(12) United States Patent
Mackenzie et al.

(10) Patent No.: US 10,272,081 B2
(45) Date of Patent: Apr. 30, 2019

(54) SHIP1 MODULATORS AND METHODS RELATED THERETO

(71) Applicant: Aquinox Pharmaceuticals (Canada) Inc., Vancouver (CA)

(72) Inventors: Lloyd F. Mackenzie, North Vancouver (CA); Thomas B. MacRury, Point Roberts, WA (US); Curtis Harwig, Vancouver (CA); David Bogucki, Surrey (CA); Jeffery R. Raymond, Vancouver (CA); Jeremy D. Pettigrew, Brunaby (CA); Vladimir Khlebnikov, Edmonton (CA); Rudong Shan, Edmonton (CA)

(73) Assignee: Aquinox Pharmaceuticals (Canada) Inc., Vancouver (CA)

( * ) Notice: Subject to any disclaimer, the term of this patent is extended or adjusted under 35 U.S.C. 154(b) by 0 days.

(21) Appl. No.: 15/884,044

(22) Filed: Jan. 30, 2018

(65) Prior Publication Data
US 2018/0161324 A1 Jun. 14, 2018
US 2018/0360828 A9 Dec. 20, 2018

Related U.S. Application Data

(62) Division of application No. 15/370,973, filed on Dec. 6, 2016, now Pat. No. 9,937,167, which is a division
(Continued)

(51) Int. Cl.
*A61K 31/05* (2006.01)
*A61K 31/09* (2006.01)
(Continued)

(52) U.S. Cl.
CPC .......... *A61K 31/4965* (2013.01); *A61K 31/05* (2013.01); *A61K 31/085* (2013.01); *A61K 31/09* (2013.01); *A61K 31/095* (2013.01); *A61K 31/10* (2013.01); *A61K 31/12* (2013.01); *A61K 31/122* (2013.01); *A61K 31/135* (2013.01); *A61K 31/155* (2013.01); *A61K 31/165* (2013.01); *A61K 31/166* (2013.01); *A61K 31/167* (2013.01); *A61K 31/192* (2013.01); *A61K 31/277* (2013.01); *A61K 31/4164* (2013.01); *A61K 31/4196* (2013.01); *A61K 31/4402* (2013.01); *A61K 31/443* (2013.01); *A61K 31/444* (2013.01); *A61K 31/4406* (2013.01); *A61K 31/4439* (2013.01); *A61K 31/4465* (2013.01); *A61K 31/495* (2013.01); *A61K 31/496* (2013.01); *C07C 39/17* (2013.01); *C07C 43/21* (2013.01); *C07C 43/215* (2013.01); *C07C 43/23* (2013.01); *C07C 49/83* (2013.01); *C07C 49/835* (2013.01); *C07C 49/84* (2013.01); *C07C 62/32* (2013.01); *C07C 62/34* (2013.01);
(Continued)

(58) Field of Classification Search
None
See application file for complete search history.

(56) References Cited

U.S. PATENT DOCUMENTS 7,601,874 B2 10/2009 Raymond et al.
7,999,010 B2 8/2011 Raymond et al.
(Continued)

FOREIGN PATENT DOCUMENTS

JP 11-349478 A 12/1999
JP 2001-31663 A 2/2001
(Continued)

OTHER PUBLICATIONS

U.S. Appl. No. 15/885,387, filed Jan. 31, 2018, Mackenzie et al.
(Continued)

*Primary Examiner* — Zinna Northington Davis
(74) *Attorney, Agent, or Firm* — Seed IP Law Group LLP

(57) ABSTRACT

Compounds of formula (I):

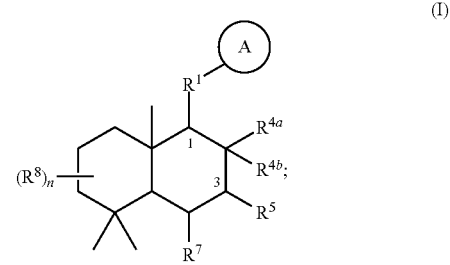

where

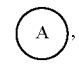

n, $R^1$, $R^{4a}$, $R^{4b}$, $R^5$, $R^7$ and $R^8$ are defined herein, or pharmaceutically acceptable salts thereof, are described herein. The disclosed compounds have activity as SHIP1 modulators, and thus may be used to treat any of a variety of diseases, disorders or conditions that would benefit from SHIP1 modulation. Compositions comprising a compound of formula (I) in combination with a pharmaceutically acceptable carrier or diluent are also disclosed, as are methods of SHIP1 modulation by administration of such compounds to an animal in need thereof.

2 Claims, No Drawings

Related U.S. Application Data of application No. 14/759,622, filed as application No. PCT/US2014/010501 on Jan. 7, 2014, now Pat. No. 9,540,353.

(60) Provisional application No. 61/750,695, filed on Jan. 9, 2013.

(51) Int. Cl.

| | | |
|---|---|---|
| A61K 31/10 | (2006.01) | |
| A61K 31/12 | (2006.01) | |
| C07C 39/17 | (2006.01) | |
| C07C 43/21 | (2006.01) | |
| C07C 43/23 | (2006.01) | |
| C07C 49/83 | (2006.01) | |
| C07C 49/84 | (2006.01) | |
| C07C 62/32 | (2006.01) | |
| C07C 62/34 | (2006.01) | |
| A61K 31/085 | (2006.01) | |
| A61K 31/095 | (2006.01) | |
| A61K 31/122 | (2006.01) | |
| A61K 31/135 | (2006.01) | |
| A61K 31/155 | (2006.01) | |
| A61K 31/165 | (2006.01) | |
| A61K 31/166 | (2006.01) | |
| A61K 31/167 | (2006.01) | |
| A61K 31/192 | (2006.01) | |
| A61K 31/4965 | (2006.01) | |
| C07D 405/12 | (2006.01) | |
| C07C 49/835 | (2006.01) | |
| C07C 43/215 | (2006.01) | |
| C07D 241/24 | (2006.01) | |
| C07D 213/81 | (2006.01) | |
| C07D 249/08 | (2006.01) | |
| C07D 295/112 | (2006.01) | |
| C07D 213/75 | (2006.01) | |
| C07D 295/215 | (2006.01) | |
| C07D 211/66 | (2006.01) | |
| C07C 311/18 | (2006.01) | |
| C07D 213/82 | (2006.01) | |
| C07D 213/89 | (2006.01) | |
| C07D 233/64 | (2006.01) | |
| C07D 401/12 | (2006.01) | |
| C07C 233/76 | (2006.01) | |
| C07D 213/38 | (2006.01) | |
| C07C 255/47 | (2006.01) | |
| C07C 275/26 | (2006.01) | |
| C07C 275/64 | (2006.01) | |
| C07C 279/16 | (2006.01) | |
| C07C 311/07 | (2006.01) | |
| C07C 311/17 | (2006.01) | |
| C07C 317/22 | (2006.01) | |
| C07C 217/84 | (2006.01) | |
| C07C 323/20 | (2006.01) | |
| C07C 225/20 | (2006.01) | |
| C07C 233/26 | (2006.01) | |
| C07C 233/28 | (2006.01) | |
| C07C 233/31 | (2006.01) | |
| C07C 233/32 | (2006.01) | |
| C07C 233/60 | (2006.01) | |
| C07C 235/82 | (2006.01) | |
| C07C 237/08 | (2006.01) | |
| A61K 31/277 | (2006.01) | |
| A61K 31/4164 | (2006.01) | |
| A61K 31/4196 | (2006.01) | |
| A61K 31/4402 | (2006.01) | |
| A61K 31/4406 | (2006.01) | |
| A61K 31/443 | (2006.01) | |
| A61K 31/4439 | (2006.01) | |
| A61K 31/444 | (2006.01) | |
| A61K 31/4465 | (2006.01) | |
| A61K 31/495 | (2006.01) | |
| A61K 31/496 | (2006.01) | |

(52) U.S. Cl.
CPC .......... C07C 217/84 (2013.01); C07C 225/20 (2013.01); C07C 233/26 (2013.01); C07C 233/28 (2013.01); C07C 233/31 (2013.01); C07C 233/32 (2013.01); C07C 233/60 (2013.01); C07C 233/76 (2013.01); C07C 235/82 (2013.01); C07C 237/08 (2013.01); C07C 255/47 (2013.01); C07C 275/26 (2013.01); C07C 275/64 (2013.01); C07C 279/16 (2013.01); C07C 311/07 (2013.01); C07C 311/17 (2013.01); C07C 311/18 (2013.01); C07C 317/22 (2013.01); C07C 323/20 (2013.01); C07D 211/66 (2013.01); C07D 213/38 (2013.01); C07D 213/75 (2013.01); C07D 213/81 (2013.01); C07D 213/82 (2013.01); C07D 213/89 (2013.01); C07D 233/64 (2013.01); C07D 241/24 (2013.01); C07D 249/08 (2013.01); C07D 295/112 (2013.01); C07D 295/215 (2013.01); C07D 401/12 (2013.01); C07D 405/12 (2013.01); C07B 2200/07 (2013.01); C07C 2602/28 (2017.05)

(56) References Cited

U.S. PATENT DOCUMENTS

| | | | |
|---|---|---|---|
| 8,084,503 | B2 | 12/2011 | Raymond et al. |
| 8,101,605 | B2 | 1/2012 | Mackenzie et al. |
| 8,673,975 | B2 | 3/2014 | Raymond et al. |
| 9,000,050 | B2 | 4/2015 | Wang et al. |
| 9,540,353 | B2 | 1/2017 | Mackenzie et al. |
| 9,765,085 | B2 | 9/2017 | Mackenzie et al. |
| 2010/0323990 | A1 | 12/2010 | Andersen et al. |
| 2011/0263539 | A1 | 10/2011 | Andersen et al. |
| 2014/0371252 | A1 | 12/2014 | Raymond et al. |
| 2016/0376222 | A1 | 12/2016 | Mackenzie et al. |
| 2017/0204048 | A1 | 7/2017 | Harwig et al. |
| 2017/0253596 | A2 | 9/2017 | Mackenzie et al. |

FOREIGN PATENT DOCUMENTS

| | | |
|---|---|---|
| JP | 2001-48873 A | 2/2001 |
| RU | 2 385 863 C2 | 4/2010 |
| WO | WO 1999/053911 A1 | 10/1999 |
| WO | WO 03/033517 A1 | 4/2003 |
| WO | WO 2004/035601 A1 | 4/2004 |
| WO | WO 2007/147251 A1 | 12/2007 |
| WO | WO 2007/147252 A1 | 12/2007 |
| WO | WO 2011/069118 A1 | 6/2011 |
| WO | WO 2014/110036 A1 | 7/2014 |

OTHER PUBLICATIONS

Barber et al., "PI3Kγ inhibition blocks glomerulonephritis and extends lifespan in a mouse model of systemic lupus," *Nature Medicine* 11(9): 933-935, Sep. 2005.

Beers et al. (eds.), *The Merck Manual of Diagnosis and Therapy, Seventeenth Edition*, Merck Research Laboratories, Division of Merck & Co., Inc., Whitehouse Station, N.J., 1999, pp. 944-955 and pp. 963-969, 11 pages.

(56) References Cited

OTHER PUBLICATIONS

Bjamer et al., "The Configuration at C(13) in Labdanolic and Eperuic Acids by an X-ray Crystal Structure Analysis of the p-Bromophenacyl Ester of Labdanolic Acid," Acta Cryst. B24: 855-865, 1968.
Bohlmann et al., "Sesquiterpenes, Guaianolides and Diterpenes from *Stevia Myriadenia,*" *Phytochemistry* 21(8): 2021-2025, 1982.
Brauer et al., "Leukemia-associated mutations in SHIP1 inhibit its enzymatic activity, interaction with the GM-CSF receptor and Grb2, and its ability to inactivate PI3K/AKT signaling," *Cellular Signalling* 24: 2095-2101, 2012.
Camps et al., "Blockade of PI3Kγ suppresses joint inflammation and damage in mouse models of rheumatoid arthritis," *Nature Medicine* 11(9): 936-943, Sep. 2005.
Coggeshall et al., "How do inhibitory phosphatases work?" *Molecular Immunology* 39: 521-529, 2002.
Damen et al., "The 145-kDa protein induced to associate with Shc by multiple cytokines is an inositol tetraphosphate and phosphatidylinositol 3,4,5-trisphosphate 5-phosphatase," *Proc. Natl. Acad. Sci. USA* 93: 1689-1693, Feb. 1996.
Deane et al., "Phosphoinositide 3-Kinase: Diverse Roles in Immune Cell Activation," *Annu. Rev. Immunol.* 22: 563-598, 2004.
Fan et al., "A dual PI3 kinase/mTOR inhibitor reveals emergent efficacy in glioma," *Cancer Cell* 9: 341-349, May 2006.
Fonseca et al., "International Myeloma Working Group molecular classification of multiple myeloma: spotlight review," NIH Public Access Author Manuscript published in final edited form as: *Leukemia.* Dec. 2009; 23(12): 2210-2221. Doi:10.1038/leu.2009.174, 27 pages.
Fukuda et al., "Alteration of phosphatidylinositol 3-kinase cascade in the multilobulated nuclear formation of adult T cell leukemia/lymphoma (ATLL)," *PNAS* 102(42): 15213-15218, Oct. 18, 2005.
Gabelloni et al., "SHIP-1 protein level and phosphorylation status differs between CLL cells segregated by ZAP-70 expression," *British Journal of Haematology* 140: 117-119, 2007.
Gallou et al., "Practical Synthesis of Unsymmetrical Ureas from Isopropenyl Carbamates," *J. Org. Chem.* 70: 6960-6963, 2005.
Garcia-Sanz et al., "Primary Plasma Cell Leukemia: Clinical, Immunophenotypic, DNA Ploidy, and Cytogenetic Characteristics," Blood 93(3): 1032-1037, Feb. 1, 1999.
Giron et al., "Evaluation of labdane derivatives as potential anti-inflammatory agents," European Journal of Medicinal Chemistry 45: 3155-3161, 2010.
Goclik et al., "Pelorol from the Tropical Marine Sponge *Dactylospongia elegans,*" *J. Nat. Prod.* 63: 1150-1152, 2000.
Halpern et al., "On the Nature of the Chemical Mediators Involved in Anaphylactic Reactions in Mice," *Brit. J. Pharmacol.* 20: 389-398, 1963.
Hashimoto et al., Chemical Conversion of Labdane-type Diterpenoid Isolated From the Liverwort Porella Perrottetiana Into (−)-Ambrox, Heterocycles 49: 315-325, 1998.
Hazen et al., "SHIP is required for a functional hematopoietic stem cell niche," *Blood* 113(13): 2924-2933, Mar. 26, 2009.
Helgason et al., "Targeted disruption of *SHIP* leads to hemopoietic perturbations, lung pathology, and a shortened life span," *Genes & Development* 12: 1610-1620, 1998.
Helgason et al., "A Dual Role for Src Homology 2 Domain-containing of Inositol-5-Phosphatase (SHIP) in Immunity: Aberrant Development and Enhanced Function of B Lymphocytes in SHIP$^{-/-\ Mice}$," *J. Exp. Med.* 191(5): 781-794, Mar. 6, 2000.
Hennessy et al., "Exploiting the PI3K/AKT Pathway for Cancer Drug Discovery," *Nat. Rev. Drug Disc.* 4: 988-1004, Dec. 2005.
Henrick et al., "Enantiomers of Labdanolic Acid and 13-EPI-Labdanolic Acid," Tetrahedron Letters 47: 3475-3480, 1964.
Kalesnikoff et al., "The role of SHIP in cytokine-induced signaling," *Rev. Physiol. Biochem. Pharmacol.* 149: 87-103, 2003.
Kennah et al., "Activation of SHIP via a small molecule agonist kills multiple myeloma cells," *Experimental Hematology* 37: 1274-1283, 2009.

King et al., "The Chemistry of Extractives from Hardwoods. Part XXI. The Structure of Eperuic Acid," Journal of Chemical Society, pp. 658-665, 1955.
Kuchkova et al., "A Short Efficient Synthesis of 11-Monoacetate of Drimane-8α,11-diol from Norambreinolide," *Synthesis*: 1045-1048, Sep. 1997.
Kuchkova et al., "Elimination of C-8-Functional Groups from Driman-8α,11-Diol-11-Monoacetate and—Diacetate," *Chemistry of Natural Compounds* 43(4): 412-416, 2007.
Knight et al., "A Pharmacological Map of the PI3-K Family Defines a Role for p110α in Insulin Signaling," *Cell* 125: 733-747, May 19, 2006.
Kwak et al., "Sesquiterpene Quinols/Quinones from the Micronesian Sponge *Petrosaspongia metachromia,*" *J. Nat. Prod.* 63: 1153-1156, 2000.
Liang et al., "Quantification of change in phosphorylation of BCR-ABL kinase and its substrates in response to Imatinib treatment in human chronic myelogenous leukemia cells," *Proteomics* 6: 4554-4564, 2006.
Lo et al., "Inactivation of SHIP1 in T-cell Acute Lymphoblastic Leukemia due to Mutation and Extensive Alternative Splicing," *Leuk. Res.* 33(11): 1562-1566, Nov. 2009.
Luo et al., "Mutation Analysis of SHIP Gene in Acute Leukemia," *Journal of Experimental Hematology* 12(4): 420-426, 2004.
Luo et al., "Possible dominant-negative mutation of the *SHIP* gene in acute myeloid leukemia," *Leukemia* 17: 1-8, 2003.
McNamara et al, "Anti-inflammatory Sesquiterpene-quinones from the New Zealand Sponge *Dysidea cf. cristagalli,*" *J. Nat. Prod.* 68: 1431-1433, 2005.
Mohanraj et al., "Photosensitized Oxygenation of Labda-8(17),12-diene, Labda-8(17)13-diene, and the Biformenes. Synthesis of Pumiloxide," *J. Org. Chem.* 46: 1362-1366, 1981.
Nodwell, "Synthesis of Biologically Active Marine Natural Product Analogues," A thesis submitted in partial fulfillment of the requirements for the degree of Doctor of Philosophy, The University of British Columbia, Vancouver, Canada, Jan. 2009, 229 pages.
Ohloff et al., "Structure-Activity Relationships in Odor Perception of Drimane Derivatives," Croatica Chemica Acta 58(4): 491-509, 1985.
Ong et al., "Small-molecule agonists of SHIP1 inhibit the phosphoinositide 3-kinase pathway in hematopoietic cells," *Blood* 110(6): 1942-1949, Sep. 15, 2007.
Ovary, "Passive Cutaneous Anaphylaxis in the Mouse," *J. Immunol.* 81: 355-357, 1958.
Pauli, "Anticandidal Low Molecular Compounds from Higher Plants with Special Reference to Compounds from Essential Oils," *Medicinal Research Reviews* 26(2): 223-268, 2006.
Rodriguez et al., "The Structures and Stereochemistry of Cytotoxic Sesquiterpene Quinones from *Dactylospongia elegans,*" *Tetrahedron* 48(32): 6667-6680, 1992.
Rohrschneider et al., "Structure, function, and biology of SHIP proteins," *Genes & Development* 14: 505-520, 2000.
Rubinstein, "Multiple Myeloma as a Form of Leukemia," *Blood* 4: 1049-1067, 1949 (20 pages).
Saint-Dic et al., "Regulation of the Src Homology 2-containing Inositol 5-Phosphatase SHIP1 in HIP1/PDGFβR-transformed Cells," The Journal of Biological Chemistry 276(24): 21192-21198, Jun. 15, 2001.
Sarragiotto et al., "Synthesis of an Enantiomerically Pure Indolosesquiterpene," J. Chem. Soc. Perkin Trans.1: 559-562, 1989.
Simon, "Using Isoform-Specific Inhibitors to Target Lipid Kinases," *Cell* 125: 647-649, May 19, 2006.
Sly et al., "SHIP, SHIP2, and PTEN activities are regulated in vivo by modulation of their protein levels: SHIP is up-regulated in macrophages and mast cells by lipopolysaccharide," *Experimental Hematology* 31: 1170-1181, 2003.
Sly et al., "LPS-Induced Upregulation of SHIP Is Essential for Endotoxin Tolerance," *Immunity* 21: 227-239, Aug. 2004.
de la Torre et al., Photochemical Access to Tetra- and Pentacyclic Terpene-like Products from R-(+)-Sclareolide, *J. Org. Chem* 68: 6611-6618, 2003.

(56) References Cited

OTHER PUBLICATIONS de la Torre et al., "Diversity Oriented Synthesis of Hispanane-like Terpene Derivatives from (R)-(+)-Sclareolide," *Chem. Eur. J.* 11: 3659-3667, 2005.
Vanderwinden et al., "Differences in signaling pathways and expression level of the phosphoinositide phosphatase SHIP1 between two oncogenic mutants of the receptor tyrosine kinase KIT," *Cellular Signalling* 18: 661-669, 2006.
Vivanco et al., "The Phosphatidylinositol 3-Kinase-AKT Pathway in Human Cancer," *Nature Reviews Cancer* 2: 489-501, Jul. 2002.
Vonakis et al., "Src homology 2 domain-containing inositol 5' phosphatase is negatively associated with histamine release to human recombinant histamine-releasing factor in human basophils," *J. Allergy Clin. Immunol.* 108(5): 822-831, Nov. 2001.
Winter et al., "Carrageenin-Induced Edema in Hind Paw of the Rat as an Assay for Antiinflammatory Drugs," *Proc. Soc. Exp. Biol. Med.* 111: 544-547, 1962.
Workman et al., "Drugging the PI3 kinome," *Nature Biotechnology* 24(7): 794-796, Jul. 2006.
Yang et al., "Synthesis of Pelorol and Analogues: Activators of the Inositol 5-Phosphatase SHIP," *Organic Letters* 7(6): 1073-1076, 2005.
Translation of Official Action from Patent Office of Japan, dated Oct. 26, 2017, for Patent Application No. 2015-551836, 8 pages.
Meimetis et al., "Synthesis of SHIP1-Activating Analogs of the Sponge Meroterpenoid Pelorol," *Eur. J. Org. Chem*, pp. 5195-5207, 2012.
Nishizawa et al., "Selective Total Synthesis of (±)-α- and γ-Polypodatetraene," *J. Chem. Soc., Chem. Commun.* 7: 467-468, 1984, 4 pages.
Official Action from European Patent Office, dated Feb. 4, 2019, for Patent Application No. 14702673.6, 5 pages.
Official Action from Japanese Patent Office (with translation), dated Dec. 28, 2018, for Patent Application No. 2018-042934, 7 pages.

SHIP1 MODULATORS AND METHODS RELATED THERETO

CROSS-REFERENCE TO RELATED APPLICATIONS

This application is a divisional application of U.S. patent application Ser. No. 15/370,973, filed on Dec. 6, 2016, now allowed; which is a divisional application of U.S. patent application Ser. No. 14/759,622, filed on Jul. 7, 2015, now U.S. Pat. No. 9,540,353, issued on Jan. 10, 2017; which is a national stage application, filed under 35 U.S.C. § 371, of International Application No. PCT/US2014/010501, accorded an international filing date of Jan. 7, 2014; which claims the benefit under 35 U.S.C. § 119(e) of U.S. Provisional Patent Application No. 61/750,695, filed on Jan. 9, 2013; the relevant disclosures of which are incorporated herein by reference in their entireties.

FIELD OF THE INVENTION

The present invention is generally directed to SHIP1 modulators, as well as to compositions and methods related to the same.

BACKGROUND OF THE INVENTION

In response to extracellular signals, phosphoinositide 3-kinase (PI3K) becomes activated and phosphorylates phosphatidylinositol-4,5-bisphosphate (PI-4,5-$P_2$) within the plasma membrane to generate phosphatidylinositol-3,4,5-trisphosphate ($PIP_3$). $PIP_3$ then initiates a cascade of downstream signaling pathways by interacting with pleckstrin homology (PH) domain-containing proteins, such as protein kinase B (PKB, also known as Akt), that regulate cellular activation, function, proliferation and/or survival, depending on the cell type and stimulus (Deane et al., *Annu Rev Immunol* 22, 563-598, 2004). Cellular levels of $PIP_3$ are normally tightly regulated by PI3K, the 5' inositol phosphatases SHIP1 (SH2 domain-containing inositol phosphatase), SHIP2, and by the 3' inositol phosphatase PTEN. SHIP1 and SHIP2 dephosphorylate $PIP_3$ to phosphatidylinositol-3,4-bisphosphate (PI-3,4-$P_2$), whereas PTEN dephosphorylates $PIP_3$ to PI-4,5-$P_2$ (Sly et al., *Exp Hematol* 31, 1170-1181, 2003; Vivanco et al., *Nat Rev Cancer* 2, 489-501, 2002). Of these three, SHIP1 is unique in that its expression is restricted primarily to immune and hematopoietic cells (Sly et al., *Exp Hematol* 31, 1170-1181, 2003; Damen et al., *Proc Natl Acad Sci USA* 93, 1689-1693, 1996).

SHIP1's role in immune cell homeostasis is shown both by the myeloproliferative syndrome observed in SHIP1$^{-/-}$ mice, as well as the hypersensitivity of SHIP1$^{-/-}$ mice and cells to immune stimulation (Helgason et al., *Genes Dev* 12, 1610-1620, 1998; Sly et al., *Immunity* 21, 227-239, 2004). SHIP1 has been shown to mediate signaling from the inhibitory FcγRIIB receptor (Coggeshall et al., *Mol Immunol* 39, 521-529, 2002), and is important in terminating signal transduction from activating immune/hematopoietic cell receptor systems (Kalesnikoff et al., *Rev Physio/Biochem Pharmacol* 149, 87-103, 2003).

Diminished SHIP1 activity or expression has been observed in human inflammatory diseases (Vonakis et al., *J Allergy Clin Immunol* 108, 822-831, 2001) and hematopoietic malignancies (Liang et al., *Proteomics* 6, 4554-4564, 2006; Fukuda et al., *Proc Natl Acad Sci USA* 102, 15213-15218, 2005; Luo et al., *Zhongguo Shi Yan Xue Ye Xue Za Zhi* 12, 420-426, 2004; Vanderwinden et al., *Cell Signal* 18, 661-669, 2006; Ong, C. J. et al., *Blood* (2007), Vol. 110, No. 6, pp. 1942-1949).

Because dysregulated activation of the PI3K pathway contributes to inflammatory/immune disorders and cancer, intense efforts have been invested into the development of inhibitors of PI3K itself, as well as downstream protein kinases (Workman et al., *Nat Biotechnol* 24, 794-796, 2006; Simon, *Cell* 125, 647-649, 2006; Hennessy et al., *Nat Rev Drug Discov* 4, 988-1004, 2005; Knight et al., *Cell* 125, 733-747, 2006; Ong, C. J. et al., *Blood* (2007), Vol. 110, No. 6, pp. 1942-1949). The precedent for discovery and biologic efficacy of kinase inhibitors is well established, and a number of promising new PI3K isoform-specific inhibitors have recently been developed and used in mouse models of inflammatory disease (Camps et al., *Nat Med* 11, 936-943, 2005; Barber et al., *Nat Med* 11, 933-935, 2005) and glioma (Fan et al., *Cancer Cell* 9, 341-349, 2006) with minimal toxicities. However, because of the dynamic interplay between phosphatases and kinases in regulating biologic processes, inositol phosphatase activators represent a complementary, alternative approach to reduce cellular $PIP_3$ levels. Of the phosphoinositol phosphatases that degrade $PIP_3$, SHIP1 is a particularly ideal target for development of therapeutics for treating immune and hemopoietic disorders because its hematopoietic-restricted expression (Hazen A L, et al. 113, 2924-33, 2009; Rohrschneider L R, Fuller J F, Wolf I, Liu Y, Lucas D M. Structure, function, and biology of SHIP proteins. *Genes Dev.* 14:505-20, 2000) would limit the effects of a specific SHIP1 agonist to target cells.

To date, a number of small molecule SHIP1 modulators have been disclosed, including sesquiterpene compounds such as pelorol. Pelorol is a natural product isolated from the topical marine sponge *Dactylospongia elegans* (Kwak et al., *J Nat Prod* 63, 1153-1156, 2000; Goclik et al., *J Nat Prod* 63, 1150-1152, 2000). Other reported SHIP1 modulators include the compounds set forth in PCT Published Patent Application Nos. WO 2003/033517, WO 2004/035601, WO 2004/092100 (or U.S. Pat. No. 7,601,874), WO 2007/147251, WO 2007/147252 and WO 2011/069118.

While significant strides have been made in this field, there remains a need for effective small molecule SHIP1 modulators. There is also a need for pharmaceutical compositions containing such compounds, as well as for methods relating to the use thereof to treat disorders or conditions that would benefit from SHIP1 modulation. The present invention fulfills these needs, and provides other related advantages.

SUMMARY OF THE INVENTION

The present invention is generally directed to compounds which are SHIP1 modulators and pharmaceutical compositions comprising the compounds and methods of using the compounds and the pharmaceutical compositions of the invention for the treatment of diseases, disorders or conditions that would benefit from SHIP1 modulation. As used herein, a SHIP1 modulator can serve as either an agonist or antagonist to SHIP1.

Accordingly, in one aspect, this invention is directed to compounds of formula (I):

(I)

[Chemical structure of formula (I): a decahydronaphthalene core with substituents R¹ (bearing group A at position 1), R⁴ᵃ and R⁴ᵇ at position 2, R⁵ at position 3, R⁷, (R⁸)ₙ, and gem-dimethyl groups]

wherein:

A is selected from:

[Chemical structures showing: a phenyl ring bearing R³, R⁶, R²; a furan bearing R⁶; a pyridine bearing R⁶; an imidazole bearing R⁶; a triazole bearing R⁶; a benzimidazole bearing R⁶; a pyrazole bearing R⁶; a pyrrole bearing R⁶; an imidazoline bearing R⁶; and a triazole bearing R⁶]

n is 1, 2, 3, 4, 5, or 6;

R¹ is —R⁹ᵃ—C(R¹⁰)₂—R⁹ᵇ—, —R⁹ᵃ—C(O)—R⁹ᵇ—, —R⁹ᵃ—S(O)ₜ—R⁹ᵇ— (where t is 0, 1 or 2), —R⁹ᵃ—O—R⁹ᵇ—, —R⁹ᵃ—C(O)N(R¹¹ᵃ)—R⁹ᵇ—, —R⁹ᵃ—N(R¹¹ᵃ)C(O)—R⁹ᵇ— or —R⁹ᵃ—N(R¹¹ᵃ)—R⁹ᵇ;

R² and R³ are each independently selected from hydrogen, alkyl or —R⁹—OR¹¹, provided that at least one of R² and R³ is —R⁹—OR¹¹ when R⁶ is hydrogen;

R⁴ᵃ and R⁴ᵇ are each independently selected from hydrogen, alkyl, —R⁹—OR¹¹ or —C(O)OR¹¹, or R⁴ᵃ is selected from hydrogen, alkyl, —R⁹—OR¹¹, or —C(O)OR¹¹ and R⁴ᵇ is a direct bond to the carbon at numeral 1 or a direct bond to the carbon at numeral 3;

or R⁴ᵃ and R⁴ᵇ together form =C(R¹³)₂;

R⁵ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —R⁹—OR¹¹, —R⁹—C(O)R¹¹, —R⁹—C(O)OR¹¹, —R⁹—N(R¹¹)R¹², —R⁹—C(O)N(R¹¹)R¹², —R⁹—N(R¹¹)C(O)R¹², —R⁹—N(R¹¹)—R¹⁴—N(R¹¹)R¹², —R⁹—N(R¹¹)C(O)—R⁹—N(R¹¹)R¹², —R⁹—N(R¹¹)C(O)N(R¹¹)—OR¹², —R⁹—N(R¹¹)C(=NR¹¹)N(R¹¹)R¹², —R⁹—N(R¹¹)S(O)ₚR¹¹ (where p is 1 or 2), —R⁹—N(R¹)C(S)N(R¹¹)R¹² or —R⁹—N(R¹¹)C(O)—R⁹—N(R¹¹)S(O)ₚR¹² (where p is 1 or 2);

each R⁶ and R⁸ is independently selected from hydrogen, alkyl, halo or haloalkyl;

R⁷ is hydrogen, alkyl, halo or haloalkyl;

each R⁹, R⁹ᵃ and R⁹ᵇ is independently a direct bond or a straight or branched alkylene chain;

each R¹⁰ is independently hydrogen, alkyl, —OR¹¹, —C(O)OR¹¹, —C(O)N(R¹¹)R¹², —N(R¹¹)R¹² or —N(R¹¹)C(O)R¹¹;

each R¹¹, R¹¹ᵃ and R¹² is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;

each R¹³ is hydrogen, alkyl or haloalkyl; and

R¹⁴ is a straight or branched alkylene chain;

or a stereoisomer thereof or a pharmaceutically acceptable salt thereof;

provided that compounds of formula (I) do not include the following compounds:

(1S,2S,4aS,8aR)-decahydro-1-[2-(3-methoxyphenyl)ethyl]-5,5,8a-trimethyl-2-naphthalenecarboxylic acid;

(1S,2S,4aS,8aR)-decahydro-1-[2-(3-methoxyphenyl)ethyl]-5,5,8a-trimethyl-2-naphthalenemethanol;

α-(3,5-dimethoxyphenyl)decahydro-2-hydroxy-2,5,5,8a-tetramethyl-1-naphthalenemethanol;

(4aS,8aS)-3,4,4a,5,6,7,8,8a-octahydro-α-(3-methoxy-5-methylphenyl)-2,5,5,8a-tetramethyl-1-naphthalenemethanol;

(1S,2R,4aS,8aS)-decahydro-2-hydroxy-α-(3-methoxy-5-methylphenyl)-2,5,5,8a-tetramethyl-1-naphthalenemethanol;

(1R,2R,4aS,8aS)-decahydro-1-[(3-methoxy-5-methylphenyl)methyl]-2,5,5,8a-tetramethyl-2-naphthalenol;

(4aS,5S,8aS)-decahydro-5-[2-(3-methoxyphenyl)ethyl]-1,1,4a-trimethyl-6-methylene-naphthalene;

2-[(1S,4aS,8aS)-decahydro-5,5,8a-trimethyl-2-methylene-1-naphthalenyl]-1-(3-methoxyphenyl)-ethanone;

(1S,2R,4aS,8aS)-1-(3-methoxy-5-methylphenoxymethyl)-2,5,5,8a-tetramethyl-decahydronaphthalen-2-ol;

(1S,2R,4aS,8aS)-1-(3,5-dimethoxyphenoxymethyl)-2,5,5,8a-tetramethyl-decahydronaphthalen-2-ol;

(1S,2R,4aS,8aS)-1-[3,5-bis(propan-2-yloxy)phenoxymethyl]-2,5,5,8a-tetramethyl-decahydronaphthalen-2-ol;

(1R,2R,8aS)-1-((3,5-dimethoxyphenylsulfonyl)methyl)-2,5,5,8a-tetramethyldecahydronaphthalen-2-ol;

(1R,2R,4aS,8aS)-1-{[(3-methoxy-5-methylphenyl)sulfanyl]methyl}-2,5,5,8a-tetramethyl-decahydronaphthalen-2-ol;

(1R,2R,4aS,8aS)-1-{[(3-methoxyphenyl)sulfanyl]methyl}-2,5,5,8a-tetramethyl-decahydronaphthalen-2-ol; and (1R,2R,4aS,8aS)-1-{[(3,5-dimethoxyphenyl)sulfanyl]methyl}-2,5,5,8a-tetramethyl-decahydronaphthalen-2-ol.

In another aspect, this invention is directed to compositions comprising a pharmaceutically acceptable excipient, carrier and/or diluent and a compound of formula (I), or a stereoisomer thereof or a pharmaceutically acceptable salt thereof.

In another aspect, this invention is directed to a method for modulating SHIP1 activity in a mammal comprising administering an effective amount of a compound of formula (I), or a pharmaceutically acceptable salt thereof or a stereoisomer thereof, or a composition comprising a compound of formula (I), or a pharmaceutically acceptable salt thereof or a stereoisomer thereof, to the mammal in need thereof.

In another aspect, this invention is directed to methods for treating a disease, disorder or condition in a mammal comprising administering an effective amount of a compound of formula (I), or a stereoisomer thereof or a pharmaceutically acceptable salt thereof, as set forth above, to the mammal in need thereof, where the disease, disorder or condition is an autoimmune disease, disorder or condition, an inflammatory disease, disorder or condition, or a neoplastic or cell proliferative disease, disorder or condition.

In another aspect, this invention is directed to methods of treating a disease, disorder or condition in a mammal comprising administering an effective amount of a compound of formula (I), or a stereoisomer thereof or a pharmaceutically acceptable salt thereof, typically in the form of a composition, to the mammal in need thereof.

Methods of this invention include administering an effective amount of a compound of formula (I), or a pharmaceutically acceptable salt thereof or a stereoisomer thereof, to the mammal in need thereof (such as a human).

In another aspect, this invention is directed to methods of preparing compounds of formula (I), or stereoisomers thereof or pharmaceutically acceptable salts thereof.

These aspects and embodiments thereof are described in more detail below. To this end, various references are set forth herein which describe in more detail certain background information, procedures, compounds and/or compositions, and are each hereby incorporated by reference in their entirety.

DETAILED DESCRIPTION OF THE INVENTION

Definitions

As used in the specification and appended claims, unless specified to the contrary, the following terms have the meaning indicated:

"Oxo" refers to =O.
"Cyano" refers to —CN.
"Nitro" refers to —$NO_2$.
"Hydroxy" refers to —OH.
"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. When specifically stated in the specification, an alkyl group may be optionally substituted by one of the following groups: alkyl, halo, haloalkyl, cyano, nitro, aryl, cycloalkyl, heterocyclyl, heteroaryl, oxo, trimethylsilanyl, —$OR^{20}$, —OC(O)—$R^{20}$, —$N(R^{20})_2$, —C(O)$R^{20}$, —C(O)O$R^{20}$, —C(O)N($R^{20})_2$, —$N(R^{20})$C(O)O$R^{22}$, —$N(R^{20})$C(O)$R^{22}$, —$N(R^{20})$S(O)$_p R^{22}$ (where p is 1 to 2), —S(O)$_p$O$R^{22}$ (where p is 1 to 2), —S(O)$_t R^{22}$ (where t is 0 to 2), and —S(O)$_p$N($R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. When specifically stated in the specification, an alkenyl group may be optionally substituted by one of the following groups: alkyl, halo, haloalkyl, cyano, nitro, aryl, cycloalkyl, heterocyclyl, heteroaryl, oxo, trimethylsilanyl, —$OR^{20}$, —OC(O)—$R^{20}$, —$N(R^{20})_2$, —C(O)$R^{20}$, —C(O)O$R^{20}$, —C(O)N($R^{20})_2$, —$N(R^{20})$C(O)O$R^{22}$, —$N(R^{20})$C(O)$R^{22}$, —$N(R^{20})$S(O)$_p R^{22}$ (where p is 1 to 2), —S(O)$_p$O$R^{22}$ (where p is 1 to 2), —S(O)$_t R^{22}$ (where t is 0 to 2), and —S(O)$_p$N($R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkoxy" refers to a radical of the formula —$OR_a$ where $R_a$ is an alkyl radical as defined above containing one to twelve carbon atoms. The alkyl part of the alkoxy radical may be optionally substituted as defined above for an alkyl radical "Alkylene" or "alkylene chain" refers to a straight or branched divalent hydrocarbon chain linking the rest of the molecule to a radical group or linking two parts of the molecule, consisting solely of carbon and hydrogen, containing no unsaturation and having from one to twelve carbon atoms, e.g., methylene, ethylene, propylene, n-butylene, and the like. The alkylene chain is attached to the rest of the molecule through a single bond and to the radical group through a single bond or is attached to two parts of the molecule through a single bond at each point of attachment. When specifically stated in the specification, an alkylene chain may be optionally substituted by one of the following groups: alkyl, alkenyl, halo, cyano, nitro, aryl, cycloalkyl, heterocyclyl, heteroaryl, oxo, trimethylsilanyl, —$OR^{20}$, —OC(O)—$R^{20}$, —$N(R^{20})_2$, —C(O)$R^{20}$, —C(O)O$R^{20}$, —C(O)N($R^{20})_2$, —$N(R^{20})$C(O)O$R^{22}$, —$N(R^{20})$C(O)$R^{22}$, —$N(R^{20})$S(O)$_p R^{22}$ (where p is 1 to 2), —S(O)$_p$O$R^{22}$ (where p is 1 to 2), —S(O)$_t R^{22}$ (where t is 0 to 2), and —S(O)$_p$N($R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. When specifically stated in the specification, an aryl group may be optionally substituted by one or more substituents independently selected from the group consisting of alkyl, alkenyl, halo, haloalkyl, cyano, nitro, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)$_2$, —$R^{21}$—C(O)$R^{20}$, —$R^{21}$—C(O)$OR^{20}$, —$R^{21}$—C(O)N($R^{20}$)$_2$, —$R^{21}$—N($R^{20}$)C(O)$R^{22}$, —$R^{21}$—N($R^{20}$)C(O)$R^{22}$, —$R^{21}$—N($R^{20}$)S(O)$_p$$R^{22}$ (where p is 1 to 2), —$R^{21}$—N=C($OR^{20}$)$R^{20}$, —$R^{21}$—S(O)$_p$$OR^{22}$ (where p is 1 to 2), —$R^{21}$—S(O)$_t$$R^{22}$ (where t is 0 to 2), and —$R^{21}$—S(O)$_p$N($R^{20}$)$_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. When specifically stated in the specification, the alkylene chain part of the aralkyl radical may be optionally substituted as described above for an optionally substituted alkylene chain. When specifically stated in the specification, the aryl part of the aralkyl radical may be optionally substituted as described above for an optionally substituted aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. When specifically stated in the specification, a cycloalkyl group may be optionally substituted by one or more substituents independently selected from the group consisting of alkyl, halo, haloalkyl, cyano, nitro, oxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)$_2$, —$R^{21}$—C(O)$R^{20}$, —$R^{21}$—C(O)$OR^{20}$, —$R^{21}$—C(O)N($R^{20}$)$_2$, —$R^{21}$—N($R^{20}$)C(O)$R^{22}$, —$R^{21}$—N($R^{20}$)C(O)$R^{22}$, —$R^{21}$—N($R^{20}$)S(O)$_p$$R^{22}$ (where p is 1 to 2), —$R^{21}$—N=C($OR^{20}$)$R^{20}$, —$R^{21}$—S(O)$_p$$OR^{22}$ (where p is 1 to 2), —$R^{21}$—S(O)$_t$$R^{22}$ (where t is 0 to 2), and —$R^{21}$—S(O)$_p$N($R^{20}$)$_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Cycloalkylalkyl" refers to a radical of the formula —$R_b$$R_g$ where $R_b$ is an alkylene chain as defined above and $R_g$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, 1,2,4-thiadiazol-5(4H)-ylidene, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. When specifically stated in the specification, a heterocyclyl group may be optionally substituted by one or more substituents selected from the group consisting of alkyl, alkenyl, halo, haloalkyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)$_2$, —$R^{21}$—C(O)$R^{20}$, —$R^{21}$—C(O)$OR^{20}$, —$R^{21}$—C(O)N($R^{20}$)$_2$, —$R^{21}$—N($R^{20}$)C(O)$OR^{22}$, —$R^{21}$—N($R^{20}$)C(O)$R^{22}$, —$R^{21}$—N($R^{20}$)S(O)$_p$$R^{22}$ (where p is 1 to 2), —$R^{21}$—N=C($OR^{20}$)$R^{20}$, —$R^{21}$—S(O)$_p$$OR^{22}$ (where p is 1 to 2), —$R^{21}$—S(O)$_t$$R^{22}$ (where t is 0 to 2), and —$R^{21}$—S(O)$_p$N($R^{20}$)$_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heterocyclyl" refers to a heterocyclyl radical as defined above containing at least one nitrogen. The point of attachment of the N-heterocyclyl to the rest of the molecule can be through a nitrogen atom or a carbon atom in the N-heterocyclyl.

When specifically stated in the specification, an N-heterocyclyl radical may be optionally substituted as described above for an optionally substituted heterocyclyl radical.

"Heterocyclylalkyl" refers to a radical of the formula —$R_b$$R_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. When specifically stated in the specification, the alkylene chain of the heterocyclylalkyl radical may be optionally substituted as defined above for an optionally substituted alkyene chain. When specifically stated in the specification, the heterocyclyl part of the heterocyclylalkyl radical may be optionally substituted as defined above for an optionally substituted heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzo[d]imidazolyl, benzthiazolyl, benzindolyl, benzodioxolyl, benzofuranyl, benzooxazolyl, benzothiazolyl, benzo[d]isoxazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazo[1,2-a]pyridinyl, imidazo[1,2-a]pyrimidinyl, imidazo[1,2-a]pyrazinyl, imidazo[1,5-a]pyrazinyl, imidazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrido[2,3-d]pyrimidinonyl, pyrazolo[1,5-a]pyrimidinyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). When specifically stated in the specification, a heteroaryl group may be optionally substituted by one or more substituents selected from the group consisting of alkyl, alkenyl, halo, haloalkyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—$OC(O)$—$R^{20}$, —$R^{21}$—$N(R^{20})_2$, —$R^{21}$—$C(O)R^{20}$, —$R^{21}$—$C(O)OR^{20}$, —$R^{21}$—$C(O)N(R^{20})_2$, —$R^{21}$—$N(R^{20})C(O)OR^{22}$, —$R^{21}$—$N(R^{20})C(O)R^{22}$, —$R^{21}$—$N(R^{20})S(O)_p R^{22}$ (where p is 1 to 2), —$R^{21}$—$N$=$C(OR^{20})R^{20}$, —$R^{21}$—$S(O)_p OR^{22}$ (where p is 1 to 2), —$R^{21}$—$S(O)_t R^{22}$ (where t is 0 to 2), and —$R^{21}$—$S(O)_p N(R^{20})_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heteroaryl" refers to a heteroaryl radical as defined above containing at least one nitrogen. The point of attachment of the N-heteroaryl to the rest of the molecule can be through a nitrogen atom or a carbon atom in the N-heteroaryl. When specifically stated in the specification, an N-heteroaryl radical may be optionally substituted as described above for an optionally substituted heteroaryl radical.

"Heteroarylalkyl" refers to a radical of the formula —$R_b R_i$ where $R_b$ is an alkylene chain as defined above and $R_i$ is a heteroaryl radical as defined above. When specifically stated in the specification, the heteroaryl part of the heteroarylalkyl radical may be optionally substituted as defined above for an optionally substituted heteroaryl group. When specifically stated in the specification, the alkylene chain part of the heteroarylalkyl radical may be optionally substituted as defined above for an optionally substituted alkylene chain.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like. Further, in the case of a carboxylic acid (—C(O)OH), esters may be employed, such as methyl esters, ethyl esters, and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted"). When a functional group is described as "optionally substituted," and in turn, substitutents on the functional group are also "optionally substituted" and so on, for the purposes of this invention, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent. Furthermore, some of the crystalline forms of the compounds of formula (I) may exist as polymorphs, which are included in the present invention.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a disease or condition alleviated by the modulation of SHIP1 in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(a) preventing the disease or condition from occurring in a mammal, in particular, when such mammal is predisposed to the condition but has not yet been diagnosed as having it;

(b) inhibiting the disease or condition, i.e., arresting its development;

(c) relieving (or ameliorating) the disease or condition, i.e., causing regression of the disease or condition; or (d) relieving (or ameliorating) the symptoms resulting from the disease or condition, i.e., relieving inflammation without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. Compounds of formula (I) may also possess axial chirality which may result in atropisomers. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes enantiomers, which refers to two stereoisomers whose molecules are nonsuperimposeable mirror images of one another. See, for example, Smith, M. B. and J. March, *March's Advanced Organic Chemistry: Reactions, Mechanisms, and Structure*, 6th edition (Wiley, 2007), for a detailed description of the structure and properties of enantiomers and stereoisomers.

A "tautomer" refers to a proton shift from one atom of a molecule to another atom of the same molecule. The present invention includes tautomers of any said compounds.

Representative isomers of the compounds of formula (I) include, but are not limited to, the following structures where $R^{4a}$ and $R^{4b}$ are each independently selected from hydrogen, alkyl, $-R^9-OR^{11}$, or $-C(O)OR^{11}$:

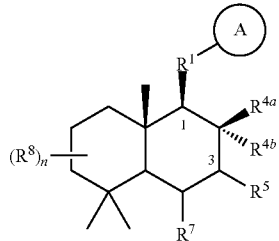

(I1)

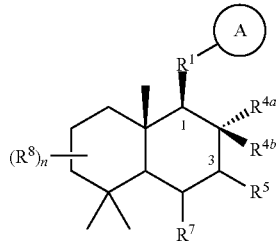

(I2)

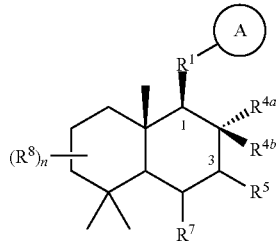

(I3)

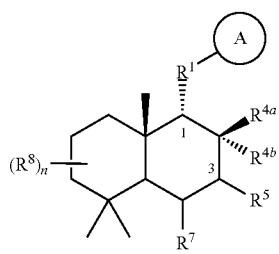

(I4)

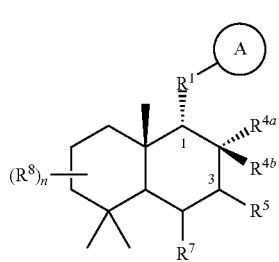

(I5)

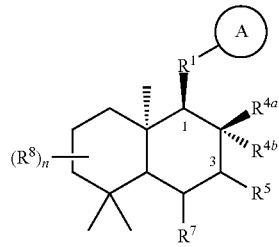

(I6)

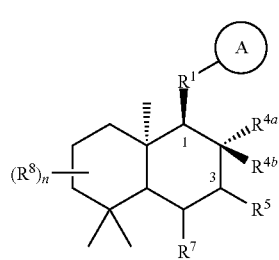

(I7)

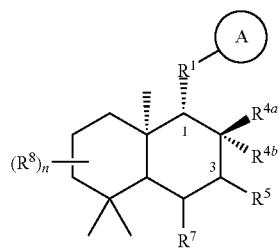

(I8)

or the following structures where $R^{4a}$ is selected from hydrogen, alkyl, $-R^9-OR^{11}$, or $-C(O)OR^{11}$ and $R^{4b}$ is a direct bond to the carbon at numeral 1 or a direct bond to the carbon at numeral 3:

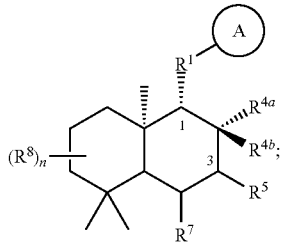

(I9)

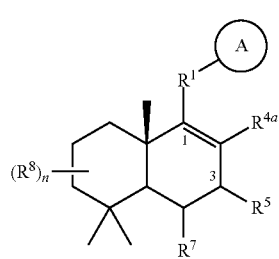

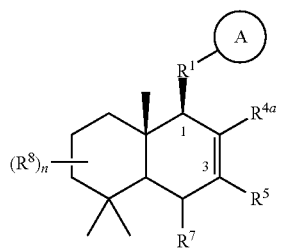
(I10)

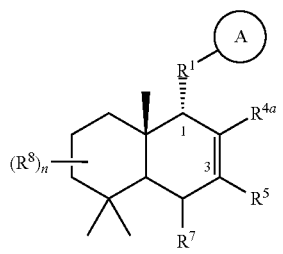
(I11)

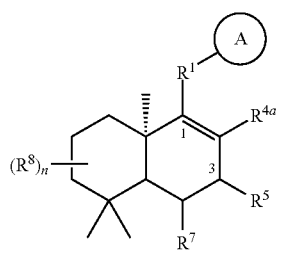
(I12)

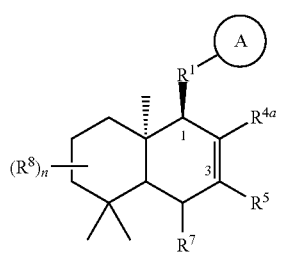
(I13)

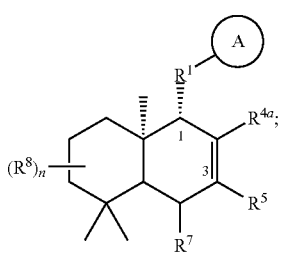
(I14)

or the following structures where $R^{4a}$ and $R^{4b}$ together form =C(R$^{13}$)$_2$:

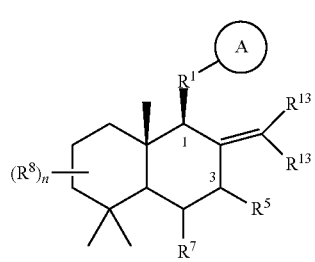
(I15)

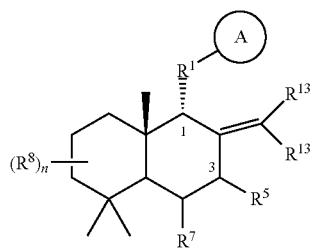
(I16)

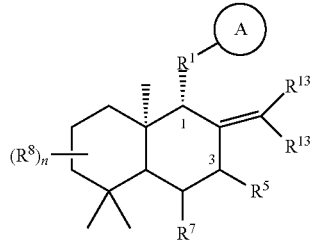
(I17)

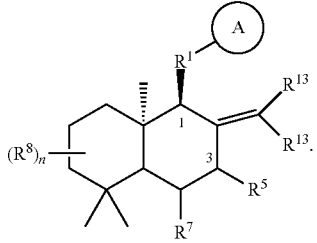
(I18)

The use of parentheses and brackets in substituent groups is used herein to conserve space. Accordingly, the use of parenthesis in a substituent group indicates that the group enclosed within the parentheses is attached directly to the atom preceding the parenthesis. For example, the following substituent group:

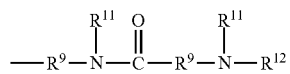

is represented herein as —R$^9$—N(R$^{11}$)C(O)—R$^9$—N(R$^{11}$)R$^{12}$.

The chemical naming protocol and structure diagrams used herein are a modified form of the I.U.P.A.C. nomenclature system, using ChemBioDraw Ultra Version 12.0 software program, wherein the compounds of the invention are named herein as derivatives of a central core structure. For complex chemical names employed herein, a substituent group is named before the group to which it attaches.

For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Certain carbons are identified by numerals in formula (I) of the compounds of the invention. Thus, the carbon in the decahydronaphthalene central moiety to which R$^1$ is attached is indicated by the numeral 1. Likewise, the carbon to which R$^5$ is attached is indicated by numeral 3. These numerals may or may not be the same as the locants in the compound names given herein.

Thus, for example, a compound of formula (I) wherein m and n are each 1, R$^1$ is —R$^{9a}$—C(O)—R$^{9b}$— where R$^{9a}$ and $R^{9b}$ are both direct bonds, $R^2$ and $R^3$ are each —$R^9$—O—$R^{11}$ where $R^9$ is a direct bond and $R^{11}$ is hydrogen, $R^{4a}$ is hydrogen and $R^{4b}$ is methyl, $R^5$ is —$R^9$—N($R^{11}$)C(O)—$R^9$—N($R^{11}$)$R^{12}$ where each $R^9$ is a direct bond, each $R^{11}$ is hydrogen and $R^{12}$ is ethyl, and $R^6$, $R^7$ and $R^8$ are each hydrogen, i.e., a compound of the following structure:

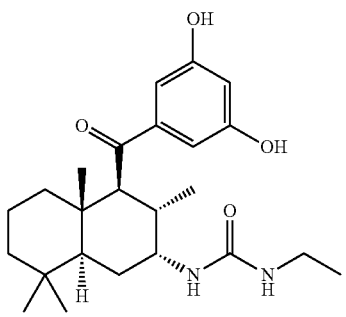 [SMILES: CCNC(=O)N[C@@H]1C[C@H]2C(C)(C)CCC[C@]2(C)[C@@H](C(=O)c2cc(O)cc(O)c2)[C@@H]1C]

is named herein as 1-[(2R,3S,4S,4aS,8aS)-4-[(3,5-dihydroxyphenyl)carbonyl]-3,4a,8,8-tetramethyl-decahydronaphthalen-2-yl]-3-ethylurea.

The following abbreviations are used herein:
Ac$_2$O for acetic anhydride;
AcOH for acetic acid;
AlMe$_3$ for trimethylaluminum;
Boc for tert-butoxycarbonyl;
BH$_3$.THF for borane tetrahydrofuran complex;
BnBr for benzyl bromide;
Bu$_3$SnH for tributyltin hydride;
n-BuLi for n-butyl lithium;
CDI for 1,1'-carbonyldiimidazole;
DABCO for 1,4-diazalbicyclo[2.2.2]octane;
DBU for 1,8-diazabicyclo[5.4.0]undec-7-ene;
DCC for N,N'-dicyclohexylcarbodiimide;
DCE for dichloroethane;
Diglyme for diethylene glycol dimethyl ether;
DIPEA/DIEA for N,N-diisopropylethylamine;
DMAP for 4-dimethylaminopyridine;
DMF for N,N-dimethylformamide;
DMSO for dimethyl sulfoxide;
Et$_2$O for diethyl ether;
Et$_3$N for triethylamine;
EtNCO for ethyl isocyanate;
EtOAc for ethyl acetate;
EtOH for ethanol;
H$_2$/Pd/C for hydrogen on palladium on charcoal;
H$_2$NMe.HCl for methylamine hydrochloride;
HBTU for O-(benzotriazol-1-yl)-N,N,N',N'-tetramethyluronium hexafluorophosphate;
IBX for 2-iodoxybenzoic acid;
i-PrOH for iso-propanol;
Imid. for imidazole;
KOtBu for potassium tert-butoxide;
LiAlH$_4$/LAH for lithium aluminum hydride;
LiEt$_3$BH for lithium triethylborohydride (Super hydride);
m-CPBA for m-chloroperoxybenzoic acid;
MeCN for acetonitrile;
MeI for methyl iodide;
MeNCS for methyl isocyanate;
2-MePhCO$_2$H for o-toluic acid;
3-MePhCO$_2$H for m-toluic acid;
4-MePhCO$_2$H for p-toluic acid;
Me$_4$Phen for 3,4,7,8-tetramethyl-[1,10]-phenanthroline;

MeOCH$_2$PPh$_3$Cl for methoxymethyl triphenylphosphonium chloride;
MeOH for methanol;
MePPh$_3$Br for methyl triphenylphosphonium bromide;
MeSO$_3$SiMe$_3$ for trimethylsilylmethanesulfonate;
MsCl for mesyl chloride;
MW for microwave;
NaSEt for sodium ethanethiolate;
NaBH(OAc)$_3$ for sodium triacetoxyborohydride;
n-BuLi for n-butyllithium;
NMP for N-methyl-2-pyrrolidone;
NMR for nuclear magnetic resonance;
PCC for pyridinium chlorochromate;
Pd/C for palladium metal on charcoal;
PhCO$_2$H for benzoic acid;
PPh$_3$ for triphenylphosphine;
PhMe for toluene;
p-TsOH.H$_2$O for p-toluenesulfonic acid monohydrate;
PyBOP for benzotriazol-1-yl-oxytripyrrolidinophosphonium hexafluorophosphate;
Pyr for pyridine;
TBAF for tetrabutylammonium fluoride;
TBDPS for tert-butyldiphenylsilyl;
TBDPSCl for tert-butyldiphenylsilyl chloride;
TBTU for O-(benzotriazol-1-yl)-N,N,N',N'-tetramethyluronium tetrafluoroborate;
TFA for trifluoroacetic acid;
THF for tetrahydrofuran;
TLC for thin layer chromatography;
TPSH for 2,4,6-triisopropylbenzenesulfonyl hydrazide; and
VAZO® for 1,1'-azobis(cyclohexanecarbonitrile).

EMBODIMENTS OF THE INVENTION

Of the various aspects of the invention set forth above in the Summary of the Invention, certain embodiments are preferred.

One embodiment of a compound of formula (I), as set forth above in the Summary of the Invention, is a compound of formula (Ia):

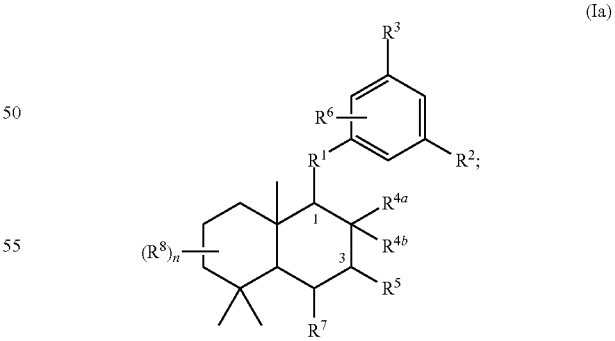

wherein n, $R^1$, $R^2$, $R^3$, $R^{4a}$, $R^{4b}$, $R^5$, $R^6$, $R^7$ and $R^8$ are as defined above for compounds of formula (I) as set forth above in the Summary of the Invention, or a stereoisomer thereof or a pharmaceutically acceptable salt thereof.

One embodiment of a compound of formula (Ia), as described above, is a compound where $R^1$ is —$R^{9a}$—C(O)—$R^{9b}$—, i.e., a compound of formula (Ia1):

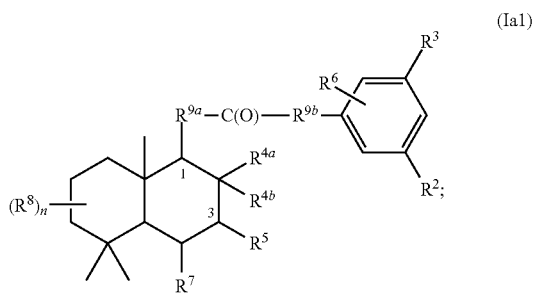

(Ia1)

wherein $R^{9a}$ and $R^{9b}$ are as defined above in the Summary of the Invention for compounds of formula (I), or a stereoisomer thereof or a pharmaceutically acceptable salt thereof.

One embodiment of a compound of formula (Ia1), as described above, or a stereoisomer thereof or a pharmaceutically acceptable salt thereof, is a compound wherein:

n is 1, 2, 3, 4, 5, or 6;

$R^2$ and $R^3$ are each independently selected from hydrogen, alkyl or —$R^9$—$OR^{11}$, provided that at least one of $R^2$ and $R^3$ is —$R^9$—$OR^{11}$ when $R^6$ is hydrogen;

$R^{4a}$ and $R^{4b}$ are each independently selected from hydrogen, alkyl, —$R^9$—$OR^{11}$, or —$C(O)OR^{11}$, $R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2);

$R^6$ and each $R^8$ are independently selected from hydrogen, alkyl, halo or haloalkyl;

$R^7$ is hydrogen, alkyl, halo or haloalkyl;

each $R^9$, $R^{9a}$ and $R^{9b}$ is independently a direct bond or a straight or branched alkylene chain;

each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and $R^{14}$ is a straight or branched alkylene chain.

Another embodiment of a compound of formula (Ia1), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;

$R^{4a}$ and $R^{4b}$ are each independently selected from hydrogen, alkyl or —$R^9$—$OR^{11}$ where $R^9$ is a direct bond and $R^{11}$ is hydrogen; $R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heteroaryl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2); where each $R^9$ is independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;

$R^6$, $R^7$ and $R^8$ are each hydrogen; and $R^{9a}$ and $R^{9b}$ are each independently a direct bond or a straight or branched alkylene chain.

Another embodiment of a compound of formula (Ia1), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;

$R^{4a}$ and $R^{4b}$ are each independently selected from hydrogen, alkyl or —$R^9$—$OR^{11}$ where $R^9$ is a direct bond and $R^{11}$ is hydrogen;

$R^5$ is independently selected from hydrogen, oxo, cyano, optionally substituted heterocyclylalkyl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2); where each $R^9$ is independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;

$R^6$, $R^7$ and $R^8$ are each hydrogen;

$R^{9a}$ and $R^{9b}$ are each independently a direct bond or a straight or branched alkylene chain.

Another embodiment of a compound of formula (Ia1), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;

$R^{4a}$ is hydrogen and $R^{4b}$ is methyl;

$R^5$ is hydrogen, oxo, cyano or —$R^9$—$OR^{11}$ where $R^9$ is a direct bond and $R^{11}$ is hydrogen;

$R^6$, $R^7$ and $R^8$ are each hydrogen; and $R^{9a}$ is a direct bond or a methylene chain and $R^{9b}$ is a direct bond.

Another embodiment of a compound of formula (Ia1), as described above, or a stereoisomer thereof or a pharmaceutically acceptable salt thereof, is a compound selected from:

(2R,3R,4S,4aS,8aS)-4-[(3-methoxy-5-methyl phenyl)carbonyl]-3,4a,8,8-tetramethyl-decahydronaphthalen-2-ol;

(2R,3R,4aS,8aS)-4-[(3-hydroxy-5-methylphenyl)carbonyl]-3,4a,8,8-tetramethyl-decahydronaphthalen-2-ol;

(3S,4S,4aS,8aS)-4-[(3-hydroxy-5-methylphenyl)carbonyl]-3,4a,8,8-tetramethyl-decahydronaphthalen-2-ol;

(2R,3R,4S,4aS,8aS)-4-[(3,5-dimethoxyphenyl)carbonyl]-3,4a,8,8-tetramethyl-decahydronaphthalen-2-ol;

(4S,4aS,8aS)-4-[(3-methoxy-5-methylphenyl)carbonyl]-3,4a,8,8-tetramethyl-decahydronaphthalene-2-carbonitrile;

(3R,4S,4aS,8aS)-4-[(3-methoxy-5-methylphenyl)carbonyl]-3,4a,8,8-tetramethyl-decahydronaphthalen-2-one;

(3S,4S,4aS,8aS)-4-[(3-hydroxy-5-methylphenyl)carbonyl]-3,4a,8,8-tetramethyl-decahydronaphthalen-2-one;

(3R,4S,4aS,8aS)-4-[(3,5-dimethoxyphenyl)carbonyl]-3,4a,8,8-tetramethyl-decahydronaphthalen-2-one;

2-[(1S,2S,4aS,8aR)-2,5,5,8a-tetramethyl-decahydronaphthalen-1-yl]-1-(3,5-dimethoxyphenyl)ethan-1-one;

2-[(1S,2S,4aS,8aR)-2,5,5,8a-tetramethyl-decahydronaphthalen-1-yl]-1-(3-hydroxy-5-methoxyphenyl)ethan-1-one; and 2-[(1S,2S,4aS,8aR)-2,5,5,8a-tetramethyl-decahydronaphthalen-1-yl]-1-(3,5-dihydroxyphenyl)ethan-1-one.

Another embodiment of a compound of formula (Ia1), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;

$R^{4a}$ is hydrogen and $R^{4b}$ is methyl;

$R^5$ is independently selected from —$R^9$—C(O)$R^{11}$, —$R^9$—C(O)$OR^{11}$ or —$R^9$—C(O)N($R^{11}$)$R^{12}$; where each $R^9$ is independently a direct bond or a straight or branched alkylene chain; and where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;

$R^6$, $R^7$ and $R^8$ are each hydrogen; and $R^{9a}$ and $R^{9b}$ are each a direct bond.

Another embodiment of a compound of formula (Ia1), as described above, or a stereoisomer thereof or a pharmaceutically acceptable salt thereof, is a compound selected from:

(3S,4S,4aS,8aS)-4-[(3-methoxy-5-methylphenyl)carbonyl]-3,4a,8,8-tetramethyl-decahydronaphthalene-2-carboxamide;

(3S,4S,4aS,8aS)-4-[(3-hydroxy-5-methylphenyl)carbonyl]-3,4a,8,8-tetramethyl-decahydronaphthalene-2-carboxamide;

(3S,4S,4aS,8aS)-4-[(3-methoxy-5-methylphenyl)carbonyl]-3,4a,8,8-tetramethyl-decahydronaphthalene-2-carboxylic acid;

(3S,4S,4aS,8aS)-4-[(3-hydroxy-5-methylphenyl)carbonyl]-3,4a,8,8-tetramethyl-decahydronaphthalene-2-carboxylic acid;

2-{[(3R,4S,4aS,8aS)-4-[(3,5-dimethoxyphenyl)carbonyl]-3,4a,8,8-tetramethyl-decahydronaphthalen-2-yl]carbonyl}pyridine; and 5-{[(1S,2R,4aS,8aS)-2,5,5,8a-tetramethyl-3-[(pyridin-2-yl)carbonyl]-decahydronaphthalen-1-yl]carbonyl}benzene-1,3-diol.

Another embodiment of a compound of formula (Ia1), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;

$R^{4a}$ is hydrogen and $R^{4b}$ is methyl;

$R^5$ is independently selected —$R^9$—N($R^{11}$)$R^{12}$ or —$R^9$—N($R^{11}$)—$R^{14}$—N($R^{11}$)$R^{12}$; where each $R^9$ is independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;

$R^6$, $R^7$ and $R^8$ are each hydrogen; and $R^{9a}$ and $R^{9b}$ are each a direct bond.

Another embodiment of a compound of formula (Ia1), as described above, or a stereoisomer thereof or a pharmaceutically acceptable salt thereof, is a compound selected from:

(3S,4S,4aS,8aS)—N-(3-aminopropyl)-4-[(3-methoxy-5-methyl phenyl)carbonyl]-3,4a,8,8-tetramethyl-decahydronaphthalen-2-amine;

3-{[(1S,4aS,8aS)-3-amino-2,5,5,8a-tetramethyl-decahydronaphthalen-1-yl]carbonyl}-5-methylphenol;

(2R,3S,4S,4aS,8aS)-4-[(3,5-dimethoxyphenyl)carbonyl]-N-[(4-methoxyphenyl)methyl]-3,4a,8,8-tetramethyl-decahydronaphthalen-2-amine;

(2R,3S,4S,4aS,8aS)-4-[(3,5-dimethoxyphenyl)carbonyl]-3,4a,8,8-tetramethyl-decahydronaphthalen-2-amine;

5-{[(1S,2S,3R,4aS,8aS)-3-amino-2,5,5,8a-tetramethyl-decahydronaphthalen-1-yl]carbonyl}benzene-1,3-diol;

5-{[(1S,2S,3R,4aS,8aS)-3-[(1H-imidazol-5-ylmethyl)amino]-2,5,5,8a-tetramethyl-decahydronaphthalen-1-yl]carbonyl}benzene-1,3-diol;

5-{[(1S,2S,3R,4aS,8aS)-2,5,5,8a-tetramethyl-3-[(1H-pyrrol-2-ylmethyl)amino]-decahydronaphthalen-1-yl]carbonyl}benzene-1,3-diol;

5-{[(1S,2S,3R,4aS,8aS)-2,5,5,8a-tetramethyl-3-[(pyridin-2-ylmethyl)amino]-decahydronaphthalen-1-yl]carbonyl}benzene-1,3-diol;

5-{[(1S,2S,3R,4aS,8aS)-2,5,5,8a-tetramethyl-3-[(pyridin-4-ylmethyl)amino]-decahydronaphthalen-1-yl]carbonyl}benzene-1,3-diol;

5-{[(1S,2S,3R,4aS,8aS)-3-[(1H-Imidazol-2-ylmethyl)amino]-2,5,5,8a-tetramethyl-decahydronaphthalen-1-yl]carbonyl}benzene-1,3-diol;

(2R,3S,4S,4aS,8aS)-4-[(3-methoxy-5-methylphenyl)carbonyl]-3,4a, 8,8-tetramethyl-decahydronaphthalen-2-amine;

3-{[(1S,2S,3R,4aS,8aS)-3-amino-2,5,5,8a-tetramethyl-decahydronaphthalen-1-yl]carbonyl}-5-methylphenol;

3-{[(1S,2S,3R,4aS,8aS)-3-[(1H-imidazol-5-ylmethyl)amino]-2,5,5,8a-tetramethyl-decahydronaphthalen-1-yl]carbonyl}-5-methylphenol; and 5-{[(1S,2S,3R,4aS,8aS)-3-[(3-aminopropyl)amino]-2,5,5,8a-tetramethyl-decahydronaphthalen-1-yl]carbonyl}benzene-1,3-diol.

Another embodiment of a compound of formula (Ia1), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;

$R^{4a}$ is hydrogen and $R^{4b}$ is methyl;

$R^5$ is independently selected from —$R^9$—$N(R^{11})C(O)R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2); where each $R^9$ is independently a direct bond or a straight or branched alkylene chain; and where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;

$R^6$, $R^7$ and $R^8$ are each hydrogen;

$R^{9a}$ and $R^{9b}$ are each a direct bond.

Another embodiment of a compound of formula (Ia1), as described above, or a stereoisomer thereof or a pharmaceutically acceptable salt thereof, is a compound selected from:

N-[(2R,3S,4S,4aS,8aS)-4-[(3,5-dihydroxyphenyl)carbonyl]-3,4a,8,8-tetramethyl-decahydronaphthalen-2-yl]acetamide;

N-[(2R,3S,4S,4aS,8aS)-4-[(3,5-dimethoxyphenyl)carbonyl]-3,4a,8,8-tetramethyl-decahydronaphthalen-2-yl]-4-methylbenzamide;

N-[(2R,3S,4S,4aS,8aS)-4-[(3,5-dihydroxyphenyl)carbonyl]-3,4a,8,8-tetramethyl-decahydronaphthalen-2-yl]-4-methylbenzamide;

N-[(2R,3S,4S,4aS,8aS)-4-[(3,5-dimethoxyphenyl)carbonyl]-3,4a,8,8-tetramethyl-decahydronaphthalen-2-yl]-3-methylbenzamide;

N-[(2R,3S,4S,4aS,8aS)-4-[(3,5-dihydroxyphenyl)carbonyl]-3,4a,8,8-tetramethyl-decahydronaphthalen-2-yl]-3-methylbenzamide;

N-[(2R,3S,4S,4aS,8aS)-4-[(3,5-dimethoxyphenyl)carbonyl]-3,4a,8,8-tetramethyl-decahydronaphthalen-2-yl]-2-methylbenzamide;

N-[(2R,3S,4S,4aS,8aS)-4-[(3,5-dihydroxyphenyl)carbonyl]-3,4a,8,8-tetramethyl-decahydronaphthalen-2-yl]-2-methylbenzamide;

N-[(2R,3S,4S,4aS,8aS)-4-[(3,5-dimethoxyphenyl)carbonyl]-3,4a,8,8-tetramethyl-decahydronaphthalen-2-yl]naphthalene-2-carboxamide;

N-[(2R,3S,4S,4aS,8aS)-4-[(3,5-dihydroxyphenyl)carbonyl]-3,4a,8,8-tetramethyl-decahydronaphthalen-2-yl]naphthalene-2-carboxamide;

N-[(3S,4S,4aS,8aS)-4-[(3,5-dihydroxyphenyl)carbonyl]-3,4a,8,8-tetramethyl-decahydronaphthalen-2-yl]pyrazine-2-carboxamide;

N-{[(2R,3R,4S,4aS,8aS)-4-[(3,5-dihydroxyphenyl)carbonyl]-3,4a,8,8-tetramethyl-decahydronaphthalen-2-yl]methyl}acetamide;

N-{[(2S,3R,4S,4aS,8aS)-4-[(3,5-dihydroxyphenyl)carbonyl]-3,4a,8,8-tetramethyl-decahydronaphthalen-2-yl]methyl}acetamide;

N-{[(2S,3R,4S,4aS,8aS)-4-[(3,5-dihydroxyphenyl)carbonyl]-3,4a,8,8-tetramethyl-decahydronaphthalen-2-yl]methyl}pyridine-3-carboxamide;

N-{[(2S,3R,4S,4aS,8aS)-4-[(3,5-dihydroxyphenyl)carbonyl]-3,4a,8,8-tetramethyl-decahydronaphthalen-2-yl]methyl}benzamide;

3-[(2R,3S,4S,4aS,8aS)-4-[(3,5-dihydroxyphenyl)carbonyl]-3,4a,8,8-tetramethyl-decahydronaphthalen-2-yl]-1-(pyridin-3-yl)urea;

1-[(2R,3S,4S,4aS,8aS)-4-[(3,5-dihydroxyphenyl)carbonyl]-3,4a,8,8-tetramethyl-decahydronaphthalen-2-yl]-3-ethylurea;

1-[(2R,3S,4S,4aS,8aS)-4-[(3,5-dihydroxyphenyl)carbonyl]-3,4a,8,8-tetramethyl-decahydronaphthalen-2-yl]-3-methoxyurea;

N-[(2R,3S,4S,4aS,8aS)-4-[(3,5-dihydroxyphenyl)carbonyl]-3,4a,8,8-tetramethyl-decahydronaphthalen-2-yl]benzamide;

N-[(2R,3S,4S,4aS,8aS)-4-[(3,5-dihydroxyphenyl)carbonyl]-3,4a,8,8-tetramethyl-decahydronaphthalen-2-yl]pyridine-3-carboxamide;

1-[(2R,3S,4S,4aS,8aS)-4-[(3,5-dihydroxyphenyl)carbonyl]-3,4a,8,8-tetramethyl-decahydronaphthalen-2-yl]-3-methylurea;

3-[(2R,3S,4S,4aS,8aS)-4-[(3-hydroxy-5-methyl phenyl)carbonyl]-3,4a,8,8-tetramethyl-decahydronaphthalen-2-yl]-1-(pyridin-3-yl)urea;

N-[(2R,3S,4S,4aS,8aS)-4-[(3-hydroxy-5-methylphenyl)carbonyl]-3,4a,8,8-tetramethyl-decahydronaphthalen-2-yl]acetamide;

N-[(2R,3S,4S,4aS,8aS)-4-[(3,5-dihydroxyphenyl)carbonyl]-3,4a,8,8-tetramethyl-decahydronaphthalen-2-yl]pyridine-2-carboxamide;

N-[(2R,3S,4S,4aS,8aS)-4-[(3,5-dihydroxyphenyl)carbonyl]-3,4a,8,8-tetramethyl-decahydronaphthalen-2-yl]pyridine-4-carboxamide;

3-{[(2R,3S,4S,4aS,8aS)-4-[(3,5-dihydroxyphenyl)carbonyl]-3,4a,8,8-tetramethyl-decahydronaphthalen-2-yl]carbamoyl}pyridin-1-ium-1-olate;

N-[(2R,3S,4S,4aS,8aS)-4-[(3,5-dihydroxyphenyl)carbonyl]-3,4a,8,8-tetramethyl-decahydronaphthalen-2-yl]-4-methylpiperazine-1-carboxamide;

N-[(2R,3S,4S,4aS,8aS)-4-[(3,5-dihydroxyphenyl)carbonyl]-3,4a,8,8-tetramethyl-decahydronaphthalen-2-yl]-3-aminopropanamide;

N-[(2R,3S,4S,4aS,8aS)-4-[(3,5-dihydroxyphenyl)carbonyl]-3,4a,8,8-tetramethyl-decahydronaphthalen-2-yl]piperidine-4-carboxamide;

N-[(2R,3S,4S,4aS,8aS)-4-[(3,5-dimethoxyphenyl)carbonyl]-3,4a,8,8-tetramethyl-decahydronaphthalen-2-yl]pyridine-3-carboxamide;

N-[(2R,3S,4S,4aS,8aS)-4-[(3,5-dihydroxyphenyl)carbonyl]-3,4a,8,8-tetramethyl-decahydronaphthalen-2-yl]-6-aminopyridine-3-carboxamide;

1-[(2R,3S,4S,4aS,8aS)-4-[(3-hydroxy-5-methyl phenyl)carbonyl]-3,4a,8,8-tetramethyl-decahydronaphthalen-2-yl]guanidine;

N-[(2R,3S,4S,4aS,8aS)-4-[(3-hydroxy-5-methylphenyl)carbonyl]-3,4a,8,8-tetramethyl-decahydronaphthalen-2-yl]methanesulfonamide;

1-[(2R,3S,4S,4aS,8aS)-4-[(3,5-dihydroxyphenyl)carbonyl]-3,4a,8,8-tetramethyl-decahydronaphthalen-2-yl]guanidine;

N-[(2R,3S,4S,4aS,8aS)-4-[(3,5-dihydroxyphenyl)carbonyl]-3,4a,8,8-tetramethyl-decahydronaphthalen-2-yl]methanesulfonamide;

1-[(2R,3S,4S,4aS,8aS)-4-[(3,5-dihydroxyphenyl)carbonyl]-3,4a,8,8-tetramethyl-decahydronaphthalen-2-yl]-3-methylthiourea;

2-[({[(2R,3S,4S,4aS,8aS)-4-[(3,5-dihydroxyphenyl)carbonyl]-3,4a,8,8-tetramethyl-decahydronaphthalen-2-yl]carbamoyl}methyl)sulfamoyl]benzoic acid.

Another embodiment of a compound of formula (Ia1), as described above, or a stereoisomer thereof or a pharmaceutically acceptable salt thereof, is a compound wherein:
n is 1;
$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;
$R^{4a}$ is hydrogen and $R^{4b}$ is methyl;
$R^5$ is independently selected from optionally substituted heterocyclylalkyl or optionally substituted heteroarylalkyl
$R^6$, $R^7$ and $R^8$ are each hydrogen; and
$R^{9a}$ and $R^{9b}$ are each independently a direct bond or a straight or branched alkylene chain.

Another embodiment of a compound of formula (Ia1), as described above, or a stereoisomer thereof or a pharmaceutically acceptable salt thereof, is a compound selected from:
5-{[(1S,2R,3S,4aS,8aS)-3-(1H-imidazol-1-ylmethyl)-2,5,5,8a-tetramethyl-decahydronaphthalen-1-yl]carbonyl}benzene-1,3-diol;
5-{[(1S,2R,3S,4aS,8aS)-2,5,5,8a-tetramethyl-3-(1H-1,2,4-triazol-1-ylmethyl)-decahydronaphthalen-1-yl]carbonyl}benzene-1,3-diol; and
5-{[(1S,2R,3S,4aS,8aS)-2,5,5,8a-tetramethyl-3-[(4-methyl piperazin-yl)methyl]-decahydronaphthalen-1-yl]carbonyl}benzene-1,3-diol.

Another embodiment of a compound of formula (Ia1), as described above, or a stereoisomer thereof or a pharmaceutically acceptable salt thereof, is a compound wherein:
n is 1;
$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;
$R^{4a}$ is alkyl and $R^{4b}$ is —$R^9$—$OR^{11}$ where $R^9$ is a direct bond and $R^{11}$ is hydrogen;
$R^5$ is independently selected from hydrogen, oxo, cyano, optionally substituted heterocyclylalkyl, optionally substituted heteroarylalkyl, —$R^9$—$OR^{11}$, —$R^9$—C(O)R, —$R^9$—C(O)$OR^{11}$, —$R^9$—N($R^{11}$)$R^{12}$, —$R^9$—C(O)N($R^{11}$)$R^{12}$, —$R^9$—N($R^{11}$)C(O)$R^{12}$, —$R^9$—N($R^{11}$)—$R^{14}$—N($R^{11}$)$R^{12}$, —$R^9$—N($R^{11}$)C(O)—$R^9$—N($R^{11}$)$R^{12}$, —$R^9$—N($R^{11}$)C(O)N($R^{11}$)—$OR^{12}$, —$R^9$—N($R^{11}$)C(=N$R^{11}$)N($R^{11}$)$R^{12}$, —$R^9$—N($R^{11}$)S(O)$_p R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p R^{12}$ (where p is 1 or 2); where each $R^9$ is independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;
$R^6$, $R^7$ and $R^8$ are each hydrogen;
$R^{9a}$ and $R^{9b}$ are each independently a direct bond or a straight or branched alkylene chain.

Another embodiment of a compound of formula (Ia1), as described above, or a stereoisomer thereof or a pharmaceutically acceptable salt thereof, is a compound wherein:
n is 1;
$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;
$R^{4a}$ is alkyl and $R^{4b}$ is —$R^9$—$OR^{11}$ where $R^9$ is a direct bond and $R^{11}$ is hydrogen;
$R^5$ is hydrogen
$R^6$, $R^7$ and $R^8$ are each hydrogen;
$R^{9a}$ and $R^{9b}$ are each independently a direct bond or a methylene chain.

Another embodiment of a compound of formula (Ia1), as described above, or a stereoisomer thereof or a pharmaceutically acceptable salt thereof, is a compound selected from:
(1R,2R,4aS,8aS)-1-[(3-methoxy-5-methylphenyl)carbonyl]-2,5,5,8a-tetramethyl-decahydronaphthalen-2-ol;
2-[(1R,2R,4aS,8aS)-2-hydroxy-2,5,5,8a-tetramethyl-decahydronaphthalen-1-yl]-1-(3,5-dimethoxyphenyl)ethan-1-one; and
(1R,2R,4aS,8aS)-1-[(3,5-dimethoxyphenyl)carbonyl]-2,5,5,8a-tetramethyl-decahydronaphthalen-2-ol.

Another embodiment of a compound of formula (Ia1), as described above, or a stereoisomer thereof or a pharmaceutically acceptable salt thereof, is a compound wherein:
n is 1, 2, 3, 4, 5, or 6;
$R^2$ and $R^3$ are each independently selected from hydrogen, alkyl or —$R^9$—$OR^1$, provided that at least one of $R^2$ and $R^3$ is —$R^9$—$OR^{11}$ when $R^6$ is hydrogen;
$R^{4a}$ is selected from hydrogen, alkyl, —$R^9$—$OR^{11}$, or —C(O)$R^{11}$ and $R^{4b}$ is a direct bond to the carbon at numeral 1 or a direct bond to the carbon at numeral 3;
$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—C(O)$R^{11}$, —$R^9$—C(O)$OR^{11}$, —$R^9$—N($R^{11}$)$R^{12}$, —$R^9$—C(O)N($R^{11}$)$R^{12}$, —$R^9$—N($R^{11}$)C(O)$R^{12}$, —$R^9$—N($R^{11}$)—$R^{14}$—N($R^{11}$)$R^{12}$, —$R^9$—N($R^{11}$)C(O)—$R^9$—N($R^{11}$)$R^{12}$, —$R^9$—N($R^{11}$)C(O)N($R^{11}$)—$OR^{12}$, —$R^9$—N($R^{11}$)C(=N$R^{11}$)N($R^{11}$)$R^{12}$, —$R^9$—N($R^{11}$)S(O)$_p R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p R^{12}$ (where p is 1 or 2);
$R^6$ and each $R^8$ are independently selected from hydrogen, alkyl, halo or haloalkyl;
$R^7$ is hydrogen, alkyl, halo or haloalkyl;
each $R^9$, $R^{9a}$ and $R^{9b}$ is independently a direct bond or a straight or branched alkylene chain;
each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and
$R^{14}$ is a straight or branched alkylene chain.

Another embodiment of a compound of formula (Ia1), as described above, or a stereoisomer thereof or a pharmaceutically acceptable salt thereof, is a compound wherein:
n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$ when $R^6$ is hydrogen;

$R^{4a}$ is selected from alkyl and $R^{4b}$ is a direct bond to the carbon at numeral 1 or a direct bond to the carbon at numeral 3;

$R^5$ is independently selected from hydrogen, oxocyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2); where each $R^9$ is a independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;

$R^6$ and $R^8$ are independently selected from hydrogen, alkyl, halo or haloalkyl;

$R^7$ is hydrogen, alkyl, halo or haloalkyl; and $R^{9a}$ and $R^{9b}$ are independently a direct bond or a straight or branched alkylene chain.

Another embodiment of a compound of formula (Ia1), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;

$R^{4a}$ is selected from alkyl and $R^{4b}$ is a direct bond to the carbon at numeral 1 or a direct bond to the carbon at numeral 3;

$R^5$ is hydrogen or —$R^9$—$OR^{11}$ where $R^9$ is a direct bond and $R^{11}$ is hydrogen;

$R^6$, $R^7$ and $R^8$ are each hydrogen; and $R^{9a}$ and $R^{9b}$ are each a direct bond.

Another embodiment of a compound of formula (Ia1), as described above, or a stereoisomer thereof or a pharmaceutically acceptable salt thereof, is a compound selected from:

[(1S,4aS,8aS)-2,5,5,8a-tetramethyl-1,4,4a,5,6,7,8,8a-octahydronaphthalen-1-yl](3-methoxy-5-methylphenyl)methanone;

3-{[(4aS,8aS)-2,5,5,8a-tetramethyl-1,4,4a,5,6,7,8,8a-octahydronaphthalen-1-yl]carbonyl}-5-methylphenol;

3-{[(4aS,8aS)-2,5,5,8a-tetramethyl-3,4,4a, 5,6,7,8,8a-octahydronaphthalen-1-yl]carbonyl}-5-methylphenol;

[(1S,4aS,8aS)-2,5,5,8a-tetramethyl-1,4,4a,5,6,7,8,8a-octahydronaphthalen-1-yl](3,5-dimethoxyphenyl)methanone; and (2R,4aS,8aS)-4-[(3,5-dimethoxyphenyl)carbonyl]-3,4a,8,8-tetramethyl-1,2,4a,5,6,7,8,8a-octahydronaphthalen-2-ol.

Another embodiment of a compound of formula (Ia1), as described above, or a stereoisomer thereof or a pharmaceutically acceptable salt thereof, is a compound wherein:

n is 1, 2, 3, 4, 5, or 6;

$R^2$ and $R^3$ are each independently selected from hydrogen, alkyl or —$R^9$—$OR^{11}$, provided that at least one of $R^2$ and $R^3$ is —$R^9$—$OR^{11}$ when $R^6$ is hydrogen;

$R^{4a}$ and $R^{4b}$ together form =$C(R^{13})_2$;

$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2);

$R^6$ and each $R^8$ are independently selected from hydrogen, alkyl, halo or haloalkyl;

$R^7$ is hydrogen, alkyl, halo or haloalkyl;

each $R^9$, $R^{9a}$ and $R^{9b}$ is independently a direct bond or a straight or branched alkylene chain;

each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and each $R^{13}$ is hydrogen, alkyl or haloalkyl; and $R^{14}$ is a straight or branched alkylene chain.

Another embodiment of a compound of formula (Ia1), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;

$R^{4a}$ and $R^{4b}$ together form =$C(R^{13})_2$;

$R^5$ is independently selected from hydrogen or —$R^9$—$OR^{11}$ where $R^9$ is a direct bond and $R^{11}$ is hydrogen;

$R^6$, $R^7$ and $R^8$ are each hydrogen;

$R^{9a}$ and $R^{9b}$ are each independently a direct bond or a straight or branched alkylene chain; and each $R^{13}$ is hydrogen, alkyl or haloalkyl.

Another embodiment of a compound of formula (Ia1), as described above, or a stereoisomer thereof or a pharmaceutically acceptable salt thereof, is (2R,4R,4aS,8aS)-4-[(3,5-dimethoxyphenyl)carbonyl]-4a,8,8-trimethyl-3-methylidene-decahydronaphthalen-2-ol.

Another embodiment of a compound of formula (Ia), as described above, is a compound where $R^1$ is —$R^{9a}$—$C(R^{10})_2$—$R^{9b}$—, i.e., the compound of formula (Ia2):

(Ia2)

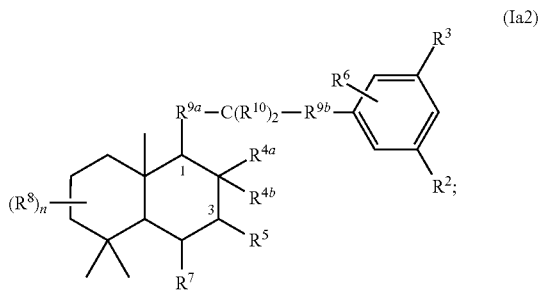

wherein $R^{9a}$, $R^{9b}$ and $R^{10}$ are as defined above in the Summary of the Invention for compounds of formula (I), or a stereoisomer thereof or a pharmaceutically acceptable salt thereof.

One embodiment of a compound of formula (Ia2), as described above, or a stereoisomer thereof or a pharmaceutically acceptable salt thereof, is a compound wherein:

n is 1, 2, 3, 4, 5, or 6;
$R^2$ and $R^3$ are each independently selected from hydrogen, alkyl or —$R^9$—$OR^{11}$, provided that at least one of $R^2$ and $R^3$ is —$R^9$—$OR^{11}$ when $R^6$ is hydrogen;
$R^{4a}$ and $R^{4b}$ are each independently selected from hydrogen, alkyl, —$R^9$—$OR^{11}$, or —$C(O)OR^{11}$,
$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(\!=\!NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2);
$R^6$ and each $R^8$ are independently selected from hydrogen, alkyl, halo or haloalkyl;
$R^7$ is hydrogen, alkyl, halo or haloalkyl;
each $R^9$, $R^{9a}$ and $R^{9b}$ is independently a direct bond or a straight or branched alkylene chain;
each $R^{10}$ is independently hydrogen, alkyl, —$OR^{11}$, —$C(O)OR^{11}$, —$C(O)N(R^{11})R^{12}$, —$N(R^{11})R^{12}$ or —$N(R^{11})C(O)R^{11}$;
each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and
$R^{14}$ is a straight or branched alkylene chain.

Another embodiment of a compound of formula (Ia2), as described above, or a stereoisomer thereof or a pharmaceutically acceptable salt thereof, is a compound wherein:
n is 1;
$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;
$R^{4a}$ and $R^{4b}$ are each independently selected from hydrogen, alkyl, —$R^9$—$OR^{11}$ or —$C(O)OR^{11}$ where $R^9$ is a direct bond or a methylene chain and each $R^{11}$ is hydrogen;
$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(\!=\!NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2); where each $R^9$ is independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;
$R^6$, $R^7$ and $R^8$ are each hydrogen;
$R^{9a}$ and $R^{9b}$ are each independently a direct bond or a straight or branched alkylene chain; and
each $R^{10}$ is independently hydrogen or —$OR^{11}$ where $R^{11}$ is hydrogen.

Another embodiment of a compound of formula (Ia2), as described above, or a stereoisomer thereof or a pharmaceutically acceptable salt thereof, is a compound wherein:
n is 1;
$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;
$R^{4a}$ and $R^{4b}$ are each independently selected from hydrogen, alkyl, —$R^9$—$OR^{11}$ or —$C(O)OR^{11}$ where $R^9$ is a direct bond or a methylene chain and each $R^{11}$ is hydrogen;
$R^5$ is independently selected from hydrogen, oxo, cyano, optionally substituted heterocyclylalkyl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(\!=\!NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2); where each $R^9$ is independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;
$R^6$, $R^7$ and $R^8$ are each hydrogen;
$R^{9a}$ and $R^{9b}$ are each independently a direct bond or a straight or branched alkylene chain; and each $R^{10}$ is independently hydrogen or —$OR^{11}$ where $R^{11}$ is hydrogen.

Another embodiment of a compound of formula (Ia2), as described above, or a stereoisomer thereof or a pharmaceutically acceptable salt thereof, is a compound wherein:

n is 1;
$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;
$R^{4a}$ is hydrogen and $R^{4b}$ is alkyl, —$R^9$—$OR^{11}$ or —C(O)$OR^{11}$ where $R^9$ is a direct bond or a methylene chain and each $R^{11}$ is hydrogen;
$R^5$ is hydrogen;
$R^6$, $R^7$ and $R^8$ are each hydrogen; and
$R^{9a}$ is a direct bond or a methylene chain and $R^{9b}$ is a direct bond; and
each $R^{10}$ is independently hydrogen or —$OR^{11}$ where $R^{11}$ is hydrogen.

Another embodiment of a compound of formula (Ia2), as described above, or a stereoisomer thereof or a pharmaceutically acceptable salt thereof, is a compound selected from:
[(1S,2S,4aS,8aR)-1-[(3-methoxy-5-methylphenyl)methyl]-5,5,8a-trimethyl-decahydronaphthalen-2-yl]methanol;
3-{[((1S,2S,4aS,8aR)-2-(hydroxymethyl)-5,5,8a-trimethyl-decahydronaphthalen-1-yl]methyl}-5-methylphenol;
(1S,2S,4aS,8aR)-1-[(3-methoxy-5-methylphenyl)methyl]-5,5,8a-trimethyl-decahydronaphthalene-2-carboxylic acid;
(1S,2S,4aS,8aR)-1-[(3-hydroxy-5-methylphenyl)methyl]-5,5,8a-trimethyl-decahydronaphthalene-2-carboxylic acid;
5-{2-[(1S,2S,4aS,8aR)-2,5,5,8a-tetramethyl-decahydronaphthalen-1-yl]-1-hydroxyethyl}benzene-1,3-diol;
2-[(1S,2S,4aS,8aR)-2,5,5,8a-tetramethyl-decahydronaphthalen-1-yl]-1-(3,5-dimethoxyphenyl)ethan-1-ol;
(4aR,5S,6S,8aS)-5-[2-(3,5-dimethoxyphenyl)ethyl]-1,1,4a,6-tetramethyl-decahydronaphthalene;
5-{2-[(1S,2S,4aS,8aR)-2,5,5,8a-tetramethyl-decahydronaphthalen-1-yl]ethyl}benzene-1,3-diol; and
(1S,2S,4aS,8aR)-1-[(3,5-dihydroxyphenyl)methyl]-5,5,8a-trimethyl-decahydronaphthalene-2-carboxylic acid.

Another embodiment of a compound of formula (Ia2), as described above, or a stereoisomer thereof or a pharmaceutically acceptable salt thereof, is a compound wherein:

n is 1;
$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;
$R^{4a}$ is alkyl and $R^{4b}$ is —$R^9$—$OR^{11}$ where $R^9$ is a direct bond and $R^{11}$ is hydrogen;
$R^5$ is independently selected from hydrogen, oxo, cyano, optionally substituted heterocyclylalkyl, optionally substituted heteroarylalkyl, —$R^9$—$OR^{11}$, —$R^9$—C(O)$R^{11}$, —$R^9$—C(O)$OR^{11}$, —$R^9$—N($R^{11}$)$R^{12}$, —$R^9$—C(O)N($R^{11}$)$R^{12}$, —$R^9$—N($R^{11}$)C(O)$R^{12}$, —$R^9$—N($R^{11}$)—$R^{14}$—N($R^{11}$)$R^{12}$, —$R^9$—N($R^{11}$)C(O)—$R^9$—N($R^{11}$)$R^{12}$, —$R^9$—N($R^{11}$)C(O)N($R^{11}$)—$OR^{12}$, —$R^9$—N($R^{11}$)C(=N$R^{11}$)N($R^{11}$)$R^{12}$, —$R^9$—N($R^{11}$)S(O)$_p$$R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p$$R^{12}$ (where p is 1 or 2); where each $R^9$ is independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;
$R^6$, $R^7$ and $R^8$ are each hydrogen; and
$R^{9a}$ and $R^{9b}$ are each independently a direct bond or a straight or branched alkylene chain; and
each $R^{10}$ is independently hydrogen or —$OR^{11}$ where $R^{11}$ is hydrogen.

Another embodiment of a compound of formula (Ia2), as described above, or a stereoisomer thereof or a pharmaceutically acceptable salt thereof, is a compound wherein:

n is 1;
$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;
$R^{4a}$ is alkyl and $R^{4b}$ is —$R^9$—$OR^{11}$ where $R^9$ is a direct bond and $R^{11}$ is hydrogen;
$R^5$ is hydrogen;
$R^6$, $R^7$ and $R^8$ are each hydrogen; and
$R^{9a}$ is a direct bond or a methylene chain and $R^{9b}$ is a direct bond; and
each $R^{10}$ is independently hydrogen or —$OR^{11}$ where $R^{11}$ is hydrogen.

Another embodiment of a compound of formula (Ia2), as described above, or a stereoisomer thereof or a pharmaceutically acceptable salt thereof, is a compound wherein:

n is 1, 2, 3, 4, 5, or 6;
$R^2$ and $R^3$ are each independently selected from hydrogen, alkyl or —$R^9$—$OR^{11}$, provided that at least one of $R^2$ and $R^3$ is —$R^9$—$OR^{11}$ when $R^6$ is hydrogen;
$R^{4a}$ is selected from hydrogen, alkyl, —$R^9$—$OR^{11}$, or —C(O)$OR^{11}$ and $R^{4b}$ is a direct bond to the carbon at numeral 1 or a direct bond to the carbon at numeral 3;
$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—C(O)$R^{11}$, —$R^9$—C(O)$OR^{11}$, —$R^9$—N($R^{11}$)$R^{12}$, —$R^9$—C(O)N($R^{11}$)$R^{12}$, —$R^9$—N($R^{11}$)C(O)$R^{12}$, —$R^9$—N($R^{11}$)—$R^{14}$—N($R^{11}$)$R^{12}$, —$R^9$—N($R^{11}$)C(O)—$R^9$—N($R^{11}$)$R^{12}$, —$R^9$—N($R^{11}$)C(O)N($R^{11}$)—$OR^{12}$, —$R^9$—N($R^{11}$)C(=N$R^{11}$)N($R^{11}$)$R^{12}$, —$R^9$—N($R^{11}$)S(O)$_p$$R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p$$R^{12}$ (where p is 1 or 2);
$R^6$ and each $R^8$ are independently selected from hydrogen, alkyl, halo or haloalkyl;
$R^7$ is hydrogen, alkyl, halo or haloalkyl;
each $R^9$, $R^{9a}$ and $R^{9b}$ is independently a direct bond or a straight or branched alkylene chain;
each $R^{10}$ is independently hydrogen, alkyl, —$OR^{11}$, —C(O)$OR^{11}$, —C(O)N($R^{11}$)$R^{12}$, —N($R^{11}$)$R^{12}$ or —N($R^{11}$)C(O)$R^{11}$;
each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and
$R^{14}$ is a straight or branched alkylene chain.

Another embodiment of a compound of formula (Ia2), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$ when $R^6$ is hydrogen;

$R^{4a}$ is selected from alkyl and $R^{4b}$ is a direct bond to the carbon at numeral 1 or a direct bond to the carbon at numeral 3;

$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2); where each $R^9$ is a independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;

$R^6$ and $R^8$ are each independently selected from hydrogen, alkyl, halo or haloalkyl;

$R^7$ is hydrogen, alkyl, halo or haloalkyl;

$R^{9a}$ and $R^{9b}$ are independently a direct bond or a straight or branched alkylene chain; and each $R^{10}$ is independently hydrogen or —$OR^{11}$ where $R^{11}$ is hydrogen.

Another embodiment of a compound of formula (Ia2), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;

$R^{4a}$ is selected from alkyl and $R^{4b}$ is a direct bond to the carbon at numeral 1 or a direct bond to the carbon at numeral 3;

$R^5$ is hydrogen;

$R^6$, $R^7$ and $R^8$ are each hydrogen;

$R^{9a}$ and $R^{9b}$ are each a direct bond; and each $R^{10}$ is hydrogen.

Another embodiment of a compound of formula (Ia2), as described above, or a stereoisomer thereof or a pharmaceutically acceptable salt thereof, is a compound selected from:

(4aS,8aS)-8-[(3-methoxy-5-methylphenyl)methyl]-4,4,7,8a-tetramethyl-1,2,3,4,4a,5,6,8a-octahydronaphthalene; and (4aS,5S,8aS)-5-[(3-methoxy-5-methylphenyl)methyl]-1,1,4a,6-tetramethyl-1,2,3,4,4a,5,8,8a-octahydronaphthalene.

Another embodiment of a compound of formula (Ia2), as described above, or a stereoisomer thereof or a pharmaceutically acceptable salt thereof, is a compound wherein:

n is 1, 2, 3, 4, 5, or 6;

$R^2$ and $R^3$ are each independently selected from hydrogen, alkyl or —$R^9$—$OR^{11}$, provided that at least one of $R^2$ and $R^3$ is —$R^9$—$OR^{11}$ when $R^6$ is hydrogen;

$R^{4a}$ and $R^{4b}$ together form =$C(R^{13})_2$;

$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2);

$R^6$ and each $R^8$ are independently selected from hydrogen, alkyl, halo or haloalkyl;

$R^7$ is hydrogen, alkyl, halo or haloalkyl;

each $R^9$, $R^{9a}$ and $R^{9b}$ is independently a direct bond or a straight or branched alkylene chain;

each $R^{10}$ is independently hydrogen, alkyl, —$OR^{11}$, —$C(O)OR^{11}$, —$C(O)N(R^{11})R^{12}$, —$N(R^{11})R^{12}$ or —$N(R^{11})C(O)R^{11}$;

each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and each $R^{13}$ is hydrogen, alkyl or haloalkyl; and $R^{14}$ is a straight or branched alkylene chain.

Another embodiment of a compound of formula (Ia2), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$ when $R^6$ is hydrogen;

$R^{4a}$ and $R^{4b}$ together form =$C(R^{13})_2$;

$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2); where each $R^9$ is independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is is a straight or branched alkylene chain;

$R^6$ and $R^8$ are each independently selected from hydrogen, alkyl, halo or haloalkyl;

$R^7$ is hydrogen, alkyl, halo or haloalkyl; and $R^{9a}$ and $R^{9b}$ are each independently a direct bond or a straight or branched alkylene chain; and each $R^{10}$ is independently hydrogen, alkyl, $-OR^{11}$, $-C(O)OR^{11}$, $-C(O)N(R^{11})R^{12}$, $-N(R^{11})R^{12}$ or $-N(R^{11})C(O)R^{11}$;

each $R^{13}$ is hydrogen, alkyl or haloalkyl.

Another embodiment of a compound of formula (Ia2), as described above, or a stereoisomer thereof or a pharmaceutically acceptable salt thereof, is a compound wherein:

n is 1;

$R^2$ and $R^3$ are each independently selected from hydrogen, alkyl or $-R^9-OR^{11}$ where $R^9$ is a direct bond and $R^{11}$ is hydrogen or methyl, provided that at least one of $R^2$ and $R^3$ is $-R^9-OR^{11}$;

$R^{4a}$ and $R^{4b}$ together form $=C(R^{13})_2$;

$R^5$ is hydrogen;

$R^6$, $R^7$ and $R^8$ are each hydrogen;

$R^{9a}$ and $R^{9b}$ are each independently a direct bond or a straight or branched alkylene chain; and each $R^{10}$ is hydrogen;

each $R^{13}$ is hydrogen, alkyl or haloalkyl.

Another embodiment of a compound of formula (Ia2), as described above, or a stereoisomer thereof or a pharmaceutically acceptable salt thereof, is (4aS,5S,8aS)-5-[(3-methoxy-5-methylphenyl)methyl]-1,1,4a-trimethyl-6-methylidene-decahydronaphthalene.

Another embodiment of a compound of formula (Ia), as described above, is a compound where $R^1$ is $-R^9-S(O)_t-R^9-$, i.e., a compound of formula (Ia3):

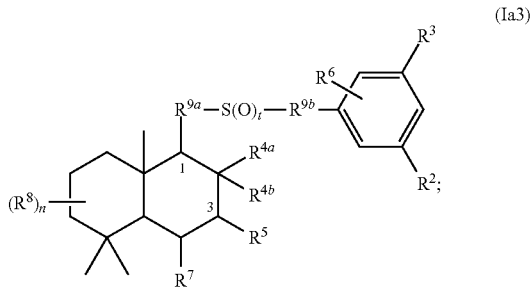

(Ia3)

wherein t, $R^{9a}$ and $R^{9b}$ are as defined above in the Summary of the Invention for compounds of formula (I), or a stereoisomer thereof or a pharmaceutically acceptable salt thereof.

One embodiment of a compound of formula (Ia3), as described above, or a stereoisomer thereof or a pharmaceutically acceptable salt thereof, is a compound wherein:

n is 1, 2, 3, 4, 5, or 6;

t is 0, 1 or 2;

$R^2$ and $R^3$ are each independently selected from hydrogen, alkyl or $-R^9-OR^{11}$, provided that at least one of $R^2$ and $R^3$ is $-R^9-OR^{11}$ when $R^6$ is hydrogen;

$R^{4a}$ and $R^{4b}$ are each independently selected from hydrogen, alkyl, $-R^9-OR^{11}$, or $-C(O)OR^{11}$, $R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, $-R^9-OR^{11}$, $-R^9-C(O)R^{11}$, $-R^9-C(O)OR^{11}$, $-R^9-N(R^{11})R^{12}$, $-R^9-C(O)N(R^{11})R^{12}$, $-R^9-N(R^{11})C(O)R^{12}$, $-R^9-N(R^{11})-R^{14}-N(R^{11})R^{12}$, $-R^9-N(R^{11})C(O)-R^9-N(R^{11})R^{12}$, $-R^9-N(R^{11})C(O)N(R^{11})-OR^{12}$, $-R^9-N(R^{11})C(=NR^{11})N(R^{11})R^{12}$, $-R^9-N(R^{11})S(O)_pR^{11}$ (where p is 1 or 2), $-R^9-N(R^{11})C(S)N(R^{11})R^{12}$ or $-R^9-N(R^{11})C(O)-R^9-N(R^{11})S(O)_pR^{12}$ (where p is 1 or 2);

$R^6$ and each $R^8$ are independently selected from hydrogen, alkyl, halo or haloalkyl;

$R^7$ is hydrogen, alkyl, halo or haloalkyl;

each $R^9$, $R^{9a}$ and $R^{9b}$ is independently a direct bond or a straight or branched alkylene chain;

each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and $R^{14}$ is a straight or branched alkylene chain.

Another embodiment of a compound of formula (Ia3), as described above, or a stereoisomer thereof or a pharmaceutically acceptable salt thereof, is a compound wherein:

n is 1;

t is 0, 1 or 2;

$R^2$ and $R^3$ are each independently selected from hydrogen, alkyl or $-R^9-OR^{11}$ where $R^9$ is a direct bond and $R^{11}$ is hydrogen or methyl, provided that at least one of $R^2$ and $R^3$ is $-R^9-OR^{11}$;

$R^{4a}$ and $R^{4b}$ are each independently selected from hydrogen, alkyl or $-R^9-OR^{11}$ where $R^9$ is a direct bond and $R^{11}$ is hydrogen;

$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, $-R^9-OR^{11}$, $-R^9-C(O)R^{11}$, $-R^9-C(O)OR^{11}$, $-R^9-N(R^{11})R^{12}$, $-R^9-C(O)N(R^{11})R^{12}$, $-R^9-N(R^{11})C(O)R^{12}$, $-R^9-N(R^{11})-R^{14}-N(R^{11})R^{12}$, $-R^9-N(R^{11})C(O)-R^9-N(R^{11})R^{12}$, $-R^9-N(R^{11})C(O)N(R^{11})-OR^{12}$, $-R^9-N(R^{11})C(=NR^{11})N(R^{11})R^{12}$, $-R^9-N(R^{11})S(O)_pR^{11}$ (where p is 1 or 2), $-R^9-N(R^{11})C(S)N(R^{11})R^{12}$ or $-R^9-N(R^{11})C(O)-R^9-N(R^{11})S(O)_pR^{12}$ (where p is 1 or 2); where each $R^9$ is independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;

$R^6$, $R^7$ and $R^8$ are each hydrogen; and $R^{9a}$ and $R^{9b}$ are each independently a direct bond or a straight or branched alkylene chain.

Another embodiment of a compound of formula (Ia3), as described above, or a stereoisomer thereof or a pharmaceutically acceptable salt thereof, is a compound wherein:

n is 1;
t is 0, 1 or 2;
$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;
$R^{4a}$ and $R^{4b}$ are each independently selected from hydrogen, alkyl or —$R^9$—$OR^{11}$ where $R^9$ is a direct bond and $R^{11}$ is hydrogen;
$R^5$ is independently selected from hydrogen, oxo, cyano, optionally substituted heterocyclylalkyl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2); where each $R^9$ is independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain.
$R^6$, $R^7$ and $R^8$ are each hydrogen; and
$R^{9a}$ and $R^{9b}$ are each independently a direct bond or a straight or branched alkylene chain.

Another embodiment of a compound of formula (Ia3), as described above, or a stereoisomer thereof or a pharmaceutically acceptable salt thereof, is a compound wherein:

n is 1;
t is 0, 1 or 2;
$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;
$R^{4a}$ and $R^{4b}$ are each independently selected from hydrogen, alkyl or —$R^9$—$OR^{11}$ where $R^9$ is a direct bond and $R^{11}$ is hydrogen;
$R^5$ is selected from hydrogen, —$R^9$—$OR^{11}$ or —$R^9$—$N(R^{11})R^{12}$; where each $R^9$ is independently a direct bond or a straight or branched alkylene chain; and where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;
$R^6$, $R^7$ and $R^8$ are each hydrogen; and
$R^{9a}$ is a methylene chain and $R^{9b}$ is a direct bond.

Another embodiment of a compound of formula (Ia3), as described above, or a stereoisomer thereof or a pharmaceutically acceptable salt thereof, is a compound selected from:
(1R,2R,3R,4aS,8aS)-3-amino-1-{[(3,5-dimethoxyphenyl)sulfanyl]methyl}-2,5,5,8a-tetramethyl-decahydronaphthalen-2-ol; and
(4S,4aS,8aS)-4-{[(3,5-dimethoxybenzene)sulfonyl]methyl}-3,4a,8,8-tetramethyl-decahydronaphthalen-2-ol.

Another embodiment of a compound of formula (Ia), as described above, is a compound where $R^1$ is —$R^{9a}$—O—$R^{9b}$—, i.e., a compound of formula (Ia4):

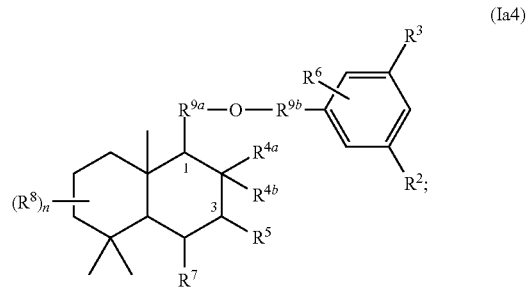

(Ia4)

wherein $R^{9a}$ and $R^{9b}$ are as defined above in the Summary of the Invention for compounds of formula (I), or a stereoisomer thereof or a pharmaceutically acceptable salt thereof.

One embodiment of a compound of formula (Ia4), as described above, or a stereoisomer thereof or a pharmaceutically acceptable salt thereof, is a compound wherein:

n is 1, 2, 3, 4, 5, or 6;
$R^2$ and $R^3$ are each independently selected from hydrogen, alkyl or —$R^9$—$OR^{11}$, provided that at least one of $R^2$ and $R^3$ is —$R^9$—$OR^{11}$ when $R^6$ is hydrogen;
$R^{4a}$ and $R^{4b}$ are each independently selected from hydrogen, alkyl, —$R^9$—$OR^{11}$, or —$C(O)OR^{11}$,
$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2);
$R^6$ and each $R^8$ are independently selected from hydrogen, alkyl, halo or haloalkyl;
$R^7$ is hydrogen, alkyl, halo or haloalkyl;
each $R^9$, $R^{9a}$ and $R^{9b}$ is independently a direct bond or a straight or branched alkylene chain;
each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and
$R^{14}$ is a straight or branched alkylene chain.

Another embodiment of a compound of formula (Ia4), as described above, or a stereoisomer thereof or a pharmaceutically acceptable salt thereof, is a compound wherein:

n is 1;
$R^2$ and $R^3$ are each independently selected from hydrogen, alkyl or —$R^9$—$OR^{11}$ where $R^9$ is a direct bond and $R^{11}$ is hydrogen, alkyl or optionally substituted aralkyl, provided that at least one of $R^2$ and $R^3$ is —$R^9$—$OR^{11}$;

$R^{4a}$ and $R^{4b}$ are each independently selected from hydrogen, alkyl or —$R^9$—$OR^{11}$ where $R^9$ is a direct bond and $R^{11}$ is hydrogen;

$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_p R^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_p R^{12}$ (where p is 1 or 2); where each $R^9$ is independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;

$R^6$, $R^7$ and $R^8$ are each hydrogen; and $R^{9a}$ and $R^{9b}$ are each independently a direct bond or a straight or branched alkylene chain.

Another embodiment of a compound of formula (Ia4), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen, alkyl or optionally substituted aralkyl, provided that at least one of $R^2$ and $R^3$ is —$R^9$—$OR^{11}$;

$R^{4a}$ and $R^{4b}$ are each independently selected from hydrogen, alkyl or —$R^9$—$OR^{11}$ where $R^9$ is a direct bond and $R^{11}$ is hydrogen;

$R^5$ is independently selected from hydrogen, oxo, cyano, optionally substituted heterocyclylalkyl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_p R^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_p R^{12}$ (where p is 1 or 2); where each $R^9$ is independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;

$R^6$, $R^7$ and $R^8$ are each hydrogen; and $R^{9a}$ and $R^{9b}$ are each independently a direct bond or a straight or branched alkylene chain.

Another embodiment of a compound of formula (Ia4), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen, alkyl or benzyl, provided that at least one of $R^2$ and $R^3$ is —$R^9$—$OR^{11}$;

$R^{4a}$ and $R^{4b}$ are each independently selected from hydrogen, alkyl or —$R^9$—$OR^{11}$ where $R^9$ is a direct bond and $R^{11}$ is hydrogen;

$R^5$ is selected from hydrogen or —$R^9$—$OR^{11}$ where $R^9$ is independently a direct bond or a straight or branched alkylene chain and $R^{11}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;

$R^6$, $R^7$ and $R^8$ are each hydrogen; and $R^{9a}$ is a methylene chain and $R^{9b}$ is a direct bond.

Another embodiment of a compound of formula (Ia4), as described above, or a stereoisomer thereof or a pharmaceutically acceptable salt thereof, is a compound selected from:
(4S,4aS,8aS)-4-(3-methoxy-5-methylphenoxymethyl)-3,4a,8,8-tetramethyl-decahydronaphthalen-2-ol; and
(1S,2R,4aS,8aS)-1-[3,5-bis(benzyloxy)-phenoxymethyl]-2,5,5,8a-tetramethyl-decahydronaphthalen-2-ol.

Another embodiment of a compound of formula (Ia4), as described above, or a stereoisomer thereof or a pharmaceutically acceptable salt thereof, is a compound wherein:

n is 1, 2, 3, 4, 5, or 6;

$R^2$ and $R^3$ are each independently selected from hydrogen, alkyl or —$R^9$—$OR^{11}$, provided that at least one of $R^2$ and $R^3$ is —$R^9$—$OR^{11}$ when $R^6$ is hydrogen;

$R^{4a}$ is selected from hydrogen, alkyl, —$R^9$—$OR^{11}$, or —$C(O)OR^{11}$ and $R^{4b}$ is a direct bond to the carbon at numeral 1 or a direct bond to the carbon at numeral 3;

$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_p R^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_p R^{12}$ (where p is 1 or 2);

$R^6$ and each $R^8$ are independently selected from hydrogen, alkyl, halo or haloalkyl;

$R^7$ is hydrogen, alkyl, halo or haloalkyl;

each $R^9$, $R^{9a}$ and $R^{9b}$ is independently a direct bond or a straight or branched alkylene chain;

each $R^{10}$ is independently hydrogen, alkyl, —$OR^{11}$, —$C(O)OR^{11}$, —$C(O)N(R^{11})R^{12}$, —$N(R^{11})R^{12}$ or —$N(R^{11})C(O)R^{11}$;

each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and $R^{14}$ is a straight or branched alkylene chain.

Another embodiment of a compound of formula (Ia4), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$ when $R^6$ is hydrogen;

$R^{4a}$ is selected from alkyl and $R^{4b}$ is a direct bond to the carbon at numeral 1 or a direct bond to the carbon at numeral 3;

$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2); where each $R^9$ is a independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;

$R^6$ and $R^8$ are each independently selected from hydrogen, alkyl, halo or haloalkyl;

$R^7$ is hydrogen, alkyl, halo or haloalkyl; and $R^{9a}$ and $R^{9b}$ are independently a direct bond or a straight or branched alkylene chain.

Another embodiment of a compound of formula (Ia4), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;

$R^{4a}$ is selected from alkyl and $R^{4b}$ is a direct bond to the carbon at numeral 1 or a direct bond to the carbon at numeral 3;

$R^5$ is hydrogen;

$R^6$, $R^7$ and $R^8$ are each hydrogen; and $R^{9a}$ is a methylene chain and $R^{9b}$ is a direct bond.

Another embodiment of a compound of formula (Ia4), as described above, or a stereoisomer thereof or a pharmaceutically acceptable salt thereof, is a compound selected from:

3-{[(1S,4aS,8aS)-2,5,5,8a-tetramethyl-1,4,4a,5,6,7,8,8a-octahydronaphthalen-1-yl]methoxy}-5-methylphenol; and 3-{[(1S,4aS,8aS)-2,5,5,8a-tetramethyl-1,4,4a,5,6,7,8,8a-octahydronaphthalen-1-yl]methoxy}-5-methoxyphenol.

Another embodiment of a compound of formula (Ia), as described above, is a compound where $R^1$ is —$R^{9a}$—$C(O)N(R^{11a})$—$R^{9b}$—, i.e., a compound of formula (Ia5):

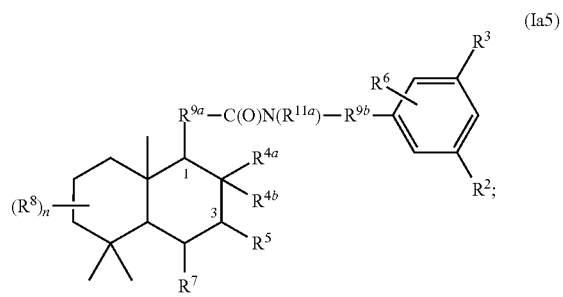

wherein $R^{9a}$, $R^{9b}$ and $R^{11a}$ are as defined above in the Summary of the Invention for compounds of formula (I), or a stereoisomer thereof or a pharmaceutically acceptable salt thereof.

One embodiment of a compound of formula (Ia5), as described above, or a stereoisomer thereof or a pharmaceutically acceptable salt thereof, is a compound wherein:

n is 1, 2, 3, 4, 5, or 6;

$R^2$ and $R^3$ are each independently selected from hydrogen, alkyl or —$R^9$—$OR^{11}$, provided that at least one of $R^2$ and $R^3$ is —$R^9$—$OR^{11}$ when $R^6$ is hydrogen;

$R^{4a}$ and $R^{4b}$ are each independently selected from hydrogen, alkyl, —$R^9$—$OR^{11}$, or —$C(O)OR^{11}$, $R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—$C(O)R^{11}$, —$R^9$—$C(O)OR^{11}$, —$R^9$—$N(R^{11})R^{12}$, —$R^9$—$C(O)N(R^{11})R^{12}$, —$R^9$—$N(R^{11})C(O)R^{12}$, —$R^9$—$N(R^{11})$—$R^{14}$—$N(R^{11})R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2);

$R^6$ and each $R^8$ are independently selected from hydrogen, alkyl, halo or haloalkyl;

$R^7$ is hydrogen, alkyl, halo or haloalkyl;

each $R^9$, $R^{9a}$ and $R^{9b}$ is independently a direct bond or a straight or branched alkylene chain;

each $R^{11}$, $R^{11a}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and $R^{14}$ is a straight or branched alkylene chain.

Another embodiment of a compound of formula (Ia5), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or alkyl, provided that at least one of $R^2$ and $R^3$ is —$R^9$—$OR^{11}$;

$R^{4a}$ and $R^{4b}$ are each independently selected from hydrogen, alkyl or —$R^9$—$OR^{11}$ where $R^9$ is a direct bond and $R^{11}$ is hydrogen;

$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—C(O)$R^{11}$, —$R^9$—C(O)$OR^{11}$, —$R^9$—N($R^{11}$)$R^{12}$, —$R^9$—C(O)N($R^{11}$)$R^{12}$, —$R^9$—N($R^{11}$)C(O)$R^{12}$, —$R^9$—N($R^{11}$)—$R^{14}$—N($R^{11}$)$R^{12}$, —$R^9$—N($R^{11}$)C(O)—$R^9$—N($R^{11}$)$R^{12}$, —$R^9$—N($R^{11}$)C(O)N($R^{11}$)—$OR^{12}$, —$R^9$—N($R^{11}$)C(=N$R^{11}$)N($R^{11}$)$R^{12}$, —$R^9$—N($R^{11}$)S(O)$_p R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p R^{12}$ (where p is 1 or 2); where each $R^9$ is independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;

$R^6$, $R^7$ and $R^8$ are each hydrogen;

$R^{9a}$ and $R^{9b}$ are each independently a direct bond or a straight or branched alkylene chain; and $R^{11a}$ is hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment of a compound of formula (Ia5), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or alkyl, provided that at least one of $R^2$ and $R^3$ is —$R^9$—$OR^{11}$;

$R^{4a}$ and $R^{4b}$ are each independently selected from hydrogen, alkyl or —$R^9$—$OR^{11}$ where $R^9$ is a direct bond and $R^{11}$ is hydrogen;

$R^5$ is independently selected from hydrogen, halo, oxo, cyano, optionally substituted heterocyclylalkyl, optionally substituted heteroarylalkyl, —$R^9$—$OR^{11}$, —$R^9$—C(O)$R^{11}$, —$R^9$—C(O)$OR^{11}$, —$R^9$—N($R^{11}$)$R^{12}$, —$R^9$—C(O)N($R^{11}$)$R^{12}$, —$R^9$—N($R^{11}$)C(O)$R^{12}$, —$R^9$—N($R^{11}$)—$R^{14}$—N($R^{11}$)$R^{12}$, —$R^9$—N($R^{11}$)C(O)—$R^9$—N($R^{11}$)$R^{12}$, —$R^9$—N($R^{11}$)C(O)N($R^{11}$)—$OR^{12}$, —$R^9$—N($R^{11}$)C(=N$R^{11}$)N($R^{11}$)$R^{12}$, —$R^9$—N($R^{11}$)S(O)$_p R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p R^{12}$ (where p is 1 or 2); where each $R^9$ is independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;

$R^6$, $R^7$ and $R^8$ are each hydrogen;

$R^{9a}$ and $R^{9b}$ are each independently a direct bond or a straight or branched alkylene chain; and $R^{11a}$ is hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment of a compound of formula (Ia5), as described above, or a stereoisomer thereof or a pharmaceutically acceptable salt thereof, is a compound wherein:

n is 1;

t is 0, 1 or 2;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;

$R^{4a}$ and $R^{4b}$ are each independently selected from hydrogen, alkyl or —$R^9$—$OR^{11}$ where $R^9$ is a direct bond and $R^{11}$ is hydrogen;

$R^5$ is selected from hydrogen, halo or —$R^9$—$OR^{11}$ where $R^9$ is independently a direct bond or a straight or branched alkylene chain and $R^{11}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;

$R^6$, $R^7$ and $R^8$ are each hydrogen;

$R^{9a}$ is a methylene chain and $R^{9b}$ is a direct bond; and;

$R^{11a}$ is hydrogen, alkyl, optionally substituted aryl or optionally substituted aralkyl.

Another embodiment of a compound of formula (Ia5), as described above, or a stereoisomer thereof or a pharmaceutically acceptable salt thereof, is a compound selected from:

2-[(1S,2S,4aS,8aR)-2,5,5,8a-tetramethyl-decahydronaphthalen-1-yl]-N-(3,5-dihydroxyphenyl)acetamide; and 2-[(1S,2R,3R,4aS,8aR)-3-bromo-2,5,5,8a-tetramethyl-decahydro-naphthalen-1-yl]-N-(3,5-dihydroxyphenyl)-N-methylacetamide.

Another embodiment of a compound of formula (Ia5), as described above, or a stereoisomer thereof or a pharmaceutically acceptable salt thereof, is a compound wherein:

n is 1, 2, 3, 4, 5, or 6;

$R^2$ and $R^3$ are each independently selected from hydrogen, alkyl or —$R^9$—$OR^{11}$, provided that at least one of $R^2$ and $R^3$ is —$R^9$—$OR^{11}$ when $R^6$ is hydrogen;

$R^{4a}$ is selected from hydrogen, alkyl, —$R^9$—$OR^{11}$, or —C(O)$OR^{11}$ and $R^{4b}$ is a direct bond to the carbon at numeral 1 or a direct bond to the carbon at numeral 3;

$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—C(O)$R^{11}$, —$R^9$—C(O)$OR^{11}$, —$R^9$—N($R^{11}$)$R^{12}$, —$R^9$—C(O)N($R^{11}$)$R^{12}$, —$R^9$—N($R^{11}$)C(O)$R^{12}$, —$R^9$—N($R^{11}$)—$R^{14}$—N($R^{11}$)$R^{12}$, —$R^9$—N($R^{11}$)C(O)—$R^9$—N($R^{11}$)$R^{12}$, —$R^9$—N($R^{11}$)C(O)N($R^{11}$)—$OR^{12}$, —$R^9$—N($R^{11}$)C(=N$R^{11}$)N($R^{11}$)$R^{12}$, —$R^9$—N($R^{11}$)S(O)$_p R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p R^{12}$ (where p is 1 or 2);

$R^6$ and each $R^8$ are independently selected from hydrogen, alkyl, halo or haloalkyl;

$R^7$ is hydrogen, alkyl, halo or haloalkyl;

each $R^9$, $R^{9a}$ and $R^{9b}$ is independently a direct bond or a straight or branched alkylene chain;

each $R^{10}$ is independently hydrogen, alkyl, —$OR^{11}$, —C(O)$OR^{11}$, —C(O)N($R^{11}$)$R^{12}$, —N($R^{11}$)$R^{12}$ or —N($R^{11}$)C(O)$R^{11}$;

each $R^{11}$, $R^{11a}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and $R^{14}$ is a straight or branched alkylene chain.

Another embodiment of a compound of formula (Ia5), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$ when $R^6$ is hydrogen;

$R^{4a}$ is selected from alkyl and $R^{4b}$ is a direct bond to the carbon at numeral 1 or a direct bond to the carbon at numeral 3;

$R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—C(O)$R^{11}$, —$R^9$—C(O)$OR^{11}$, —$R^9$—N($R^{11}$)$R^{12}$, —$R^9$—C(O)N($R^{11}$)$R^{12}$, —$R^9$—N($R^{11}$)C(O)$R^{12}$, —$R^9$—N($R^{11}$)—$R^{14}$—N($R^{11}$)$R^{12}$, —$R^9$—N($R^{11}$)C(O)—$R^9$—N($R^{11}$)$R^{12}$, —$R^9$—N($R^{11}$)C(O)N($R^{11}$)—$OR^{12}$, —$R^9$—N($R^{11}$)C(=N$R^{11}$)N($R^{11}$)$R^{12}$, —$R^9$—N($R^{11}$)S(O)$_p$$R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p$$R^{12}$ (where p is 1 or 2); where each $R^9$ is a independently a direct bond or a straight or branched alkylene chain; where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and where $R^{14}$ is a straight or branched alkylene chain;

$R^6$ and $R^8$ are each independently selected from hydrogen, alkyl, halo or haloalkyl;

$R^7$ is hydrogen, alkyl, halo or haloalkyl;

$R^{9a}$ and $R^{9b}$ are independently a direct bond or a straight or branched alkylene chain and $R^{11a}$ is hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment of a compound of formula (Ia5), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen or methyl, provided that at least one of $R^2$ and $R^3$ is —$R^9$—$OR^{11}$;

$R^{4a}$ is selected from alkyl and $R^{4b}$ is a direct bond to the carbon at numeral 1 or a direct bond to the carbon at numeral 3;

$R^5$ is hydrogen;

$R^6$, $R^7$ and $R^8$ are each hydrogen;

$R^{9a}$ is a direct bond or methylene and $R^{9b}$ is a direct bond; and $R^{11a}$ is hydrogen, alkyl, optionally substituted aryl or optionally substituted aralkyl.

Another embodiment of a compound of formula (Ia5), as described above, or a stereoisomer thereof or a pharmaceutically acceptable salt thereof, is a compound selected from:

2-[(1S,4aS,8aS)-2,5,5,8a-tetramethyl-1,4,4a,5,6,7,8,8a-octahydronaphthalen-1-yl]-N-(3,5-dihydroxyphenyl)-N-methylacetamide;

(4aS,8aS)—N-(3,5-dimethoxyphenyl)-2,5,5,8a-tetramethyl-3,4,4a,5,6,7,8,8a-octahydronaphthalene-1-carboxamide;

(4aS,8aS)—N-(3-hydroxy-5-methoxyphenyl)-2,5,5,8a-tetramethyl-3,4,4a,5,6,7,8,8a-octahydronaphthalene-1-carboxamide; and (4aS,8aS)—N-(3,5-dihydroxyphenyl)-2,5,5,8a-tetramethyl-3,4,4a,5,6,7,8,8a-octahydronaphthalene-1-carboxamide.

Another embodiment of a compound of formula (Ia), as described above, is a compound where $R^1$ is —$R^{9a}$—N($R^{11a}$)C(O)—$R^{9b}$—, i.e., a compound of formula (Ia6):

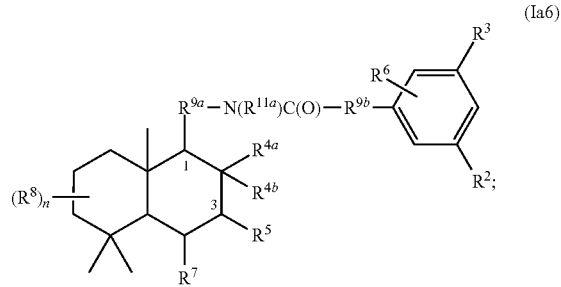

(Ia6)

wherein $R^{9a}$, $R^{9b}$ and $R^{11a}$ are as defined above in the Summary of the Invention for compounds of formula (I), or a stereoisomer thereof or a pharmaceutically acceptable salt thereof.

One embodiment of a compound of formula (Ia6), as described above, or a stereoisomer thereof or a pharmaceutically acceptable salt thereof, is a compound wherein:

n is 1, 2, 3, 4, 5, or 6;

$R^2$ and $R^3$ are each independently selected from hydrogen, alkyl or —$R^9$—$OR^{11}$, provided that at least one of $R^2$ and $R^3$ is —$R^9$—$OR^{11}$ when $R^6$ is hydrogen;

$R^{4a}$ and $R^{4b}$ are each independently selected from hydrogen, alkyl, —$R^9$—$OR^{11}$, or —C(O)$OR^{11}$, $R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—C(O)$R^{11}$, —$R^9$—C(O)$OR^{11}$, —$R^9$—N($R^{11}$)$R^{12}$, —$R^9$—C(O)N($R^{11}$)$R^{12}$, —$R^9$—N($R^{11}$)C(O)$R^{12}$, —$R^9$—N($R^{11}$)—$R^{14}$—N($R^{11}$)$R^{12}$, —$R^9$—N($R^{11}$)C(O)—$R^9$—N($R^{11}$)$R^{12}$, —$R^9$—N($R^{11}$)C(O)N($R^{11}$)—$OR^{12}$, —$R^9$—N($R^{11}$)C(=N$R^{11}$)N($R^{11}$)$R^{12}$, —$R^9$—N($R^{11}$)S(O)$_p$$R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p$$R^{12}$ (where p is 1 or 2);

$R^6$ and each $R^8$ are independently selected from hydrogen, alkyl, halo or haloalkyl;

$R^7$ is hydrogen, alkyl, halo or haloalkyl;

each $R^9$, $R^{9a}$ and $R^{9b}$ is independently a direct bond or a straight or branched alkylene chain;

each $R^{11}$, $R^{11a}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and $R^{14}$ is a straight or branched alkylene chain.

Another embodiment of a compound of formula (Ia6), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$, provided that at least one of $R^2$ and $R^3$ is —$R^9$—$OR^{11}$ when $R^6$ is hydrogen;

$R^{4a}$ and $R^{4b}$ are each independently selected from hydrogen, alkyl, —$R^9$—$OR^{11}$, or —C(O)$OR^{11}$, $R^5$ is independently selected from —$R^9$—N($R^{11}$)C(O)$R^{12}$, —$R^9$—N($R^{11}$)C(O)—$R^9$—N($R^{11}$)$R^{12}$, —$R^9$—N($R^{11}$)C(O)N($R^{11}$)—$OR^{12}$, —$R^9$—N($R^{11}$)C(=N$R^{11}$)N($R^{11}$)$R^{12}$, —$R^9$—N($R^{11}$)S(O)$_p R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p R^{12}$ (where p is 1 or 2); where each $R^9$ is independently a direct bond or a straight or branched alkylene chain; and where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;

$R^6$ and each $R^8$ are independently selected from hydrogen, alkyl, halo or haloalkyl;

$R^7$ is hydrogen, alkyl, halo or haloalkyl;

$R^{9a}$ is a straight or branched alkylene chain;

$R^{9b}$ is a direct bond or a straight or branched alkylene chain; and $R^{11a}$ is hydrogen, alkyl, optionally substituted aryl or optionally substituted aralkyl.

Another embodiment of a compound of formula (Ia6), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$, provided that at least one of $R^2$ and $R^3$ is —$R^9$—$OR^{11}$ when $R^6$ is hydrogen;

$R^{4a}$ is hydrogen and $R^{4b}$ is methyl;

$R^5$ is —$R^9$—N($R^{11}$)C(O)$R^{12}$ where each $R^9$ is a direct bond, $R^{11}$ is hydrogen or alkyl, and $R^{12}$ is optionally substituted aryl, optionally substituted heterocyclyl, optionally substituted heterocyclylalkyl or optionally substituted heteroaryl;

$R^6$ is hydrogen, halo or haloalkyl;

$R^7$ and $R^8$ are each hydrogen;

$R^{9a}$ is methylene or ethylene;

$R^{9b}$ is a direct bond; and $R^{11a}$ is hydrogen.

Another embodiment of a compound of formula (Ia6), as described above, or a stereoisomer thereof or a pharmaceutically acceptable salt thereof, is a compound selected from:

N-((2R,3S,4S,4aS)-3,4a,8,8-tetramethyl-4-((4-(trifluoromethyl)benzamido)methyl)-decahydronaphthalen-2-yl)nicotinamide;

4-methyl-N-((2R,3S,4S,4aS)-3,4a,8,8-tetramethyl-4-((4-(trifluoromethyl)benzamido)methyl)-decahydronaphthalen-2-yl)piperazine-1-carboxamide;

N-((2R,3S,4S,4aS)-4-((4-fluorobenzamido)methyl)-3,4a,8,8-tetramethyldecahydronaphthalen-2-yl)-4-methyl piperazine-1-carboxamide;

4-methyl-N-((2R,3S,4S,4aR)-3,4a,8,8-tetramethyl-4-(2-(4-(trifluoromethyl)benzamido)ethyl)-decahydronaphthalen-2-yl)piperazine-1-carboxamide; and N-((2R,3S,4S,4aR)-4-(2-(4-fluorobenzamido)ethyl)-3,4a,8,8-tetramethyldecahydronaphthalen-2-yl)-4-methyl piperazine-1-carboxamide.

Another embodiment of a compound of formula (Ia), as described above, is a compound where $R^1$ is —$R^{9a}$—N($R^{11a}$)—$R^{9b}$—, i.e., a compound of formula (Ia7):

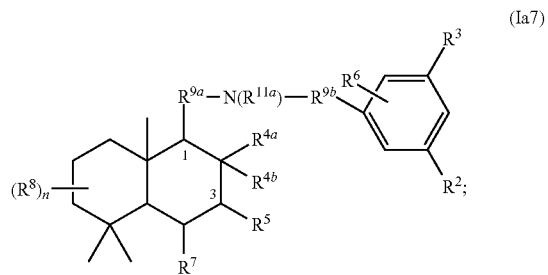

(Ia7)

wherein $R^{9a}$, $R^{9b}$ and $R^{11a}$ are as defined above in the Summary of the Invention for compounds of formula (I), or a stereoisomer thereof or a pharmaceutically acceptable salt thereof.

One embodiment of a compound of formula (Ia7), as described above, or a stereoisomer thereof or a pharmaceutically acceptable salt thereof, is a compound wherein:

n is 1, 2, 3, 4, 5, or 6;

$R^2$ and $R^3$ are each independently selected from hydrogen, alkyl or —$R^9$—$OR^{11}$, provided that at least one of $R^2$ and $R^3$ is —$R^9$—$OR^{11}$ when $R^6$ is hydrogen;

$R^{4a}$ and $R^{4b}$ are each independently selected from hydrogen, alkyl, —$R^9$—$OR^{11}$, or —C(O)$OR^{11}$, $R^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^9$—$OR^{11}$, —$R^9$—C(O)$R^{11}$, —$R^9$—C(O)$OR^{11}$, —$R^9$—N($R^{11}$)$R^{12}$, —$R^9$—C(O)N($R^{11}$)$R^{12}$, —$R^9$—N($R^{11}$)C(O)$R^{12}$, —$R^9$—N($R^{11}$)—$R^{14}$—N($R^{11}$)$R^{12}$, —$R^9$—N($R^{11}$)C(O)—$R^9$—N($R^{11}$)$R^{12}$, —$R^9$—N($R^{11}$)C(O)N($R^{11}$)—$OR^{12}$, —$R^9$—N($R^{11}$)C(=N$R^{11}$)N($R^{11}$)$R^{12}$, —$R^9$—N($R^{11}$)S(O)$_p R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p R^{12}$ (where p is 1 or 2);

$R^6$ and each $R^8$ are independently selected from hydrogen, alkyl, halo or haloalkyl;

$R^7$ is hydrogen, alkyl, halo or haloalkyl;

each $R^9$, $R^{9a}$ and $R^{9b}$ is independently a direct bond or a straight or branched alkylene chain;

each $R^{11}$, $R^{11a}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and $R^{14}$ is a straight or branched alkylene chain.

Another embodiment of a compound of formula (Ia7), as described above, or a stereoisomer thereof or a pharmaceutically acceptable salt thereof, is a compound wherein:

n is 1;

$R^2$ and $R^3$ are each independently selected from hydrogen, alkyl or —$R^9$—$OR^{11}$ where $R^9$ is a direct bond and $R^{11}$ is hydrogen, alkyl or benzyl, provided that at least one of $R^2$ and $R^3$ is —$R^9$—$OR^{11}$;

$R^{4a}$ and $R^{4b}$ are each independently selected from hydrogen, alkyl or —$R^9$—$OR^{11}$ where $R^9$ is a direct bond and $R^{11}$ is hydrogen;

$R^5$ is selected from hydrogen or —$R^9$—$OR^{11}$ where $R^9$ is independently a direct bond or a straight or branched alkylene chain and $R^{11}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;

$R^6$, $R^7$ and $R^8$ are each hydrogen; and $R^{9a}$ is a methylene chain and $R^{9b}$ is a direct bond.

Another embodiment of a compound of formula (Ia7), as described above, or a stereoisomer thereof or a pharmaceutically acceptable salt thereof, is the compound which is (2R,4aS,8aS)-1-{[(3-hydroxy-5-methoxyphenyl)amino]methyl}-2,5,5,8a-tetramethyl-decahydronaphthalen-2-ol.

Another embodiment of a compound of formula (I), as set forth above in the Summary of the Invention, is a compound of formula (Ib):

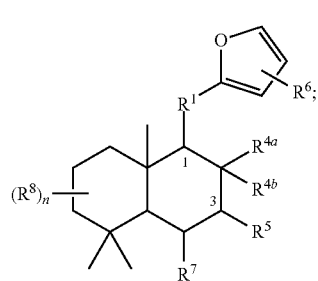

(Ib)

wherein n, $R^1$, $R^{4a}$, $R^{4b}$, $R^5$, $R^6$, $R^7$ and $R^8$ are as defined above in the Summary of the Invention for compounds of formula (I), or a stereoisomer thereof or a pharmaceutically acceptable salt thereof.

One embodiment of a compound of formula (Ib), as described above, is a compound wherein $R^1$ is —$R^{9a}$—N($R^{11a}$)C(O)—$R^{9b}$—, i.e., a compound of formula (Ib1):

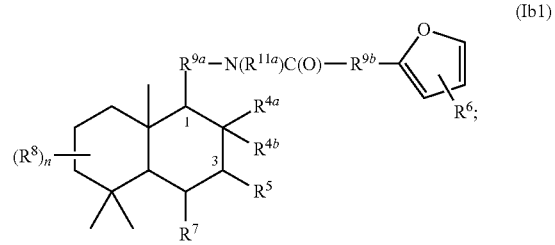

(Ib1)

wherein $R^{9a}$, $R^{9b}$ and $R^{11a}$ are as defined above in the Summary of the Invention for compounds of formula (I), or a stereoisomer thereof or a pharmaceutically acceptable salt thereof.

One embodiment of a compound of formula (Ib1), as described above, or a stereoisomer thereof or a pharmaceutically acceptable salt thereof, is a compound wherein:

n is 1;

$R^{4a}$ and $R^{4b}$ are each independently selected from hydrogen, alkyl, —$R^9$—$OR^{11}$, or —C(O)$OR^{11}$, $R^5$ is independently selected from —$R^9$—N($R^{11}$)C(O)$R^{12}$, —$R^9$—N($R^{11}$)C(O)—$R^9$—N($R^{11}$)$R^{12}$, —$R^9$—N($R^{11}$)C(O)N($R^{11}$)—$OR^{12}$, —$R^9$—N($R^{11}$)C(=N$R^{11}$)N($R^{11}$)$R^{12}$, —$R^9$—N($R^{11}$)S(O)$_p R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p R^{12}$ (where p is 1 or 2); where each $R^9$ is independently a direct bond or a straight or branched alkylene chain; and where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;

$R^6$ and each $R^8$ are independently selected from hydrogen, alkyl, halo or haloalkyl;

$R^7$ is hydrogen, alkyl, halo or haloalkyl;

$R^{9a}$ is a straight or branched alkylene chain;

$R^{9b}$ is a direct bond or a straight or branched alkylene chain; and $R^{11a}$ is hydrogen, alkyl, optionally substituted aryl or optionally substituted aralkyl.

Another embodiment of a compound of formula (Ib1), as described above, or a stereoisomer thereof or a pharmaceutically acceptable salt thereof, is a compound wherein:

n is 1;

$R^{4a}$ is hydrogen and $R^{4b}$ is methyl;

$R^5$ is —$R^9$—N($R^{11}$)C(O)$R^{12}$ where each $R^9$ is a direct bond, $R^{11}$ is hydrogen or alkyl, and $R^{12}$ is optionally substituted aryl, optionally substituted heterocyclyl, optionally substituted heterocyclylalkyl or optionally substituted heteroaryl;

$R^6$ is hydrogen, halo or haloalkyl;

$R^7$ and $R^8$ are each hydrogen;

$R^{9a}$ is methylene or ethylene;

$R^{9b}$ is a direct bond; and $R^{11a}$ is hydrogen.

Another embodiment of a compound of formula (Ib1), as described above, or a stereoisomer thereof or a pharmaceutically acceptable salt thereof, is a compound selected from:
N-((2R,3S,4S,4aS)-4-((furan-2-carboxamido)methyl)-3,4a,8,8-tetramethyldecahydronaphthalen-2-yl) nicotinamide;
N-((2R,3S,4S,4aS)-4-((furan-2-carboxamido)methyl)-3,4a,8,8-tetramethyldecahydronaphthalen-2-yl)-4-methylpiperazine-1-carboxamide; and N-((2R,3S,4S,4aR)-4-(2-(furan-2-carboxamido)ethyl)-3,4a,8,8-tetramethyldecahydronaphthalen-2-yl)-4-methylpiperazine-1-carboxamide.

Another embodiment of a compound of formula (I), as set forth above in the Summary of the Invention, is a compound of formula (Ic):

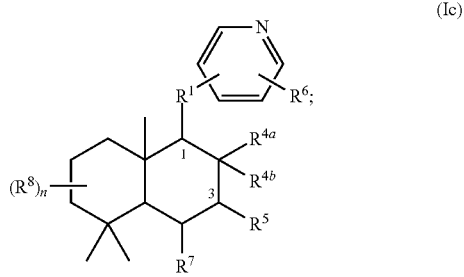

wherein n, $R^1$, $R^{4a}$, $R^{4b}$, $R^5$, $R^6$, $R^7$ and $R^8$ are as defined above in the Summary of the Invention for compounds of formula (I), or a stereoisomer thereof or a pharmaceutically acceptable salt thereof.

One embodiment of a compound of formula (Ic), as described above, is a compound wherein $R^1$ is —$R^{9a}$—N($R^{11a}$)C(O)—$R^{9b}$—, i.e., a compound of formula (Ic1):

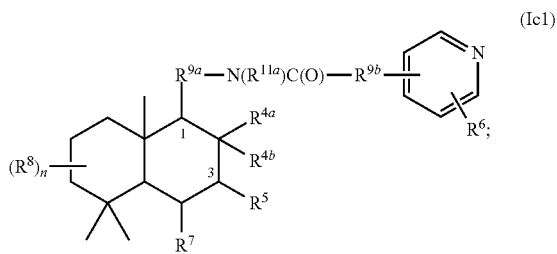

wherein $R^{9a}$, $R^{9b}$ and $R^{11a}$ are as defined above in the Summary of the Invention for compounds of formula (I), or a stereoisomer thereof or a pharmaceutically acceptable salt thereof.

One embodiment of a compound of formula (Ic1), as described above, or a stereoisomer thereof or a pharmaceutically acceptable salt thereof, is a compound wherein:
n is 1;
$R^{4a}$ and $R^{4b}$ are each independently selected from hydrogen, alkyl, —$R^9$—$OR^{11}$, or —C(O)$OR^{11}$,
$R^5$ is independently selected from —$R^9$—N($R^{11}$)C(O)$R^{12}$, —$R^9$—N($R^{11}$)C(O)—$R^9$—N($R^{11}$)$R^{12}$, —$R^9$—N($R^{11}$)C(O)N($R^{11}$)—$OR^{12}$, —$R^9$—N($R^{11}$)C(=N$R^{11}$)N($R^{11}$)$R^{12}$, —$R^9$—N($R^{11}$)S(O)$_p R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p R^{12}$ (where p is 1 or 2); where each $R^9$ is independently a direct bond or a straight or branched alkylene chain; and where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;
$R^6$ and each $R^8$ are independently selected from hydrogen, alkyl, halo or haloalkyl;
$R^7$ is hydrogen, alkyl, halo or haloalkyl;

$R^{9a}$ is a straight or branched alkylene chain;
$R^{9b}$ is a direct bond or a straight or branched alkylene chain; and
$R^{11a}$ is hydrogen, alkyl, optionally substituted aryl or optionally substituted aralkyl.

Another embodiment of a compound of formula (Ic1), as described above, or a stereoisomer thereof or a pharmaceutically acceptable salt thereof, is a compound wherein:
n is 1;
$R^{4a}$ is hydrogen and $R^{4b}$ is methyl;
$R^5$ is —$R^9$—N($R^{11}$)C(O)$R^{12}$ where each $R^9$ is a direct bond, $R^{11}$ is hydrogen or alkyl, and $R^{12}$ is optionally substituted aryl, optionally substituted heterocyclyl, optionally substituted heterocyclylalkyl or optionally substituted heteroaryl;
$R^6$ is hydrogen;
$R^7$ and $R^8$ are each hydrogen;
$R^{9a}$ is methylene or ethylene;
$R^{9b}$ is a direct bond; and
$R^{11a}$ is hydrogen.

Another embodiment of a compound of formula (Ic1), as described above, or a stereoisomer thereof or a pharmaceutically acceptable salt thereof, is a compound selected from:

N-((2R,3S,4S,4aS)-4-(isonicotinamidomethyl)-3,4a,8,8-tetramethyldecahydronaphthalen-2-yl) nicotinamide;

N-(((1S,2S,3R,8aS)-2,5,5,8a-tetramethyl-3-(nicotinamido)decahydronaphthalen-1-yl)methyl)nicotinamide;

N-((2R,3S,4S,4aS)-4-(isonicotinamidomethyl)-3,4a,8,8-tetramethyldecahydronaphthalen-2-yl)-4-methylpiperazine-1-carboxamide;

4-methyl-N-((2R,3S,4S,4aS)-3,4a,8,8-tetramethyl-4-(nicotinamidomethyl)decahydronaphthalen-2-yl)piperazine-1-carboxamide; and 4-methyl-N-((2R,3S,4S,4aR)-3,4a,8,8-tetramethyl-4-(2-(nicotinamido)ethyl)decahydronaphthalen-2-yl)piperazine-1-carboxamide.

Another embodiment of a compound of formula (I), as set forth above in the Summary of the Invention, is a compound of formula (Id):

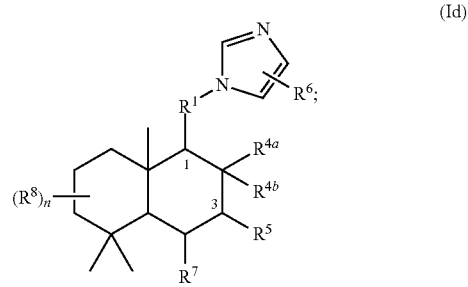

wherein n, $R^1$, $R^{4a}$, $R^{4b}$, $R^5$, $R^6$, $R^7$ and $R^8$ are as defined above in the Summary of the Invention for compounds of formula (I), or a stereoisomer thereof or a pharmaceutically acceptable salt thereof.

One embodiment of a compound of formula (Id), as described above, is a compound wherein $R^1$ is —$R^{9a}$—C($R^{10}$)$_2$—$R^{9b}$—, i.e., a compound of formula (Id1):

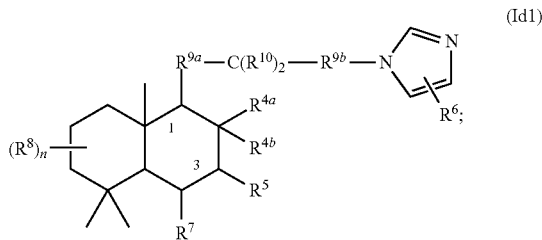

(Id1)

wherein $R^{9a}$, $R^{9b}$ and $R^{10}$ are as defined above in the Summary of the Invention for compounds of formula (I), or a stereoisomer thereof or a pharmaceutically acceptable salt thereof.

One embodiment of a compound of formula (Id1), as described above, or a stereoisomer thereof or a pharmaceutically acceptable salt thereof, is a compound wherein:

n is 1;

$R^{4a}$ and $R^{4b}$ are each independently selected from hydrogen, alkyl, —$R^9$—$OR^{11}$, or —C(O)$OR^{11}$, $R^5$ is independently selected from —$R^9$—$N(R^{11})C(O)R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2); where each $R^9$ is independently a direct bond or a straight or branched alkylene chain; and where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;

$R^6$ and each $R^8$ are independently selected from hydrogen, alkyl, halo or haloalkyl;

$R^7$ is hydrogen, alkyl, halo or haloalkyl;

$R^{9a}$ and $R^{9b}$ are independently a direct bond or a straight or branched alkylene chain; and each $R^{10}$ is hydrogen or alkyl.

Another embodiment of a compound of formula (Id1), as described above, or a stereoisomer thereof or a pharmaceutically acceptable salt thereof, is a compound wherein:

n is 1;

$R^{4a}$ is hydrogen and $R^{4b}$ is methyl;

$R^5$ is —$R^9$—$N(R^{11})C(O)R^{12}$ where each $R^9$ is a direct bond, $R^{11}$ is hydrogen or alkyl, and $R^{12}$ is optionally substituted aryl, optionally substituted heterocyclyl, optionally substituted heterocyclylalkyl or optionally substituted heteroaryl;

$R^6$ is hydrogen, halo or haloalkyl;

$R^7$ and $R^8$ are each hydrogen;

$R^{9a}$ and $R^{9b}$ are each a direct bond; and each $R^{10}$ is hydrogen.

Another embodiment of a compound of formula (Id1), as described above, or a stereoisomer thereof or a pharmaceutically acceptable salt thereof, is N-((2R,3S,4S,4aS)-4-((1H-imidazol-1-yl)methyl)-3,4a,8,8-tetramethyldecahydronaphthalen-2-yl) nicotinamide.

Another embodiment of a compound of formula (I), as set forth above in the Summary of the Invention, is a compound of formula (Ie):

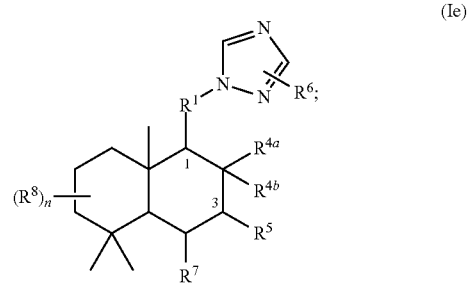

(Ie)

wherein n, $R^1$, $R^{4a}$, $R^{4b}$, $R^5$, $R^6$, $R^7$ and $R^8$ are as defined above in the Summary of the Invention for compounds of formula (I), or a stereoisomer thereof or a pharmaceutically acceptable salt thereof.

One embodiment of a compound of formula (Ie), as described above, is a compound wherein $R^1$ is —$R^{9a}$—C$(R^{10})_2$—$R^{9b}$—, i.e., a compound of formula (Ie1):

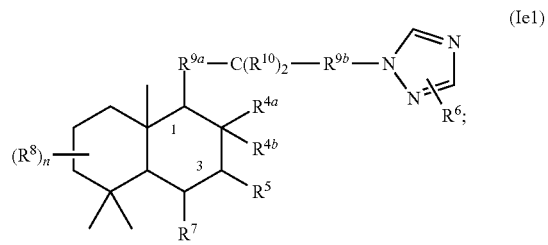

(Ie1)

wherein $R^{9a}$, $R^{9b}$ and $R^{10}$ are as defined above in the Summary of the Invention for compounds of formula (I), or a stereoisomer thereof or a pharmaceutically acceptable salt thereof.

One embodiment of a compound of formula (Ie1), as described above, or a stereoisomer thereof or a pharmaceutically acceptable salt thereof, is a compound wherein:

n is 1;

$R^{4a}$ and $R^{4b}$ are each independently selected from hydrogen, alkyl, —$R^9$—$OR^{11}$, or —C(O)$OR^{11}$, $R^5$ is independently selected from —$R^9$—$N(R^{11})C(O)R^{12}$, —$R^9$—$N(R^{11})C(O)$—$R^9$—$N(R^{11})R^{12}$, —$R^9$—$N(R^{11})C(O)N(R^{11})$—$OR^{12}$, —$R^9$—$N(R^{11})C(=NR^{11})N(R^{11})R^{12}$, —$R^9$—$N(R^{11})S(O)_pR^{11}$ (where p is 1 or 2), —$R^9$—$N(R^{11})C(S)N(R^{11})R^{12}$ or —$R^9$—$N(R^{11})C(O)$—$R^9$—$N(R^{11})S(O)_pR^{12}$ (where p is 1 or 2); where each $R^9$ is independently a direct bond or a straight or branched alkylene chain; and where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;

$R^6$ and each $R^8$ are independently selected from hydrogen, alkyl, halo or haloalkyl;

$R^7$ is hydrogen, alkyl, halo or haloalkyl;

$R^{9a}$ and $R^{9b}$ are independently a direct bond or a straight or branched alkylene chain; and each $R^{10}$ is hydrogen or alkyl.

Another embodiment of a compound of formula (Ie1), as described above, or a stereoisomer thereof or a pharmaceutically acceptable salt thereof, is a compound wherein:

n is 1;

$R^{4a}$ is hydrogen and $R^{4b}$ is methyl;

$R^5$ is —$R^9$—N($R^{11}$)C(O)$R^{12}$ where each $R^9$ is a direct bond, $R^{11}$ is hydrogen or alkyl, and $R^{12}$ is optionally substituted aryl, optionally substituted heterocyclyl, optionally substituted heterocyclylalkyl or optionally substituted heteroaryl;

$R^6$ is hydrogen, halo or haloalkyl;

$R^7$ and $R^8$ are each hydrogen;

$R^{9a}$ and $R^{9b}$ are each a direct bond; and each $R^{10}$ is hydrogen.

Another embodiment of a compound of formula (Ie1), as described above, or a stereoisomer thereof or a pharmaceutically acceptable salt thereof, is N-((2R,3S,4S,4aS)-4-((1H-1,2,4-triazol-1-yl)methyl)-3,4a,8,8-tetramethyldecahydronaphthalen-2-yl) nicotinamide.

Another embodiment of a compound of formula (I), as set forth above in the Summary of the Invention, is a compound of formula (If):

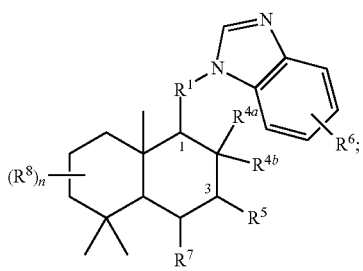

(If)

wherein n, $R^1$, $R^{4a}$, $R^{4b}$, $R^5$, $R^6$, $R^7$ and $R^8$ are as defined above in the Summary of the Invention for compounds of formula (I), or a stereoisomer thereof or a pharmaceutically acceptable salt thereof.

One embodiment of a compound of formula (If), as described above, is a compound wherein $R^1$ is —$R^{9a}$—C($R^{10}$)$_2$—$R^{9b}$—, i.e., a compound of formula (If1):

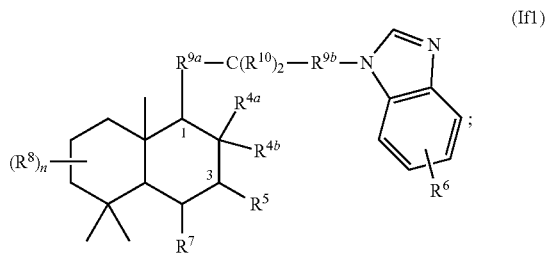

(If1)

wherein $R^{9a}$, $R^{9b}$ and $R^{10}$ are as defined above in the Summary of the Invention for compounds of formula (I), or a stereoisomer thereof or a pharmaceutically acceptable salt thereof.

One embodiment of a compound of formula (If1), as described above, or a stereoisomer thereof or a pharmaceutically acceptable salt thereof, is a compound wherein:

n is 1;

$R^{4a}$ and $R^{4b}$ are each independently selected from hydrogen, alkyl, —$R^9$—O$R^{11}$, or —C(O)O$R^{11}$, $R^5$ is independently selected from —$R^9$—N($R^{11}$)C(O)$R^{12}$, —$R^9$—N($R^{11}$)C(O)—$R^9$—N($R^{11}$)$R^{12}$, —$R^9$—N($R^{11}$)C(O)N($R^{11}$)—O$R^{12}$, —$R^9$—N($R^{11}$)C(=N$R^{11}$)N($R^{11}$)$R^{12}$, —$R^9$—N($R^{11}$)S(O)$_p$$R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p$$R^{12}$ (where p is 1 or 2); where each $R^9$ is independently a direct bond or a straight or branched alkylene chain; and where each $R^{11}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;

$R^6$ and each $R^8$ are independently selected from hydrogen, alkyl, halo or haloalkyl;

$R^7$ is hydrogen, alkyl, halo or haloalkyl;

$R^{9a}$ and $R^{9b}$ are independently a direct bond or a straight or branched alkylene chain; and each $R^{10}$ is hydrogen or alkyl.

Another embodiment of a compound of formula (If1), as described above, or a stereoisomer thereof or a pharmaceutically acceptable salt thereof, is a compound wherein:

n is 1;

$R^{4a}$ is hydrogen and $R^{4b}$ is methyl;

$R^5$ is —$R^9$—N($R^{11}$)C(O)$R^{12}$ where each $R^9$ is a direct bond, $R^{11}$ is hydrogen or alkyl, and $R^{12}$ is optionally substituted aryl, optionally substituted heterocyclyl, optionally substituted heterocyclylalkyl or optionally substituted heteroaryl;

$R^6$ is hydrogen, halo or haloalkyl;

$R^7$ and $R^8$ are each hydrogen;

$R^{9a}$ and $R^{9b}$ are each a direct bond; and each $R^{10}$ is hydrogen.

Another embodiment of a compound of formula (If1), as described above, or a stereoisomer thereof or a pharmaceutically acceptable salt thereof, is N-((2R,3S,4S,4aS)-4-((1H-benzo[d]imidazol-1-yl)methyl)-3,4a,8,8-tetramethyldecahydronaphthalen-2-yl) nicotinamide.

Another embodiment of a compound of formula (I), as set forth above in the Summary of the Invention, is a compound of formula (I) wherein:

is selected from:

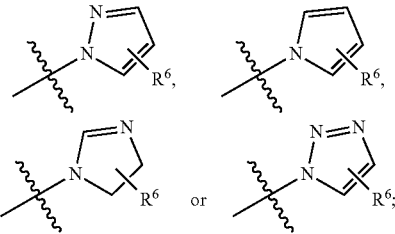

n is 1, 2, 3, 4, 5, or 6;

$R^1$ is —$R^{9a}$—C($R^{10}$)$_2$—$R^{9b}$—, —$R^{9a}$—C(O)—$R^{9b}$—, —$R^{9a}$—S(O)$_t$-$R^{9b}$— (where t is 0, 1 or 2), —$R^{9a}$—O—$R^{9b}$—, or —$R^{9a}$—C(O)N($R^{11a}$)—$R^{9b}$— or —$R^{9a}$—N($R^{11a}$)C(O)—$R^{9b}$—;

$R^{4a}$ and $R^{4b}$ are each independently selected from hydrogen, alkyl, —$R^9$—O$R^{11}$ or —C(O)O$R^{11}$, or $R^{4a}$ is selected from hydrogen, alkyl, —$R^9$—O$R^{11}$, or —C(O)O$R^{11}$ and $R^{4b}$ is a direct bond to the carbon at numeral 1 or a direct bond to the carbon at numeral 3;

or $R^{4a}$ and $R^{4b}$ together form =C($R^{13}$)$_2$;

R$^5$ is independently selected from hydrogen, oxo, cyano, nitro, halo, alkyl, haloalkyl, optionally substituted cycloalkyl, optionally substituted cycloakylalkyl, optionally substituted aryl, optionally substituted aralkyl, optionally substituted heterocyclyl, optionally substituted heterocyclylalkyl, optionally substituted heteroaryl, optionally substituted heteroarylalkyl, —R$^9$—OR$^{11}$, —R$^9$—C(O)R$^{11}$, —R$^9$—C(O)OR$^{11}$, —R$^9$—N(R$^{11}$)R$^{12}$, —R$^9$—C(O)N(R$^{11}$)R$^{12}$, —R$^9$—N(R$^{11}$)C(O)R$^{12}$, —R$^9$—N(R$^{11}$)—R$^{14}$—N(R$^{11}$)R$^{12}$, —R$^9$—N(R$^{11}$)C(O)—R$^9$—N(R$^{11}$)R$^{12}$, —R$^9$—N(R$^{11}$)C(O)N(R$^{11}$)—OR$^{12}$, —R$^9$—N(R$^{11}$)C(=NR$^{11}$)N(R$^{11}$)R$^{12}$, —R$^9$—N(R$^{11}$)S(O)$_p$R$^{11}$ (where p is 1 or 2), —R$^9$—N(R$^{11}$)C(S)N(R$^{11}$)R$^{12}$ or —R$^9$—N(R$^{11}$)C(O)—R$^9$—N(R$^{11}$)S(O)$_p$R$^{12}$ (where p is 1 or 2);

each R$^6$ and R$^8$ is independently selected from hydrogen, alkyl, halo or haloalkyl;

R$^7$ is hydrogen, alkyl, halo or haloalkyl;

each R$^9$, R$^{9a}$ and R$^{9b}$ is independently a direct bond or a straight or branched alkylene chain;

each R$^{10}$ is independently hydrogen, alkyl, —OR$^{11}$, —C(O)OR$^{11}$, —C(O)N(R$^{11}$)R$^{12}$, —N(R$^{11}$)R$^{12}$ or —N(R$^{11}$)C(O)R$^{11}$;

each R$^{11}$, R$^{11a}$ and R$^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;

each R$^{13}$ is hydrogen, alkyl or haloalkyl; and

R$^{14}$ is a straight or branched alkylene chain;

or a stereoisomer thereof or a pharmaceutically acceptable salt thereof.

One embodiment of the methods for treating a disease, disorder or condition in a mammal in need thereof is where the disease, disorder or condition is an autoimmune disease, disorder or condition, an inflammatory disease, disorder or condition, or a neoplastic or cell proliferative disease, disorder or condition.

Another embodiment of the methods for treating a disease, disorder or condition in a mammal in need thereof is where the disease, disorder or condition is an autoimmune disease, disorder or condition selected from idiopathic pulmonary fibrosis, an inflammatory bowel disease, rheumatoid arthritis, Still's Disease, Sjögren's Syndrome, systemic lupus erythematosus, multiple sclerosis, psoriasis and systemic sclerosis.

Another embodiment of the methods for treating a disease, disorder or condition in a mammal in need thereof is where the disease, disorder or condition is an inflammatory bowel disease selected from Crohn's Disease and ulcerative colitis.

Another embodiment of the methods for treating a disease, disorder or condition in a mammal in need thereof is where the disease, disorder or condition is an inflammatory disease, disorder or condition selected from acute respiratory distress syndrome, allergic rhinitis, Alzheimer's Disease, asthma, an ocular inflammatory disease, atopic dermatitis, bladder pain syndrome/interstitial cystitis, chronic obstructive pulmonary disease (COPD) including emphysematous, bronchitic, and alpa 1 anti-trypsin deficiency related COPD; dermal contact hypersensitivity, eczema, eosinophilic gastrointestinal disorder, fibromyalgia, gout, hepatic fibrosis, irritable bowel syndrome, ischemic reperfusion disease, kidney fibrosis, pancreatitis, Parkinsons Disease, post operative inflammation, a seronegative spondyloarthropathy, and vasculitis.

Another embodiment of the methods for treating a disease, disorder or condition in a mammal in need thereof is where the disease, disorder or condition is an ocular inflammatory disease selected from allergic conjunctivitis, dry eye, and uveitis.

Another embodiment of the methods for treating a disease, disorder or condition in a mammal in need thereof is where the disease, disorder or condition is a seronegative spondyloarthropathy selected from ankylosing spondylitis, psoriatic arthritis, and Reiter's Syndrome.

Another embodiment of the methods for treating a disease, disorder or condition in a mammal in need thereof is where the disease, disorder or condition is vasculitis selected from Wegener's Granulomatosis, polyarteritis nodosa, leucocytoclastic vasculitis, Churg-Strauss Syndrome, cryoglobulinemic vasculitis, and giant cell arteritis.

Another embodiment of the methods for treating a disease, disorder or condition in a mammal in need thereof is where the disease, disorder or condition is a neoplastic or cell proliferative disease, disorder or condition selected from acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia.

Another embodiment of the invention is a method of using the compounds of formula (I) as standards or controls in in vitro or in vivo assays in determining the efficacy of test compounds in modulating SHIP1 activity.

In another embodiment of the invention, the compounds of formula (I) are isotopically-labeled by having one or more atoms therein replaced by an atom having a different atomic mass or mass number. Such isotopically-labeled (i.e., radiolabelled) compounds of formula (I) are considered to be within the scope of this invention.

Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These isotopically-labeled compounds would be useful to help determine or measure the effectiveness of the compounds, by characterizing, for example, the site or mode of action for SHIP1 modulation, or binding affinity to pharmacologically important site of action for SHIP1 modulation. Certain isotopically-labeled compounds of formula (I), for example, those incorporating a radioactive isotope, are useful in drug and/or substrate tissue distribution studies. The radioactive isotopes tritium, i.e. $^3$H, and carbon-14, i.e., $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

In other embodiments, compounds of formula (I) exclude the following compounds:

1. (1S,2S,4aS,8aR)-decahydro-1-[2-(3-methoxyphenyl)ethyl]-5,5,8a-trimethyl-2-naphthalenecarboxylic acid, having the following formula (a):

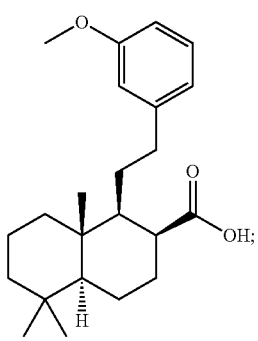

(a)

2. (1S,2S,4aS,8aR)-decahydro-1-[2-(3-methoxyphenyl)ethyl]-5,5,8a-trimethyl-2-naphthalenemethanol, having the following formula (b):

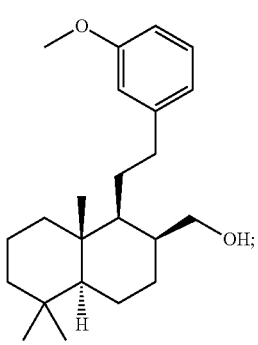

(b)

3. α-(3,5-dimethoxyphenyl)decahydro-2-hydroxy-2,5,5,8a-tetramethyl-1-naphthalenemethanol, having the following formula (c):

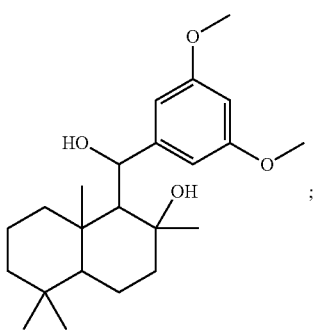 [SMILES: COc1cc(OC)cc(C(O)C2C(C)(O)CCC3C(C)(C)CCCC32C)c1]

(c)

4. (4aS,8aS)-3,4,4a,5,6,7,8,8a-octahydro-α-(3-methoxy-5-methylphenyl)-2,5,5,8a-tetramethyl-1-naphthalenemethanol, having the following formula (d):

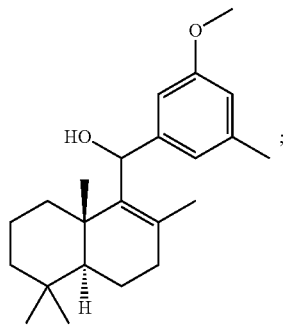

(d)

5. (1S,2R,4aS,8aS)-decahydro-2-hydroxy-α-(3-methoxy-5-methylphenyl)-2,5,5,8a-tetramethyl-1-naphthalenemethanol, having the following formula (e):

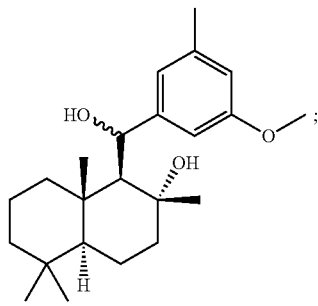

(e)

6. (1R,2R,4aS,8aS)-decahydro-1-[(3-methoxy-5-methylphenyl)methyl]-2,5,5,8a-tetramethyl-2-naphthalenol, having the following formula (f):

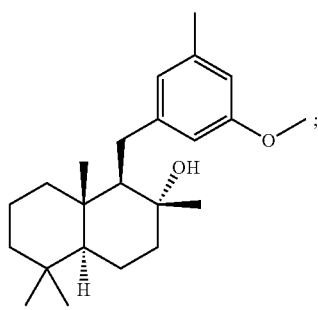

(f)

7. (4aS,5S,8aS)-decahydro-5-[2-(3-methoxyphenyl)ethyl]-1,1,4a-trimethyl-6-methylene-naphthalene, having the following formula (g):

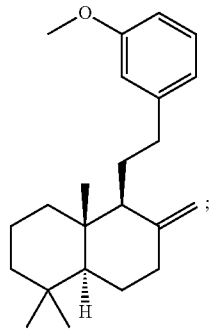

(g)

8. 2-[(1S,4aS,8aS)-decahydro-5,5,8a-trimethyl-2-methyl-ene-1-naphthalenyl]-1-(3-methoxyphenyl)-ethanone, having the following formula (h):

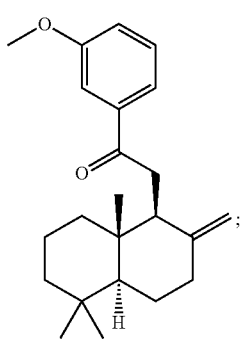

(h)

9. (1S,2R,4aS,8aS)-1-(3-methoxy-5-methylphenoxymethyl)-2,5,5,8a-tetramethyl-decahydronaphthalen-2-ol, having the following formula (i):

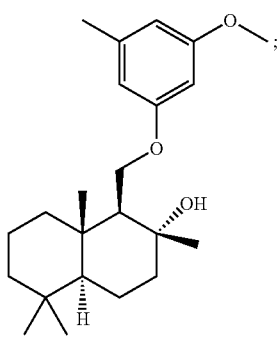

(i)

10. (1S,2R,4aS,8aS)-1-(3,5-dimethoxyphenoxymethyl)-2,5,5,8a-tetramethyl-decahydronaphthalen-2-ol, having the following formula (j):

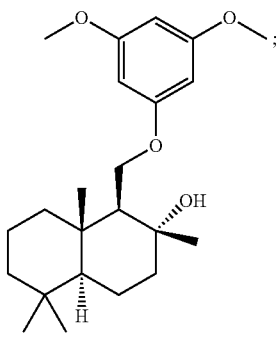

(j)

11. (1S,2R,4aS,8aS)-1-[3,5-bis(propan-2-yloxy)phenoxymethyl]-2,5,5,8a-tetramethyl-decahydronaphthalen-2-ol, having the following formula (k):

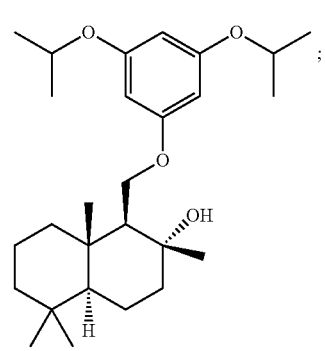

(k)

12. (1R,2R,8aS)-1-((3,5-dimethoxyphenylsulfonyl)methyl)-2,5,5,8a-tetramethyldecahydronaphthalen-2-ol, having the following formula (m):

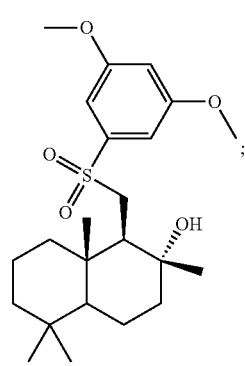

(m)

13. (1R,2R,4aS,8aS)-1-{[(3-methoxy-5-methylphenyl)sulfanyl]methyl}-2,5,5,8a-tetramethyl-decahydronaphthalen-2-ol, having the following formula (n):

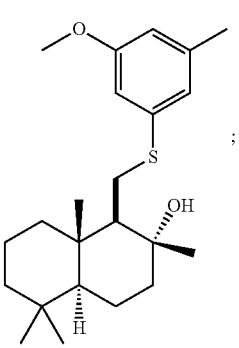

14. (1R,2R,4aS,8aS)-1-{[(3-methoxyphenyl)sulfanyl]methyl}-2,5,5,8a-tetramethyl-decahydronaphthalen-2-ol, having the following formula (o):

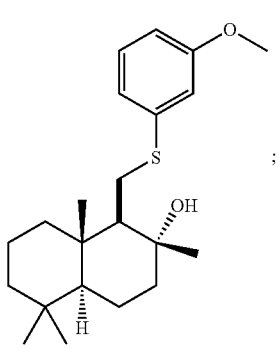

and 15. (1R,2R,4aS,8aS)-1-{[(3,5-dimethoxyphenyl)sulfanyl]methyl}-2,5,5,8a-tetramethyl-decahydronaphthalen-2-ol, having the following formula (p):

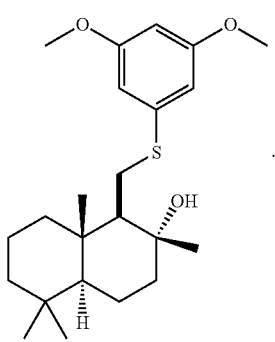

In other embodiments, compounds of formula (I) exclude all isomeric forms of compounds (a) through (p) above.

In further embodiments, compounds of formula (Ia) exclude embodiments wherein $R^1$ is —$CH_2$—, —$(CH_2)_2$—, —CH(OH)— and/or —$CH_2C(O)$—. In still further embodiments, compounds of formula (Ia) exclude compounds wherein one or both of $R^2$ and $R^3$ is alkoxy (e.g., wherein $R^2$ and $R^3$ are independently hydrogen, hydroxy or alkyl, provided that at least one of $R^2$ and $R^3$ is hydroxy).

In other embodiments, preferred stereochemistry of the compounds of formula (I) is shown below:

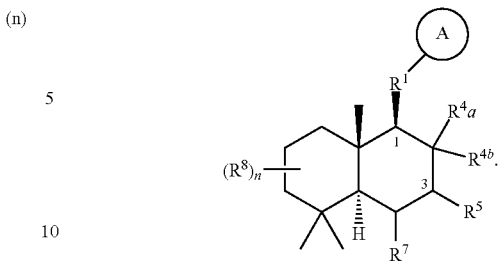

Specific embodiments of the compounds of the invention are described in more detail below in the Preparation of the Compounds of the Invention.

Utility and Testing of the Compounds of the Invention

Compounds of formula (I) above have activity as SHIP1 modulators and utility over a wide range of therapeutic applications, and may be used to treat any of a variety of diseases, disorders or conditions that would benefit from SHIP1 modulation. For example, such diseases, disorders or conditions include (but are not limited to) autoimmune diseases such as idiopathic pulmonary fibrosis, inflammatory bowel disease (including Crohn's Disease and ulcerative colitis), rheumatoid arthritis, Still's Disease, Sjögren's Syndrome, systemic lupus erythematosus, multiple sclerosis, psoriasis, and systemic sclerosis; inflammatory diseases such as acute respiratory distress syndrome (ARDS), allergic rhinitis, Alzheimer's Disease, asthma, ocular inflammatory diseases (including allergic conjunctivitis, dry eye, and uveitis), chronic obstructive pulmonary disease (COPD) including emphysematous, bronchitic, and COPD due to alpha 1 anti-trypsin deficiency, atopic dermatitis, dermal contact hypersensitivity, eczema, eosinophilic gastrointestinal disorder, fibromyalgia, gout, hepatic fibrosis, irritable bowl syndrome, bladder pain syndrome/interstitial cystitis, post operative inflammation, ischemic reperfusion disease, kidney fibrosis, pancreatitis, Parkinsons Disease, seronegative spondyloarthropathies (including ankylosing spondylitis, psoriatic arthritis, and Reiter's Syndrome), and vasculitis (including Wegener's Granulomatosis, polyarteritis nodosa, leucocytoclastic vasculitis, Churg-Strauss Syndrome, cryoglobulinemic vasculitis and giant cell arteritis); and neoplastic diseases or other cell proliferative disorders such as acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia.

The effectiveness of a compound as a SHIP1 modulator may be determined by any number of known techniques, including the assays set forth in Examples 120-123.

Pharmaceutical Compositions of the Invention and Administration

For the purposes of administration, the compounds of the present invention may be formulated as pharmaceutical compositions. Pharmaceutical compositions comprise one or more compounds of this invention in combination with a pharmaceutically acceptable carrier and/or diluent. The compound is present in the composition in an amount which is effective to treat a particular disorder—that is, in an amount sufficient to achieve SHIP1 modulation activity, and preferably with acceptable toxicity to the patient. Typically, the pharmaceutical compositions of the present invention may include a compound in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds in an appropriate manner, and in accordance with accepted practices, such as those disclosed in *Remington's Pharmaceutical Sciences* (Mack Pub. Co., N.J. current edition).

In another embodiment, the present invention provides a method for modulation SHIP1 generally and, more specifically, to treating the diseases, disorders and conditions as discussed above. Such methods include administering of a compound of the present invention to a mammal, preferably a human, in an amount sufficient to treat the condition. In this context, "treat" includes prophylactic administration. Such methods include systemic administration of a compound of this invention, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parenteral administration, the compounds of the present invention can be prepared in aqueous injection solutions which may contain buffers, antioxidants, bacteriostats, and other additives commonly employed in such solutions.

Preparation of the Compounds of the Invention

The following Reaction Schemes illustrate methods to make compounds of the present invention, i.e., compounds of formula (I), as set forth above in the Summary of the Invention.

The compounds of the present invention may be prepared by known organic synthesis techniques, including the methods described in more detail in the Examples. In general, the compounds of formula (I) may be made by the following Reaction Schemes, wherein all substituents are as defined above unless indicated otherwise.

Although not generally depicted in the following schemes, one skilled in the art will understand that appropriate protecting group strategies may be useful in preparing compounds of formula (I). Protecting group methodology is well known to those skilled in the art (see, for example, Greene, T. W. and Wuts, P. G. M. Greene's *Protective Groups in Organic Synthesis* (2006), 4th Ed. Wiley).

It is also understood that one skilled in the art would be able to make the compounds of the invention by similar methods or by methods known to one skilled in the art. It is also understood that one skilled in the art would be able to make in a similar manner as described below other compounds of the invention not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *March's Advanced Organic Chemistry: Reactions, Mechanisms, and Structure,* 6th edition (Wiley, 2007)) or prepared as described herein.

It is also understood that in the following description, combinations of substituents and/or variables of the depicted formulae are permissible only if such contributions result in stable compounds.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

A. Preparation of Compounds of Formulae (Ia1a), (Ia1b), (Ia1c), (Ia1d), (Ia1e), (Ia1f) and (Ia1g)

Compounds of formulae (Ia1a), (Ia1b), (Ia1c), (Ia1d), (Ia1e), (Ia1f) and (Ia1g) are compounds of formula (Ia1), as set forth above in the Embodiments of the Invention, where $R^{9b}$ is a direct bond, $R^{4b}$ is —$R^9$—$OR^{11}$ (where $R^9$ is a direct bond and $R^{11}$ is hydrogen), $R^{4a}$ is hydrogen, alkyl or —$R^9$—$OR^{11}$ (where $R^9$ is an alkylene chain and $R^{11}$ is as described above for $R^{11}$ in the Summary of the Invention for compounds of formula (I)), and n, $R^2$, $R^3$, $R^5$, $R^6$, $R^7$, $R^8$, $R^{9a}$ and $R^{13}$ are as described above in the Summary of the Invention for compounds of formula (I), and are prepared below in Reaction Scheme 1:

REACTION SCHEME 1

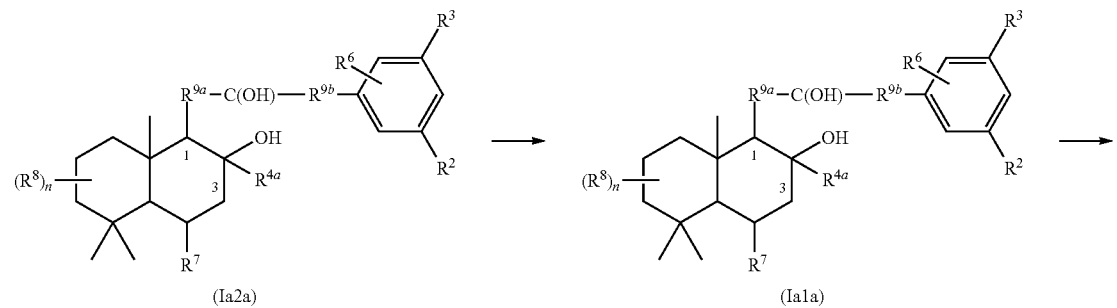

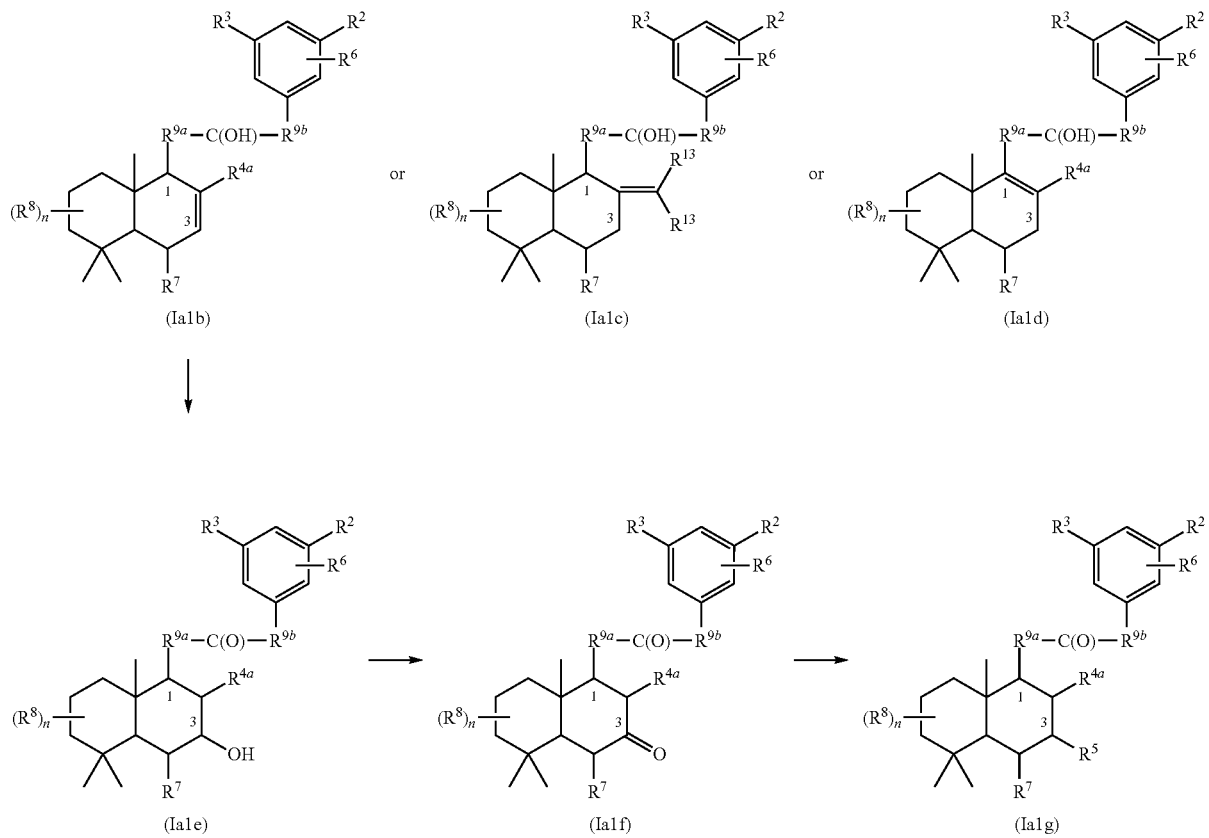

Compounds of formula (Ia2a) are compounds of formula (Ia2), as described above in the Embodiments, where $R^{9b}$ is a direct bond and one $R^{10}$ is hydrogen and the other $R^{10}$ is hydroxy, $R^{4a}$ is —$R^9$—$OR^{11}$ (where $R^9$ is a direct bond and $R^{11}$ is hydrogen), $R^{4b}$ is hydrogen, alkyl or —$R^9$—$OR^{11}$ (where $R^9$ is an alkylene chain and $R^{11}$ is as described above for $R^{11}$ in the Summary of the Invention for compounds of formula (I)), and m, n, $R^2$, $R^3$, $R^5$, $R^6$, $R^7$, $R^8$, $R^{9a}$ and $R^{13}$ are as described above in the Summary of the Invention for compounds of formula (I), and may be purchased or prepared according to methods known in the art or by methods disclosed herein.

In general, oxidation of the benzylic alcohol of compound of formula (Ia2a) with an appropriate reagent, for example pyridinium chlorochromate (PCC), results in ketone compound of formula (Ia1a). Elimination of the tertiary alcohol of compound of formula (Ia1a) under appropriate conditions, for example Tin (IV) chloride, produces compounds of formula (Ia1b), compounds of formula (Ia1c) or compounds of formula (Ia1d). Further treatment of compound of formula (Ia1 b) with an appropriate reagent, for example $BH_3$-THF followed by NaOH, yields alcohol compound of formula (Ia1e). Alcohol compound of formula (Ia1e) may then be oxidized, for example with PCC, to yield ketone compound of formula (Ia1f). The non-benzylic keto moiety of compound of formula (Ia1f) may be partially reduced to the corresponding alcohol or completely reduced to the corresponding methylene using methods known in the art to produce a compound of formula (Ia1g) wherein $R^5$ is hydrogen or hydroxy. Alternatively, a compound of formula (Ia1f) may be treated under reductive alkylation or reductive amination conditions to produce a compound of formula (Ia1g) wherein, for example, $R^5$ is optionally substituted amino, or converted to another functional group, such as a cyano, amide or carboxylic acid, using methods known in the art. One skilled in the art will recognize that, instead of starting with a compound comprising the $R^6$, $R^7$ and $R^8$ moiety, the $R^6$, $R^7$ and $R^8$ moiety may be installed at a later point in the synthesis using methods known to one skilled in the art.

B. Preparation of Compounds of Formulae (1a2b), (1a2c), (1a2d), (1a2e) and (1a2f)

Compounds of formulae (1a2b), (1a2c), (1a2d), (1a2e) and (1a2f) are compounds of formula (Ia2), as set forth above in the Embodiments of the Invention, where $R^{9b}$ is a direct bond and both $R^{10}$'s are hydrogen, $R^{4b}$ is —$R^9$—$OR^{11}$ where $R^9$ is a direct bond and $R^{11}$ is hydrogen, $R^{4a}$ is hydrogen, alkyl or —$R^9$—$OR^{11}$ where $R^9$ is an alkylene chain and $R^{11}$ is as described above for $R^{11}$ in the Summary of the Invention for compounds of formula (I), $R^5$ is hydrogen, and m, n, $R^2$, $R^3$, $R^6$, $R^7$, $R^8$, $R^{9a}$ and $R^{13}$ are as described above in the Summary of the Invention for compounds of formula (I), and are prepared below in Reaction Scheme 2:

REACTION SCHEME 2

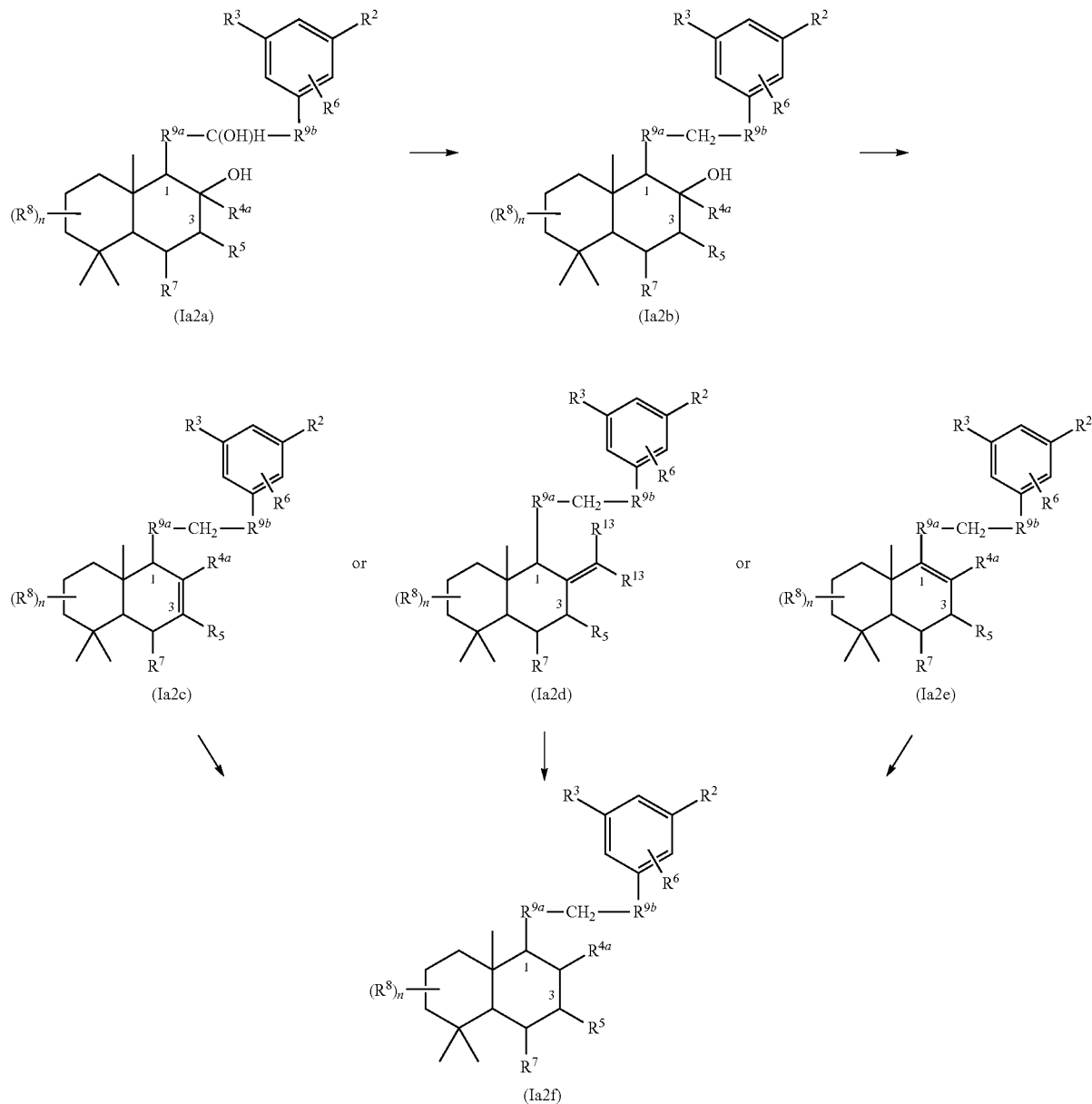

Compounds of formula (Ia2a) are described above in Reaction Scheme 1.

In general, complete reduction of the benzylic alcohol of compound of formula (1a2a) under conditions known in the art results in alcohol compound of formula (1a2b). Elimination of the tertiary alcohol of compound of formula (1a2b) under appropriate conditions, for example, Tin (IV) chloride, produces compounds of formulae (1a2c), (1a2d) or (1a2e). Further reduction of a compound of formulae (1a2c), (1a2d) or (1a2e) under appropriate conditions, for example catalytic hydrogenation or other suitable method, yields compounds of formula (1a2f). One skilled in the art will recognize that, instead of starting with a compound comprising the $R^5$, $R^6$, $R^7$ and/or $R^8$ moiety, the $R^5$, $R^6$, $R^7$ and/or $R^8$ moiety may be installed at a later point in the synthesis using methods analogous to those described herein.

C. Preparation of Compounds of Formulae (Ia3a), (Ia3b), (Ia3c), (Ia3d) and (Ia3f)

Compounds of formulae (Ia3a), (Ia3b), (Ia3c), (Ia3d) and (Ia3e) are compounds of formula (Ia3), as set forth above in the Embodiments of the Invention, where t is 0, $R^{9a}$ is straight or branched alkylene chain, $R^{4b}$ is —$R^9$—$OR^{11}$ (where $R^9$ is a direct bond and $R^{11}$ is hydrogen), $R^{4a}$ is hydrogen, alkyl or —$R^9$—$OR^{11}$ (where $R^9$ is an straight or branched alkylene chain and $R^{11}$ is as described above in the Summary of the Invention for compounds of formula (I)), $R^5$ is hydrogen and m, n, $R^2$, $R^3$, $R^6$, $R^7$, $R^8$, $R^{9b}$ and $R^{13}$ are as described above in the Summary of the Invention for compounds of formula (I), and are prepared below in Reaction Scheme 3:

REACTION SCHEME 3

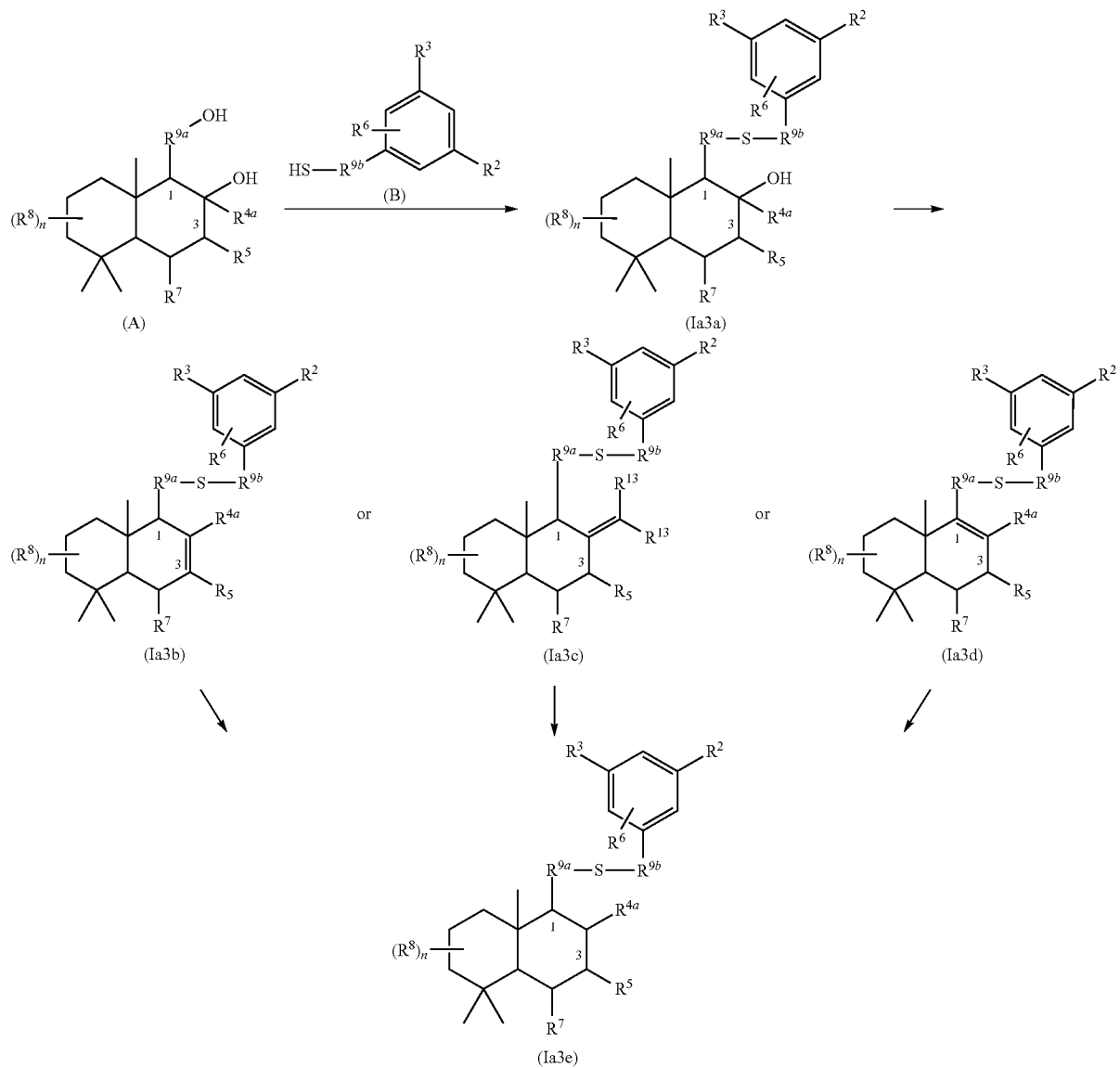

Compounds of formula (A) and formula (B) may be purchased or prepared by methods known in the art.

In general, activation of the primary alcohol in compound of formula (A), for example by conversion to the mesylate using methods known in the art, and reaction of the activated compound of formula (A) with the phenyl compound of formula (B) results in compound of formula (Ia3a). Compounds of formulae (Ia3b), (Ia3c) and (Ia3c) may be produced from compounds of formula (Ia3a) using methods analogous to those described above in Reaction Scheme 1, and compounds of formula (Ia3e) may be produced from compounds of formulae (Ia3b), (Ia3c) and (Ia3d) using methods analogous to those described above in Reaction Scheme 1. One skilled in the art will recognize that compounds of formulae (Ia3a), (Ia3b), (Ia3c), (Ia3d) and (Ia3e) may be further oxidized under the appropriate oxidizing conditions to produce the corresponding compounds of formula (Ia3) where t is 1 or 2. One skilled in the art will also recognize that, instead of starting with a compound comprising the $R^5$, $R^6$, $R^7$ and/or $R^8$ moiety, the $R^5$, $R^6$, $R^7$ and/or $R^8$ moiety may be installed at a later point in the synthesis using methods analogous to those described herein.

D. Preparation of Compounds of Formulae (Ia4a), (Ia4b), (Ia4c), (Ia4d) and (Ia4e)

Compounds of formulae (Ia4a), (Ia4b), (Ia4c), (Ia4d) and (Ia4e) are compounds of formula (Ia4), as set forth above in the Embodiments of the invention, where $R^{9b}$ is a direct bond, $R^{4b}$ is —$R^9$—$OR^{11}$ (where $R^9$ is a direct bond and $R^{11}$ is hydrogen), $R^{4a}$ is hydrogen, alkyl or —$R^9$—$OR^{11}$ (where $R^9$ is an alkylene chain and $R^{11}$ is as described above in the Summary of the Invention for compounds of formula (I)), $R^5$ is hydrogen and m, n, $R^2$, $R^3$, $R^6$, $R^7$, $R^8$, $R^{9a}$ and $R^{13}$ are as described above in the Summary of the Invention for compounds of formula (I), and are prepared below in Reaction Scheme 4 where W is a suitable leaving group, such as halogen:

REACTION SCHEME 4

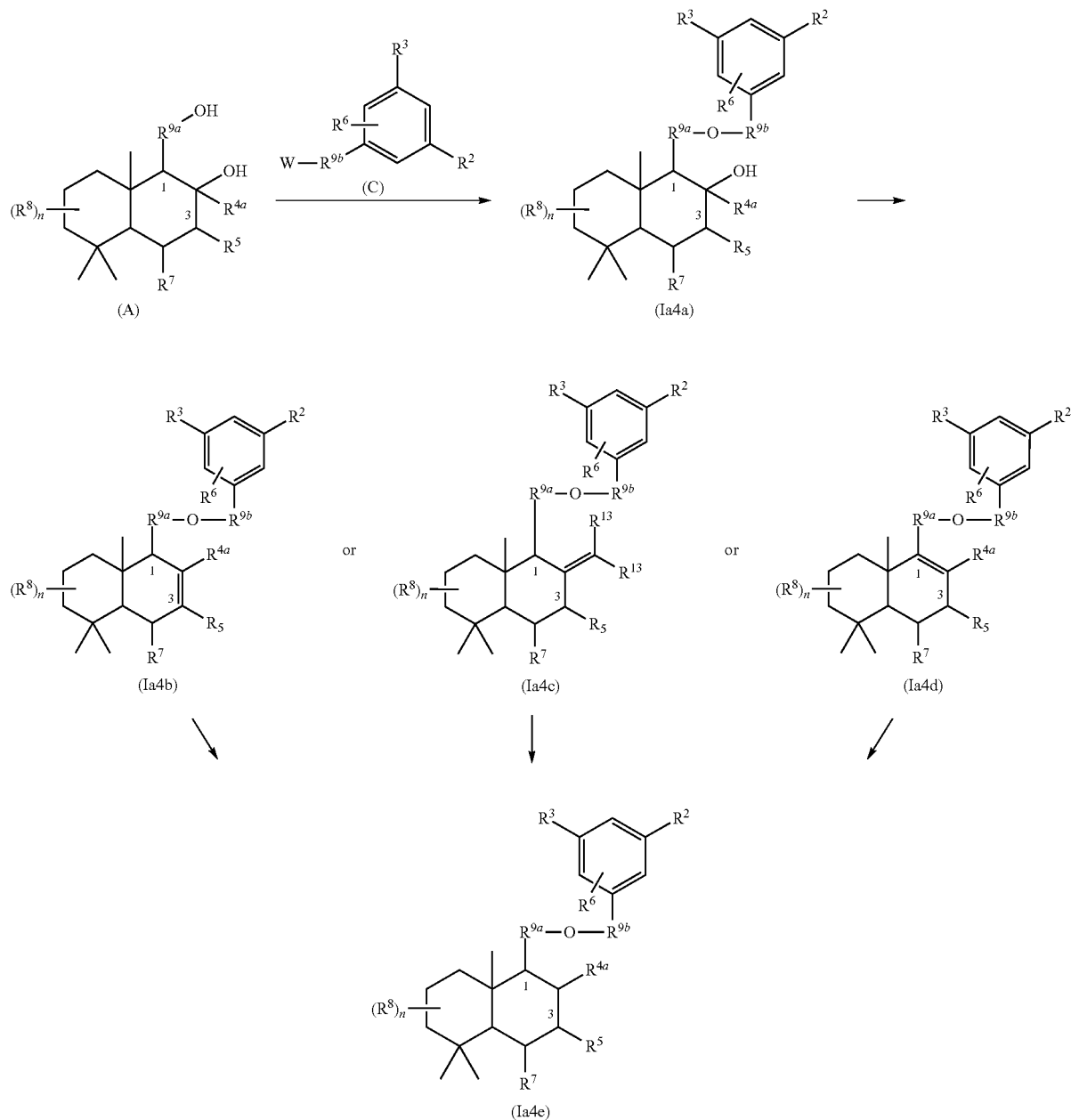

Compounds of formula (A) and formula (C) may be purchased or prepared by methods known in the art or by methods disclosed herein.

In general, reaction of the primary alcohol in compound of formula (A) with the phenyl compound of formula (C) results in compound of formula (Ia4a). Compounds of formulae (Ia4b), (Ia4c) and (Ia4d) may be produced from compounds of formula (Ia4a) using methods analogous to those described above in Reaction Scheme 1. Compounds of formula (Ia4e) may be produced from compounds of formulae (Ia4b), (Ia4b) and (Ia4c) using methods analogous to those described above in Reaction Scheme 2. One skilled in the art will recognize that, instead of starting with a compound comprising the $R^5$, $R^6$, $R^7$ and/or $R^8$ moiety, the $R^5$, $R^6$, $R^7$ and/or $R^8$ moiety may be installed at a later point in the synthesis using methods analogous to those described herein.

E. Preparation of Compounds of Formulae (Ia5a), (Ia5b), (Ia5c) and (Ia5d)

Compounds of formulae (Ia5a), (Ia5b), (Ia5c) and (Ia5d) are compounds of formula (Ia5), as set forth above in the Embodiments of the invention, where $R^{11a}$ is hydrogen, $R^{4b}$ is —$R^9$—$OR^{11}$ (where $R^9$ is a direct bond and $R^{11}$ is hydrogen), $R^{4a}$ is hydrogen, alkyl or —$R^9$—$OR^{11}$ (where $R^9$ is an alkylene chain and $R^{11}$ is as described above for $R^{11}$ in the Summary of the Invention for compounds of formula (I)), $R^5$ is hydrogen and m, n, $R^2$, $R^3$, $R^6$, $R^7$, $R^8$, $R^{9a}$, $R^{9b}$ and $R^{13}$ are as described above in the Summary of the Invention for compounds of formula (I), and are prepared below in Reaction Scheme 5:

REACTION SCHEME 5
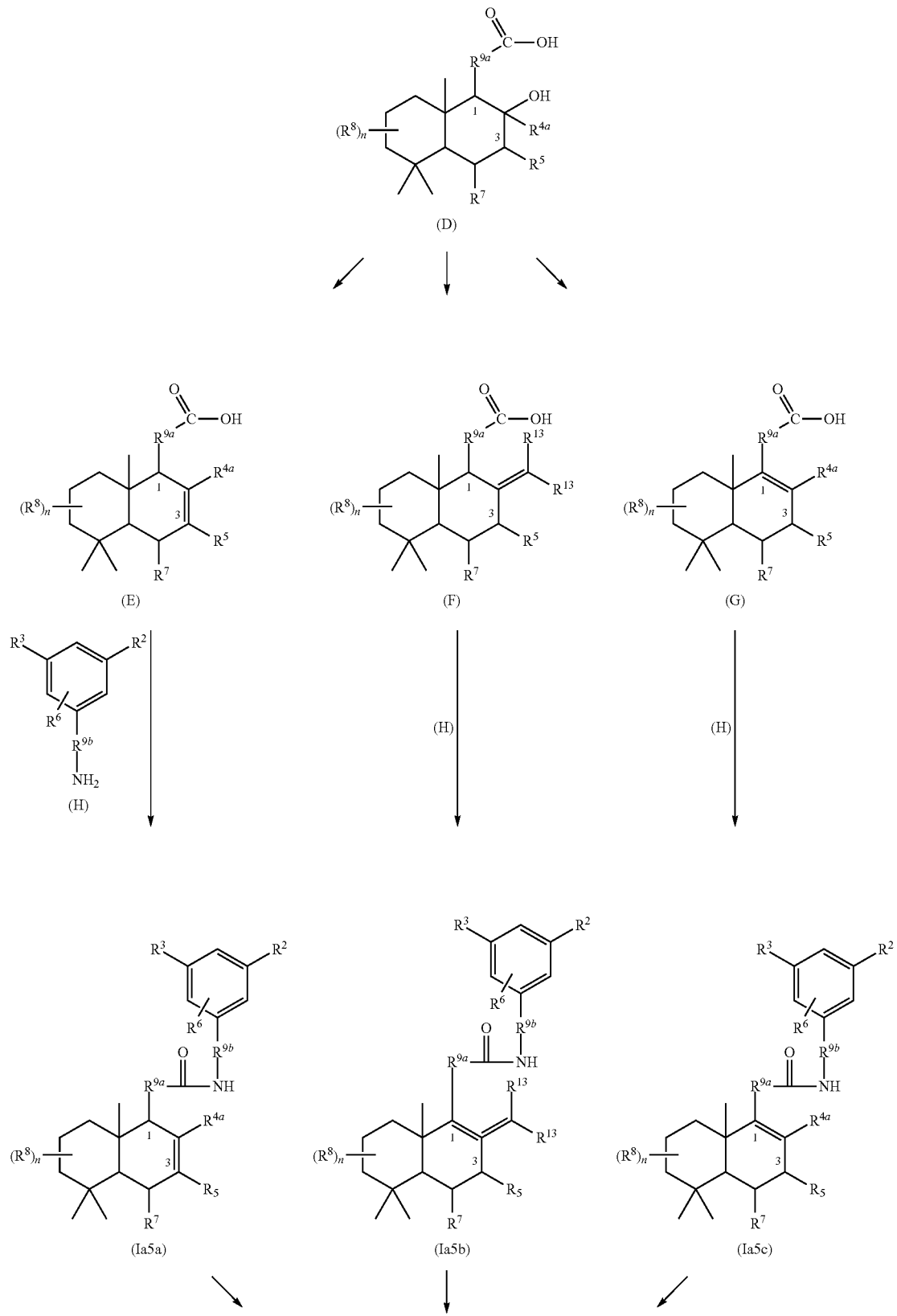

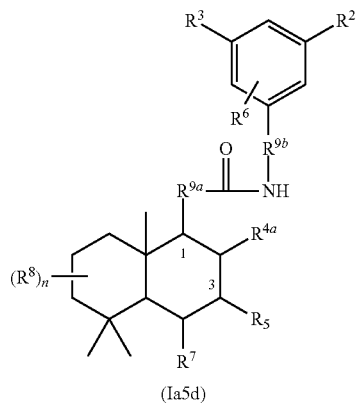

(Ia5d)

Compounds of formula (D) and formula (H) may be purchased or prepared by methods known in the art.

In general, elimination of the tertiary alcohol in the compound of formula (D) under appropriate conditions, for example with p-toluene sulphonic acid, followed by oxidation of the aldehyde to the corresponding carboxylic acid under conditions known in the art results in the formation of a compound of formulae (E), (F) or (G). Activation of the carboxylic acid in these compounds under appropriate conditions, for example with oxalic acid, followed by reaction with aniline compound of formula (H) results in a compound of formulae (Ia5a), (Ia5b) or (Ia5c). Compounds of formula (Ia5d) may then be produced using methods analogous to those described above in Reaction Scheme 2. One skilled in the art will recognize that, instead of starting with a compound comprising the $R^5$, $R^6$, $R^7$ and/or $R^8$ moiety, the $R^5$, $R^6$, $R^7$ and/or $R^8$ moiety may be installed at a later point in the synthesis using methods analogous to those described herein.

F. Preparation of Compounds of Formulae (Ia1h), (Ia1i), (Ia1j), (Ia1k) and (Ia1l)

Compounds of formulae (Ia1h), (Ia1i), (Ia1j), (Ia1k) and (Ia1l) are compounds of formula (Ia1), as set forth above in the Embodiments of the Invention, where $R^{9a}$ is methylene, ethylene or propylene and $R^{9b}$ is a direct bond, $R^{4b}$ is —$R^9$—$OR^{11}$ (where $R^9$ is a direct bond and $R^{11}$ is hydrogen), $R^{4a}$ is hydrogen, alkyl or —$R^9$—$OR^{11}$ (where $R^9$ is an alkylene chain and $R^{11}$ is as described above for $R^{11}$ in the Summary of the Invention for compounds of formula (I)), $R^5$ is hydrogen and m, n, $R^2$, $R^3$, $R^6$, $R^7$, $R^8$ and $R^{13}$ are as described above in the Summary of the Invention for compounds of formula (I), and are prepared below in Reaction Scheme 6:

REACTION SCHEME 6

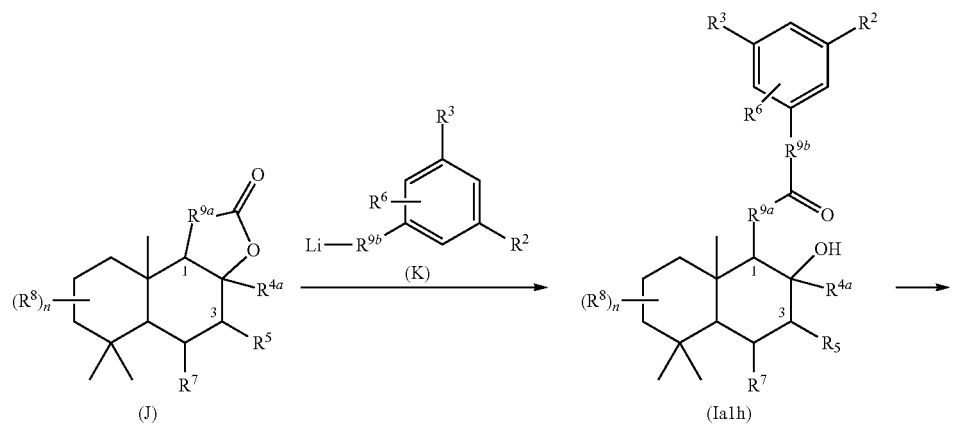

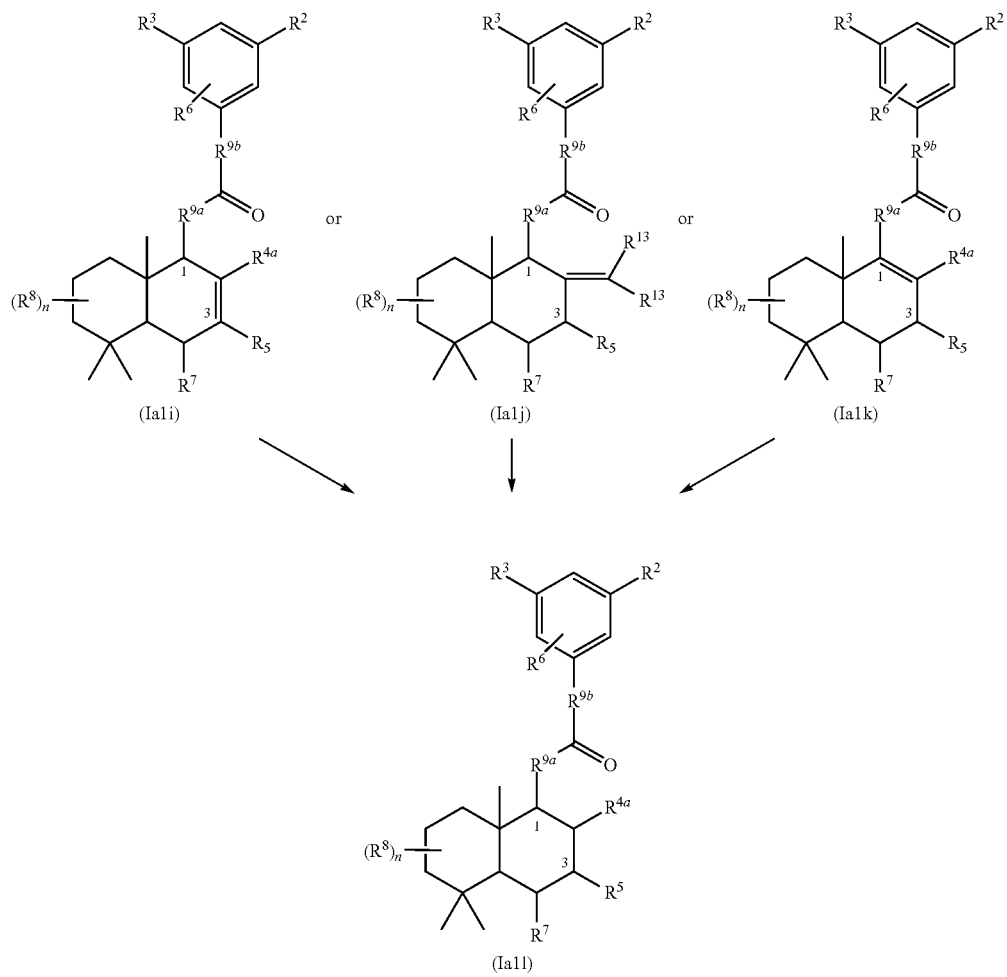

Compounds of formula (J) and formula (K) may be purchased or prepared by methods known in the art.

Utilizing organometallic methodologies, the reaction of a compound of formula (J) with phenyllithium compound of formula (K) results in ketone compound of formula (Ia1h). Compounds of formulae (Ia1i), (Ia1j), (Ia1k) and (Ia1l) may then be produced using methods analogous to those described above in Reaction Scheme 2. The keto moiety of compounds of formulae (Ia1h), (Ia1i), (Ia1j), (Ia1k) and (Ia1l) may also be partially reduced to the corresponding hydroxyl compound or completely reduced to a methylene to yield compounds of formula (Ia2) wherein one $R^{10}$ is hydrogen and the other is hydroxy or wherein both $R^{10}$'s are hydrogen, which may be further functionalized. Methods for such reduction are well known in the art. One skilled in the art will recognize that, instead of starting with a compound comprising the $R^5$, $R^6$, $R^7$ and/or $R^8$ moiety, the $R^5$, $R^6$, $R^7$ and/or $R^8$ moiety may be installed at a later point in the synthesis using methods analogous to those described herein.

G. Preparation of Compounds of Formulae (Ia1f2), (Ia1g1), (Ia1g2), (Ia1g3) and (Ia1g4)

Compound of formula (Ia1f2) are compounds of formula (Ia1f), as described above in Reaction Scheme 1, and compounds of formulae (Ia1g1), (Ia1g2), (Ia1g3) and (Ia1g4) are compounds of formula (Ia1g), as described above in Reaction Scheme 1, and are prepared below in Reaction Scheme 7 where $R^{4a1}$ is alkyl, $R^{11b}$ is optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl, and X is halo:

REACTION SCHEME 7

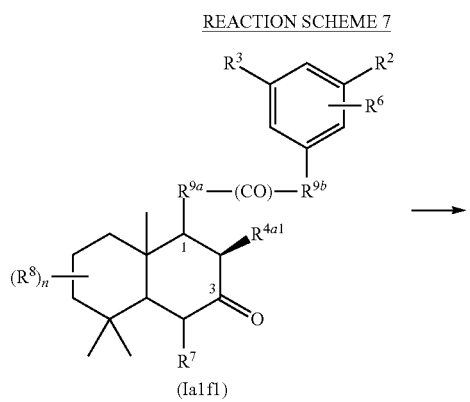

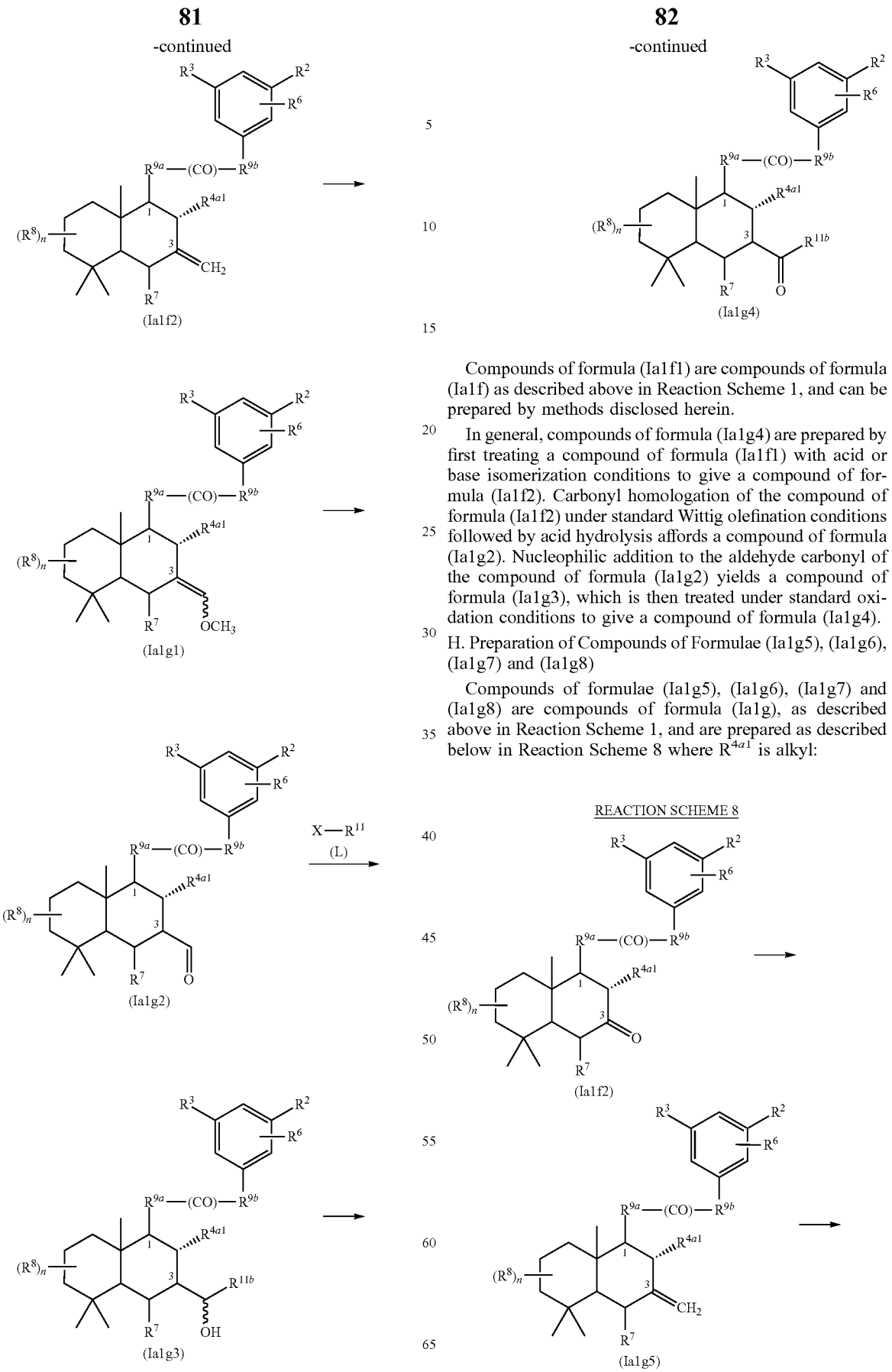

Compounds of formula (Ia1f1) are compounds of formula (Ia1f) as described above in Reaction Scheme 1, and can be prepared by methods disclosed herein.

In general, compounds of formula (Ia1g4) are prepared by first treating a compound of formula (Ia1f1) with acid or base isomerization conditions to give a compound of formula (Ia1f2). Carbonyl homologation of the compound of formula (Ia1f2) under standard Wittig olefination conditions followed by acid hydrolysis affords a compound of formula (Ia1g2). Nucleophilic addition to the aldehyde carbonyl of the compound of formula (Ia1g2) yields a compound of formula (Ia1g3), which is then treated under standard oxidation conditions to give a compound of formula (Ia1g4).

H. Preparation of Compounds of Formulae (Ia1g5), (Ia1g6), (Ia1g7) and (Ia1g8)

Compounds of formulae (Ia1g5), (Ia1g6), (Ia1g7) and (Ia1g8) are compounds of formula (Ia1g), as described above in Reaction Scheme 1, and are prepared as described below in Reaction Scheme 8 where $R^{4a1}$ is alkyl:

REACTION SCHEME 8

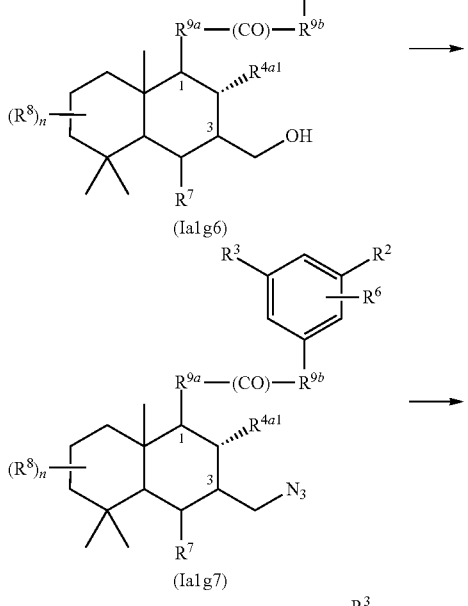

(Ia1g6)

(Ia1g7)

(Ia1g8)

Compounds of formula (Ia1f2) are described above in Reaction Scheme 7 and are prepared by methods disclosed herein.

In general, compounds of formula (Ia1g8) are prepared by first treating a compound of formula (Ia1f2) under standard Wittig reaction conditions to form the methylidene compound of formula (Ia1g5). Hydroboration of the methylidene of the compound of formula (Ia1g5) with oxidative work up affords the primary alcohol compound of formula (Ia1g6). In addition to direct methods, the alcohol of the compound of formula (Ia1g5) is converted to an azide compound of formula (Ia1g7) by first activation of the hydroxyl by standard conditions, such as treatment with methanesulfonyl chloride, followed by treatment with sodium azide under standard conditions. Reduction of the azide of the compound of formula (Ia1g7), for example using Staudinger conditions, affords a compound of formula (Ia1g8).

I. Preparation of Compounds of Formulae (Ia-2) and (Ia-3)

Compounds of formulae (Ia-2) and (Ia-3) are compounds of formula (Ia), as described above in the Embodiments of the Invention where $R^5$ is —$R^9$—$N(R^{11})C(O)$—$R^9$—$N(R^{11})R^{12}$ (where the first $R^9$, $R^{11}$ and $R^{12}$ are as described above in the Summary of the Invention for compounds of formula (I) and the second $R^9$ is a direct bond), and are prepared as described below in Reaction Scheme 9 where n, $R^1$, $R^2$, $R^3$, $R^{4a}$, $R^{4b}$, $R^6$, $R^7$, $R^8$, $R^{11}$ and $R^{12}$ are as described above in the Summary of the Invention for compounds of formula (I):

REACTION SCHEME 9

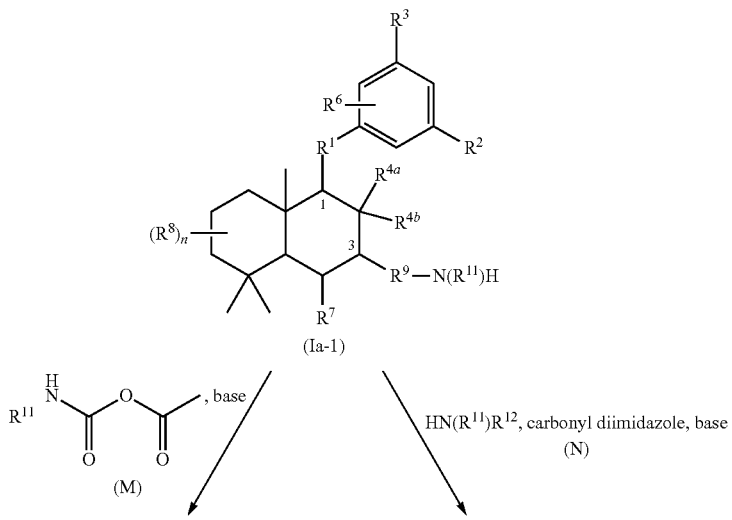

(Ia-1)

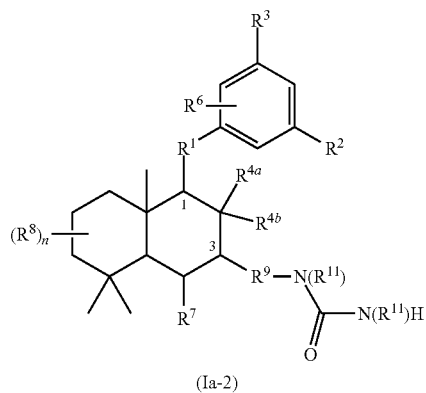

(Ia-2)

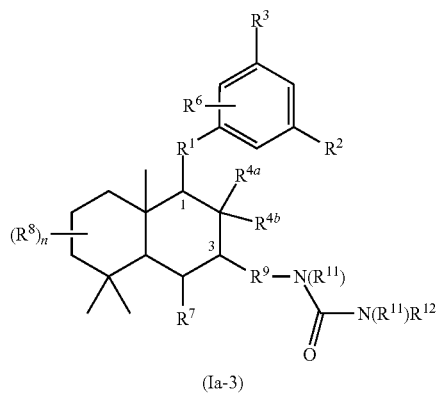

(Ia-3)

Compounds of formula (Ia-1) are compounds of formula (Ia) as described herein and are prepared by the methods described herein or by methods known to one skilled in the art. Compounds of formula (M) can be prepared by methods known to one skilled in the art. Compounds of formula (N) are commercially available or can be prepared by the methods known to one skilled in the art.

In general, compounds of formula (Ia-2) are prepared by reaction of the amine compound of formula (Ia-1) with the anhydride activated compound of formula (M) under standard conditions.

In general, compounds of formula (Ia-3) are prepared by reaction of the amine compound of formula (N) with carbonyl diimidazole under standard conditions, followed by reaction of the resulting intermediate with the amine compound of formula (Ia-1).

J. Preparation of Compounds of Formula (Ia3f)

Compounds of formula (Ia3f) are compounds of formula (Ia3), as described above in the Embodiments of the Invention where $R^5$ is $—R^9—N(R^{11})R^{12}$ (where $R^9$ is a direct bond and $R^{11}$ and $R^{12}$ are as described above in the Summary of the Invention for compounds of formula (I)), and are prepared as described below in Reaction Scheme 10 where $R^{23}$ is an acyl group such as acetyl, $R^5$ is hydrogen, each $R^{13}$ is hydrogen, $R^{9a}$ is straight or branched alkylene chain, and n, $R^2$, $R^3$, $R^6$, $R^7$, $R^8$ and $R^{9b}$ are as described above in the Summary of the Invention for compounds of formula (I):

REACTION SCHEME 10

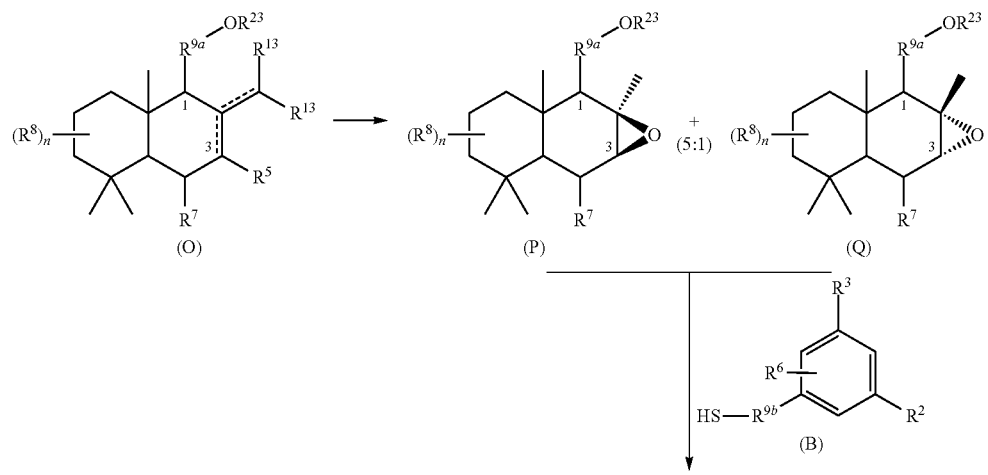

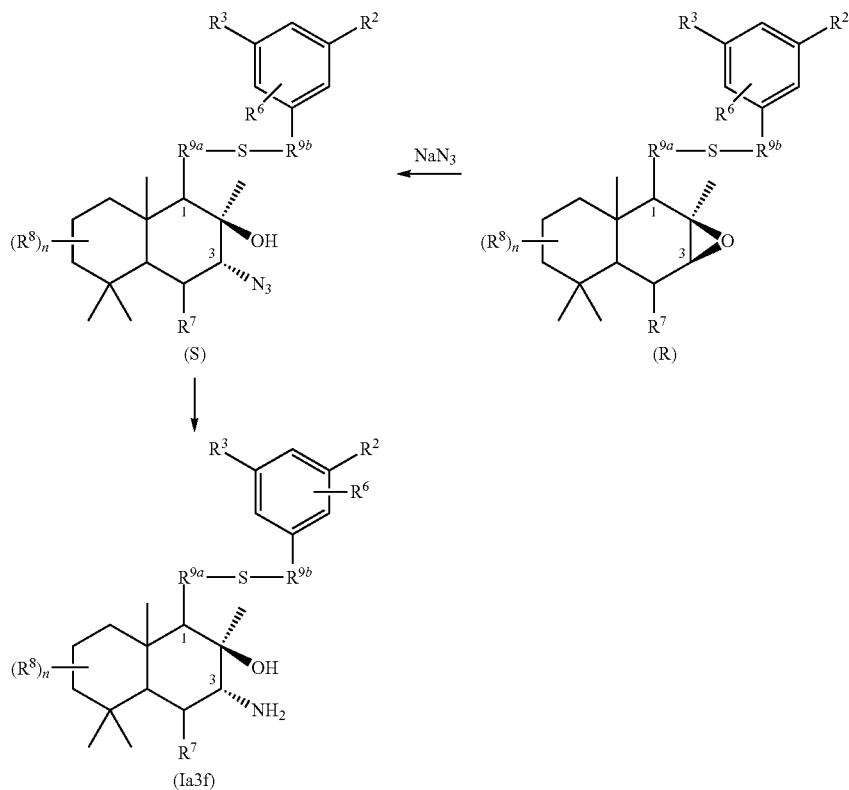

(Ia3f)

Compounds of formulae (O) and (B) may be prepared by methods disclosed herein or by methods known to one skilled in the art.

In general, compounds of formula (Ia3f) are prepared by the method shown above in Reaction Scheme 10 by first treating a compound of formula (O) (where ----- indicates an optional double bond), under standard epoxidation conditions, such as treatment with a suitable oxidizing agent in an aprotic solvent, to form a (5:1) mixture of a compound of formula (P) and a compound of formula (Q). Activation of the primary alcohol in the compounds of formulae (P) and (Q), for example by conversion to the mesylate using methods known in the art, and reaction of the activated compounds of formulae (P) and (Q) with the phenyl compound of formula (B) results in compound of formula (R). Treatment of the compound of formula (R) with sodium azide under standard conditions produces the compound of formula (S), which is then reduced under standard conditions to form the compound of formula (Ia3f). One skilled in the art will recognize that, instead of starting with a compound comprising the $R^6$, $R^7$ and/or $R^8$ moiety, the $R^6$, $R^7$ and/or $R^8$ moiety may be installed at a later point in the synthesis using methods analogous to those described herein. Furthermore, one skilled in the art will recognize that the compound of formula (Ia3f) may be further functionalized to produce compounds of formula (Ia3) wherein $R^5$ is —$R^9$—N($R^{11}$)C(O)$R^{12}$, —$R^9$—N($R^{11}$)—$R^{14}$—N($R^{11}$)$R^{12}$, —$R^9$—N($R^{11}$)C(O)—$R^9$—N($R^{11}$)$R^{12}$, —$R^9$—N($R^{11}$)C(O)N($R^{11}$)$R^{12}$, —$R^9$—N($R^{11}$)—OR$^{12}$, —$R^9$—N($R^{11}$)C(=NR$^{11}$)N($R^{11}$)$R^{12}$, —$R^9$—N($R^{11}$)S(O)$_p$$R^{11}$ (where p is 1 or 2), —$R^9$—N($R^{11}$)C(S)N($R^{11}$)$R^{12}$ or —$R^9$—N($R^{11}$)C(O)—$R^9$—N($R^{11}$)S(O)$_p$$R^{12}$ (where p is 1 or 2), where each $R^9$, $R^{11}$, $R^{12}$ and $R^{14}$ are as described above in the Summary of the Invention for compounds of formula (I). It is also understood that other compounds of formula (I) where $R^5$ is —$R^9$—N($R^{11}$)$R^{12}$ (where $R^9$ is a direct bond and $R^{11}$ and $R^{12}$ are as described above in the Summary of the Invention for compounds of formula (I)) may be prepared by this method utilizing the appropriate starting materials.

K. Preparation of Compounds of Formulae (Ia-4)

Compounds of formula (Ia-4) are compounds of formula (Ia), as described above in the Embodiments of the Invention where $R^{4a}$ and $R^{4b}$ together form =C($R^{13}$)$_2$ (where each $R^{13}$ is hydrogen), and are prepared as described below in Reaction Scheme 11 where n, $R^2$, $R^3$, $R^6$, $R^7$, $R^8$, $R^{9a}$ and $R^{9b}$ are as described above in the Summary of the Invention for compounds of formula (I):

REACTION SCHEME 11

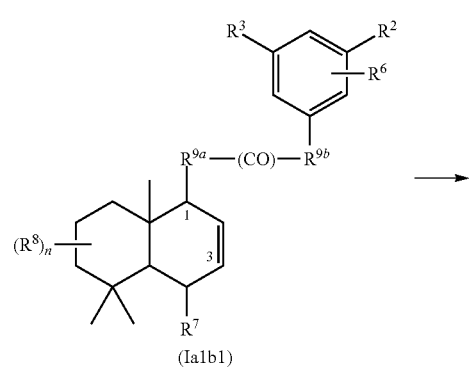

(Ia1b1)

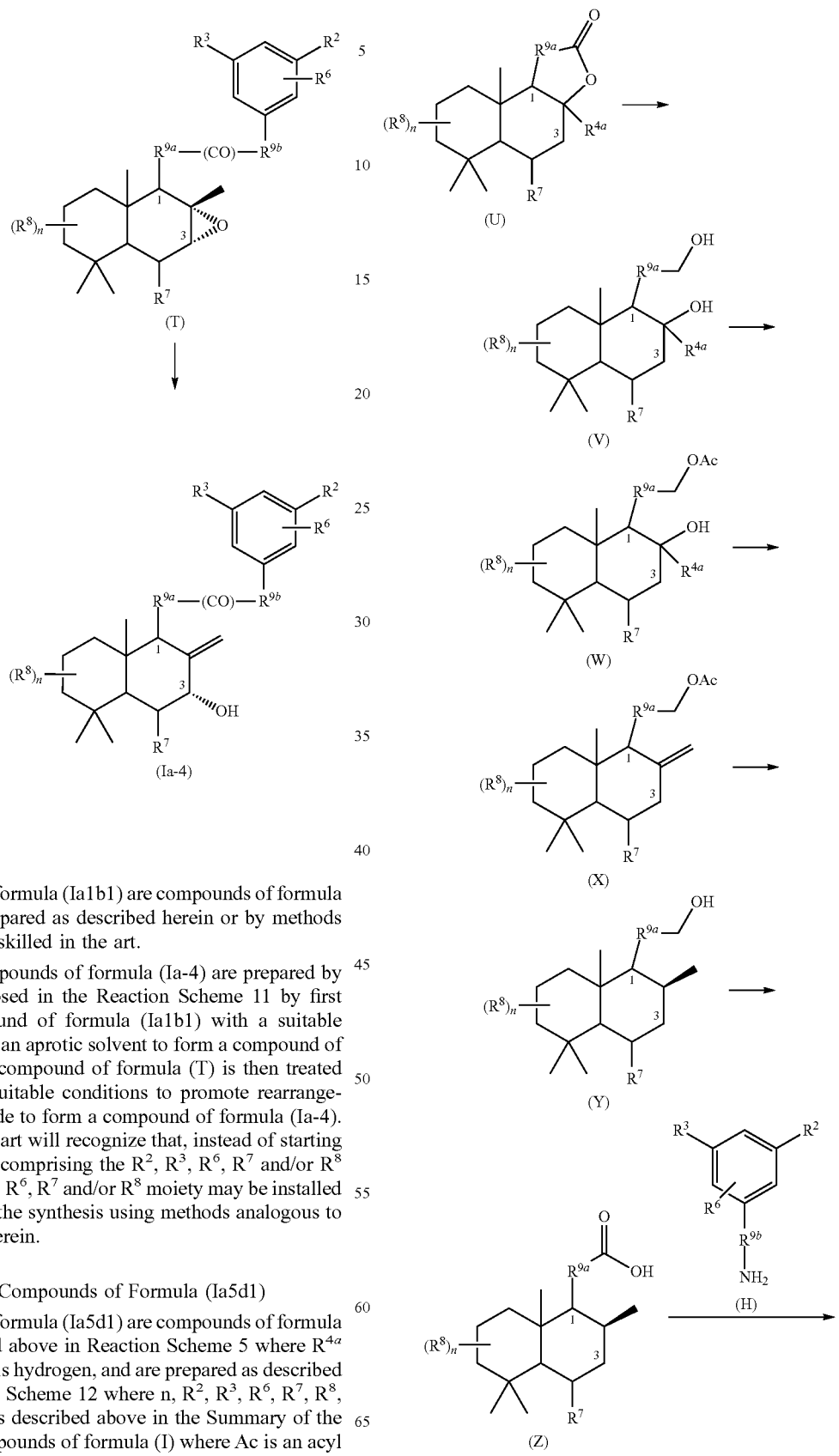

REACTION SCHEME 12

Compounds of formula (Ia1b1) are compounds of formula (Iab1) and are prepared as described herein or by methods described by one skilled in the art.

In general, compounds of formula (Ia-4) are prepared by the method disclosed in the Reaction Scheme 11 by first treating a compound of formula (Ia1b1) with a suitable oxidizing agent in an aprotic solvent to form a compound of formula (T). The compound of formula (T) is then treated with acid under suitable conditions to promote rearrangement of the epoxide to form a compound of formula (Ia-4). One skilled in the art will recognize that, instead of starting with a compound comprising the $R^2$, $R^3$, $R^6$, $R^7$ and/or $R^8$ moiety, the $R^2$, $R^3$, $R^6$, $R^7$ and/or $R^8$ moiety may be installed at a later point in the synthesis using methods analogous to those described herein.

L. Preparation of Compounds of Formula (Ia5d1)

Compounds of formula (Ia5d1) are compounds of formula (Ia5), as described above in Reaction Scheme 5 where $R^{4a}$ is methyl and $R^{4b}$ is hydrogen, and are prepared as described below in Reaction Scheme 12 where n, $R^2$, $R^3$, $R^6$, $R^7$, $R^8$, $R^{9a}$ and $R^{9b}$ are as described above in the Summary of the Invention for compounds of formula (I) where Ac is an acyl group, such as acetyl:

-continued

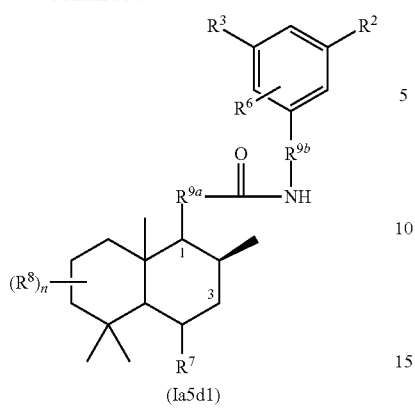
(Ia5d1)

Compounds of formulae (U) and (H) may be prepared by one skilled in the art by methods known to one skilled in the art or by methods disclosed herein.

In general, compound of formula (Ia5d1) are prepared by first treating a compound of formula (U) under standard reduction conditions to form a compound of formula (V). The primary hydroxyl in the compound of formula (V) is then protected, for example, with an acyl group, such as acetyl, under standard conditions to form the compound of formula (W). Dehydration of the tertiary alcohol in the compound of formula (W) affords the methylidene compound of formula (X). Reduction of the methylidene of the compound of formula (X) under standard hydrogenation conditions followed by removal of the hydroxyl protecting group affords a compound of formula (Y). Oxidation of the primary alcohol of the compound of formula (Y) under standard conditions yields the carboxylic acid compound of formula (Z). The compound of formula (Z) undergoes standard amide coupling with a compound of formula (H) to afford a compound of formula (Ia5d1).

M. Preparation of Compounds of Formulae (Ia2g1), (Ia2g2) and (Ia2g3)

Compounds of formulae (Ia2g1), (Ia2g2) and (Ia2g3) are compounds of formula (Ia2g), as described above in Reaction Scheme 2 where $R^5$ is hydrogen, and are prepared as described below in Reaction Scheme 13 where n, $R^2$, $R^3$, $R^6$, $R^7$, $R^8$, $R^{9a}$ and $R^{9b}$ are as described above in the Summary of the Invention for compounds of formula (I):

REACTION SCHEME 13

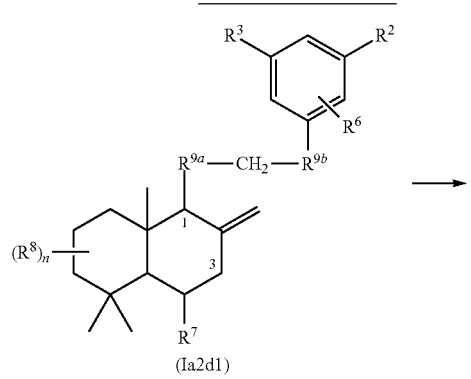
(Ia2d1)

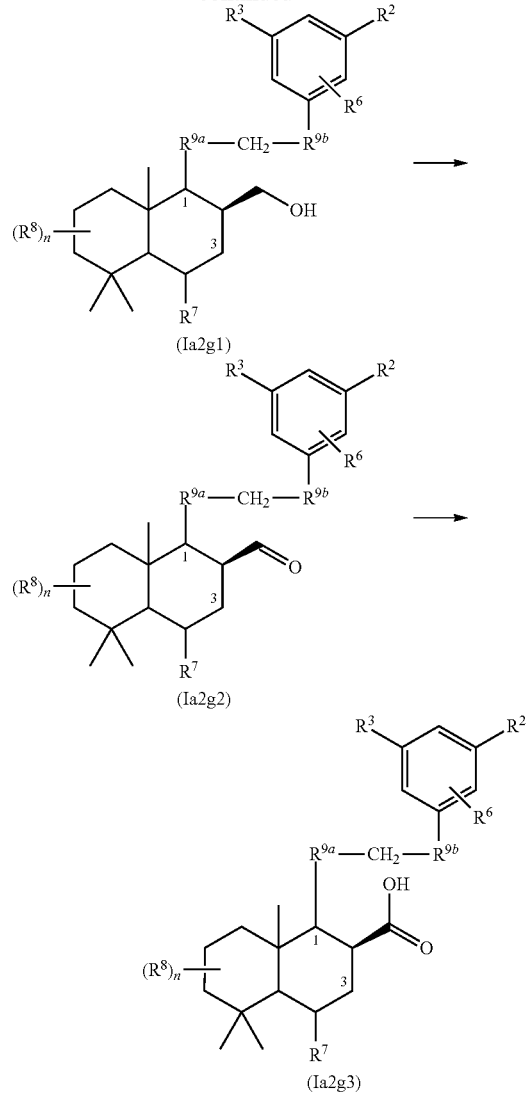

Compounds of formula (Ia2d1) are compounds of formula (Ia2d), as described above in Reaction Scheme 2 where each $R^{13}$ is hydrogen and $R^5$ is hydrogen, and may be prepared by methods disclosed herein or by methods known to one skilled in the art.

In general, compounds of formulae (Ia2g1), (Ia2g2) and (Ia2g3) are prepared by the method shown above in Reaction Scheme 13 by first treating a compound of formula (Ia2d1) under hydroboration conditions with oxidative work up. The resulting primary alcohol compound of formula (Ia2g1) can be selectively oxidized to the aldehyde compound of formula (Ia2g2) and can be further oxidized to the carboxylic acid compound of formula (Ia2g3).

N. Preparation of Compounds of Formula (I-1)

Compounds of formula (I-1) are compounds of formula (I), as described above in the Summary of the Invention where $R^1$ is —$R^{9a}$—N($R^{11a}$)C(O)—$R^{9b}$— (where $R^{11a}$ is hydrogen and $R^{9a}$ and $R^{9b}$ are as described above in the Summary of the Invention for compounds of formula (I)), and are prepared as described below in Reaction Scheme 14 where

, n, $R^7$, $R^8$, $R^{9a}$ and $R^{9b}$ are as described above in the Summary of the Invention for compounds of formula (I), $R^{4a}$ is methyl, $R^{24}$ is $R^{12}$, $-R^9-N(R^{11})R^{12}$, $-N(R^{11})-OR^{12}$, $-R^9-N(R^{11})S(O)_pR^{12}$ (where p is 1 or 2 and each $R^9$, $R^{11}$ and $R^{12}$ is as described above in the Summary of the Invention), $Pg^1$ is an oxygen protecting group, such as tert-butyldimethylphenylsilyl, and $Pg^2$ is a nitrogen protecting group, such as para-methoxybenzyl:

REACTION SCHEME 14

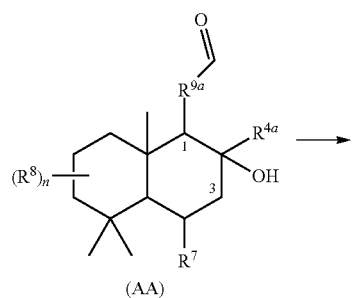
(AA)

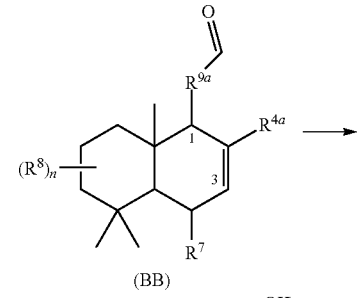
(BB)

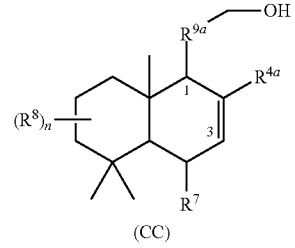
(CC)

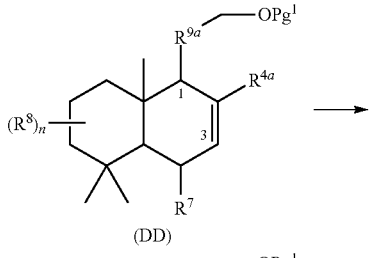
(DD)

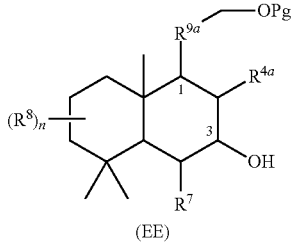
(EE)

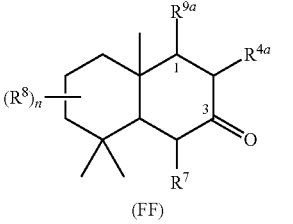
(FF)

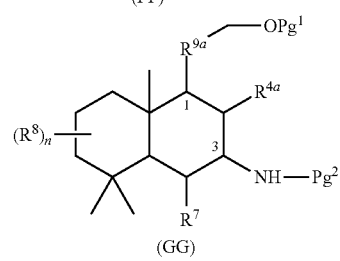
(GG)

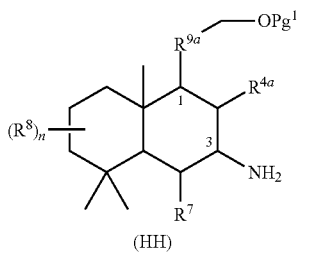
(HH)

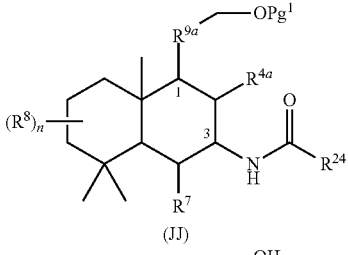
(JJ)

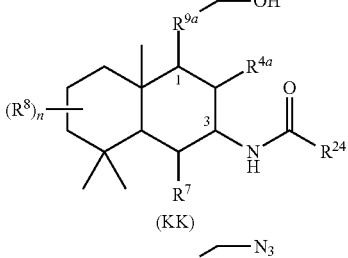
(KK)

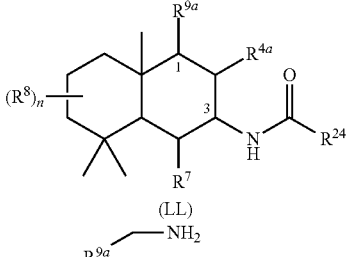
(LL)

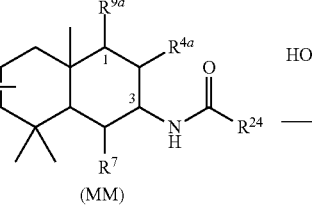
(MM)

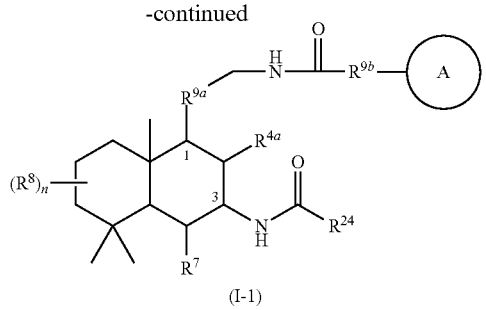

(I-1)

Compounds of formula (AA) may be prepared according to the methods disclosed in PCT Published Patent Application No. WO 2007/147251 or by methods known to one skilled in the art. Compounds of formula (II) and (NN) are commercially available or can be prepared by methods known to one skilled in the art or by methods disclosed herein.

In general, compounds of formula (I-1) are prepared by the method disclosed above in Reaction Scheme 14 by first treating a compound of formula (AA) under standard dehydration conditions, for example, Tin (IV) chloride, to afford a compound of formula (BB). Standard reduction of the aldehyde of the compound of formula (BB) affords a primary alcohol compound of formula (CC). The hydroxyl is protected under standard conditions to form a compound of formula (DD), then the double bond in the compound of formula (DD) is hydroborated with oxidative work up to give the secondary alcohol compound of formula (EE). The hydroxyl in the compound of formula (EE) is oxidized to the ketone compound of formula (FF), which undergoes reductive amination with a suitably protected amine to give a compound of formula (GG). The protecting group is removed from the amine to give a compound of formula (HH) which undergoes amide coupling chemistry with a carboxylic acid compound of formula (II) to afford an amide compound of formula (JJ). The hydroxyl protecting group is removed to give a compound of formula (KK). In addition to direct methods, the hydroxyl of the compound of formula (KK) is converted to an azide compound of formula (LL) by first activation of the hydroxyl by standard conditions, such as treatment with methanesulfonyl chloride, followed by treatment with sodium azide under standard conditions. Reduction of the azide of the compound of formula (LL), for example, using Staudinger conditions, affords a compound of formula (MM). Amide compounds of formula (I-1) are prepared by amide coupling chemistry between the amine compounds of the formula (MM) with carboxylic acid compounds of the formula (NN).

O. Preparation of Compounds of Formula (I-2)

Compounds of formula (I-2) are compounds of formula (I), as described above in the Summary of the Invention where $R^1$ is —$R^{9a}$—$C(R^{10})_2$—$R^{9b}$— (where $R^{9a}$ is as defined above in the Summary of the Invention for compounds of formula (I), each $R^{10}$ is hydrogen and $R^{9b}$ is a directed bond), and are prepared as described below in Reaction Scheme 15 where

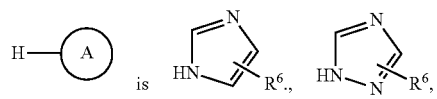

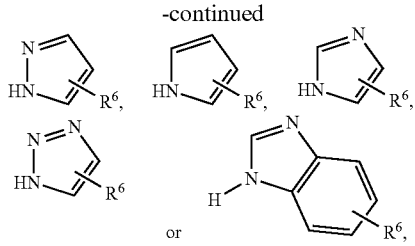

and n, $R^{4a}$, $R^7$, $R^8$ and $R^{9a}$ are as described above in the Summary of the Invention for compounds of formula (I), and $R^{24}$ is $R^{12}$, —$R^9$—N($R^{11}$)$R^{12}$, —N($R^{11}$)—O$R^{12}$, or —$R^9$—N($R^{11}$)S(O)$_p$$R^{12}$ (where p is 1 or 2 and each $R^9$, $R^{11}$ and $R^{12}$ is as described above in the Summary of the Invention):

REACTION SCHEME 15

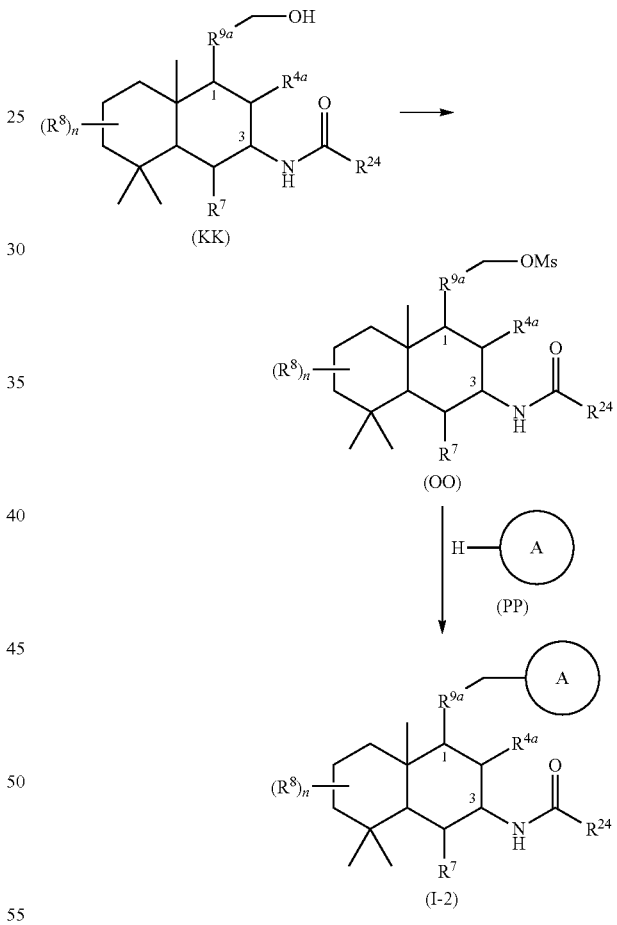

Compounds of formula (KK) may be prepared by methods known one skilled in the art or by methods described herein. Compounds of formula (PP) are commercially available.

In general, compounds of formula (I-2) are prepared by the method described above in Reaction Scheme 15 by first activating the hydroxyl of the compound of formula (KK) by treating the compound of formula (KK) with methanesulfonyl chloride (MsCl) under standard conditions to form the compound of formula (OO). The compound of formula (OO) is then treated with a compound of formula (PP) under nucleophilic displacement conditions in polar aprotic solvent to form a compound of formula (I-2). One skilled in the art will recognize that, instead of starting with a compound comprising the $R^7$ and/or $R^8$ moiety, the $R^7$ and/or $R^8$ moiety may be installed at a later point in the synthesis using methods analogous to those described herein.

P. Preparation of Compounds of Formula (I-3)

Compounds of formula (I-3) are compounds of formula (I), as described above in the Summary of the Invention where $R^1$ is $-R^{9a}-N(R^{11a})C(O)-R^{9b}-$ (where $R^{11a}$ is hydrogen and $R^{9a}$ and $R^{9b}$ are as described above in the Summary of the Invention for compounds of formula (I)), and are prepared as described below in Reaction Scheme 16 where

, n, $R^7$, $R^8$, $R^{9a}$ and $R^{9b}$ are as described above in the Summary of the Invention for compounds of formula (I), $R^{4a}$ is methyl, and $R^{24}$ is $R^{12}$, $-R^9-N(R^{11})R^{12}$, $-N(R^{11})-OR^{12}$, Or $-R^9-N(R^{11})S(O)_pR^{12}$ (where p is 1 or 2 and each $R^9$, $R^{11}$ and $R^{12}$ is as described above in the Summary of the Invention):

REACTION SCHEME 16

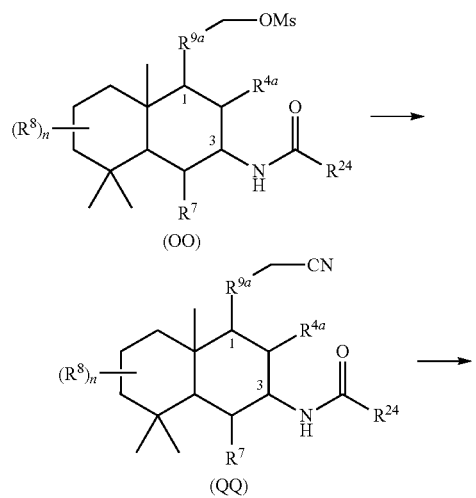

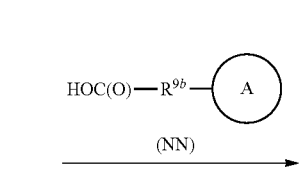

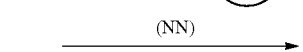

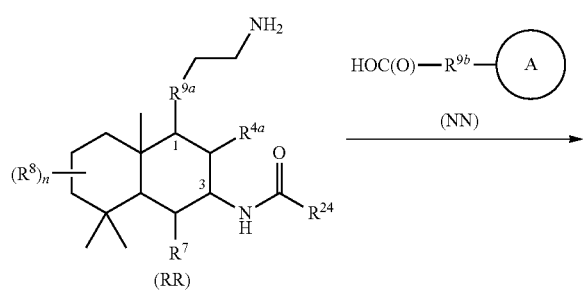

-continued

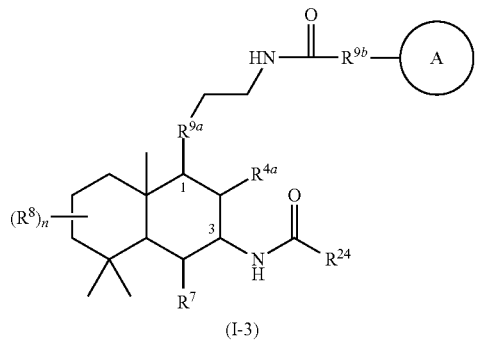

Compounds of formula (OO) may be prepared as described above in Reaction Scheme 16 or by methods known to one skilled in the art. Compounds of formula (NN) are commercially available or can be prepared by methods known to ones skilled in the art.

In general, compounds of formula (I-3) are prepared by the method disclosed above in Reaction Scheme 16 by first treating a compound of formula (OO) under nucleophilic displacement conditions with potassium cyanide in polar aprotic solvent to form a compound of formula (QQ), which is then reduced under standard reduction conditions to form the compound of formula (RR). The compound of formula (RR) is then treated with the compound of formula (NN) under standard amide coupling conditions to form the compound of formula (I-3). One skilled in the art will recognize that, instead of starting with a compound comprising the $R^7$ and/or $R^8$ moiety, the $R^7$ and/or $R^8$ moiety may be installed at a later point in the synthesis using methods analogous to those described herein.

Q. Preparation of Compounds of Formula (Ia7a)

Compounds of formula (Ia7a) are compounds of formula (Ia7), as described above in the Embodiments of the Invention, where $R^{9a}$ is methylene and n, $R^2$, $R^3$, $R^{4a}$, $R^{4b}$, $R^6$, $R^7$, $R^8$, $R^{9b}$ and $R^{11a}$ are as described above in the Embodiments of the Invention for compounds of formula (Ia7), and are prepared below in Reaction Scheme 17:

REACTION SCHEME 17

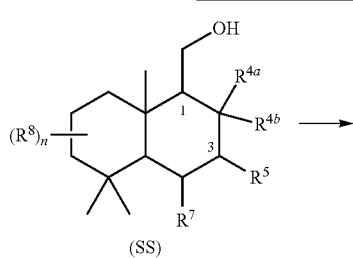

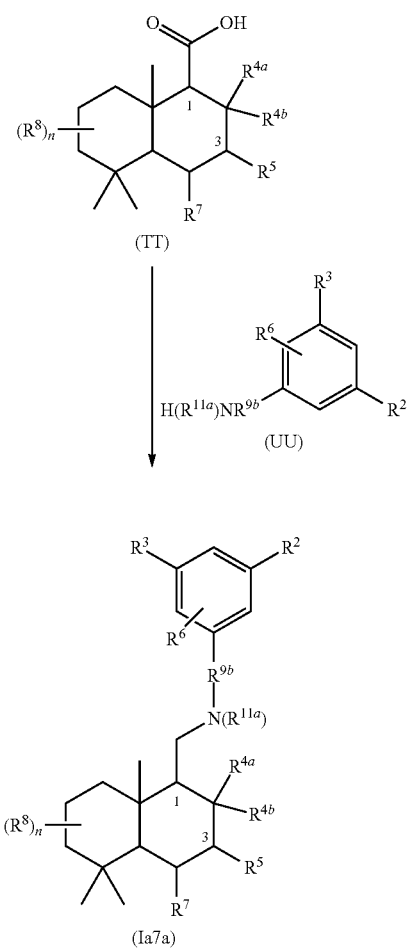

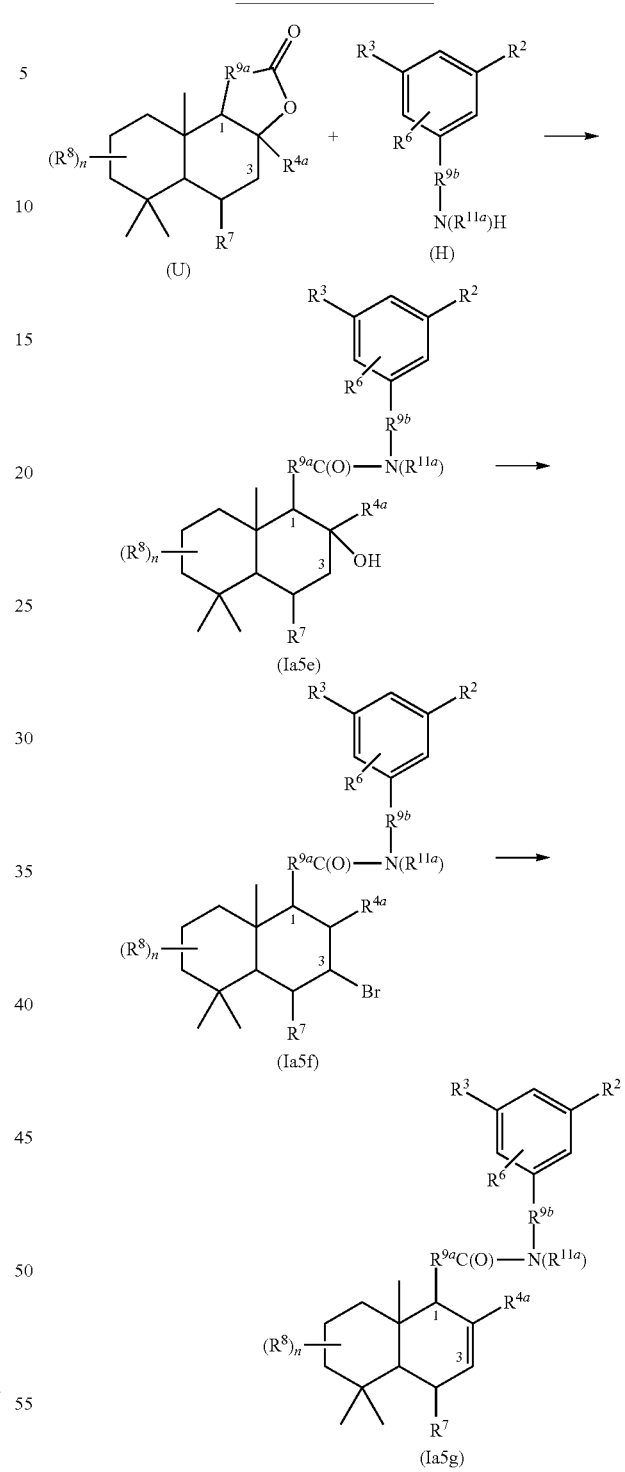

REACTION SCHEME 18

Compounds of formula (SS) and formula (UU) may be purchased or prepared by methods known in the art or by methods disclosed herein.

In general, compounds of formula (Ia7a) are prepared by first oxidizing a compound of formula (SS) with an appropriate reagent, for example, pyridinium chlorochromate, to form a compound of formula (TT). Treatment of the compound of formula (TT) with a compound of formula (UU) under standard reductive amination conditions results in a compound of formula (Ia7a). One skilled in the art will recognize that, instead of starting with a compound comprising the $R^2$, $R^3$, $R^5$, $R^6$, $R^7$ and $R^8$, the $R^2$, $R^3$, $R^5$, $R^6$, $R^7$ and $R^8$ moiety may be installed at a later point in the synthesis using methods analogous to those described herein.

R. Preparation of Compounds of Formulae (Ia5e), (Ia5f) and (Ia5g)

Compounds of formulae (Ia5e), (Ia5f) and (Ia5g) are compounds of formula (Ia5), as described above in the Embodiments of the Invention, where $R^{9a}$ is an alkylene chain and n, $R^2$, $R^3$, $R^{4a}$, $R^6$, $R^7$, $R^8$, $R^{9b}$ and $R^{11a}$ are as described above in the Embodiments of the Invention for compounds of formula (Ia5), and are prepared below in Reaction Scheme 18:

Compounds of formula (U) and formula (H) may be purchased or prepared by methods known in the art or by methods disclosed herein.

In general, compounds of formulae (Ia5e), (Ia5f) and (Ia5g) are prepared by utilizing organometallic methodologies by first treating a compound of formula (H) with an organometallic compound, such as trimethylaluminum and then treating the resulting product with a compound of formula (H) under suitable conditions to yield a compound of formula (Ia5e). The compound of formula (Ia5e) is then treated with a brominating agent to yield a compound of formula (Ia5f), which is then treated under standard elimination conditions to yield a compound of formula (Ia5g).

All of the compounds described herein as being prepared which may exist in free base or acid form may be converted to their pharmaceutically acceptable salts by treatment with the appropriate inorganic or organic base or acid. Salts of the compounds prepared below may be converted to their free base or acid form by standard techniques. Furthermore, all compounds of the invention which contain an acid or an ester group can be converted to the corresponding ester or acid, respectively, by methods known to one skilled in the art or by methods described herein.

Representative compounds of the invention which were prepared by the methods disclosed herein include (but are not limited to) the compounds listed below in Table 1.

TABLE 1

| Cpd. No. | Compound Name | Ex. # |
|---|---|---|
| 2 | (1R,2R,4aS,8aS)-1-[(3-methoxy-5-methylphenyl)carbonyl]-2,5,5,8a-tetramethyl-decahydronaphthalen-2-ol | 1 |
| 3 | [(1S,4aS,8aS)-2,5,5,8a-tetramethyl-1,4,4a,5,6,7,8,8a-octahydronaphthalen-1-yl](3-methoxy-5-methylphenyl)methanone | 2 |
| 4 | 3-{[(4aS,8aS)-2,5,5,8a-tetramethyl-1,4,4a,5,6,7,8,8a-octahydronaphthalen-1-yl]carbonyl}-5-methylphenol | 3 |
| 5 | 3-{[(4aS,8aS)-2,5,5,8a-tetramethyl-3,4,4a,5,6,7,8,8a-octahydronaphthalen-1-yl]carbonyl}-5-methylphenol | 3 |
| 6 | (2R,3R,4S,4aS,8aS)-4-[(3-methoxy-5-methylphenyl)carbonyl]-3,4a,8,8-tetramethyl-decahydronaphthalen-2-ol | 4 |
| 7 | (3R,4S,4aS,8aS)-4-[(3-methoxy-5-methylphenyl)carbonyl]-3,4a,8,8-tetramethyl-decahydronaphthalen-2-one | 5 |
| 8 | (3S,4S,4aS,8aS)-4-[(3-hydroxy-5-methylphenyl)carbonyl]-3,4a,8,8-tetramethyl-decahydronaphthalen-2-one | 6 |
| 9 | (2R,3R,4aS,8aS)-4-[(3-hydroxy-5-methylphenyl)carbonyl]-3,4a,8,8-tetramethyl-decahydronaphthalen-2-ol | 7 |
| 11 | (3S,4S,4aS,8aS)-N-(3-aminopropyl)-4-[(3-methoxy-5-methylphenyl)carbonyl]-3,4a,8,8-tetramethyl-decahydronaphthalen-2-amine dihydrochloride | 8 |
| 13 | (4aS,8aS)-8-[(3-methoxy-5-methylphenyl)methyl]-4,4,7,8a-tetramethyl-1,2,3,4,4a,5,6,8a-octahydronaphthalene | 9 |
| 14 | (4aS,5S,8aS)-5-[(3-methoxy-5-methylphenyl)methyl]-1,1,4a,6-tetramethyl-1,2,3,4,4a,5,8,8a-octahydronaphthalene | 9 |
| 15 | (4aS,5S,8aS)-5-[(3-methoxy-5-methylphenyl)methyl]-1,1,4a-trimethyl-6-methylidene-decahydronaphthalene | 9 |
| 16 | [(1S,2S,4aS,8aR)-1-[(3-methoxy-5-methylphenyl)methyl]-5,5,8a-trimethyl-decahydronaphthalen-2-yl]methanol | 10 |
| 17 | 3-{[(1S,2S,4aS,8aR)-2-(hydroxymethyl)-5,5,8a-trimethyl-decahydronaphthalen-1-yl]methyl}-5-methylphenol | 11 |
| 19 | (1S,2S,4aS,8aR)-1-[(3-methoxy-5-methylphenyl)methyl]-5,5,8a-trimethyl-decahydronaphthalene-2-carboxylic acid | 12 |
| 20 | (1S,2S,4aS,8aR)-1-[(3-hydroxy-5-methylphenyl)methyl]-5,5,8a-trimethyl-decahydronaphthalene-2-carboxylic acid | 13 |
| 22 | 3-{[(1S,4aS,8aS)-3-amino-2,5,5,8a-tetramethyl-decahydronaphthalen-1-yl]carbonyl}-5-methylphenol hydrochloride | 14 |
| 23 | (3S,4S,4aS,8aS)-4-[(3-hydroxy-5-methylphenyl)carbonyl]-3,4a,8,8-tetramethyl-decahydronaphthalen-2-ol | 15 |
| 27 | (1S,2R,4aS,8aS)-1-(3-methoxy-5-methylphenoxymethyl)-2,5,5,8a-tetramethyl-decahydronaphthalen-2-ol | 16 |
| 29 | 3-{[(1S,4aS,8aS)-2,5,5,8a-tetramethyl-1,4,4a,5,6,7,8,8a-octahydronaphthalen-1-yl]methoxy}-5-methylphenol | 17 |
| 30 | (4S,4aS,8aS)-4-(3-methoxy-5-methylphenoxymethyl)-3,4a,8,8-tetramethyl-decahydronaphthalen-2-ol | 18 |
| 33 | (1S,2R,4aS,8aS)-1-[3,5-bis(benzyloxy)-phenoxymethyl]-2,5,5,8a-tetramethyl-decahydronaphthalen-2-ol | 19 |
| 34 | (1S,2R,4aS,8aS)-1-(3,5-dimethoxyphenoxymethyl)-2,5,5,8a-tetramethyl-decahydronaphthalen-2-ol | 20 |
| 37 | (1S,2R,4aS,8aS)-1-[3,5-bis(propan-2-yloxy)phenoxymethyl]-2,5,5,8a-tetramethyl-decahydronaphthalen-2-ol | 21 |
| 38 | 5-{[(1S,2R,4aS,8aS)-2-hydroxy-2,5,5,8a-tetramethyl-decahydronaphthalen-1-yl]methoxy}benzene-1,3-diol | 22 |
| 41 | (4aS,8aS)-N-(3,5-dimethoxyphenyl)-2,5,5,8a-tetramethyl-3,4,4a,5,6,7,8,8a-octahydronaphthalene-1-carboxamide | 23 |
| 42 | (4aS,8aS)-N-(3-hydroxy-5-methoxyphenyl)-2,5,5,8a-tetramethyl-3,4,4a,5,6,7,8,8a-octahydronaphthalene-1-carboxamide | 24 |
| 43 | (4aS,8aS)-N-(3,5-dihydroxyphenyl)-2,5,5,8a-tetramethyl-3,4,4a,5,6,7,8,8a-octahydronaphthalene-1-carboxamide | 24 |
| 45 | 2-[(1R,2R,4aS,8aS)-2-hydroxy-2,5,5,8a-tetramethyl-decahydronaphthalen-1-yl]-1-(3,5-dimethoxyphenyl)ethan-1-one | 25 |
| 46 | 2-[(1S,2S,4aS,8aR)-2,5,5,8a-tetramethyl-decahydronaphthalen-1-yl]-1-(3,5-dimethoxyphenyl)ethan-1-one | 26 |
| 47 | 2-[(1S,2S,4aS,8aR)-2,5,5,8a-tetramethyl-decahydronaphthalen-1-yl]-1-(3-hydroxy-5-methoxyphenyl)ethan-1-one | 27 |
| 48 | 2-[(1S,2S,4aS,8aR)-2,5,5,8a-tetramethyl-decahydronaphthalen-1-yl]-1-(3,5-dihydroxyphenyl)ethan-1-one | 27 |
| 49 | (1S,2R,4aS,8aS)-1-[(3,5-dimethoxyphenyl)(hydroxy)methyl]-2,5,5,8a-tetramethyl-decahydronaphthalen-2-ol | 28 |
| 50 | (1R,2R,4aS,8aS)-1-[(3,5-dimethoxyphenyl)carbonyl]-2,5,5,8a-tetramethyl-decahydronaphthalen-2-ol | 29 |
| 51 | [(1S,4aS,8aS)-2,5,5,8a-tetramethyl-1,4,4a,5,6,7,8,8a-octahydronaphthalen-1-yl](3,5-dimethoxyphenyl)methanone | 30 |
| 52 | (2R,3R,4S,4aS,8aS)-4-[(3,5-dimethoxyphenyl)carbonyl]-3,4a,8,8-tetramethyl-decahydronaphthalen-2-ol | 31 |
| 53 | (3R,4S,4aS,8aS)-4-[(3,5-dimethoxyphenyl)carbonyl]-3,4a,8,8-tetramethyl-decahydronaphthalen-2-one | 32 |
| 54 | (2R,3S,4S,4aS,8aS)-4-[(3,5-dimethoxyphenyl)carbonyl]-N-[(4-methoxyphenyl)methyl]-3,4a,8,8-tetramethyl-decahydronaphthalen-2-amine | 33 |
| 55 | (2R,3S,4S,4aS,8aS)-4-[(3,5-dimethoxyphenyl)carbonyl]-3,4a,8,8-tetramethyl-decahydronaphthalen-2-amine | 34 |
| 56 | 5-{[(1S,2S,3R,4aS,8aS)-3-amino-2,5,5,8a-tetramethyl-decahydronaphthalen-1-yl]carbonyl}benzene-1,3-diol | 35 |
| 57 | N-[(2R,3S,4S,4aS,8aS)-4-[(3,5-dihydroxyphenyl)carbonyl]-3,4a,8,8-tetramethyl-decahydronaphthalen-2-yl]acetamide | 36 |
| 58 | 5-{2-[(1S,2S,4aS,8aR)-2,5,5,8a-tetramethyl-decahydronaphthalen-1-yl]-1-hydroxyethyl}benzene-1,3-diol | 37 |
| 59 | 2-[(1S,2S,4aS,8aR)-2,5,5,8a-tetramethyl-decahydronaphthalen-1-yl]-1-(3,5-dimethoxyphenyl)ethan-1-ol | 38 |
| 61 | (4aR,5S,6S,8aS)-5-[2-(3,5-dimethoxyphenyl)ethyl]-1,1,4a,6-tetramethyl-decahydronaphthalene | 39 |
| 62 | 5-{2-[(1S,2S,4aS,8aR)-2,5,5,8a-tetramethyl-decahydronaphthalen-1-yl]ethyl}benzene-1,3-diol | 40 |
| 63 | (4S,4aS,8aS)-4-[(3-methoxy-5-methylphenyl)carbonyl]-3,4a,8,8-tetramethyl-decahydronaphthalene-2-carbonitrile | 41 |
| 64 | (3S,4S,4aS,8aS)-4-[(3-methoxy-5-methylphenyl)carbonyl]-3,4a,8,8-tetramethyl-decahydronaphthalene-2-carboxamide | 42 |
| 65 | (3S,4S,4aS,8aS)-4-[(3-hydroxy-5-methylphenyl)carbonyl]-3,4a,8,8-tetramethyl-decahydronaphthalene-2-carboxamide | 43 |
| 67 | (3S,4S,4aS,8aS)-4-[(3-methoxy-5-methylphenyl)carbonyl]-3,4a,8,8-tetramethyl-decahydronaphthalene-2-carboxylic acid | 44 |
| 68 | (3S,4S,4aS,8aS)-4-[(3-hydroxy-5-methylphenyl)carbonyl]-3,4a,8,8-tetramethyl-decahydronaphthalene-2-carboxylic acid | 45 |

TABLE 1-continued

| Cpd. No. | Compound Name | Ex. # |
|---|---|---|
| 75 | (1R,2R,4aS,8aS)-1-{[(3-methoxy-5-methylphenyl)sulfanyl]methyl}-2,5,5,8a-tetramethyl-decahydronaphthalen-2-ol | 46 |
| 76 | (1R,2R,4aS,8aS)-1-{[(3-methoxyphenyl)sulfanyl]methyl}-2,5,5,8a-tetramethyl-decahydronaphthalen-2-ol | 47 |
| 80 | (1R,2R,4aS,8aS)-1-{[(3,5-dimethoxyphenyl)sulfanyl]methyl}-2,5,5,8a-tetramethyl-decahydronaphthalen-2-ol | 48 |
| 81 | N-[(2R,3S,4S,4aS,8aS)-4-[(3,5-dimethoxyphenyl)carbonyl]-3,4a,8,8-tetramethyl-decahydronaphthalen-2-yl]-4-methylbenzamide | 49 |
| 82 | N-[(2R,3S,4S,4aS,8aS)-4-[(3,5-dihydroxyphenyl)carbonyl]-3,4a,8,8-tetramethyl-decahydronaphthalen-2-yl]-4-methylbenzamide | 50 |
| 83 | N-[(2R,3S,4S,4aS,8aS)-4-[(3,5-dimethoxyphenyl)carbonyl]-3,4a,8,8-tetramethyl-decahydronaphthalen-2-yl]-3-methylbenzamide | 51 |
| 84 | N-[(2R,3S,4S,4aS,8aS)-4-[(3,5-dihydroxyphenyl)carbonyl]-3,4a,8,8-tetramethyl-decahydronaphthalen-2-yl]-3-methylbenzamide | 52 |
| 85 | N-[(2R,3S,4S,4aS,8aS)-4-[(3,5-dimethoxyphenyl)carbonyl]-3,4a,8,8-tetramethyl-decahydronaphthalen-2-yl]-2-methylbenzamide | 53 |
| 86 | N-[(2R,3S,4S,4aS,8aS)-4-[(3,5-dihydroxyphenyl)carbonyl]-3,4a,8,8-tetramethyl-decahydronaphthalen-2-yl]-2-methylbenzamide | 54 |
| 87 | N-[(2R,3S,4S,4aS,8aS)-4-[(3,5-dimethoxyphenyl)carbonyl]-3,4a,8,8-tetramethyl-decahydronaphthalen-2-yl]naphthalene-2-carboxamide | 55 |
| 88 | N-[(2R,3S,4S,4aS,8aS)-4-[(3,5-dihydroxyphenyl)carbonyl]-3,4a,8,8-tetramethyl-decahydronaphthalen-2-yl]naphthalene-2-carboxamide | 56 |
| 89 | N-[(3S,4S,4aS,8aS)-4-[(3,5-dihydroxyphenyl)carbonyl]-3,4a,8,8-tetramethyl-decahydronaphthalen-2-yl]pyrazine-2-carboxamide | 57 |
| 94 | 2-{[(3R,4S,4aS,8aS)-4-[(3,5-dimethoxyphenyl)carbonyl]-3,4a,8,8-tetramethyl-decahydronaphthalen-2-yl]carbonyl}pyridine | 58 |
| 95 | 5-{[(1S,2R,4aS,8aS)-2,5,5,8a-tetramethyl-3-[(pyridin-2-yl)carbonyl]-decahydronaphthalen-1-yl]carbonyl}benzene-1,3-diol | 59 |
| 102 | N-{[(2R,3R,4S,4aS,8aS)-4-[(3,5-dihydroxyphenyl)carbonyl]-3,4a,8,8-tetramethyl-decahydronaphthalen-2-yl]methyl}acetamide | 60 |
| 103 | N-{[(2S,3R,4S,4aS,8aS)-4-[(3,5-dihydroxyphenyl)carbonyl]-3,4a,8,8-tetramethyl-decahydronaphthalen-2-yl]methyl}acetamide | 61 |
| 109 | N-{[(2S,3R,4S,4aS,8aS)-4-[(3,5-dihydroxyphenyl)carbonyl]-3,4a,8,8-tetramethyl-decahydronaphthalen-2-yl]methyl}pyridine-3-carboxamide | 62 |
| 111 | N-{[(2S,3R,4S,4aS,8aS)-4-[(3,5-dihydroxyphenyl)carbonyl]-3,4a,8,8-tetramethyl-decahydronaphthalen-2-yl]methyl}benzamide | 63 |
| 113 | 5-{[(1S,2R,3S,4aS,8aS)-3-(1H-imidazol-1-ylmethyl)-2,5,5,8a-tetramethyl-decahydronaphthalen-1-yl]carbonyl}benzene-1,3-diol | 64 |
| 115 | 5-{[(1S,2R,3S,4aS,8aS)-2,5,5,8a-tetramethyl-3-(1H-1,2,4-triazol-1-ylmethyl)-decahydronaphthalen-1-yl]carbonyl}benzene-1,3-diol | 65 |
| 117 | 5-{[(1S,2R,3S,4aS,8aS)-2,5,5,8a-tetramethyl-3-[(4-methylpiperazin-1-yl)methyl]-decahydronaphthalen-1-yl]carbonyl}benzene-1,3-diol dihydrochloride salt | 66 |
| 118 | 3-[(2R,3S,4S,4aS,8aS)-4-[(3,5-dihydroxyphenyl)carbonyl]-3,4a,8,8-tetramethyl-decahydronaphthalen-2-yl]-1-(pyridin-3-yl)urea | 67 |
| 119 | 5-{[(1S,2S,3R,4aS,8aS)-3-[(1H-imidazol-5-ylmethyl)amino]-2,5,5,8a-tetramethyl-decahydronaphthalen-1-yl]carbonyl}benzene-1,3-diol | 68 |
| 120 | 1-[(2R,3S,4S,4aS,8aS)-4-[(3,5-dihydroxyphenyl)carbonyl]-3,4a,8,8-tetramethyl-decahydronaphthalen-2-yl]-3-ethylurea | 69 |
| 121 | 1-[(2R,3S,4S,4aS,8aS)-4-[(3,5-dihydroxyphenyl)carbonyl]-3,4a,8,8-tetramethyl-decahydronaphthalen-2-yl]-3-methoxyurea | 70 |
| 122 | N-[(2R,3S,4S,4aS,8aS)-4-[(3,5-dihydroxyphenyl)carbonyl]-3,4a,8,8-tetramethyl-decahydronaphthalen-2-yl]benzamide | 71 |
| 123 | N-[(2R,3S,4S,4aS,8aS)-4-[(3,5-dihydroxyphenyl)carbonyl]-3,4a,8,8-tetramethyl-decahydronaphthalen-2-yl]pyridine-3-carboxamide | 72 |
| 124 | 1-[(2R,3S,4S,4aS,8aS)-4-[(3,5-dihydroxyphenyl)carbonyl]-3,4a,8,8-tetramethyl-decahydronaphthalen-2-yl]-3-methylurea | 73 |
| 125 | 5-{[(1S,2S,3R,4aS,8aS)-2,5,5,8a-tetramethyl-3-[(1H-pyrrol-2-ylmethyl)amino]-decahydronaphthalen-1-yl]carbonyl}benzene-1,3-diol | 74 |
| 126 | 5-{[(1S,2S,3R,4aS,8aS)-2,5,5,8a-tetramethyl-3-[(pyridin-2-ylmethyl)amino]-decahydronaphthalen-1-yl]carbonyl}benzene-1,3-diol | 75 |
| 127 | 5-{[(1S,2S,3R,4aS,8aS)-2,5,5,8a-tetramethyl-3-[(pyridin-4-ylmethyl)amino]-decahydronaphthalen-1-yl]carbonyl}benzene-1,3-diol | 76 |
| 132 | (1R,2R,3R,4aS,8aS)-3-amino-1-{[(3,5-dimethoxyphenyl)sulfanyl]methyl}-2,5,5,8a-tetramethyl-decahydronaphthalen-2-ol | 77 |
| 133 | 5-{[(1S,2S,3R,4aS,8aS)-3-[(1H-Imidazol-2-ylmethyl)amino]-2,5,5,8a-tetramethyl-decahydronaphthalen-1-yl]carbonyl}benzene-1,3-diol | 78 |
| 135 | (2R,4S,4aS,8aS)-4-[(3-methoxy-5-methylphenyl)carbonyl]-3,4a,8,8-tetramethyl-decahydronaphthalen-2-amine | 79 |
| 136 | 3-{[(1S,2S,3R,4aS,8aS)-3-amino-2,5,5,8a-tetramethyl-decahydronaphthalen-1-yl]carbonyl}-5-methylphenol | 80 |
| 137 | 3-{[(1S,2S,3R,4aS,8aS)-3-[(1H-imidazol-5-ylmethyl)amino]-2,5,5,8a-tetramethyl-decahydronaphthalen-1-yl]carbonyl}-5-methylphenol | 81 |
| 138 | 3-[(2R,3S,4S,4aS,8aS)-4-[(3-hydroxy-5-methylphenyl)carbonyl]-3,4a,8,8-tetramethyl-decahydronaphthalen-2-yl]-1-(pyridin-3-yl)urea | 82 |
| 139 | N-[(2R,3S,4S,4aS,8aS)-4-[(3-hydroxy-5-methylphenyl)carbonyl]-3,4a,8,8-tetramethyl-decahydronaphthalen-2-yl]acetamide | 83 |
| 141 | (2R,4R,4aS,8aS)-4-[(3,5-dimethoxyphenyl)carbonyl]-4a,8,8-trimethyl-3-methylidene-decahydronaphthalen-2-ol | 84 |
| 142 | (2R,4aS,8aS)-4-[(3,5-dimethoxyphenyl)carbonyl]-3,4a,8,8-tetramethyl-1,2,4a,5,6,7,8,8a-octahydronaphthalen-2-ol | 85 |
| 149 | 2-[(1S,2S,4aS,8aR)-2,5,5,8a-tetramethyl-decahydronaphthalen-1-yl]-N-(3,5-dihydroxyphenyl)acetamide | 86 |
| 157 | (1S,2S,4aS,8aR)-1-[(3,5-dihydroxyphenyl)methyl]-5,5,8a-trimethyl-decahydronaphthalene-2-carboxylic acid | 87 |
| 158 | N-[(2R,3S,4S,4aS,8aS)-4-[(3,5-dihydroxyphenyl)carbonyl]-3,4a,8,8-tetramethyl-decahydronaphthalen-2-yl]pyridine-2-carboxamide | 88 |
| 159 | N-[(2R,3S,4S,4aS,8aS)-4-[(3,5-dihydroxyphenyl)carbonyl]-3,4a,8,8-tetramethyl-decahydronaphthalen-2-yl]pyridine-4-carboxamide | 89 |
| 160 | 3-{[(2R,3S,4S,4aS,8aS)-4-[(3,5-dihydroxyphenyl)carbonyl]-3,4a,8,8-tetramethyl-decahydronaphthalen-2-yl]carbamoyl}pyridin-1-ium-1-olate | 90 |
| 163 | N-[(2R,3S,4S,4aS,8aS)-4-[(3,5-dihydroxyphenyl)carbonyl]-3,4a,8,8-tetramethyl-decahydronaphthalen-2-yl]-4-methylpiperazine-1-carboxamide | 91 |
| 165 | N-[(2R,3S,4S,4aS,8aS)-4-[(3,5-dihydroxyphenyl)carbonyl]-3,4a,8,8-tetramethyl-decahydronaphthalen-2-yl]-3-aminopropanamide | 92 |
| 167 | N-[(2R,3S,4S,4aS,8aS)-4-[(3,5-dihydroxyphenyl)carbonyl]-3,4a,8,8-tetramethyl-decahydronaphthalen-2-yl]piperidine-4-carboxamide | 93 |
| 168 | N-[(2R,3S,4S,4aS,8aS)-4-[(3,5-dimethoxyphenyl)carbonyl]-3,4a,8,8-tetramethyl-decahydronaphthalen-2-yl]pyridine-3-carboxamide | 94 |
| 170 | 5-{[(1S,2S,3R,4aS,8aS)-3-[(3-aminopropyl)amino]-2,5,5,8a-tetramethyl-decahydronaphthalen-1-yl]carbonyl}benzene-1,3-diol dihydrochloride | 95 |
| 171 | N-[(2R,3S,4S,4aS,8aS)-4-[(3,5-dihydroxyphenyl)carbonyl]-3,4a,8,8-tetramethyl-decahydronaphthalen-2-yl]-6-aminopyridine-3-carboxamide | 96 |
| 173 | (4S,4aS,8aS)-4-{[(3,5-dimethoxybenzene)sulfonyl]methyl}-3,4a,8,8-tetramethyl-decahydronaphthalen-2-ol | 97 |

TABLE 1-continued

| Cpd. No. | Compound Name | Ex. # |
|---|---|---|
| 175 | 1-[(2R,3S,4S,4aS,8aS)-4-[(3-hydroxy-5-methylphenyl)carbonyl]-3,4a,8,8-tetramethyl-decahydronaphthalen-2-yl]guanidine | 98 |
| 176 | N-[(2R,3S,4S,4aS,8aS)-4-[(3-hydroxy-5-methylphenyl)carbonyl]-3,4a,8,8-tetramethyl-decahydronaphthalen-2-yl]methanesulfonamide | 99 |
| 178 | 1-[(2R,3S,4S,4aS,8aS)-4-[(3,5-dihydroxyphenyl)carbonyl]-3,4a,8,8-tetramethyl-decahydronaphthalen-2-yl]guanidine | 100 |
| 179 | N-[(2R,3S,4S,4aS,8aS)-4-[(3,5-dihydroxyphenyl)carbonyl]-3,4a,8,8-tetramethyl-decahydronaphthalen-2-yl]methanesulfonamide | 101 |
| 180 | 1-[(2R,3S,4S,4aS,8aS)-4-[(3,5-dihydroxyphenyl)carbonyl]-3,4a,8,8-tetramethyl-decahydronaphthalen-2-yl]-3-methylthiourea | 102 |
| 181 | 2-[({[(2R,3S,4S,4aS,8aS)-4-[(3,5-dihydroxyphenyl)carbonyl]-3,4a,8,8-tetramethyl-decahydronaphthalen-2-yl]carbamoyl}methyl)sulfamoyl]benzoic acid | 103 |
| 196 | N-((2R,3S,4S,4aS)-3,4a,8,8-tetramethyl-4-((4-(trifluoromethyl)benzamido)methyl)-decahydronaphthalen-2-yl)nicotinamide | 104 |
| 197 | N-((2R,3S,4S,4aS)-4-((furan-2-carboxamido)methyl)-3,4a,8,8-tetramethyldecahydronaphthalen-2-yl)nicotinamide | 105 |
| 198 | N-((2R,3S,4S,4aS)-4-(isonicotinamidomethyl)-3,4a,8,8-tetramethyldecahydronaphthalen-2-yl)nicotinamide | 106 |
| 199 | N-(((1S,2S,3R,8aS)-2,5,5,8a-tetramethyl-3-(nicotinamido)decahydronaphthalen-1-yl)methyl)nicotinamide | 107 |
| 200 | N-((2R,3S,4S,4aS)-4-((1H-imidazol-1-yl)methyl)-3,4a,8,8-tetramethyldecahydronaphthalen-2-yl)nicotinamide | 108 |
| 201 | N-((2R,3S,4S,4aS)-4-((1H-1,2,4-triazol-1-yl)methyl)-3,4a,8,8-tetramethyldecahydronaphthalen-2-yl)nicotinamide | 109 |
| 202 | N-((2R,3S,4S,4aS)-4-((1H-benzo[d]imidazol-1-yl)methyl)-3,4a,8,8-tetramethyldecahydronaphthalen-2-yl)nicotinamide | 110 |
| 208 | 4-methyl-N-((2R,3S,4S,4aS)-3,4a,8,8-tetramethyl-4-((4-(trifluoromethyl)benzamido)methyl)-decahydronaphthalen-2-yl)piperazine-1-carboxamide | 111 |
| 209 | N-((2R,3S,4S,4aS)-4-((4-fluorobenzamido)methyl)-3,4a,8,8-tetramethyldecahydronaphthalen-2-yl)-4-methylpiperazine-1-carboxamide | 112 |
| 210 | N-((2R,3S,4S,4aS)-4-(isonicotinamidomethyl)-3,4a,8,8-tetramethyldecahydronaphthalen-2-yl)-4-methylpiperazine-1-carboxamide | 113 |
| 211 | 4-methyl-N-((2R,3S,4S,4aS)-3,4a,8,8-tetramethyl-4-(nicotinamidomethyl)decahydronaphthalen-2-yl)piperazine-1-carboxamide | 114 |
| 212 | N-((2R,3S,4S,4aS)-4-((furan-2-carboxamido)methyl)-3,4a,8,8-tetramethyldecahydronaphthalen-2-yl)-4-methylpiperazine-1-carboxamide | 115 |
| 215 | 4-methyl-N-((2R,3S,4S,4aR)-3,4a,8,8-tetramethyl-4-(2-(4-(trifluoromethyl)benzamido)ethyl)-decahydronaphthalen-2-yl)piperazine-1-carboxamide | 116 |
| 216 | N-((2R,3S,4S,4aR)-4-(2-(4-fluorobenzamido)ethyl)-3,4a,8,8-tetramethyldecahydronaphthalen-2-yl)-4-methylpiperazine-1-carboxamide | 117 |
| 217 | N-((2R,3S,4S,4aR)-4-(2-(furan-2-carboxamido)ethyl)-3,4a,8,8-tetramethyldecahydronaphthalen-2-yl)-4-methylpiperazine-1-carboxamide | 118 |
| 218 | 4-methyl-N-((2R,3S,4S,4aR)-3,4a,8,8-tetramethyl-4-(2-(nicotinamido)ethyl)decahydronaphthalen-2-yl)piperazine-1-carboxamide | 119 |
| 220 | 3-{[(1S,4aS,8aS)-2,5,5,8a-tetramethyl-1,4,4a,5,6,7,8,8a-octahydronaphthalen-1-yl]methoxy}-5-methoxyphenol. | 120 |
| 223 | (2R,4aS,8aS)-1-{[(3-hydroxy-5-methoxyphenyl)amino]methyl}-2,5,5,8a-tetramethyl-decahydronaphthalen-2-ol | 121 |
| 225 | 2-[(1S,2R,3R,4aS,8aR)-3-bromo-2,5,5,8a-tetramethyl-decahydro-naphthalen-1-yl]-N-(3,5-dihydroxyphenyl)-N-methylacetamide | 122 |
| 226 | 2-[(1S,4aS,8aS)-2,5,5,8a-tetramethyl-1,4,4a,5,6,7,8,8a-octahydronaphthalen-1-yl]-N-(3,5-dihydroxyphenyl)-N-methylacetamide | 122 |

The following Examples are provided for purposes of illustration, not limitation. In summary, the following Examples disclose the synthesis of representative compounds of this invention and compounds used in the preparation of compounds of the invention, as well as representative assays for the same.

EXAMPLE 1

Synthesis of (1R,2R,4aS,8aS)-1-[(3-methoxy-5-methylphenyl)carbonyl]-2,5,5,8a-tetramethyl-decahydronaphthalen-2-ol (Compound No. 2)

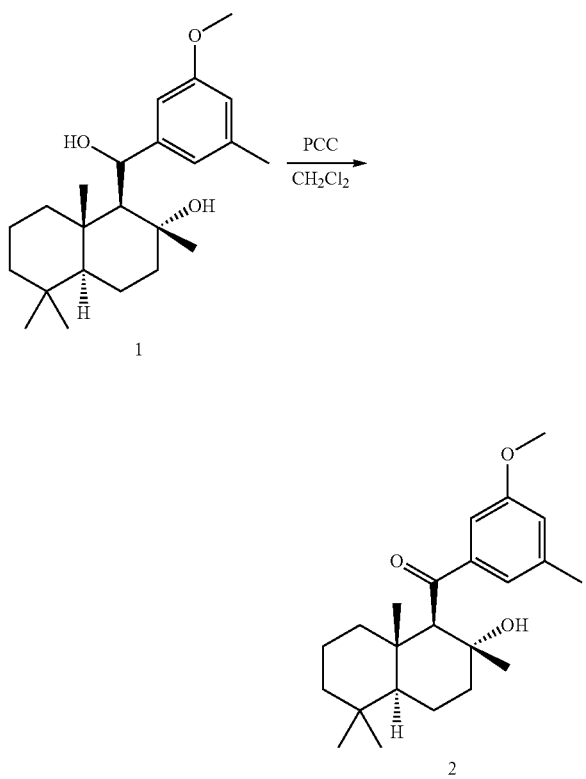

To a solution of (1S,2R,4aS,8aS)-1-[hydroxy(3-methoxy-5-methylphenyl)methyl]-2,5,5,8a-tetramethyl-decahydronaphthalen-2-ol (Compound No. 1, prepared according to Andersen, R. et al. PCT Int. Patent Appl. WO 2007/147251 A1, 5.00 g, 13.9 mmol) in CH$_2$Cl$_2$ (50 mL) under argon was added pyridinium chlorochromate (PCC) (3.32 g, 15.4 mmol) as a solid in one portion and the mixture stirred at room temperature for 1.5 h. The reaction was concentrated to ~10-15 mL and filtered through a pad of Celite and silica gel, washing with Et$_2$O (500 mL). The filtrate was concentrated and purified by column chromatography through a plug of silica gel (Et$_2$O) to afford (1R,2R,4aS,8aS)-1-[(3-methoxy-5-methylphenyl)carbonyl]-2,5,5,8a-tetramethyl-decahydronaphthalen-2-ol (Compound No. 2, 4.44 g, 88%) as a yellow foam. $^1$H NMR (CDCl$_3$): δ7.40 (s, 1H), 7.31 (s, 1H), 6.88 (s, 1H), 3.83 (s, 3H), 3.56 (s, 1H), 2.39 (s, 3H), 1.88 (dt, J=12, 3.6 Hz, 1H), 1.79-0.96 (m, 17H), 0.90 (s, 3H), 0.83 (s, 3H).

EXAMPLE 2

Synthesis of [(1S,4aS,8aS)-2,5,5,8a-tetramethyl-1,4,4a,5,6,7,8,8a-octahydronaphthalen-1-yl](3-methoxy-5-methylphenyl)methanone (Compound No. 3)

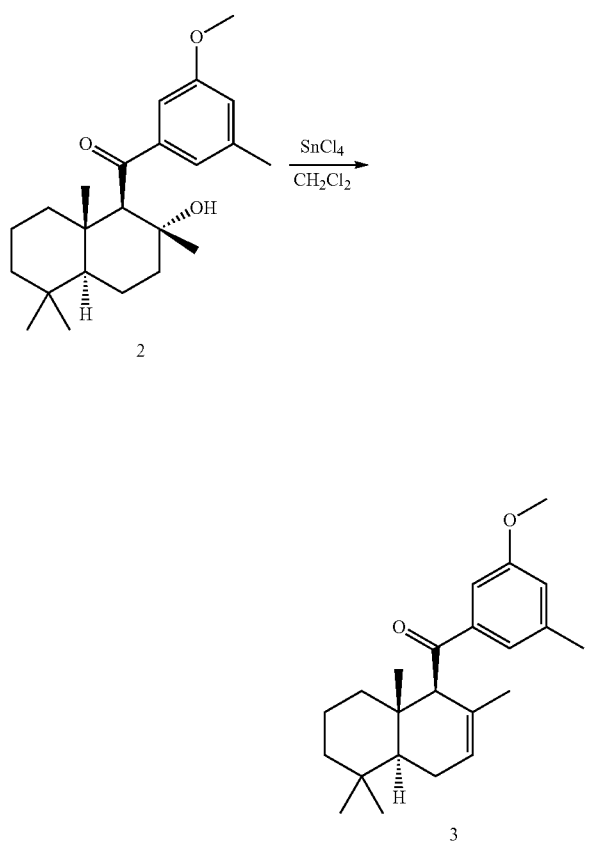

To a solution of (1R,2R,4aS,8aS)-1-[(3-methoxy-5-methylphenyl)-carbonyl]-2,5,5,8a-tetramethyl-decahydronaphthalen-2-ol (Compound No. 2, 0.49 g, 1.37 mmol) in $CH_2Cl_2$ (20 mL) at 0° C. under argon was added $SnCl_4$ (0.48 mL, 4.1 mmol) and the reaction stirred at 0° C. for 10 min. The mixture was warmed to room temperature and diluted with $CH_2Cl_2$ (40 mL) and water (30 mL). The aqueous layer was extracted with $CH_2Cl_2$ (2×20 mL) and the combined organic extracts washed with saturated aqueous $NaHCO_3$ (1×40 mL), dried ($Na_2SO_4$) and concentrated. The resulting crude brown oil was purified by column chromatography on silica gel (hexanes/EtOAc, 9:1) to give [(1S,4aS,8aS)-2,5,5,8a-tetramethyl-1,4,4a,5,6,7,8,8a-octahydronaphthalen-1-yl](3-methoxy-5-methylphenyl)methanone (Compound No. 3, 0.35 g, 75%) as a clear oil. $^1$H NMR ($CDCl_3$): δ7.33 (s, 1H), 7.24 (m, 1H), 6.91 (m, 1H), 5.61 (m, 1H), 4.12 (m, 1H), 3.85 (s, 3H), 2.40 (s, 3H), 2.12-1.92 (m, 2H), 1.55-1.37 (m, 6H), 1.30-1.14 (m, 4H), 0.96 (s, 3H), 0.91 (s, 3H), 0.90 (s, 3H).

EXAMPLE 3

Synthesis of 3-{[(4aS,8aS)-2,5,5,8a-tetramethyl-1,4,4a,5,6,7,8,8a-octahydronaphthalen-1-yl]carbonyl}-5-methylphenol (Compound No. 4) and 3-{[(4aS,8aS)-2,5,5,8a-tetramethyl-3,4,4a,5,6,7,8,8a-octahydronaphthalen-1-yl]carbonyl}-5-methylphenol (Compound No. 5)

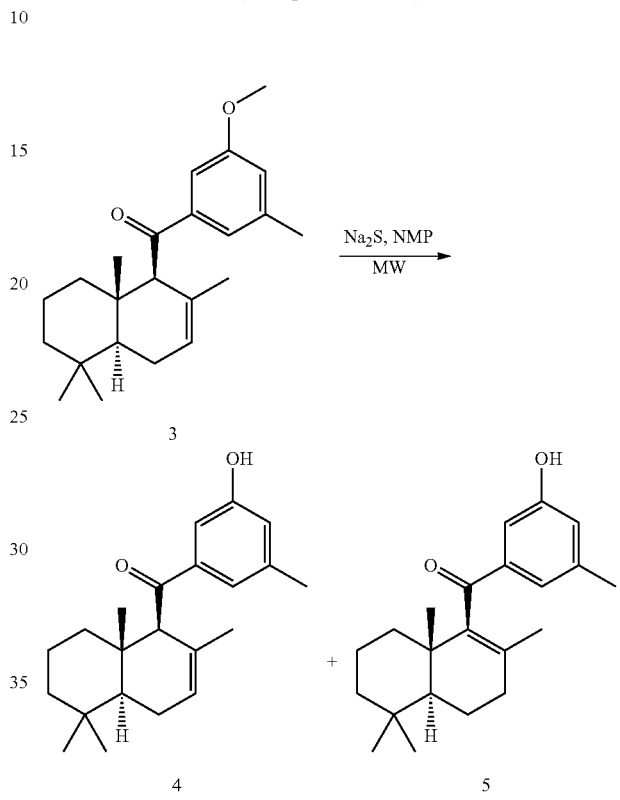

To a microwave (MW) vessel (2-5 mL) was added $Na_2S$ (109 mg, 1.40 mmol) and a solution of [(1S,4aS,8aS)-2,5,5,8a-tetramethyl-1,4,4a,5,6,7,8,8a-octahydronaphthalen-1-yl](3-methoxy-5-methylphenyl)methanone (Compound No. 3, 98 mg, 0.29 mmol) in NMP (1.5 mL). The reaction vessel was sealed and placed in a Biotage Microwave Initiator reactor and irradiated at 180° C. for 30 min. The reaction mixture was allowed to cool to room temperature and then quenched with 10% aqueous HCl (5 mL) and diluted with EtOAc (20 mL). The organic layer was washed with brine (3×10 mL), dried ($Na_2SO_4$) and concentrated. The crude product was purified by flash chromatography on silica gel (hexanes/EtOAc, 85:15) to afford a mixture of 3-{[(4aS,8aS)-2,5,5,8a-tetramethyl-1,4,4a,5,6,7,8,8a-octahydronaphthalen-1-yl]carbonyl}-5-methylphenol and 3-{[(4aS,8aS)-2,5,5,8a-tetramethyl-3,4,4a,5,6,7,8,8a-octahydronaphthalen-1-yl]carbonyl}-5-methylphenol (Compound No. 4 and Compound No. 5 respectively, 71 mg, 78%) as a white foam. $^1$H NMR ($CDCl_3$): δ7.40-7.20 (m, total 3H), 6.93-6.86 (m, total 1H), 5.72-5.61 (m, total 1H), 2.38-2.35 (m, total 3H), 2.17-1.52 (m, total 3H), 1.40-1.08 (m, 12H), 0.95-0.86 (m, total 7H). ES-MS m/z 327 ([M+1]$^+$).

EXAMPLE 4

Synthesis of (2R,3R,4S,4aS,8aS)-4-[(3-methoxy-5-methylphenyl)carbonyl]-3,4a,8,8-tetramethyl-decahydronaphthalen-2-ol (Compound No. 6)

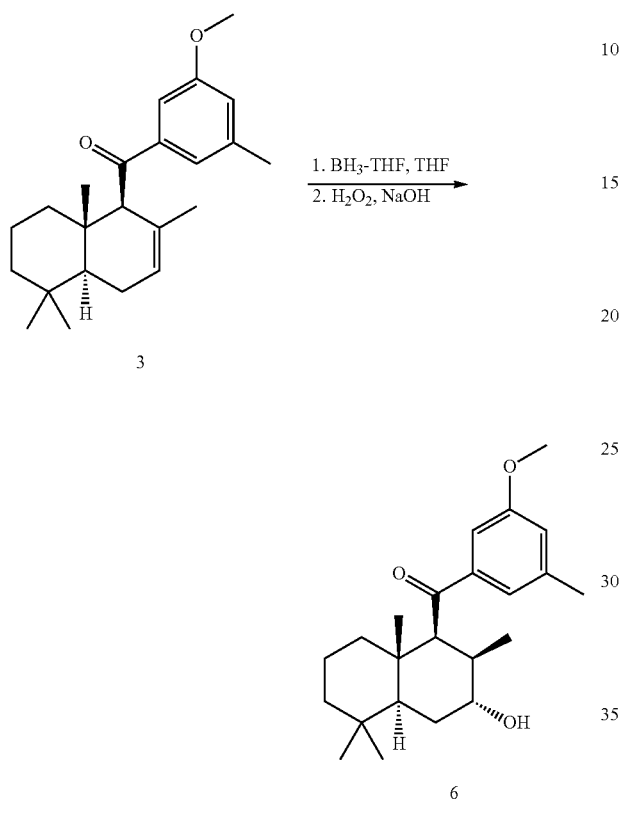

To a solution of [(1S,4as,8aS)-2,5,5,8a-tetramethyl-1,4,4a,5,6,7,8,8a-octahydronaphthalen-1-yl](3-methoxy-5-methylphenyl)methanone (Compound No. 3, 2.26 g, 6.65 mmol) in anhydrous THF (70 mL) at 0° C. under argon was added a solution of $BH_3$-THF (1.0 M in THF, 10.0 mL, 10.0 mmol) and the reaction stirred at 0° C. for 1.5 h before warming to room temperature and stirring for another 30 min. The reaction was then quenched carefully at 0° C. with MeOH (2 mL), 15% aqueous NaOH (2 mL) and 50% aqueous $H_2O_2$ (2 mL) and stirred at room temperature for 30 min. The mixture was diluted with EtOAc (50 mL), water (40 mL) and saturated aqueous sodium thiosulfate (30 mL) and stirred for another 15 min. The layers were separated and the organic layer washed with brine (1×40 mL). The combined aqueous layers were extracted with EtOAc (1×30 mL) and the organic extracts dried ($Na_2SO_4$) and concentrated to afford a white foam (2.50 g). The crude product was purified by column chromatography on silica gel (hexanes/EtOAc, 3:1) to give (2R,3R,4S,4aS,8aS)-4-[(3-methoxy-5-methyl phenyl)carbonyl]-3,4a,8,8-tetramethyl-decahydronaphthalen-2-ol (Compound No. 6, 1.60 g, 67%) as a white solid. $^1$H NMR ($CDCl_3$): δ7.32 (s, 1H), 7.26-7.24 (m, 1H), 6.90-6.87 (m, 1H), 3.96 (q, J=2.1 Hz, 1H), 3.82 (s, 3H), 3.72 (d, J=4.5 Hz, 1H), 2.37 (s, 3H), 2.16-2.06 (m, 1H), 1.85-1.52 (m, 7H), 1.46-1.18 (m, 3H), 1.36 (s, 3H), 0.99 (d, J=8.1 Hz, 3H), 0.89 (s, 3H), 0.86 (s, 3H). ES-MS m/z 359 ([M+1]$^+$).

EXAMPLE 5

Synthesis of (3R,4S,4aS,8aS)-4-[(3-methoxy-5-methylphenyl)carbonyl]-3,4a,8,8-tetramethyl-decahydronaphthalen-2-one (Compound No. 7)

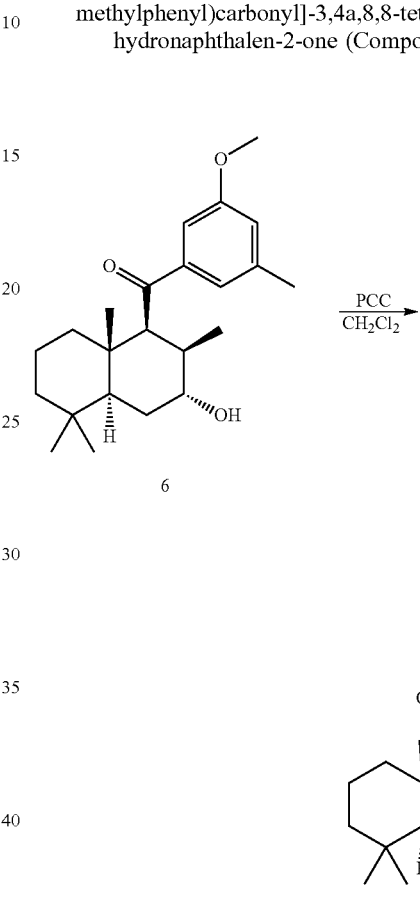

To a solution of (2R,3R,4S,4aS,8aS)-4-[(3-methoxy-5-methylphenyl)carbonyl]-3,4a,8,8-tetramethyl-decahydronaphthalen-2-ol (Compound No. 6, 1.05 g, 2.93 mmol) in $CH_2Cl_2$ (25 mL) under argon was added PCC (782 mg, 3.63 mmol) and the mixture stirred for 1 h. TLC analysis showed some remaining starting alcohol so another portion of PCC (178 mg, 0.830 mmol) was added and the mixture stirred another 1 h. The reaction was concentrated, diluted with $Et_2O$ (150 mL), filtered and re-concentrated. The resultant brown oil was purified by column chromatography on silica gel (hexanes/EtOAc, 3:1) to afford (3R,4S,4aS,8aS)-4-[(3-methoxy-5-methylphenyl)carbonyl]-3,4a,8,8-tetramethyl-decahydronaphthalen-2-one (Compound No. 7, 0.93 g, 89%) as a pale yellow oil. $^1$H NMR ($CDCl_3$): δ7.23 (s, 1H), 7.20 (m, 1H), 6.91 (m, 1H), 3.83 (s, 3H), 3.63 (d, J=6.9 Hz, 1H), 2.82 (m, J=7.5 Hz, 1H), 2.60-2.41 (m, 2H), 2.38 (m, 3H), 2.17 (s, 1H), 1.87 (m, 1H), 1.72-1.40 (m, 4H), 1.35 (s, 2H), 1.27-1.08 (m, 5H), 0.90 (s, 6H).

EXAMPLE 6

Synthesis of (3S,4S,4aS,8aS)-4-[(3-hydroxy-5-methylphenyl)carbonyl]-3,4a,8,8-tetramethyl-decahydronaphthalen-2-one (Compound No. 8)

EXAMPLE 7

Synthesis of (2R,3R,4aS,8aS)-4-[(3-hydroxy-5-methylphenyl)carbonyl]-3,4a,8,8-tetramethyl-decahydronaphthalen-2-ol (Compound No. 9)

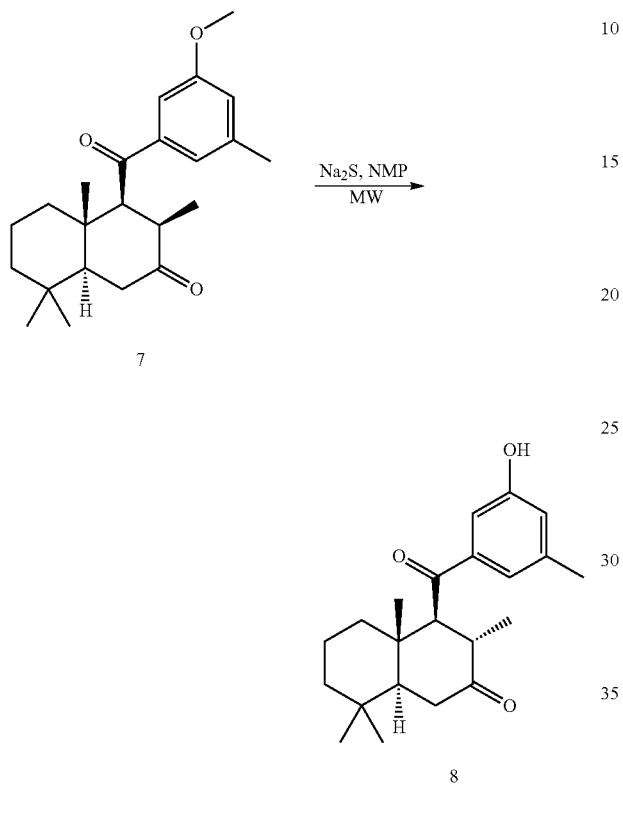

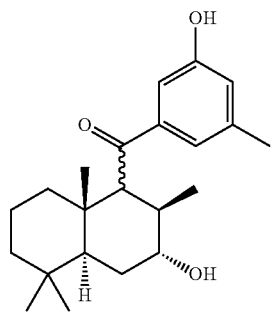

To a microwave (MW) vessel (2-5 mL) was added $Na_2S$ (65 mg, 0.83 mmol) and a solution of (3R,4S,4aS,8aS)-4-[(3-methoxy-5-methylphenyl)carbonyl]-3,4a,8,8-tetramethyl-decahydronaphthalen-2-one (Compound No. 7, 59 mg, 0.17 mmol) in NMP (1.5 mL). The reaction vessel was sealed and placed in a Biotage Microwave Initiator reactor and irradiated at 180° C. for 30 min. The reaction mixture was allowed to cool to room temperature and then quenched with 10% aqueous HCl (5 mL) and diluted with EtOAc (20 mL). The organic layer was washed with brine (3×10 mL), dried ($Na_2SO_4$) and concentrated. The crude product was purified by flash chromatography on silica gel (hexanes/EtOAc, 4:1 then 7:3) to afford (3S,4S,4aS,8aS)-4-[(3-hydroxy-5-methylphenyl)carbonyl]-3,4a,8,8-tetramethyl-decahydronaphthalen-2-one (Compound No. 8, 25 mg, 44%) a white solid. $^1$H NMR ($CDCl_3$): δ7.16 (s, 1H), 7.09 (s, 1H), 6.85 (s, 1H), 3.30 (d, J=12 Hz, 1H), 3.04-2.93 (m, 1H), 2.50-2.43 (m, 1H), 2.42 (d, J=12 Hz, 1H), 2.34 (s, 3H), 1.52-1.06 (m, 8H), 1.21 (s, 3H), 0.88 (d, J=6.3 Hz, 3H), 0.87 (s, 3H), 0.86 (s, 3H). ES-MS m/z 343 ([M+1]$^+$).

To a MW vessel (2-5 mL) was added $Na_2S$ (71 mg, 0.91 mmol) and a solution of (2R,3R,4S,4aS,8aS)-4-[(3-methoxy-5-methyl phenyl)carbonyl]-3,4a,8,8-tetramethyl-decahydronaphthalen-2-ol (Compound No. 6, 64 mg, 0.18 mmol) in NMP (1 mL). The reaction vessel was sealed and placed in a Biotage Microwave Initiator reactor and irradiated at 180° C. for 30 min. The reaction mixture was allowed to cool to room temperature and then quenched with 10% aqueous HCl (5 mL) and diluted with EtOAc (20 mL). The organic layer was washed with brine (3×10 mL), dried ($Na_2SO_4$) and concentrated. The crude product was purified by flash chromatography on silica gel (hexanes/EtOAc, 2:1) to afford (2R,3R,4aS,8aS)-4-[(3-hydroxy-5-methylphenyl)carbonyl]-3,4a,8,8-tetramethyl-decahydronaphthalen-2-ol (Compound No. 9, 23 mg, 37%) as a mixture of diastereomers (white solid). $^1$H NMR ($CDCl_3$): δ7.40-7.20 (m, total 2H), 6.92-6.83 (m, total 1H), 4.10-3.25 (m, total 2H), 2.37 and 2.35 (2 s, total 3H), 2.18-2.02 (m, total 1H), 1.86-1.19 (m, total 6H), 1.42-1.20 (m, 8H), 0.99-0.94 (m, total 3H), 0.90-0.82 (m, total 6H). ES-MS m/z 345 ([M+1]$^+$).

EXAMPLE 8

Synthesis of (3S,4S,4aS,8aS)-N-(3-aminopropyl)-4-[(3-methoxy-5-methyl phenyl)carbonyl]-3,4a,8,8-tetramethyl-decahydronaphthalen-2-amine dihydrochloride (Compound No. 11)

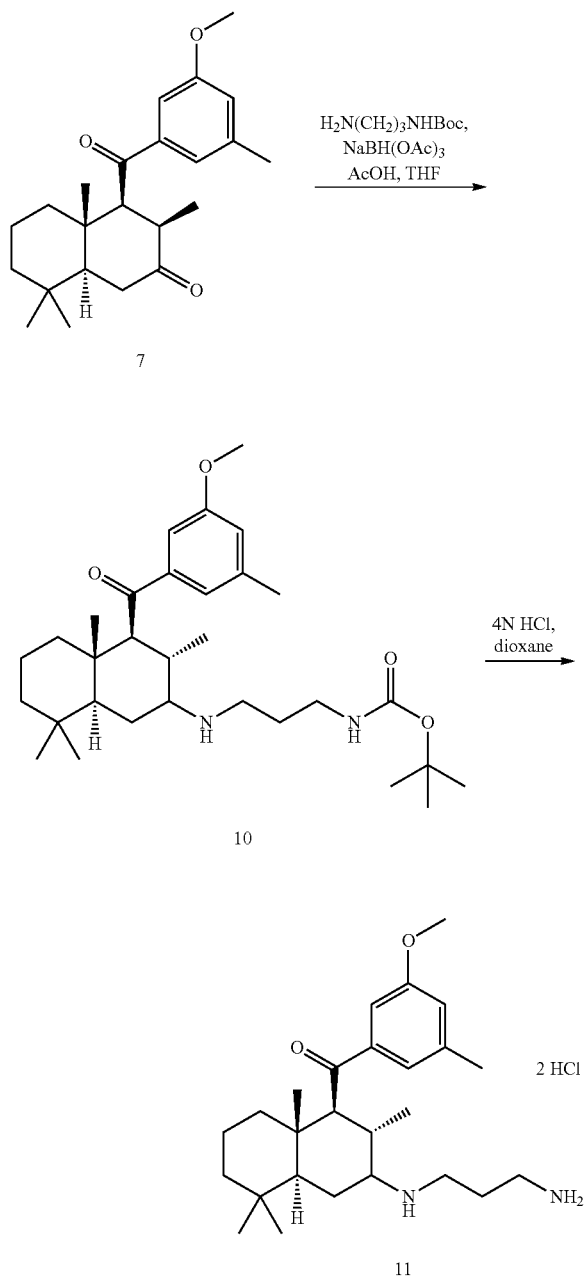

A. To a solution of (3R,4S,4aS,8aS)-4-[(3-methoxy-5-methylphenyl)carbonyl]-3,4a,8,8-tetramethyl-decahydronaphthalen-2-one (Compound No. 7, 158 mg, 0.44 mmol) in THF (2 mL) under argon was added a solution of tert-butyl N-(3-aminopropyl)carbamate (90 mg, 0.52 mmol) in THF (2 mL) followed by glacial AcOH (40 uL, 0.70 mmol) and the reaction stirred at room temperature for 40 min. Solid NaBH(OAc)$_3$ (135 mg, 0.636 mmol) was then added and the mixture stirred for 2 d before diluting with CH$_2$Cl$_2$ (30 mL) and saturated aqueous NaHCO$_3$ (20 mL). The aqueous layer was extracted with CH$_2$Cl$_2$ (2×15 mL) and the combined organic extracts dried (Na$_2$SO$_4$) and concentrated. The resultant yellow foam was purified by column chromatography on silica gel (EtOAc then CH$_2$Cl$_2$/MeOH, 9:1) to afford tert-butyl N-(3-{[(3S,4S,4aS,8aS)-4-[(3-methoxy-5-methylphenyl)carbonyl]-3,4a,8,8-tetramethyl-decahydronaphthalen-2-yl]amino}propyl)carbamate (Compound No. 10, 103 mg, 62%) as a yellow oil.

B. To a solution of tert-butyl N-(3-{[(3S,4S,4aS,8aS)-4-[(3-methoxy-5-methylphenyl)carbonyl]-3,4a,8,8-tetramethyl-decahydronaphthalen-2-yl]amino}propyl)-carbamate (Compound No. 10, 39 mg, 0.076 mmol) in MeOH (0.5 mL) was added a solution of HCl in dioxane (4.0 M, 0.30 mL, 1.2 mmol) and the mixture stirred at room temperature for 1.5 h before concentrating in vacuo. The product was diluted with MeOH (2-3 mL) and concentrated and this process was repeated (2×). Et$_2$O (10 mL) was added to precipitate a white solid and the supernatant solution was decanted. The solid was washed by decantation with Et$_2$O (3×5 mL) and the remaining traces of solvent removed under vacuum to give (3S,4S,4aS,8aS)-N-(3-aminopropyl)-4-[(3-methoxy-5-methylphenyl)carbonyl]-3,4a,8,8-tetramethyl-decahydronaphthalen-2-amine dihydrochloride (Compound No. 11, 23 mg, 62%) as a white solid. $^1$H NMR (CD$_3$OD): δ7.69 (s, 1H), 7.40 (s, 1H), 7.00 (s, 1H), 3.96 (d, J=9.9 Hz, 1H), 3.85 (s, 3H), 3.65-3.60 (m, 1H), 3.24-3.02 (m, 4H), 2.70-2.58 (m, 1H), 2.41 (s, 3H), 2.37-2.22 (m, 2H), 2.2 (d, J=9.9 Hz, 1H), 1.92-1.78 (m, 1H), 1.64 (d, J=9.9 Hz, 1H), 1.56-1.26 (m, 6H), 1.05 (s, 3H), 1.00 (s, 3H), 0.95 (d, J=6.9 Hz, 3H), 0.90 (s, 3H). ES-MS m/z 415 ([M+1]$^+$).

EXAMPLE 9

Synthesis of (4aS,8aS)-8-[(3-methoxy-5-methylphenyl)methyl]-4,4,7,8a-tetramethyl-1,2,3,4,4a,5,6,8a-octahydronaphthalene (Compound No. 13), (4aS,5S,8aS)-5-[(3-methoxy-5-methylphenyl)methyl]-1,1,4a,6-tetramethyl-1,2,3,4,4a,5,8,8a-octahydronaphthalene (Compound No. 14) and (4aS,5S,8aS)-5-[(3-methoxy-5-methylphenyl)methyl]-1,1,4a-trimethyl-6-methylidene-decahydronaphthalene (Compound No. 15)

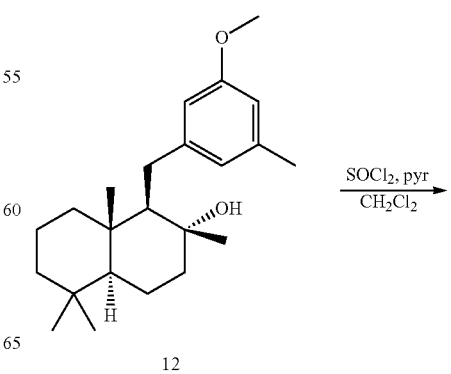

EXAMPLE 10

Synthesis of [(1S,2S,4aS,8aR)-1-[(3-methoxy-5-methylphenyl)methyl]-5,5,8a-trimethyl-decahydronaphthalen-2-yl]methanol (Compound No. 16)

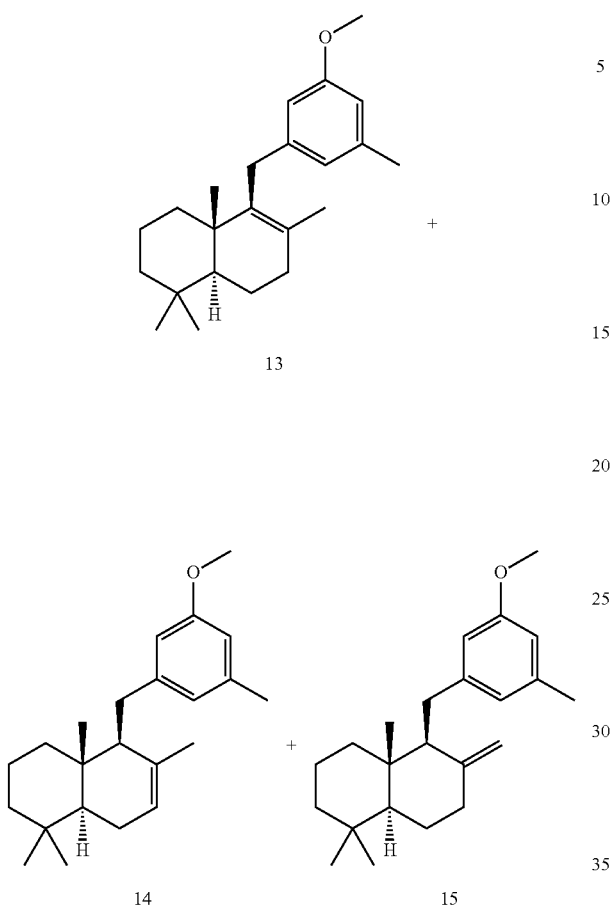

13

14    15

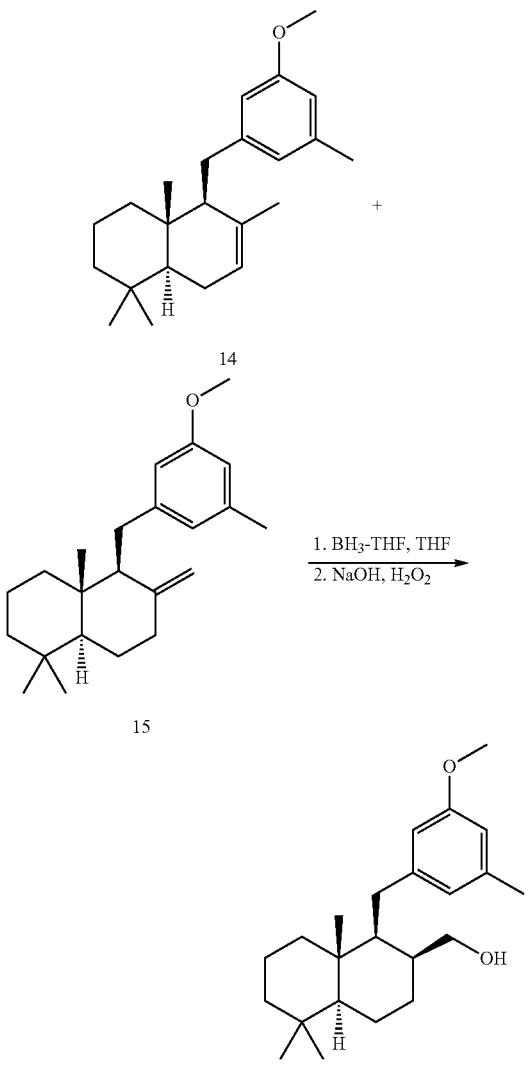

To a solution of (1R,2R,4aS,8aS)-1-[(3-methoxy-5-methylphenyl)methyl]-2,5,5,8a-tetramethyl-decahydronaphthalen-2-ol (Compound No. 12, prepared according to Andersen, R. et al. PCT Int. Patent Appl. WO 2007/147251 A1, 470 mg, 1.37 mmol) and pyridine (1.10 mL, 13.6 mmol) in CH$_2$Cl$_2$ (20 mL) at −78° C. under argon was added thionyl chloride (0.50 mL, 6.9 mmol) dropwise neat. The reaction was stirred at −78° C. for 1 h then quenched with saturated aqueous sodium bicarbonate (30 mL) and diluted with CH$_2$Cl$_2$ (20 mL). The mixture was warmed to room temperature, the layers separated and the aqueous layer extracted with CH$_2$Cl$_2$ (3×15 mL). The combined organic extracts were washed with brine (1×40 mL), dried (Na$_2$SO$_4$) and concentrated to afford a mixture of (4aS,8aS)-8-[(3-methoxy-5-methylphenyl)methyl]-4,4,7,8a-tetramethyl-1,2,3,4,4a,5,6,8a-octahydronaphthalene, (4aS,5S,8aS)-5-[(3-methoxy-5-methylphenyl)methyl]-1,1,4a,6-tetramethyl-1,2,3,4,4a,5,8,8a-octahydronaphthalene and (4aS,5S,8aS)-5-[(3-methoxy-5-methylphenyl)methyl]-1,1,4a-trimethyl-6-methylidene-decahydronaphthalene (Compound No. 13, Compound No. 14, and Compound No. 15, respectively, 0.44 g, 1.3 mmol) as a clear oil.

To a mixture of (4aS,8aS)-8-[(3-methoxy-5-methylphenyl)methyl]-4,4,7,8a-tetramethyl-1,2,3,4,4a,5,6,8a-octahydronaphthalene, (4aS,5S,8aS)-5-[(3-methoxy-5-methylphenyl)methyl]-1,1,4a,6-tetramethyl-1,2,3,4,4a,5,8,8a-octahydronaphthalene and (4aS,5S,8aS)-5-[(3-methoxy-5-methylphenyl)methyl]-1,1,4a-trimethyl-6-methylidene-decahydronaphthalene (Compound No. 13, Compound No. 14, and Compound No. 15 respectively, 0.44 g, 1.3 mmol) in anhydrous THF (11 mL) at OoC under argon was added a solution of BH$_3$-THF (1.0 M in THF, 2.6 mL, 2.6 mmol) and the reaction stirred for 2 d before quenching carefully with MeOH (4 mL), 15% aqueous NaOH (2 mL) and 50% aqueous H$_2$O$_2$ (3 mL). The mixture was stirred at room temperature for 5 h then diluted with EtOAc (25 mL) and water (20 mL). The layers were separated and the aqueous layer extracted with EtOAc (2×20 mL). The combined organic extracts were washed with brine (1×40 mL), dried (Na$_2$SO$_4$) and concentrated. The resultant white foam (0.46 g) was purified by column chromatography on silica gel (hexanes/EtOAc, 3:1 then 7:3) to give [(1S,2S,4aR)-1-[(3-methoxy-5-methylphenyl)methyl]-5,5,8a-trimethyl-decahydronaphthalen-2-yl]methanol (Compound No. 16, 191 mg, 41% from Compound No. 12) as clear oil. $^1$H NMR (CDCl$_3$): δ6.59 (s, 1H), 6.54 (s, 2H), 3.90 (d, J=9.9 Hz, 1H), 3.77 (s, 3H), 3.57 (t, J=9.9 Hz, 1H), 2.80 (dd, J=13.5, 3.2 Hz, 1H), 2.37 (dd, J=13.5, 11.4 Hz, 1H), 2.30 (s, 3H), 2.04 (s, 1H), 1.96-1.90 (m, 1H), 1.84-1.74 (m, 1H), 1.64-1.14 (m, 9H), 1.08-0.86 (m, 2H), 0.86 (s, 3H), 0.83 (s, 3H), 0.79 (s, 3H). ES-MS m/z 345 ([M+1]$^+$).

EXAMPLE 11

Synthesis of 3-{[(1S,2S,4aS,8aR)-2-(hydroxymethyl)-5,5,8a-trimethyl-decahydronaphthalen-1-yl]methyl}-5-methylphenol (Compound No. 17)

5-methylphenyl)methyl]-5,5,8a-trimethyl-decahydronaphthalen-2-yl]methanol (Compound No. 16, 190 mg, 0.55 mmol) in NMP (3 mL). The reaction vessel was sealed and placed in a Biotage Microwave Initiator reactor and irradiated at 180° C. for 3 h. The reaction mixture was allowed to cool to room temperature and then quenched with 10% aqueous HCl (10 mL) and diluted with EtOAc (30 mL). The organic layer was washed with brine (3×10 mL), dried (Na$_2$SO$_4$) and concentrated. The crude product was purified by flash chromatography on silica gel (hexanes/EtOAc, 3:2) to afford 3-{[(1S,2S,4aS,8aR)-2-(hydroxymethyl)-5,5,8a-trimethyl-decahydronaphthalen-1-yl]methyl}-5-methylphenol (Compound No. 17, 90 mg, 50%) as a white foam. $^1$H NMR (CDCl$_3$): δ6.54 (s, 1H), 6.48 (s, 2H), 5.78 (br s, 1H), 3.91 (d, J=10.5 Hz, 1H), 3.60 (t, J=10.2 Hz, 1H), 2.76 (dd, J=13.2, 2.9 Hz, 1H), 2.33 (dd, J=13.5, 11.7 Hz, 1H), 2.26 (s, 3H), 2.05 (s, 1H), 1.94-1.86 (m, 1H), 1.84-1.74 (m, 1H), 1.68-1.14 (m, 9H), 1.09-0.86 (m, 2H), 0.86 (s, 3H), 0.82 (s, 3H), 0.77 (s, 3H). ES-MS m/z 331 ([M+1]$^+$).

EXAMPLE 12

Synthesis of (1S,2S,4aS,8aR)-1-[(3-methoxy-5-methylphenyl)methyl]-5,5,8a-trimethyl-decahydronaphthalene-2-carboxylic acid (Compound No. 19)

To a MW vessel (2-5 mL) was added Na$_2$S (226 mg, 2.90 mmol) and a solution of [(1S,2S,4aS,8aR)-1-[(3-methoxy-

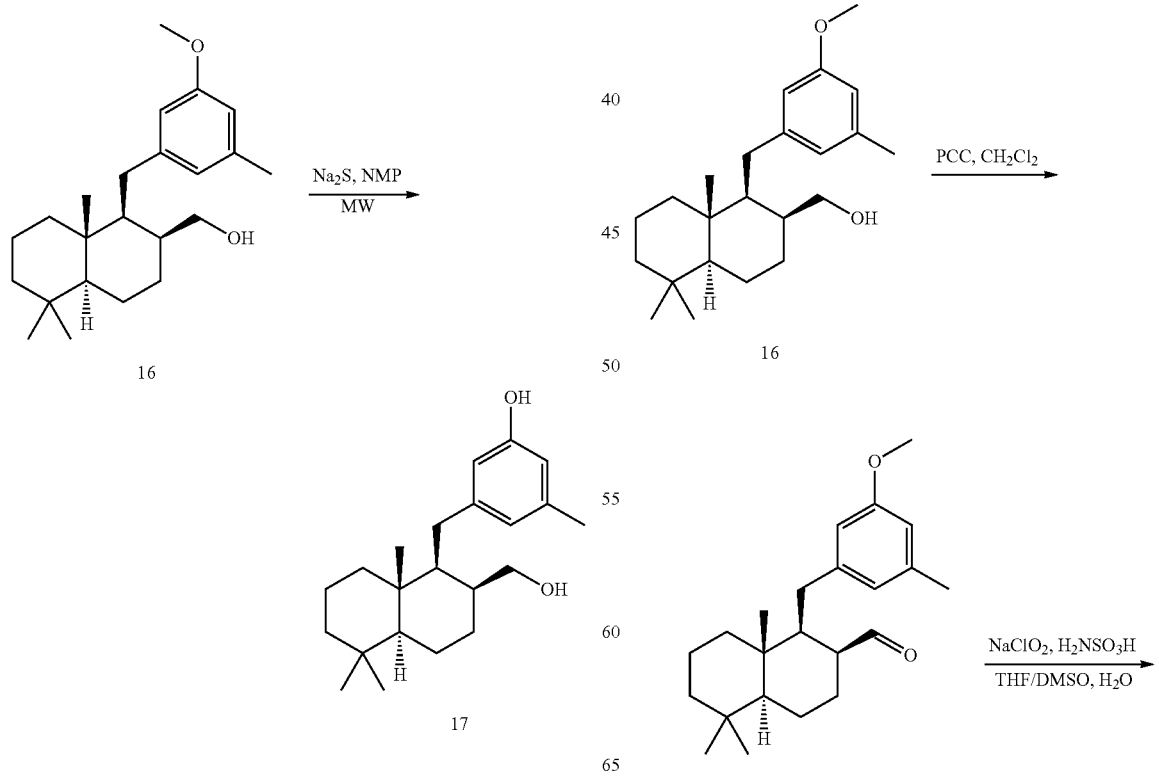

-continued

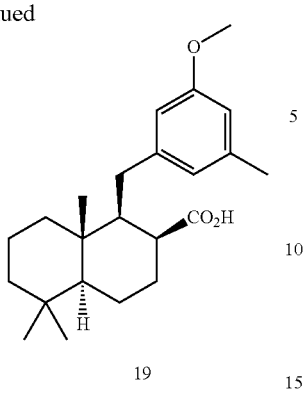

19

A. To a solution of [(1S,2S,4aS,8aR)-1-[(3-methoxy-5-methylphenyl)methyl]-5,5,8a-trimethyl-decahydronaphthalen-2-yl]methanol (Compound No. 16, 236 mg, 0.686 mmol) in $CH_2Cl_2$ (10 mL) under argon was added PCC (155 mg, 0.719 mmol) and the reaction stirred at room temperature for 1 h. Another portion of PCC (44 mg, 0.20 mmol) was then added and the mixture stirred an additional 2 h before concentrating and diluting with $Et_2O$ (10 mL). The mixture was then filtered through a plug of silica gel, washing with $Et_2O$. The resultant filtrate was concentrated to give crude (1S,2S,4aS,8aR)-1-[(3-methoxy-5-methylphenyl)methyl]-5,5,8a-trimethyl-decahydronaphthalene-2-carbaldehyde (Compound No. 18, 201 mg, ~0.6 mmol).

B. To a solution of crude (1S,2S,4aS,8aR)-1-[(3-methoxy-5-methylphenyl)methyl]-5,5,8a-trimethyl-decahydronaphthalene-2-carbaldehyde (Compound No. 18, 201 mg, ~0.6 mmol) and sulfamic acid (410 mg, 4.22 mmol) in THF/DMSO (10:1, 11 mL) at 0° C. was added a solution of sodium chlorite (235 mg, 2.08 mmol) in water (10 mL) and the reaction stirred at 0° C. for 1 h before warming to room temperature and stirring for 2 d. The reaction was diluted with EtOAc (25 mL) and the organic phase washed with saturated aqueous $NH_4Cl$ (2×10 mL) and brine (2×10 mL), dried ($Na_2SO_4$) and concentrated. Purification of the crude product by column chromatography on silica gel (hexanes/EtOAc, 9:1) gave (1S,2S,4aS,8aR)-1-[(3-methoxy-5-methylphenyl)methyl]-5,5,8a-trimethyl-decahydronaphthalene-2-carboxylic acid (Compound No. 19, 105 mg, 49%) as a pale yellow oil. $^1$H NMR ($CDCl_3$): δ6.72 (s, 2H), 6.55 (s, 1H), 3.78 (s, 3H), 3.01 (t, J=12 Hz, 1H), 2.82 (dd, J=12, 3 Hz, 1H), 2.47-2.42 (m, 1H), 2.31 (s, 3H), 2.24-2.16 (m, 1H), 1.92-1.83 (m, 1H), 1.75-1.38 (m, 7H), 1.30-0.98 (m, 4H), 0.95 (s, 3H), 0.87 (s, 3H), 0.85 (s, 3H).

EXAMPLE 13

Synthesis of (1S,2S,4aS,8aR)-1-[(3-hydroxy-5-methylphenyl)methyl]-5,5,8a-trimethyl-decahydronaphthalene-2-carboxylic acid (Compound No. 20)

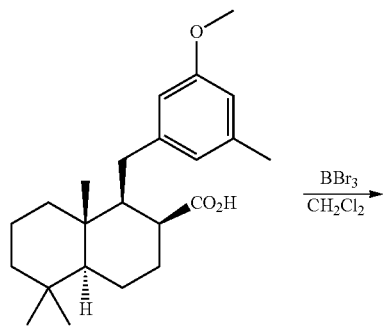

-continued

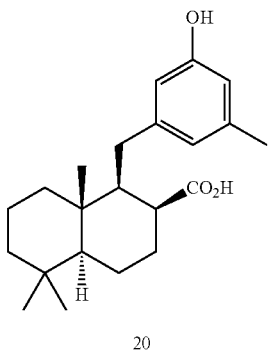

20

To a solution of (1S,2S,4aS,8aR)-1-[(3-methoxy-5-methylphenyl)methyl]-5,5,8a-trimethyl-decahydronaphthalene-2-carboxylic acid (Compound No. 19, 105 mg, 0.293 mmol) in $CH_2Cl_2$ (5 mL) at -78° C. under argon was added a solution of $BBr_3$ (1 M in $CH_2Cl_2$, 1.5 mL, 1.5 mmol) and the mixture allowed to stir from -78° C. to room temperature overnight. The reaction was quenched with MeOH (10 mL) and concentrated. This was repeated 2× and the residue diluted with i-PrOH (10 mL) and 1 N HCl (3 mL) and heated to reflux for 1 h. The mixture was cooled, concentrated and diluted with EtOAc (25 mL) and water (10 mL). The layers were separated and the aqueous layer extracted with EtOAc (1×10 mL). The combined organic extracts were dried ($Na_2SO_4$), concentrated and purified by column chromatography on silica gel (hexanes/EtOAc, 3:1) to afford (1S,2S,4aS,8aR)-1-[(3-methoxy-5-methylphenyl)methyl]-5,5,8a-trimethyl-decahydronaphthalene-2-carboxylic acid (Compound No. 20, 53 mg, 53%) as a brown foam. $^1$H NMR ($CDCl_3$): δ6.68 (s, 1H), 6.65 (s, 1H), 6.48 (s, 1H), 2.97 (t, J=12.6 Hz, 1H), 2.80 (dd, J=13.2, 3.3 Hz, 1H), 2.47-2.42 (m, 1H), 2.28 (s, 3H), 2.24-2.16 (m, 1H), 1.90-1.81 (m, 1H), 1.78-0.92 (m, 10H), 0.94 (s, 3H), 0.87 (s, 3H), 0.87-0.83 (m, 2H), 0.84 (s, 3H). ES-MS m/z 345 ([M+1]$^+$).

EXAMPLE 14

Synthesis of 3-{[(1S,4aS,8aS)-3-amino-2,5,5,8a-tetramethyl-decahydronaphthalen-1-yl]carbonyl}-5-methylphenol hydrochloride (Compound No. 22)

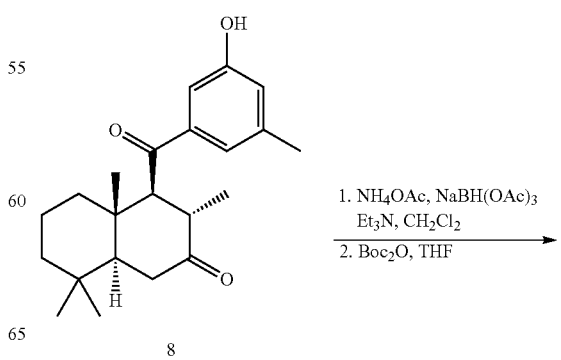

8 dronaphthalen-1-yl]carbonyl}-5-methylphenol hydrochloride (Compound No. 22, 10 mg, 39%) as a white solid. $^1$H NMR (CD$_3$OD): δ7.27 (s, 1H), 7.13 (s, 1H), 6.87 (s, 1H), 3.12-3.01 (m, 1H), 2.35 (s, 3H), 2.30-2.16 (m, 1H), 2.06-1.96 (m, 1H), 1.62-1.08 (m, 9H), 1.05 (s, 3H), 0.96 (s, 3H), 0.90 (s, 3H), 0.89 (d, J=6 Hz, 3H). ES-MS m/z 344 ([M+1]$^+$).

EXAMPLE 15

Synthesis of (3S,4S,4aS,8aS)-4-[(3-hydroxy-5-methylphenyl)carbonyl]-3,4a,8,8-tetramethyl-decahydronaphthalen-2-ol (Compound No. 23)

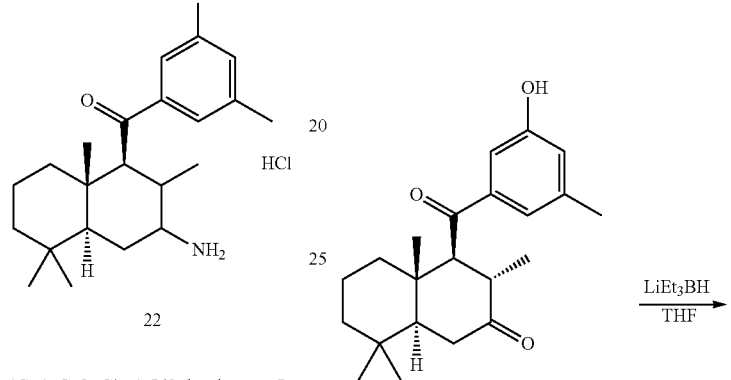

A. To a solution of (3S,4S,4aS,8aS)-4-[(3-hydroxy-5-methylphenyl)carbonyl]-3,4a,8,8-tetramethyl-decahydronaphthalen-2-one (Compound No. 8, 110 mg, 0.32 mmol) in THF (4 mL) under argon was added NH$_4$OAc (230 mg, 2.99 mmol), Et$_3$N (0.10 mL, 0.72 mmol) and NaBH(OAc)$_3$ (118 mg, 0.557 mmol) and the mixture stirred at room temperature overnight before adding another portion of NaBH(OAc)$_3$ (118 mg, 0.557 mmol) and stirring for 2 d. The reaction was then diluted with CH$_2$Cl$_2$ (30 mL) and saturated aqueous NaHCO$_3$ (25 mL). The aqueous layer was extracted with CH$_2$Cl$_2$ (2×10 mL) and the combined organic extracts dried (Na$_2$SO$_4$) and concentrated. The resultant yellow foam was purified by column chromatography on silica gel (CH$_2$Cl$_2$/MeOH/NH$_4$OH, 96:4:0 then 88:10:2) to afford the desired amine (40 mg) as an impure mixture (yellow oil).

B. To a solution of the crude amine from above (40 mg) in THF (1 mL) under argon was added a solution of di-tert-butyl dicarbonate (40 mg, 0.18 mmol) in THF (1 mL) and the reaction stirred overnight. The mixture was concentrated and purified by column chromatography on silica gel (hexanes/EtOAc, 4:1 then 7:3) to give tert-butyl N-[(4S,4aS,8aS)-4-[(3-hydroxy-5-methylphenyl)carbonyl]-3,4a,8,8-tetramethyl-decahydronaphthalen-2-yl]carbamate (Compound No. 21, 30 mg, 58%) as a white foam.

C. To a solution of tert-butyl N-[(4S,4aS,8aS)-4-[(3-hydroxy-5-methylphenyl)carbonyl]-3,4a,8,8-tetramethyl-decahydronaphthalen-2-yl]carbamate (Compound No. 21, 30 mg, 0.068 mmol) in MeOH (0.5 mL) was added a solution of HCl in dioxane (4.0 M, 0.30 mL, 1.2 mmol) and the mixture stirred at room temperature for 2 h before concentrating in vacuo. The product was diluted with MeOH (2-3 mL) and concentrated and this process was repeated (2×). Et$_2$O (10 mL) was added to precipitate a white solid and the supernatant solution was decanted. The solid was washed by decantation with Et$_2$O (3×5 mL) and the remaining traces of solvent removed under vacuum to give 3-{[(1S,4aS,8aS)-3-amino-2,5,5,8a-tetramethyl-decahy- To a solution of (3S,4S,4aS,8aS)-4-[(3-hydroxy-5-methylphenyl)carbonyl]-3,4a,8,8-tetramethyl-decahydronaphthalen-2-one (Compound No. 8, 202 mg, 0.590 mmol) in anhydrous THF (12 mL) at 0° C. under argon was added a solution of Super-Hydride in THF (1.0 M in THF, 3.6 mL, 3.6 mmol) and the reaction stirred to room temperature overnight. The mixture was quenched with water (10 mL), diluted with EtOAc (20 mL) and brine (20 mL) and the layers separated. The organic phase was washed with brine (1×25 mL), dried (Na$_2$SO$_4$), concentrated and purified by column chromatography on silica gel (hexanes/EtOAc, 3:1 then 65:35) to afford (3R,4S,4aS)-4-[(3-hydroxy-5-methylphenyl)carbonyl]-3,4a,8,8-tetramethyl-decahydronaphthalen-2-ol (Compound No. 23, 75 mg, 37%) as a white solid. $^1$H NMR (CDCl$_3$): δ7.28-7.26 (m, 1H), 7.20-7.18 (m, 1H), 6.87-6.86 (m, 1H), 5.45 (s, 1H), 3.40-3.28 (m, 1H), 2.97 (d, J=11.4 Hz, 1H), 2.38 (s, 3H), 2.12-1.94 (m, 2H), 1.61 (s, 3H), 1.50-1.35 (m, 2H), 1.30-1.22 (m, 1H), 1.18-1.00 (m, 3H), 1.07 (s, 3H), 0.90 (s, 3H), 0.89 (d, J=6 Hz, 3H), 0.86 (s, 3H). ES-MS m/z 345 ([M+1]$^+$).

EXAMPLE 16

Synthesis of (1S,2R,4aS,8aS)-1-(3-methoxy-5-methylphenoxymethyl)-2,5,5,8a-tetramethyl-decahydronaphthalen-2-ol (Compound No. 27)

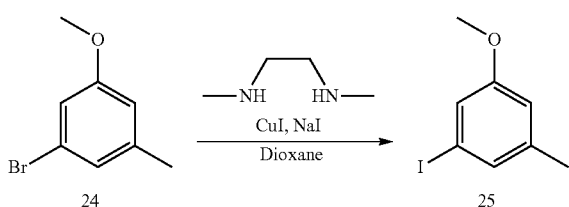

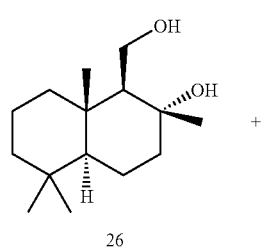

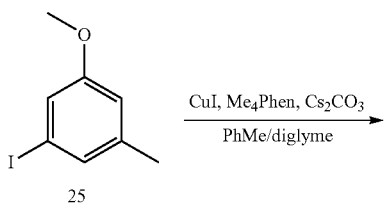

A. Cu(I)I (0.05 g, 0.25 mmol) and NaI (1.49 g, 10 mmol) were added to an oven dried sealed tube and the tube sealed with a rubber septum and flushed with a stream of nitrogen for 15 min. Anhydrous dioxane (5 mL), N,N'-dimethyl ethylenediamine (0.055 mL, 0.50 mmol) and 1-bromo-3-methoxy-5-methylbenzene (Compound No. 24, 1.0 g, 5 mmol) were added via a syringe with vigorous stirring under a stream of nitrogen at room temperature. The rubber septum was replaced with the Teflon cap and the sealed tube was heated at 110° C. in an oil bath for 18 h. The reaction was allowed to cool to room temperature and then quenched with a saturated aqueous solution of ammonium chloride. The reaction mixture was extracted with $CH_2Cl_2$. The organic layer was washed with water, and then concentrated to dryness to give 1-iodo-3-methoxy-5-methylbenzene (Compound No. 25, 1.05 g, 87% yield) as a pale yellow oil.

B. (1S,2R,4aS,8aS)-1-(Hydroxymethyl)-2,5,5,8a-tetramethyl-decahydro-naphthalen-2-ol (Compound No. 26, prepared according to Kuchkova et al. *Synthesis*, 1997, 1045, 938 mg, 3.90 mmol), CuI (84 mg, 0.44 mmol), 3,4,7,8-tetramethyl-[1,10]phenanthroline (188 mg, 0.796 mmol), and $Cs_2CO_3$ (1.91 g, 5.86 mmol) were weighed into a sealed flask and degassed with Ar for 2 min. A solution of 1-iodo-3-methoxy-5-methylbenzene (Compound No 25, 1.04 g, 4.19 mmol) in toluene (20 mL) and diglyme (4 mL) was added to the flask and the reaction heated to 120° C. for 3 d. The mixture was filtered through Celite, washed with EtOAc (300 mL), dried ($MgSO_4$) and concentrated. The crude product was purified by chromatography on silica gel (EtOAc/hexanes, 1:9 to 1:4) to afford (1S,2R,4aS,8aS)-1-(3-methoxy-5-methylphenoxymethyl)-2,5,5,8a-tetramethyl-decahydronaphthalen-2-ol (Compound No. 27, 1.18 g, 84%) as a yellow oil. $^1H$ NMR ($CDCl_3$): δ6.36-6.35 (d, J=2.1 Hz, 2H), 6.30 (t, J=2.4 Hz, 1H), 4.24-4.16 (m, 2H), 3.77 (s, 3H), 2.30 (s, 3H), 3.23 (br s, 1H), 1.96-1.88 (m, 1H), 1.82-1.10 (m, 10H), 1.27 (s, 3H), 1.06-1.00 (m, 1H), 0.91 (s, 3H), 0.90 (s, 3H), 0.82 (s, 3H). ES-MS m/z 361 ($[M+1]^+$).

EXAMPLE 17

Synthesis of 3-{[(1S,4aS,8aS)-2,5,5,8a-tetramethyl-1,4,4a,5,6,7,8,8a-octahydronaphthalen-1-yl]methoxy}-5-methylphenol (Compound No. 29)

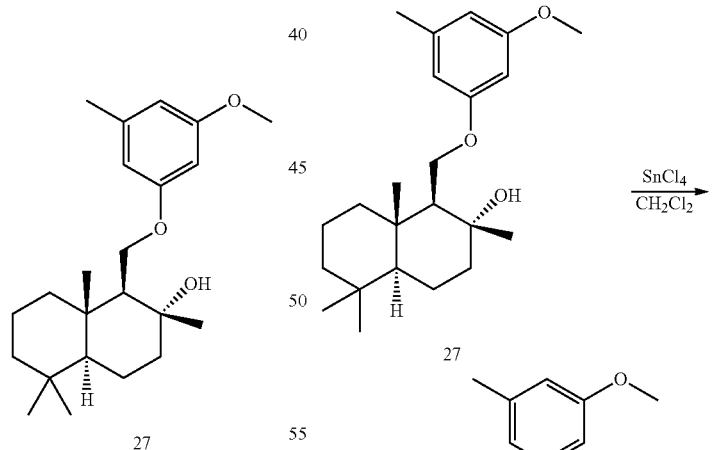

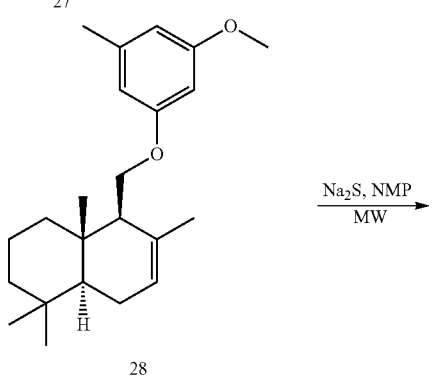

EXAMPLE 18

Synthesis of (4S,4aS,8aS)-4-(3-methoxy-5-methyl-phenoxymethyl)-3,4a,8,8-tetramethyl-decahydronaphthalen-2-ol (Compound No. 30)

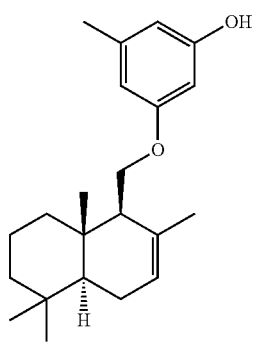

29

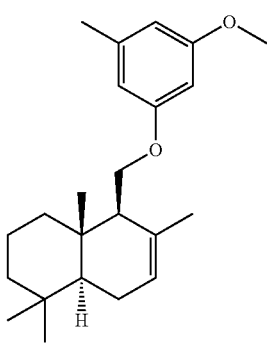

28

1. BH₃—THF, THF
2. NaOH, H₂O₂

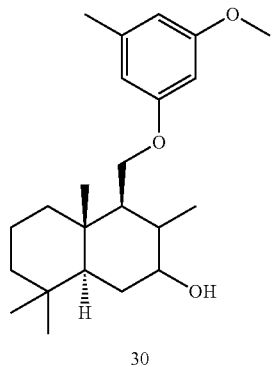

30

A. To a solution of (1S,2R,4aS,8aS)-1-(3-methoxy-5-methylphenoxymethyl)-2,5,5,8a-tetramethyl-decahydronaphthalen-2-ol (Compound No. 27, 1.18 g, 32.8 mmol) in CH₂Cl₂ (70 mL) at −78° C. under argon was added neat SnCl₄ (0.88 mL, 7.5 mmol) dropwise and the reaction stirred at −78° C. for 3.5 h before adding another portion of SnCl₄ (0.88 mL, 7.5 mmol). The mixture was stirred another 2 h at −78° C. then quenched at −78° C. with water (50 mL). The reaction was warmed to room temperature, the layers separated and the aqueous layer extracted with CH₂Cl₂ (1×40 mL). The combined organic extracts were washed with saturated aqueous NaHCO₃ (1×60 mL), dried (Na₂SO₄) and concentrated to afford a yellow oil (1.1 g). Purification of the crude product by column chromatography on silica gel (hexanes/EtOAc, 98:2) gave an impure mixture containing (4aS,5S,8aS)-5-(3-methoxy-5-methylphenoxymethyl)-1,1,4a,6-tetramethyl-1,2,3,4,4a,5,8,8a-octahydronaphthalene (Compound No. 28, 1.16 g) as a clear oil.

B. To a MW vessel (2-5 mL) was added Na₂S (460 mg, 5.89 mmol) and a solution of the impure mixture containing (4aS,5S,8aS)-5-(3-methoxy-5-methylphenoxymethyl)-1,1,4a,6-tetramethyl-1,2,3,4,4a,5,8,8a-octahydronaphthalene (Compound No. 28, ~1 mmol) in NMP (6 mL). The reaction vessel was sealed and placed in a Biotage Microwave Initiator reactor and irradiated at 180° C. for 1.5 h. The reaction mixture was allowed to cool to room temperature and then quenched with 1 N HCl (20 mL) and diluted with EtOAc (40 mL). The organic layer was washed with water (1×40 mL), dried (Na₂SO₄) and concentrated. The crude product was purified by flash chromatography on silica gel (hexanes/EtOAc, 92:8 then 85:15) to afford 3-{[(1S,8aS)-2,5,5,8a-tetramethyl-1,4,4a,5,6,7,8,8a-octahydronaphthalen-1-yl]methoxy}-5-methylphenol (Compound No. 29, 40 mg, 10%) as a colorless oil. $^1$H NMR (CDCl₃): δ6.31 (s, 1H), 6.24-6.20 (m, 2H), 5.50 (br s, 1H), 4.71 (br s, 1H), 4.07 (dd, J=9.6, 3 Hz, 1H), 3.88 (dd, J=9.6, 6.3 Hz, 1H), 2.26 (s, 3H), 2.20-1.83 (m, 4H), 1.70 (s, 3H), 1.66-1.38 (m, 6H), 0.90 (s, 3H), 0.88 (s, 6H). ES-MS m/z 329 ([M+1]⁺).

To a solution of the impure mixture containing (4aS,5S,8aS)-5-(3-methoxy-5-methylphenoxymethyl)-1,1,4a,6-tetramethyl-1,2,3,4,4a,5,8,8a-octahydronaphthalene (Compound No. 28, ~0.7 mmol) in dry THF (9 mL) at 0° C. under argon was added a solution of BH₃-THF (1.0 M in THF, 1.0 mL, 1.0 mmol) dropwise. The reaction was stirred under argon for 1.5 h, then allowed to warm to room temperature and stirred for an additional 1.5 h. The reaction was quenched with MeOH (7 mL), 15% aqueous NaOH (0.23 mL) and 50% aqueous H₂O₂ (0.23 mL) and allowed to stir at room temperature overnight. The mixture was diluted with EtOAc (25 mL) and water (25 mL). The layers were separated and the organic layer washed with brine (1×25 mL), dried (MgSO₄) and concentrated. The crude material was purified by chromatography on silica gel (EtOAc/hexanes, 91:9 then 4:1) to yield (4S,4aS,8aS)-4-(3-methoxy-5-methylphenoxymethyl)-3,4a,8,8-tetramethyl-decahydronaphthalen-2-ol (Compound No. 30, 50 mg, 21%) as a white solid. $^1$H NMR (CDCl₃): δ6.33-6.30 (m, 2H), 6.29-6.26 (m, 1H), 4.12 (dd, J=9.3, 4.8 Hz, 1H), 3.94 (br s, 1H), 3.86 (t, J=9.3 Hz, 1H), 3.77 (s, 3H), 2.29 (s, 3H), 2.20-2.04 (m, 2H), 1.76-1.04 (m, 10H), 0.96 (d, J=8.1 Hz, 3H), 0.94 (s, 3H), 0.88 (s, 3H), 0.84 (s, 3H). ES-MS m/z 361 ([M+1]⁺).

EXAMPLE 19

Synthesis of (1S,2R,4aS,8aS)-1-[3,5-bis(benzyloxy)-phenoxymethyl]-2,5,5,8a-tetramethyl-decahydronaphthalen-2-ol (Compound No. 33)

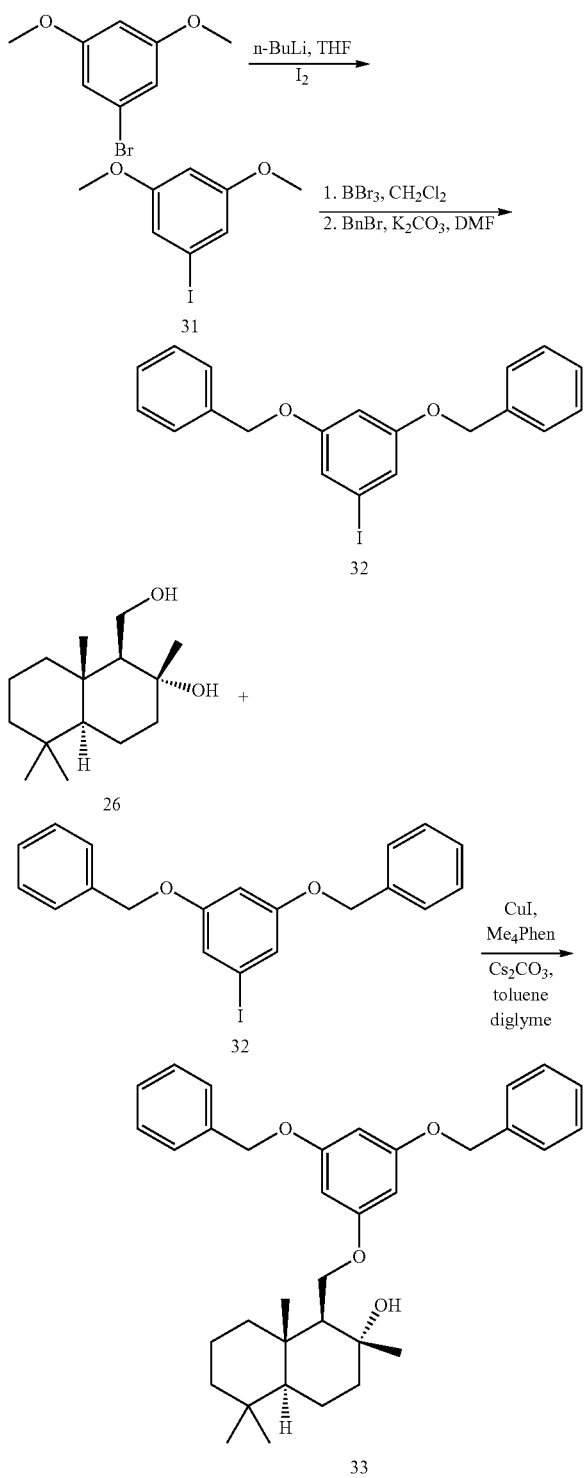

A. To a solution of 1-bromo-3,5-dimethoxybenzene (3.01 g, 13.9 mmol) in dry THF (25 mL) at −78° C. under argon was added a solution of n-BuLi (2.2 M in hexanes, 7.00 mL, 15.4 mmol) dropwise and the mixture stirred for 40 min. A solution of iodine in dry THF (20 mL) was then added dropwise and the reaction allowed to stir for an additional 45 min at −78° C. before quenching with 20% aqueous $Na_2S_2O_3$ (45 mL) and warming to room temperature. The mixture was diluted with EtOAc (50 mL), the layers separated and the organic layer washed with brine (50 mL), dried ($MgSO_4$) and concentrated to a yellow solid (3.12 g). Purification of the crude product by chromatography on silica gel (20% EtOAc/hexanes) gave 1-iodo-3,5-dimethoxybenzene (Compound No. 31, 2.01 g, 55%) as a white solid.

B. To a solution of 1-iodo-3,5-dimethoxybenzene (Compound No. 31, 2.01 g, 7.61 mmol) in $CH_2Cl_2$ (20 mL) at 0° C. under argon was added a solution of $BBr_3$ (1 M in $CH_2Cl_2$, 11.4 mL, 11.4 mmol) and the mixture allowed to stir for 17 h. The reaction was quenched with MeOH (13 mL) and concentrated. The residue was diluted with EtOAc (25 mL) and the organic layer washed with water (3×20 mL) and brine (20 mL), dried ($MgSO_4$) and concentrated to a brown oil.

C. To a solution of the crude residue from above in DMF (20 mL) under argon was added $K_2CO_3$ (2.32 g, 16.8 mmol) and benzyl bromide (2.00 mL, 16.8 mmol) and the mixture was allowed to stir for 2 d. The mixture was diluted with EtOAc (40 mL) and the organic layer washed with water (3×30 mL), dried ($MgSO_4$) and concentrated to a dark yellow oil. The crude material was purified by chromatography on silica gel (EtOAc/hexanes, 5:95 to 15:85) to yield 1,3-bis(benzyloxy)-5-iodobenzene (Compound No. 32, 2.66 g, 84% over 2 steps) as an off-white solid.

D. (1S,2R,4aS,8aS)-1-(Hydroxymethyl)-2,5,5,8a-tetramethyl-decahydro-naphthalen-2-ol (Compound No. 26, 1.54 g, 6.41 mmol), CuI (0.12 g, 0.63 mmol), 3,4,7,8-tetramethyl-[1,10]phenanthroline (0.30 g, 1.3 mmol), and $Cs_2CO_3$ (3.19 g, 9.79 mmol) were weighed into a sealed flask and degassed with Ar for 2 min. A solution of 1,3-bis(benzyloxy)-5-iodobenzene (Compound No. 32, 2.66 g, 6.39 mmol) in toluene (30 mL) and diglyme (6 mL) was added to the flask and the reaction heated to 120° C. for 2 d. The mixture was filtered through Celite, washed with EtOAc (300 mL), dried ($MgSO_4$) and concentrated. The crude product was purified by chromatography on silica gel (EtOAc/hexanes, 8:92) to afford (1S,2R,4aS,8aS)-1-[3,5-bis(benzyloxy)-phenoxymethyl]-2,5,5,8a-tetramethyl-decahydronaphthalen-2-ol (Compound No. 33, 1.48 g, 44%) as a white foam. $^1$H NMR ($CDCl_3$): δ7.45-7.32 (m, 10H), 6.27 (t, J=2.1 Hz, 1H), 6.21 (d, J=2.1 Hz, 2H), 5.00 (s, 4H), 4.10-4.23 (m, 2H), 1.95-1.88 (m, 1H), 1.81-1.28 (m, 8H), 1.25 (s, 3H), 1.24-0.98 (m, 4H), 0.90 (s, 3H), 0.89 (s, 3H), 0.82 (s, 3H).

EXAMPLE 20

Synthesis of (1S,2R,4aS,8aS)-1-(3,5-dimethoxyphenoxymethyl)-2,5,5,8a-tetramethyl-decahydronaphthalen-2-ol (Compound No. 34)

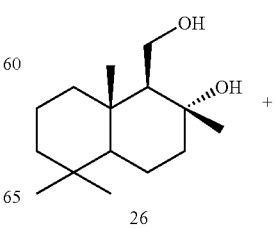

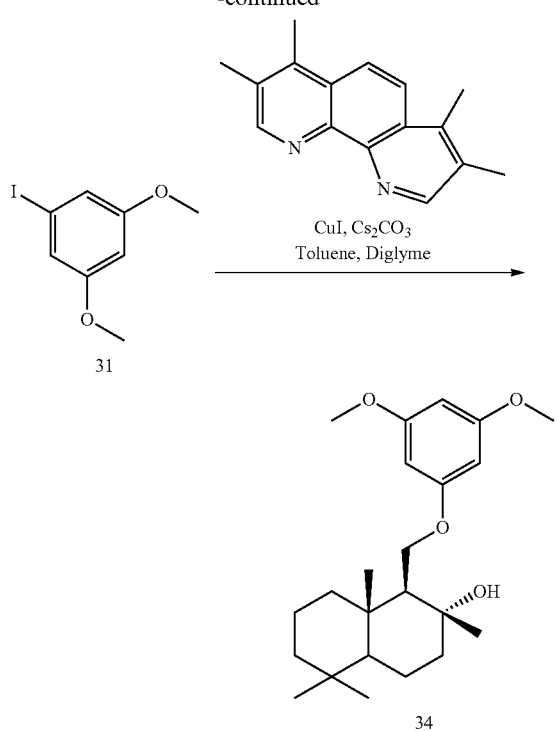

In a sealed tube purged with nitrogen, 1-iodo-3,5-dimethoxybenzene (Compound No. 31, 0.78 g, 2.95 mmol), (1S,2R,4aS,8aS)-1-(hydroxymethyl)-2,5,5,8a-tetramethyl-decahydronaphthalen-2-ol (Compound No. 26, 0.65 g, 2.68 mmol), $Cs_2CO_3$ (1.3 g, 3.99 mmol), 3,4,7,8-tetramethyl-[1,10]-phenylthroline (0.12 g, 0.50 mmol), CuI (0.05 g, 0.26 mmol), diglyme (2 mL) and toluene (10 mL) were added. The reaction mixture was stirred at 120° C. for 18 h. The reaction was cooled to room temperature, diluted with EtOAc (300 mL) and washed with water (100 mL). The organic layer was dried ($Na_2SO_4$) and concentrated. Purification by column chromatography on silica gel (Hexanes/EtOAc, 2:1) gave (1S,2R,4aS,8aS)-1-(3,5-dimethoxyphenoxymethyl)-2,5,5,8a-tetramethyl-decahydronaphthalen-2-ol (Compound No. 34, 0.71 g, 70%) as a colorless oil. $^1H$ NMR ($CDCl_3$): δ6.08 (s, 3H), 4.20 (m, 2H), 3.75 (s, 6H), 3.08 (s, 1H), 1.95-1.30 (m, 10H), 1.30 (s, 3H), 1.25-1.00 (m, 2H), 0.90 (s, 6H), 0.88 (m, 2H), 0.80 (s, 3H).

EXAMPLE 21

Synthesis of (1S,2R,4aS,8aS)-1-[3,5-bis(propan-2-yloxy)phenoxymethyl]-2,5,5,8a-tetramethyl-decahydronaphthalen-2-ol (Compound No. 37)

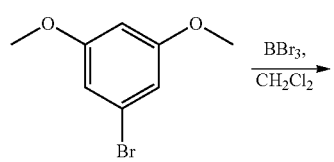

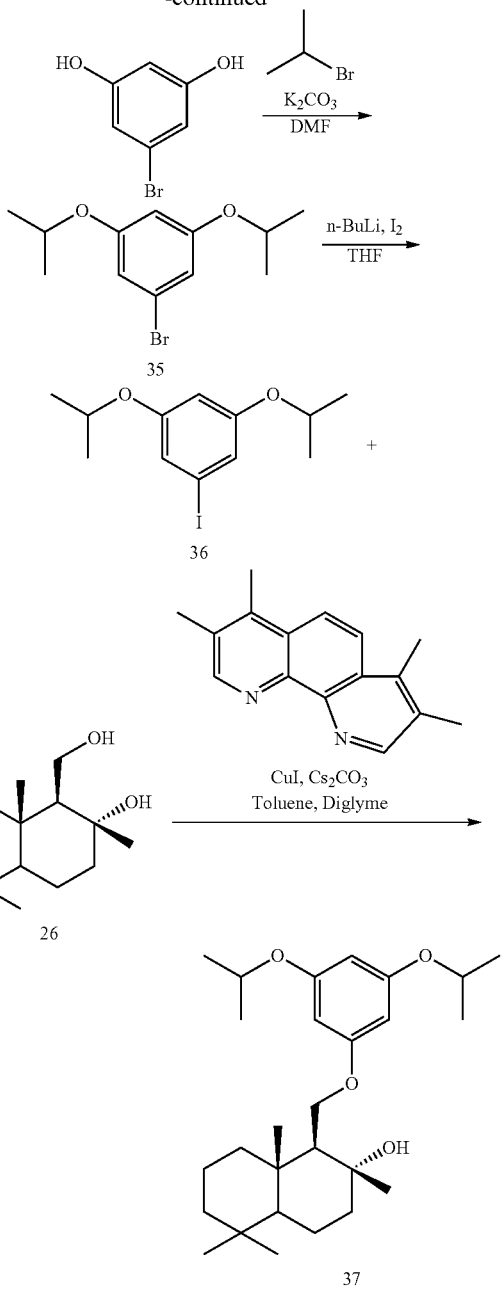

A. To a solution of 1-bromo-3,5-dimethoxybenzene (15.0 g, 69.0 mmol) in $CH_2Cl_2$ (40 mL) at 0° C. under argon was added dropwise a 1 M $BBr_3$ solution in $CH_2Cl_2$ (140 mL, 140 mmol). The ice bath was removed and the reaction was stirred at room temperature for 18 h. The reaction was quenched with MeOH and concentrated. The residue was dissolved in EtOAc (500 mL) and washed with water (300 mL). The organic layer was separated, dried ($Na_2SO_4$) and concentrated to give 5-bromobenzene-1,3-diol (13.03 g, 69.0 mmol) as an orange oil.

B. To a solution of 5-bromobenzene-1,3-diol (13.03 g, 69.0 mmol) in DMF (150 mL) under argon was added $K_2CO_3$ (38.08 g, 276 mmol) followed by 2-bromopropane (26.0 mL, 276 mmol). The mixture was heated to 60° C. and stirred for 18 h. The reaction was cooled to room temperature, quenched with water (700 mL) and extracted with EtOAc (3×300 mL). The organic layer was separated, dried (Na₂SO₄) and concentrated. Purification by column chromatography on silica gel (Hexanes/EtOAc, 10:1) gave 1-bromo-3,5-bis(propan-2-yloxy)benzene (Compound No. 35, 17.6 g, 93%) as an orange oil.

C. To a solution of 1-bromo-3,5-bis(propan-2-yloxy)benzene (Compound No. 35, 2.0 g, 7.32 mmol) in THF (100 mL) at −78° C. under argon was added dropwise a 1.6 M n-BuLi solution in hexanes (9.16 mL, 14.65 mmol). The temperature was maintained at −78° C. for 30 min, after which a solution of iodine (3.17 g, 29.3 mmol) in THF (15 mL) was added dropwise. The mixture was warmed to −35° C. and maintained at this temperature for 1.5 h. ¹H NMR indicated that the reaction was complete. The reaction mixture was diluted with EtOAc (100 mL) and washed with water (2×50 mL) and brine (50 mL). The organic layer was separated, dried (Na₂SO₄) and concentrated. Purification by column chromatography on silica gel (Hexanes/EtOAc, 4:1) gave 1-iodo-3,5-bis(propan-2-yloxy)benzene (Compound No. 36, 1.85 g, 79%) as a viscous orange oil.

D. In a sealed tube purged with nitrogen, 1-iodo-3,5-bis(propan-2-yloxy)benzene (Compound No. 36, 1.85 g, 5.78 mmol), (1S,2R,4aS,8aS)-1-(hydroxymethyl)-2,5,5,8a-tetramethyl-decahydronaphthalen-2-ol (Compound No. 26, 1.26 g, 5.25 mmol), Cs₂CO₃ (2.56 g, 7.87 mmol), 3,4,7,8-tetramethyl-[1,10]-phenylthroline (0.25 g, 1.04 mmol), CuI (0.10 g, 0.70 mmol), diglyme (5 mL) and toluene (20 mL) were placed. The reaction mixture was stirred at 120° C. for 18 h. The reaction was cooled to room temperature, diluted with EtOAc (600 mL) and washed with water (200 mL). The solid material was removed by filtration. The organic layer was separated, dried (Na₂SO₄) and concentrated. Purification by column chromatography on silica gel (Hexanes/EtOAc, 4:1) gave (1S,2R,4aS,8aS)-1-[3,5-bis(propan-2-yloxy)phenoxymethyl]-2,5,5,8a-tetramethyl-decahydronaphthalen-2-ol (Compound No. 37, 1.50 g, 66%) as a colorless oil. ¹H NMR (CDCl₃): δ6.05 (s, 3H), 4.47 (m, 2H), 4.20 (m, 2H), 3.28 (s, 1H), 1.95-1.35 (m, 8H), 1.32 (d, 12H), 1.30 (s, 3H), 1.29-1.00 (m, 4H), 0.90 (s, 3H), 0.88 (s, 3H), 0.80 (s, 3H).

EXAMPLE 22

Synthesis of 5-{[(1S,2R,4aS,8aS)-2-hydroxy-2,5,5,8a-tetramethyl-decahydronaphthalen-1-yl]methoxy}benzene-1,3-diol (Compound No. 38)

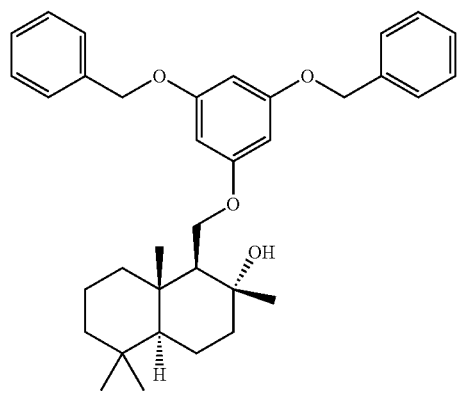

33

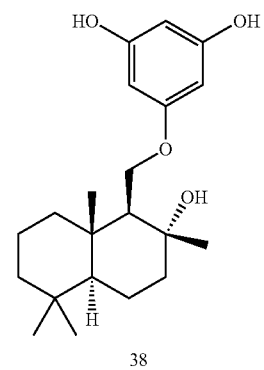

38

To a solution of (1S,2R,4aS,8aS)-1-[3,5-bis(benzyloxy)phenoxymethyl]-2,5,5,8a-tetramethyl-decahydronaphthalen-2-ol (Compound No. 33, 0.30 g, 0.57 mmol) in EtOH (10 mL) was added 10% Pd/C (0.06 g) and ammonium formate (0.63 g, 10 mmol) and the solution refluxed for 2 h then cooled to room temperature and stirred 2 d. The reaction was filtered through Celite, washed with MeOH (75 mL), and concentrated. The residue was re-dissolved in EtOAc (25 mL) and washed with water (15 mL) and brine (20 mL). The organic layer was dried (MgSO₄) and concentrated then purified by chromatography on silica gel (EtOAc/hexanes, 12:88 to 40:60) to give 5-{[(1S,2R,4aS,8aS)-2-hydroxy-2,5,5,8a-tetramethyl-decahydronaphthalen-1-yl]methoxy}benzene-1,3-diol (Compound No. 38, 141 mg, 71%) as a white foam. ¹H NMR (CDCl₃): δ7.10 (br s, 2H), 6.01 (s, 1H), 5.97 (d, J=2.1 Hz, 2H), 4.5 (br s, 1H), 4.26-4.12 (m, 2H), 1.99-1.82 (m, 2H), 1.78-1.50 (m, 5H), 1.48-1.32 (m, 2H), 1.31 (s, 3H), 1.29-0.90 (m, 3H), 0.87 (s, 6H), 0.80 (s, 3H). ES-MS m/z 331 ([M−17]⁺).

EXAMPLE 23

Synthesis of (4aS,8aS)-N-(3,5-dimethoxyphenyl)-2,5,5,8a-tetramethyl-3,4,4a,5,6,7,8,8a-octahydronaphthalene-1-carboxamide (Compound No. 41)

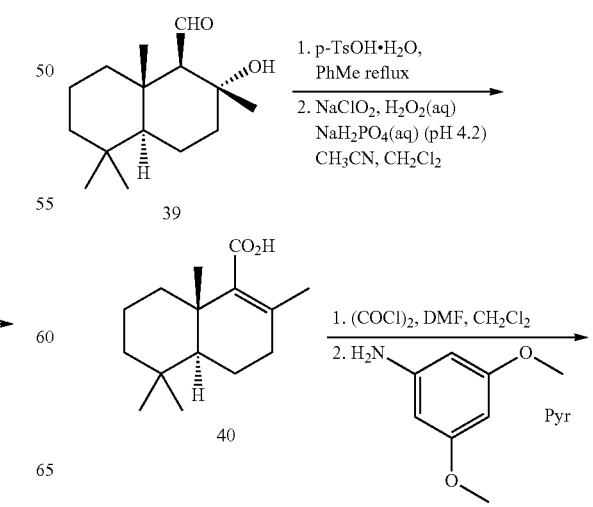

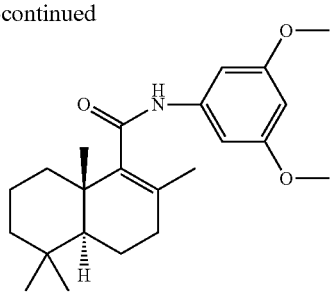

41

A. A solution of (1R,2R,4aS,8aS)-2-hydroxy-2,5,5,8a-tetramethyl-decahydronaphthalene-1-carbaldehyde (Compound No. 39, prepared according to Andersen, R. et al. PCT Int. Patent Appl. WO 2007/147251 A1, 2.94 g, 12.3 mmol) and p-TsOH.H₂O (117 mg, 0.615 mmol) in toluene (100 mL) under argon was heated to reflux under a Dean-Stark trap for 1 h 45 min. The solution was washed with saturated aqueous NaHCO₃ (25 mL), and the aqueous layer was extracted with EtOAc (15 mL). The combined organic layers were dried (Na₂SO₄) and concentrated. The residue was purified by chromatography on silica gel (EtOAc/hexanes, 1:99 then 98:2) to give (4aS,8aS)-2,5,5,8a-tetramethyl-3,4,4a,5,6,7,8,8a-octahydronaphthalene-1-carbaldehyde (1.33 g, 49%) as colorless crystals.

B. A solution of NaClO₂ (440 mg, 3.89 mmol) in water (7.8 mL) was added to a mixture of (4aS,8aS)-2,5,5,8a-tetramethyl-3,4,4a,5,6,7,8,8a-octahydronaphthalene-1-carbaldehyde (612 mg, 2.78 mmol), aqueous NaH₂PO₄ (2.6 mL, pH 4.2), 50% aqueous H₂O₂ (0.18 mL, 3.1 mmol), CH₃CN (5.6 mL), and CH₂Cl₂ (0.5 mL) then stirred at room temperature for 19.5 h. The mixture was diluted with water (10 mL), and excess peroxide was destroyed with solid Na₂SO₃. The aqueous phase was extracted with CH₂Cl₂ (4×10 mL) then dried (Na₂SO₄) and concentrated to give (8aS)-2,5,5,8a-tetramethyl-3,4,4a,5,6,7,8,8a-octahydronaphthalene-1-carboxylic acid (Compound No. 40, 582 mg, 89%) as colorless crystals.

C. To a solution of (4aS,8aS)-2,5,5,8a-tetramethyl-3,4,4a,5,6,7,8,8a-octahydronaphthalene-1-carboxylic acid (Compound No. 40, 148 mg, 0.626 mmol) in CH₂Cl₂ (6 mL) under argon was added DMF (cat.) and oxalyl chloride (0.16 mL, 1.8 mmol) then stirred at room temperature for 1 h. The solution was concentrated then azeotroped with CH₂Cl₂ (3×8 mL). The acid chloride residue was dissolved in pyridine (3 mL), and 3,5-dimethoxyaniline (101 mg, 0.659 mmol) was added. The solution was stirred at room temperature for 1.5 h then concentrated. The residue was dissolved in EtOAc (30 mL), washed with saturated aqueous NaHCO₃ (2×10 mL) and brine (10 mL) then dried (Na₂SO₄) and concentrated. The residue was purified by chromatography on silica gel (EtOAc/hexanes, 1:9) to give (4aS,8aS)-N-(3,5-dimethoxyphenyl)-2,5,5,8a-tetramethyl-3,4,4a,5,6,7,8,8a-octahydronaphthalene-1-carboxamide (Compound No. 41, 56 mg, 24%) as a yellow foam.

EXAMPLE 24

Synthesis of (4aS,8aS)-N-(3-hydroxy-5-methoxyphenyl)-2,5,5,8a-tetramethyl-3,4,4a,5,6,7,8,8a-octahydronaphthalene-1-carboxamide (Compound No. 42) and (4aS,8aS)-N-(3,5-dihydroxyphenyl)-2,5,5,8a-tetramethyl-3,4,4a,5,6,7,8,8a-octahydronaphthalene-1-carboxamide (Compound No. 43)

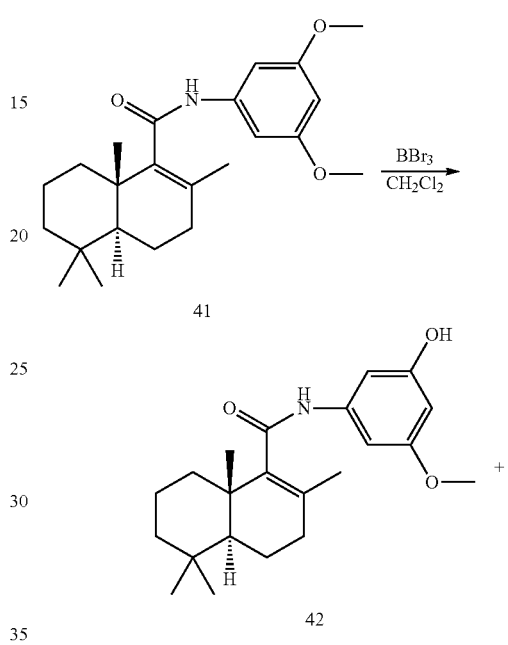

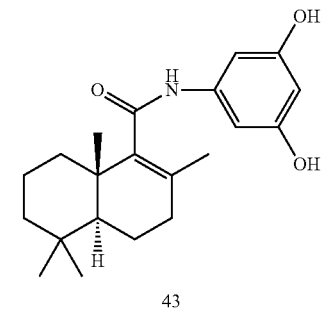

43

A. To a solution of (4aS,8aS)-N-(3,5-dimethoxyphenyl)-2,5,5,8a-tetramethyl-3,4,4a,5,6,7,8,8a-octahydronaphthalene-1-carboxamide (Compound No. 41, 56 mg, 0.15 mmol) in CH₂Cl₂ (3 mL) at −78° C. under argon was added BBr₃ (1.0 M in CH₂Cl₂, 0.60 mL, 0.60 mmol). The solution was stirred at −78° C. for 10 min then at room temperature for 2 h. Methanol (10 mL) was carefully added to the solution then concentrated (3×). The residue was dissolved in i-PrOH/10% aqueous HCl (3:1, 4 mL) and heated to 80° C. for 45 min. The solution was diluted with EtOAc (30 mL) and washed with brine (2×10 mL) then dried (MgSO₄) and concentrated. The residue was purified by chromatography on silica gel (hexanes/acetone, 4:1 then 3:2) to give (4aS,8aS)-N-(3-hydroxy-5-methoxyphenyl)-2,5,5,8a-tetramethyl-3,4,4a,5,6,7,8,8a-octahydronaphthalene-1-carboxamide (Compound No. 42, 16 mg, 30%) as a yellow solid and (4aS,8aS)-N-(3,5-dihydroxyphenyl)-2,5,5,8a-tetramethyl-3,4,4a,5,6,7,8,8a-octahydronaphthalene-1-carboxamide (Compound No. 43, 17 mg, 33%) as a yellow solid.

B. (8aS)-N-(3-hydroxy-5-methoxyphenyl)-2,5,5,8a-tetramethyl-3,4,4a,5,6,7,8,8a-octahydro-naphthalene-1-carboxamide (Compound No. 42): $^1$H NMR (CDCl$_3$): δ8.38 (brs, 1H), 7.61 (m, 1H), 7.06 (s, 1H), 6.26 (m, 1H), 6.16 (m, 1H), 3.75 (s, 3H), 2.09 (m, 2H), 0.87-1.70 (m, 21H). ES-MS m/z 358 ([M+1]$^+$).

C. (8aS)-N-(3,5-dihydroxyphenyl)-2,5,5,8a-tetramethyl-3,4,4a,5,6,7,8,8a-octahydronaphthalene-1-carboxamide (Compound No. 43): $^1$H NMR (CDCl$_3$): δ7.75 (br s, 2H), 7.18 (s, 1H), 6.79 (s, 1H), 6.75 (s, 1H), 6.26 (s, 1H), 2.05 (m, 2H), 1.65-0.82 (m, 21 H). ES-MS m/z 344 ([M+1]$^+$).

EXAMPLE 25

Synthesis of 2-[(1R,2R,4aS,8aS)-2-hydroxy-2,5,5,8a-tetramethyl-decahydronaphthalen-1-yl]-1-(3,5-dimethoxyphenyl)ethan-1-one (Compound No. 45)

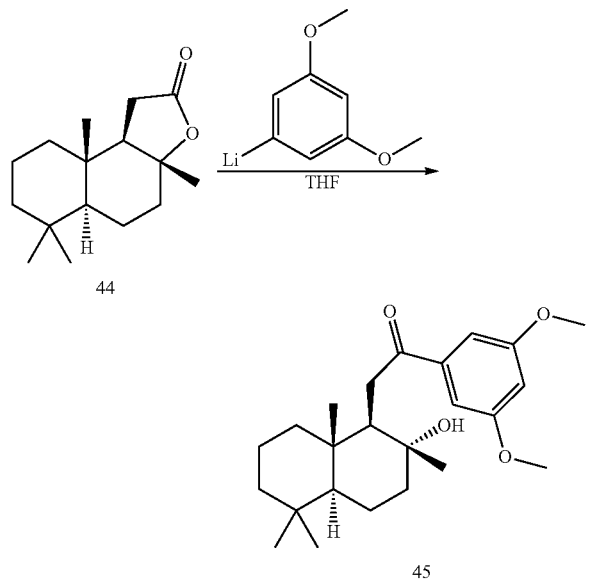

To a solution of 1-bromo-3,5-dimethoxybenzene (3.34 g, 15.4 mmol) in THF (28 mL) under argon at −78° C. was added n-BuLi (2.2 M in hexanes, 6.35 mL, 14.0 mmol). The solution was stirred at −78° C. for 15 min then added via cannula to a solution of sclareolide (Compound No. 44, 3.50 g, 14.0 mmol) in THF (28 mL) at −78° C. After stirring at −78° C. for 2.5 h, saturated aqueous NH$_4$Cl (25 mL) was added, and the mixture was allowed to warm to room temperature. The mixture was acidified with 1N HCl (25 mL), and the aqueous phase was extracted with EtOAc (30 mL). The combined organic layers were washed with brine (20 mL) then dried (MgSO$_4$) and concentrated. The residue was purified by chromatography on silica gel (EtOAc/hexanes, 1:4) to give 2-[(1R,2R,4aS,8aS)-2-hydroxy-2,5,5,8a-tetramethyl-decahydronaphthalen-1-yl]-1-(3,5-dimethoxyphenyl)ethan-1-one (Compound No. 45, 3.06 g, 56%) as colorless crystals. $^1$H NMR (CDCl$_3$): δ7.13 (d, J=2.4 Hz, 2H), 6.64 (t, J=2.4 Hz, 1H), 3.84 (s, 6H), 3.06 (dd, J=18, 5.0 Hz, 1H), 2.94 (dd, J=18, 5.1 Hz, 1H), 2.19 (t, J=5.1 Hz, 1H), 1.97 (m, 1H), 1.71 (m, 1H), 1.59-1.24 (m, 7H), 1.12 (s, 3H), 1.11 (m, 2H), 0.92 (m, 1H), 0.88 (s, 3H), 0.87 (s, 3H), 0.80 (s, 3H). ES-MS m/z 371 ([M−17]$^+$).

EXAMPLE 26

Synthesis of 2-[(1S,2S,4aS,8aR)-2,5,5,8a-tetramethyl-decahydronaphthalen-1-yl]-1-(3,5-dimethoxyphenyl)ethan-1-one (Compound No. 46)

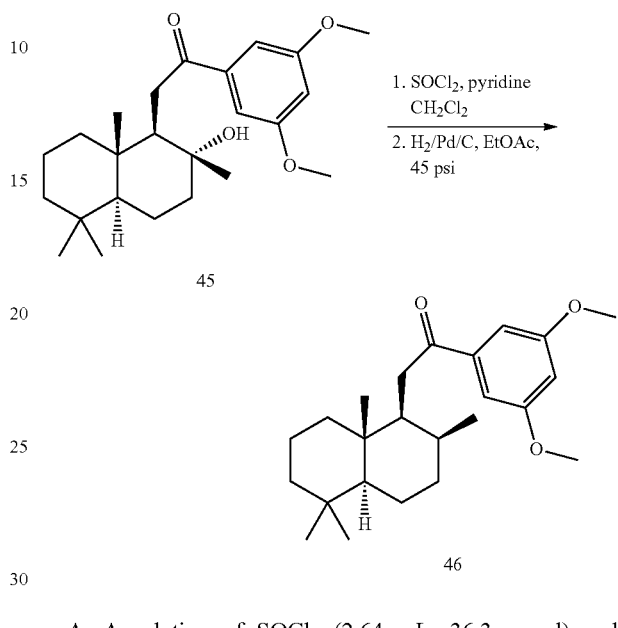

A. A solution of SOCl$_2$ (2.64 mL, 36.3 mmol) and pyridine (4.70 mL, 58.1 mmol) in CH$_2$Cl$_2$ (18 mL) was added to a solution of 2-[(1R,2R,4aS,8aS)-2-hydroxy-2,5,5,8a-tetramethyl-decahydronaphthalen-1-yl]-1-(3,5-dimethoxyphenyl)ethan-1-one (Compound No. 45, 2.82 g, 7.26 mmol) and pyridine (1.17 mL, 14.5 mmol) in CH$_2$Cl$_2$ (73 mL) at −78° C. under argon. After stirring at −78° C. for 55 min, saturated aqueous NaHCO$_3$ (30 mL) was added, and the mixture was allowed to warm to room temperature. The aqueous phase was extracted with CH$_2$Cl$_2$ (2×10 mL), and the combined organic layers were dried (MgSO$_4$), concentrated, and azeotroped with hexanes (3×30 mL). The residue was filtered through silica gel using 5% EtOAc/hexanes to give a colorless oil (2.43 g) that was used in the next step without further purification.

B. To a solution of the colorless oil from above (2.43 g) in EtOAc (20 mL) was added 10% Pd/C (224 mg) then shaken under an atmosphere of H$_2$(g) at 45 psi for 2 h. The mixture was filtered through Celite then concentrated. The residue was dissolved in THF (66 mL), cooled to 0° C. under argon, and BH$_3$.THF (1.0 M in THF, 4.6 mL, 4.6 mmol) was added. After stirring at room temperature for 1.5 h, the solution was cooled to 0° C. and 10 N NaOH (0.62 mL, 6.2 mmol) was added followed by 50% aqueous H$_2$O$_2$(0.53 mL, 9.2 mmol). The mixture was stirred at room temperature for 0.5 h then at 60° C. for 1 h. The mixture was diluted with water (20 mL), excess peroxide was destroyed with solid Na$_2$SO$_3$ and the organic layer was washed with brine (15 mL). The combined aqueous layers were extracted with EtOAc (20 mL), and the combined organic layers were dried (MgSO$_4$) and concentrated. The residue was purified by chromatography on silica gel (EtOAc/hexanes, 2:98) to give 2-[(1S,2S,4aS,8aR)-2,5,5,8a-tetramethyl-decahydronaphthalen-1-yl]-1-(3,5-dimethoxyphenyl)ethan-1-one (Compound No. 46, 947 mg, 35% over 2 steps) as colorless crystals. $^1$H NMR (CDCl$_3$): δ7.11 (d, J=2.4 Hz, 2H), 6.64 (t, J=2.4 Hz, 1H), 3.84 (s, 6H), 2.85 (dd, J=18, 3.2 Hz, 1H), 2.75 (dd, J=19, 6.2 Hz, 1H), 1.84-1.72 (m, 2H), 1.65-0.82 (m, 20H), 0.68 (d, J=6.6 Hz, 3H). ES-MS m/z 373 ([M+1]+).

EXAMPLE 27

Synthesis of 2-[(1S,2S,4aS,8aR)-2,5,5,8a-tetramethyl-decahydronaphthalen-1-yl]-1-(3-hydroxy-5-methoxyphenyl)ethan-1-one (Compound No. 47) and 2-[(1S,2S,4aS,8aR)-2,5,5,8a-tetramethyl-decahydronaphthalen-1-yl]-1-(3,5-dihydroxyphenyl)ethan-1-one (Compound No. 48)

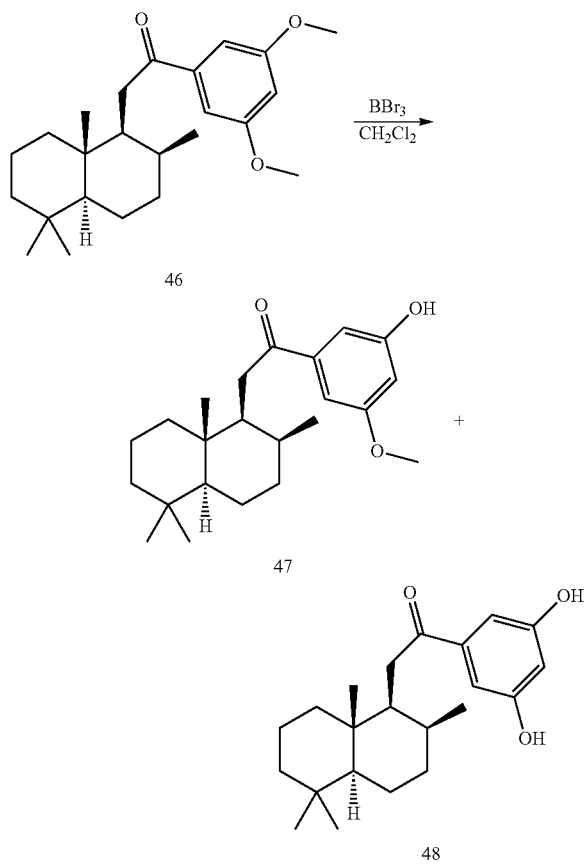

A. A solution of 2-[(1S,2S,4aS,8aR)-2,5,5,8a-tetramethyl-decahydronaphthalen-1-yl]-1-(3,5-dimethoxyphenyl)ethan-1-one (Compound No. 46, 200 mg, 0.537 mmol) in CH$_2$Cl$_2$ (5.4 mL) was cooled to −78° C. under argon. BBr$_3$ (1.0 M in CH$_2$Cl$_2$, 2.15 mL, 2.15 mmol) was added, and the solution was stirred at room temperature for 2 h. Methanol (5 mL) was carefully added to the solution then concentrated (3×). The residue was dissolved in i-PrOH/10% aqueous HCl (3:1, 5.5 mL) and heated to 85° C. for 35 min. The solution was concentrated, diluted with EtOAc (30 mL), washed with brine (2×10 mL) then dried (MgSO$_4$) and concentrated. The residue was purified by chromatography on silica gel (EtOAc/hexanes, 3:7) to give 2-[(1S,2S,4aS,8aR)-2,5,5,8a-tetramethyl-decahydronaphthalen-1-yl]-1-(3-hydroxy-5-methoxyphenyl)ethan-1-one (Compound No. 47, 37 mg, 19%) as a colorless foam and 2-[(1S,2S,4aS,8aR)-2,5,5,8a-tetramethyl-decahydronaphthalen-1-yl]-1-(3,5-dihydroxyphenyl)ethan-1-one (Compound No. 48, 149 mg, 81%) as a colorless foam. 2-[(1S,2S,4aS,8aR)-2,5,5,8a-Tetramethyl-decahydronaphthalen-1-yl]-1-(3-hydroxy-5-methoxyphenyl)ethan-1-one (Compound No. 47): $^1$H NMR (CDCl$_3$): δ7.11 (m, 2H), 6.63 (m, 1H), 5.81 (s, 1H), 3.83 (s, 3H), 2.84 (dd, J=19, 3.3 Hz, 1H), 2.45 (dd, J=19, 6.0 Hz, 1H), 1.82-1.71 (m, 2H), 1.73-0.82 (m, 20H), 0.67 (d, J=6.3 Hz, 3H). ES-MS m/z 359 ([M+1]+). 2-[(1S,2S,4aS,8aR)-2,5,5,8a-tetramethyl-decahydronaphthalen-1-yl]-1-(3,5-dihydroxyphenyl)ethan-1-one (Compound No. 48): $^1$H NMR (CDCl$_3$): δ7.08 (d, J=2.4 Hz, 2H), 6.58 (t, J=2.1 Hz, 1H), 5.43 (s, 2H), 2.83 (dd, J=19. 3.2 Hz, 1H), 2.73 (dd, J=19, 6.2 Hz, 1H), 1.76 (m, 2H), 1.66-0.82 (m, 20H), 0.66 (d, J=6.3 Hz, 3H). ES-MS m/z 345 ([M+1]+).

EXAMPLE 28

Synthesis of (1S,2R,4aS,8aS)-1-[(3,5-dimethoxyphenyl)(hydroxy)methyl]-2,5,5,8a-tetramethyl-decahydronaphthalen-2-ol (Compound No. 49)

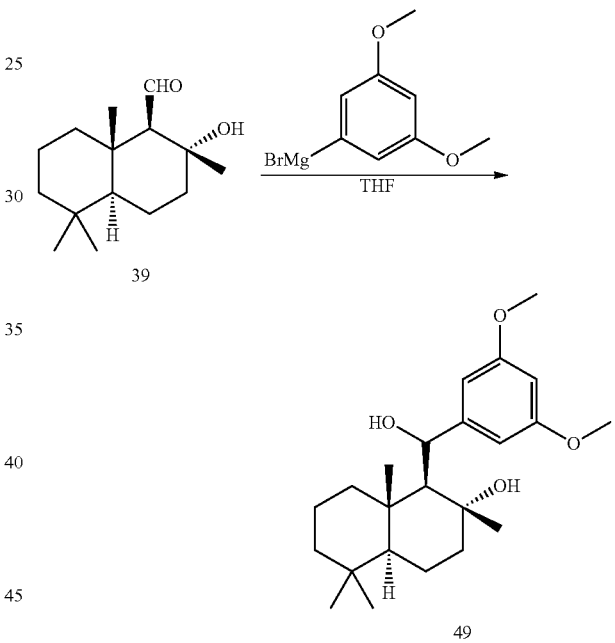

To dried magnesium turnings (530 mg, 21.8 mmol) under argon was added THF (7 mL) followed by 1,2-dibromoethane (0.18 mL, 2.1 mmol) and a few drops of a solution of 1-bromo-3,5-dimethoxybenzene (4.73 g, 21.8 mmol) in THF (15 mL). Once the reaction initiated, the remainder of the 1-bromo-3,5-dimethoxybenzene solution was added over 10 min. After stirring at room temperature for 1 h, the mixture was cooled to −15° C. and a solution of (1R,2R,4aS,8aS)-2-hydroxy-2,5,5,8a-tetramethyl-decahydronaphthalene-1-carbaldehyde (Compound No. 39, 2.60 g, 10.9 mmol) in THF (20 mL) was added over 10 min. The mixture was stirred at −15° C. for 0.5 h then 0° C. for 2.5 h. The mixture was acidified to pH 2 using 10% aqueous HCl then diluted with water (20 mL) and EtOAc (60 mL). The organic phase was washed with brine (10 mL) then dried (MgSO$_4$) and concentrated. The residue was purified by chromatography on silica gel (EtOAc/hexanes, 1:3 to 3:7) to give (1S,2R,4aS,8aS)-1-[(3,5-dimethoxyphenyl)(hydroxy)methyl]-2,5,5,8a-tetramethyl-decahydronaphthalen-2-ol (Compound No. 49, 1.01 g, 25%) as a colorless foam. $^1$H NMR (CDCl$_3$): δ6.61 (d, J=2.4 Hz, 2H), 6.37 (t, J=2.3 Hz, 1H), 4.80 (dd, J=8.1, 3.9 Hz, 1H), 4.02 (s, 1H), 3.81 (s, 6H), 2.76 (d, J=3.9 Hz, 1H), 2.12 (d, J=7.8 Hz, 1H), 1.85 (m, 1H), 1.68-1.17 (m, 9H), 1.04 (s, 3H), 0.96 (m, 2H), 0.84 (s, 3H), 0.79 (s, 3H), 0.42 (m, 1H).

EXAMPLE 29

Synthesis of (1R,2R,4aS,8aS)-1-[(3,5-dimethoxyphenyl)carbonyl]-2,5,5,8a-tetramethyl-decahydronaphthalen-2-ol (Compound No. 50)

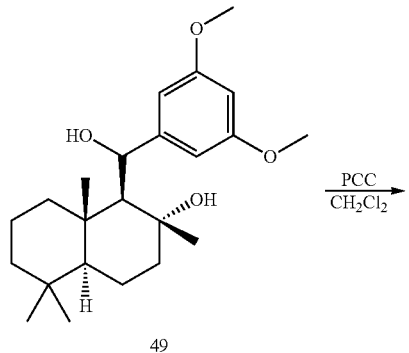

To a solution of (1S,2R,4aS,8aS)-1-[(3,5-dimethoxyphenyl)(hydroxy)methyl]-2,5,5,8a-tetramethyl-decahydronaphthalen-2-ol (Compound No. 49, 3.01 g, 7.99 mmol) in CH$_2$Cl$_2$ (32 mL) was added PCC (1.90 g, 8.81 mmol) and the mixture was stirred at room temperature for 2 h then filtered and concentrated. The residue was purified by chromatography on silica gel (EtOAc/hexanes, 3:17 to 1:4) to afford (1R,2R,4aS,8aS)-1-[(3,5-dimethoxyphenyl)carbonyl]-2,5,5,8a-tetramethyl-decahydronaphthalen-2-ol (Compound No. 50, 1.94 g, 65%) as a colorless foam. $^1$H NMR (CDCl$_3$): δ7.14 (d, J=2.1 Hz, 2H), 6.61 (t, J=2.3 Hz, 1H), 3.84 (s, 6H), 3.53 (s, 1H), 1.87 (m, 1H), 1.77-1.00 (m, 17H), 0.90 (s, 3H), 0.83 (s, 3H). ES-MS m/z 357 ([M-17]$^+$).

EXAMPLE 30

Synthesis of [(1S,4aS,8aS)-2,5,5,8a-tetramethyl-1,4,4a,5,6,7,8,8a-octahydronaphthalen-1-yl](3,5-dimethoxyphenyl)methanone (Compound No. 51)

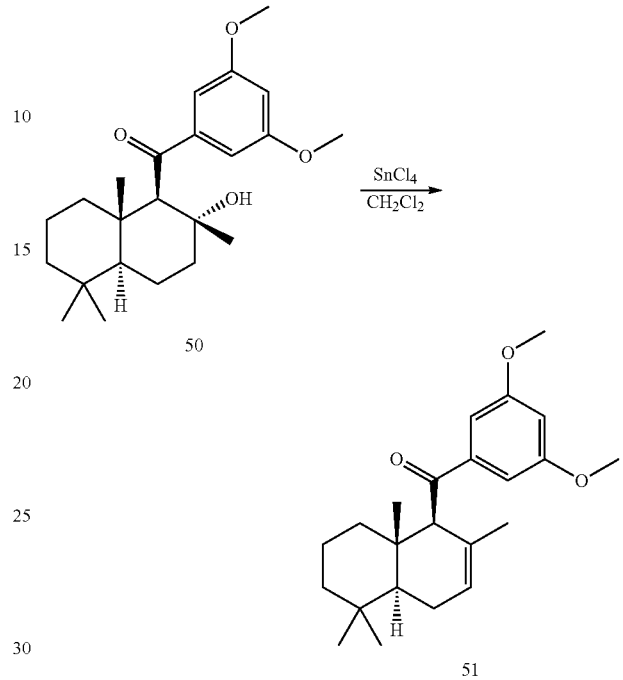

A solution of (1R,2R,4aS,8aS)-1-[(3,5-dimethoxyphenyl)carbonyl]-2,5,5,8a-tetramethyl-decahydronaphthalen-2-ol (Compound No. 50, 1.92 g, 5.13 mmol) in CH$_2$Cl$_2$ (70 mL) was cooled to 0° C. under argon and SnCl$_4$ (1.80 mL, 15.4 mmol) was added. The solution was stirred at 0° C. for 10 min then washed with water (30 mL). The aqueous phase was extracted with CH$_2$Cl$_2$ (2×10 mL), and the combined organic phases were washed with saturated aqueous NaHCO$_3$ (30 mL) then dried (MgSO$_4$) and concentrated. The residue was purified by chromatography on silica gel (EtOAc/hexanes, 1:19) to afford [(1S,4aS,8aS)-2,5,5,8a-tetramethyl-1,4,4a,5,6,7,8,8a-octahydronaphthalen-1-yl](3,5-dimethoxyphenyl)methanone (Compound No. 51, 1.54 g, 84%) as a colorless oil. $^1$H NMR (CDCl$_3$): δ7.06 (d, J=2.4 Hz, 2H), 6.63 (t, J=2.3 Hz, 1H), 5.62 (br s, 1H), 4.09 (br s, 1H), 3.85 (s, 6H), 2.02 (m, 2H), 1.55-1.13 (m, 10H), 0.96 (s, 3H), 0.91 (s, 3H), 0.90 (s, 3H). ES-MS m/z 357 ([M+1]$^+$).

EXAMPLE 31

Synthesis of (2R,3R,4S,4aS,8aS)-4-[(3,5-dimethoxyphenyl)carbonyl]-3,4a,8,8-tetramethyl-decahydronaphthalen-2-ol (Compound No. 52)

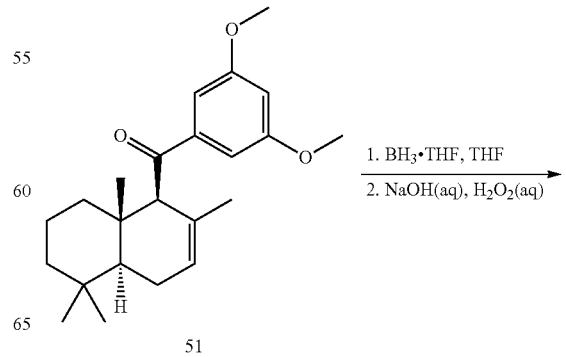

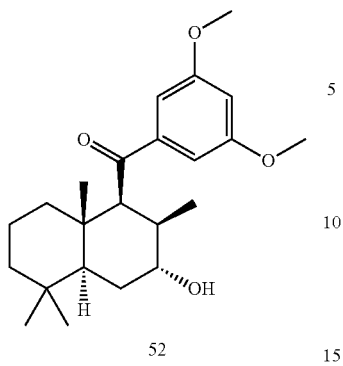

52

To a solution of [(1S,4aS,8aS)-2,5,5,8a-tetramethyl-1,4,4a,5,6,7,8,8a-octahydronaphthalen-1-yl](3,5-dimethoxyphenyl)methanone (Compound No. 51, 1.52 g, 4.26 mmol) in THF (100 mL) was added $BH_3$.THF (1.0 M in THF, 6.40 mL, 6.40 mmol) at 0° C. under argon. The solution was stirred at 0° C. for 10 min then room temperature for 1.5 h. The solution was cooled to 0° C., and a solution containing 15% aqueous NaOH (2.24 mL) and 50% aqueous $H_2O_2$ (0.74 mL, 13 mmol) was added dropwise. The mixture was stirred at room temperature for 20 min and 65° C. for 1 h then allowed to cool to room temperature. To the mixture was added saturated aqueous $NH_4Cl$ (30 mL) and acidified to pH 2 using concentrated HCl. The aqueous phase was extracted with EtOAc (30 mL), and the combined organic layers were dried ($MgSO_4$) and concentrated. The residue was purified by chromatography on silica gel (EtOAc/hexanes, 1:4) to afford (2R,3R,4S,4aS,8aS)-4-[(3,5-dimethoxyphenyl)carbonyl]-3,4a,8,8-tetramethyl-decahydronaphthalen-2-ol (Compound No. 52, 0.60 g, 38%) as colorless crystals. $^1$H NMR ($CDCl_3$): δ7.08 (d, J=2.4 Hz, 2H), 6.61 (t, J=2.4 Hz, 1H), 3.95 (br s, 1H), 3.83 (s, 6H), 3.70 (d, J=4.5 Hz, 1H), 2.14 (m, 1H), 1.84-1.18 (m, 12H), 0.98 (m, 4H), 0.89 (s, 3H), 0.86 (s, 3H). ES-MS m/z 375 ([M+1]$^+$).

EXAMPLE 32

Synthesis of (3R,4S,4aS,8aS)-4-[(3,5-dimethoxyphenyl)carbonyl]-3,4a,8,8-tetramethyl-decahydronaphthalen-2-one (Compound No. 53)

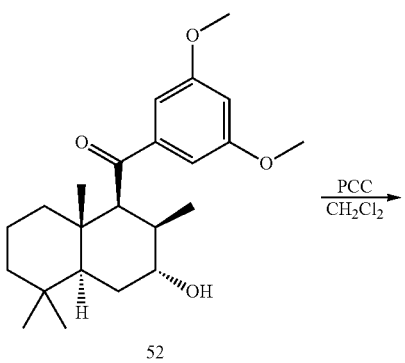

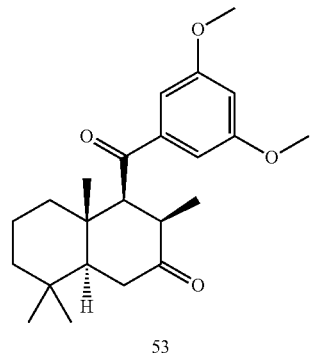

53

To a solution of (2R,3R,4S,4aS,8aS)-4-[(3,5-dimethoxyphenyl)carbonyl]-3,4a,8,8-tetramethyl-decahydronaphthalen-2-ol (Compound No. 52, 0.58 g, 1.5 mmol) in $CH_2Cl_2$ (15 mL) was added PCC (0.50 g, 2.3 mmol), and the mixture was stirred at room temperature for 4 h then filtered and concentrated. The residue was purified by chromatography on silica gel (EtOAc/hexanes, 3:17) to afford (3R,4S,4aS,8aS)-4-[(3,5-dimethoxyphenyl)carbonyl]-3,4a,8,8-tetramethyl-decahydronaphthalen-2-one (Compound No. 53, 543 mg, 93%) as a colorless oil. $^1$H NMR ($CDCl_3$): δ6.99 (d, J=2.4 Hz, 2H), 6.63 (t, J=2.1 Hz, 1H), 3.83 (s, 6H), 3.62 (d, J=6.6 Hz, 1H), 2.83 (m, 1H), 2.53 (dd, J=17, 13 Hz, 1H), 2.44 (dd, J=17, 4.2 Hz, 1H), 1.86 (m, 1H), 1.72-1.40 (m, 4H), 1.32 (s, 3H), 1.19 (m, 2H), 1.08 (d, J=7.5 Hz, 3H), 0.90 (s, 6H). ES-MS m/z 373 ([M+1]$^+$).

EXAMPLE 33

Synthesis of (2R,3S,4S,4aS,8aS)-4-[(3,5-dimethoxyphenyl)carbonyl]-N-[(4-methoxyphenyl)methyl]-3,4a,8,8-tetramethyl-decahydronaphthalen-2-amine (Compound No. 54)

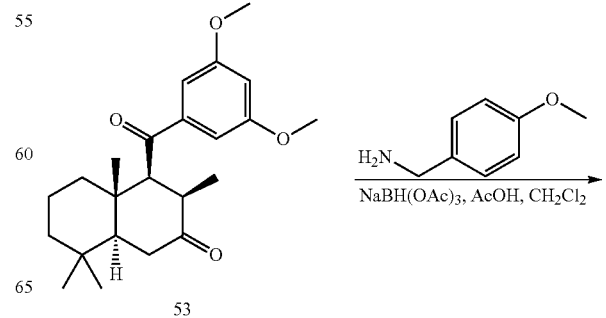

53

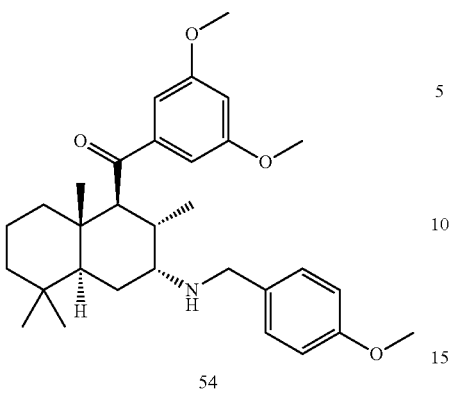

54

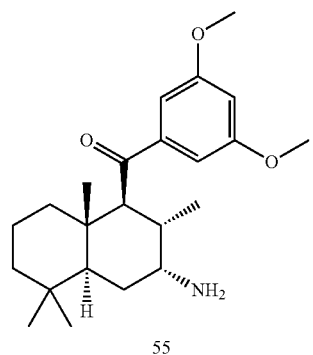

55

A mixture of (3R,4S,4aS,8S)-4-[(3,5-dimethoxyphenyl)carbonyl]-3,4a,8,8-tetramethyl-decahydronaphthalen-2-one (Compound No. 53, 531 mg, 1.43 mmol), 4-methoxybenzylamine (0.19 mL, 1.5 mmol), sodium triacetoxyborohydride (906 mg, 4.27 mmol), and AcOH (0.082 mL, 1.4 mmol) in $CH_2Cl_2$ (14 mL) was stirred at room temperature under argon for 22.5 h then washed with 1 N NaOH (10 mL). The aqueous phase was extracted with $CH_2Cl_2$ (3×10 mL), and the combined organic layers were dried ($MgSO_4$) and concentrated. The residue was purified by chromatography on silica gel (EtOAc/hexanes, 1:9) to afford (2R,3S,4S,4aS,8aS)-4-[(3,5-dimethoxyphenyl)carbonyl]-N-[(4-methoxyphenyl)methyl]-3,4a,8,8-tetramethyl-decahydronaphthalen-2-amine (Compound No. 54, 443 mg, 63%) as a colorless oil. $^1$H NMR ($CDCl_3$): δ7.27 (m, 2H), 7.07 (d, J=2.4 Hz, 2H), 6.88 (m, 2H), 6.61 (t, J=2.4 Hz, 1H), 3.84 (d, 1H), 3.84 (s, 6H), 3.82 (s, 3H), 3.54 (m, 2H), 2.87 (m, 1H), 2.34 (m, 1H), 1.86 (m, 1H), 1.66-1.06 (m, 12H), 0.92 (s, 3H), 0.86 (s, 3H), 0.75 (d, J=6.9 Hz, 3H). ES-MS m/z 494 ([M+1]$^+$).

To a suspension of (2R,3S,4S,4aS,8aS)-4-[(3,5-dimethoxyphenyl)carbonyl]-N-[(4-methoxyphenyl)methyl]-3,4a,8,8-tetramethyl-decahydronaphthalen-2-amine (Compound No. 54, 433 mg, 0.877 mmol) in MeOH (10 mL) was carefully added 10% aqueous HCl (0.5 mL) and 10% Pd/C (90 mg), and the mixture was stirred under $H_2$(g) at 1 atm at room temperature for 23 h. The mixture was filtered through Celite then concentrated. To the residue was added water (10 mL) then adjusted to pH 10 with 1 N NaOH. The mixture was extracted with $CH_2Cl_2$ (3×10 mL), and the combined organic extracts were dried ($MgSO_4$) and concentrated. The residue was purified by chromatography on silica gel ($CH_2Cl_2$/MeOH/$NH_4$OH, 200:2:1-200:10:1) to afford (2R,3S,4S,4aS,8aS)-4-[(3,5-dimethoxyphenyl)carbonyl]-3,4a,8,8-tetramethyl-decahydronaphthalen-2-amine (Compound No. 55, 208 mg, 63%) as colorless crystals. $^1$H NMR ($CDCl_3$): δ7.09 (d, J=1.8 Hz, 2H), 6.62 (t, J=2.3 Hz, 1H), 3.84 (s, 6H), 3.47 (d, J=11 Hz, 1H), 3.22 (m, 1H), 2.31 (m, 1H), 1.79-1.07 (m, 14H), 0.88 (s, 3H), 0.84 (s, 3H), 0.77 (d, J=7.2 Hz, 3H). ES-MS m/z 374 ([M+1]$^+$).

EXAMPLE 34

Synthesis of (2R,3S,4S,4aS,8aS)-4-[(3,5-dimethoxyphenyl)carbonyl]-3,4a,8,8-tetramethyl-decahydronaphthalen-2-amine (Compound No. 55)

EXAMPLE 35

Synthesis of 5-{[(1S,2S,3R,4aS,8aS)-3-amino-2,5,5,8a-tetramethyl-decahydronaphthalen-1-yl]carbonyl}benzene-1,3-diol (Compound No. 56)

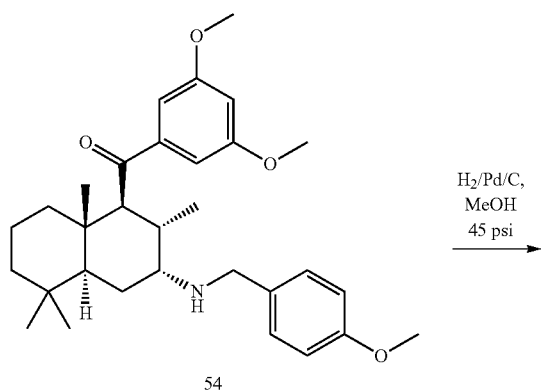

54

H$_2$/Pd/C,
MeOH
45 psi

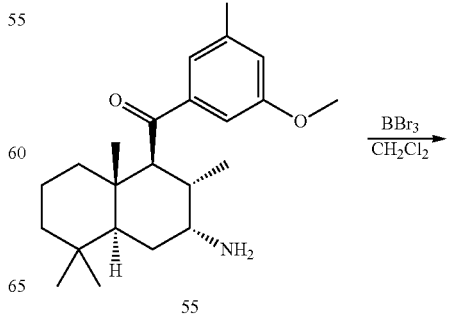

55

BBr$_3$
CH$_2$Cl$_2$

-continued

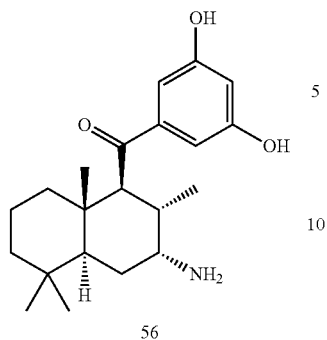

56

A solution of (2R,3S,4S,4aS,8aS)-4-[(3,5-dimethoxyphenyl)carbonyl]-3,4a,8,8-tetramethyl-decahydronaphthalen-2-amine (Compound No. 55, 197 mg, 0.527 mmol) in CH$_2$Cl$_2$ (5.3 mL) was cooled to −78° C. under argon, BBr$_3$ (1.0 M in CH$_2$Cl$_2$, 2.64 mL, 2.64 mmol) was added, and the solution was stirred at room temperature for 3.5 h. Methanol (10 mL) was carefully added to the solution then concentrated (3×). The residue was dissolved in i-PrOH/10% aqueous HCl (3:1, 5.5 mL) and heated to 85° C. for 40 min. The solution was concentrated, diluted with EtOAc (30 mL) and water (10 mL), then neutralized to pH 7 using 1N NaOH. The aqueous phase was extracted with EtOAc (10 mL), and the combined organic layers were dried (MgSO$_4$) and concentrated. The residue was purified by chromatography on silica gel (CH$_2$Cl$_2$/MeOH/NH$_4$OH, 100:10:1) to afford 5-{[(1S,2S,3R,4aS,8aS)-3-amino-2,5,5,8a-tetramethyl-decahydronaphthalen-1-yl]carbonyl}benzene-1,3-diol (Compound No. 56, 162 mg, 89%) as a yellow foam. $^1$H NMR (CD$_3$OD): δ6.88 (d, J=2.1 Hz, 2H), 6.47 (t, J=2.3 Hz, 1H), 3.45 (d, J=12 Hz, 1H), 3.27 (m, 1H), 2.31 (m, 1H), 1.78 (m, 2H), 1.55-1.18 (m, 6H), 1.06 (m, 4H), 0.92 (s, 3H), 0.87 (s, 3H), 0.77 (d, J=6.6 Hz, 3H). ES-MS m/z 346 ([M+1]$^+$).

EXAMPLE 36

Synthesis of N-[(2R,3S,4S,4aS,8aS)-4-[(3,5-dihydroxyphenyl)carbonyl]-3,4a,8,8-tetramethyl-decahydronaphthalen-2-yl]acetamide (Compound No. 57)

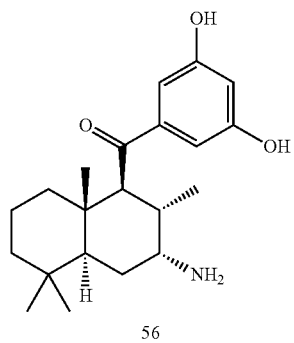

56

-continued

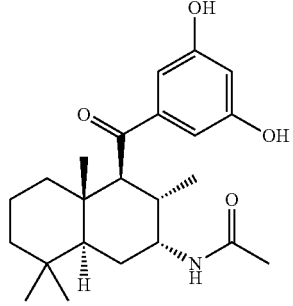

57

A. To a solution of 5-{[(1S,2S,3R,4aS,8aS-3-amino-2,5,5,8a-tetramethyl-decahydronaphthalen-1-yl]carbonyl}benzene-1,3-diol (Compound No. 56, 111 mg, 0.321 mmol), DMAP (4 mg, 0.03 mmol), and Et$_3$N (0.16 mL, 1.1 mmol) in THF (3.2 mL) at 0° C. was added Ac$_2$O (0.10 mL, 1.1 mmol), and the solution was stirred under argon at 0° C. for 5 min then room temperature for 3 h. The solution was concentrated, dissolved in EtOAc (40 mL), washed with saturated aqueous NaHCO$_3$ (5×10 mL) and brine (10 mL) then dried (MgSO$_4$) and concentrated. The yellow foam (150 mg) that was obtained was used in the next step without further purification.

B. To a solution of the yellow foam from above (150 mg) in MeOH (3.5 mL) was added 10 N NaOH (0.3 mL), and the solution was stirred at room temperature for 40 min then concentrated. The residue was diluted with water (10 mL) and neutralized to pH 7 with 10% aqueous HCl then the mixture was extracted with EtOAc (35 mL). The organic extract was washed with brine (10 mL) then dried (MgSO$_4$) and concentrated to afford N-[(2R,3S,4S,4aS,8aS)-4-[(3,5-dihydroxyphenyl)carbonyl]-3,4a,8,8-tetramethyl-decahydronaphthalen-2-yl]acetamide (Compound No. 57, 124 mg, 99% over 2 steps) as a light yellow solid. $^1$H NMR (CD$_3$OD): δ8.21 (d, J=9.3 Hz, 1H), 6.93 (d, J=2.4 Hz, 2H), 6.49 (t, J=2.1 Hz, 1H), 4.25 (m, 1H), 3.42 (d, J=12 Hz, 1H), 2.36 (m, 1H), 2.04 (s, 3H), 1.69-1.21 (m, 8H), 1.07 (m, 1H), 1.02 (s, 3H), 0.85 (s, 6H), 0.68 (d, J=6.6 Hz, 3H). ES-MS m/z 388 ([M+1]$^+$).

EXAMPLE 37

Synthesis of 5-{2-[(1S,2S,4aS,8aR)-2,5,5,8a-tetramethyl-decahydronaphthalen-1-yl]-1-hydroxyethyl}benzene-1,3-diol (Compound No. 58)

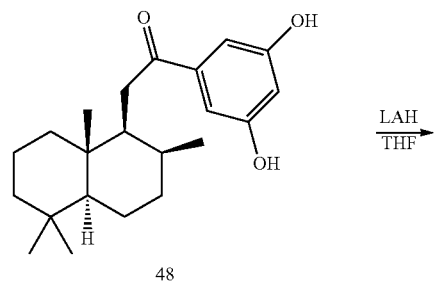

48

1. Ac$_2$O, DMAP Et$_3$N, THF
2. NaOH(aq)/MeOH

LAH / THF

-continued

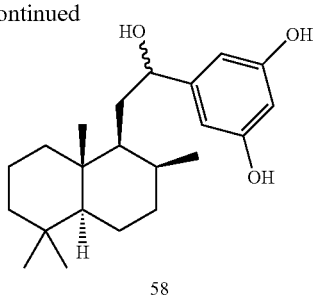

58

A solution of 2-[(1S,2S,4aS,8aR)-2,5,5,8a-tetramethyl-decahydronaphthalen-1-yl]-1-(3,5-dihydroxyphenyl)ethan-1-one (Compound No. 48, 473 mg, 1.37 mmol) in THF (14 mL) under argon was stirred at 0° C. while LiAlH$_4$ (182 mg, 4.80 mmol) was added. The solution was stirred at 0° C. for 0.5 h then room temperature for 1.5 h. The solution was treated with water (1 mL), acidified to pH 3 using 10% aqueous HCl then diluted with EtOAc (20 mL). The aqueous layer was extracted with EtOAc (2×20 mL), and the combined organic layers were washed with brine (10 mL) then dried (MgSO$_4$) and concentrated. The residue was heated to reflux in CH$_2$Cl$_2$ (15 mL) for 5 min then allowed to cool to room temperature. The insoluble material was collected by filtration to afford 5-{2-[(1S,2S,4aS,8aR)-2,5,5,8a-tetramethyl-decahydronaphthalen-1-yl]-1-hydroxyethyl}benzene-1,3-diol (Compound No. 58, 375 mg, 79%) as a colorless solid (1:1 mixture of epimers). $^1$H NMR (CD$_3$OD): δ6.30 (m, 4H), 6.16 (t, J=2.1 Hz, 1H), 6.14 (t, J=2.1 Hz, 1H), 4.41 (m, 2H), 1.88-0.68 (m, 19H), 0.59 (m, 2H), 0.15 (m, 2H). ES-MS m/z 329 ([M−17]$^+$).

EXAMPLE 38

Synthesis of 2-[(1S,2S,4aS,8aR)-2,5,5,8a-tetramethyl-decahydronaphthalen-1-yl]-1-(3,5-dimethoxyphenyl)ethan-1-ol (Compound No. 59)

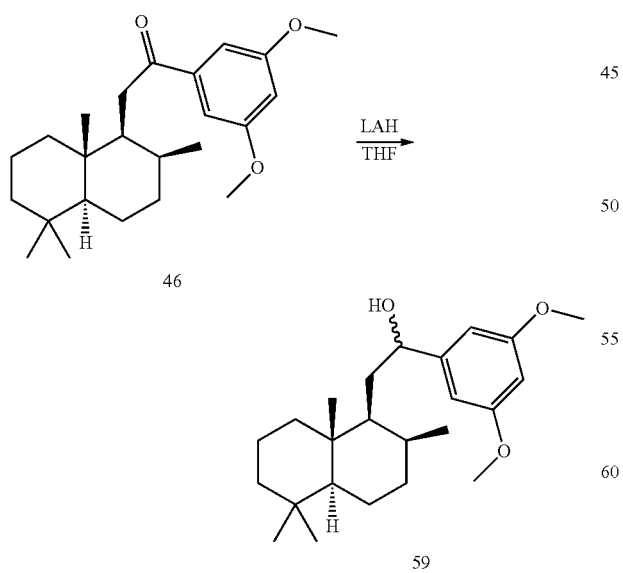

A solution of 2-[(1S,2S,4aS,8aR)-2,5,5,8a-tetramethyl-decahydronaphthalen-1-yl]-1-(3,5-dimethoxyphenyl)ethan-1-one (Compound No. 46, 128 mg, 0.344 mmol) in THF (3.5 mL) under argon was stirred at 0° C. while LiAlH$_4$ (13 mg, 0.34 mmol) was added. The solution was stirred at 0° C. for 15 min then water (0.013 mL) was added followed by 15% aqueous NaOH (0.013 mL) and water (0.039 mL). The mixture was stirred at room temperature for 10 min then diluted with EtOAc (10 mL), dried (MgSO$_4$), filtered and concentrated to give 2-[(1S,2S,4aS,8aR)-2,5,5,8a-tetramethyl-decahydronaphthalen-1-yl]-1-(3,5-dimethoxyphenyl)ethan-1-ol (Compound No. 59, 124 mg, 96%) as a colorless oil.

EXAMPLE 39

Synthesis of (4aR,5S,6S,8aS)-5-[2-(3,5-dimethoxyphenyl)ethyl]-1,1,4a,6-tetramethyl-decahydronaphthalene (Compound No. 61)

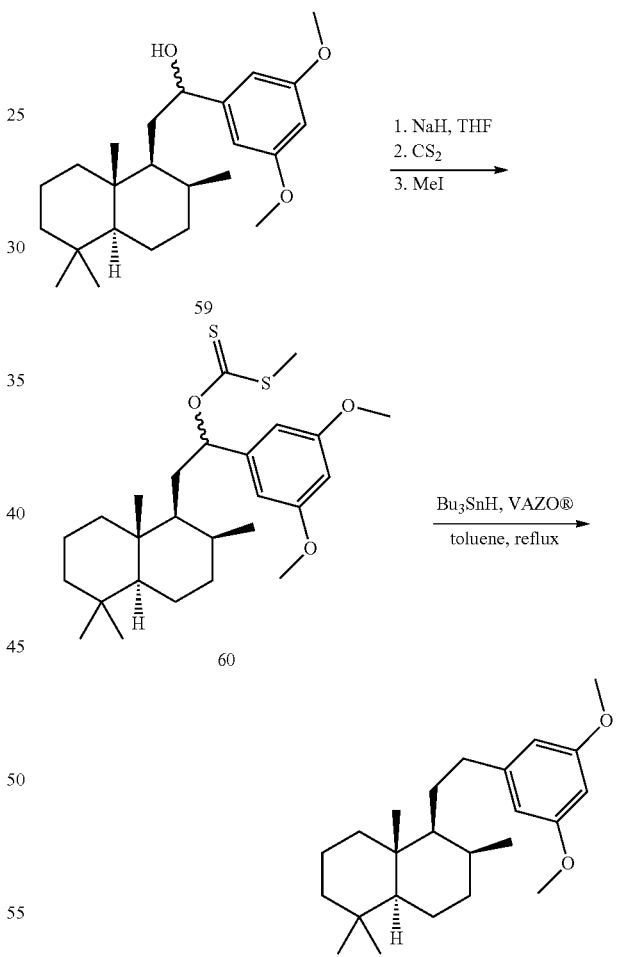

A. A solution of 2-[(1S,2S,4aS,8aR)-2,5,5,8a-tetramethyl-decahydronaphthalen-1-yl]-1-(3,5-dimethoxyphenyl)ethan-1-ol (Compound No. 59, 98 mg, 0.26 mmol) in THF (1.7 mL) under argon was stirred at room temperature while NaH (60% dispersion in mineral oil, 34 mg, 0.85 mmol) was added. The mixture was heated to 40° C. for 1 h then cooled to 0° C. and CS$_2$ (0.094 mL, 1.6 mmol) was added. The mixture was stirred at 0° C. for 20 min then at room temperature for 25 min, and MeI (0.098 mL, 1.6 mmol) was added. After stirring at room temperature for 1.5 h, the mixture was concentrated then partitioned between EtOAc (35 mL) and water (10 mL). The organic phase was washed with water (2×10 mL) and brine (10 mL) then dried (MgSO$_4$) and concentrated to give the desired xanthate (Compound No. 60, 147 mg) as a yellow oil that was used in the next step without further purification.

B. A solution of the yellow oil from above (Compound No. 60, 147 mg) and tributyltin hydride (0.10 mL, 0.38 mmol) in toluene (1.7 mL) was heated to reflux under argon then 1,1'-azobis(cyclohexanecarbonitrile) (VAZO®)(6 mg, 0.02 mmol) was added. The mixture was heated at reflux for 1.5 h, additional 1,1'-azobis(cyclohexanecarbonitrile) (14 mg, 0.057 mmol) was added and heating was continued for 3 h. The mixture was concentrated, and the residue was purified by chromatography on silica gel (EtOAc/hexanes, 2:98) to give (4aR,5S,6S,8aS)-5-[2-(3,5-dimethoxyphenyl)ethyl]-1,1,4a,6-tetramethyl-decahydronaphthalene as a colorless oil (Compound No. 61, 79 mg, 84% over 2 steps). $^1$H NMR (CDCl$_3$): δ6.34 (d, J=2.1 Hz, 2H), 6.29 (t, J=2.4 Hz, 1H), 3.78 (s, 6H), 2.59 (td, J=13, 5.3 Hz, 1H), 2.44 (td, J=13, 6.0 Hz, 1H), 1.82-0.77 (m, 26H), 0.54 (m, 1H).

EXAMPLE 40

Synthesis of 5-{2-[(1S,2S,4aS,8aR)-2,5,5,8a-tetramethyl-decahydronaphthalen-1-yl]ethyl}benzene-1,3-diol (Compound No. 62)

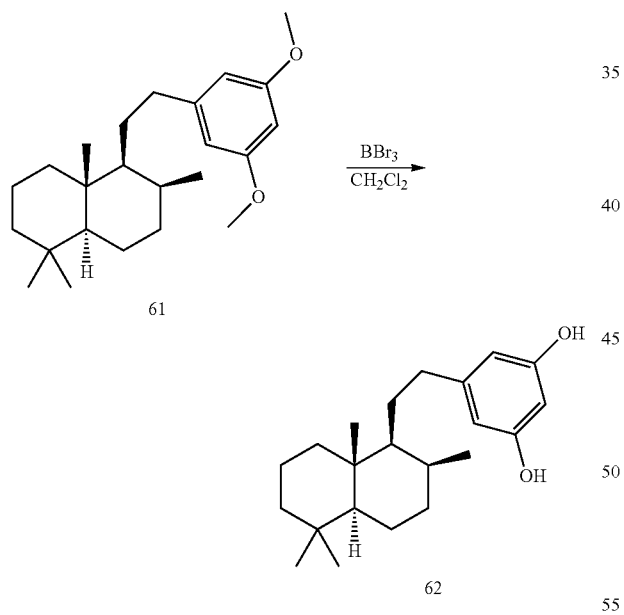

A solution of (4aR,5S,6S,8aS)-5-[2-(3,5-dimethoxyphenyl)ethyl]-1,1,4a,6-tetramethyl-decahydronaphthalene (Compound No. 61, 79 mg, 0.22 mmol) in CH$_2$Cl$_2$ (2.2 mL) was cooled to –78° C. under argon, BBr$_3$ (1.0 M in CH$_2$Cl$_2$, 1.10 mL, 1.10 mmol) was added, and the solution was stirred at room temperature for 15 h. Methanol (5 mL) was carefully added to the solution then concentrated (2×). The residue was dissolved in i-PrOH/10% aqueous HCl (3:1, 3.0 mL) and heated to 85° C. for 45 min. The solution was concentrated and the residue was partitioned between EtOAc (30 mL) and water (5 mL). The organic layer was washed with water (5 mL) and brine (5 mL) then dried (MgSO$_4$) and concentrated. The residue was purified by chromatography on silica gel (MeOH/CH$_2$Cl$_2$, 1:24) to afford 5-{2-[(1S,2S,4aS,8aR)-2,5,5,8a-tetramethyl-decahydronaphthalen-1-yl]ethyl}benzene-1,3-diol (Compound No. 62, 53 mg, 73%) as a colorless foam. $^1$H NMR (CDCl$_3$): δ6.25 (d, J=2.1 Hz, 2H), 6.17 (t, J=2.3 Hz, 1H), 4.64 (s, 2H), 2.53 (td, J=13, 5.1 Hz, 1H), 2.38 (td, J=13, 6.0 Hz, 1H), 1.80-0.77 (m, 26H), 0.53 (m, 1H). ES-MS m/z 331 ([M+1]$^+$).

EXAMPLE 41

Synthesis of (4S,4aS,8aS)-4-[(3-methoxy-5-methylphenyl)carbonyl]-3,4a,8,8-tetramethyl-decahydronaphthalene-2-carbonitrile (Compound No. 63)

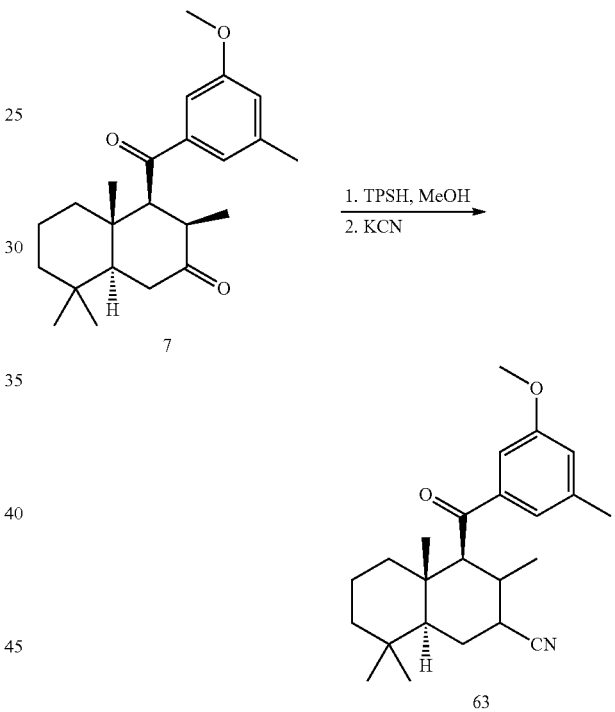

A suspension of (3R,4S,4aS,8aS)-4-[(3-methoxy-5-methylphenyl)carbonyl]-3,4a,8,8-tetramethyl-decahydronaphthalen-2-one (Compound No. 7, 702 mg, 1.97 mmol) and 2,4,6-triisopropylbenzenesulfonyl hydrazide (705 mg, 2.36 mmol) in MeOH (6.6 mL) was stirred at room temperature under argon for 1 h 10 min then KCN (449 mg, 6.89 mmol) was added. After heating to reflux for 2 h 45 min, the mixture was allowed to cool to room temperature then concentrated. The residue was partitioned between CH$_2$Cl$_2$ (20 mL) and water (20 mL), and the aqueous phase was extracted with CH$_2$Cl$_2$ (2×10 mL). The combined organic layers were dried (MgSO$_4$) and concentrated. The residue was purified by chromatography on silica gel (EtOAc/hexanes, 1:9) to give (4S,4aS,8aS)-4-[(3-methoxy-5-methylphenyl)carbonyl]-3,4a,8,8-tetramethyl-decahydronaphthalene-2-carbonitrile (Compound No. 63) (contaminated with (4S,4aS,8aS)-4-[(3-methoxy-5-methylphenyl)carbonyl]-3,4a,8,8-tetramethyl-decahydronaphthalen-2-one) as a colorless foam (242 mg).

EXAMPLE 42

Synthesis of (3S,4S,4aS,8aS)-4-[(3-methoxy-5-methylphenyl)carbonyl]-3,4a,8,8-tetramethyl-decahydronaphthalene-2-carboxamide (Compound No. 64)

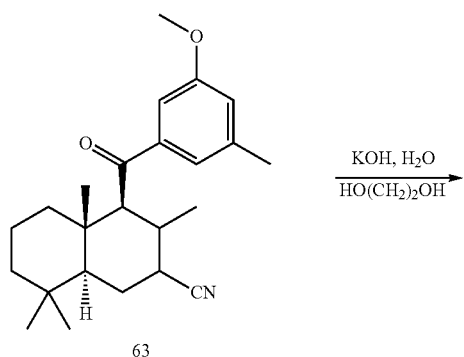

63

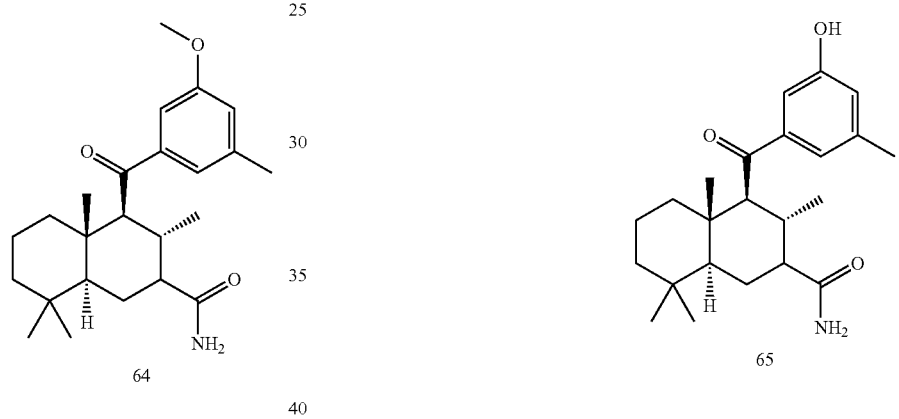

64

A mixture containing (4S,4aS,8aS)-4-[(3-methoxy-5-methyl phenyl)carbonyl]-3,4a,8,8-tetramethyl-decahydronaphthalene-2-carbonitrile (Compound No. 63) from above (196 mg) and solid KOH (450 mg, 8.0 mmol) in ethylene glycol/water (4:1, 2.5 mL) was heated to 120° C. under argon for 22 h then allowed to cool to room temperature. The mixture was adjusted to pH 1 using 1 N HCl then partitioned between water (40 mL) and EtOAc (30 mL). The organic phase was washed with water (10 mL), and the combined aqueous layers were extracted with EtOAc (20 mL). The combined organic layers were washed with brine (2×15 mL) then dried (MgSO$_4$) and concentrated. The residue was purified by chromatography on silica gel (MeOH/CH$_2$Cl$_2$, 1:24) to give (4S,4aS,8aS)-4-[(3-methoxy-5-methylphenyl)carbonyl]-3,4a,8,8-tetramethyl-decahydronaphthalene-2-carboxamide (Compound No. 64, 116 mg, 19% over 2 steps) as a colorless solid. $^1$H NMR (CDCl$_3$): δ7.30 (s, 1H), 7.24 (m, 1H), 6.91 (s, 1H), 5.47 (br s, 1H), 5.36 (br s, 1H), 3.85 (s, 3H), 3.01 (d, J=11 Hz, 1H), 2.43 (m, 1H), 2.41 (s, 3H), 2.01 (m, 1H), 1.86 (m, 1H), 1.66 (m, 1H), 1.51-1.37 (m, 2H), 1.30-1.00 (m, 8H), 0.90 (s, 3H), 0.86 (s, 3H), 0.80 (d, J=6.6 Hz, 3H).

EXAMPLE 43

Synthesis of (3S,4S,4aS,8aS)-4-[(3-hydroxy-5-methylphenyl)carbonyl]-3,4a,8,8-tetramethyl-decahydronaphthalene-2-carboxamide (Compound No. 65)

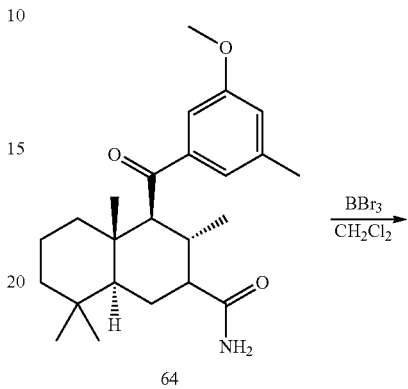

64

65

A suspension of (4S,4aS,8aS)-4-[(3-methoxy-5-methylphenyl)carbonyl]-3,4a,8,8-tetramethyl-decahydronaphthalene-2-carboxamide (Compound No. 64, 116 mg, 0.301 mmol) in CH$_2$Cl$_2$ (3.0 mL) was cooled to −78° C. under argon, BBr$_3$ (1.0 M in CH$_2$Cl$_2$, 2.30 mL, 2.30 mmol) was added, and the solution was stirred at room temperature for 23 h. Methanol (10 mL) was carefully added to the solution then concentrated. The residue was dissolved in i-PrOH/10% aqueous HCl (3:1, 4 mL) and heated to 80° C. for 30 min. The solution was concentrated, diluted with water (10 mL) then adjusted to pH 6 using 1 N NaOH. The mixture was extracted with EtOAc (30 mL), and the organic layer was washed with brine (10 mL) then dried (MgSO$_4$) and concentrated. The residue was purified by chromatography on silica gel (MeOH/CH$_2$Cl$_2$, 3:97) to afford (3S,4S,4aS,8aS)-4-[(3-hydroxy-5-methylphenyl)carbonyl]-3,4a,8,8-tetramethyl-decahydronaphthalene-2-carboxamide (Compound No. 65, 46 mg, 41%) as a yellow solid. $^1$H NMR (CD$_3$OD): δ7.24 (s, 1H), 7.12 (s, 1H), 6.85 (m, 1H), 3.11 (d, J=11 Hz, 1H), 2.38 (m, 1H), 2.35 (s, 3H), 2.12 (td, J=12, 4.4 Hz, 1H), 1.79 (m, 1H), 1.71-1.03 (m, 11H), 0.92 (s, 3H), 0.88 (s, 3H), 0.73 (d, J=6.3 Hz, 3H). ES-MS m/z 372 ([M+1]$^+$).

EXAMPLE 44

Synthesis of (3S,4S,4aS,8aS)-4-[(3-methoxy-5-methylphenyl)carbonyl]-3,4a,8,8-tetramethyl-decahydronaphthalene-2-carboxylic acid (Compound No. 67)

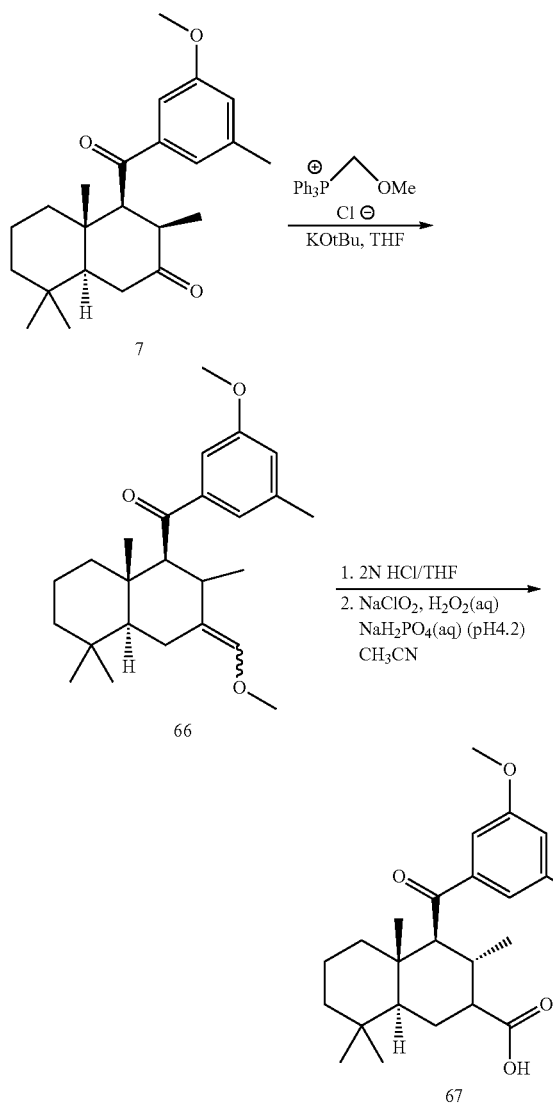

A. To a suspension of (methoxymethyl)triphenylphosphonium chloride (687 mg, 2.00 mmol) in THF (5.0 mL) at 0° C. under argon was added potassium t-butoxide (1.0 M in THF, 2.00 mL, 2.00 mmol) dropwise. The mixture was stirred at 0° C. for 25 min then a solution of (3R,4S,4aS,8aS)-4-[(3-methoxy-5-methyl phenyl)carbonyl]-3,4a,8,8-tetramethyl-decahydronaphthalen-2-one (Compound No. 7, 357 mg, 1.00 mmol) in THF (2.9 mL) was added dropwise at 0° C. The mixture was stirred at 0° C. for 5 min then room temperature for 1 h 40 min. The mixture was diluted with EtOAc (30 mL), washed with brine (10 mL) then dried (MgSO$_4$) and concentrated. The residue was purified by chromatography on silica gel (EtOAc/hexanes, 1:19) to give [(1S,4aS,8aS)-3-(methoxymethylidene)-2,5,5,8a-tetramethyl-decahydronaphthalen-1-yl](3-methoxy-5-methylphenyl)methanone (Compound No. 66, 373 mg, 97%) as colorless crystals.

B. To a solution of [(1S,4aS,8aS)-3-(methoxymethylidene)-2,5,5,8a-tetramethyl-decahydronaphthalen-1-yl](3-methoxy-5-methylphenyl)methanone (Compound No. 66, 373 mg, 0.970 mmol) in THF (8 mL) was added 2 N HCl (2 mL), and the mixture was heated to reflux for 0.5 h. The mixture was diluted with EtOAc (30 mL), washed with brine (10 mL) then dried (MgSO$_4$) and concentrated to give a colorless oil (389 mg) that was used in the next step without further purification.

C. To a solution of the colorless oil from above (389 mg) in CH$_3$CN (2 mL) was added aqueous NaH$_2$PO$_4$ (pH 4.2, 1.1 mL) followed by 50% aqueous H$_2$O$_2$(0.073 mL, 1.3 mmol) and a solution of 80% NaClO$_2$ (186 mg, 1.65 mmol) in water (3.3 mL). The mixture was stirred at room temperature for 27 h then diluted with EtOAc (20 mL) and water (5 mL). Excess peroxide was destroyed with solid Na$_2$SO$_3$, and the aqueous phase was acidified to pH 2 with concentrated HCl then extracted with EtOAc (2×10 mL). The combined organic layers were dried (MgSO$_4$) and concentrated to give impure (3S,4S,4aS,8aS)-4-[(3-methoxy-5-methylphenyl)carbonyl]-3,4a,8,8-tetramethyl-decahydronaphthalene-2-carboxylic acid (Compound No. 67, 395 mg) as a colorless foam.

EXAMPLE 45

Synthesis of (3S,4S,4aS,8aS)-4-[(3-hydroxy-5-methylphenyl)carbonyl]-3,4a,8,8-tetramethyl-decahydronaphthalene-2-carboxylic acid (Compound No. 68)

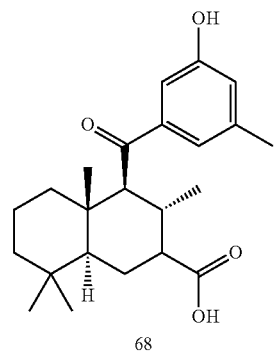

A solution of impure (3S,4S,4aS,8aS)-4-[(3-methoxy-5-methyl phenyl)carbonyl]-3,4a,8,8-tetramethyl-decahydronaphthalene-2-carboxylic acid from above (Compound No. 67, 395 mg) in CH$_2$Cl$_2$ (10 mL) was cooled to −78° C. under argon, BBr$_3$ (1.0 M in CH$_2$Cl$_2$, 4.9 mL, 4.9 mmol) was added, and the solution was stirred at room temperature for 4 h. Methanol (10 mL) was carefully added to the solution then concentrated (4×). The residue was dissolved in i-PrOH/10% aqueous HCl (2.5:1, 14 mL) and heated to 85° C. for 45 min. The solution was concentrated and the residue was partitioned between EtOAc (30 mL) and water (10 mL). The aqueous phase was extracted with EtOAc (10 mL), and the combined organic layers were dried (MgSO$_4$) and concentrated. The residue was dissolved in 1 N NaOH (2 mL) and diluted with water (20 mL) then extracted with EtOAc (2×10 mL). The aqueous phase was acidified to pH 1 using 1 N HCl and extracted with CH$_2$Cl$_2$ (4×8 mL). The combined CH$_2$Cl$_2$ extracts were dried (MgSO$_4$) and concentrated. The residue was purified by chromatography on silica gel (MeOH/CH$_2$Cl$_2$, 3:97) to afford (3S,4S,4aS,8aS)-4-[(3-hydroxy-5-methylphenyl)carbonyl]-3,4a,8,8-tetramethyl-decahydronaphthalene-2-carboxylic_acid (Compound No. 68, 174 mg, 48%) as colorless crystals. $^1$H NMR (CDCl$_3$): δ7.29 (s, 1H), 7.20 (s, 1H), 6.87 (s, 1H), 2.98 (d, J=11 Hz, 1H), 2.50 (m, 1H), 2.38 (s, 3H), 2.23 (td, J=12, 4.2 Hz, 1H), 1.93 (m, 1H), 1.73-1.01 (m, 12H), 0.91 (s, 3H), 0.86 (s, 3H), 0.81 (d, J=6.3 Hz, 3H). ES-MS m/z 373 ([M+1]$^+$).

EXAMPLE 46

Synthesis of (1R,2R,4aS,8aS)-1-{[(3-methoxy-5-methylphenyl)sulfanyl]methyl}-2,5,5,8a-tetramethyl-decahydro-naphthalen-2-ol (Compound No. 75)

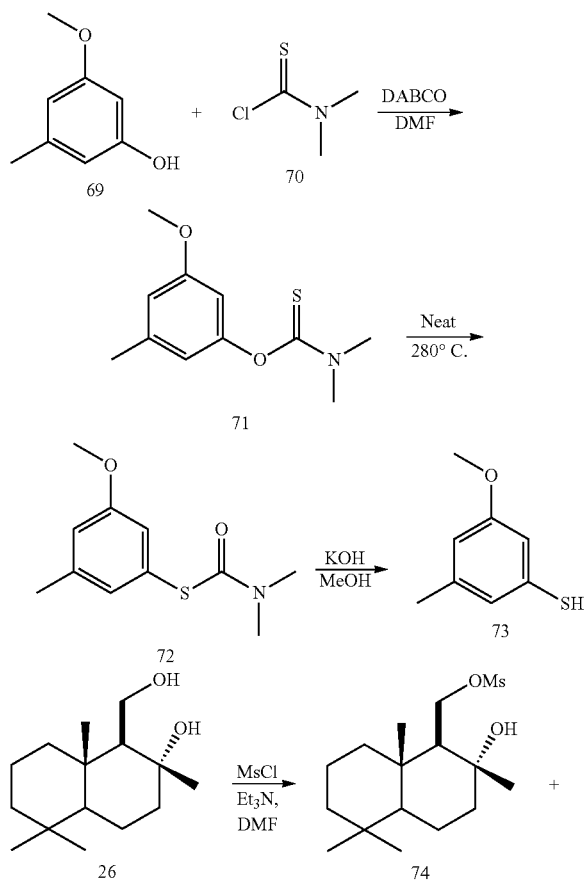

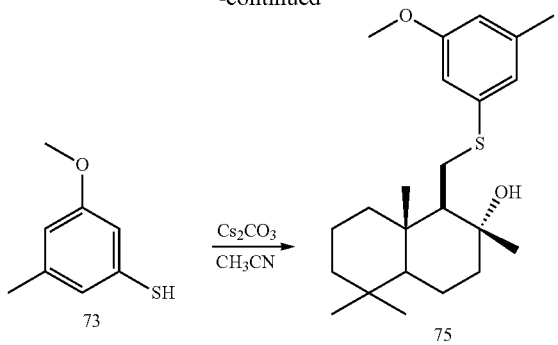

A. To a mixture of 3-methoxy-5-methylphenol (Compound No. 69, 3.39 g, 24.5 mmol) and 1,4-diazabicyclo [2.2.2]octane (5.50 g, 49.0 mmol) in DMF (20 mL) under argon was added dimethylthiocarbamoyl chloride (Compound No. 70, 6.06 g, 49.0 mmol) portionwise. The reaction mixture was stirred at room temperature overnight and 500 mL of ether was added. The organics were washed with water (150 mL), brine (2×50 mL), dried (Na$_2$SO$_4$), and concentrated. Purification by chromatography on silica gel (Hexanes/EtOAc, 4:1) gave O-3-methoxy-5-methylphenyl dimethylcarbamothioate (Compound No. 71, 5.05 g, 91%) as a colorless solid.

B. O-3-Methoxy-5-methylphenyl dimethylcarbamothioate (Compound No. 71, 5.0 g, 22.2 mmol) was vacuum-degassed (4 cycles, flask was backfilled with nitrogen) and heated to 280° C. for 4 h, then cooled to room temperature. Purification by chromatography on silica gel (Hexanes/EtOAc, 85:15) gave S-3-methoxy-5-methylphenyl dimethylcarbamothioate (Compound No. 72, 4.10 g, 82%) as a light yellow oil.

C. A mixture of S-3-methoxy-5-methylphenyl dimethylcarbamothioate (Compound No. 72, 4.10 g, 18.2 mmol) and KOH (6.0 g) in MeOH (200 mL) was refluxed for 2 h. After cooling, the mixture was concentrated and diluted with EtOAc (500 mL). The organics were washed with 1N HCl (50 mL), brine (2×50 mL), dried (Na$_2$SO$_4$), and concentrated to give 3-methoxy-5-methylbenzenethiol (Compound No. 73, 2.80 g, quant.) as a colorless oil.

D. To a mixture of (1S,2R,4aS,8aS)-1-(hydroxymethyl)-2,5,5,8a-tetramethyl-decahydronaphthalen-2-ol (Compound No. 26, 4.66 g, 19.39 mmol) and Et$_3$N (7.01 mL, 50.41 mmol) in DMF (40 mL) under argon was added methanesulfonyl chloride (2.66 g, 23.27 mmol) dropwise at 0° C. After stirring at room temperature for 3 h, ether (400 mL) was added. The organics were washed with 1N HCl (20 mL), saturated aqueous NaHCO$_3$ (20 mL), brine (2×20 mL), dried (Na$_2$SO$_4$), and concentrated to give ((1S,2R,4aS,8aS)-2-hydroxy-2,5,5,8a-tetramethyldecahydronaphthalen-1-yl) methyl methanesulfonate (Compound No. 74, 5.90 g, 96%) as a light yellow sticky mass.

E. A mixture of 3-methoxy-5-methylbenzenethiol (Compound No. 73, 3.14 g, 20.36 mmol), ((1S,2R,4aS,8aS)-2-hydroxy-2,5,5,8a-tetramethyldecahydronaphthalen-1-yl) methyl methanesulfonate (Compound No. 74, 6.48 g, 20.36 mmol), and Cs$_2$CO$_3$ (19.90 g, 61.08 mmol) in CH$_3$CN (300 mL) under argon was stirred at room temperature for 1 h, then refluxed for 24 h. After cooling, the mixture was concentrated. Purification by chromatography on silica gel (Hexanes/EtOAc, 4:1) gave (1R,2R,4aS,8aS)-1-{[(3-methoxy-5-methylphenyl)sulfanyl]methyl}-2,5,5,8a-tetramethyl-decahydro-naphthalen-2-ol (Compound No. 75, 5.70 g, purity ~75%) as a yellow sticky mass.

EXAMPLE 47

Synthesis of (1R,2R,4aS,8aS)-1-{[(3-methoxyphenyl)sulfanyl]methyl}-2,5,5,8a-tetramethyl-decahydronaphthalen-2-ol (Compound No. 76)

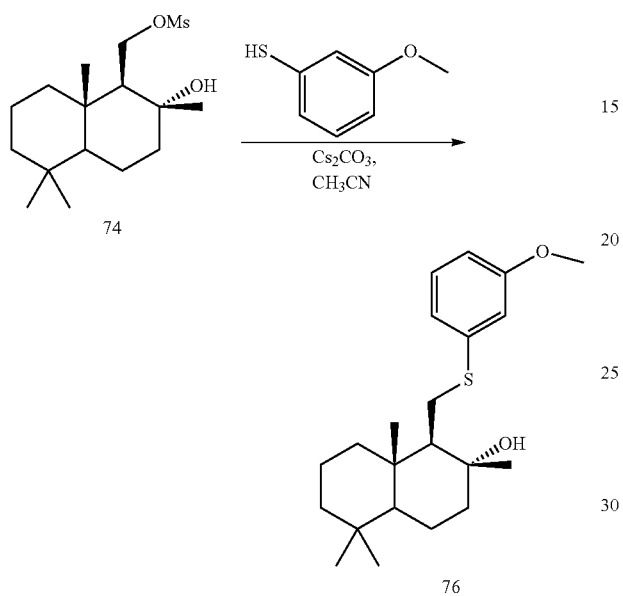

A mixture of 3-methoxythiophenol (2.20 g, 15.72 mmol), [(1S,2R,4aS,8aS)-2-hydroxy-2,5,5,8a-tetramethyl-decahydronaphthalen-1-yl]methyl methanesulfonate (Compound No. 74, 5.0 g, 15.72 mmol), and Cs$_2$CO$_3$ (15.30 g, 47.16 mmol) in CH$_3$CN (600 mL) under argon was stirred at room temperature for 1 h, then refluxed for 24 h. After cooling, the mixture was concentrated and purified by column chromatography on silica gel (Hexanes/EtOAc, 10:1 to 6:1) to give (1R,2R,4aS,8aS)-1-{[(3-methoxyphenyl)sulfanyl]methyl}-2,5,5,8a-tetramethyl-decahydronaphthalen-2-ol (Compound No. 76, 4.03 g, 71%) as a yellow oil. $^1$H NMR (CDCl$_3$): δ7.20 (t, 1H), 6.95 (m, 2H), 6.71 (d, 1H), 3.78 (s, 3H), 3.02 (ABq, 2H), 2.00 (s, 1H), 1.90 (m, 1H) 1.78-1.22 (m, 8H), 1.21 (s, 3H), 1.20-0.98 (m, 3H), 0.90 (s, 3H), 0.85 (s, 3H), 0.80 (s, 3H).

EXAMPLE 48

Synthesis of (1R,2R,4aS,8aS)-1-{[(3,5-dimethoxyphenyl)-sulfanyl]methyl}-2,5,5,8a-tetramethyl-decahydronaphthalen-2-ol (Compound No. 80)

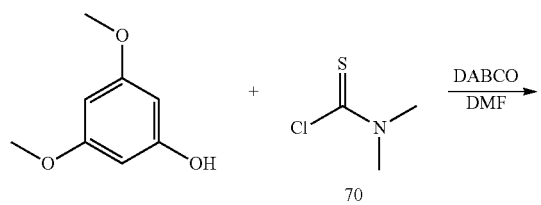

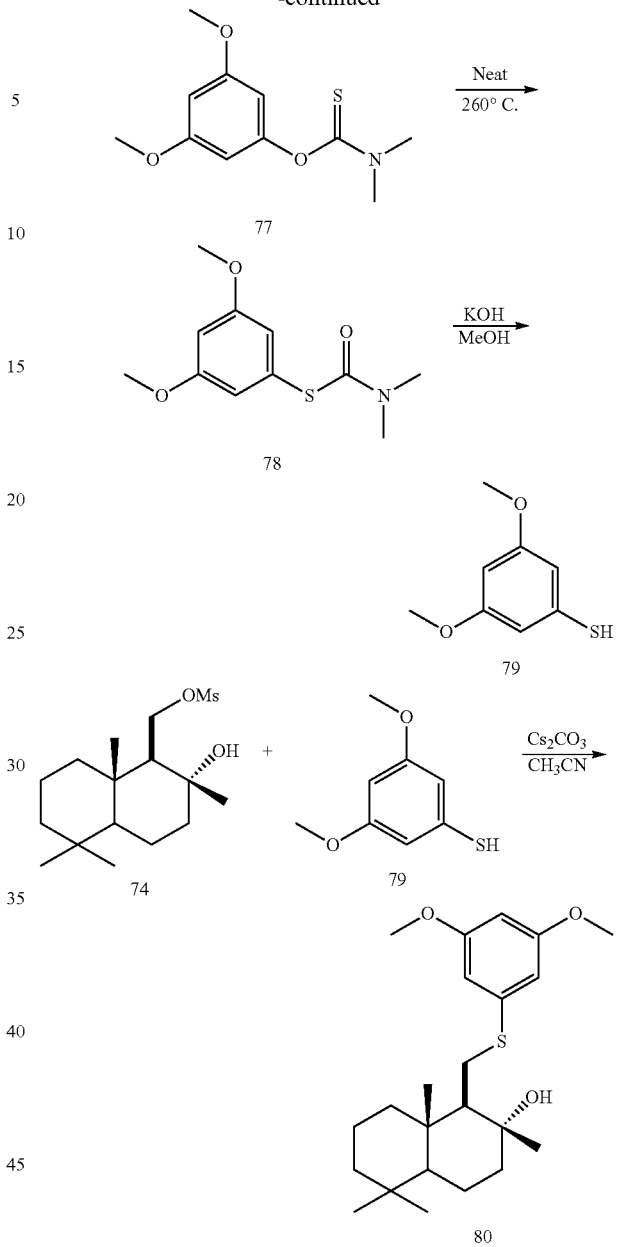

A. To a mixture of 3,5-dimethoxyphenol (7.70 g, 50 mmol) and 1,4-diazabicyclo[2.2.2]octane (11.22 g, 100 mmol) in DMF (40 mL) under argon was added dimethylthiocarbamoyl chloride (Compound No. 70, 12.36 g, 100 mmol) portionwise. The reaction mixture was stirred at room temperature overnight and 500 mL of ether was added. The organics were washed with water (150 mL), brine (2×50 mL), dried (Na$_2$SO$_4$), and concentrated. Purification by chromatography on silica gel (Hexanes/EtOAc, 4:1) gave O-3,5-dimethoxyphenyl dimethylcarbamothioate (Compound No. 77, 10.88 g, 90%) as a white solid.

B. O-3,5-Dimethoxyphenyl dimethylcarbamothioate (Compound No. 77, 1.0 g, 4.14 mmol) was vacuum-degassed (4 cycles, flask was backfilled with nitrogen) and heated to 260° C. for 3 h, then cooled to room temperature to give S-3,5-dimethoxyphenyl dimethylcarbamothioate (Compound No. 78, 1.0 g, quant.) as a light brown oil.

C. A mixture of S-3,5-dimethoxyphenyl dimethylcarbamothioate (Compound No. 78, 1.0 g, 4.14 mmol) and KOH (1.5 g) in MeOH (20 mL) was refluxed for 2 h. After cooling, it was concentrated. EtOAc (100 mL) was added. The organics were washed with 1N HCl (20 mL), brine (3×20 mL), dried ($Na_2SO_4$), and concentrated to give 3,5-dimethoxybenzenethiol (Compound No. 79, 0.70 g, quant.) as a light brown oil.

D. A mixture of 3,5-dimethoxybenzenethiol (Compound No. 79, 6.74 g, 39.60 mmol), ((1S,2R,4aS,8aS)-2-hydroxy-2,5,5,8a-tetramethyldecahydronaphthalen-1-yl)methyl methanesulfonate (Compound No. 74, 12.62 g, 39.60 mmol), and $Cs_2CO_3$ (38.70 g, 118.77 mmol) in $CH_3CN$ (560 mL) under argon was stirred at room temperature for 1 h, then refluxed for 24 h. After cooling, the mixture was concentrated. Purification by chromatography on silica gel (Hexanes/EtOAc, 4:1) gave (1R,2R,4aS,8aS)-1-{[(3,5-dimethoxyphenyl)-sulfanyl]methyl}-2,5,5,8a-tetramethyl-decahydronaphthalen-2-ol (Compound No. 80, 9.40 g, 60%) as a light yellow sticky mass. $^1$H NMR ($CDCl_3$): δ6.52 (d, 2H), 6.30 (d, 1H), 3.78 (2s, 6H), 3.01 (AB, 2H), 1.90-1.30 (m, 10H), 1.22 (s, 3H), 1.20-0.98 (m, 3H), 0.90 (2s, 6H), 0.82 (s, 3H).

EXAMPLE 49

Synthesis of N-[(2R,3S,4S,4aS,8aS)-4-[(3,5-dimethoxyphenyl)carbonyl]-3,4a,8,8-tetramethyl-decahydronaphthalen-2-yl]-4-methylbenzamide (Compound No. 81)

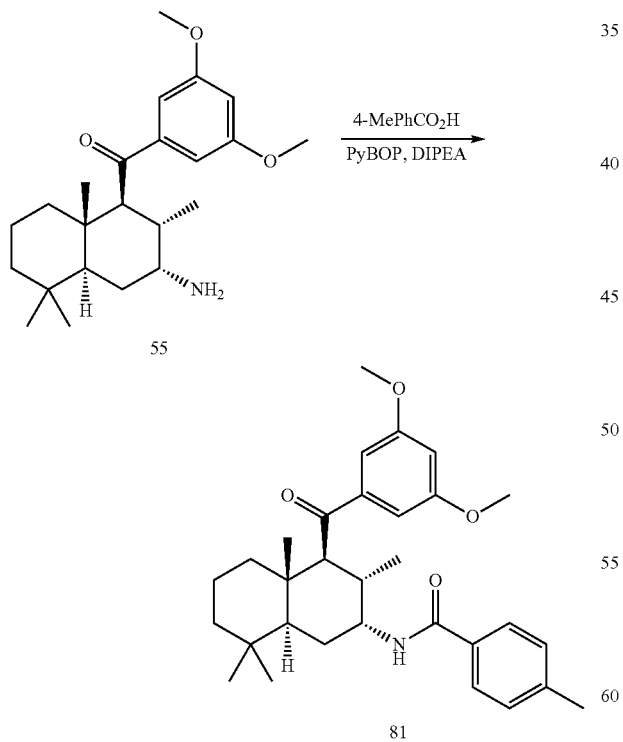

A mixture of (2R,3S,4S,4aS,8aS)-4-[(3,5-dimethoxyphenyl)carbonyl]-3,4a,8,8-tetramethyl-decahydronaphthalen-2-amine (Compound No. 55, 125 mg, 0.33 mmol), benzotriazol-1-yl-oxytripyrrolidinophosphonium hexafluorophosphate (230 mg, 0.440 mmol), p-toluic acid (52 mg, 0.38 mmol), N,N-diisopropylethylamine (0.15 mL, 0.86 mmol) and DMF (3.5 mL) under argon was allowed to stir at room temperature for 18 h. EtOAc (20 mL) was added to the solution, and the mixture washed with saturated aqueous $NaHCO_3$ (3×10 mL) and saturated aqueous NaCl (2×10 mL). The organic layer was concentrated and the residue was purified by flash chromatography using hexanes/EtOAc (3:1) to afford the product, N-[(2R,3S,4S,4aS,8aS)-4-[(3,5-dimethoxyphenyl)carbonyl]-3,4a,8,8-tetramethyl-decahydronaphthalen-2-yl]-4-methylbenzamide (Compound No. 81, 100 mg, 62%) as a clear colourless oil. $^1$H NMR (300 MHz, $CDCl_3$) δ7.66 (d, J=8.0 Hz, 2H), 7.26 (d, J=7.9 Hz, 2H), 7.03 (s, 2H), 6.63 (s, 1H) 6.47 (d, J=9.2 Hz, 1H), 4.56 (s, 1H), 3.83 (s, 6H), 3.10 (d, J=11.7 Hz, 1H), 2.54 (m, 1H), 2.41 (s, 3H), 1.01 (s, 3H), 1.3 (m, 7H), 0.85 (s, 3H), 0.83 (s, 3H), 0.79 (d, J=6.6 Hz, 3H); $^{13}$C NMR (75 MHz, $CDCl_3$) δ203.0, 167.7, 161.1, 142.9, 142.0, 132.9, 129.6, 127.0, 106.4, 104.4, 58.9, 55.8, 49.9, 49.6, 42.0, 41.5, 39.6, 33.9, 33.6, 33.2, 27.9, 22.9, 21.2, 18.6, 16.6, 13.7; MS m/z: 492.4 ([M+1]$^+$).

EXAMPLE 50

Synthesis of N-[(2R,3S,4S,4aS,8aS)-4-[(3,5-dihydroxyphenyl)carbonyl]-3,4a,8,8-tetramethyl-decahydronaphthalen-2-yl]-4-methylbenzamide (Compound No. 82)

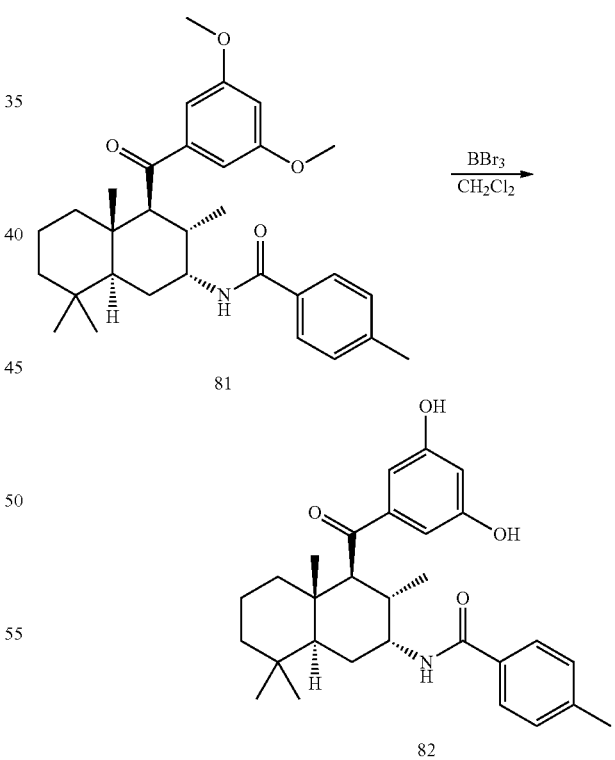

A solution of N-[(2R,3S,4S,4aS,8aS)-4-[(3,5-dimethoxyphenyl)carbonyl]-3,4a,8,8-tetramethyl-decahydronaphthalen-2-yl]-4-methylbenzamide (Compound No. 81, 71 mg, 0.14 mmol) in $CH_2Cl_2$ (1.5 mL) under argon was cooled to −78° C. Boron tribromide (1 M in $CH_2Cl_2$, 1.0 mL, 1.0 mmol) was added and the mixture was stirred at −78° C. for 10 min. The reaction was warmed up to room temperature and stirred for 19 h. Methanol (3 mL) was carefully added and the resultant mixture was concentrated in vacuo. This was repeated three times. Isopropanol/1 M HCl (3:1, 2 mL) was added, and the solution was heated to 85° C. for 45 min. The solution was concentrated, EtOAc (10 mL) and water (5 mL) were added, and the pH was adjusted to approximately 7 (1 M HCl and 1 M NaOH). The mixture was extracted with EtOAc (2×10 mL), dried over anhydrous $Na_2SO_4$, filtered, and concentrated in vacuo. Purification by flash chromatography using $CH_2Cl_2$/MeOH (20:1 to 10:1, EtOAc to load) afforded the impure product (53 mg, 82%) as a white solid. Additional purification via radial chromatography using hexanes/EtOAc (5:2) afforded pure N-[(2R,3S,4S,4aS,8aS)-4-[(3,5-dihydroxyphenyl)carbonyl]-3,4a,8,8-tetramethyl-decahydronaphthalen-2-yl]-4-methylbenzamide (Compound No. 82, 27 mg, 42%). $^1$H NMR (300 MHz, $CD_3OD$) δ8.30 (d, J=10.0 Hz, 1H), 7.70 (d, J=8.1 Hz, 2H), 7.29 (d, J=8.1 Hz, 2H), 6.94 (s, 2H), 6.48 (s, 1H), 4.87 (s, 2H), 3.59 (d, J=12.3 Hz, 1H), 3.30 (s, 1H), 2.47 (m, 1H), 2.40 (s, 3H), 1.77 (m, 2H), 1.35 (m, 3H), 1.04 (s, 4H), 0.87 (s, 9H), 0.76 (d, J=6.5 Hz, 3H); $^{13}$C NMR (75 MHz, $CD_3OD$) δ206.4, 171.8, 159.8, 144.6, 139.4, 132.9, 129.3, 129.1, 125.7, 108.0, 58.9, 51.6, 42.9, 42.4, 40.2, 34.1, 33.9, 33.8, 28.9, 22.1, 21.4, 19.5, 16.7, 14.2; MS m/z: 464.3 ([M+1]$^+$).

EXAMPLE 51

Synthesis of N-[(2R,3S,4S,4aS,8aS)-4-[(3,5-dimethoxyphenyl)carbonyl]-3,4a,8,8-tetramethyl-decahydronaphthalen-2-yl]-3-methylbenzamide (Compound No. 83)

A mixture of (2R,3S,4S,4aS,8aS)-4-[(3,5-dimethoxyphenyl)carbonyl]-3,4a,8,8-tetramethyl-decahydronaphthalen-2-amine (Compound No. 55, 125 mg, 0.33 mmol), benzotriazol-1-yl-oxytripyrrolidinophosphonium hexafluorophosphate (230 mg, 0.440 mmol), m-toluic acid (52 mg, 0.38 mmol), N,N-diisopropylethylamine (0.15 mL, 0.86 mmol) and DMF (3.5 mL) under argon was allowed to stir at room temperature for 20 h. EtOAc (20 mL) was added to the solution, and the mixture washed with saturated aqueous $NaHCO_3$ (3×10 mL) and saturated aqueous NaCl (2×10 mL). The organic layer was concentrated and the residue was purified by flash chromatography using hexanes/EtOAc (3:1) to afford the product N-[(2R,3S,4S,4aS,8aS)-4-[(3,5-dimethoxyphenyl)carbonyl]-3,4a,8,8-tetramethyl-decahydronaphthalen-2-yl]-3-methylbenzamide (Compound No. 83, 95 mg, 59%) as a white solid. $^1$H NMR (300 MHz, $CDCl_3$) δ7.49 (s, 1H), 7.44 (d, J=7.4 Hz, 1H), 7.21 (d, J=4.7 Hz, 2H), 7.02 (d, J=2.2 Hz, 2H), 6.60 (d, J=9.6 Hz, 1H), 6.57 (d, J=1.9 Hz, 1H), 4.54 (m, 1H), 3.75 (s, 6H), 3.18 (d, J=12.2 Hz, 1H), 2.48 (m, 1H), 2.30 (s, 3H), 1.70 (m, 2H), 1.16 (m, 3H), 1.05 (s, 4H), 0.85 (d, J=2.5 Hz, 6H), 0.81 (s, 3H), 0.78 (s, 3H); $^{13}$C NMR (75 MHz, $CDCl_3$) δ202.9, 167.9, 160.9, 142.8, 138.8, 135.7, 132.2, 128.7, 127.9, 123.7, 106.3, 104.3, 58.7, 55.7, 49.8, 49.5, 41.9, 41.4, 39.5, 33.8, 33.5, 33.1, 27.8, 21.8, 21.5, 18.6, 16.5, 13.6; MS m/z: 492.4 ([M+1]$^+$).

EXAMPLE 52

Synthesis of N-[(2R,3S,4S,4aS,8aS)-4-[(3,5-dihydroxyphenyl)carbonyl]-3,4a,8,8-tetramethyl-decahydronaphthalen-2-yl]-3-methylbenzamide (Compound No. 84)

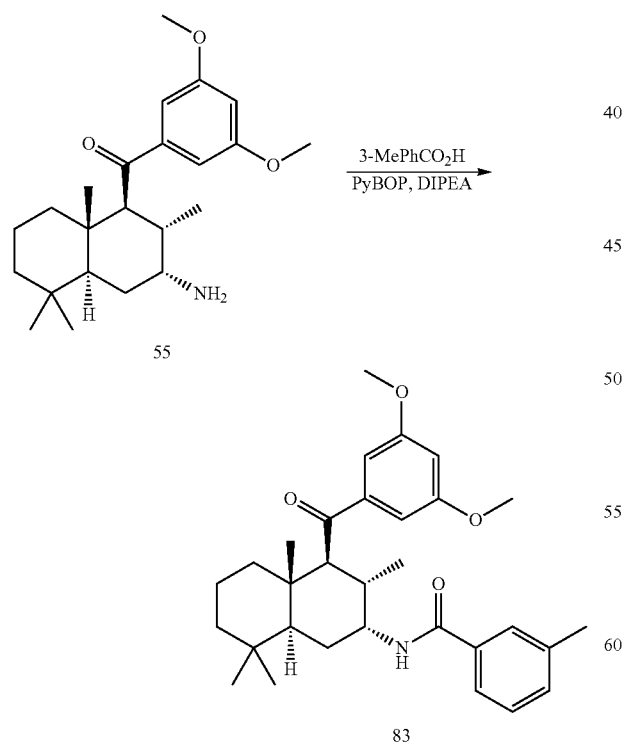

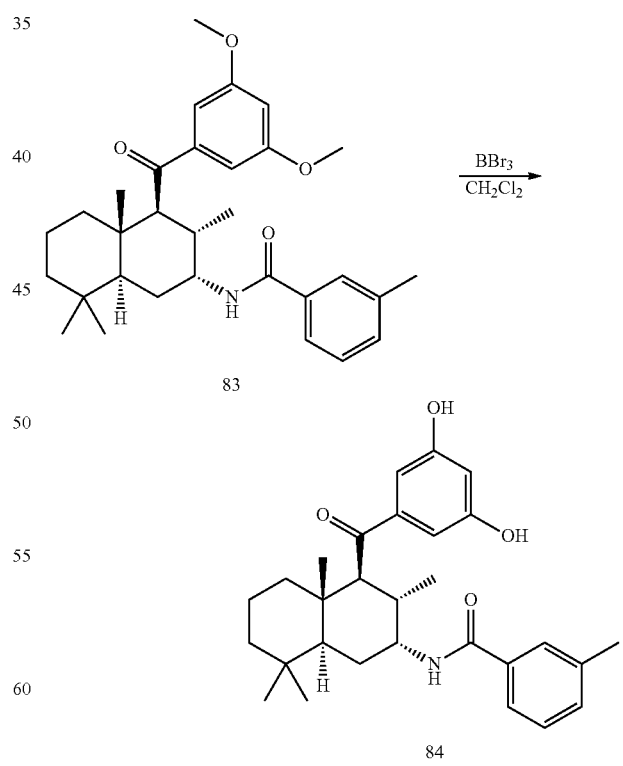

A solution of N-[(2R,3S,4S,4aS,8aS)-4-[(3,5-dimethoxyphenyl)carbonyl]-3,4a,8,8-tetramethyl-decahydronaphthalen-2-yl]-3-methylbenzamide (Compound No. 83, 110 mg, 0.22 mmol) in CH$_2$Cl$_2$ (2.2 mL) under argon was cooled to −78° C. Boron tribromide (1 M in CH$_2$Cl$_2$, 1.1 mL, 1.1 mmol) was added and the mixture was stirred at −78° C. for 10 min. The reaction was warmed up to room temperature and stirred overnight. Methanol (3 mL) was carefully added and the resultant mixture was concentrated in vacuo. This was repeated three times. Isopropanol/1 M HCl (3:1, 4 mL) was added, and the solution was heated to 85° C. for 45 min. The solution was concentrated, EtOAc (20 mL) and water (10 mL) were added, and the pH was adjusted to approximately 7 (1 M HCl and 1 M NaOH). The mixture was extracted with EtOAc (2×20 mL), dried over anhydrous Na$_2$SO$_4$, filtered, and concentrated in vacuo. Purification by flash chromatography using CH$_2$Cl$_2$/MeOH (20:1, EtOAc to load) afforded the impure product (92 mg, 89%) as a white solid. Additional purification via radial chromatography using hexanes/EtOAc (5:2) afforded pure N-[(2R,3S,4S,4aS,8aS)-4-[(3,5-dihydroxyphenyl)carbonyl]-3,4a,8,8-tetramethyl-decahydronaphthalen-2-yl]-3-methylbenzamide (Compound No. 84, 56 mg, 54%). $^1$H NMR (300 MHz, CD$_3$OD) δ8.35 (d, J=9.3 Hz, 1H), 7.56 (s, 2H), 7.35 (s, 2H), 6.95 (s, 2H), 6.49 (d, J=1.5 Hz, 1H), 4.88 (s, 2H), 4.52 (s, 1H), 3.59 (d, J=12.0 Hz, 1H), 3.30 (s, 1H), 2.41 (s, 3H), 1.99 (s, 1H), 1.78 (s, 2H), 1.45 (q, J=15.6, 6.3 Hz, 2H), 1.28 (m, 4H) 1.04 (s, 6H), 0.78 (s, 3H), 0.75 (s, 3H); $^{13}$C NMR (75 MHz, CD$_3$OD) δ206.4, 171.8, 159.8, 144.6, 139.4, 137.0, 132.9, 129.3, 129.1, 125.7, 107.9, 58.5, 51.6, 42.9, 42.4, 40.2, 34.1, 33.9, 28.9, 22.1, 21.4, 19.5, 16.7, 14.2; MS m/z: 464.3 ([M+1]$^+$).

A mixture of (2R,3S,4S,4aS,8aS)-4-[(3,5-dimethoxyphenyl)carbonyl]-3,4a,8,8-tetramethyl-decahydronaphthalen-2-amine (Compound No. 55, 125 mg, 0.33 mmol), benzotriazol-1-yl-oxytripyrrolidinophosphonium hexafluorophosphate (230 mg, 0.440 mmol), o-toluic acid (52 mg, 0.38 mmol), N,N-diisopropylethylamine (0.15 mL, 0.86 mmol) and DMF (3.5 mL) under argon was allowed to stir at room temperature for 20 h. EtOAc (20 mL) was added to the solution, and the mixture washed with saturated aqueous NaHCO$_3$ (3×10 mL) and saturated aqueous NaCl (2×10 mL). The organic layer was concentrated and the residue was purified by flash chromatography using hexanes/EtOAc (3:1) to afford the product N-[(2R,3S,4S,4aS,8aS)-4-[(3,5-dimethoxyphenyl)carbonyl]-3,4a,8,8-tetramethyl-decahydronaphthalen-2-yl]-2-methylbenzamide (Compound No. 85, 100 mg, 62%) as a white solid. $^1$H NMR (300 MHz, CDCl$_3$) δ7.66 (d, J=8.1 Hz, 2H), 7.27 (d, J=7.8 Hz, 2H), 7.04 (s, 2H), 6.62 (s, 1H), 6.31 (d, J=8.1 Hz, 1H), 4.55 (m, 1H), 3.83 (s, 6H), 3.10 (d, J=11.7 Hz, 1H), 2.53 (m, 1H), 2.41 (s, 3H), 1.80 (m, 2H), 1.41 (m, 1H), 1.27 (m, 4H), 1.15 (m, 2H), 1.10 (s, 3H), 0.86 (d, J=4.80 Hz, 6H), 0.84 (s, 3H), 0.81 (s, 3H); $^{13}$C NMR (75 MHz, CDCl$_3$) δ203.0, 170.2, 161.1, 142.8, 137.8, 136.0, 131.2, 130.0, 126.8, 126.2, 106.5, 104.4, 55.9, 49.9, 49.3, 42.1, 41.6, 39.6, 33.9, 33.3, 33.2, 28.0, 22.0, 18.7, 16.7, 14.5, 13.8; MS m/z: 492.4 ([M+1]$^+$).

EXAMPLE 53

Synthesis of N-[(2R,3S,4S,4aS,8aS)-4-[(3,5-dimethoxyphenyl)carbonyl]-3,4a,8,8-tetramethyl-decahydronaphthalen-2-yl]-2-methylbenzamide (Compound No. 85)

EXAMPLE 54

Synthesis of N-[(2R,3S,4S,4aS,8aS)-4-[(3,5-dihydroxyphenyl)carbonyl]-3,4a,8,8-tetramethyl-decahydronaphthalen-2-yl]-2-methylbenzamide (Compound No. 86)

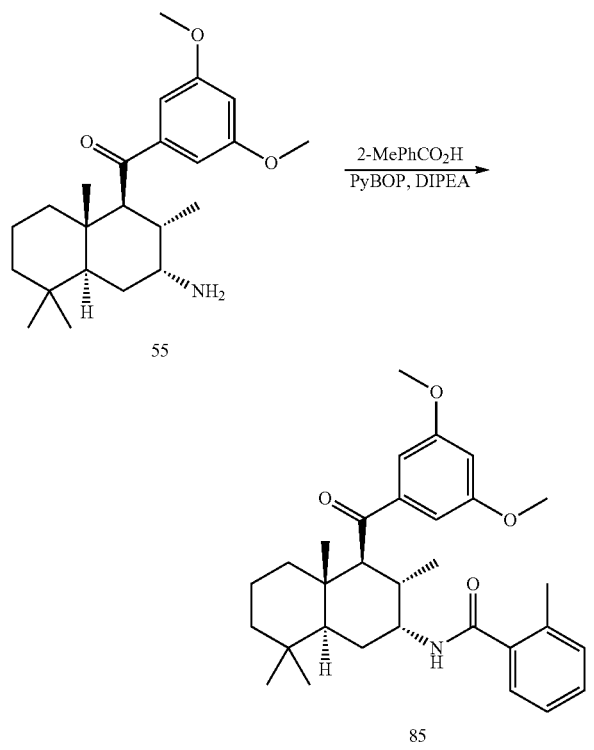

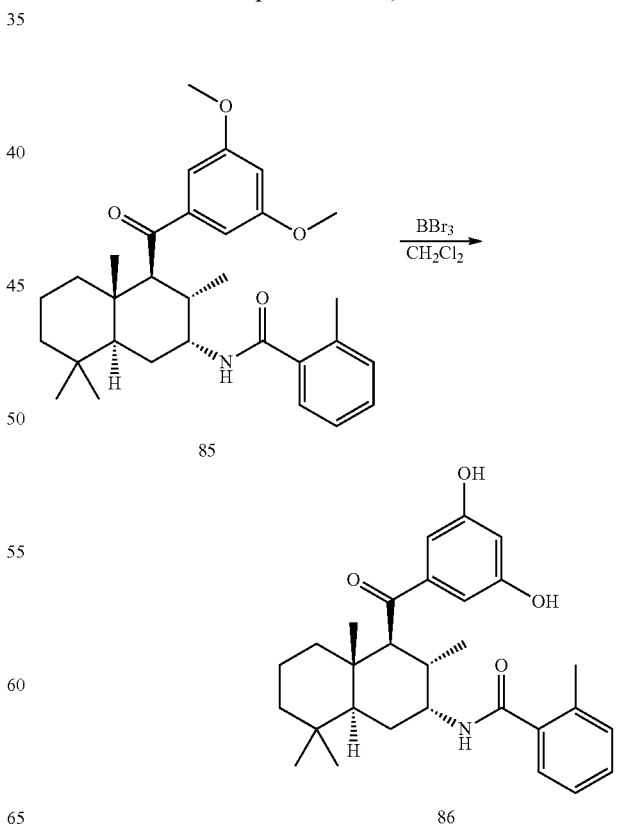

A solution of N-[(2R,3S,4S,4aS,8aS)-4-[(3,5-dimethoxyphenyl)carbonyl]-3,4a,8,8-tetramethyl-decahydronaphthalen-2-yl]-2-methylbenzamide (Compound No. 85, 46 mg, 0.09 mmol) in CH$_2$Cl$_2$ (1.0 mL) under argon was cooled to −78° C. Boron tribromide (1 M in CH$_2$Cl$_2$, 0.7 mL, 0.7 mmol) was added and the mixture was stirred at −78° C. for 10 min. The reaction was warmed up to room temperature and stirred overnight. Methanol (3 mL) was carefully added and the resultant mixture was concentrated in vacuo. This was repeated three times. Isopropanol/1 M HCl (3:1, 2 mL) was added, and the solution was heated to 85° C. for 45 min. The solution was concentrated, EtOAc (10 mL) and water (5 mL) were added, and the pH was adjusted to approximately 7 (1 M HCl and 1 M NaOH). The mixture was extracted with EtOAc (2×10 mL), dried over anhydrous Na$_2$SO$_4$, filtered, and concentrated in vacuo. Purification by flash chromatography using CH$_2$Cl$_2$/MeOH (20:1, EtOAc to load) afforded the impure product (36 mg, 86%) as a white solid. Additional purification of this material with 20 mg from another reaction via radial chromatography using hexanes/EtOAc (5:2) afforded pure N-[(2R,3S,4S,4aS,8aS)-4-[(3,5-dihydroxyphenyl)carbonyl]-3,4a,8,8-tetramethyl-decahydronaphthalen-2-yl]-2-methylbenzamide (Compound No. 86). $^1$H NMR (300 MHz, CD$_3$OD) δ8.67 (d, J=9.3 Hz, 1H), 7.26 (m, 4H), 6.92 (s, 2H), 6.46 (s, 1H), 4.88 (s, 2H), 4.49 (s, 1H), 3.51 (d, J=12.3 Hz, 1H), 3.31 (s, 1H), 2.38 (s, 3H), 2.00 (s, 2H), 1.50 (m, 1H), 1.25 (m, 6H), 0.89 (d, J=10.5 Hz, 6H), 0.81 (s, 3H), 0.78 (s, 3H); $^{13}$C NMR (75 MHz, CD$_3$OD) δ206.3, 173.4, 159.7, 144.5, 139.0, 136.1, 131.4, 130.5, 128.0, 126.7, 108.0, 58.7, 51.5, 42.9, 42.3, 40.1, 34.0, 33.9, 33.8, 28.9, 22.2, 19.7, 19.5, 16.8, 14.1; MS m/z: 464.4 ([M+1]$^+$).

EXAMPLE 55

Synthesis of N-[(2R,3S,4S,4aS,8aS)-4-[(3,5-dimethoxyphenyl)carbonyl]-3,4a,8,8-tetramethyl-decahydronaphthalen-2-yl]naphthalene-2-carboxamide (Compound No. 87)

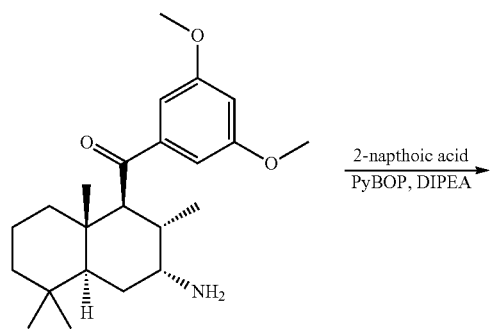

A mixture of (2R,3S,4S,4aS,8aS)-4-[(3,5-dimethoxyphenyl)carbonyl]-3,4a,8,8-tetramethyl-decahydronaphthalen-2-amine (Compound No. No. 55, 80 mg, 0.02 mmol), benzotriazol-1-yl-oxytripyrrolidinophosphonium hexafluorophosphate (135 mg, 0.260 mmol), 2-napthoic acid (45 mg, 0.26 mmol), N,N-diisopropylethylamine (0.10 mL, 0.52 mmol) and DMF (2.3 mL) under argon was allowed to stir at room temperature for 15 h. EtOAc (15 mL) was added to the solution, and the mixture washed with saturated aqueous NaHCO$_3$ (3×10 mL) and saturated aqueous NaCl (2×10 mL). The organic layer was concentrated and the residue was purified via radial chromatography using hexanes/EtOAc (5:1) to afford pure N-[(2R,3S,4S,4aS,8aS)-4-[(3,5-dimethoxyphenyl)carbonyl]-3,4a,8,8-tetramethyl-decahydronaphthalen-2-yl]naphthalene-2-carboxamide (Compound No. 87, 69 mg, 66%) as a white solid. $^1$H NMR (300 MHz, CDCl$_3$) δ8.23 (s, 1H), 7.86 (m, 4H), 7.56 (m, 2H), 7.07 (d, J=2.0 Hz, 2H), 6.62 (t, J=4.2, 2.1 Hz, 1H), 6.57 (d, J=8.5 Hz, 1H), 4.65 (m, 1H), 3.82 (s, 6H), 3.19 (d, J=11.7 Hz, 1H), 2.59 (m, 1H), 2.01 (s, 1H), 1.83 (m, 2H), 1.13 (s, 4H), 0.96 (d, J=6.6 Hz, 1H), 0.85 (m, 12H); $^{13}$C NMR (75 MHz, CDCl$_3$) δ203.1, 168.0, 161.1, 142.9, 134.9, 133.0, 132.9, 129.1, 128.8, 128.0, 127.8, 127.4, 127.0, 123.8, 106.5, 104.3, 58.8, 55.8, 50.1, 49.6, 42.0, 41.4, 39.7, 33.9, 33.7, 33.3, 27.9, 21.9, 18.7, 16.7, 13.7; MS m/z: 528.4 ([M+1]$^+$).

EXAMPLE 56

Synthesis of N-[(2R,3S,4S,4aS,8aS)-4-[(3,5-dihydroxyphenyl)carbonyl]-3,4a,8,8-tetramethyl-decahydronaphthalen-2-yl]naphthalene-2-carboxamide (Compound No. 88)

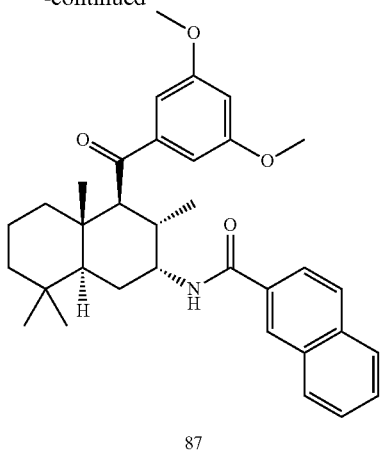

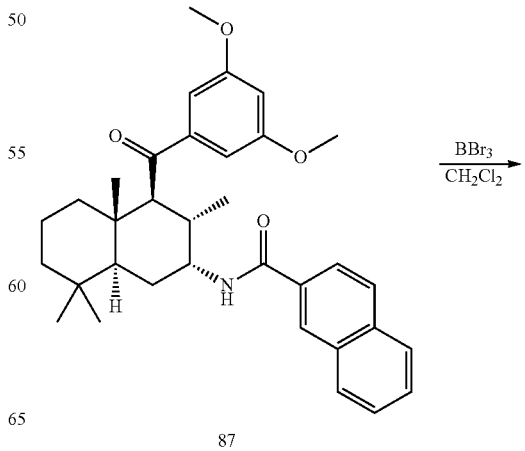

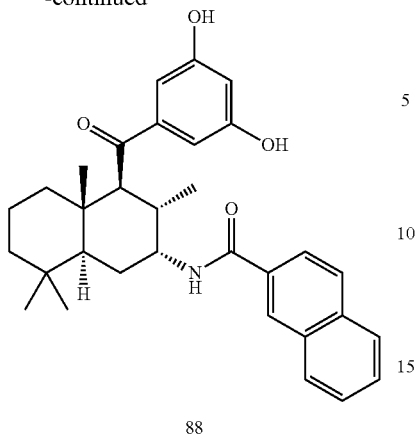

88

A solution of N-[(2R,3S,4S,4aS,8aS)-4-[(3,5-dimethoxyphenyl)carbonyl]-3,4a,8,8-tetramethyl-decahydronaphthalen-2-yl]naphthalene-2-carboxamide (Compound No. 87) (19 mg, 0.04 mmol) in CH$_2$Cl$_2$ (2.0 mL) under argon was cooled to −78° C. Boron tribromide (1 M in CH$_2$Cl$_2$, 0.3 mL, 0.3 mmol) was added and the mixture was stirred at −78° C. and allowed to warm to room temperature over 2 days. Methanol (6 mL) was carefully added and the resultant mixture was concentrated in vacuo. This was repeated three times. Isopropanol/1 M HCl (3:1, 4 mL) was added, and the solution was heated to 85° C. for 40 min. The solution was concentrated, EtOAc (25 mL) and water (10 mL) were added, and the pH was adjusted to approximately 9 (2 M NaOH). The mixture was extracted with EtOAc (3×10 mL), dried over anhydrous Na$_2$SO$_4$, filtered, and concentrated in vacuo. Purification by radial chromatography using hexanes/EtOAc (3:1 to 1:1 to 1:3) afforded pure N-[(2R,3S,4S,4aS,8aS)-4-[(3,5-dihydroxyphenyl)carbonyl]-3,4a,8,8-tetramethyl-decahydronaphthalen-2-yl]naphthalene-2-carboxamide (Compound No. 88, 13 mg, 72%) as a white solid. $^1$H NMR (300 MHz, CD$_3$OD) δ8.56 (d, J=9.1 Hz, 1 H), 8.30 (s, 1 H), 7.97 (m, 3 H), 7.81 (dd, J=8.5, 1.5 Hz, 1 H), 7.59 (m, 2 H), 6.96 (d, J=2.1 Hz, 2 H), 6.48 (t, J=2.0 Hz, 1 H), 4.59 (m, 1 H), 3.65 (d, J=12.1 Hz, 1 H), 2.52 (m, 1 H), 1.95-1.18 (m, 9 H), 1.07 (s, 3 H), 0.92 (s, 3 H), 0.90 (s, 3 H), 0.82 (d, J=7.0 Hz, 3 H); $^{13}$C NMR (75 MHz, CD$_3$OD) δ205.2, 170.4, 158.6, 143.4, 135.0, 133.0, 132.8, 128.8, 128.0, 127.63, 127.56, 127.4, 126.6, 124.2, 106.8, 57.7, 50.7, 41.7, 41.2, 39.0, 33.0, 32.7, 27.7, 21.0, 18.4, 15.6, 13.1; MS m/z: 500.3 ([M+1]$^+$).

EXAMPLE 57

Synthesis of N-[(3S,4S,4aS,8aS)-4-[(3,5-dihydroxyphenyl)carbonyl]-3,4a,8,8-tetramethyl-decahydronaphthalen-2-yl]pyrazine-2-carboxamide (Compound No. 89)

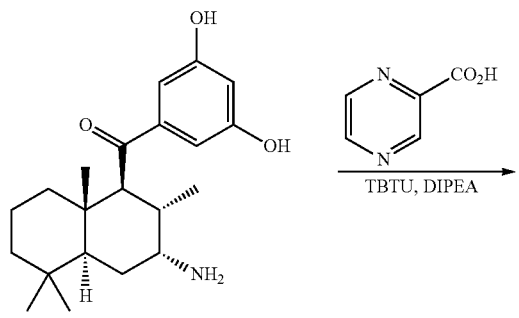

56

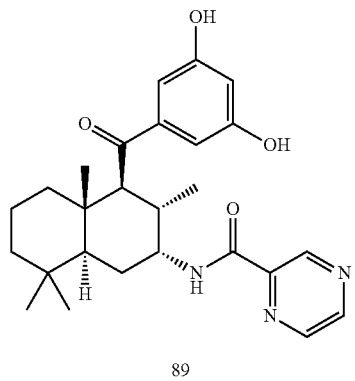

89

A mixture of 5-{[(1S,2S,3R,4aS,8aS)-3-amino-2,5,5,8a-tetramethyl-decahydronaphthalen-1-yl]carbonyl}benzene-1,3-diol (Compound No. 56, 145 mg, 0.42 mmol), O-(Benzotriazol-1-yl)-N,N,N',N'-tetramethyluronium tetrafluoroborate (519 mg, 1.62 mmol), pyrazine-2-carboxylic acid (172 mg, 1.39 mmol), N,N-diisopropylethylamine (0.60 mL, 3.4 mmol) and DMF (8 mL) under argon was allowed to stir at room temperature for 22 h. EtOAc (90 mL) was added to the solution, and the mixture washed with saturated aqueous NaHCO$_3$ (3×20 mL), water (20 mL) and saturated aqueous NaCl (2×20 mL). The organic layer was dried over anhydrous Na$_2$SO$_4$, concentrated and the residue was purified via radial chromatography using EtOAc to afford impure N-[(2R,3S,4S,4aS,8aS)-4-[(3,5-dihydroxyphenyl)carbonyl]-3,4a,8,8-tetramethyl-decahydronaphthalen-2-yl]pyrazine-2-carboxamide (Compound No. 89). The impure material was dissolved in MeOH (8 mL). Aqueous NaOH (2 M, 2 mL, 4 mmol) was added and the resultant mixture was stirred at room temperature for two days before being concentrated in vacuo. The residue was partitioned between EtOAc (90 mL) and water (30 mL). The organic layer was washed with saturated aqueous NaHCO$_3$ (3×30 mL), saturated aqueous NaCl (20 mL) and dried over anhydrous Na$_2$SO$_4$. The organic layer was concentrated and the residue was purified via radial chromatography using a gradient of 10% EtOAc/hexanes to 100% EtOAc to afford N-[(2R,3S,4S,4aS,8aS)-4-[(3,5-dihydroxyphenyl)carbonyl]-3,4a,8,8-tetramethyl-decahydronaphthalen-2-yl]pyrazine-2-carboxamide (Compound No. 89, 40 mg, 21%) as a white solid. $^1$H NMR (300 MHz, CD$_3$OD) δ9.26 (d, J=1.4 Hz, 1 H), 8.85 (d, J=2.4 Hz, 1 H), 8.78 (m, 1 H), 6.88 (d, J=2.1 Hz, 2 H), 6.48 (m, 1 H), 4.51 (m, 1 H), 3.38 (d, J=11.5 Hz, 1 H), 2.53 (m, 1 H), 1.94-1.18 (m, 9 H), 1.09 (s, 3 H), 0.88 (s, 3 H), 0.83 (s, 3 H), 0.75 (d, J=6.3 Hz, 3 H); $^{13}$C NMR (75 MHz, CD$_3$OD) δ204.2, 163.7, 163.3, 147.6, 143.7, 143.6, 143.2, 106.5, 58.1, 50.3, 41.7, 41.1, 39.2, 33.2, 32.7, 27.4, 20.9, 18.3, 15.5, 12.9; MS m/z: 452.4 ([M+1]$^+$).

EXAMPLE 58

Synthesis of 2-{[(3R,4S,4aS,8aS)-4-[(3,5-dimethoxyphenyl)carbonyl]-3,4a,8,8-tetramethyl-decahydronaphthalen-2-yl]carbonyl}pyridine (Compound No. 94)

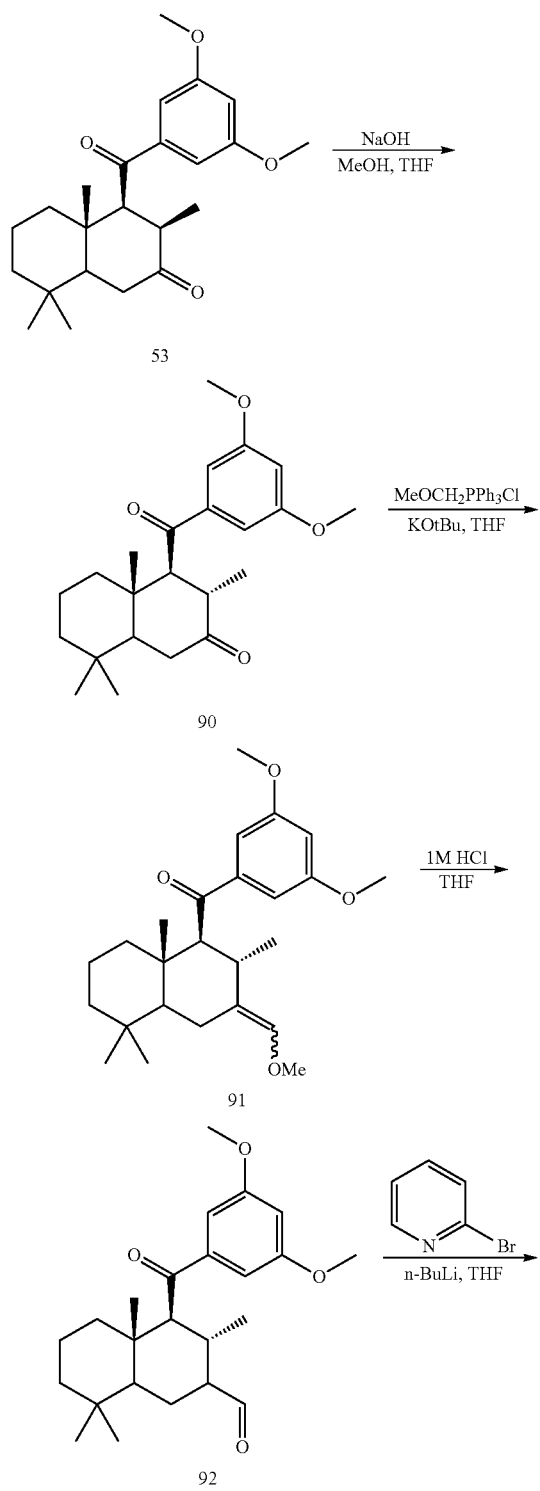

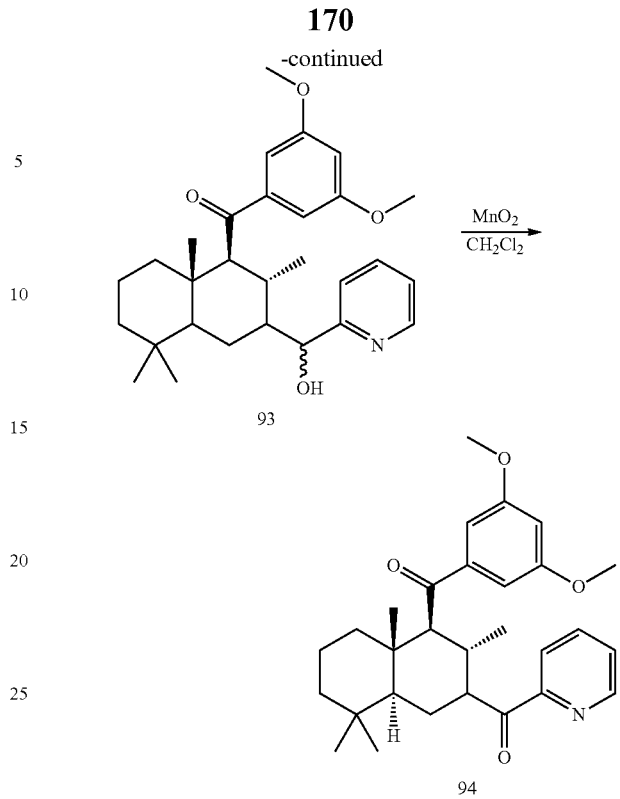

A. A mixture of (3R,4S,4aS,8aS)-4-[(3,5-dimethoxyphenyl)carbonyl]-3,4a,8,8-tetramethyl-decahydronaphthalen-2-one (Compound No. 53, 1.74 g, 4.68 mmol) and NaOH (2 M, 2.35 mL, 4.70 mmol) in MeOH/THF (2:1, 75 mL) was heated to 80° C. for 210 min. After cooling, the mixture was concentrated in vacuo and the resulting residue was partitioned between $CH_2Cl_2$ and saturated aqueous $NH_4Cl$. The aqueous layer was extracted with $CH_2Cl_2$ (3×) and the combined organic layers were washed with brine (1×), dried over anhydrous $Na_2SO_4$ and concentrated to afford (3S,4S,4aS,8aS)-4-[(3,5-dimethoxyphenyl)carbonyl]-3,4a, 8,8-tetramethyl-decahydronaphthalen-2-one (Compound No. 90, 1.59 g, 91%) as a white solid.

B. To a suspension of methoxymethyl triphenylphosphonium chloride (1.37 g, 4.00 mmol) in THF (15 mL) at room temperature under argon was added potassium t-butoxide (448 mg, 4.00 mmol) and resultant mixture was stirred for 20 min. To the resulting red mixture was added (3S,4S,4aS,8aS)-4-[(3,5-dimethoxyphenyl)carbonyl]-3,4a,8,8-tetramethyl-decahydronaphthalen-2-one (Compound No. 90, 500 mg, 1.34 mmol). After 1 h at room temperature, the reaction was quenched with saturated aqueous $NaHCO_3$ (20 mL) and EtOAc (60 mL) was added. The organic layer was washed with brine (3×20 mL), dried over anhydrous $Na_2SO_4$ and concentrated in vacuo. Purification by flash chromatography using EtOAc/hexanes (gradient from 5% to 10% to 20%) afforded a mixture of the desired enol ethers, [(1S,2S,4aS,8aS)-3-(methoxymethylidene)-2,5,5,8a-tetramethyl-decahydronaphthalen-1-yl](3,5-dimethoxyphenyl)methanone, (Compound No. 91, 424 mg, 81%) as a white foam.

C. A mixture of the enol ethers (Compound No. 91, 183 mg, 0.457 mmol) and HCl (1M, 0.5 mL, 0.5 mmol) in THF (2 mL) was heated at reflux for 30 min. After cooling to room temperature, the mixture was diluted with EtOAc (25 mL), washed with brine (3×5 mL), dried over anhydrous $Na_2SO_4$ and concentrated in vacuo to afford the aldehyde, (3R,4S,4aS,8aS)-4-[(3,5-dimethoxyphenyl)carbonyl]-3,4a,
8,8-tetramethyl-decahydronaphthalene-2-carbaldehyde,
(Compound No. 92, dr~10:1, 167 mg, 95%) as a white foam.

D. To a solution of 2-bromopyridine (91 μL, 0.95 mmol) in THF (5 mL) at −78° C. under argon was added n-butyllithium (1.9 M in hexanes, 0.45 mL, 0.86 mmol). After 10 min, a solution of (3R,4S,4aS,8aS)-4-[(3,5-dimethoxyphenyl)carbonyl]-3,4a,8,8-tetramethyl-decahydronaphthalene-2-carbaldehyde (Compound No. 92, 167 mg, 0.432 mg) in THF (2 mL) at −78° C. was added via cannula. After 3 h at this temperature, a saturated aqueous solution of NH$_4$Cl (10 mL) was added and the mixture was allowed to warm to room temperature. The mixture was extracted with EtOAc (3×15 mL), dried over anhydrous Na$_2$SO$_4$ and concentrated in vacuo. Purification by radial chromatography with EtOAc/hexanes (gradient from 20% to 35% to 50%) afforded a ca. 1:1 mixture of the diastereomeric alcohols, [(3R,4S,4aS,8aS)-4-[(3,5-dimethoxyphenyl)carbonyl]-3,4a,8,8-tetramethyl-decahydronaphthalen-2-yl](pyridin-2-yl)methanol, (Compound No. 93, 145 mg, 72%) as a thick oil.

E. A mixture of the alcohols from above (Compound No. 93, 145 mg, 0.311 mmol) and manganese dioxide (1.45 g) in CH$_2$Cl$_2$ (15 mL) under argon was stirred at room temperature overnight. Additional manganese dioxide (1.73 g) was added and the resultant mixture was stirred for the weekend. The mixture was filtered through a pad of celite and concentrated in vacuo. Purification by radial chromatography with EtOAc/hexanes (1:3) afforded 2-{[(3R,4S,4aS,8aS)-4-[(3,5-dimethoxyphenyl)carbonyl]-3,4a,8,8-tetramethyl-decahydronaphthalen-2-yl]carbonyl}pyridine (Compound No. 94, 108 mg, 75%) as a white solid. $^1$H NMR (300 MHz, CDCl$_3$) δ8.72 (d, J=4.2 Hz, 1 H), 8.10 (d, J=7.8 Hz, 1 H), 7.86 (td, J=7.8, 1.6 Hz, 1 H), 7.48 (m, 1 H), 7.09 (d, J=2.7 Hz, 2 H), 6.63 (m, 1 H), 3.99 (td, J=11.3, 3.8 Hz, 1 H), 3.85 (s, 6 H), 3.19 (d, J=11.9 Hz, 1 H), 2.76 (m, 1 H), 1.87 (m, 1 H), 1.59-1.00 (m, 7 H), 0.96 (d, J=6.4 Hz, 1H), 1.16 (s, 3 H), 0.86 (s, 3 H), 0.80 (s, 3 H), 0.67 (d, J=6.3 Hz, 3 H); $^{13}$C NMR (75 MHz, CDCl$_3$) δ204.7, 204.1, 161.0, 153.6, 149.2, 143.2, 137.2, 127.2, 122.7, 106.3, 104.8, 62.8, 55.8, 54.5, 50.7, 42.2, 41.2, 39.4, 33.7, 33.6, 32.1, 31.8, 26.3, 22.0, 19.2, 18.7, 14.3; MS m/z: 464.1 ([M+1]$^+$).

EXAMPLE 59

Synthesis of 5-{[(1S,2R,4aS,8aS)-2,5,5,8a-tetramethyl-3-[(pyridin-2-yl)carbonyl]-decahydronaphthalen-1-yl]carbonyl}benzene-1,3-diol (Compound No. 95)

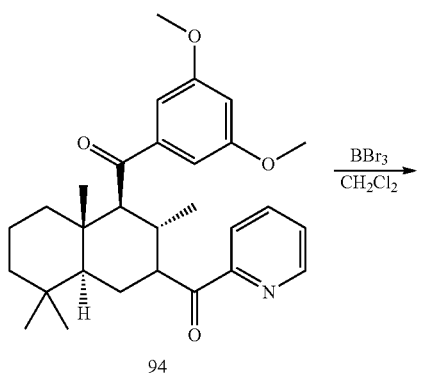

94

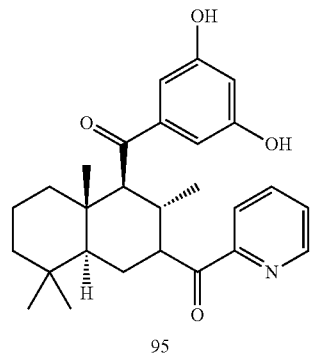

95

A solution of 2-{[(3R,4S,4aS,8aS)-4-[(3,5-dimethoxyphenyl)carbonyl]-3,4a,8,8-tetramethyl-decahydronaphthalen-2-yl]carbonyl}pyridine (Compound No. 94, 73 mg, 0.16 mmol) in CH$_2$Cl$_2$ (10 mL) under argon was cooled to −78° C. Boron tribromide (1 M in CH$_2$Cl$_2$, 0.8 mL, 0.8 mmol) was added and the mixture was stirred at −78° C. and allowed to warm to room temperature overnight. Methanol (10 mL) was carefully added and the resultant mixture was concentrated in vacuo. This was repeated three times. Isopropanol/1 M HCl (3:1, 8 mL) was added, and the solution was heated to 85° C. for 45 min. The solution was concentrated, EtOAc (40 mL) and water (20 mL) were added, and the pH was adjusted to approximately 9 (2 M NaOH). The mixture was extracted with EtOAc (3×20 mL), dried over anhydrous Na$_2$SO$_4$, filtered, and concentrated in vacuo. $^1$H NMR of the resultant residue indicated that the reaction had not gone to completion. The residue was dissolved in CH$_2$Cl$_2$ (10 mL) at room temperature under argon. Boron tribromide (1 M in CH$_2$Cl$_2$, 1.6 mL, 1.6 mmol) was added and the resultant mixture was stirred for 24 h. Methanol (10 mL) was carefully added and the resultant mixture was concentrated in vacuo. This was repeated three times. Isopropanol/1 M HCl (3:1, 8 mL) was added, and the solution was heated to 85° C. for 45 min. The solution was concentrated, EtOAc (40 mL) and water (20 mL) were added, and the pH was adjusted to approximately 9 (2 M NaOH). The mixture was extracted with EtOAc (3×20 mL), dried over anhydrous Na$_2$SO$_4$, filtered, and concentrated in vacuo. Purification by radial chromatography using hexanes/EtOAc (gradient from 3:1 to 2:1) afforded pure 5-{[(1S,2R,4aS,8aS)-2,5,5,8a-tetramethyl-3-[(pyridin-2-yl)carbonyl]-decahydronaphthalen-1-yl]carbonyl}benzene-1,3-diol (Compound No. 95, 57 mg, 84%) as a white solid. $^1$H NMR (300 MHz, CDCl$_3$) δ8.75 (dm, J=4.2 Hz, 1 H), 8.16 (d, J=7.3 Hz, 1 H), 7.93 (td, J=7.8, 1.3 Hz, 1 H), 7.57 (m, 1 H), 7.21 (br s, 2 H), 6.99 (d, J=1.7 Hz, 2 H), 6.70 (m, 1 H), 3.88 (td, J=11.4, 3.5 Hz, 1 H), 2.95 (d, J=11.4 Hz, 1 H), 2.71 (m, 1 H), 1.84 (m, 1 H), 1.69 (m, 2 H), 1.51-0.96 (m, 6 H), 1.08 (s, 3 H), 0.84 (s, 3 H), 0.76 (s, 3 H), 0.62 (d, J=8.0 Hz, 3 H); $^{13}$C NMR (75 MHz, CDCl$_3$) δ205.9, 204.4, 157.8, 153.1, 148.9, 143.3, 138.2, 127.9, 123.4, 108.4, 108.2, 63.0, 54.1, 50.6, 42.0, 41.2, 39.4, 33.6, 32.0, 26.2, 22.0, 19.0, 18.6, 14.3; MS m/z: 436.3 ([M+1]$^+$).

EXAMPLE 60

Synthesis of N-{[(2R,3R,4S,4aS,8aS)-4-[(3,5-dihydroxyphenyl)carbonyl]-3,4a,8,8-tetramethyl-decahydronaphthalen-2-yl]methyl}acetamide (Compound No. 102)

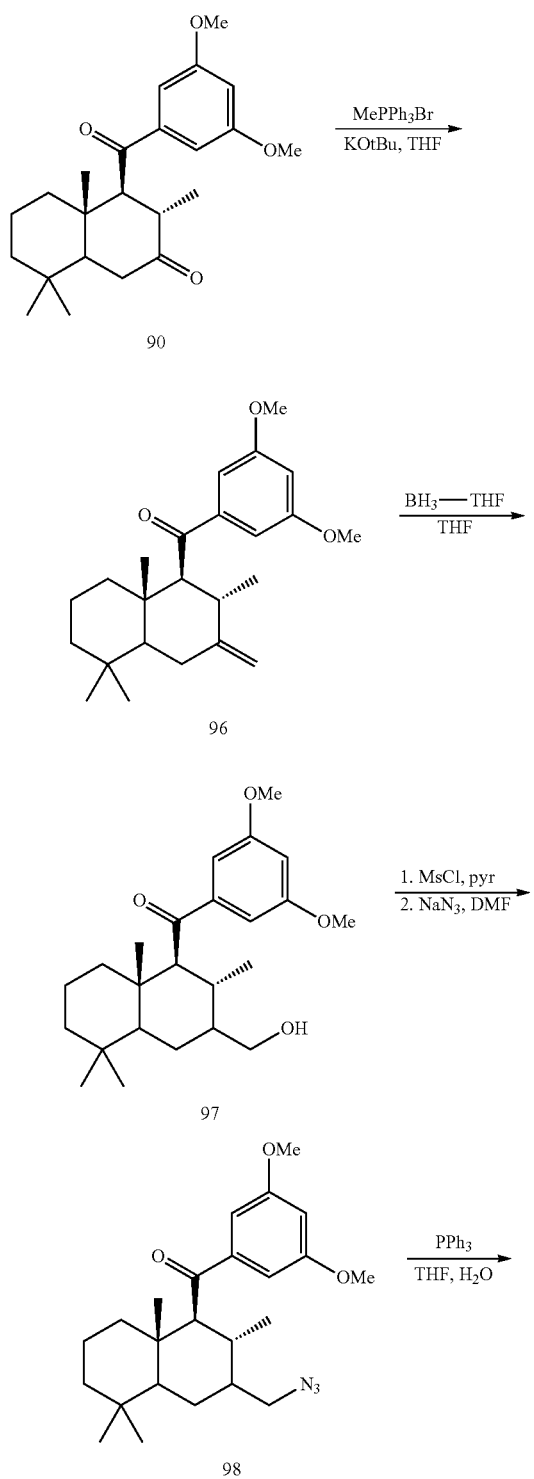

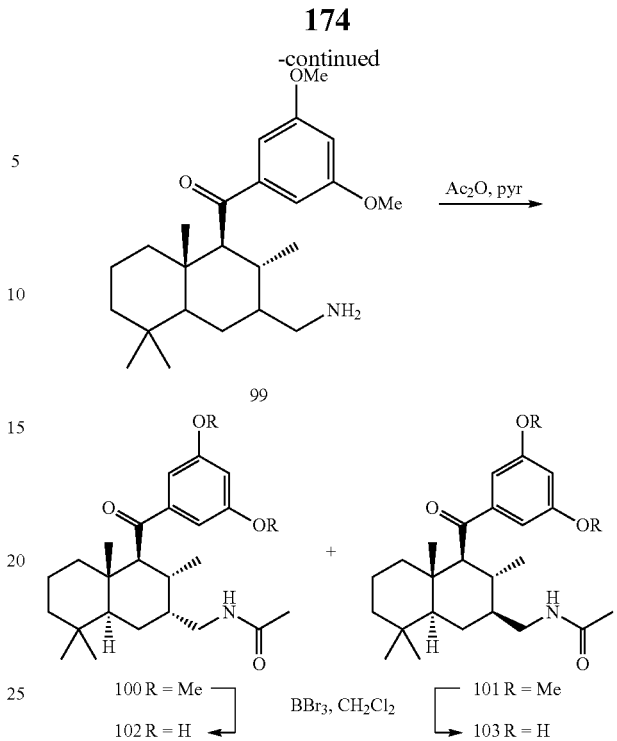

A. A solution of Ph₃PMeBr (863 mg, 2.42 mmol), KO'Bu (277 mg, 2.42 mmol) and THF (10 mL) was stirred at room temperature under argon. After 1 h, (3S,4S,4aS,8aS)-4-[(3,5-di methoxyphenyl)carbonyl]-3,4a, 8,8-tetramethyl-decahydronaphthalen-2-one (Compound No. 90, 300 mg, 0.805 mmol) was added to the bright yellow reaction mixture. After 2 h, the reaction mixture was cooled in ice then saturated NaHCO₃ solution (5 mL) was added. The mixture was diluted with EtOAc (75 mL) and was washed with half-saturated NaCl solution (2×15 mL). The EtOAc solution was dried over MgSO₄, filtered and concentrated. Purification using radial chromatography, eluting with 5% EtOAc/Hexanes afforded [(1S,2S,4aS,8aS)-2,5,5,8a-tetramethyl-3-methyl idene-decahydronaphthalen-1-yl](3,5-dimethoxyphenyl)methanone as a colourless film (Compound No. 96, 258 mg, 87% yield).

B. Borane (1.4 mL of a 1 M solution in THF, 1.4 mmol) was added to a −78° C. solution of [(1S,2S,4aS,8aS)-2,5,5,8a-tetramethyl-3-methylidene-decahydronaphthalen-1-yl](3,5-dimethoxyphenyl)methanone (Compound No. 96, 258 mg, 0.69 mmol) in THF (5 mL) under argon. The reaction was allowed to warm to room temperature. After 2 h, the reaction was cooled in ice then water (5 mL) was slowly added followed by NaBO₃ (215 mg). After 15 min, the ice bath was removed and the reaction was allowed to continue at room temperature for 2 h. The reaction mixture was diluted with EtOAc (75 mL) and was washed with half-saturated NaCl solution (3×15 mL). The EtOAc solution was dried over MgSO₄, filtered and concentrated. Purification using radial chromatography, eluting with 25% EtOAc/Hexanes afforded a mixture of diastereomers of [(3R,4S,4aS,8aS)-4-[(3,5-dimethoxyphenyl)carbonyl]-3,4a,8,8-tetramethyl-decahydronaphthalen-2-yl]methanol as a white foam (Compound No. 97, 216 mg, 80% yield).

C. Methanesulfonyl chloride (0.13 mL, 1.67 mmol) was added to an ice cold solution of [(3R,4S,4aS,8aS)-4-[(3,5-dimethoxyphenyl)carbonyl]-3,4a,8,8-tetramethyl-decahydronaphthalen-2-yl]methanol (Compound No. 97, 216 mg, 0.55 mmol) in pyridine (5 mL) under argon. After 1 h, saturated NaHCO₃ solution (5 mL) was added and the resulting solution was stirred at room temperature for 20 min. The mixture was diluted with EtOAc (75 mL) and was washed with half-saturated NaCl solution (3×15 mL). The EtOAc solution was dried over MgSO₄, filtered and concentrated. Residual pyridine was co-distilled with toluene (3×15 mL) to afford the desired mesylates as a white foam (253 mg, 97% yield).

D. A solution of the above mesylates (253 mg, 0.54 mmol), NaN₃ (106 mg, 1.6 mmol) and DMF (5 mL) under argon was heated at 60° C. for 2 days. The reaction mixture was cooled in ice, then saturated NaHCO₃ solution (2 mL) was added. The mixture was diluted with Et₂O (75 mL) and was washed with half-saturated NaCl solution (3×15 mL). The Et₂O solution was dried over MgSO₄, filtered and concentrated to afford [(1S,2R,4aS,8aS)-3-(azidomethyl)-2,5,5,8a-tetramethyl-decahydronaphthalen-1-yl](3,5-dimethoxyphenyl)methanone as a brown oil (Compound No. 98, 236 mg, quantitative yield).

E. A solution of [(1S,2R,4aS,8aS)-3-(azidomethyl)-2,5,5,8a-tetramethyl-decahydronaphthalen-1-yl](3,5-dimethoxyphenyl)methanone (Compound No. 98, 263 mg, 0.54 mmol), triphenylphosphine (715 mg, 2.7 mmol), water (0.05 mL 2.7 mmol) and THF (5 mL) was stirred at room temperature for 19 h then was heated at reflux for 5 h. The reaction was cooled to below room temperature then was concentrated. Purification using radial chromatography, eluting with 5% MeOH/CH₂Cl₂ then 5% MeOH/CH₂Cl₂ with 2% Et₃N afforded [(3R,4S,4aS,8aS)-4-[(3,5-dimethoxyphenyl)carbonyl]-3,4a,8,8-tetramethyl-decahydronaphthalen-2-yl]methanamine as an off-white solid (Compound No. 99, 263 mg, quantitative yield).

F. Acetic anhydride (0.15 mL, 1.6 mmol) was added to room temperature solution of [(3R,4S,4aS,8aS)-4-[(3,5-dimethoxyphenyl)carbonyl]-3,4a,8,8-tetramethyl-decahydronaphthalen-2-yl]methanamine (Compound No. 99, 263 mg, 0.54 mmol) in pyridine (5 mL) under argon. After 17 h, the reaction mixture was cooled in ice then saturated NaHCO₃ solution (1.5 mL) was added. The mixture was diluted with EtOAc (75 mL) and was washed with half-saturated NaCl solution (3×15 mL). The EtOAc solution was dried over MgSO₄, filtered and concentrated. Residual pyridine was co-distilled with toluene (3×15 mL). Purification using radial chromatography, eluting with 2% MeOH/CH₂Cl₂ afforded N-{[(2R,3R,4S,4aS,8aS)-4-[(3,5-dimethoxyphenyl)carbonyl]-3,4a,8,8-tetramethyl-decahydronaphthalen-2-yl]methyl}acetamide as a white solid (Compound No. 100, 104 mg, 44% yield from Compound No. 97) and N-{[(2S,3R,4S,4aS,8aS)-4-[(3,5-dimethoxyphenyl)carbonyl]-3,4a,8,8-tetramethyl-decahydronaphthalen-2-yl]methyl}acetamide as a white solid (Compound No. 101, 34 mg, 16% yield from Compound No. 97).

G. BBr₃ (1.2 mL of a 1 M solution in CH₂Cl₂) was added to a −78° C. solution of N-{[(2R,3R,4S,4aS,8aS)-4-[(3,5-dimethoxyphenyl)carbonyl]-3,4a,8,8-tetramethyl-decahydronaphthalen-2-yl]methyl}acetamide (Compound No. 100, 102 mg, 0.237 mmol) in CH₂Cl₂ (5 mL) under argon. The reaction mixture was allowed to warm to room temperature while allowed to react for 24 h. MeOH (10 mL) was added and the resulting mixture concentrated. The MeOH addition/concentration cycle was repeated twice more. The residue was taken up into i-PrOH (4.5 mL) and 1 N HCl (1.5 mL), then was heated at 85° C. for 45 min. The mixture was cooled to below room temperature and then was concentrated. CH₂Cl₂ (30 mL) and water (10 mL) were added then the pH was adjusted to approximately 9 by addition of 2 N NaOH solution. The layers were separated and the aqueous layer was extracted with EtOAc (25 mL). The CH₂Cl₂ and EtOAc extracts were combined and dried over MgSO₄, filtered and concentrated. Purification using radial chromatography, eluting with 80% EtOAc/Hexanes afforded N-{[(2R,3R,4S,4aS,8aS)-4-[(3,5-dihydroxyphenyl)carbonyl]-3,4a,8,8-tetramethyl-decahydronaphthalen-2-yl]methyl}acetamide as a white solid (Compound No. 102, 87 mg, 91% yield). ¹H NMR (CDCl₃): δ6.80 (s, 2H), 6.55 (br s, 1H), 6.45 (s, 1H), 3.25 (m, 2H), 3.15 (d, 1H), 2.35 (m, 1H), 1.90 (s, 3H), 1.90 (1H), 1.6-1.0 (7H), 0.95 (s, 3H), 0.78 (s, 3H), 0.76 (s, 3H), 0.70 (d, 3H). MS m/z 400.1 ([M−1]⁻).

EXAMPLE 61

Synthesis of N-{[(2S,3R,4S,4aS,8aS)-4-[(3,5-dihydroxyphenyl)carbonyl]-3,4a,8,8-tetramethyl-decahydronaphthalen-2-yl]methyl}acetamide (Compound No. 103)

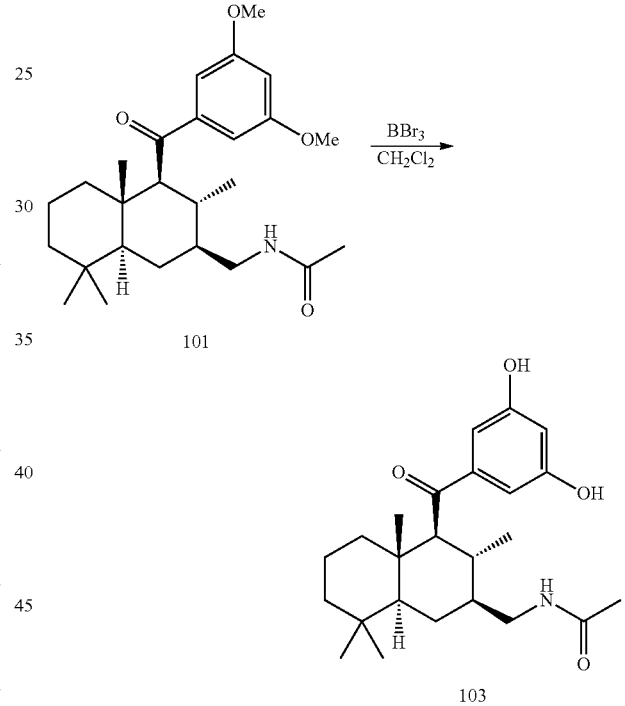

BBr₃ (0.8 mL of a 1 M solution in CH₂Cl₂) was added to an ice cooled solution of N-{[(2S,3R,4S,4aS,8aS)-4-[(3,5-dimethoxyphenyl)carbonyl]-3,4a,8,8-tetramethyl-decahydronaphthalen-2-yl]methyl}acetamide (Compound No. 101, 34 mg, 0.079 mmol) in CH₂Cl₂ (10 mL) under argon. After 5 min, the ice bath was removed then after 10 min the reaction vessel was fitted with a reflux condenser and the solution was heated in a 50° C. oil bath for 6.5 h. The reaction was then allowed to continue at room temperature for 17 h. MeOH (10 mL) was added and the resulting mixture was concentrated. The MeOH addition/concentration cycle was repeated twice more. The residue was taken up into i-PrOH (4.5 mL) and 1 N HCl (1.5 mL) then was heated at 85° C. for 45 min. The mixture was cooled to below room temperature then was concentrated. CH₂Cl₂ (30 mL) and water (10 mL) were added then the pH was adjusted to approximately 9 by addition of 2 N NaOH solution. The layers were separated and the aqueous layer was extracted with EtOAc (25 mL). The CH$_2$Cl$_2$ and EtOAc extracts were combined and dried over MgSO$_4$, filtered and concentrated. Purification using radial chromatography, eluting with 80% EtOAc/Hexanes then 1% MeOH/EtOAc afforded N-{[(2S,3R,4S,4aS,8aS)-4-[(3,5-dihydroxyphenyl)carbonyl]-3,4a,8,8-tetramethyl-decahydronaphthalen-2-yl]methyl}acetamide as a white solid (Compound No. 103, 32 mg, 100% yield). $^1$H NMR (CDCl$_3$): δ7.10 (1H), 6.70 (s, 2H), 6.40 (s, 1H), 3.35 (m, 1H), 2.95 (m, 1H), 2.85 (d, 1H), 1.85 (s, 3H), 1.75 (m, 1H), 1.50 (m, 1H), 1.4-0.9 (7H), 0.90 (s, 3H), 0.70 (s, 3H), 0.65 (6H). MS m/z 402.1 ([M+1]$^+$).

EXAMPLE 62

Synthesis of N-{[(2S,3R,4S,4aS,8aS)-4-[(3,5-dihydroxyphenyl)carbonyl]-3,4a,8,8-tetramethyl-decahydronaphthalen-2-yl]methyl}pyridine-3-carboxamide (Compound No. 109)

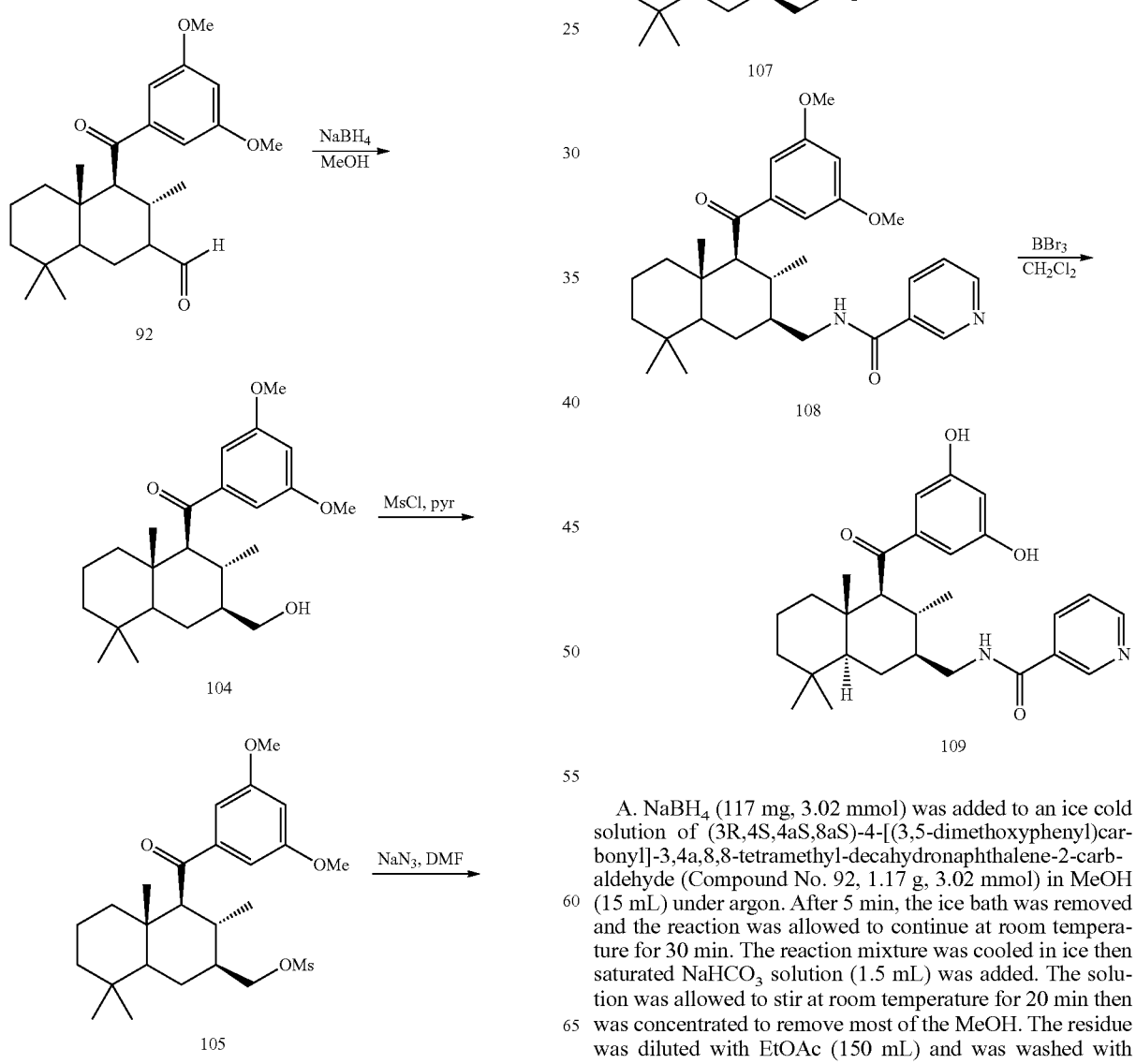

A. NaBH$_4$ (117 mg, 3.02 mmol) was added to an ice cold solution of (3R,4S,4aS,8aS)-4-[(3,5-dimethoxyphenyl)carbonyl]-3,4a,8,8-tetramethyl-decahydronaphthalene-2-carbaldehyde (Compound No. 92, 1.17 g, 3.02 mmol) in MeOH (15 mL) under argon. After 5 min, the ice bath was removed and the reaction was allowed to continue at room temperature for 30 min. The reaction mixture was cooled in ice then saturated NaHCO$_3$ solution (1.5 mL) was added. The solution was allowed to stir at room temperature for 20 min then was concentrated to remove most of the MeOH. The residue was diluted with EtOAc (150 mL) and was washed with half-saturated NaCl solution (3×30 mL). The EtOAc solution was dried over MgSO$_4$, filtered and concentrated. Purification using flash chromatography, eluting with 25% EtOAc/Hexanes, afforded [(2S,3R,4S,4aS,8aS)-4-[(3,5-dimethoxyphenyl)carbonyl]-3,4a,8,8-tetramethyl-decahydronaphthalen-2-yl]methanol as a white foam (Compound No. 104, 1.13 g, 96% yield).

D. Methanesulfonyl chloride (0.31 mL, 3.9 mmol) was added to an ice cold solution of [(2S,3R,4S,4aS,8aS)-4-[(3,5-dimethoxyphenyl)carbonyl]-3,4a,8,8-tetramethyl-decahydronaphthalen-2-yl]methanol (Compound No. 104, 505 mg, 1.3 mmol) in pyridine (6.5 mL) under argon. After 1.5 h, saturated NaHCO$_3$ solution (5 mL) was added and the resulting solution was stirred at room temperature for 40 min. The mixture was diluted with EtOAc (150 mL) and was washed with half-saturated NaCl solution (3×30 mL). The EtOAc solution was dried over MgSO$_4$, filtered and concentrated. Residual pyridine was co-distilled with toluene (3×40 mL) to afford [(2S,3R,4S,4aS,8aS)-4-[(3,5-dimethoxyphenyl)carbonyl]-3,4a,8,8-tetramethyl-decahydronaphthalen-2-yl]methyl methanesulfonate as a white foam (Compound No. 105, 601 mg, 99% yield).

E. A solution of [(2S,3R,4S,4aS,8aS)-4-[(3,5-dimethoxyphenyl)carbonyl]-3,4a,8,8-tetramethyl-decahydronaphthalen-2-yl]methyl methanesulfonate (Compound No. 105, 290 mg, 0.62 mmol), NaN$_3$ (121 mg, 1.86 mmol) and DMF (5 mL) under argon was heated at 60° C. for 18 h. The reaction mixture was cooled to room temperature then was diluted with Et$_2$O (75 mL) and was washed with half-saturated NaCl solution (3×15 mL). The Et$_2$O solution was dried over MgSO$_4$, filtered and concentrated to afford [(1S,2R,3S,4aS,8aS)-3-(azidomethyl)-2,5,5,8a-tetramethyl-decahydronaphthalen-1-yl](3,5-dimethoxyphenyl)methanone as a yellow oil (Compound No. 106, 260 mg, quantitative yield).

F. A solution of [(1S,2R,3S,4aS,8aS)-3-(azidomethyl)-2,5,5,8a-tetramethyl-decahydronaphthalen-1-yl](3,5-dimethoxyphenyl)methanone (Compound No. 106, 257 mg, 0.62 mmol), triphenylphosphine (815 mg, 3.1 mmol), water (0.05 mL 2.7 mmol) and THF (5 mL) was stirred at room temperature for 19 h then was heated at reflux for 6 h. The reaction was cooled to room temperature then was concentrated. Purification using radial chromatography, eluting with 5% MeOH/CH$_2$Cl$_2$ then 5% MeOH/CH$_2$Cl$_2$ with 2% Et$_3$N afforded [(2S,3R,4S,4aS,8aS)-4-[(3,5-dimethoxyphenyl)carbonyl]-3,4a,8,8-tetramethyl-decahydronaphthalen-2-yl]methanamine as a foam (Compound No. 107, 221 mg, 92%).

G. A solution of [(2S,3R,4S,4aS,8aS)-4-[(3,5-dimethoxyphenyl)carbonyl]-3,4a,8,8-tetramethyl-decahydronaphthalen-2-yl]methanamine (Compound No. 107, 50 mg, 0.13 mmol), nicotinic acid (21 mg, 0.17 mmol) and dicyclohexylcarbodiimide (DCC) (31 mg, 0.15 mmol) in CH$_2$Cl$_2$ (5 mL) was stirred at room temperature under argon. After 22 h, the reaction mixture was filtered through a plug of silica gel, eluting with CH$_2$Cl$_2$ then EtOAc. The filtrate was concentrated and purified using radial chromatography, eluting with 40%, 60% then 80% EtOAc/Hexanes to afford N-[(2S,3R,4S,4aS,8aS)-4-[(3,5-dimethoxyphenyl)carbonyl]-3,4a,8,8-tetramethyl-decahydronaphthalen-2-yl]methyl}pyridine-3-carboxamide as a white solid (Compound No. 108, 50 mg, 78% yield).

H. BBr$_3$ (1.0 mL of a 1 M solution in CH$_2$Cl$_2$) was added to a room temperature solution of N-[(2S,3R,4S,4aS,8aS)-4-[(3,5-dimethoxyphenyl)carbonyl]-3,4a,8,8-tetramethyl-decahydronaphthalen-2-yl]methyl}pyridine-3-carboxamide (Compound No. 108, 50 mg, 0.10 mmol) in CH$_2$Cl$_2$ (10 mL) under argon. The reaction mixture was heated at reflux for 2 h then allowed to react at room temperature for 3 days. Added MeOH (10 mL) then concentrated. The MeOH addition/concentration cycle was repeated twice more. The residue was taken up into i-PrOH (4.5 mL) and 1 N HCl (1.5 mL) then was heated at 85° C. for 45 min. The mixture was cooled to below room temperature then was concentrated. CH$_2$Cl$_2$ (30 mL) and water (10 mL) were added then the pH was adjusted to approximately 9 by addition of 2 N NaOH solution. The layers were separated and the aqueous layer was extracted with EtOAc (25 mL). The CH$_2$Cl$_2$ and EtOAc extracts were combined and dried over MgSO$_4$, filtered and concentrated. Purification using radial chromatography, eluting with 2% MeOH/EtOAc afforded N-{[(2S,3R,4S,4aS,8aS)-4-[(3,5-dihydroxyphenyl)carbonyl]-3,4a,8,8-tetramethyl-decahydronaphthalen-2-yl]methyl}pyridine-3-carboxamide as a white solid (Compound No. 109, 33 mg, 70% yield). $^1$H NMR (CDCl$_3$): δ8.90 (s, 1H), 8.60 (m, 1H), 8.15 (m, 1H), 7.70 (m, 1H), 7.40 (m, 1H), 6.90 (s, 2H), 6.45 (s, 1H), 3.70 (m, 1H), 3.25 (m, 1H), 2.97 (d, 1H), 1.90 (m, 1H), 1.70 (m, 1H), 1.4-1.0 (9H), 0.95 (s, 3H), 0.75 (9H). MS m/z 465.3 ([M+1]$^+$).

EXAMPLE 63

Synthesis of N-{[(2S,3R,4S,4aS,8aS)-4-[(3,5-dihydroxyphenyl)carbonyl]-3,4a,8,8-tetramethyl-decahydronaphthalen-2-yl]methyl}benzamide (Compound No. 111)

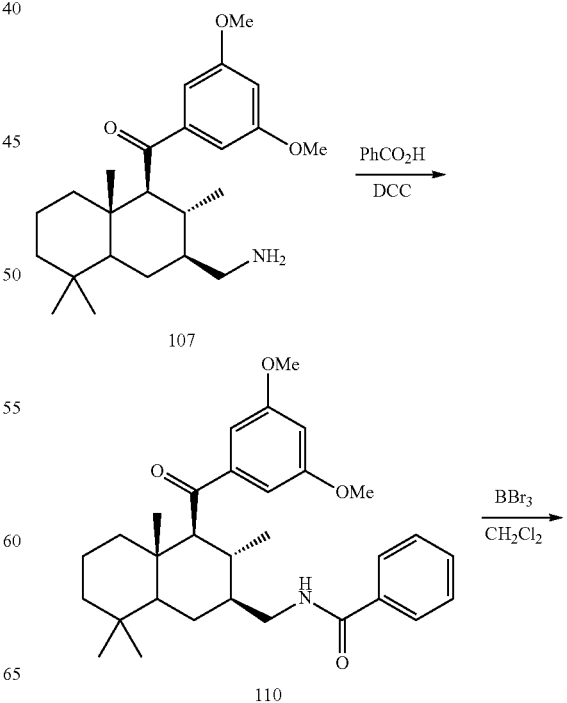

181
-continued

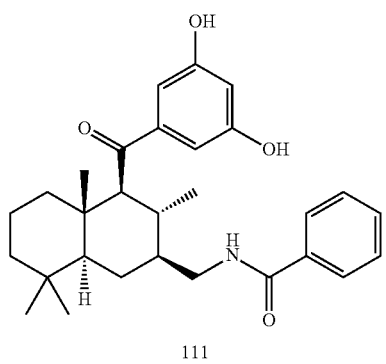

111

A. A solution of [(2S,3R,4S,4aS,8aS)-4-[(3,5-dimethoxyphenyl)carbonyl]-3,4a,8,8-tetramethyl-decahydronaphthalen-2-yl]methanamine (Compound No. 107, 56 mg, 0.14 mmol), benzoic acid (23 mg, 0.19 mmol) and DCC (40 mg, 0.19 mmol) in CH$_2$Cl$_2$ (5 mL) was stirred at room temperature under argon. After 19 h, the reaction mixture was filtered through a plug of silica gel, eluting with CH$_2$Cl$_2$ then EtOAc. The filtrate was concentrated and purified using radial chromatography, eluting with 20% EtOAc/Hexanes to afford N-{[(2S,3R,4S,4aS,8aS)-4-[(3,5-dimethoxyphenyl)carbonyl]-3,4a,8,8-tetramethyl-decahydronaphthalen-2-yl]methyl}benzamide as a white solid (Compound No. 110, 49 mg, 69% yield).

B. BBr$_3$ (0.5 mL of a 1 M solution in CH$_2$Cl$_2$) was added to an ice cooled solution of N-{[(2S,3R,4S,4aS,8aS)-4-[(3,5-dimethoxyphenyl)carbonyl]-3,4a,8,8-tetramethyl-decahydronaphthalen-2-yl]methyl}benzamide (Compound No. 110, 49 mg, 0.10 mmol) in CH$_2$Cl$_2$ (10 mL) under argon. The reaction mixture was allowed to react at room temperature for 6 days. Added MeOH (10 mL) then concentrated. The MeOH addition/concentration cycle was repeated twice more. The residue was taken up into i-PrOH (4.5 mL) and 1 N HCl (1.5 mL) then was heated at 85° C. for 45 min. The mixture was cooled to below room temperature then was concentrated. CH$_2$Cl$_2$ (30 mL) and water (10 mL) were added then the pH was adjusted to approximately 9 by addition of 2 N NaOH solution. The layers were separated and the aqueous layer was extracted with EtOAc (25 mL). The CH$_2$Cl$_2$ and EtOAc extracts were combined and dried over MgSO$_4$, filtered and concentrated. Purification using radial chromatography, eluting with 40% EtOAc/Hexanes afforded N-{[(2S,3R,4S,4aS,8aS)-4-[(3,5-dihydroxyphenyl)carbonyl]-3,4a,8,8-tetramethyl-decahydronaphthalen-2-yl]methyl}benzamide as a white solid (Compound No. 111, 26 mg, 56% yield). $^1$H NMR (CDCl$_3$): δ8.90 (s, 1H), 7.70 (m, 2H), 7.40 (m, 3H), 7.10 (1H), 6.78 (s, 2H), 6.42 (s, 1H), 3.65 (m, 1H), 3.20 (m, 1H), 2.95 (d, 1H), 1.85 (m, 1H), 1.65 (m, 1H), 1.4-1.0 (7H), 0.90 (s, 3H), 0.70 (9H). MS m/z 478.2 ([M+1]$^+$).

182
EXAMPLE 64

Synthesis of 5-{[(1S,2R,3S,4aS,8aS)-3-(1H-imidazol-1-ylmethyl)-2,5,5,8a-tetramethyl-decahydronaphthalen-1-yl]carbonyl}benzene-1,3-diol (Compound No. 113)

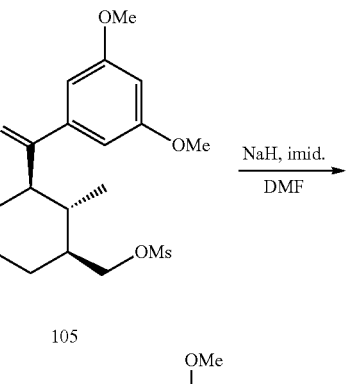

105

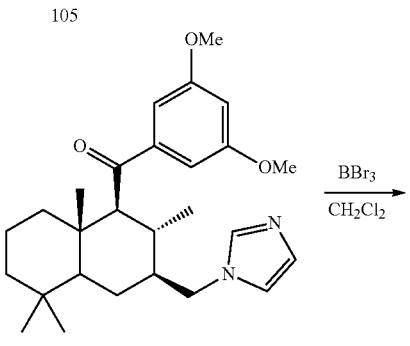

112

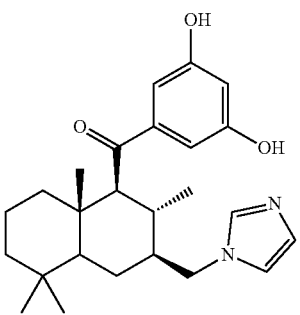

113

A. NaH (86 mg of a 60% dispersion in mineral oil, 2.1 mmol) was added to an ice cold solution of imidazole (146 mg, 2.1 mmol) in DMF (5 mL) under argon. After 1 h, [(2S,3R,4S,4aS,8aS)-4-[(3,5-dimethoxyphenyl)carbonyl]-3,4a,8,8-tetramethyl-decahydronaphthalen-2-yl]methyl methanesulfonate (Compound No. 105, 100 mg, 0.21 mmol) was added and the reaction was allowed to warm to room temperature. After 17 h, the reaction mixture was cooled in ice and saturated NaHCO$_3$ solution (5 mL) was added. The solution was diluted with Et$_2$O (75 mL) and was washed with half-saturated NaCl solution (3×15 mL). The Et$_2$O solution was dried over MgSO$_4$, filtered and concentrated. Purification using radial chromatography, eluting with 5% MeOH/CH$_2$Cl$_2$, afforded 1-{[(2S,3R,4S,4aS,8aS)-4-[(3,5-dimethoxyphenyl)carbonyl]-3,4a,8,8-tetramethyl-decahydronaphthalen-2-yl]methyl}-1H-imidazole as a white solid (Compound No. 112, 79 mg, 84% yield).

B. BBr₃ (0.74 mL of a 1 M solution in CH₂Cl₂) was added to a −78° C. solution of 1-{[(2S,3R,4S,4aS,8aS)-4-[(3,5-dimethoxyphenyl)carbonyl]-3,4a,8,8-tetramethyl-decahydronaphthalen-2-yl]methyl}-1H-imidazole (Compound No. 112, 65 mg, 0.15 mmol) in CH₂Cl₂ (5 mL) under argon. The reaction mixture was allowed to warm to room temperature while allowed to react for 21 h. Added MeOH (10 mL) then concentrated. The MeOH addition/concentration cycle was repeated twice more. The residue was taken up into i-PrOH (4.5 mL) and 1 N HCl (1.5 mL) then was heated at 85° C. for 45 min. The mixture was cooled to room temperature then was concentrated. CH₂Cl₂ (30 mL) and water (10 mL) were added then the pH was adjusted to approximately 9 by addition of 2 N NaOH solution. The layers were separated and the aqueous layer was extracted with EtOAc (25 mL). The CH₂Cl₂ and EtOAc extracts were combined and dried over MgSO₄, filtered and concentrated to afford 5-{[(1S,2R,3S,4aS,8aS)-3-(1H-imidazol-1-ylmethyl)-2,5,5,8a-tetramethyl-decahydronaphthalen-1-yl]carbonyl}benzene-1,3-diol as a tan solid (Compound No. 113, 40 mg, 65% yield). ¹H NMR (CDCl₃): δ7.42 (s, 1H), 6.95 (s, 1H), 6.85 (s, 1H), 6.78 (s, 2H), 6.42 (s, 1H), 4.15 (m, 1H), 3.72 (m, 1H), 2.97 (d, 1H), 1.95 (m, 1H), 1.50 (m, 1H), 1.4-1.1 (4H), 1.0 (6H), 0.8 (7H), 0.65 (6H). MS m/z 409.3 ([M−1]⁻).

EXAMPLE 65

Synthesis of 5-{[(1S,2R,3S,4aS,8aS)-2,5,5,8a-tetramethyl-3-(1H-1,2,4-triazol-1-ylmethyl)-decahydronaphthalen-1-yl]carbonyl}benzene-1,3-diol (Compound No. 115)

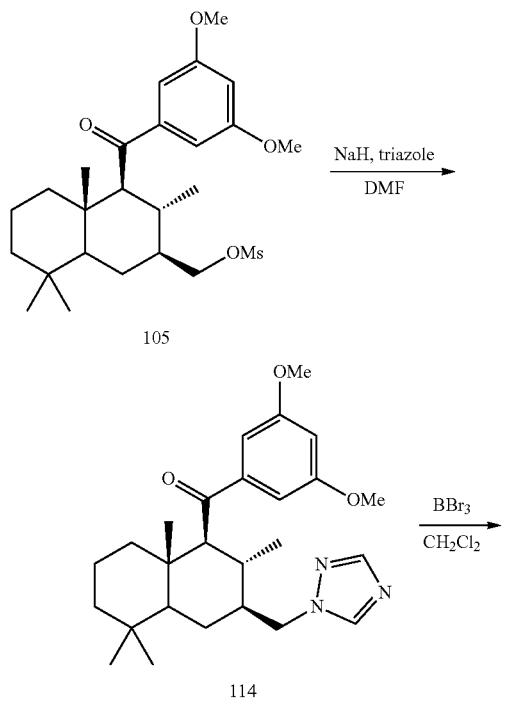

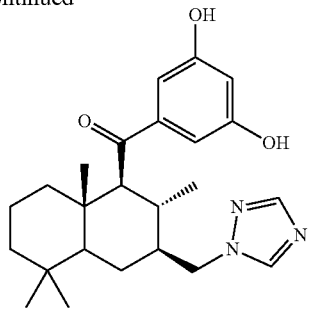

A. NaH (86 mg of a 60% dispersion in mineral oil, 2.1 mmol) was added to an ice cold solution of 1,2,4-triazole (148 mg, 2.1 mmol) in DMF (5 mL) under argon. After 1 h, [(2S,3R,4S,4aS,8aS)-4-[(3,5-dimethoxyphenyl)carbonyl]-3,4a,8,8-tetramethyl-decahydronaphthalen-2-yl]methyl methanesulfonate (Compound No. 105, 100 mg, 0.21 mmol) was added and the reaction was allowed to warm to room temperature. After 3 days, the reaction mixture was cooled in ice and saturated NaHCO₃ solution (3 mL) was added. The solution was diluted with Et₂O (75 mL) and was washed with half-saturated NaCl solution (3×15 mL). The Et₂O solution was dried over MgSO₄, filtered and concentrated. Purification using radial chromatography, eluting with 40% then 60% EtOAc/Hexanes, afforded 1-{[(2S,3R,4S,4aS,8aS)-4-[(3,5-dimethoxyphenyl)carbonyl]-3,4a,8,8-tetramethyl-decahydronaphthalen-2-yl]methyl}-1H-1,2,4-triazole as a white solid (Compound No. 114, 84 mg, 89% yield).

B. BBr₃ (0.93 mL of a 1 M solution in CH₂Cl₂) was added to a −78° C. solution of 1-{[(2S,3R,4S,4aS,8aS)-4-[(3,5-dimethoxyphenyl)carbonyl]-3,4a,8,8-tetramethyl-decahydronaphthalen-2-yl]methyl}-1H-1,2,4-triazole (Compound No. 114, 82 mg, 0.19 mmol) in CH₂Cl₂ (5 mL) under argon. The reaction mixture was allowed to warm to room temperature while allowed to react for 18 h. Added MeOH (10 mL) then concentrated. The MeOH addition/concentration cycle was repeated twice more. The residue was taken up into i-PrOH (4.5 mL) and 1 N HCl (1.5 mL) then was heated at 85° C. for 45 min. The mixture was cooled to room temperature then was concentrated. CH₂Cl₂ (30 mL) and water (10 mL) were added then the pH was adjusted to approximately 9 by addition of 2 N NaOH solution. The layers were separated and the aqueous layer was extracted with EtOAc (25 mL). The CH₂Cl₂ and EtOAc extracts were combined and dried over MgSO₄, filtered and concentrated. ¹H NMR indicated the reaction was not complete therefore the reaction was set up again with the modification that 10 mL CH₂Cl₂ was used as reaction solvent. After 2 days, the work up procedure was repeated. Purification using radial chromatography, eluting with 50% then 80% EtOAc/Hexanes afforded 5-{[(1S,2R,3S,4aS,8aS)-2,5,5,8a-tetramethyl-3-(1H-1,2,4-triazol-1-ylmethyl)-decahydronaphthalen-1-yl]carbonyl}benzene-1,3-diol as a white solid ((Compound No. 115, 51 mg, 66% yield). ¹H NMR (CDCl₃): δ8.10 (s, 1H), 7.90 (2, 1H), 6.78 (s, 2H), 6.45 (s, 1H), 4.35 (m, 1H), 3.98 (m, 1H), 2.97 (d, 1H), 1.90 (m, 1H), 1.70 (m, 1H), 1.4-1.1 (4H), 1.0 (6H), 0.80 (7H), 0.65 (6H). MS m/z 412.3 ([M+1]⁺).

EXAMPLE 66

Synthesis of 5-{[(1S,2R,3S,4aS,8aS)-2,5,5,8a-tetramethyl-3-[(4-methylpiperazin-1-yl)methyl]-decahydronaphthalen-1-yl]carbonyl}benzene-1,3-diol dihydrochloride salt (Compound No. 117)

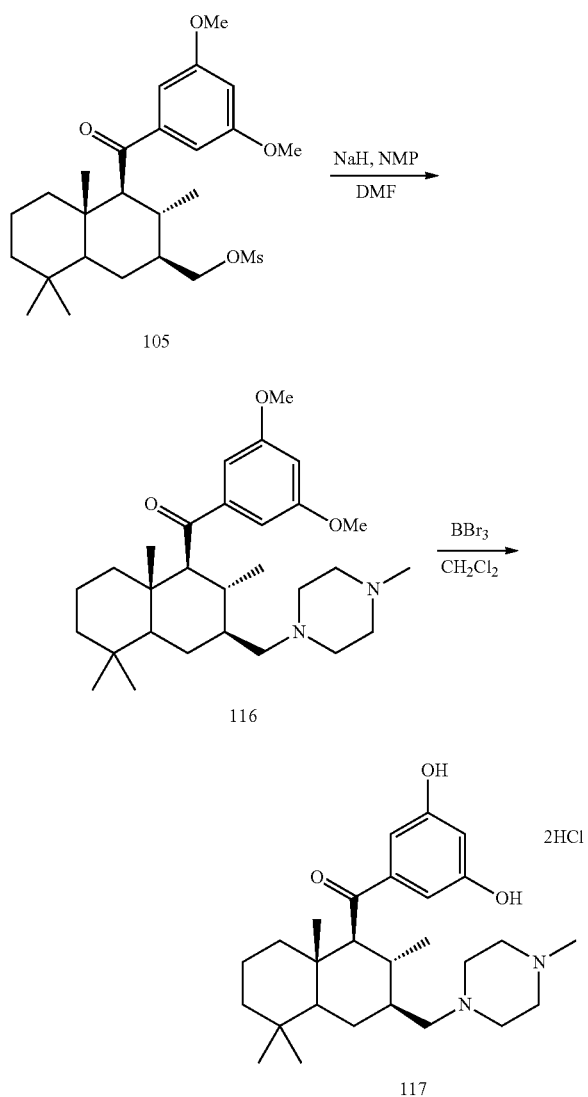

A. NaH (86 mg of a 60% dispersion in mineral oil, 2.1 mmol) was added to an ice cold solution of 1-methylpiperazine ("NMP") (0.24 mL, 2.1 mmol) in DMF (5 mL) under argon. After 1 h, [(2S,3R,4S,4aS,8aS)-4-[(3,5-dimethoxyphenyl)carbonyl]-3,4a,8,8-tetramethyl-decahydronaphthalen-2-yl]methyl methanesulfonate (Compound No. 105, 100 mg, 0.21 mmol) was added and the reaction was allowed to warm to room temperature. After 1 day, the reaction was heated at 50° C. for 23 h then the mixture was cooled in ice and saturated NaHCO$_3$ solution (3 mL) was added. The solution was diluted with Et$_2$O (75 mL) and was washed with half-saturated NaCl solution (3×15 mL). The Et$_2$O solution was dried over MgSO$_4$, filtered and concentrated. Purification using radial chromatography, eluting with 2% then 5%, then 10% MeOH/CH$_2$Cl$_2$, afforded 1-{[(2S,3R,4S,4aS,8aS)-4-[(3,5-dimethoxyphenyl)carbonyl]-3,4a,8,8-tetramethyl-decahydronaphthalen-2-yl]methyl}-4-methylpiperazine as a colourless film (Compound No. 116, 54 mg, 53% yield).

B. BBr$_3$ (0.6 mL of a 1 M solution in CH$_2$Cl$_2$) was added to a −78° C. solution of 1-{[(2S,3R,4S,4aS,8aS)-4-[(3,5-dimethoxyphenyl)carbonyl]-3,4a,8,8-tetramethyl-decahydronaphthalen-2-yl]methyl}-4-methylpiperazine (Compound No. 116, 54 mg, 0.12 mmol) in CH$_2$Cl$_2$ (5 mL) under argon. The reaction mixture was allowed to warm to room temperature while allowed to react for 23 h. Added MeOH (10 mL) then concentrated. The MeOH addition/concentration cycle was repeated twice more. The residue was taken up into i-PrOH (4.5 mL) and 1 N HCl (1.5 mL) then was heated at 85° C. for 45 min. The mixture was cooled to room temperature then was concentrated. CH$_2$Cl$_2$ (30 mL) and water (10 mL) were added then the pH was adjusted to approximately 9 by addition of 2 N NaOH solution. The layers were separated and the aqueous layer was extracted with EtOAc (25 mL). The CH$_2$Cl$_2$ and EtOAc extracts were combined and dried over MgSO$_4$, filtered and concentrated. $^1$H NMR indicated the reaction was not complete therefore the reaction was set up again with the modifications that the reaction was begun at 0° C. and that 10 mL CH$_2$Cl$_2$ was used as reaction solvent. After 3 days, the work up procedure was repeated. Purification using radial chromatography, eluting with 5% MeOH/CH$_2$Cl$_2$ with 2% Et$_3$N afforded 26 mg of a white solid. The material was taken up into MeCN (6 mL) then HCl (0.15 mL of a 1.25 M solution in i-PrOH) was added resulting in formation of a white precipitate. Most of the liquid was decanted then MeCN (5 mL) was added to the solid. The suspension was concentrated and dried to afford 5-{[(1S,2R,3S,4aS,8aS)-2,5,5,8a-tetramethyl-3-[(4-methylpiperazin-1-yl)methyl]-decahydronaphthalen-1-yl]carbonyl}benzene-1,3-diol dihydrochloride salt as a white solid (Compound No. 117, 26 mg, 44% yield). $^1$H NMR (CD$_3$OD): δ 6.85 (2H), 6.50 (1H), 3.8 (br s, 10H), 3.45 (m, 1H), 3.2 (m, 1H), 3.15 (d, 1H), 3.0 (s, 3H), 2.15 (m, 1H), 1.90 (m, 1H), 1.78 (m, 1H), 1.6-1.1 (6H), 1.00 (s, 3H), 0.97 (s, 3H), 0.90 (s, 3H), 0.85 (d, 3H). MS m/z 443.4 ([M+1]$^+$).

EXAMPLE 67

Synthesis of 3-[(2R,3S,4S,4aS,8aS)-4-[(3,5-dihydroxyphenyl)carbonyl]-3,4a,8,8-tetramethyl-decahydronaphthalen-2-yl]-1-(pyridin-3-yl)urea (Compound No. 118)

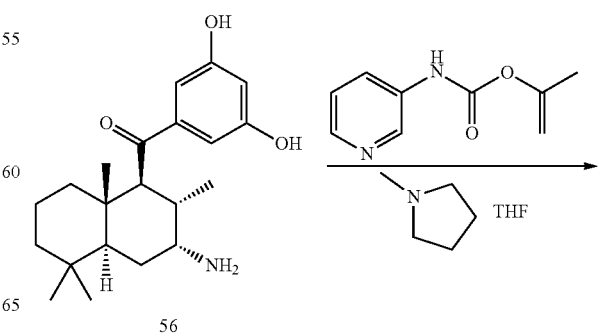

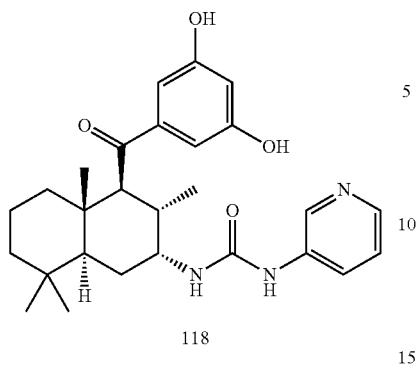

118

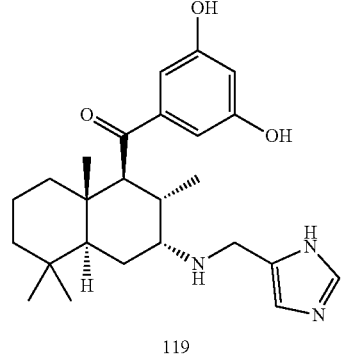

119

To a suspension of 5-{[(1S,2S,3R,4aS,8aS)-3-amino-2,5,5,8a-tetramethyl-decahydronaphthalen-1-yl]carbonyl}benzene-1,3-diol (Compound No. 56, 61 mg, 0.18 mmol) and pyridin-3-yl-carbamic acid isopropenyl ester (39 mg, 0.22 mmol, prepared according to Gallou, I. et al. *J. Org. Chem.*, 2005, 70 (17), pp 6960-6963) in THF (1.00 mL) was added 1-methylpyrrolidine (0.018 mL, 0.17 mmol) under argon then heated to 55° C. for 24 h. The suspension was allowed to cool to room temperature and stirred for another 17 h. The mixture was concentrated, and the residue was purified by chromatography on silica gel (MeOH/EtOAc, 1:9) to give 3-[(2R,3S,4S,4aS,8aS)-4-[(3,5-dihydroxyphenyl)carbonyl]-3,4a,8,8-tetramethyl-decahydronaphthalen-2-yl]-1-(pyridin-3-yl)urea as a colourless powder (Compound No. 118, 59 mg, 72%). $^1$H NMR (CD$_3$OD): δ8.56 (s, 1H), 8.14 (m, 1H), 7.97 (m, 1H), 7.34 (dd, J=8.3, 4.7 Hz, 1H), 6.88 (d, J=2.4 Hz, 1H), 6.51 (t, J=2.3 Hz, 1H), 4.13 (m, 1H), 3.23 (d, J=12 Hz, 1H), 2.42 (m, 1H), 1.11-1.85 (m, 10H), 1.08 (s, 3H), 0.88 (s, 6H), 0.77 (d, J=6.6 Hz, 3H). $^{13}$C NMR (CD$_3$OD): δ204.6, 158.7 (2C), 156.3, 143.4, 142.1, 139.3, 126.3, 124.1, 106.8, 106.5 (2C), 58.2, 50.3, 41.9, 41.3, 39.2, 33.3, 32.8, 32.7, 27.8, 20.9, 18.4, 15.5, 12.7. ES-MS m/z 466 ([M+1]$^+$).

A. To a suspension of 5-{[(1S,2S,3R,4aS,8aS)-3-amino-2,5,5,8a-tetramethyl-decahydronaphthalen-1-yl]carbonyl}benzene-1,3-diol (Compound No. 56, 81 mg, 0.23 mmol) and 4-imidazolecarboxaldehyde (34 mg, 0.35 mmol) in CH$_2$Cl$_2$ (2.3 mL) was added acetic acid (0.013 mL, 0.23 mmol) and sodium triacetoxyborohydride (158 mg, 0.745 mmol) under argon. The solution was stirred for 72 h, diluted with 10% MeOH/CH$_2$Cl$_2$ (20 mL), and washed with saturated aqueous NaHCO$_3$ (20 mL). The aqueous layer was extracted with 10% MeOH/CH$_2$Cl$_2$ (3×10 mL), and the combined organic layers were dried (MgSO$_4$) and concentrated. The residue was purified by chromatography on silica gel (CH$_2$Cl$_2$/MeOH/NH$_4$OH, 100:10:1) to give 5-{[(1S,2S,3R,4aS,8aS)-3-[(1H-imidazol-5-ylmethyl)amino]-2,5,5,8a-tetramethyl-decahydronaphthalen-1-yl]carbonyl}benzene-1,3-diol as a colourless powder (Compound No. 119, 24 mg, 24%). $^1$H NMR (CD$_3$OD): δ7.69 (s, 1H), 7.07 (s, 1H), 6.87 (d, J=2.1 Hz, 2H), 6.46 (t, J=2.3 Hz, 1H), 3.93 (d, J=14 Hz, 1H), 3.74 (d, J=14 Hz, 1H), 3.53 (d, J=12 Hz, 1H), 3.00 (br s, 1H), 2.33 (m, 1H), 1.95 (m, 1H), 1.19-1.60 (m, 7H), 1.06 (m, 1H), 1.04 (s, 3H), 0.96 (s, 3H), 0.89 (s, 3H), 0.77 (d, J=6.6 Hz, 3H). $^{13}$C NMR (CD$_3$OD): δ206.5, 159.9 (2C), 144.5, 136.7 (2C), 118.2, 108.1, 107.8 (2C), 58.4, 58.0, 47.3, 44.2, 42.9, 42.1, 40.5, 35.0, 34.0 (2C), 25.4, 22.2, 19.6, 16.5, 14.1. ES-MS m/z 426 ([M+1]$^+$).

EXAMPLE 68

Synthesis of 5-{[(1S,2S,3R,4aS,8aS)-3-[(1H-imidazol-5-ylmethyl)amino]-2,5,5,8a-tetramethyl-decahydronaphthalen-1-yl]carbonyl}benzene-1,3-diol (Compound No. 119)

EXAMPLE 69

Synthesis of 1-[(2R,3S,4S,4aS,8aS)-4-[(3,5-dihydroxyphenyl)carbonyl]-3,4a,8,8-tetramethyl-decahydronaphthalen-2-yl]-3-ethylurea (Compound No. 120)

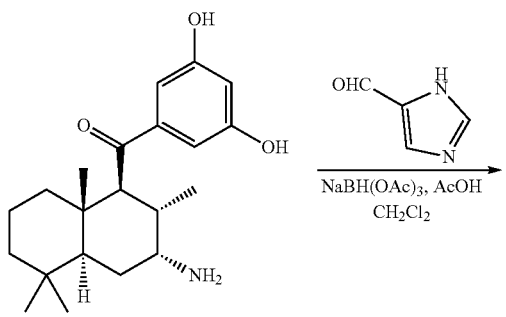

56

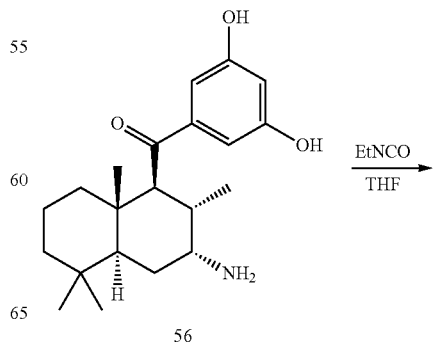

56

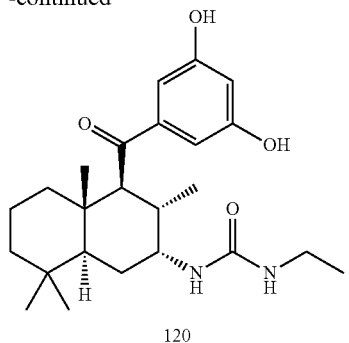

120

To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 50 mg, 0.14 mmol) in THF (1.46 mL) was added ethyl isocyanate (0.023 mL, 0.29 mmol) under argon. The solution was stirred at room temperature for 6 h then another equivalent of ethyl isocyanate (0.010 mL, 0.13 mmol) was added. The solution was stirred for another 60 h then concentrated. The residue was purified by chromatography on silica gel (CH$_2$Cl$_2$/MeOH/NH$_4$OH, 100:10:2) to give 1-[(2R,3S,4S,4aS,8aS)-4-[(3,5-dihydroxyphenyl)carbonyl]-3,4a,8,8-tetramethyl-decahydronaphthalen-2-yl]-3-ethylurea as a colourless solid (Compound No. 120, 45 mg, 75%). $^1$H NMR (CD$_3$OD): δ6.87 (d, J=1.8 Hz, 2H), 6.49 (s, 1H), 6.29 (d, J=9.0 Hz, 1H), 4.02 (m, 1H), 3.18 (m, 3H), 2.34 (m, 1H), 1.03-1.75 (m, 15H), 0.85 (s, 6H), 0.70 (d, J=6.6 Hz, 3H). $^{13}$C NMR (CD$_3$OD): δ206.1, 161.0, 159.8 (2C), 144.6, 108.0, 107.7 (2C), 59.2, 51.2, 49.2, 43.0, 42.4, 40.3, 35.7, 34.6, 33.9 (2C), 29.2, 22.1, 19.5, 16.7, 15.9, 14.0. ES-MS m/z 417 ([M+1]$^+$).

EXAMPLE 70

Synthesis of 1-[(2R,3S,4S,4aS,8aS)-4-[(3,5-dihydroxyphenyl)carbonyl]-3,4a,8,8-tetramethyl-decahydronaphthalen-2-yl]-3-methoxyurea (Compound No. 121)

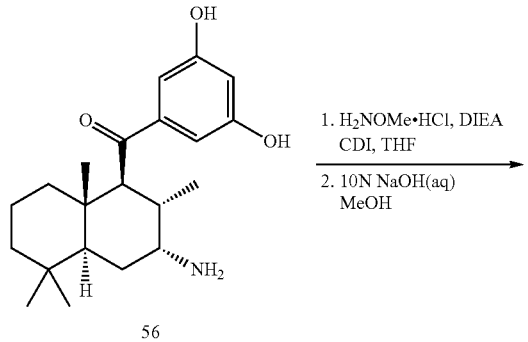

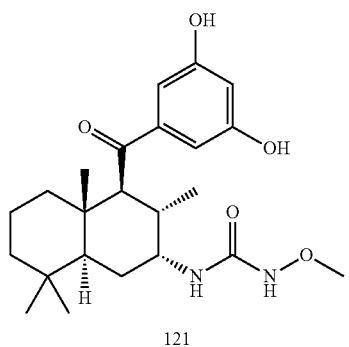

121

To a suspension of methoxylamine hydrochloride (291 mg, 3.48 mmol) in THF (5.0 mL) was added 1,1'-carbonyldiimidazole (564 mg, 3.48 mmol) and N,N-diisopropylethylamine (1.10 mL, 6.31 mmol) under argon. The solution was stirred at room temperature for 1 h then 5-{[(1S,2S,3R,4aS,8aS)-3-amino-2,5,5,8a-tetramethyl-decahydronaphthalen-1-yl]carbonyl}benzene-1,3-diol (Compound No. 56, 109 mg, 0.316 mmol) in THF (10.8 mL) was added, and the solution was heated to 60° C. overnight. After 20 h, the solution was allowed to cool to room temperature and saturated aqueous NaHCO$_3$ (20 mL) was added. The aqueous layer was extracted with EtOAc (3×20 mL), and the combined organic layers were dried (MgSO$_4$) and concentrated. The residue was partially purified by chromatography on silica gel (MeOH/EtOAc, 1:49) to give a colourless solid (112 mg). To a solution of the colourless solid (112 mg) in MeOH (5.0 mL) was added 10N NaOH (0.50 mL, 5.0 mmol) at room temperature. The solution was stirred for 1 h then concentrated, and the residue was partitioned between EtOAc (40 mL) and H$_2$O (20 mL). The aqueous layer was adjusted to pH 9 and extracted with EtOAc (2×30 mL). The combined organic layers were dried (MgSO$_4$) and concentrated. The residue was suspended in CH$_2$Cl$_2$, heated to a boil, and allowed to cool to room temperature. 1-[(2R,3S,4S,4aS,8aS)-4-[(3,5-dihydroxyphenyl)carbonyl]-3,4a,8,8-tetramethyl-decahydronaphthalen-2-yl]-3-methoxyurea, a colourless solid (Compound No. 121, 19 mg, 14%), was collected by filtration. $^1$H NMR (CD$_3$OD): δ6.86 (d, J=1.8 Hz, 2H), 6.53 (d, J=9.9 Hz, 1H), 6.49 (s, 1H), 4.15 (m, 1H), 3.74 (s, 3H), 3.25 (d, J=12 Hz, 1H), 2.41 (m, 1H), 1.75 (m, 2H), 1.06-1.57 (m, 10H), 0.87 (s, 6H), 0.72 (d, J=6.6 Hz, 3H). $^{13}$C NMR (CD$_3$OD): δ205.7, 162.1, 159.9 (2C), 144.4, 108.1, 107.7 (2C), 64.7, 59.3, 51.2, 49.5, 42.9, 42.3, 40.3, 34.4, 34.0, 33.9, 29.0, 22.1, 19.5, 16.7, 14.0. ES-MS m/z 419 ([M+1]$^+$).

EXAMPLE 71

Synthesis of N-[(2R,3S,4S,4aS,8aS)-4-[(3,5-dihydroxyphenyl)carbonyl]-3,4a,8,8-tetramethyl-decahydronaphthalen-2-yl]benzamide (Compound No. 122)

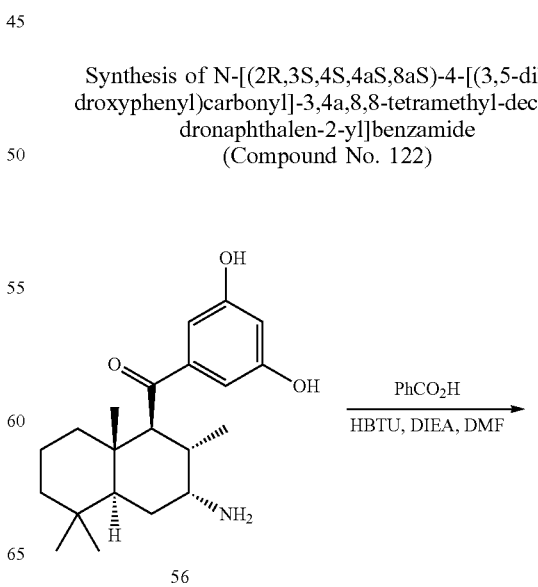

191

-continued

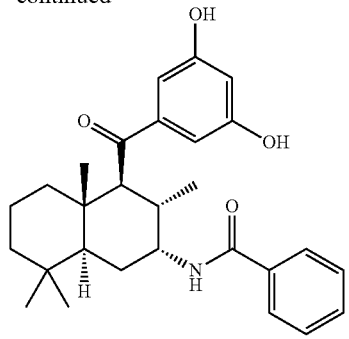

122

To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 149 mg, 0.431 mmol), O-(benzotriazol-1-yl)-N,N,N',N'-tetramethyluronium hexafluorophosphate (170 mg, 0.448 mmol), and benzoic acid (63 mg, 0.52 mmol) in DMF (4.32 mL) was added N,N-diisopropylethylamine (0.11 mL, 0.63 mmol) under argon. The solution was stirred at room temperature for 66 h then concentrated. The residue was dissolved in EtOAc (40 mL) and washed with saturated aqueous NaHCO$_3$ (5×10 mL) and brine (2×10 mL) then dried (MgSO$_4$) and concentrated. The residue was purified by chromatography on silica gel (MeOH/CH$_2$Cl$_2$, 1:24) to give N-[(2R,3S,4S,4aS,8aS)-4-[(3,5-di hydroxyphenyl)carbonyl]-3,4a,8,8-tetramethyl-decahydronaphthalen-2-yl]benzamide as a colourless powder (Compound No. 122, 130 mg, 67%). $^1$H NMR (CD$_3$OD): δ8.41 (d, J=9.3 Hz, 1H), 7.75 (d, J=8.1 Hz, 2H), 7.52 (m, 3H), 6.95 (d, J=1.8 Hz, 2H), 6.48 (s, 1H), 4.51 (m, 1H), 3.60 (d, J=12 Hz, 1H), 2.49 (m, 1H), 1.79 (m, 2H), 1.28-1.56 (m, 6H), 1.08 (m, 4H), 0.88 (s, 6H), 0.78 (d, J=6.6 Hz, 3H). $^{13}$C NMR (CD$_3$OD): δ206.3, 171.5, 159.6 (2C), 144.5, 136.9, 132.2, 129.3 (2C), 128.5 (2C), 108.0, 107.9 (2C), 58.8, 51.6, 48.6, 42.8, 42.3, 40.1, 34.0, 33.9, 33.8, 28.8, 22.1, 19.5, 16.7, 14.2. ES-MS m/z 450 ([M+1]$^+$).

EXAMPLE 72

Synthesis of N-[(2R,3S,4S,4aS,8aS)-4-[(3,5-dihydroxyphenyl)carbonyl]-3,4a,8,8-tetramethyl-decahydronaphthalen-2-yl]pyridine-3-carboxamide (Compound No. 123)

192

-continued

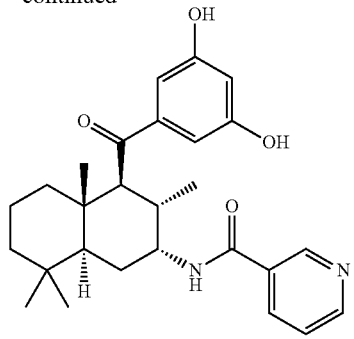

123

To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 147 mg, 0.425 mmol), O-(benzotriazol-1-yl)-N,N,N',N'-tetramethyluronium hexafluorophosphate (164 mg, 0.432 mmol), and nicotinic acid (64 mg, 0.52 mmol) in DMF (4.27 mL) was added N,N-diisopropylethylamine (0.10 mL, 0.57 mmol) under argon. The solution was stirred at room temperature for 66 h then concentrated. The residue was dissolved in EtOAc (40 mL) and washed with saturated aqueous NaHCO$_3$ (5×10 mL) and brine (2×10 mL) then dried (MgSO$_4$) and concentrated. The residue was suspended in CH$_2$Cl$_2$, heated to a boil, and allowed to cool to room temperature. A pink solid was collected by filtration then purified by chromatography on silica gel (EtOAc) to give N-[(2R,3S,4S,4aS,8aS)-4-[(3, 5-dihydroxyphenyl)carbonyl]-3,4a,8,8-tetramethyl-decahydronaphthalen-2-yl]pyridine-3-carboxamide as a colourless solid (Compound No. 123, 72 mg, 38%). $^1$H NMR (CD$_3$OD): δ8.88 (s, 1H), 8.70 (d, J=3.6 Hz, 1H), 8.16 (d, J=8.7 Hz, 1H), 7.57 (m, 1H), 6.94 (d, J=2.1 Hz, 2H), 6.48 (s, 1H), 4.54 (m, 1H), 3.57 (d, J=13 Hz, 1H), 2.50 (m, 1H), 1.81 (m, 2H), 1.24-1.56 (m, 6H), 1.09 (m, 4H), 0.89 (s, 6H), 0.78 (d, J=6.3 Hz, 3H). $^{13}$C NMR (CD$_3$OD): δ206.2, 169.0, 164.5, 159.8 (2C), 152.3, 149.1, 144.6, 137.3, 133.4, 125.0, 107.9 (2C), 58.9, 52.0, 48.8, 42.9, 42.5, 40.2, 34.0, 33.9 (2C), 28.8, 22.1, 19.5, 16.7, 14.2. ES-MS m/z 451 ([M+1]$^+$).

EXAMPLE 73

Synthesis of 1-[(2R,3S,4S,4aS,8aS)-4-[(3,5-dihydroxyphenyl)carbonyl]-3,4a,8,8-tetramethyl-decahydronaphthalen-2-yl]-3-methylurea (Compound No. 124)

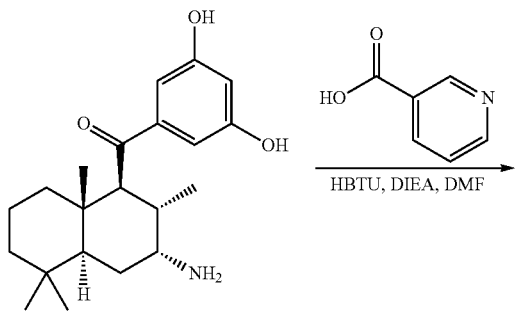

56

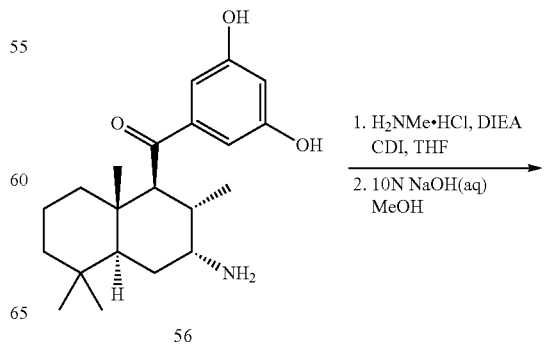

56

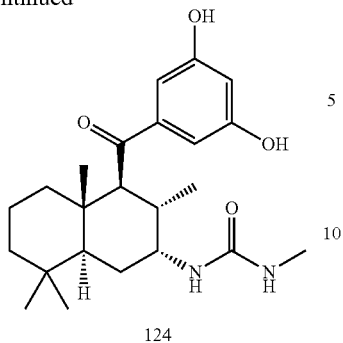

124

To a suspension of methylamine hydrochloride (130 mg, 1.93 mmol) and 1,1'-carbonyldiimidazole (306 mg, 1.89 mmol) in THF (5.0 mL) was added N,N-diisopropylethylamine (0.61 mL, 3.5 mmol) under argon. The solution was stirred at room temperature for 1 h then 5-{[(1S,2S,3R,4aS,8aS)-3-amino-2,5,5,8a-tetramethyl-decahydronaphthalen-1-yl]carbonyl}benzene-1,3-diol (Compound No. 56, 62 mg, 0.18 mmol) in THF (3.68 mL) was added, and the solution was heated to 60° C. overnight. After 17 h, the solution was allowed to cool to room temperature and saturated aqueous NaHCO$_3$ (20 mL) was added. The aqueous layer was extracted with EtOAc (3×20 mL), and the combined organic layers were dried (MgSO$_4$) and concentrated to give a yellow oil (229 mg). To a solution of the yellow oil (229 mg) in MeOH (5.69 mL) was added 10N NaOH (0.57 mL, 5.7 mmol) at room temperature. The solution was stirred for 2 h then concentrated, and the residue was partitioned between EtOAc (20 mL) and H$_2$O (30 mL). The aqueous layer was adjusted to pH 8 and extracted with EtOAc (3×20 mL). The combined organic layers were dried (MgSO$_4$) and concentrated. The residue was purified by chromatography on silica gel (EtOAc) to give 1-[(2R,3S,4S,4aS,8aS)-4-[(3,5-dihydroxyphenyl)carbonyl]-3,4a,8,8-tetramethyl-decahydronaphthalen-2-yl]-3-methylurea as a colourless solid (Compound No. 124, 38 mg, 53%). $^1$H NMR (CD$_3$OD): δ6.87 (d, J=2.1 Hz, 2H), 6.50 (t, J=2.1 Hz, 1H), 6.34 (d, J=8.4 Hz, 1H), 4.03 (m, 1H), 3.21 (d, J=12 Hz, 1H), 2.73 (s, 3H), 2.34 (m, 1H), 1.17-1.74 (m, 8H), 1.08 (m, 4H), 0.86 (s, 6H), 0.70 (d, J=6.6 Hz, 3H). $^{13}$C NMR (CD$_3$OD): δ206.1, 161.8, 159.8 (2C), 144.6, 108.0, 107.7 (2C), 59.2, 51.3, 49.2, 43.1, 42.4, 40.3, 34.6, 33.9 (2C), 29.3, 26.9, 22.1, 19.5, 16.7, 14.0. ES-MS m/z 403 ([M+1]$^+$).

EXAMPLE 74

Synthesis of 5-{[(1S,2S,3R,4aS,8aS)-2,5,5,8a-tetramethyl-3-[(1H-pyrrol-2-ylmethyl)amino]-decahydronaphthalen-1-yl]carbonyl}benzene-1,3-diol (Compound No. 125)

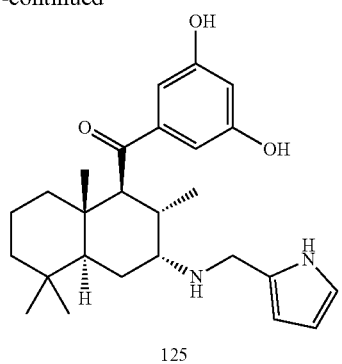

125

To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 70 mg, 0.20 mmol) in THF (2.05 mL) was added pyrrole-2-carboxaldehyde (25 mg, 0.26 mmol), acetic acid (0.016 mL, 0.28 mmol) and sodium triacetoxyborohydride (141 mg, 0.665 mmol) under argon. The mixture was stirred for 17 h, diluted with EtOAc (30 mL), and washed with saturated aqueous NaHCO$_3$ (20 mL). The aqueous layer was extracted with EtOAc (3×20 mL), and the combined organic layers were dried (MgSO$_4$) and concentrated. The residue was purified by chromatography on silica gel (MeOH/EtOAc, 1:49) to give 5-{[(1S,2S,3R,4aS,8aS)-2,5,5,8a-tetramethyl-3-[(1H-pyrrol-2-ylmethyl)amino]-decahydronaphthalen-1-yl]carbonyl}benzene-1,3-diol as a colourless powder (Compound No. 125, 29 mg, 34%). $^1$H NMR (CD$_3$OD): δ6.87 (d, J=2.1 Hz, 2H), 6.71 (m, 1H), 6.46 (m, 1H), 6.04 (m, 2H), 3.93 (d, J=14 Hz, 1H), 3.73 (d, J=14 Hz, 1H), 3.51 (d, J=12 Hz, 1H), 2.95 (br s, 1H), 2.31 (m, 1H), 1.93 (m, 1H), 1.19-1.54 (m, 7H), 1.06 (m, 4H), 0.97 (s, 3H), 0.88 (s, 3H), 0.74 (d, J=6.6 Hz, 3H). $^{13}$C NMR (CD$_3$OD): δ206.8, 159.9 (2C), 144.5, 130.2, 118.5, 108.6, 108.1, 108.0, 107.8 (2C), 58.1, 57.9, 47.3, 44.8, 43.0, 42.2, 40.5, 35.1, 34.1, 33.9, 25.6, 22.2, 19.6, 16.5, 14.1. ES-MS m/z 423 ([M−1]$^−$).

EXAMPLE 75

Synthesis of 5-{[(1S,2S,3R,4aS,8aS)-2,5,5,8a-tetramethyl-3-[(pyridin-2-ylmethyl)amino]-decahydronaphthalen-1-yl]carbonyl}benzene-1,3-diol (Compound No. 126)

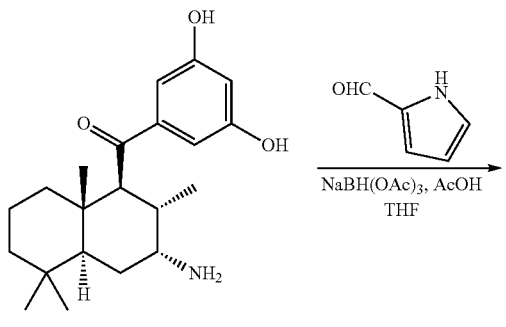

56

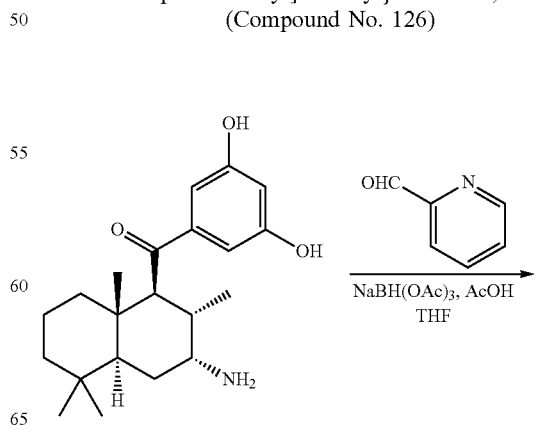

56

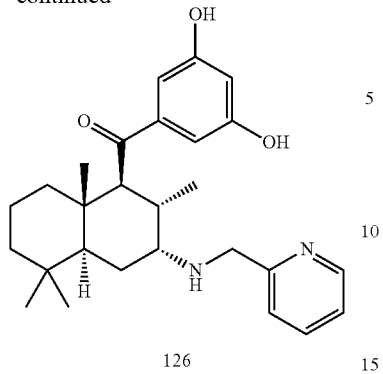

126

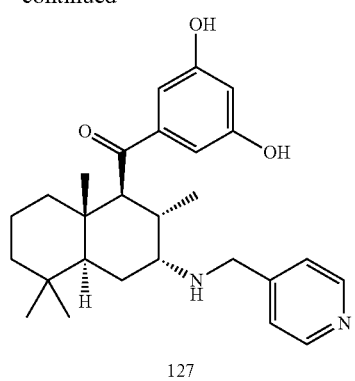

127

To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 72 mg, 0.21 mmol) in THF (2.09 mL) was added 2-pyridinecarboxaldehyde (0.024 mL, 0.25 mmol), acetic acid (0.012 mL, 0.21 mmol) and sodium triacetoxyborohydride (144 mg, 0.679 mmol) under argon. The mixture was stirred for 16 h, diluted with saturated aqueous NaHCO$_3$ (20 mL), and the aqueous layer was extracted with EtOAc (3×30 mL). The combined organic layers were dried (MgSO$_4$) and concentrated. The residue was partially purified by chromatography on silica gel (CH$_2$Cl$_2$/MeOH/NH$_4$OH, 100:10:2) to give a yellow solid (63 mg). The yellow solid (63 mg) was suspended in CH$_2$Cl$_2$, heated to a boil, and allowed to cool to room temperature. 5-{[(1S,2S,3R,4aS,8aS)-2,5,5,8a-Tetramethyl-3-[(pyridin-2-ylmethyl)amino]-decahydronaphthalen-1-yl]carbonyl}benzene-1,3-diol, a colourless solid (Compound No. 126, 49 mg, 54%), was collected by filtration. $^1$H NMR (CD$_3$OD): δ8.52 (d, J=4.2 Hz, 1H), 7.83 (m, 1H), 7.51 (d, J=7.8 Hz, 1H), 7.32 (m, 1H), 6.87 (s, 2H), 6.46 (s, 1H), 4.00 (d, J=14 Hz, 1H), 3.81 (d, J=14 Hz, 1H), 3.58 (d, J=11 Hz, 1H), 2.87 (br s, 1H), 2.31 (m, 1H), 1.93 (m, 1H), 1.18-1.67 (m, 7H), 1.06 (m, 4H), 0.93 (s, 3H), 0.88 (s, 3H), 0.81 (d, J=6.6 Hz, 3H). $^{13}$C NMR (CD$_3$OD): δ206.7, 160.6, 159.4 (2C), 149.6, 144.2, 138.2, 124.0, 123.3, 107.9, 107.6 (2C), 58.6, 57.8, 53.4, 47.0, 42.7, 41.9, 40.3, 35.2, 34.0, 33.7, 25.9, 22.2, 19.4, 16.6, 14.0. ES-MS m/z 437 ([M+1]$^+$).

EXAMPLE 76

Synthesis of 5-{[(1S,2S,3R,4aS,8aS)-2,5,5,8a-tetramethyl-3-[(pyridin-4-ylmethyl)amino]-decahydronaphthalen-1-yl]carbonyl}benzene-1,3-diol (Compound No. 127)

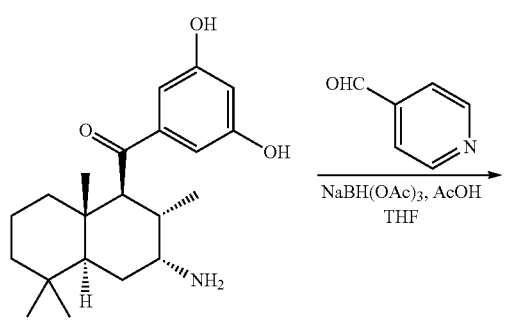

56

To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 70 mg, 0.20 mmol) in THF (2.03 mL) was added 4-pyridinecarboxaldehyde (0.023 mL, 0.24 mmol), acetic acid (0.012 mL, 0.21 mmol) and sodium triacetoxyborohydride (139 mg, 0.656 mmol) under argon. The mixture was stirred for 14 h, diluted with saturated aqueous NaHCO$_3$ (30 mL), and the aqueous layer was extracted with EtOAc (3×30 mL). The combined organic layers were dried (MgSO$_4$) and concentrated. The residue was purified by chromatography on silica gel (MeOH/EtOAc, 1:49) to give 5-{[(1S,2S,3R,4aS,8aS)-2,5,5,8a-tetramethyl-3-[(pyridin-4-ylmethyl)amino]-decahydronaphthalen-1-yl]carbonyl}benzene-1,3-diol as a colourless solid (Compound No. 127, 40 mg, 45%). $^1$H NMR (CD$_3$OD): δ8.48 (d, J=5.4 Hz, 2H), 7.50 (d, J=5.4 Hz, 2H), 6.87 (d, J=1.8, 2H), 6.47 (m, 1H), 3.96 (d, J=14 Hz, 1H), 3.77 (d, J=15 Hz, 1H), 3.56 (d, J=12 Hz, 1H), 2.86 (m, 1H), 2.30 (m, 1H), 1.88 (m, 1H), 1.18-1.66 (m, 7H), 1.06 (m, 4H), 0.89 (s, 3H), 0.87 (s, 3H), 0.80 (d, J=6.9 Hz, 3H). $^{13}$C NMR (CD$_3$OD): δ206.8, 159.6 (2C), 152.9, 149.8 (2C), 144.4, 124.8 (2C), 107.9, 107.6 (2C), 58.3, 58.0, 51.2, 47.4, 42.9, 42.1, 40.4, 35.4, 34.0, 33.8, 26.0, 22.2, 19.5, 16.7, 14.0. ES-MS m/z 437 ([M+1]$^+$).

EXAMPLE 77

Synthesis of (1R,2R,3R,4aS,8aS)-3-amino-1-{[(3,5-dimethoxyphenyl)sulfanyl]methyl}-2,5,5,8a-tetramethyl-decahydronaphthalen-2-ol (Compound No. 132)

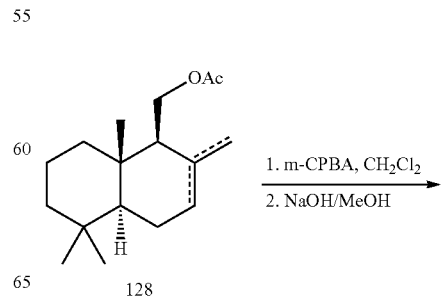

128

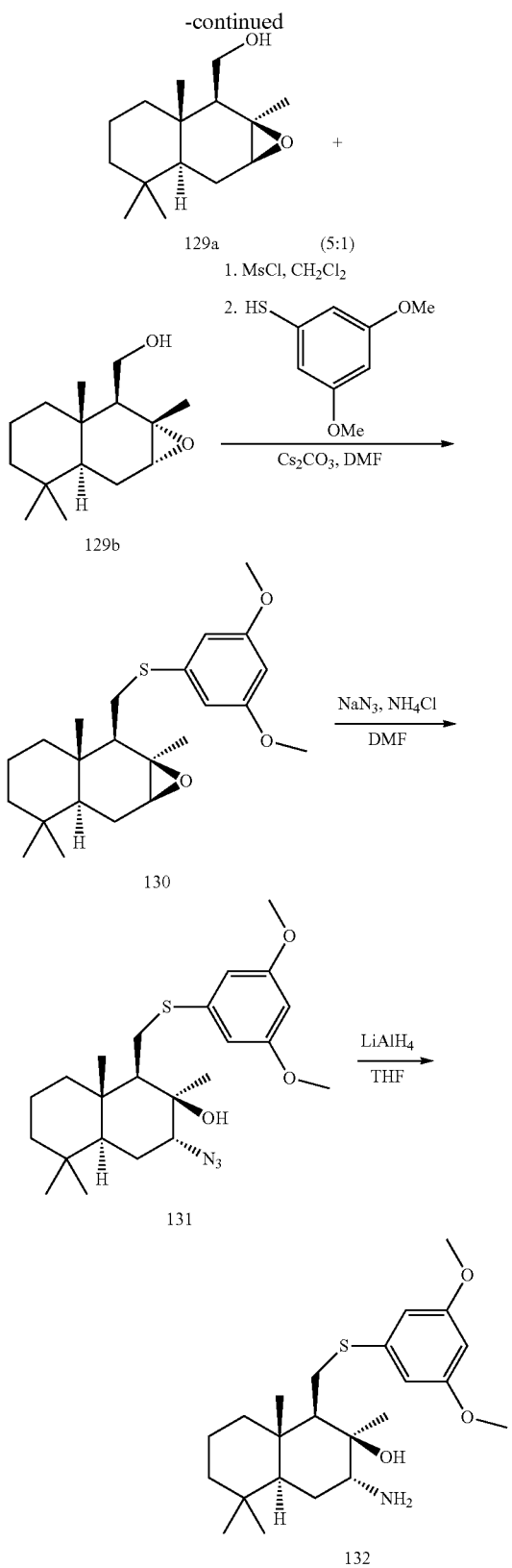

A. A solution of the mixture of [(1S,4aS,8aS)-2,5,5,8a-tetramethyl-1,4,4a,5,6,7,8,8a-octahydronaphthalen-1-yl] methyl acetate (8 parts) and [(1S,4aS,8aS)-5,5,8a-trimethyl-2-methylidene-decahydronaphthalen-1-yl]methyl acetate (1 part) (Compound No. 128, prepared according to Kuchkova et al. *Chem. Nat. Comp.* 2007, 43(4), pp 412-416, 2.02 g, 7.64 mmol) and m-chloroperoxybenzoic acid (3.33 g, 14.9 mmol) in $CH_2Cl_2$ (52 mL) under argon was stirred at room temperature for 1 h. Water (30 mL) and as solution of 10% aqueous $Na_2SO_3$ (30 mL) were added and the mixture stirred at room temperature for 15 min. The layers were partitioned, and the organic layer washed with saturated aqueous $NaHCO_3$ (3×30 mL) and brine (30 mL) then dried ($MgSO_4$) and concentrated to afford a colourless oil (2.01 g) that was used in the next step without further purification.

B. A solution of the colourless oil from above (2.01 g) in 6:1 MeOH/10 N NaOH was stirred at room temperature for 2 h. Water (50 mL) was added, and the mixture was extracted with EtOAc (4×50 mL). The organic layers were combined, washed with brine (50 mL) then dried ($MgSO_4$) and concentrated. The residue was purified by silica gel chromatography (25%-35% EtOAc/hexanes) to afford a 5:1 mixture of [(1aR,2S,2aS,6aS,7aS)-1a,2a,6,6-tetramethyl-decahydronaphtho[2,3-b]oxiren-2-yl]methanol and [(1aS,2S,2aS,6aS,7aR)-1a,2a,6,6-tetramethyl-decahydronaphtho[2,3-b]oxiren-2-yl]methanol as a colourless solid (Compounds No. 129a and 129b, 1.71 g, 81% over 2 steps).

C. To a solution of the 5:1 mixture of [(1aR,2S,2aS,6aS,7aS)-1a,2a,6,6-tetramethyl-decahydronaphtho[2,3-b]oxiren-2-yl]methanol and [(1aS,2S,2aS,6aS,7aR)-1a,2a,6,6-tetramethyl-decahydronaphtho[2,3-b]oxiren-2-yl]methanol from above (Compounds No. 129a and 129b, 1.53 g, 6.42 mmol) and triethylamine (1.20 mL, 8.61 mmol) in $CH_2Cl_2$ at 0° C. under argon was added methanesulfonyl chloride (0.55 mL, 7.1 mmol). The solution was stirred at 0° C. for 5 min then at room temperature for 1.5 h. The solution was diluted with ethyl acetate (180 mL) and washed with saturated aqueous $NaHCO_3$ (5×35 mL) and brine (35 mL) then dried ($MgSO_4$) and concentrated, affording a yellow solid (1.97 g), that was used in the next step without further purification.

D. A mixture of the yellow solid from above (1.97 g), $Cs_2CO_3$ (6.34 g, 19.4 mmol), and 3,5-dimethoxythiophenol (Compound No. 79, 1.13 g, 6.65 mmol) in DMF (32 mL) under argon was stirred at 80° C. for 17 h. The mixture was diluted with EtOAc (300 mL) and saturated aqueous $NH_4Cl$ (100 mL). The aqueous layer was extracted with EtOAc (100 mL), and the organic layers combined, washed with brine (5×100 mL), dried ($MgSO_4$) and concentrated. The residue was purified on silica gel (15% EtOAc/hexanes) to afford (1aR,2R,2aS,6aS,7aS)-2-{[(3,5-dimethoxyphenyl)sulfanyl]methyl}-1a,2a,6,6-tetramethyl-decahydronaphtho[2,3-b]oxirene as a green oil (Compound No. 130, 2.73 g, 82% over 2 steps).

E. To a solution of (1aR,2R,2aS,6aS,7aS)-2-{[(3,5-dimethoxyphenyl)sulfanyl]methyl}-1a,2a,6,6-tetramethyl-decahydronaphtho[2,3-b]oxirene (Compound No. 130, 507 mg, 1.30 mmol) in DMF (13.0 mL) under argon was added sodium azide (549 mg, 8.45 mmol) and ammonium chloride (209 mg, 3.90 mmol). The mixture was heated to 80° C. for 5 days then allowed to cool to room temperature and diluted with EtOAc (150 mL). The organic layer was washed with $H_2O$ (20 mL) and brine (5×40 mL) then dried ($MgSO_4$) and concentrated. The residue was purified by chromatography on silica gel (EtOAc/hexanes, 15:185) to give (1R,2R,3R,4aS,8aS)-3-azido-1-{[(3,5-dimethoxyphenyl)sulfanyl]methyl}-2,5,5,8a-tetramethyl-decahydronaphthalen-2-ol as a yellow oil (Compound No. 131, 299 mg, 53%).

F. To a solution of (1R,2R,3R,4aS,8aS)-3-azido-1-{[(3,5-dimethoxyphenyl)sulfanyl]methyl}-2,5,5,8a-tetramethyl-decahydronaphthalen-2-ol (Compound No. 131, 299 mg, 0.690 mmol) in THF (6.88 mL) was added lithium aluminum hydride (2.0 M in THF, 0.69 mL, 1.4 mmol) dropwise at 0° C. under argon. The mixture was stirred for 20 min at 0° C. then at room temperature for 3 h. The mixture was cooled to 0° C., and $H_2O$ (0.06 mL) was added followed by 15% aqueous NaOH (0.06 mL) and $H_2O$ (0.16 mL). The mixture was stirred for 30 min at 0° C. then dried ($MgSO_4$) and stirred at room temperature for 10 min. The mixture was filtered and concentrated, and the residue was purified by chromatography on silica gel (MeOH/$CH_2Cl_2$, 1:19) to give (1R,2R,3R,4aS,8aS)-3-amino-1-{[(3,5-dimethoxyphenyl)sulfanyl]methyl}-2,5,5,8a-tetramethyl-decahydronaphthalen-2-ol as a colourless foam (Compound No. 132, 163 mg, 58%). $^1$H NMR ($CDCl_3$): δ6.46 (s, 2H), 6.24 (s, 1H), 3.78 (s, 6H), 3.55 (br s, 1H), 3.06 (dd, J=12, 4.5 Hz, 1H), 2.83 (m, 1H), 0.97-1.87 (m, 16H), 0.88 (s, 3H), 0.82 (s, 3H). $^{13}$C NMR ($CDCl_3$): δ161.0 (2C), 141.0, 106.1 (2C), 97.9, 77.5, 56.1, 55.5 (2C), 53.6, 46.8, 41.9, 39.4, 39.2, 33.1, 32.9, 29.1, 27.9, 25.5, 21.7, 18.2, 15.5. ES-MS m/z 408 ([M+1]$^+$).

EXAMPLE 78

Synthesis of 5-{[(1S,2S,3R,4aS,8aS)-3-[(1H-imidazol-2-ylmethyl)amino]-2,5,5,8a-tetramethyl-decahydronaphthalen-1-yl]carbonyl}benzene-1,3-diol (Compound No. 133)

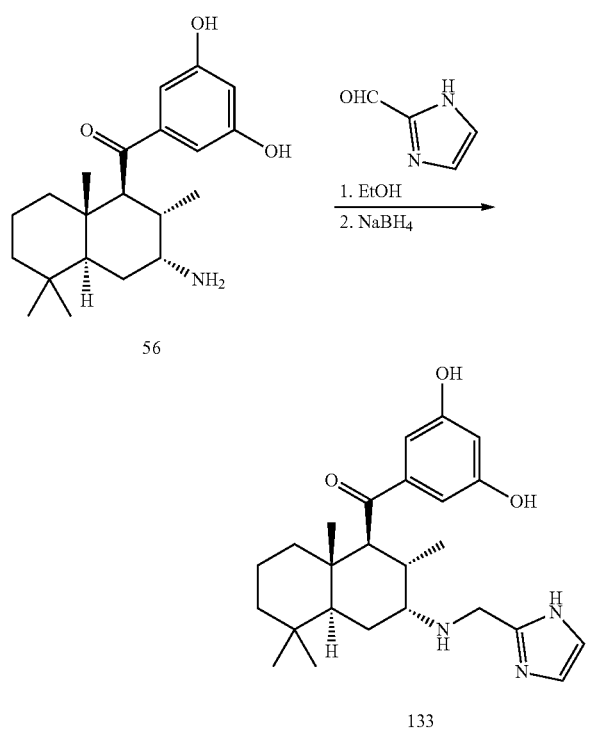 [SMILES: C[C@@H]1[C@H](N)C[C@H]2C(C)(C)CCC[C@]2(C)[C@H]1C(=O)c1cc(O)cc(O)c1 ; O=Cc1ncc[nH]1 ; C[C@@H]1[C@H](NCc2ncc[nH]2)C[C@H]2C(C)(C)CCC[C@]2(C)[C@H]1C(=O)c1cc(O)cc(O)c1]

To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 75 mg, 0.22 mmol) in EtOH (2.2 mL) under argon was added 2-imidazolecarboxaldehyde (26 mg, 0.27 mmol), and the mixture was heated to reflux for 2 h. After allowing the solution to cool to room temperature, sodium borohydride (26 mg, 0.69 mmol) was added, and the mixture was stirred for 30 min then partitioned between $H_2O$ (10 mL) and EtOAc (20 mL). The aqueous layer was adjusted to pH 10 and extracted with EtOAc (2×10 mL). The combined organic layers were dried ($MgSO_4$) and concentrated. The residue was suspended in $CH_2Cl_2$, heated to a boil, and allowed to cool to room temperature. 5-{[(1S,2S,3R,4aS,8aS)-3-[(1H-Imidazol-2-ylmethyl)amino]-2,5,5,8a-tetramethyl-decahydronaphthalen-1-yl]carbonyl}benzene-1,3-diol, a colourless solid (Compound No. 133, 49 mg, 53%), was collected by filtration. $^1$H NMR ($CD_3OD$): δ6.99 (s, 2H), 6.86 (d, J=2.1 Hz, 2H), 6.46 (m, 1H), 3.92 (d, J=14 Hz, 1H), 3.77 (d, J=14 Hz, 1H), 3.52 (d, J=12 Hz, 1H), 2.80 (brs, 1H), 2.28 (m, 1H), 1.90 (m, 1H), 1.17-1.62 (m, 7H), 1.06 (m, 4H), 0.92 (s, 3H), 0.87 (s, 3H), 0.76 (d, J=6.9 Hz, 3H). $^{13}$C NMR ($CD_3OD$): δ206.9, 159.8 (2C), 148.7, 144.5, 122.5 (2C), 108.1, 107.8 (2C), 58.5, 58.0, 47.3, 45.1, 43.0, 42.2, 40.5, 35.4, 34.1, 33.9, 25.9, 22.3, 19.6, 16.7, 14.1. ES-MS m/z 426 ([M+1]$^+$).

EXAMPLE 79

Synthesis of (2R,3S,4S,4aS,8aS)-4-[(3-methoxy-5-methylphenyl)carbonyl]-3,4a,8,8-tetramethyl-decahydronaphthalen-2-amine (Compound No. 135)

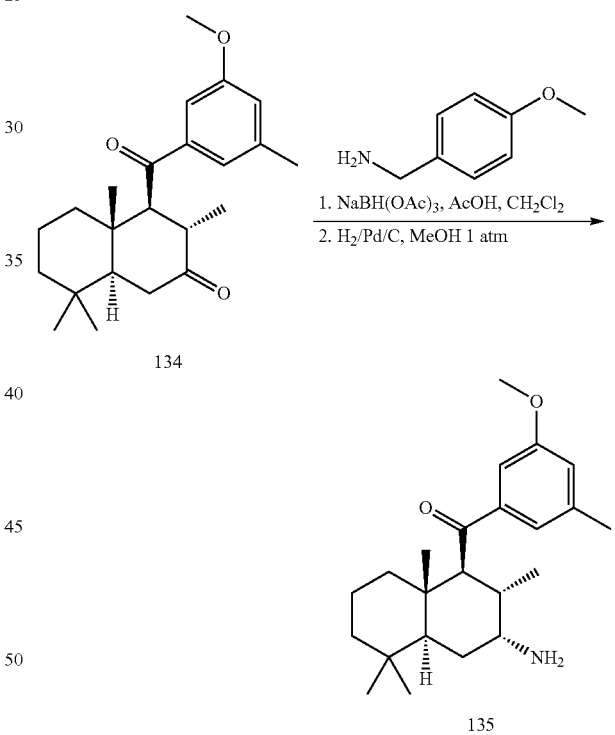

A. Sodium triacetoxyborohydride (6.96 g, 32.8 mmol) was added to a solution of (3S,4S,4aS,8aS)-4-[(3-methoxy-5-methylphenyl)carbonyl]-3,4a,8,8-tetramethyl-decahydronaphthalen-2-one (Compound No. 134, prepared from Compound No. 7 in similar manner as described for Compound No. 90, 3.87 g, 10.9 mmol), 4-methoxybenzylamine (1.56 mL, 12.0 mmol), and acetic acid (0.63 mL, 11 mmol) in $CH_2Cl_2$ (110 mL), under argon and the mixture was stirred at room temperature for 25 h. The mixture was diluted with $CH_2Cl_2$ (70 mL) then washed with 1 N NaOH (100 mL). The aqueous layer was extracted with $CH_2Cl_2$ (3×75 mL), and the organic layers were combined, dried ($MgSO_4$) and concentrated. The residue was partially purified by chromatography on silica gel (EtOAc/CH$_2$Cl$_2$, 1:19-1:9) to give (2R,3S,4S,4aS,8aS)-4-[(3-methoxy-5-methylphenyl)carbonyl]-N-[(4-methoxyphenyl)methyl]-3,4a,8,8-tetramethyl-decahydronaphthalen-2-amine as a yellow foam (3.72 g).

B. Methanol (80 mL) was carefully added under argon to (2R,3S,4S,4aS,8aS)-4-[(3-methoxy-5-methylphenyl)carbonyl]-N-[(4-methoxyphenyl)methyl]-3,4a,8,8-tetramethyl-decahydronaphthalen-2-amine (3.72 g) and 10% Pd/C (788 mg) followed by the addition of 10% aqueous HCl (4.0 mL). The mixture was stirred at room temperature under H$_2$(g) at 1 atm for 16 h then filtered through Celite and concentrated. The residue was purified by chromatography on silica gel (CH$_2$Cl$_2$/MeOH/NH$_4$OH, 200:10:1) to afford (2R,3S,4S,4aS,8aS)-4-[(3-methoxy-5-methylphenyl)carbonyl]-3,4a,8,8-tetramethyl-decahydronaphthalen-2-amine as a colourless solid (Compound No. 135, 1.62 g, 42% over 2 steps). $^1$H NMR: (CDCl$_3$): δ7.36 (s, 1H), 7.27 (s, 1H), 6.90 (s, 1H), 3.84 (s, 3H), 3.51 (d, J=11.6 Hz, 1H), 3.25 (m, 1H), 2.40 (s, 3H), 2.30 (m, 1H), 1.75 (m, 1H), 1.62-1.09 (m, 8H), 1.07 (s, 3H), 0.89 (s, 3H), 0.84 (s, 3H), 0.78 (d, J=6.8 Hz, 3H).

EXAMPLE 80

Synthesis of 3-{[(1S,2S,3R,4aS,8aS)-3-amino-2,5,5,8a-tetramethyl-decahydronaphthalen-1-yl]carbonyl}-5-methylphenol (Compound No. 136)

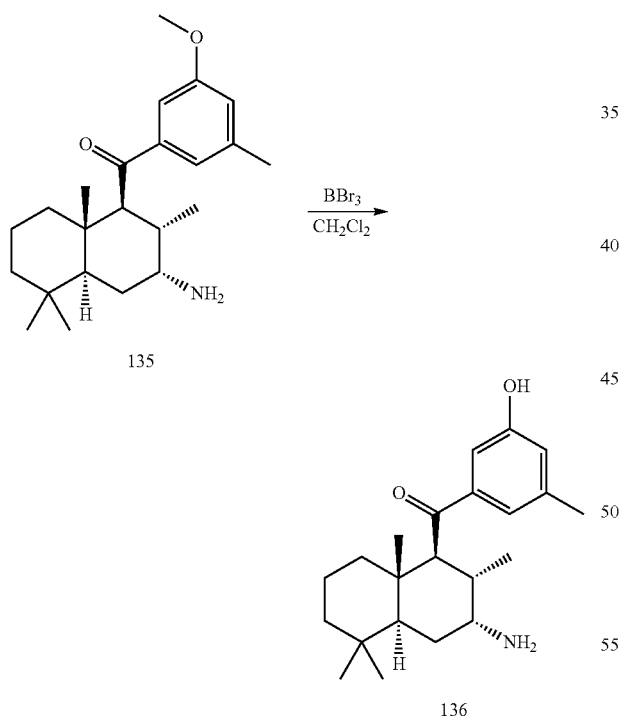

Boron tribromide (1.0 M in CH$_2$Cl$_2$, 18.1 mL, 18.1 mmol) was added to a solution of (2R,3S,4S,4aS,8aS)-4-[(3-methoxy-5-methylphenyl)carbonyl]-3,4a,8,8-tetramethyl-decahydronaphthalen-2-amine (Compound No. 135, 1.62 g, 4.53 mmol) in CH$_2$Cl$_2$ (45 mL) at −78° C. under argon. The solution was stirred for 5 min at −78° C. then at room temperature for 3.25 h. The solution was carefully quenched with MeOH (60 mL) and concentrated. The residue was dissolved in i-PrOH (45 mL) and 10% aqueous HCl (15 mL), and the solution was stirred at 85° C. for 100 min. The solution was concentrated, diluted with EtOAc (180 mL) and H$_2$O (60 mL), then neutralized to pH 7 with 1 N NaOH. The aqueous layer was extracted with EtOAc (2×60 mL), and the organic layers were combined, dried (MgSO$_4$) and concentrated. The residue was purified by chromatography on silica gel (CH$_2$Cl$_2$/MeOH/NH$_4$OH, 100:10:0.9) to give 3-{[(1S,2S,3R,4aS,8aS)-3-amino-2,5,5,8a-tetramethyl-decahydronaphthalen-1-yl]carbonyl}-5-methylphenol as a colourless solid (Compound No. 136, 1.51 g, 97%). $^1$H NMR (CD$_3$OD): δ7.34 (s, 1H), 7.17 (s, 1H), 6.84 (s, 1H), 3.54 (d, J=11.8 Hz, 1H), 3.17 (m, 1H), 2.34 (s, 3H), 2.26 (m, 1H), 1.82-1.68 (m, 2H), 1.58-1.14 (m, 6H), 1.02 (m, 4H), 0.91 (s, 3H), 0.86 (s, 3H), 0.76 (d, J=6.8 Hz, 3H). $^{13}$C NMR (CD$_3$OD): δ207.0, 159.2, 143.8, 140.9, 121.8, 121.4, 113.1, 57.2, 52.4, 47.5, 43.0, 42.3, 40.4, 35.0, 34.0, 33.8, 30.2, 22.1, 21.4, 19.6, 16.7, 13.9. ES-MS m/z 344 ([M+1]$^+$).

EXAMPLE 81

Synthesis of 3-{[(1S,2S,3R,4aS,8aS)-3-[(1H-imidazol-5-ylmethyl)amino]-2,5,5,8a-tetramethyl-decahydronaphthalen-1-yl]carbonyl}-5-methylphenol (Compound No. 137)

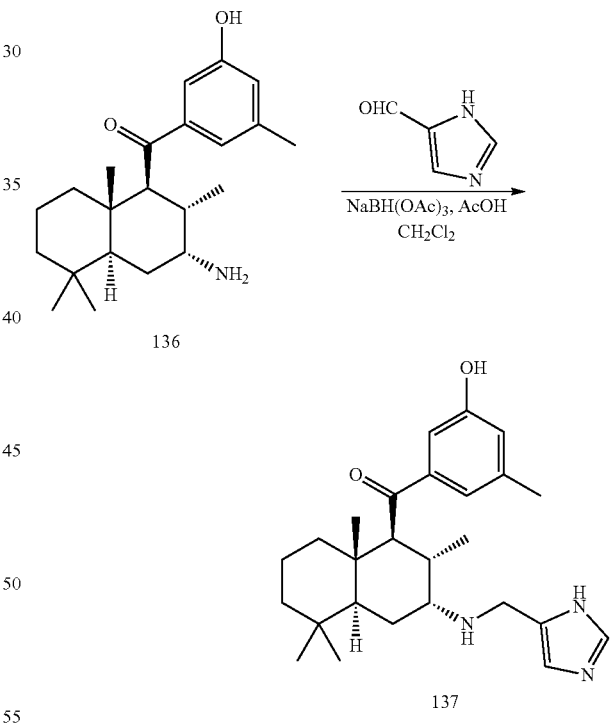

To a suspension of 3-{[(1S,2S,3R,4aS,8aS)-3-amino-2,5,5,8a-tetramethyl-decahydronaphthalen-1-yl]carbonyl}-5-methylphenol (Compound No. 136, 61.6 mg, 0.179 mmol), 4(5)-imidazolecarboxaldehyde (20.7 mg, 0.215 mmol), and acetic acid (0.010 mL, 0.17 mmol) in CH$_2$Cl$_2$ (1.7 mL) under argon was added sodium triacetoxyborohydride (120 mg, 0.566 mmol), and the mixture was stirred for 24 h at room temperature. The mixture was diluted with 10% MeOH/CH$_2$Cl$_2$ (10 mL) and washed with saturated aqueous NaHCO$_3$ (5 mL). The aqueous layer was extracted with 10% MeOH/CH$_2$Cl$_2$ (2×10 mL), and the organic layers were combined, dried (MgSO$_4$) and concentrated. The residue was purified by chromatography on silica gel (acetone/toluene/NH$_4$OH, 40:50:1) to give 3-{[(1S,2S,3R,4aS,8aS)-3-[(1H-imidazol-5-ylmethyl)amino]-2,5,5,8a-tetramethyl-decahydronaphthalen-1-yl]carbonyl}-5-methylphenol as a colourless solid (Compound No. 137, 40 mg, 53%). $^1$H NMR (CDCl$_3$): δ7.82 (s, 1H), 7.53 (s, 1H), 7.26 (s, 1H), 6.86 (s, 1H), 6.76 (s, 1H), 4.00 (d, J=12.6 Hz, 1H), 3.69 (d, J=11.7 Hz, 1H), 3.62 (d, J=13.0 Hz, 1H), 3.00 (br s, 1H), 2.36 (m, 1H), 2.22 (s, 3H), 2.01 (m, 1H), 1.91 (m, 1H), 1.55-1.05 (m, 4H), 1.01 (s, 3H), 0.90-0.78 (m, 8H), 0.72 (d, J=6.9 Hz, 3H), 0.50 (m, 1H). ES-MS m/z 424 ([M+1]$^+$).

EXAMPLE 82

Synthesis of 3-[(2R,3S,4S,4aS,8aS)-4-[(3-hydroxy-5-methylphenyl)carbonyl]-3,4a,8,8-tetramethyl-decahydronaphthalen-2-yl]-1-(pyridin-3-yl)urea (Compound No. 138)

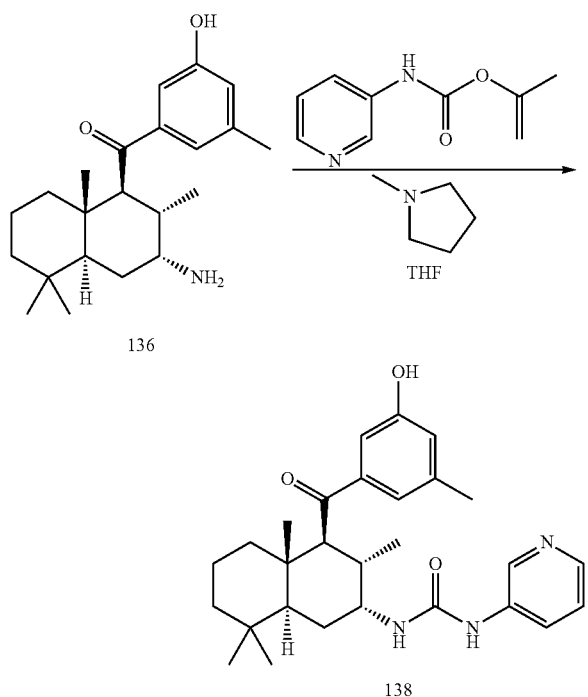

To a suspension of 3-{[(1S,2S,3R,4aS,8aS)-3-amino-2,5,5,8a-tetramethyl-decahydronaphthalen-1-yl]carbonyl}-5-methylphenol (Compound No. 136, 61 mg, 0.18 mmol) and pyridin-3-yl-carbamic acid isopropenyl ester (39 mg, 0.22 mmol) in THF (0.35 mL) was added 1-methylpyrrolidine (0.020 mL, 0.19 mmol) under argon then heated to 55° C. for 16 h. The mixture was concentrated, and the residue was purified by chromatography on silica gel (MeOH/CH$_2$Cl$_2$, 1:9-15:85) to give 3-[(2R,3S,4S,4aS,8aS)-4-[(3-hydroxy-5-methylphenyl)carbonyl]-3,4a,8,8-tetramethyl-decahydronaphthalen-2-yl]-1-(pyridin-3-yl)urea as a light yellow solid (Compound No. 138, 70 mg, 85%). $^1$H NMR (CD$_3$OD): δ8.55 (br s, 1H), 8.14 (d, J=4.5 Hz, 1H), 7.98 (m, 1H), 7.35 (dd, J=8.4, 4.9 Hz, 1H), 7.28 (s, 1H), 7.17 (m, 1H), 6.87 (m, 1H), 6.67 (d, J=9.3 Hz, 1H), 4.14 (m, 1H), 3.28 (m, 1H), 2.44 (m, 1H), 2.38 (s, 3H), 1.87-1.12 (m, 9H), 1.08 (s, 3H), 0.89 (s, 3H), 0.88 (s, 3H), 0.77 (d, J=6.7 Hz, 3H). $^{13}$C NMR (CD$_3$OD): δ205.8, 158.9, 157.4, 143.8, 143.4, 141.0, 140.6, 127.5, 125.3, 121.6, 121.1, 113.1, 59.3, 51.5, 43.1, 42.7, 40.3, 34.4, 34.0, 33.9, 29.0, 22.1, 21.5, 19.5, 16.7, 14.0. ES-MS m/z 464 ([M+1]$^+$).

EXAMPLE 83

Synthesis of N-[(2R,3S,4S,4aS,8aS)-4-[(3-hydroxy-5-methylphenyl)carbonyl]-3,4a,8,8-tetramethyl-decahydronaphthalen-2-yl]acetamide (Compound No. 139)

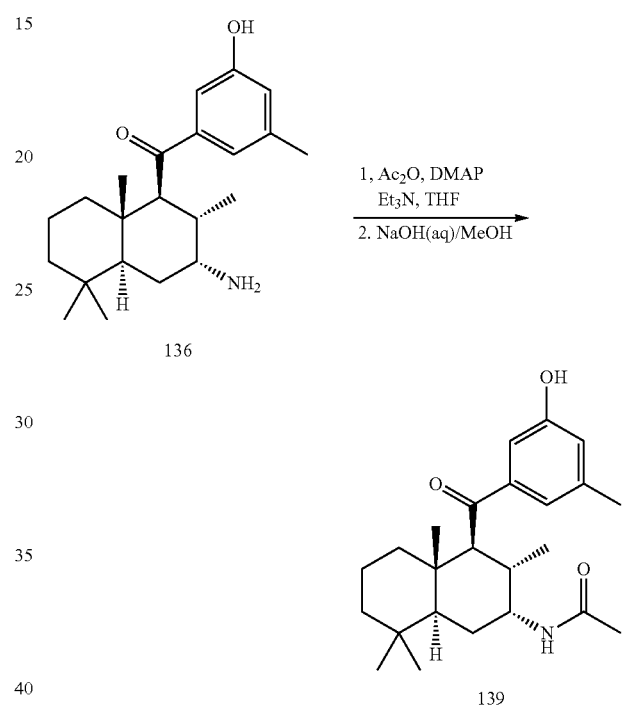

A. Acetic anhydride (0.040 mL, 0.42 mmol) was added to a solution of 3-{[(1S,2S,3R,4aS,8aS)-3-amino-2,5,5,8a-tetramethyl-decahydronaphthalen-1-yl]carbonyl}-5-methylphenol (Compound No. 136, 62 mg, 0.18 mmol), DMAP (2.2 mg, 0.018 mmol), and Et$_3$N (0.059 mL, 0.42 mmol) in THF (1.8 mL) at 0° C. under argon. The solution was stirred for 5 min at 0° C. then at room temperature for 3 h. The solution was concentrated, dissolved in EtOAc (40 mL), washed with saturated aqueous NaHCO$_3$ (5×10 mL) and brine (10 mL) then dried (MgSO$_4$) and concentrated. The colourless crystals (75 mg) that were obtained were used in the next step without further purification.

B. The colourless crystals from above (75 mg) were dissolved in MeOH (2 mL) and 10 N NaOH (0.2 mL) was added. The solution was stirred for 35 min at room temperature then concentrated. The residue was diluted with H$_2$O (10 mL) and adjusted to pH 6 with 10% aqueous HCl. The mixture was extracted with EtOAc (40 mL), and the organic extract was dried (MgSO$_4$) and concentrated to give N-[(2R,3S,4S,4aS,8aS)-4-[(3-hydroxy-5-methylphenyl)carbonyl]-3,4a,8,8-tetramethyl-decahydronaphthalen-2-yl]acetamide as a colourless solid (Compound No. 139, 70 mg, quantitative over 2 steps). $^1$H NMR (CDCl$_3$): δ7.26 (br s, 1H), 6.88 (s, 1H), 6.55 (br s, 1H), 5.99 (br s, 1H), 4.37 (m, 1H), 3.03 (d, J=11.9 Hz, 1H), 2.43 (m, 1H), 2.37 (s, 3H), 2.14 (s, 3H), 1.77-1.02 (m, 12H), 0.84 (s, 3H), 0.82 (s, 3H), 0.71 (d, J=6.7 Hz, 3H). $^{13}$C NMR (CDCl$_3$): δ203.5 s, 171.2, 156.2, 142.3, 140.5, 121.3, 121.0, 113.0, 58.2, 50.1, 48.6, 41.6, 41.3, 39.3, 33.5, 33.0, 32.8, 27.7, 23.6, 21.8, 21.6, 18.5, 16.5, 13.5. ES-MS m/z 386 ([M+1]$^+$).

EXAMPLE 84

Synthesis of (2R,4R,4aS,8aS)-4-[(3,5-dimethoxyphenyl)carbonyl]-4a,8,8-trimethyl-3-methylidene-decahydronaphthalen-2-ol (Compound No. 141

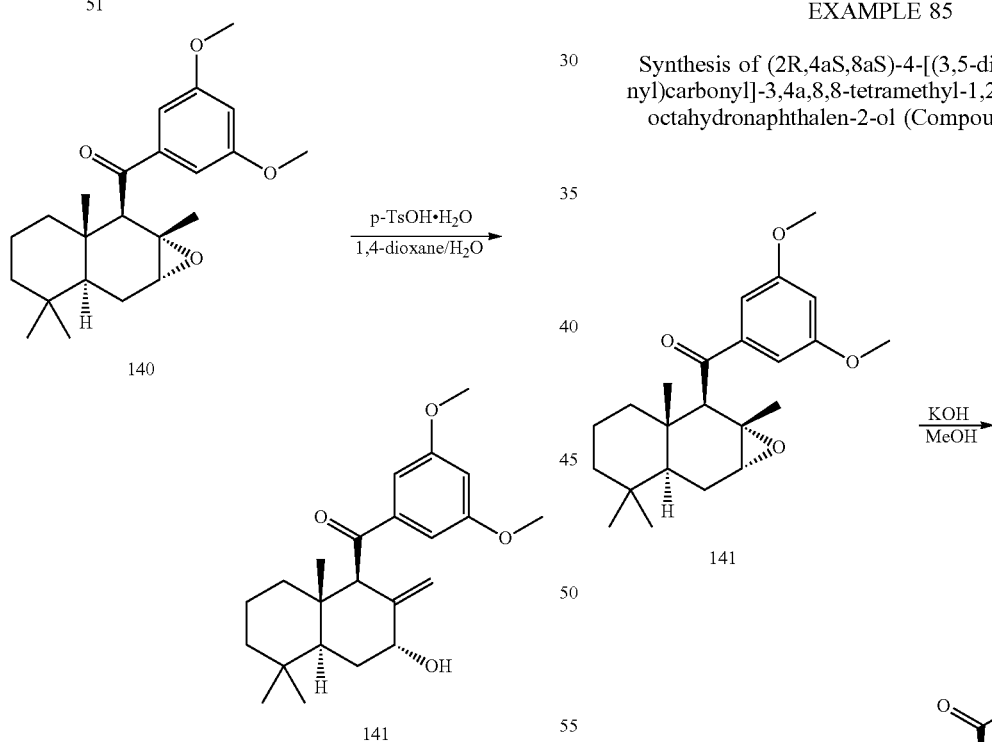

A. A solution of [(1S,4aS,8aS)-2,5,5,8a-tetramethyl-1,4,4a,5,6,7,8,8a-octahydronaphthalen-1-yl](3,5-dimethoxyphenyl)methanone (Compound No. 51, 208 mg, 0.583 mmol) and m-chloroperoxybenzoic acid (154 mg, 0.687 mmol) in CH$_2$Cl$_2$ (5.8 mL) was stirred under argon at 0° C. for 2 h. The reaction was quenched with 10% aqueous Na$_2$SO$_3$ (3.0 mL) and allowed to stir at room temperature for 1 h. The mixture was extracted with EtOAc (20 mL), and the organic layer was washed with saturated aqueous NaHCO$_3$ (5×10 mL) and brine (10 mL) then dried (MgSO$_4$) and concentrated. The residue was purified by chromatography on silica gel (EtOAc/hexanes, 1:9) to afford (1aS,2R,2aS,6aS,7aR)-2-[(3,5-dimethoxyphenyl)carbonyl]-1a,2a,6,6-tetramethyl-decahydronaphtho[2,3-b]oxirene as a colourless oil (Compound No. 140, 158 mg, 73%).

B. A solution of (1aS,2R,2aS,6aS,7aR)-2-[(3,5-dimethoxyphenyl)carbonyl]-1a,2a,6,6-tetramethyl-decahydronaphtho[2,3-b]oxirene (Compound No. 140, 103 mg, 0.277 mmol) and p-toluenesulfonic acid (2.6 mg, 0.014 mmol) in 1,4-dioxane/H$_2$O (9:1, 2.0 mL) was heated to reflux for 2 h. The solution was diluted with saturated aqueous NaHCO$_3$ (10 mL) and EtOAc (30 mL), and the aqueous layer was extracted with EtOAc (2×10 mL). The organic layers were combined, washed with brine (10 mL), then dried (MgSO$_4$) and concentrated. The residue was purified by chromatography on silica gel (EtOAc/hexanes, 1:9-2:3) to afford (2R,4R,4aS,8aS)-4-[(3,5-dimethoxyphenyl)carbonyl]-4a,8,8-trimethyl-3-methylidene-decahydronaphthalen-2-ol as colourless crystals (Compound No. 141, 40 mg, 39%). $^1$H NMR (CDC$_3$): δ7.11 (d, J=2.2 Hz, 2H), 6.61 (t, J=2.2 Hz, 1H), 5.03 (s, 1H), 4.58 (s, 1H), 4.47 (br s, 1H), 4.37 (s, 1H), 3.82 (s, 6H), 1.96-1.06 (m, 12H), 0.91 (s, 3H), 0.86 (s, 3H). $^{13}$C NMR (CDCl$_3$): δ200.5, 160.9 (2C), 146.9, 141.2, 112.6, 106.2 (2C), 105.0, 73.5, 57.6, 55.7 (2C), 48.0, 42.2, 41.1, 38.8, 33.5, 33.2, 31.0, 21.8, 19.1, 14.1. ES-MS m/z 373 ([M+1]$^+$).

EXAMPLE 85

Synthesis of (2R,4aS,8aS)-4-[(3,5-dimethoxyphenyl)carbonyl]-3,4a,8,8-tetramethyl-1,2,4a,5,6,7,8,8a-octahydronaphthalen-2-ol (Compound No. 142)

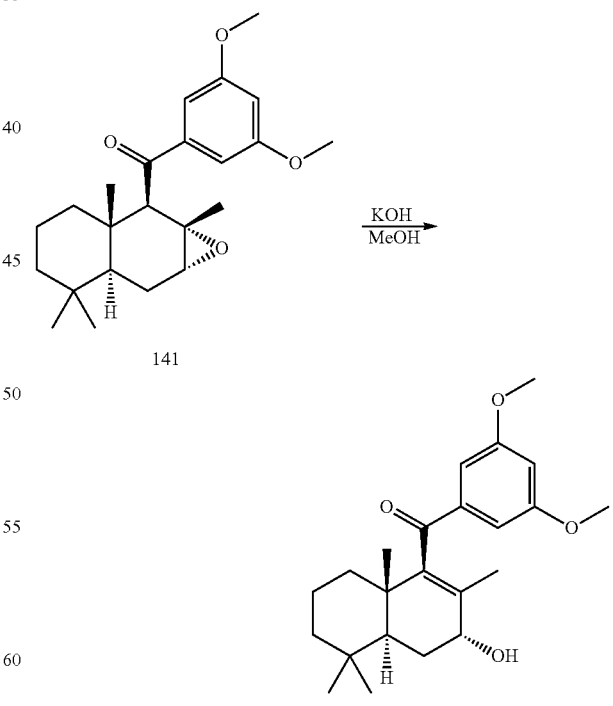

A solution of (1aS,2R,2aS,6aS,7aR)-2-[(3,5-dimethoxyphenyl)carbonyl]-1a,2a,6,6-tetramethyl-decahydronaphtho[2,3-b]oxirene (Compound No. 140, 55 mg, 0.15 mmol) and KOH (29 mg, 0.52 mmol) in MeOH (1.5 mL) was heated to reflux for 18 h then saturated aqueous NH₄Cl (10 mL) was added. The mixture was extracted with 10% MeOH/CH$_2$Cl$_2$ (2×10 mL), and the organic layers were combined, washed with brine (10 mL), dried (MgSO$_4$) and concentrated. The residue was purified by chromatography on silica gel (EtOAc/hexanes, 3:7-3:2) to afford (2R,4aS,8aS)-4-[(3,5-dimethoxyphenyl)carbonyl]-3,4a,8,8-tetramethyl-1,2,4a,5,6,7,8,8a-octahydronaphthalen-2-ol as a colourless solid (Compound No. 142, 28 mg, 51%). $^1$H NMR (CDCl$_3$): δ7.09 (d, J=2.3 Hz, 2H), 6.65 (t, J=2.3 Hz, 1H), 4.07 (m, 1H), 3.84 (s, 6H), 1.90 (m, 2H), 1.59-1.22 (m, 13H), 0.96 (s, 3H), 0.88 (s, 3H). $^{13}$C NMR (CDCl$_3$): δ200.3, 161.1 (2C), 146.2, 139.9, 130.5, 107.4 (2C), 105.6, 69.4, 55.7 (2C), 45.4, 41.7, 39.1, 37.1, 33.2, 33.0, 29.0, 21.7, 19.5, 18.9, 18.7. ES-MS m/z 355 ([M−17]$^+$).

EXAMPLE 86

Synthesis of 2-[(1S,2S,4aS,8aR)-2,5,5,8a-tetramethyl-decahydronaphthalen-1-yl]-N-(3,5-dihydroxyphenyl)acetamide (Compound No. 149)

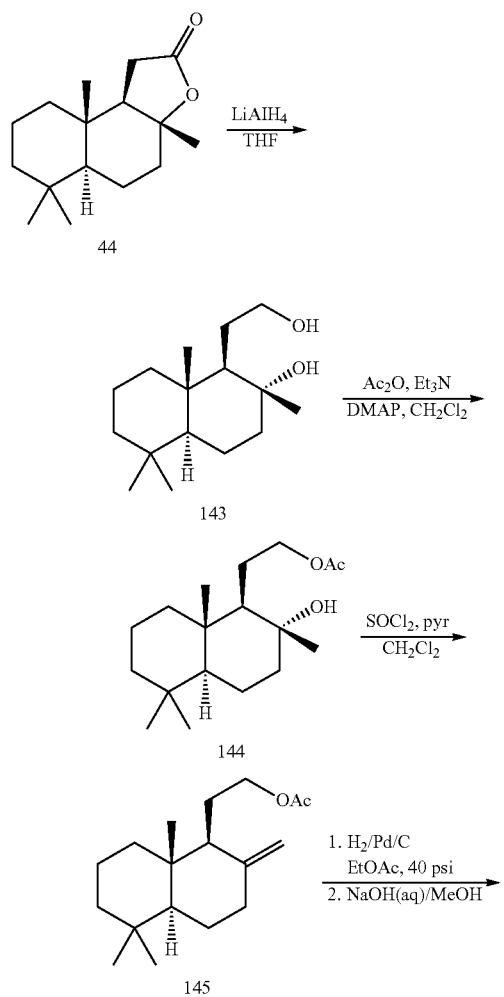

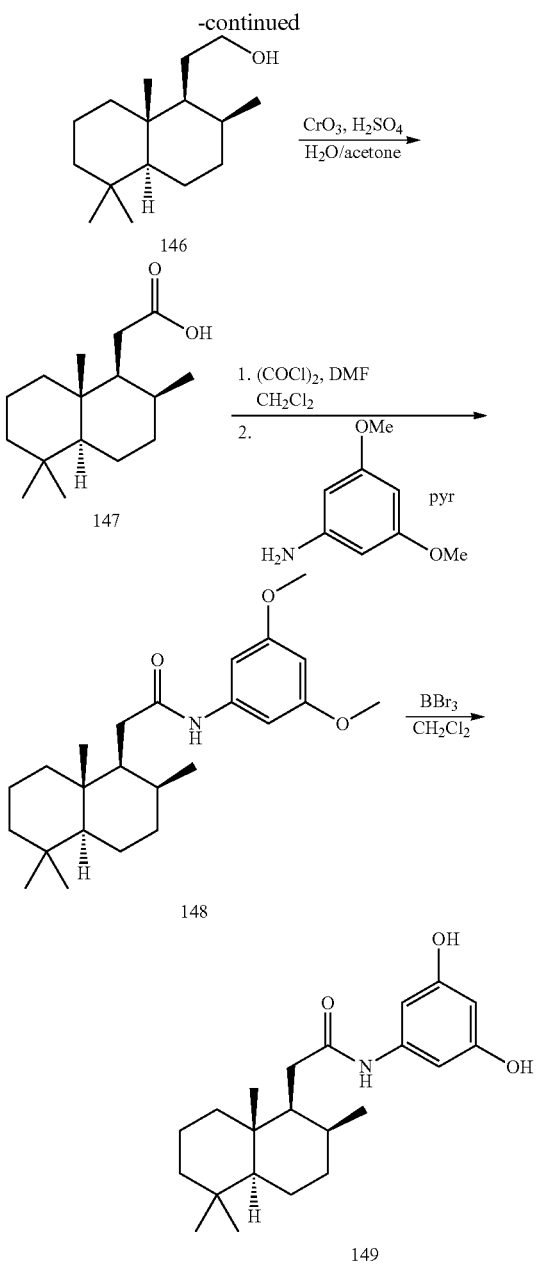

A. A solution of sclareolide (Compound No. 44, 5.76 g, 23.0 mmol) in THF (115 mL) was cooled to 0° C. under argon and lithium aluminum hydride (1.92 g, 50.6 mmol) was added. After stirring at room temperature for 2 h, the mixture was cooled to 0° C. and H$_2$O (1.9 mL) was carefully added followed by 15% aqueous NaOH (1.9 mL) and H$_2$O (5.7 mL). The mixture was stirred for 1 h at room temperature then dried (MgSO$_4$), filtered and concentrated to give (1R,2R,4aS,8aS)-1-(2-hydroxyethyl)-2,5,5,8a-tetramethyl-decahydronaphthalen-2-ol as a colourless solid (Compound No. 143, 5.51 g, 94%).

B. Acetic anhydride (2.04 mL, 21.6 mmol) was added to a solution of (1R,2R,4aS,8aS)-1-(2-hydroxyethyl)-2,5,5,8a-tetramethyl-decahydronaphthalen-2-ol (Compound No. 143, 5.51 g, 21.7 mmol), DMAP (132 mg, 1.08 mmol), and Et$_3$N (3.32 mL, 23.8 mmol) in CH$_2$Cl$_2$ (108 mL) at 0° C. under argon. The solution was stirred at 0° C. for 20 min then at room temperature for 40 min. The solution was concentrated, dissolved in EtOAc (100 mL), washed with saturated aqueous NaHCO$_3$ (5×30 mL) and brine (20 mL) then dried (MgSO$_4$) and concentrated. The colourless oil, 2-[(1R,2R,4aS,8aS)-2-hydroxy-2,5,5,8a-tetramethyl-decahydronaphthalen-1-yl]ethyl acetate, (Compound No. 144, 7.03 g) that was obtained was used in the next step without further purification.

C. To a solution of 2-[(1R,2R,4aS,8aS)-2-hydroxy-2,5,5,8a-tetramethyl-decahydronaphthalen-1-yl]ethyl acetate (Compound No. 144, 7.03 g) and pyridine (3.51 mL, 434 mmol) in CH$_2$Cl$_2$ (217 mL) was added a solution of thionyl chloride (7.89 mL, 108 mmol) and pyridine (14.0 mL, 173 mmol) in CH$_2$Cl$_2$ (54 mL) at −78° C. under argon over 30 min. The solution was stirred at −78° C. for 40 min then saturated aqueous NaHCO$_3$ (50 mL) was added and allowed to warm to room temperature. The organic phase was washed with H$_2$O (30 mL) and concentrated followed by azeotropic removal of pyridine using hexanes (50 mL). The residue was partitioned between EtOAc (100 mL) and saturated aqueous NaHCO$_3$ (40 mL). The organic phase was washed with saturated aqueous NaHCO$_3$ (4×40 mL) and brine (15 mL) then dried (MgSO$_4$) and concentrated. The residue was filtered through silica gel (EtOAc/hexanes, 1:19) to give 2-[(1S,4aS,8aS)-5,5,8a-trimethyl-2-methylidene-decahydronaphthalen-1-yl]ethyl acetate as a light yellow oil (Compound No. 145, 6.01 g) that was used in the next step without further purification.

D. To a solution of 2-[(1S,4aS,8aS)-5,5,8a-trimethyl-2-methylidene-decahydronaphthalen-1-yl]ethyl acetate (Compound No. 145, 6.01 g) in EtOAc (40 mL) was added 10% Pd/C (600 mg) then shaken under an atmosphere of H$_2$(g) at 45 psi for 1.5 h. The mixture was filtered through Celite then concentrated to give a colourless oil (5.53 g). The colourless oil (5.53 g) was dissolved in MeOH (100 mL) and 10 N NaOH (9.9 mL) was slowly added. The solution was stirred for 20 min at room temperature then cooled to 0° C. and adjusted to pH 2 with concentrated HCl. The mixture was concentrated then partitioned between CH$_2$Cl$_2$ (40 mL) and H$_2$O (30 mL). The aqueous layer was extracted with CH$_2$Cl$_2$ (2×20 mL), and the combined organic layers were dried (MgSO$_4$) and concentrated to give a pale oil, 2-[(1S,2S,4aS,8aR)-2,5,5,8a-tetramethyl-decahydronaphthalen-1-yl]ethan-1-ol (Compound No. 146, 5.21 g) that was used in the next step without further purification.

E. Jones reagent was freshly prepared by adding CrO$_3$ (6.56 g, 65.6 mmol) to H$_2$SO$_4$ (5.89 mL, 105 mmol) at 0° C. then slowly diluting the mixture with H$_2$O (24 mL) at 0° C. The Jones reagent was added dropwise over 10 min to a solution of 2-[(1S,2S,4aS,8aR)-2,5,5,8a-tetramethyl-decahydronaphthalen-1-yl]ethan-1-ol (Compound No. 146, 5.21 g) in acetone (73 mL) at 0° C., and the mixture was stirred at 0° C. for 1 h then at room temperature for 2 days. The mixture was diluted with i-PrOH (40 mL) then concentrated. The residue was diluted with H$_2$O (100 mL) and extracted with CH$_2$Cl$_2$ (50 mL then 3×15 mL). The combined organic extracts were dried (MgSO$_4$) and concentrated, and the residue was partially purified by chromatography on silica gel (MeOH/CH$_2$Cl$_2$, 1:24) to give 2-[(1S,2S,4aS,8aR)-2,5,5,8a-tetramethyl-decahydronaphthalen-1-yl]acetic acid as yellow crystals (Compound No. 147, 4.87 g).

F. To a solution of 2-[(1S,2S,4aS,8aR)-2,5,5,8a-tetramethyl-decahydronaphthalen-1-yl]acetic acid (Compound No. 147, 302 mg) in CH$_2$Cl$_2$ (6 mL) under argon was added DMF (cat.) and oxalyl chloride (0.31 mL, 3.6 mmol) then stirred at room temperature for 45 min. The solution was concentrated followed by azeotropic removal of excess oxalyl chloride with CH$_2$Cl$_2$ (3×10 mL). The acid chloride residue was dissolved in pyridine (3 mL), and 3,5-dimethoxyaniline (202 mg, 1.32 mmol) was added. The solution was stirred at room temperature for 17 h then concentrated. The residue was partitioned between EtOAc (35 mL) and saturated aqueous NaHCO$_3$ (15 mL), and the organic layer was washed with saturated aqueous NaHCO$_3$ (2×15 mL) and brine (10 mL) then dried (MgSO$_4$) and concentrated. The residue was purified by chromatography on silica gel (EtOAc/hexanes, 15:85) to give 2-[(1S,2S,4aS,8aR)-2,5,5,8a-tetramethyl-decahydronaphthalen-1-yl]-N-(3,5-dimethoxyphenyl)acetamide as a colourless solid (Compound No. 148, 151 mg, 29% over 6 steps).

G. A solution of 2-[(1S,2S,4aS,8aR)-2,5,5,8a-tetramethyl-decahydronaphthalen-1-yl]-N-(3,5-dimethoxyphenyl)acetamide (Compound No. 148, 151 mg, 0.390 mmol) in CH$_2$Cl$_2$ (4 mL) under argon was stirred at room temperature while BBr$_3$ (1.0 M in CH$_2$Cl$_2$, 2.5 mL, 2.5 mmol) was added then the solution was stirred at room temperature for 3 h. Methanol (10 mL) was carefully added to the solution then concentrated (3×). The residue was dissolved in i-PrOH/10% aqueous HCl (3:1, 4 mL) and heated to 85° C. for 40 min. The solution was concentrated, and the residue was partitioned between EtOAc (20 mL) and H$_2$O (10 mL). The aqueous phase was adjusted to pH 9 using 1 N NaOH and extracted with EtOAc (20 mL). The combined organic layers were dried (MgSO$_4$) and concentrated, and the residue was purified by chromatography on silica gel (acetone/hexanes, 33:67) to give 2-[(1S,2S,4aS,8aR)-2,5,5,8a-tetramethyl-decahydronaphthalen-1-yl]-N-(3,5-dihydroxyphenyl)acetamide as a tan solid (Compound No. 149, 116 mg, 83%). $^1$H NMR (CD$_3$OD): δ6.55 (d, J=2.4 Hz, 2H), 6.01 (t, J=2.1 Hz, 1H), 2.46 (dd, J=16.2, 2.1 Hz, 1H), 2.07 (dd, J=16.4, 6.2 Hz, 1H), 1.80-0.94 (m, 13H), 0.87 (m, 12H). $^{13}$C NMR (CD$_3$OD): δ175.1, 159.5 (2C), 141.6, 100.2 (2C), 99.5, 56.3, 54.1, 43.1, 40.0, 38.8, 38.0, 37.3, 35.3, 34.2, 33.9, 23.0, 22.2, 21.2, 19.8, 15.0. ES-MS m/z 360 ([M+1]$^+$).

EXAMPLE 87

Synthesis of (1S,2S,4aS,8aR)-1-[(3,5-dihydroxyphenyl)methyl]-5,5,8a-trimethyl-decahydronaphthalene-2-carboxylic acid (Compound No. 157)

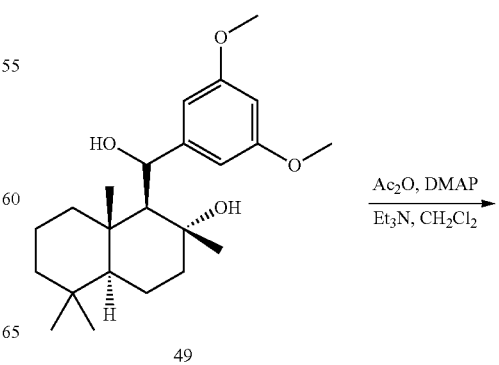

49

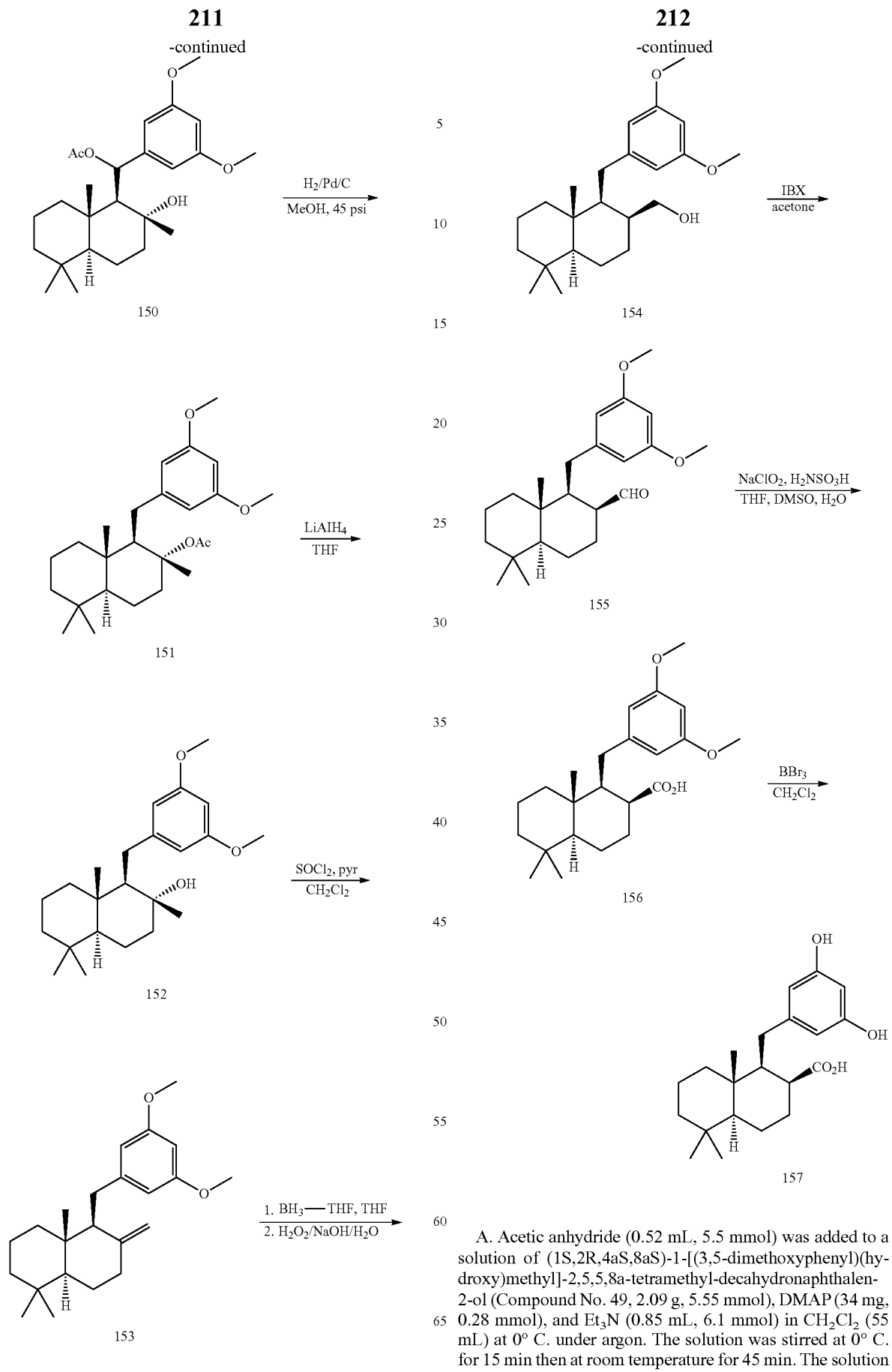
A. Acetic anhydride (0.52 mL, 5.5 mmol) was added to a solution of (1S,2R,4aS,8aS)-1-[(3,5-dimethoxyphenyl)(hydroxy)methyl]-2,5,5,8a-tetramethyl-decahydronaphthalen-2-ol (Compound No. 49, 2.09 g, 5.55 mmol), DMAP (34 mg, 0.28 mmol), and Et$_3$N (0.85 mL, 6.1 mmol) in CH$_2$Cl$_2$ (55 mL) at 0° C. under argon. The solution was stirred at 0° C. for 15 min then at room temperature for 45 min. The solution was concentrated, dissolved in EtOAc (100 mL), washed with saturated aqueous NaHCO$_3$ (5×20 mL) and brine (15 mL) then dried (MgSO$_4$) and concentrated. The residue was purified by chromatography on silica gel (EtOAc/hexanes, 1:3) to give [(1S,2R,4aS,8aS)-2-hydroxy-2,5,5,8a-tetramethyl-decahydronaphthalen-1-yl](3,5-dimethoxyphenyl) methyl acetate as a light yellow oil (Compound No. 150, 2.26 g, 97%).

B. To a solution of [(1S,2R,4aS,8aS)-2-hydroxy-2,5,5,8a-tetramethyl-decahydronaphthalen-1-yl](3,5-dimethoxyphenyl)methyl acetate (Compound No. 150, 2.26 g, 5.40 mmol) in MeOH (20 mL) was carefully added 10% Pd/C (228 mg) portionwise then shaken under an atmosphere of H$_2$(g) at 45 psi for 17 h. The mixture was filtered through Celite then concentrated to give a colourless oil, (1R,2R,4aS,8aS)-1-[(3,5-dimethoxyphenyl)methyl]-2,5,5,8a-tetramethyl-decahydronaphthalen-2-yl acetate (Compound No. 151, 2.10 g).

C. A solution of (1R,2R,4aS,8aS)-1-[(3,5-dimethoxyphenyl)methyl]-2,5,5,8a-tetramethyl-decahydronaphthalen-2-yl acetate (Compound No. 151, 2.10 g) in THF (35 mL) was cooled to 0° C. under argon and lithium aluminum hydride (297 mg, 7.83 mmol) was added. After stirring at room temperature for 2 h, the mixture was cooled to 0° C. and H$_2$O (0.3 mL) was carefully added followed by 15% aqueous NaOH (0.3 mL) and H$_2$O (0.9 mL). The mixture was stirred for 30 min at room temperature then dried (MgSO$_4$), filtered and concentrated. The residue was purified by chromatography on silica gel (EtOAc/hexanes, 1:3) to give (1R,2R,4aS,8aS)-1-[(3,5-dimethoxyphenyl)methyl]-2,5,5,8a-tetramethyl-decahydronaphthalen-2-ol as a colourless oil (Compound No. 152, 1.53 g, 78% over 2 steps).

D. To a solution of (1R,2R,4aS,8aS)-1-[(3,5-dimethoxyphenyl)methyl]-2,5,5,8a-tetramethyl-decahydronaphthalen-2-ol (Compound No. 152, 1.53 g, 4.24 mmol) and pyridine (0.69 mL, 8.5 mmol) in CH$_2$Cl$_2$ (42 mL) was added a solution of thionyl chloride (1.54 mL, 21.2 mmol) and pyridine (2.75 mL, 34.0 mmol) in CH$_2$Cl$_2$ (11 mL) at −78° C. under argon over 30 min. The solution was stirred at −78° C. for 40 min then saturated aqueous NaHCO$_3$ (20 mL) was added and allowed to warm to room temperature. The aqueous phase was extracted with CH$_2$Cl$_2$ (20 mL), and the combined organic layers were concentrated followed by azeotropic removal of pyridine using hexanes (3×10 mL). The residue was partitioned between EtOAc (80 mL) and saturated aqueous NaHCO$_3$ (15 mL). The organic phase was washed with saturated aqueous NaHCO$_3$ (3×15 mL) and brine (10 mL) then dried (MgSO$_4$) and concentrated to give a yellow oil, (4aS,5S,8aS)-5-[(3,5-dimethoxyphenyl)methyl]-1,1,4a-trimethyl-6-methylidene-decahydronaphthalene (Compound No. 153, 1.50 g) that was used in the next step without further purification.

E. To a solution of (4aS,5S,8aS)-5-[(3,5-dimethoxyphenyl)methyl]-1,1,4a-trimethyl-6-methylidene-decahydronaphthalene (Compound No. 153, 1.50 g) in THF (42 mL) under argon was added BH$_3$.THF (1.0 M in THF, 6.3 mL, 6.3 mmol) at 0° C., and the solution was stirred at 0° C. for 5 min then at room temperature for 1.8 h. The solution was cooled to 0° C., and 10 N NaOH (0.84 mL) was added followed by dropwise addition of 50% aqueous H$_2$O$_2$ (0.73 mL, 13 mmol). The mixture was stirred at room temperature for 20 min and 65° C. for 50 min then allowed to cool to room temperature. The mixture was diluted with H$_2$O (25 mL), and saturated aqueous Na$_2$SO$_3$ was added until excess peroxide was destroyed. The organic layer was washed with brine (15 mL), and the combined aqueous layers were extracted with EtOAc (20 mL). The combined organic layers were dried (MgSO$_4$) and concentrated, and the residue was purified by chromatography on silica gel (EtOAc/hexanes, 1:3) to give [(1S,2S,4aS,8aR)-1-[(3,5-dimethoxyphenyl) methyl]-5,5,8a-trimethyl-decahydronaphthalen-2-yl]methanol as a colourless oil (Compound No. 154, 0.59 g, 39% over 2 steps).

F. To a solution of [(1S,2S,4aS,8aR)-1-[(3,5-dimethoxyphenyl)methyl]-5,5,8a-trimethyl-decahydronaphthalen-2-yl]methanol (Compound No. 154, 0.59 g, 1.6 mmol) in acetone (11 mL) under argon was added 2-iodoxybenzoic acid (1.37 g, 4.89 mmol), and the mixture was heated to 60° C. for 3 h. The mixture was allowed to cool to room temperature then filtered and concentrated to give a yellow oil, (1S,2S,4aS,8aR)-1-[(3,5-dimethoxyphenyl)methyl]-5,5,8a-trimethyl-decahydronaphthalene-2-carbaldehyde (Compound No. 155, 605 mg) that was used in the next step without further purification.

G. To a solution of (1S,2S,4aS,8aR)-1-[(3,5-dimethoxyphenyl)methyl]-5,5,8a-trimethyl-decahydronaphthalene-2-carbaldehyde (Compound No. 155, 605 mg) and sulfamic acid (544 mg, 5.60 mmol) in THF/DMSO (10:1, 18 mL) at 0° C. was added a solution of 80% sodium chlorite (543 mg, 4.80 mmol) in H$_2$O (16 mL), and the mixture was stirred at 0° C. for 3 h. The mixture was diluted with EtOAc (50 mL), H$_2$O (10 mL) and saturated aqueous NH$_4$Cl (10 mL). The organic layer was washed with brine (3×15 mL) then dried (MgSO$_4$) and concentrated. The residue was partially purified by chromatography on silica gel (EtOAc/hexanes, 1:4) to give (1S,2S,4aS,8aR)-1-[(3,5-dimethoxyphenyl)methyl]-5,5,8a-trimethyl-decahydronaphthalene-2-carboxylic acid as a yellow oil (Compound No. 156, 374 mg).

H. A solution of (1S,2S,4aS,8aR)-1-[(3,5-dimethoxyphenyl)methyl]-5,5,8a-trimethyl-decahydronaphthalene-2-carboxylic acid (Compound No. 156, 99 mg) in CH$_2$Cl$_2$ (2.6 mL) under argon was stirred at 0° C. while BBr$_3$ (1.0 M in CH$_2$Cl$_2$, 1.6 mL, 1.6 mmol) was added then the solution was stirred at room temperature for 23 h. Methanol (5 mL) was carefully added to the solution then concentrated (2×). The residue was diluted with i-PrOH/10% aqueous HCl (2:1, 3 mL) and heated to 90° C. for 45 min. The solution was concentrated, and the residue was partitioned between EtOAc (30 mL) and brine (15 mL). The organic layer was dried (MgSO$_4$) and concentrated, and the residue was purified by chromatography on silica gel (MeOH/CH$_2$Cl$_2$, 3:97) to give (1S,2S,4aS,8aR)-1-[(3,5-dihydroxyphenyl)methyl]-5,5,8a-trimethyl-decahydronaphthalene-2-carboxylic acid as a pale solid (Compound No. 157, 11 mg, 7% over 3 steps). $^1$H NMR (CD$_3$OD): δ6.28 (d, J=2.4 Hz, 2H), 6.08 (t, J=2.3 Hz, 1H), 2.96 (m, 1H), 2.68 (dd, J=13.2, 3.0 Hz, 1H), 2.40 (m, 1H), 2.19 (m, 1H), 1.85 (m, 1H), 1.79-0.95 (m, 13H), 0.87 (s, 3H), 0.85 (s, 3H). $^{13}$C NMR (CD$_3$OD): δ179.2, 159.0 (2C), 146.3, 109.1 (2C), 101.0, 58.1, 58.0, 43.3, 40.7, 40.0 (2C), 34.3, 34.0, 32.7, 30.9, 21.9, 20.5, 19.8, 15.3. ES-MS m/z 345 ([M−1]$^-$).

EXAMPLE 88

Synthesis of N-[(2R,3S,4S,4aS,8aS)-4-[(3,5-dihydroxyphenyl)carbonyl]-3,4a,8,8-tetramethyl-decahydronaphthalen-2-yl]pyridine-2-carboxamide (Compound No. 158)

EXAMPLE 89

Synthesis of N-[(2R,3S,4S,4aS,8aS)-4-[(3,5-dihydroxyphenyl)carbonyl]-3,4a,8,8-tetramethyl-decahydronaphthalen-2-yl]pyridine-4-carboxamide (Compound No. 159)

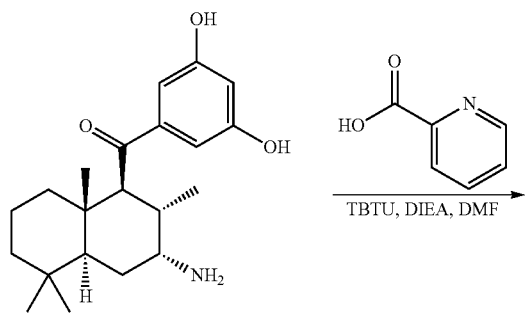

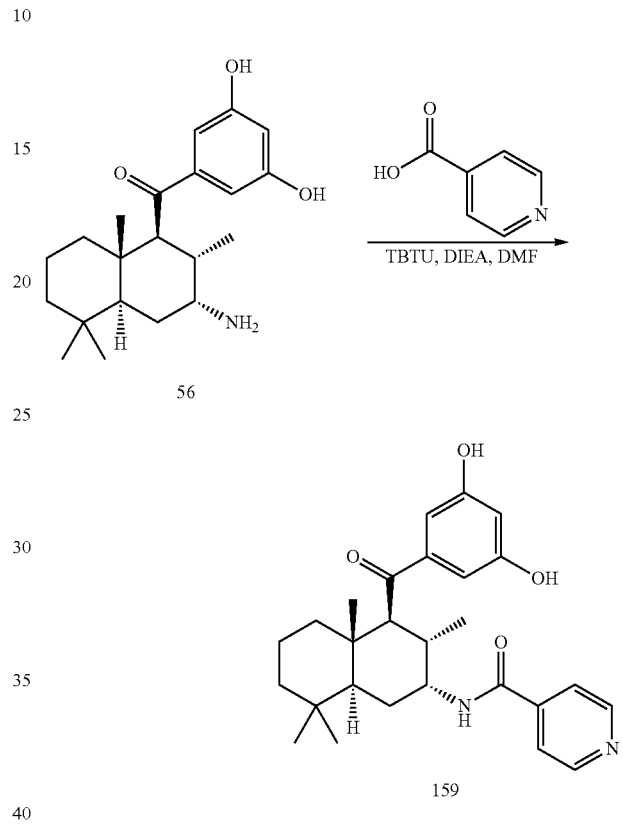

To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 79 mg, 0.23 mmol), O-(benzotriazol-1-yl)-N,N,N',N'-tetramethyluronium tetrafluoroborate (88 mg, 0.27 mmol), and 2-picolinic acid (34 mg, 0.28 mmol) in DMF (1.1 mL) under argon was added N,N-diisopropylethylamine (0.056 mL, 0.32 mmol), and the solution was stirred at room temperature for 19.5 h then concentrated. The residue was dissolved in EtOAc (40 mL) and washed with saturated aqueous NaHCO₃ (10 mL) and brine (5×10 mL) then dried (MgSO₄) and concentrated. The residue was purified by chromatography on silica gel (EtOAc/CH₂Cl₂, 2:3) to give N-[(2R,3S,4S,4aS,8aS)-4-[(3,5-di hydroxyphenyl)carbonyl]-3,4a,8,8-tetramethyl-decahydronaphthalen-2-yl]pyridine-2-carboxamide as a colourless foam (Compound No. 158, 73 mg, 71%). $^1$H NMR (CD₃OD): δ8.74 (d, J=4.2 Hz, 1H), 8.14 (d, J=7.5 Hz, 1H), 8.00 (m, 1H), 7.61 (m, 1H), 6.90 (d, J=2.1 Hz, 2H), 6.50 (t, J=2.3 Hz, 1H), 4.47 (m, 1H), 3.37 (d, J=12.0 Hz, 1H), 2.52 (m, 1H), 1.84 (m, 2H), 1.61-1.09 (m, 10H), 0.87 (s, 3H), 0.81 (s, 3H), 0.75 (d, J=6.9 Hz, 3H). $^{13}$C NMR (CD₃OD): δ205.4, 165.9, 159.9 (2C), 150.8, 149.8, 144.3, 139.2, 128.0, 123.3, 108.2, 107.6 (2C), 59.3, 51.3, 49.8, 42.8, 42.3, 40.3, 34.4, 33.9, 33.8, 28.6, 22.0, 19.5, 16.8, 14.0. ES-MS m/z 451 ([M+1]⁺).

To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 79 mg, 0.23 mmol), O-(benzotriazol-1-yl)-N,N,N',N'-tetramethyluronium tetrafluoroborate (88 mg, 0.27 mmol), and isonicotinic acid (34 mg, 0.28 mmol) in DMF (1.1 mL) under argon was added N,N-diisopropylethylamine (0.056 mL, 0.32 mmol), and the solution was stirred at room temperature for 19.5 h then concentrated. The residue was dissolved in EtOAc (40 mL) and washed with saturated aqueous NaHCO₃ (10 mL) and brine (5×10 mL) then dried (MgSO₄) and concentrated. The residue was purified by chromatography on silica gel (MeOH/EtOAc, 1:99) to give N-[(2R,3S,4S,4aS,8aS)-4-[(3,5-di hydroxyphenyl)carbonyl]-3,4a,8,8-tetramethyl-decahydronaphthalen-2-yl]pyridine-4-carboxamide as a colourless solid (Compound No. 159, 53 mg, 51%). $^1$H NMR (CD₃OD): δ8.70 (d, J=5.7 Hz, 2H), 7.68 (m, 2H), 6.94 (d, J=2.4 Hz, 2H), 6.48 (t, J=2.0 Hz, 1H), 4.53 (m, 1H), 3.57 (d, J=12.0 Hz, 1H), 2.50 (m, 1H), 1.80 (m, 2H), 1.60-1.29 (m, 6H), 1.08 (m, 4H), 0.88 (s, 6H), 0.77 (d, J=6.6 Hz, 3H). $^{13}$C NMR (CD₃OD): δ206.2, 169.3, 159.8 (2C), 150.7 (2C), 145.4, 144.5, 123.3 (2C), 107.9 (3C), 58.8, 52.1, 48.8, 42.9, 42.5, 40.1, 33.9 (3C), 28.7, 22.1, 19.5, 16.6, 14.2. ES-MS m/z 451 ([M+1]⁺).

EXAMPLE 90

Synthesis of 3-{[(2R,3S,4S,4aS,8aS)-4-[(3,5-dihydroxyphenyl)carbonyl]-3,4a,8,8-tetramethyl-decahydronaphthalen-2-yl]carbamoyl}pyridin-1-ium-1-olate (Compound No. 160)

EXAMPLE 91

Synthesis of N-[(2R,3S,4S,4aS,8aS)-4-[(3,5-dihydroxyphenyl)carbonyl]-3,4a,8,8-tetramethyl-decahydronaphthalen-2-yl]-4-methylpiperazine-1-carboxamide (Compound No. 163)

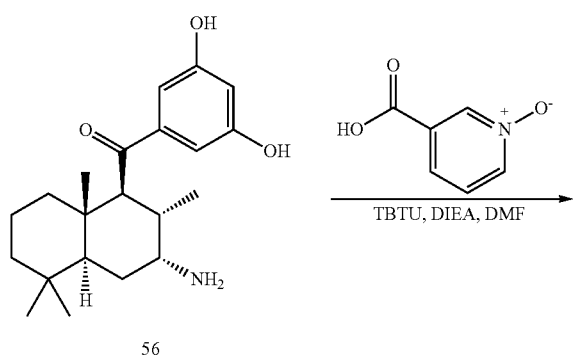

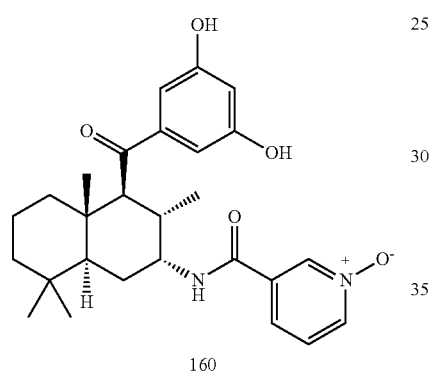

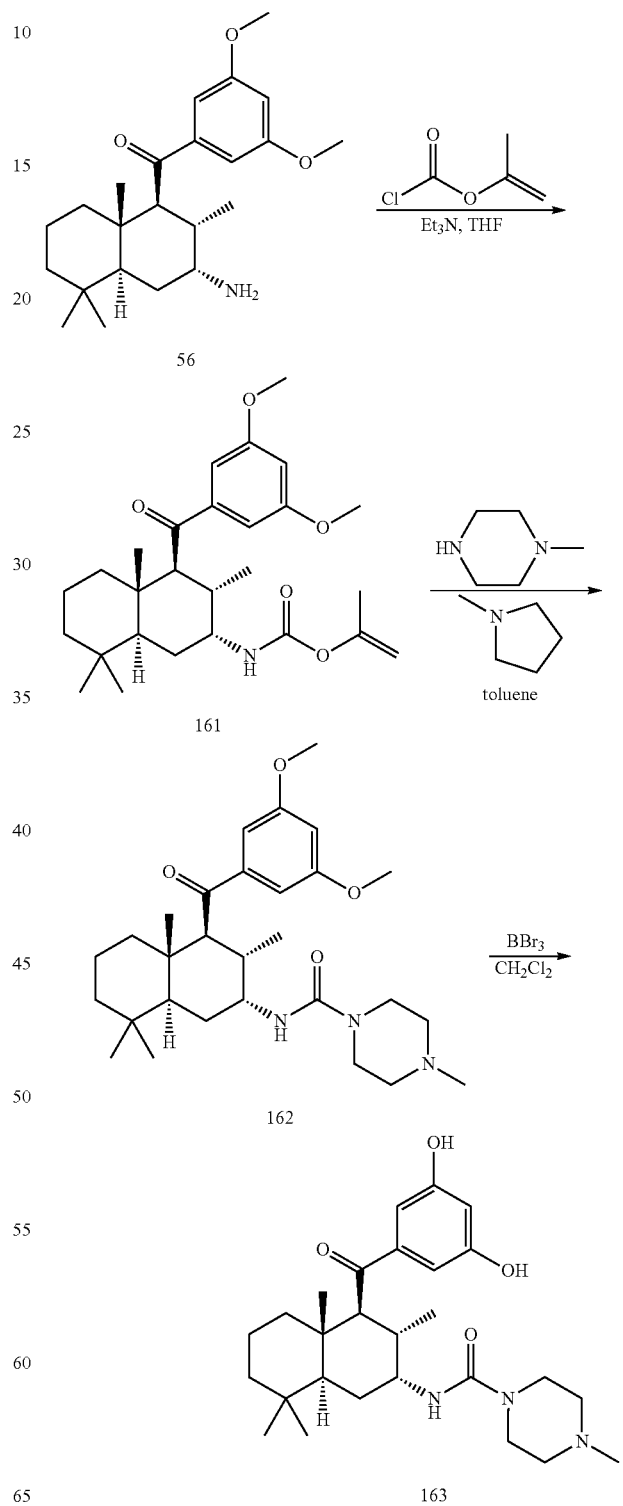

To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 74 mg, 0.21 mmol), O-(benzotriazol-1-yl)-N,N,N',N'-tetramethyluronium tetrafluoroborate (185 mg, 0.58 mmol), and nicotinic acid N-oxide (80 mg, 0.58 mmol) in DMF (1.1 mL) under argon was added N,N-diisopropylethylamine (0.12 mL, 0.69 mmol), and the solution was stirred at room temperature for 21 h then concentrated. The residue was partitioned between EtOAc (40 mL) and saturated aqueous NaHCO$_3$ (10 mL). The organic phase was washed with brine (5×10 mL) then dried (MgSO$_4$) and concentrated. The residue was purified by chromatography on silica gel (CH$_2$Cl$_2$/MeOH/NH$_4$OH, 100:10:2) to give 3-{[(2R,3S,4S,4aS,8aS)-4-[(3,5-dihydroxyphenyl)carbonyl]-3,4a,8,8-tetramethyl-decahydronaphthalen-2-yl]carbamoyl}pyridin-1-ium-1-olate as a pale solid (Compound No. 160, 39 mg, 39%). $^1$H NMR (DMSO-d6): δ9.59 (s, 2H), 8.60 (s, 1H), 8.50 (d, J=9.3 Hz, 1H), 8.39 (d, J=5.7 Hz, 1H), 7.67 (d, J=7.8 Hz, 1H), 7.55 (m, 1H), 6.89 (d, J=1.8 Hz, 2H), 6.47 (s, 1H), 4.40 (br s, 1H), 3.60 (d, J=11.7 Hz, 1H), 2.31 (m, 1H), 1.66-1.15 (m, 8H), 0.94 (s, 4H), 0.79 (s, 6H), 0.61 (d, J=6.3 Hz, 3H). $^{13}$C NMR (DMSO-d6): δ203.8, 163.2, 158.3 (2C), 142.9, 140.4, 137.5, 134.5, 126.5, 124.6, 106.7, 106.3 (2C), 55.8, 49.5, 48.6, 46.0, 41.5, 38.4, 33.1, 32.4, 32.1, 27.3, 21.4, 18.0, 15.9, 13.2. ES-MS m/z 467 ([M+1]$^+$).

A. A solution of isopropenyl chloroformate (51 mg, 0.42 mmol) in THF (1.0 mL) was added to a solution of (2R,3S,4S,4aS,8aS)-4-[(3,5-dimethoxyphenyl)carbonyl]-3,4a,8,8-tetramethyl-decahydronaphthalen-2-amine (Compound No. 55, 122 mg, 0.327 mmol) and Et₃N (0.059 mL, 0.42 mmol) in THF (0.6 mL) at 0° C. under argon then stirred at room temperature for 23 h. The mixture was diluted with EtOAc (40 mL) and washed with saturated aqueous NaHCO₃ (5×10 mL) and brine (10 mL) then dried (MgSO₄) and concentrated. After azeotropic distillation using toluene (3×10 mL), prop-1-en-2-yl N-[(2R,3S,4S,4aS,8aS)-4-[(3,5-dimethoxyphenyl)carbonyl]-3,4a,8,8-tetramethyl-decahydronaphthalen-2-yl]carbamate was obtained as a yellow solid (Compound No. 161, 144 mg, 97%) and used in the next step without further purification.

B. A solution of prop-1-en-2-yl N-[(2R,3S,4S,4aS,8aS)-4-[(3,5-dimethoxyphenyl)carbonyl]-3,4a,8,8-tetramethyl-decahydronaphthalen-2-yl]carbamate (Compound No. 161, 144 mg, 0.315 mmol), 1-methylpiperazine (38 mg, 0.38 mmol) and 1-methylpyrrolidine (29 mg, 0.34 mmol) in toluene (1.0 mL) was heated to 100° C. for 25 h under argon. The mixture was allowed to cool to room temperature and partitioned between EtOAc (35 mL) and saturated aqueous NaHCO₃ (10 mL). The organic layer was washed with saturated aqueous NaHCO₃ (2×10 mL) and brine (10 mL) then dried (MgSO₄) and concentrated. The residue was purified by chromatography on silica gel (MeOH/CH₂Cl₂, 3:47) to give N-[(2R,3S,4S,4aS,8aS)-4-[(3,5-dimethoxyphenyl)carbonyl]-3,4a,8,8-tetramethyl-decahydronaphthalen-2-yl]-4-methylpiperazine-1-carboxamide as a light yellow film (Compound No. 162, 128 mg, 82%).

C. A solution of N-[(2R,3S,4S,4aS,8aS)-4-[(3,5-dimethoxyphenyl)carbonyl]-3,4a,8,8-tetramethyl-decahydronaphthalen-2-yl]-4-methylpiperazine-1-carboxamide (Compound No. 162, 128 mg, 0.256 mmol) in CH₂Cl₂ (2.6 mL) under argon was stirred at −78° C. while BBr₃ (1.0 M in CH₂Cl₂, 1.5 mL, 1.5 mmol) was added then the solution was stirred at room temperature for 6 h. Methanol (10 mL) was carefully added to the solution at 0° C. then concentrated. After azeotropic distillation using MeOH (3×10 mL), the residue was diluted with i-PrOH (3.5 mL) and 10% aqueous HCl (1 mL) then heated to 80° C. for 40 min. The solution was concentrated, diluted with H₂O (1 mL) then adjusted to pH 8 using saturated aqueous NaHCO₃. The mixture was extracted with EtOAc (20 mL then 2×10 mL), and the organic extracts were combined, dried (MgSO₄) and concentrated. The residue was purified by chromatography on silica gel (CH₂Cl₂/MeOH/NH₄OH, 100:10:1) to afford N-[(2R,3S,4S,4aS,8aS)-4-[(3,5-dihydroxyphenyl)carbonyl]-3,4a,8,8-tetramethyl-decahydronaphthalen-2-yl]-4-methylpiperazine-1-carboxamide as a colourless solid (Compound No. 163, 51 mg, 42%). ¹H NMR (CD₃OD): δ6.92 (d, J=2.1 Hz, 2H), 6.49 (s, 1H), 6.15 (d, J=7.5 Hz, 1H), 4.19 (m, 1H), 3.52 (m, 4H), 3.42 (d, J=12.0 Hz, 1H), 2.49 (m, 4H), 2.38 (m, 1H), 2.34 (s, 3H), 1.68 (m, 2H), 1.59-1.22 (m, 6H), 1.07 (m, 1H), 1.02 (s, 3H), 0.85 (s, 6H), 0.70 (d, J=6.9 Hz, 3H). ¹³C NMR (CD₃OD): δ206.3, 160.4, 159.8 (2C), 144.6, 107.9, 107.8 (2C), 59.1, 55.7 (2C), 52.3, 48.6, 46.1, 45.2 (2C), 42.9, 42.4, 40.1, 34.3, 33.9 (2C), 29.4, 22.2, 19.6, 16.8, 14.2. ES-MS m/z 472 ([M+1]⁺).

EXAMPLE 92

Synthesis of N-[(2R,3S,4S,4aS,8aS)-4-[(3,5-dihydroxyphenyl)carbonyl]-3,4a,8,8-tetramethyl-decahydronaphthalen-2-yl]-3-aminopropanamide (Compound No. 165)

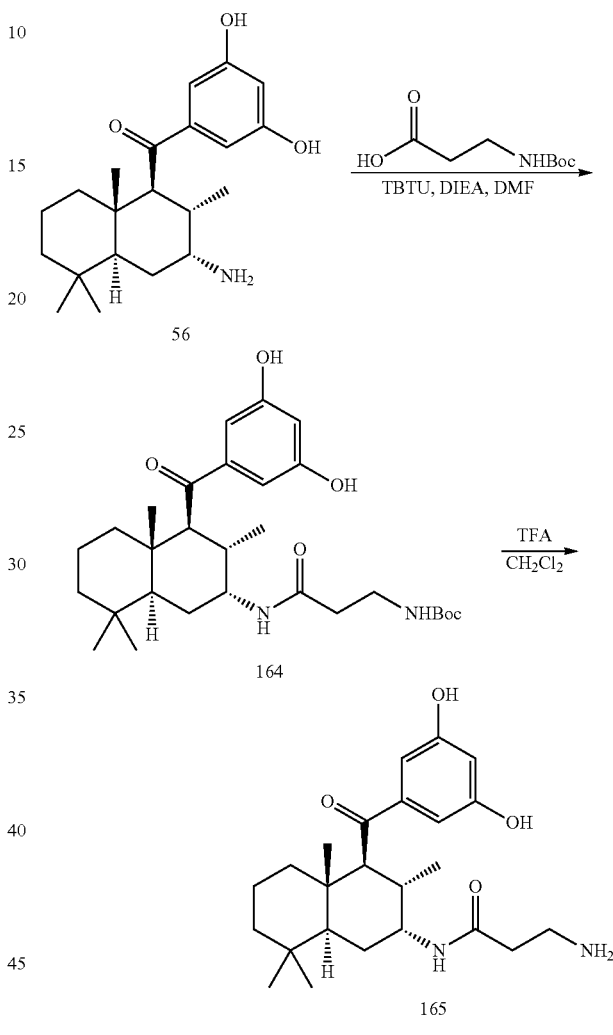

A. To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 76 mg, 0.22 mmol), O-(benzotriazol-1-yl)-N,N,N',N'-tetramethyluronium tetrafluoroborate (85 mg, 0.26 mmol), and N-(tert-butoxycarbonyl)-beta-alanine (50 mg, 0.26 mmol) in DMF (1.1 mL) under argon was added N,N-diisopropylethylamine (0.054 mL, 0.31 mmol), and the solution was stirred at room temperature for 16 h then concentrated. The residue was dissolved in EtOAc (40 mL) and washed with saturated aqueous NaHCO₃ (10 mL) and brine (5×10 mL) then dried (MgSO₄) and concentrated. The residue was partially purified by chromatography on silica gel (EtOAc/CH₂Cl₂, 3:1) to give tert-butyl N-(2-{[(2R,3S,4S,4aS,8aS)-4-[(3,5-dihydroxyphenyl)carbonyl]-3,4a,8,8-tetramethyl-decahydronaphthalen-2-yl]carbamoyl}ethyl)carbamate as a colourless solid (Compound No. 164, 103 mg).

B. Trifluoroacetic acid (1 mL) was added to a solution of tert-butyl N-(2-{[(2R,3S,4S,4aS,8aS)-4-[(3,5-dihydroxyphenyl)carbonyl]-3,4a,8,8-tetramethyl-decahydronaphthalen-2-yl]carbamoyl}ethyl)carbamate (Compound No. 164, 103 mg) in CH₂Cl₂ (3 mL) under argon, and the solution was stirred at room temperature for 50 min. The solution was cooled to 0° C. and adjusted to pH 8 using 10 N NaOH then diluted with H₂O (10 mL) and EtOAc (15 mL). The aqueous layer was extracted with EtOAc (15 mL), and the combined organic layers were dried (MgSO₄) and concentrated. The residue was stirred in H₂O (2 mL), and N-[(2R,3S,4S,4aS,8aS)-4-[(3,5-dihydroxyphenyl)carbonyl]-3,4a,8,8-tetramethyl-decahydronaphthalen-2-yl]-3-aminopropanamide, a pale solid (Compound No. 165, 52 mg, 57% over 2 steps), was collected by filtration. ¹H NMR (CD₃OD): δ6.93 (d, J=1.8 Hz, 2H), 6.49 (s, 1H), 4.28 (br s, 1H), 3.42 (d, J=12.3 Hz, 1H), 3.02 (br s, 2H), 2.57 (m, 2H), 2.37 (m, 1H), 1.68 (m, 2H), 1.55-1.22 (m, 6H), 1.08 (m, 1H), 1.03 (s, 3H), 0.85 (s, 6H), 0.69 (d, J=6.3 Hz, 3H). ¹³C NMR (CD₃OD): δ206.3, 173.7, 160.0 (2C), 144.5, 108.2, 107.9 (2C), 58.8, 50.9, 48.8, 42.9, 42.3, 40.2, 38.7, 36.9, 33.9, 33.8 (2C), 28.7, 22.1, 19.5, 16.6, 14.0. ES-MS m/z 415 ([M−1]⁻).

EXAMPLE 93

Synthesis of N-[(2R,3S,4S,4aS,8aS)-4-[(3,5-dihydroxyphenyl)carbonyl]-3,4a,8,8-tetramethyl-decahydronaphthalen-2-yl]piperidine-4-carboxamide (Compound No. 167)

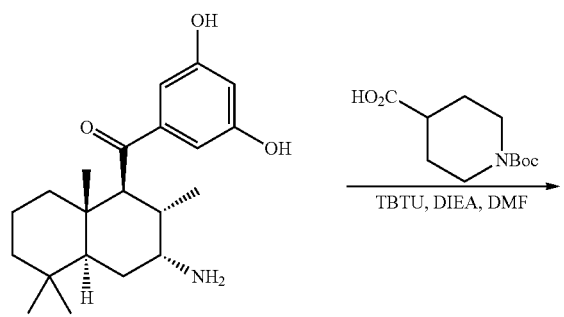

56

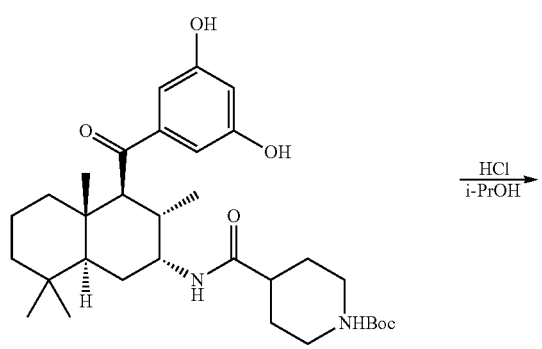

166

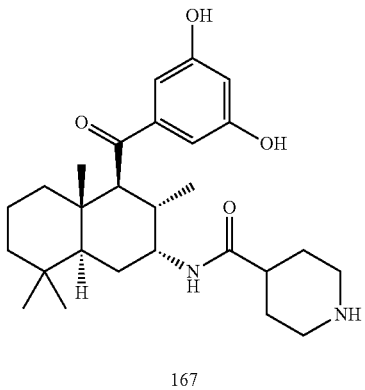

167

A. To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 73 mg, 0.21 mmol), O-(benzotriazol-1-yl)-N,N,N',N'-tetramethyluronium tetrafluoroborate (81 mg, 0.25 mmol), and 1-(tert-butoxycarbonyl)piperidine-4-carboxylic acid (58 mg, 0.25 mmol) in DMF (1.1 mL) under argon was added N,N-diisopropylethylamine (0.052 mL, 0.30 mmol), and the solution was stirred at room temperature for 17 h then concentrated. The residue was dissolved in EtOAc (40 mL) and washed with saturated aqueous NaHCO₃ (10 mL) and brine (5×10 mL) then dried (MgSO₄) and concentrated. The residue was partially purified by chromatography on silica gel (EtOAc/CH₂Cl₂, 3:2) to give tert-butyl 4-{[(2R,3S,4S,4aS,8aS)-4-[(3,5-dihydroxyphenyl)carbonyl]-3,4a,8,8-tetramethyl-decahydronaphthalen-2-yl]carbamoyl}piperidine-1-carboxylate as a colourless solid (Compound No. 166, 112 mg).

B. tert-Butyl 4-{[(2R,3S,4S,4aS,8aS)-4-[(3,5-dihydroxyphenyl)carbonyl]-3,4a,8,8-tetramethyl-decahydronaphthalen-2-yl]carbamoyl}piperidine-1-carboxylate (Compound No. 166, 112 mg) was dissolved in a solution of 1.25 M HCl in i-PrOH (4 mL) and stirred at room temperature for 24 h. The solution was concentrated, and the residue was partitioned between EtOAc (20 mL) and saturated aqueous NaHCO₃ (20 mL). The aqueous layer was extracted with EtOAc (2×20 mL), and the combined organic layers were washed with brine (10 mL) then dried (MgSO₄) and concentrated. The residue was briefly stirred as a suspension in CH₂Cl₂ (2 mL), and N-[(2R,3S,4S,4aS,8aS)-4-[(3,5-dihydroxyphenyl)carbonyl]-3,4a,8,8-tetramethyl-decahydronaphthalen-2-yl]piperidine-4-carboxamide, a light yellow solid (Compound No. 167, 61 mg, 64% over 2 steps), was collected by filtration. ¹H NMR (CD₃OD): δ8.14 (d, J=7.8 Hz, 1H), 6.96 (d, J=2.1 Hz, 2H), 6.50 (s, 1H), 4.24 (m, 1H), 3.45 (d, J=12.0 Hz, 1H), 3.31 (m, 2H), 2.89 (m, 2H), 2.74 (m, 1H), 2.39 (m, 1H), 1.88-1.22 (m, 12H), 1.08 (m, 1H), 1.02 (s, 3H), 0.85 (s, 6H), 0.69 (d, J=6.3 Hz, 3H). ¹³C NMR (CD₃OD): δ206.2, 176.6, 160.0 (2C), 144.5, 108.2, 107.9 (2C), 58.9, 50.8, 48.6, 45.2 (2C), 42.8, 42.3, 41.9, 40.1, 33.8 (3C), 28.6, 28.5, 28.2, 22.1, 19.5, 16.6, 14.1. ES-MS m/z 457 ([M+1]⁺).

EXAMPLE 94

Synthesis of N-[(2R,3S,4S,4aS,8aS)-4-[(3,5-dimethoxyphenyl)carbonyl]-3,4a,8,8-tetramethyl-decahydronaphthalen-2-yl]pyridine-3-carboxamide (Compound No. 168)

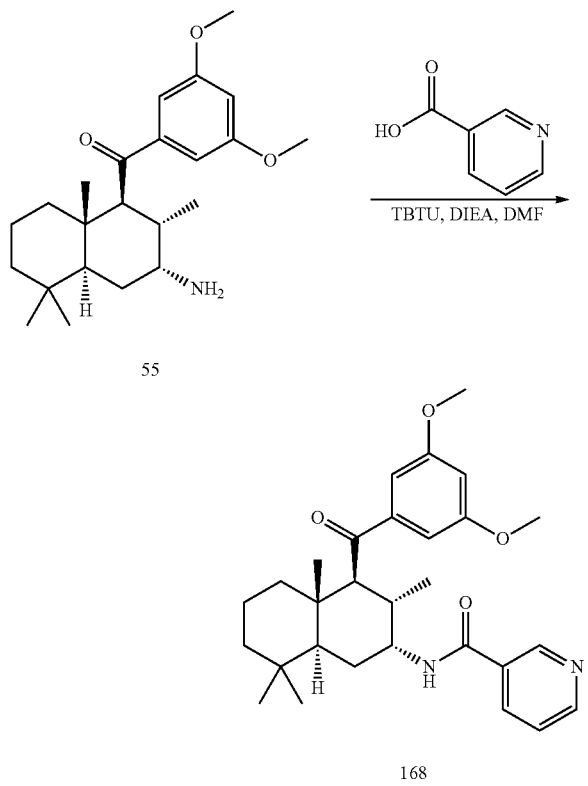

To a solution of (2R,3S,4S,4aS,8aS)-4-[(3,5-dimethoxyphenyl)carbonyl]-3,4a,8,8-tetramethyl-decahydronaphthalen-2-amine (Compound No. 55, 72 mg, 0.19 mmol), O-(benzotriazol-1-yl)-N,N,N',N'-tetramethyluronium tetrafluoroborate (74 mg, 0.23 mmol), and nicotinic acid (28 mg, 0.23 mmol) in DMF (1.0 mL) under argon was added N,N-diisopropylethylamine (0.047 mL, 0.27 mmol), and the solution was stirred at room temperature for 18 h then concentrated. The residue was partitioned between EtOAc (40 mL) and saturated aqueous NaHCO$_3$ (10 mL). The organic phase was washed with brine (5×10 mL) then dried (MgSO$_4$) and concentrated. The residue was purified by chromatography on silica gel (EtOAc/CH$_2$Cl$_2$, 3:7) to give N-[(2R,3S,4S,4aS,8aS)-4-[(3,5-dimethoxyphenyl)carbonyl]-3,4a,8,8-tetramethyl-decahydronaphthalen-2-yl]pyridine-3-carboxamide as a colourless solid (Compound No. 168, 69 mg, 75%). $^1$H NMR (CDCl$_3$): δ8.98 (brs, 1H), 8.76 (brs, 1H), 8.11 (d, J=8.1 Hz, 1H), 7.43 (dd, J=7.7, 5.0 Hz, 1H), 7.02 (d, J=1.8 Hz, 2H), 6.62 (s, 1H), 6.36 (d, J=9.0 Hz, 1H), 4.60 (m, 1H), 3.83 (s, 6H), 3.09 (d, J=12.3 Hz, 1H), 2.57 (m, 1H), 1.91-1.02 (m, 12H), 0.86 (s, 3H), 0.85 (s, 3H), 0.80 (d, J=6.6 Hz, 3H). $^{13}$C NMR (CDCl$_3$): δ202.7, 165.8, 161.0 (2C), 152.2, 147.6, 142.6, 135.4, 131.4, 123.8, 106.4 (2C), 104.2, 58.7, 55.7 (2C), 50.2, 49.4, 41.9, 41.4, 39.5, 33.8, 33.3, 33.1, 27.8, 21.8, 18.5, 16.5, 13.6. ES-MS m/z 479 ([M+1]$^+$).

EXAMPLE 95

Synthesis of 5-{[(1S,2S,3R,4aS,8aS)-3-[(3-aminopropyl)amino]-2,5,5,8a-tetramethyl-decahydronaphthalen-1-yl]carbonyl}benzene-1,3-diol dihydrochloride (Compound No. 170)

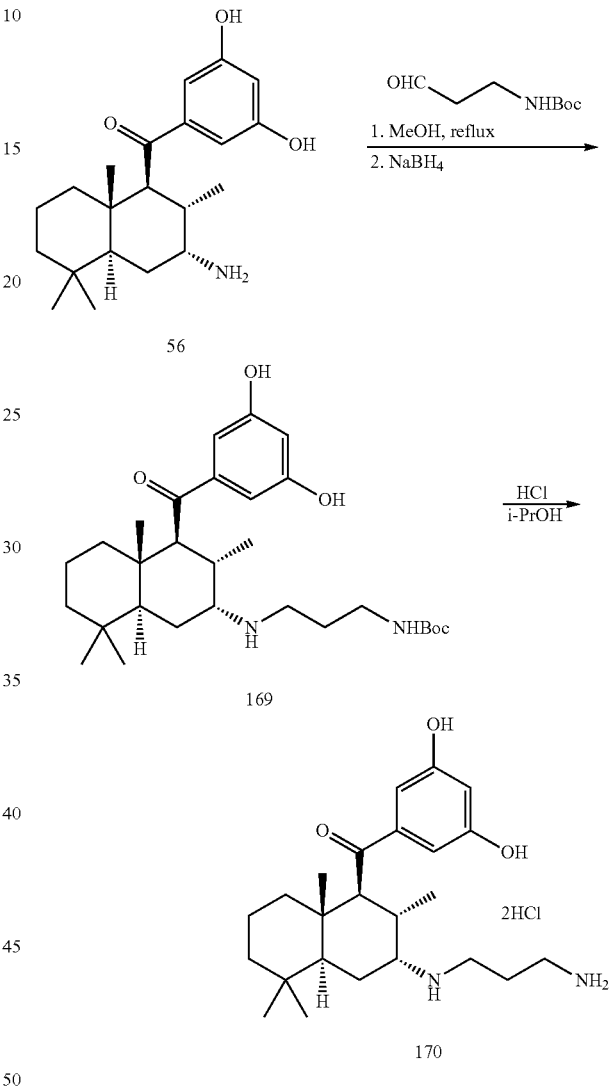

A. A solution of 5-{[(1S,2S,3R,4aS,8aS)-3-amino-2,5,5,8a-tetramethyl-decahydronaphthalen-1-yl]carbonyl}benzene-1,3-diol (Compound No. 56, 73 mg, 0.21 mmol) and tert-butyl N-(3-oxopropyl)carbamate (45 mg, 0.26 mmol) in MeOH (4.2 mL) was heated to reflux under argon for 35 min. After allowing the solution to cool to room temperature, sodium borohydride (16 mg, 0.42 mmol) was added, and the mixture was stirred for 2 h then concentrated. The residue was dissolved in EtOAc (30 mL) and washed with brine (10 mL). The aqueous phase was extracted with EtOAc (10 mL), and the combined organic layers were dried (MgSO$_4$) and concentrated. The residue was partially purified by chromatography on silica gel (CH$_2$Cl$_2$/MeOH/ NH$_4$OH, 100:5:1) to give a colourless solid (87 mg). The colourless solid (87 mg) was dissolved in EtOAc (30 mL) and washed with H$_2$O (18×15 mL) and brine (10 mL) then dried (MgSO$_4$) and concentrated to give tert-butyl N-(3-{[(2R,3S,4S,4aS,8aS)-4-[(3,5-dihydroxyphenyl)carbonyl]-3,4a,8,8-tetramethyl-decahydronaphthalen-2-yl]amino}propyl)carbamate as a colourless solid (Compound No. 169, 78 mg, 74%).

B. tert-Butyl N-(3-{[(2R,3S,4S,4aS,8aS)-4-[(3,5-dihydroxyphenyl)carbonyl]-3,4a,8,8-tetramethyl-decahydronaphthalen-2-yl]amino}propyl)carbamate (Compound No. 169, 78 mg, 0.16 mmol) was dissolved in a solution of 1.25 M HCl in i-PrOH (4 mL) and stirred at room temperature for 18.5 h. The solution was concentrated followed by azeotropic distillation using MeOH (3 mL). The residue was dissolved in MeOH (0.5 mL), and Et$_2$O (40 mL) was added to precipitate a colourless solid. The supernatant was decanted, and the remaining solid was washed by decantation with Et$_2$O (4×10 mL). Remaining traces of solvent were removed under vacuum to afford 5-{[(1S,2S,3R,4aS,8aS)-3-[(3-aminopropyl)amino]-2,5,5,8a-tetramethyl-decahydronaphthalen-1-yl]carbonyl}benzene-1,3-diol dihydrochloride as a colourless solid (Compound No. 170, 57 mg, 77%). $^1$H NMR (CD$_3$OD): δ6.99 (d, J=2.1 Hz, 2H), 6.49 (t, J=2.0 Hz, 1H), 3.73 (d, J=12.3 Hz, 1H), 3.63 (br s, 1H), 3.26-3.07 (m, 4H), 2.63 (m, 1H), 2.28 (m, 2H), 2.04 (m, 1H), 1.84 (m, 1H), 1.63-1.31 (m, 6H), 1.06 (m, 4H), 1.01 (s, 3H), 0.94 (d, J=7.2 Hz, 3H), 0.90 (s, 3H). $^{13}$C NMR (CD$_3$OD): δ204.4, 160.0 (2C), 143.8, 108.6, 108.0 (2C), 61.5, 57.5, 46.9, 44.2, 42.4, 41.7, 40.1, 38.2, 34.2, 33.8, 33.5, 24.9, 23.1, 21.9, 19.3, 16.2, 14.2. ES-MS m/z 403 ([M+1]$^+$).

EXAMPLE 96

Synthesis of N-[(2R,3S,4S,4aS,8aS)-4-[(3,5-dihydroxyphenyl)carbonyl]-3,4a,8,8-tetramethyl-decahydronaphthalen-2-yl]-6-aminopyridine-3-carboxamide (Compound No. 171)

To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 69 mg, 0.20 mmol), O-(benzotriazol-1-yl)-N,N,N',N'-tetramethyluronium tetrafluoroborate (77 mg, 0.24 mmol), and 6-aminonicotinic acid (33 mg, 0.24 mmol) in DMF (1.0 mL) under argon was added N,N-diisopropylethylamine (0.049 mL, 0.28 mmol), and the solution was stirred at room temperature for 21 h then concentrated. The residue was partitioned between EtOAc (30 mL) and H$_2$O (10 mL). The organic phase was washed with brine (3×10 mL) then dried (MgSO$_4$) and concentrated. The residue was purified by chromatography on silica gel (CH$_2$Cl$_2$/MeOH/NH$_4$OH, 100:10:1) to give N-[(2R,3S,4S,4aS,8aS)-4-[(3,5-dihydroxyphenyl)carbonyl]-3,4a,8,8-tetramethyl-decahydronaphthalen-2-yl]-6-aminopyridine-3-carboxamide as a colourless solid (Compound No. 171, 40 mg, 43%). $^1$H NMR (CD$_3$OD): δ8.39 (d, J=2.1 Hz, 1H), 8.18 (d, J=9.3 Hz, 1H), 7.86 (dd, J=8.9, 2.3 Hz, 1H), 6.95 (d, J=1.8 Hz, 2H), 6.61 (d, J=8.7 Hz, 1H), 6.49 (t, J=2.0 Hz, 1H), 4.50 (m, 1H), 3.58 (d, J=12.0 Hz, 1H), 2.47 (m, 1H), 1.77 (m, 2H), 1.60-1.24 (m, 6H), 1.08 (m, 1H), 1.05 (s, 3H), 0.87 (s, 6H), 0.75 (d, J=6.9 Hz, 3H). $^{13}$C NMR (CD$_3$OD): δ206.4, 169.5, 169.4, 162.6, 159.8 (2C), 148.6, 144.6, 138.7, 121.2, 109.1, 107.9 (2C), 58.9, 51.5, 51.4, 42.8, 42.4, 40.1, 34.1, 33.9 (2C), 29.0, 22.1, 19.5, 16.7, 14.2. ES-MS m/z 466 ([M+1]$^+$).

EXAMPLE 97

Synthesis of (4S,4aS,8aS)-4-{[(3,5-dimethoxybenzene)sulfonyl]methyl}-3,4a,8,8-tetramethyl-decahydronaphthalen-2-ol (Compound No. 173)

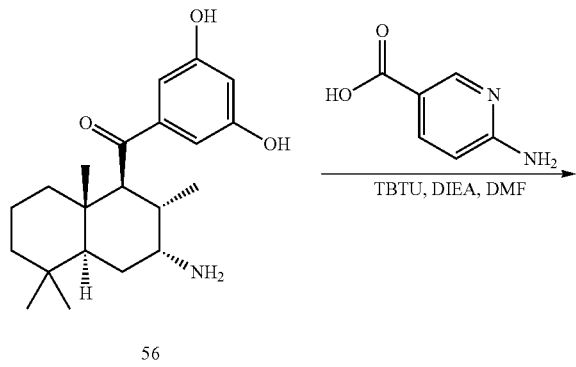

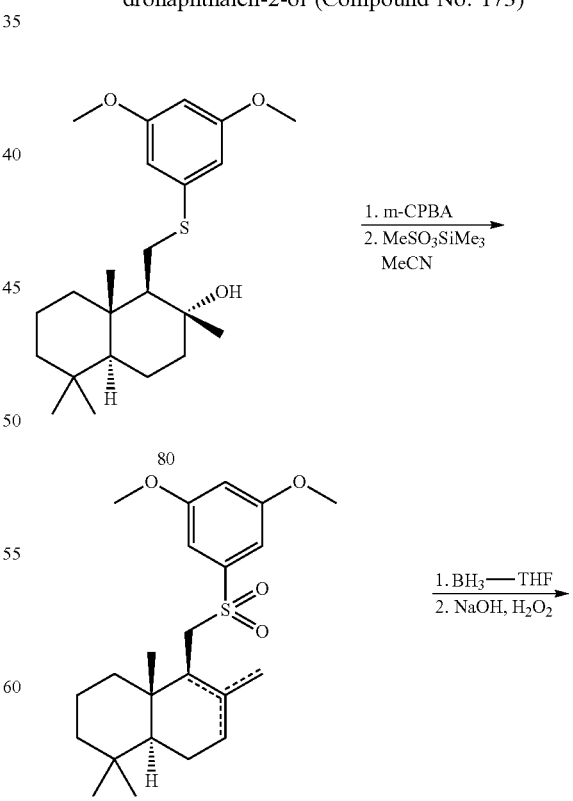

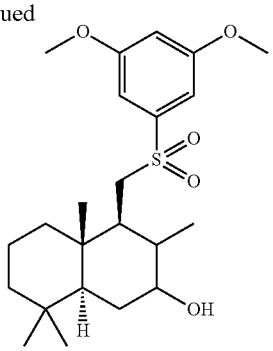

173

A. A solution of (1R,2R,4aS,8aS)-1-{[(3,5-dimethoxyphenyl)-sulfanyl]methyl}-2,5,5,8a-tetramethyl-decahydronaphthalen-2-ol (Compound No. 80, 40 mg, 0.1 mmol) and m-chloroperoxybenzoic acid (77%, 53 mg, 0.24 mmol) in $CH_2Cl_2$ (3 mL) under argon was stirred at room temperature for 4 h. The mixture was concentrated, diluted with saturated aqueous $NaHCO_3$ (15 mL) and EtOAc (15 mL). The organic layer was washed with brine (1×15 mL), dried ($Na_2SO_4$), concentrated and purified by silica gel chromatography (hexanes:EtOAc, 3:1 to 1:1) to afford (1R,2R,4aS,8aS)-1-{[(3,5-dimethoxybenzene)sulfonyl]methyl}-2,5,5,8a-tetramethyl-decahydronaphthalen-2-ol as a red solid (29 mg, 67%).

B. To a solution of (1R,2R,4aS,8aS)-1-{[(3,5-dimethoxybenzene)sulfonyl]methyl}-2,5,5,8a-tetramethyl-decahydronaphthalen-2-ol from above (50 mg, 0.118 mmol) in MeCN (0.3 ml) under argon was added trimethylsilylmethanesulfonate (0.03 mL, 0.177 mmol) and the reaction mixture stirred for 24 h. The reaction mixture was diluted with water (5 mL), washed with saturated aqueous $NaHCO_3$ (5 mL), and water (5 mL), dried over $Na_2SO_4$, filtered and concentrated to afford Compound No. 172 as a mixture of double bond isomers (46 mg, 96%, ~1:1) as a red oil.

C. To the reaction mixture containing Compound No. 172 (46 mg, 0.113 mmol) in THF (1 mL) under argon at 0° C. was slowly added $BH_3$.THF (1.0 M, 0.2 mL, 0.170 mmol) and stirred for 15 min. The reaction mixture was then warmed to room temperature and stirred for another 90 min. The mixture was cooled to 0° C. and aqueous NaOH (10 M, 0.1 mL, 0.226 mmol) was carefully added, followed by the addition of $H_2O_2$(50% wt, 0.02 mL, 0.339 mmol), and stirred for 45 min. The reaction was allowed to warm to room temperature and was stirred for 24 h after which water (5 mL) and solid $Na_2SO_3$ (excess) were added. The resultant mixture was extracted using EtOAc (5 mL), then washed with brine (5 mL), dried over $Na_2SO_4$, filtered and concentrated under vacuum. The crude product was then purified using column chromatography (hexanes:EtOAc, 4:1 to 3:1 to 2:1 to 1:1 to 1:2) to afford (4S,4aS,8aS)-4-{[(3,5-dimethoxybenzene)sulfonyl]methyl}-3,4a,8,8-tetramethyl-decahydronaphthalen-2-ol as a colourless oil (Compound No. 173, 11 mg, 23%). $^1$H NMR ($CDCl_3$): δ7.05 (s, 1H), 6.70 (s, 1H), 3.90 (s, 6H), 3.10 (m, 2H), 2.30 (d, 1H), 1.75-1.45 (m, 6H), 1.44 (s, 3H), 1.42-1.02 (m, 4H), 0.98 (s, 3H), 0.89 (s, 3H), 0.85 (s, 3H). ES-MS m/z 442.3 ([M+18]$^+$).

EXAMPLE 98

Synthesis of 1-[(2R,3S,4S,4aS,8aS)-4-[(3-hydroxy-5-methylphenyl)carbonyl]-3,4a,8,8-tetramethyl-decahydronaphthalen-2-yl]guanidine (Compound No. 175)

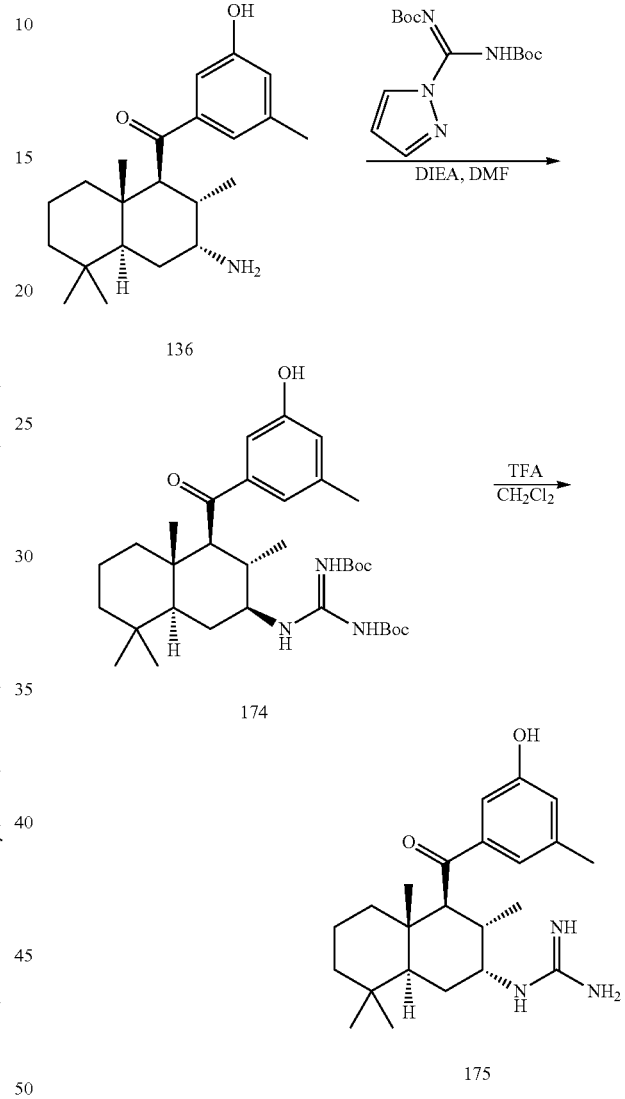

A. A solution of 3-{[(1S,2S,3R,4aS,8aS)-3-amino-2,5,5,8a-tetramethyl-decahydronaphthalen-1-yl]carbonyl}-5-methylphenol (Compound No. 136, 60 mg, 0.17 mmol), N,N'-bis(tert-butoxycarbonyl)-1H-pyrazole-1-carboxamidine (65 mg, 0.21 mmol), and N,N-diisopropylethylamine (0.035 mL, 0.20 mmol) in DMF (0.25 mL) under argon was stirred at room temperature for 18 h then concentrated. The residue was dissolved in EtOAc (30 mL) and washed with $H_2O$ (10 mL), saturated aqueous $NaHCO_3$ (4×10 mL) and brine (10 mL) then dried ($MgSO_4$) and concentrated. The residue was purified by chromatography on silica gel ($MeOH/CH_2Cl_2$, 1:99) to give tert-butyl N-[(1Z)-{[(2R,3S, 4S,4aS,8aS)-4-[(3-hydroxy-5-methylphenyl)carbonyl]-3,4a, 8,8-tetramethyl-decahydronaphthalen-2-yl]amino}({[(tert-butoxy)carbonyl]imino})methyl]carbamate as a colourless solid (Compound No. 174, 86 mg, 84%).

B. To a suspension of tert-butyl N-[(1Z)-{[(2R,3S,4S,4aS,8aS)-4-[(3-hydroxy-5-methylphenyl)carbonyl]-3,4a,8,8-tetramethyl-decahydronaphthalen-2-yl]amino}({[(tert-butoxy)carbonyl]imino})methyl]carbamate (Compound No. 174, 85 mg, 0.15 mmol) in $CH_2Cl_2$ (1.5 mL) was added trifluoroacetic acid (0.75 mL, 10 mmol) under argon at room temperature. The resulting homogeneous solution was stirred at room temperature for 2 h then concentrated, and the residue was partitioned between EtOAc (40 mL) and saturated aqueous $NaHCO_3$ (10 mL). The aqueous phase was extracted with EtOAc (2×10 mL), and the organic layers were combined, dried ($MgSO_4$) and concentrated. The residue was purified by chromatography on silica gel ($CH_2Cl_2$/MeOH/$NH_4OH$, 100:10:1), giving a green solid (53 mg). The solid was suspended in 10% aqueous HCl and ether, then filtered and washed with ether. The solid was dissolved in MeOH and concentrated. The residue was diluted with EtOAc (12 mL) and washed with saturated aqueous $NaHCO_3$ (10 mL). The aqueous layer was extracted with EtOAc (5 mL), and the organic layers were combined, dried ($MgSO_4$) and concentrated to afford 1-[(2R,3S,4S,4aS,8aS)-4-[(3-hydroxy-5-methylphenyl)carbonyl]-3,4a,8,8-tetramethyl-decahydronaphthalen-2-yl]guanidine as a colourless solid (Compound No. 175, 34 mg, 61%). $^1$H NMR ($CD_3OD$): δ7.66 (s, 1H), 7.22 (s, 1H), 6.82 (s, 1H), 3.81 (m, 1H), 3.58 (d, J=12.1 Hz, 1H), 2.45 (m, 1H), 2.33 (s, 3H), 1.82-1.21 (m, 8H), 1.01 (m, 4H), 0.86 (s, 6H), 0.80 (d, J=6.7 Hz, 3H). ES-MS m/z 386 ([M+1]$^+$).

EXAMPLE 99

Synthesis of N-[(2R,3S,4S,4aS,8aS)-4-[(3-hydroxy-5-methylphenyl)carbonyl]-3,4a,8,8-tetramethyl-decahydronaphthalen-2-yl]methanesulfonamide (Compound No. 176)

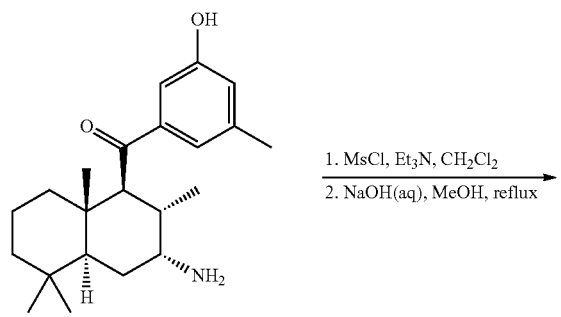

A. To a solution of 3-{[(1S,2S,3R,4aS,8aS)-3-amino-2,5,5,8a-tetramethyl-decahydronaphthalen-1-yl]carbonyl}-5-methylphenol (Compound No. 136, 73 mg, 0.21 mmol) and $Et_3N$ (0.070 mL, 0.50 mmol) in $CH_2Cl_2$ (2.1 mL) under argon was added methanesulfonyl chloride (0.035 mL, 0.45 mmol) at 0° C. The solution was stirred for 30 min at 0° C. then at room temperature for 21 h. The solution was concentrated, and the residue was dissolved in EtOAc (40 mL) then washed with saturated aqueous $NaHCO_3$ (3×10 mL) and brine (10 mL). The organic phase was dried ($MgSO_4$) and concentrated, and the residue was purified by chromatography on silica gel (MeOH/$CH_2Cl_2$, 1:99-$CH_2Cl_2$/MeOH/$NH_4OH$, 100:10:0.6) to give 3-{[(1S,2S,3R,4aS,8aS)-3-methanesulfonamido-2,5,5,8a-tetramethyl-decahydronaphthalen-1-yl]carbonyl}-5-methylphenyl methanesulfonate as a colourless film (42 mg, 40%).

B. A solution of 3-{[(1S,2S,3R,4aS,8aS)-3-methanesulfonamido-2,5,5,8a-tetramethyl-decahydronaphthalen-1-yl]carbonyl}-5-methylphenyl methanesulfonate (42 mg, 0.084 mmol) and sodium hydroxide (25 mg, 0.63 mmol) in 10:1 MeOH/$H_2O$ (4.4 mL) was heated to reflux for 20 h. The solution was concentrated, and the residue was partitioned between 10% MeOH/$CH_2Cl_2$ (40 mL) and $H_2O$ (10 mL). The aqueous layer was adjusted to pH 8 with 10% aqueous HCl and extracted with 10% MeOH/$CH_2Cl_2$ (2×10 mL). The organic layers were combined, dried ($MgSO_4$) and concentrated. The residue was purified by chromatography on silica gel (EtOAc/hexanes, 1:4-3:2) to give N-[(2R,3S,4S,4aS,8aS)-4-[(3-hydroxy-5-methylphenyl)carbonyl]-3,4a,8,8-tetramethyl-decahydronaphthalen-2-yl]methanesulfonamide as a light yellow solid (Compound No. 176, 33 mg, 94%). $^1$H NMR ($CD_3OD$): δ7.38 (s, 1H), 7.16 (s, 1H), 6.85 (s, 1H), 3.74 (m, 1H), 3.39 (d, J=12.0 Hz, 1H), 2.97 (s, 3H), 2.37 (m, 4H), 1.90-1.15 (m, 8H), 1.02 (m, 4H), 0.92 (s, 3H), 0.87 (s, 3H), 0.79 (d, J=6.6 Hz, 3H). ES-MS m/z 422 ([M+1]$^+$).

EXAMPLE 100

Synthesis of 1-[(2R,3S,4S,4aS,8aS)-4-[(3,5-dihydroxyphenyl)carbonyl]-3,4a,8,8-tetramethyl-decahydronaphthalen-2-yl]guanidine (Compound No. 178)

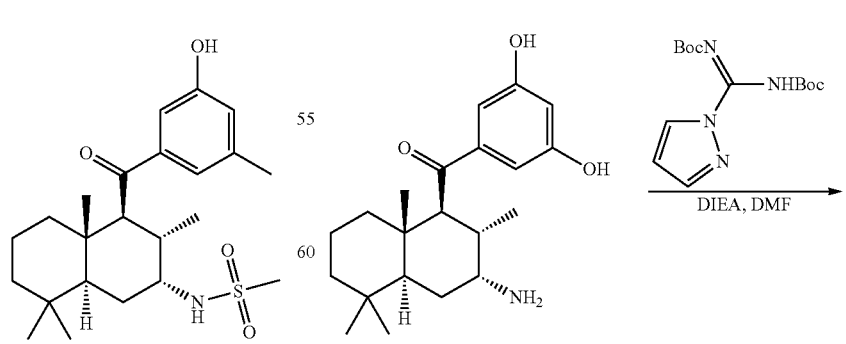

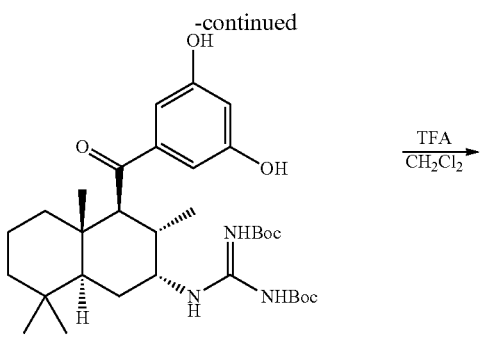

177

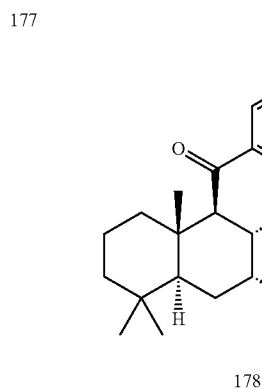

178

144.2, 108.4, 107.8 (2C), 58.3, 54.1, 48.9, 42.7, 42.3, 40.2, 34.0, 33.9, 33.7, 28.4, 22.1, 19.4, 16.5, 13.9. ES-MS m/z 388 ([M+1]+).

EXAMPLE 101

Synthesis of N-[(2R,3S,4S,4aS,8aS)-4-[(3,5-dihydroxyphenyl)carbonyl]-3,4a,8,8-tetramethyl-decahydronaphthalen-2-yl]methanesulfonamide (Compound No. 179)

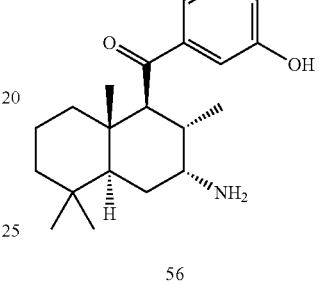

56

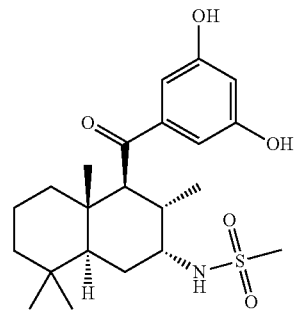

179

A. A solution of 5-{[(1S,2S,3R,4aS,8aS)-3-amino-2,5,5,8a-tetramethyl-decahydronaphthalen-1-yl]carbonyl}benzene-1,3-diol (Compound No. 56, 148 mg, 0.428 mmol), N,N'-bis(tert-butoxycarbonyl)-1H-pyrazole-1-carboxamidine (162 mg, 0.522 mmol), and N,N-diisopropylethylamine (0.09 mL, 0.5 mmol) in DMF (1.1 mL) under argon was stirred at room temperature for 19 h then concentrated. The residue was dissolved in EtOAc (30 mL) and washed with H₂O (10 mL), saturated aqueous NaHCO₃ (2×10 mL) and brine (5×10 mL) then dried (MgSO₄) and concentrated. The residue was purified by chromatography on silica gel (MeOH/CH₂Cl₂, 1:99) to give tert-butyl N-[(1Z)-{[(2R,3S,4S,4aS,8aS)-4-[(3,5-dihydroxyphenyl)carbonyl]-3,4a,8,8-tetramethyl-decahydronaphthalen-2-yl]amino}({[(tert-butoxy)carbonyl]imino})methyl]carbamate as a colourless solid (Compound No. 177, 179 mg, 71%).

B. To a suspension of tert-butyl N-[(1Z)-{[(2R,3S,4S,4aS,8aS)-4-[(3,5-dihydroxyphenyl)carbonyl]-3,4a,8,8-tetramethyl-decahydronaphthalen-2-yl]amino}({[(tert-butoxy)carbonyl]imino})methyl]carbamate (Compound No. 177, 179 mg, 0.305 mmol) in CH₂Cl₂ (3.2 mL) was added trifluoroacetic acid (1.59 mL) under argon at room temperature. The resulting homogeneous solution was stirred at room temperature for 1.5 h then concentrated. After azeotropic distillation using CH₂Cl₂ (2×5 mL), the residue was partitioned between 10% MeOH/CH₂Cl₂ (40 mL) and saturated aqueous NaHCO₃ (20 mL). The aqueous phase was extracted with 10% MeOH/EtOAc (4×15 mL), and the organic layers were combined, dried (MgSO₄) and concentrated to afford 1-[(2R,3S,4S,4aS,8aS)-4-[(3,5-dihydroxyphenyl)carbonyl]-3,4a,8,8-tetramethyl-decahydronaphthalen-2-yl]guanidine as a colourless solid (Compound No. 178, 115 mg, 97%). ¹H NMR (CD₃OD): δ6.91 (d, J=2.1 Hz, 2H), 6.51 (t, J=2.3 Hz, 1H), 3.84 (m, 1H), 3.31 (m, 1H), 2.47 (m, 1H), 1.74 (m, 2H), 1.56-1.09 (m, 7H), 1.04 (s, 3H), 0.88 (s, 6H), 0.77 (d, J=6.6 Hz, 3H). ¹³C NMR (CD₃OD): δ205.3, 160.2 (2C), 158.6, A. To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 118 mg, 0.342 mmol) and Et₃N (0.16 mL, 1.1 mmol) in CH₂Cl₂ (3.4 mL) under argon was added methanesulfonyl chloride (0.08 mL, 1 mmol) at 0° C. The solution was stirred for 17 h at room temperature then concentrated. The residue was dissolved in EtOAc (40 mL) and washed with saturated aqueous NaHCO₃ (5×10 mL) and brine (10 mL) then dried (MgSO₄) and concentrated to give a brown oil (169 mg).

B. To a solution of the brown oil from above (169 mg) in MeOH (5.8 mL) was added 10 N NaOH (0.29 mL, 2.9 mmol), and the solution was heated to reflux for 72 h then concentrated. The residue was partitioned between 10% MeOH/CH₂Cl₂ (40 mL) and H₂O (10 mL), and the aqueous layer was adjusted to pH 9 with 10% aqueous HCl. The aqueous layer was extracted with 10% MeOH/CH₂Cl₂ (3×10 mL), and the organic layers were combined, dried (MgSO₄) and concentrated. The residue was purified by chromatography on silica gel (MeOH/CH₂Cl₂, 1:19) to give N-[(2R,3S,4S,4aS,8aS)-4-[(3,5-dihydroxyphenyl)carbonyl]-3,4a,8,8-tetramethyl-decahydronaphthalen-2-yl]methanesulfonamide as a colourless solid (Compound No. 179, 23 mg, 16% over 2 steps). ¹H NMR (CD₃OD): δ6.90 (d, J=1.9 Hz, 2H), 6.48 (m, 1H), 3.73 (m, 1H), 3.30 (m, 1H), 2.97 (s, 3H), 2.35 (m, 1H), 1.85 (m, 1H), 1.71 (m, 1H), 1.59-1.19 (m, 6H), 1.05 (m, 1H), 1.03 (s, 3H), 0.91 (s, 3H), 0.86 (s, 3H), 0.79 (d, J=6.6 Hz, 3H). $^{13}$C NMR (CD$_3$OD): δ206.1, 159.8 (2C), 144.5, 108.0, 107.9 (2C), 58.6, 56.3, 48.1, 42.9, 42.1 (2C), 40.2, 34.7, 33.8 (2C), 30.0, 22.2, 19.5, 17.1, 14.0. ES-MS m/z 424 ([M+1]$^+$).

EXAMPLE 102

Synthesis of 1-[(2R,3S,4S,4aS,8aS)-4-[(3,5-dihydroxyphenyl)carbonyl]-3,4a,8,8-tetramethyl-decahydronaphthalen-2-yl]-3-methylthiourea (Compound No. 180)

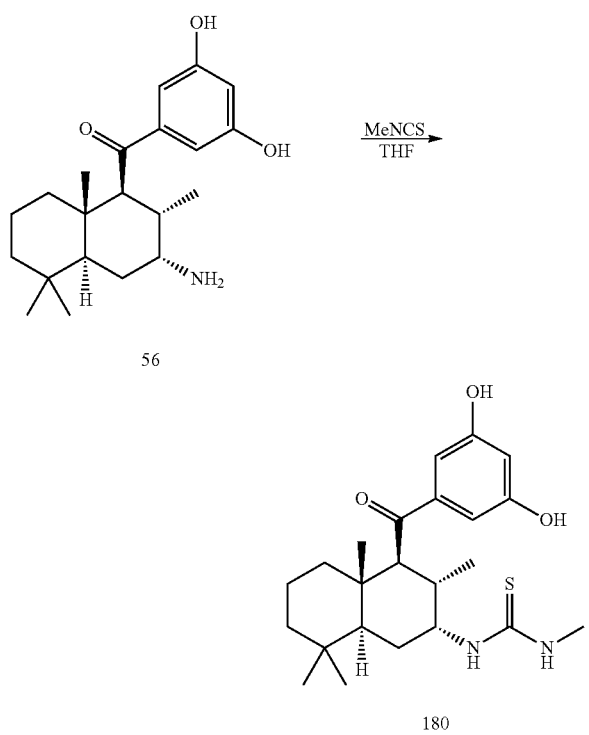

To a solution of 5-{[(1S,2S,3R,4aS,8aS)-3-amino-2,5,5,8a-tetramethyl-decahydronaphthalen-1-yl]carbonyl}benzene-1,3-diol (Compound No. 56, 54 mg, 0.16 mmol) in THF (1.0 mL) was added methyl isothiocyanate (24 mg, 0.33 mmol) under argon. The solution was stirred at room temperature for 66 h then concentrated. The residue was purified by chromatography on silica gel (CH$_2$Cl$_2$/MeOH/NH$_4$OH, 100:10:2) to give 1-[(2R,3S,4S,4aS,8aS)-4-[(3,5-dihydroxyphenyl)carbonyl]-3,4a,8,8-tetramethyl-decahydronaphthalen-2-yl]-3-methylthiourea as a colourless solid (Compound No. 180, 46 mg, 71%). $^1$H NMR (CD$_3$OD): δ6.89 (m, 2H), 6.50 (s, 1H), 4.60 (br s, 1H), 3.29 (m, 1H), 3.04 (s, 3H), 2.41 (m, 1H), 1.87 (m, 1H), 1.68-1.04 (m, 11H), 0.86 (s, 3H), 0.84 (s, 3H), 0.73 (d, J=6.6 Hz, 3H). $^{13}$C NMR (CD$_3$OD): δ205.9, 184.5, 159.8 (2C), 144.5, 108.1, 107.7 (2C), 59.4, 55.3, 49.3, 42.9, 42.4, 40.3, 34.4, 33.9 (2C), 31.6, 28.3, 22.1, 19.5, 16.6, 14.0. ES-MS m/z 419 ([M+1]$^+$).

EXAMPLE 103

Synthesis of 2-[({[(2R,3S,4S,4aS,8aS)-4-[(3,5-dihydroxyphenyl)carbonyl]-3,4a,8,8-tetramethyl-decahydronaphthalen-2-yl]carbamoyl}methyl)sulfamoyl]benzoic acid (Compound No. 181)

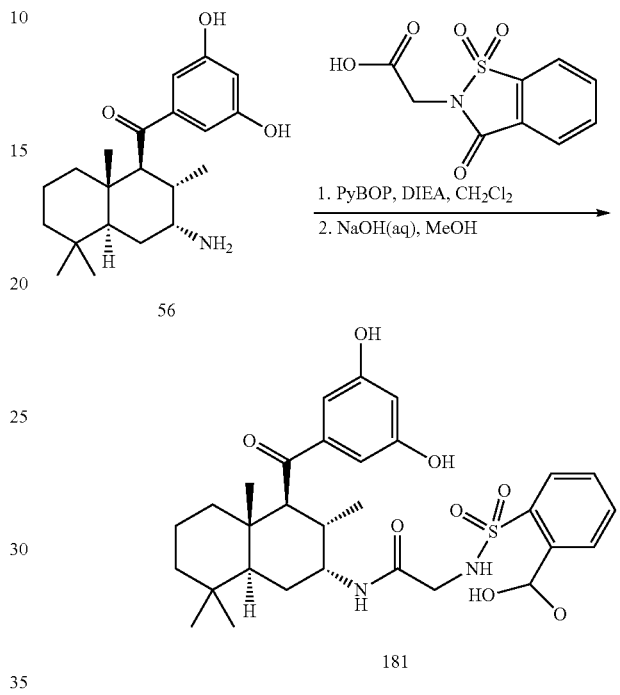

A. A solution of 5-{[(1S,2S,3R,4aS,8aS)-3-amino-2,5,5,8a-tetramethyl-decahydronaphthalen-1-yl]carbonyl}benzene-1,3-diol (Compound No. 56, 143 mg, 0.414 mmol), 2-(1,1,3-trioxo-2,3-dihydro-1λ$^6$,2-benzothiazol-2-yl)acetic acid (120 mg, 0.497), (benzotriazol-1-yloxy)tripyrrolidinophosphonium hexafluorophosphate (237 mg, 0.455 mmol) and N,N-diisopropylethylamine (0.22 mL, 1.3 mmol) in CH$_2$Cl$_2$ (2.8 mL) under argon was stirred at room temperature for 42 h then concentrated. The residue was partitioned between EtOAc (40 mL) and saturated aqueous NaHCO$_3$ (10 mL). The organic layer was washed with saturated aqueous NaHCO$_3$ (3×10 mL) and brine (10 mL) then dried (MgSO$_4$) and concentrated. The residue was partially purified by chromatography on silica gel (CH$_2$Cl$_2$/MeOH/NH$_4$OH, 100:10:1) then filtered through silica gel (acetone/CH$_2$Cl$_2$, 1:4) to give a colourless film (137 mg).

B. The colourless film from above (137 mg) was dissolved in 1 N NaOH (2 mL) and stirred at room temperature for 1 h. The solution was diluted with MeOH (1 mL) and stirred at room temperature for 1.2 h then adjusted to pH 2 with concentrated HCl. The mixture was diluted with EtOAc (40 mL) and H$_2$O (10 mL), and the organic layer was washed with brine (2×10 mL) then dried (MgSO$_4$) and concentrated to give 2-[({[(2R,3S,4S,4aS,8aS)-4-[(3,5-dihydroxyphenyl)carbonyl]-3,4a,8,8-tetramethyl-decahydronaphthalen-2-yl]carbamoyl}methyl)sulfamoyl]benzoic acid as a colourless solid (Compound No. 181, 134 mg, 55% over 2 steps). $^1$H NMR (DMSO-d$_6$): δ9.58 (s, 2H), 8.07 (d, J=9.6 Hz, 1H), 7.92 (m, 1H), 7.78 (m, 1H), 7.67 (m, 2H), 7.20 (m, 1H), 6.83 (d, J=1.5 Hz, 2H), 6.47 (t, J=2.1 Hz, 1H), 4.00 (m, 1H), 3.70 (m, 2H), 3.31 (m, 1H), 2.14 (m, 1H), 1.56-1.06 (m, 8H), 0.89 (m, 4H), 0.74 (s, 3H), 0.72 (s, 3H), 0.39 (d, J=6.6 Hz, 3H). $^{13}$C NMR (CD$_3$OD): δ205.9, 170.2 (2C), 159.8 (2C), 144.4, 139.3, 134.0, 133.3, 132.5, 132.0, 130.5, 108.0, 107.9 (2C), 58.9, 51.2, 46.7, 42.8, 42.3, 40.2, 34.0, 33.9, 33.8, 28.4, 22.1, 19.5, 16.5, 13.9. ES-MS m/z 585 ([M−1]$^-$).
EXAMPLE 104
Synthesis of N-((2R,3S,4S,4aS)-3,4a,8,8-tetramethyl-4-((4-(trifluoromethyl)benzamido)methyl)-decahydronaphthalen-2-yl) nicotinamide (Compound No. 196)
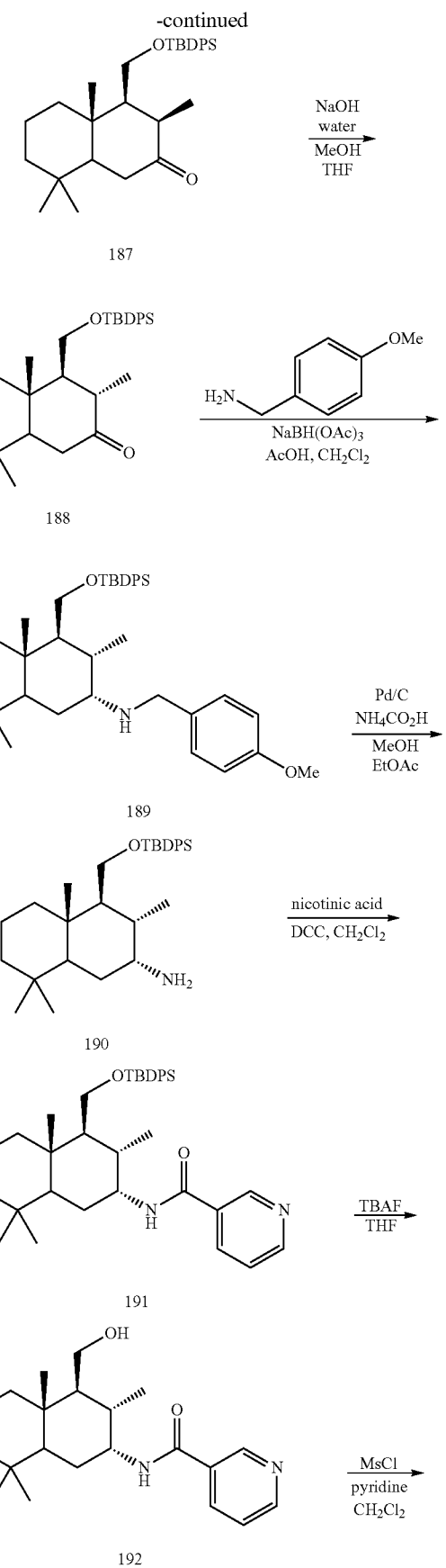

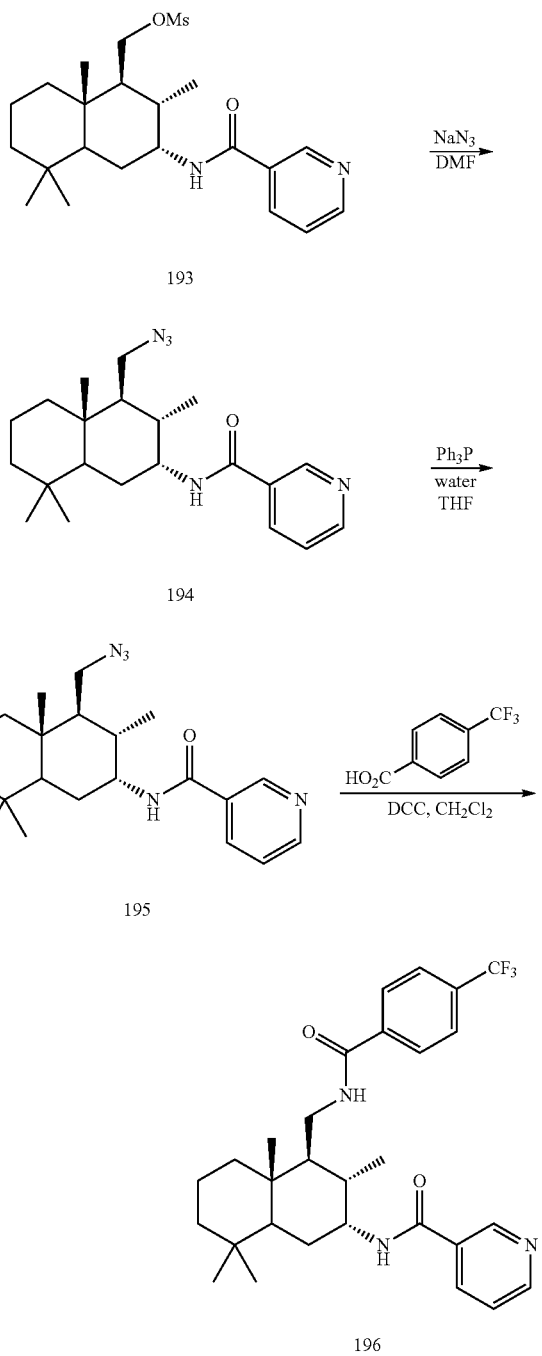

A. To a solution of Compound No. 39 (3.85 g, 16.2 mmol) in CH$_2$Cl$_2$ (75 mL) at 0° C. under argon was added SnCl$_4$ (3.8 mL, 32.3 mmol) and the reaction stirred at 0° C. for 1 hour then at room temperature for 2 hours. The mixture was cooled to 0° C. and diluted with water (25 mL) then was stirred vigorously for 30 minutes while warming to room temperature. To the mixture was added brine (25 mL) then the layers were separated. The aqueous layer was further extracted with CH$_2$Cl$_2$ (2×75 mL) and the combined organic extracts dried (MgSO$_4$) and concentrated to a green oil.

B. To solution of the above crude green oil (Compound No. 183, 3.56 g, 16.2 mmol) in MeOH (75 mL) at 0° C. under argon was added NaBH$_4$ (625 mg, 16.2 mmol) and the reaction was allowed to warm to room temperature while stirring for 3 days. The reaction was cooled to 0° C. then was added saturated NaHCO$_3$ solution (10 mL). The mixture was concentrated to remove most of the MeOH. The residue was taken up in EtOAc (300 mL) and washed with half-saturated NaCl solution (3×30 mL), dried (MgSO$_4$) and concentrated to a yellow oil.

C. To a solution of the above crude yellow oil (Compound No. 184, 3.59 g, 16.2 mmol) and imidazole (4.4 g, 64.8 mmol) in DMF (40 mL) at 0° C. under argon was added TBDPSCl (8.3 mL, 32.4 mmol) and the reaction was allowed to warm to room temperature while stirring for 18 hours. The mixture was diluted with Et$_2$O (300 mL) and washed with half-saturated NaCl solution (3×30 mL), dried (MgSO$_4$) and concentrated. The resulting yellow oil was filtered through a silica gel plug, eluting with 10% EtOAc/Hexanes (300 mL) and concentrated to a yellow oil.

D. To a solution of the above yellow oil (Compound No. 185, 7.44 g, 16.2 mmol) in THF (40 mL) at 0° C. under argon was added BH$_3$-THF (1.0 M in THF, 48.6 mL, 48.6 mmol) and the reaction was allowed to warm to room temperature while stirring for 20 hours. The mixture was cooled to 0° C. then water (25 mL) was slowly added followed by NaBO$_3$.4H$_2$O (7.5 g). The mixture was stirred at room temperature for 30 minutes then heated at reflux for 2.5 hours. The mixture was cooled to room temperature and was concentrated to remove most of the THF. The residue was taken up in EtOAc (300 mL) and washed with half-saturated NaCl solution (6×30 mL), dried (MgSO$_4$) and concentrated to a colourless oil.

E. A solution of the above colourless oil (Compound No. 186, 7.90 g, 16.2 mmol) and IBX (9.07 g, 32.4 mmol) in MeCN (100 mL) under argon was heated at 75° C. for 3.5 hours. The mixture was cooled to room temperature then was filtered through a silica gel plug eluting with 30% EtOAc/Hexanes (300 mL) and concentrated. The crude product was purified by flash chromatography on silica gel (5% EtOAc/hexanes) to afford Compound No. 187 (3.95 g, 51%) as a colourless oil.

F. A solution of Compound No. 187 (3.95 g, 8.28 mmol) and NaOH (2 M in water, 4.1 mL, 8.3 mmol) in MeOH (28 mL) and THF (14 mL) was heated at reflux for 1.5 hours. The mixture was cooled to 0° C. then diluted with saturated NaHCO$_3$ solution (40 mL) and concentrated to remove most of the MeOH and THF. The residue was taken up in EtOAc (350 mL), washed with half-saturated NaCl solution (3×30 mL), dried (MgSO$_4$) and concentrated to afford Compound No. 188 (3.86 g, 98%) as slightly yellow oil.

G. A mixture of Compound No. 188 (3.86 g, 8.10 mmol), 4-methoxybenzylamine (3.20 mL, 24.3 mmol), sodium triacetoxyborohydride (15.5 mg, 72.9 mmol), and AcOH (1.4 mL, 24 mmol) in CH$_2$Cl$_2$ (100 mL) under argon was stirred at room temperature for 17 hours. The mixture was cooled to 0° C. then was added saturated NaHCO$_3$ solution (120 mL). After stirring 15 minutes at 0° C. and 45 minutes at room temperature the mixture was extracted with EtOAc (300 mL). The organic extract was washed with half-saturated NaCl solution (3×30 mL), dried (MgSO$_4$) and concentrated. The residue was purified by chromatography on silica gel (EtOAc/hexanes, 1:9) to afford Compound No. 189 (3.80 g, 78%) as a slightly yellow oil.

H. To a solution of Compound No. 189 (3.80 g, 6.35 mmol) and NH$_4$CO$_2$H (4.13 g, 63.5 mmol) in MeOH (100 mL) and EtOAc (12 mL) flushed thoroughly with Argon was added a slurry of Pd (10% on carbon, 675 mg, 0.63 mmol) in MeOH (15 mL). The reaction was heated at reflux for 18 hours then was cooled to room temperature. The mixture was filtered through a Celite pad eluting with EtOAc (200 mL) then was concentrated. The residue was taken up in 0.5 M aqueous NaOH solution (300 mL) and extracted with $CH_2Cl_2$ (3×100 mL). The combined organic extracts were dried ($MgSO_4$) and concentrated. The residue was purified by chromatography on silica gel (30% EtOAc/hexanes then 10% MeOH/EtOAc with 1% $NH_4OH$) to afford Compound No. 190 (2.44 g, 80%) as a viscous oil.

I. A mixture of Compound No. 190 (466 mg, 0.975 mmol), nicotinic acid (245 mg, 1.95 mmol) and DCC (366 mg, 1.76 mmol) in $CH_2Cl_2$ (20 mL) under argon was stirred at room temperature for 18 hours. The mixture was filtered through a silica gel plug eluting with EtOAc (150 mL) and concentrated to a white solid.

J. A mixture of crude Compound No. 191 (568 mg, 0.975 mmol) and TBAF (1.0 M in THF, 2.9 mL, 2.9 mmol) in THF (20 mL) under argon was heated at reflux for 2 hours then was cooled and concentrated. The residue was purified by chromatography on silica gel (50% then 80% EtOAc/hexanes then 10% MeOH/EtOAc) to afford Compound No. 192 (308 mg, 92%) as a white solid.

K. To a solution of Compound No. 192 (241 mg, 0.70 mmol) in pyridine (3.5 mL) and $CH_2Cl_2$ (3 mL) at 0° C. under argon was added MsCl (0.17 mL, 2.1 mmol). After 45 minutes saturated $NaHCO_3$ solution (3 mL) was added and the mixture stirred at room temperature for 30 minutes. The mixture was diluted with EtOAc (75 mL) and washed with half-saturated NaCl solution (3×15 mL), dried ($MgSO_4$) and concentrated to afford Compound No. 193 (289 mg, 97%) as a white solid.

L. A mixture of Compound No. 193 (284 mg, 0.67 mmol) and $NaN_3$ (131 mg, 2.0 mmol) in DMF (6 mL) at 60° C. under argon was stirred for 16 hours. The mixture was cooled, diluted with $Et_2O$ (75 mL), washed with half-saturated NaCl solution (3×15 mL), dried ($MgSO_4$) and concentrated. The residue was purified by chromatography on silica gel (50% then 80% EtOAc/hexanes) to afford Compound No. 194 (211 mg, 85%) as a white foam.

M. A solution of Compound No. 194 (207 mg, 0.56 mmol), triphenylphosphine (742 mg, 2.8 mmol) and water (0.05 mL, 2.8 mmol) in THF (10 mL) was stirred at room temperature for 24 hours. The mixture was concentrated and the residue was purified by chromatography on silica gel (10% MeOH/EtOAc with 1% $NH_4OH$ then 15% MeOH/EtOAc with 3% $NH_4OH$) to afford Compound No. 195 (175 mg, 91%) as a white foam.

N. A mixture of Compound No. 195 (25 mg, 0.073 mmol), 4-trifluoromethyl benzoic acid (43 mg, 0.22 mmol) and DCC (38 mg, 0.18 mmol) in $CH_2Cl_2$ (4 mL) under argon was stirred at room temperature for 18 hours. The mixture was purified by chromatography on silica gel (50% then 66% EtOAc/hexanes) to afford Compound No. 196 (41 mg, 100%) as a white solid. $^1$H NMR ($CDCl_3$): δ8.95 (m, 1H), 8.73 (m, 1H), 8.08 (m, 1H), 7.80 (m, 2H), 7.67 (m, 2H), 7.40 (m, 1H), 6.30 (m, 1H), 6.18 (m, 1H), 4.50 (m, 1H), 4.10 (m, 1H), 3.75 (m, 1H), 3.43 (m, 1H), 3.25 (m, 1H), 2.1-1.0 (12H), 0.98 (s, 3H), 0.85 (s, 3H), 0.80 (s, 3H). ES-MS m/z 516 ($[M+1]^+$).

EXAMPLE 105

Synthesis of N-((2R,3S,4S,4aS)-4-((furan-2-carboxamido)methyl)-3,4a,8,8-tetramethyldecahydronaphthalen-2-yl)nicotinamide (Compound No. 197)

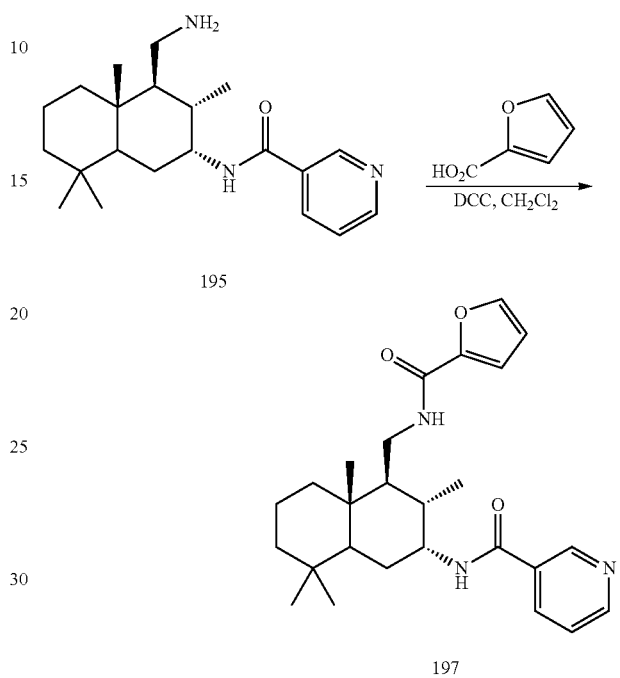

A mixture of Compound No. 195 (25 mg, 0.073 mmol), 2-furoic acid (25 mg, 0.22 mmol) and DCC (38 mg, 0.18 mmol) in $CH_2Cl_2$ (4 mL) under argon was stirred at room temperature for 18 hours. The mixture was purified by chromatography on silica gel (EtOAc) to afford Compound No. 197 (33 mg, 100%) as a white solid. $^1$H NMR ($CDCl_3$): δ8.95 (m, 1H), 8.73 (m, 1H), 8.08 (m, 1H), 7.40 (2H), 7.06 (m, 1H), 6.45 (m, 1H), 6.28 (2H), 4.50 (m, 1H), 4.05 (m, 1H), 3.75 (m, 1H), 3.45 (m, 1H), 3.19 (m, 1H), 2.1-1.0 (12H), 0.98 (s, 3H), 0.85 (s, 3H), 0.80 (s, 3H). ES-MS m/z 438 ($[M+1]^+$).

EXAMPLE 106

Synthesis of N-((2R,3S,4S,4aS)-4-(isonicotinamidomethyl)-3,4a,8,8-tetramethyldecahydronaphthalen-2-yl)nicotinamide (Compound No. 198)

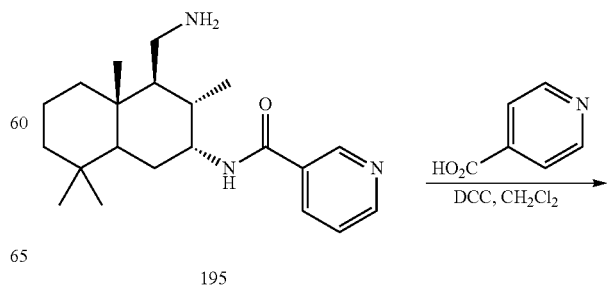

-continued

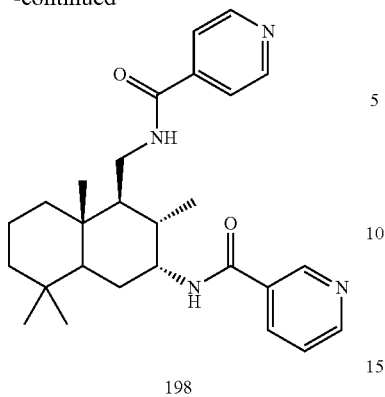

198

A mixture of Compound No. 195 (25 mg, 0.073 mmol), isonicotinic acid (27 mg, 0.22 mmol) and DCC (38 mg, 0.18 mmol) in CH$_2$Cl$_2$ (4 mL) under argon was stirred at room temperature for 18 hours. The mixture was purified by chromatography on silica gel (EtOAc then 10% MeOH/EtOAc) to afford Compound No. 198 (31 mg, 94%) as a white solid. $^1$H NMR (CDCl$_3$): δ8.95 (m, 1H), 8.73 (3H), 8.08 (m, 1H), 7.55 (2H), 7.40 (m, 1H), 6.23 (m, 1H), 6.10 (m, 1H), 4.50 (m, 1H), 3.78 (m, 1H), 3.5 (m, 1H), 3.25 (m, 1H), 2.1-1.4 (5H), 1.3-1.0 (6H), 0.98 (s, 3H), 0.85 (s, 3H), 0.80 (s, 3H). ES-MS m/z 449 ([M+1]$^+$).

EXAMPLE 107

Synthesis of N-((((1S,2S,3R,8aS)-2,5,5,8a-tetramethyl-3-(nicotinamido)decahydronaphthalen-1-yl)methyl)nicotinamide (Compound No. 199)

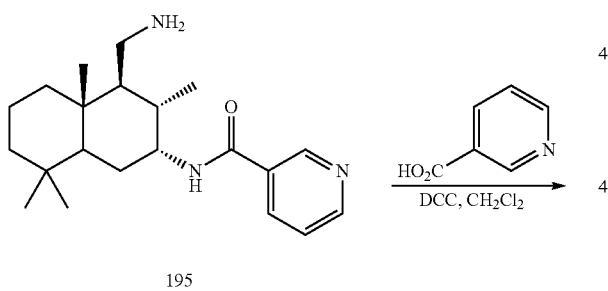

199

A mixture of Compound No. 195 (25 mg, 0.073 mmol), nicotinic acid (27 mg, 0.22 mmol) and DCC (38 mg, 0.18 mmol) in CH$_2$Cl$_2$ (5 mL) under argon was stirred at room temperature for 18 hours. The mixture was purified by chromatography on silica gel (EtOAc then 10% MeOH/EtOAc) to afford Compound No. 198 (36 mg, 100%) as a white solid. $^1$H NMR (CDCl$_3$): δ8.92 (2H), 8.70 (2H), 8.08 (2H), 7.39 (2H), 6.38 (m, 1H), 6.08 (m, 1H), 4.50 (m, 1H), 3.78 (m, 1H), 3.5 (m, 1H), 3.25 (m, 1H), 2.05 (2H), 1.90 (m, 1H), 1.8-1.4 (3H), 1.3-1.0 (6H), 0.98 (s, 3H), 0.87 (s, 3H), 0.82 (s, 3H). ES-MS m/z 449 ([M+1]$^+$).

EXAMPLE 108

Synthesis of N-((2R,3S,4S,4aS)-4-((1H-imidazol-1-yl)methyl)-3,4a,8,8-tetramethyldecahydronaphthalen-2-yl)nicotinamide (Compound No. 200)

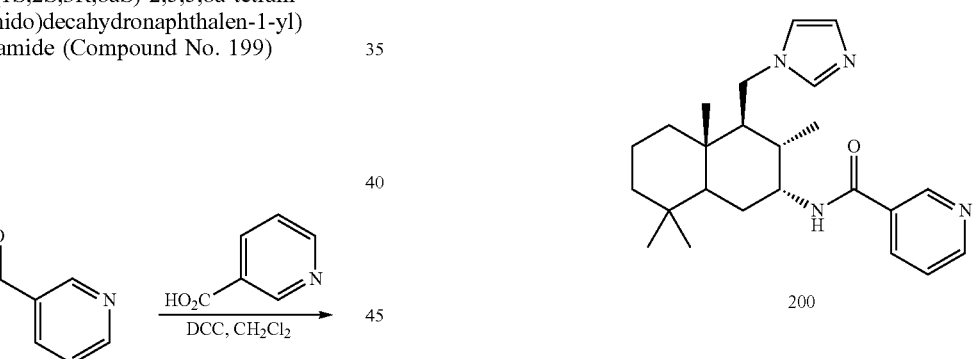

To a solution of imidazole (81 mg, 1.2 mmol) in DMF (3 mL) at 0° C. under argon was added NaH (60% in mineral oil, 48 mg, 1.2 mmol). After 1.5 hours Compound No. 193 (50 mg, 0.12 mmol) was added and the reaction was stirred at room temperature. After 17 hours the reaction was stirred at 60° C. for 4 hours then cooled to 0° C., quenched with saturated NaHCO$_3$ solution (3 mL), diluted with Et$_2$O (40 mL), washed with half-saturated NaCl solution (3×8 mL), dried (MgSO$_4$) and concentrated. The residue was purified by chromatography (50% then 100% EtOAc/hexanes then 10% then 20% MeOH/EtOAc) to afford Compound No. 200 (24 mg, 51%) as a white solid. $^1$H NMR (CDCl$_3$): δ8.85 (m, 1H), 8.62 (m, 1H), 8.00 (m, 1H), 7.33 (2H), 7.10 (m, 1H), 6.85 (2H), 4.53 (m, 1H), 4.02 (m, 1H), 3.70 (m, 1H), 2.02 (1H), 1.85 (2H), 1.8-1.4 (5H), 1.30-1.05 (3H), 1.00 (d, 3H), 0.95 (s, 3H), 0.85 (6H). ES-MS m/z 395 ([M+1]$^+$).

EXAMPLE 109

Synthesis of N-((2R,3S,4S,4aS)-4-((1H-1,2,4-triazol-1-yl)methyl)-3,4a,8,8-tetramethyldecahydronaphthalen-2-yl)nicotinamide (Compound No. 201)

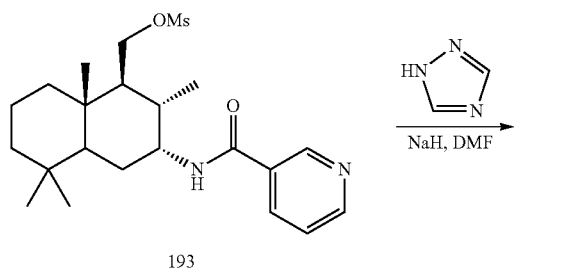

To a solution of 1,2,4-triazole (85 mg, 1.2 mmol) in DMF (3 mL) at 0° C. under argon was added NaH (60% in mineral oil, 48 mg, 1.2 mmol). After 1.5 hours Compound No. 193 (50 mg, 0.12 mmol) was added and the reaction was stirred at room temperature for 18 hours. The reaction cooled to 0° C., quenched with saturated NaHCO$_3$ solution (3 mL), diluted with Et$_2$O (40 mL), washed with half-saturated NaCl solution (3×8 mL), dried (MgSO$_4$) and concentrated. The residue was purified by chromatography (50% then 100% EtOAc/hexanes then 10% then 20% MeOH/EtOAc) to afford Compound No. 201 (37 mg, 79%) as a white solid. $^1$H NMR (CDCl$_3$): δ8.92 (m, 1H), 8.72 (m, 1H), 8.02 (2H), 7.92 (s, 1H), 7.40 (m, 1H), 6.35 (m, 1H), 4.48 (m, 1H), 4.25 (m, 1H), 3.98 (m, 1H), 2.10 (m, 1H), 1.95-1.45 (6H), 1.35-1.05 (4H), 0.98 (s, 3H), 0.90 (d, 3H), 0.85 (s, 3H), 0.80 (s, 3H). ES-MS m/z 396 ([M+1]$^+$).

EXAMPLE 110

Synthesis of N-((2R,3S,4S,4aS)-4-((1H-benzo[d]imidazol-1-yl)methyl)-3,4a,8,8-tetramethyldecahydronaphthalen-2-yl)nicotinamide (Compound No. 202)

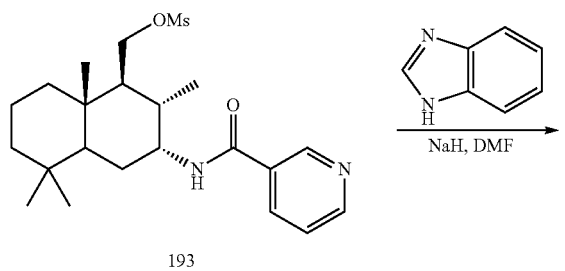

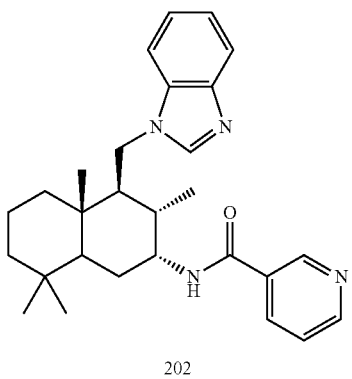

To a solution of benzimidazole (145 mg, 1.2 mmol) in DMF (3 mL) at 0° C. under argon was added NaH (60% in mineral oil, 48 mg, 1.2 mmol). After 1.5 hours Compound No. 193 (50 mg, 0.12 mmol) was added and the reaction was stirred at room temperature for 18 hours. The reaction cooled to 0° C., quenched with saturated NaHCO$_3$ solution (3 mL), diluted with Et$_2$O (40 mL), washed with half-saturated NaCl solution (3×8 mL), dried (MgSO$_4$) and concentrated. The residue was purified by chromatography (80% then 100% EtOAc/hexanes then 20% MeOH/EtOAc) to afford Compound No. 201 (34 mg, 64%) as a white solid. $^1$H NMR (CDCl$_3$): δ8.82 (m, 1H), 8.59 (m, 1H), 7.95 (m, 1H), 7.87 (s, 1H), 7.75 (m, 1H), 7.42 (m, 1H), 7.25 (3H), 6.65 (m, 1H), 4.50 (m, 1H), 4.25 (m, 1H), 3.95 (m, 1H), 2.15 (m, 1H), 1.90 (2H), 1.75 (2H), 1.60 (m, 1H), 1.50 (2H), 1.1 (3H), 1.05 (s, 3H), 0.95 (9H). ES-MS m/z 445 ([M+1]$^+$).

EXAMPLE 111

Synthesis of 4-methyl-N-((2R,3S,4S,4aS)-3,4a,8,8-tetramethyl-4-((4-(trifluoromethyl)benzamido)methyl)-decahydronaphthalen-2-yl)piperazine-1-carboxamide (Compound No. 208)

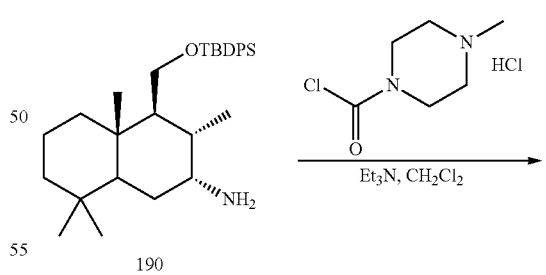

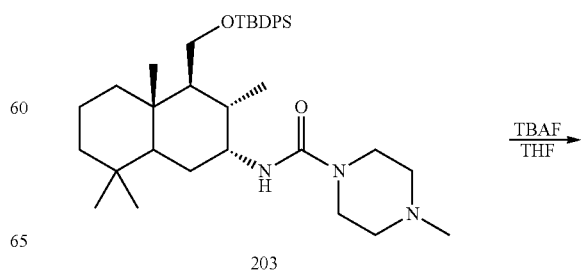

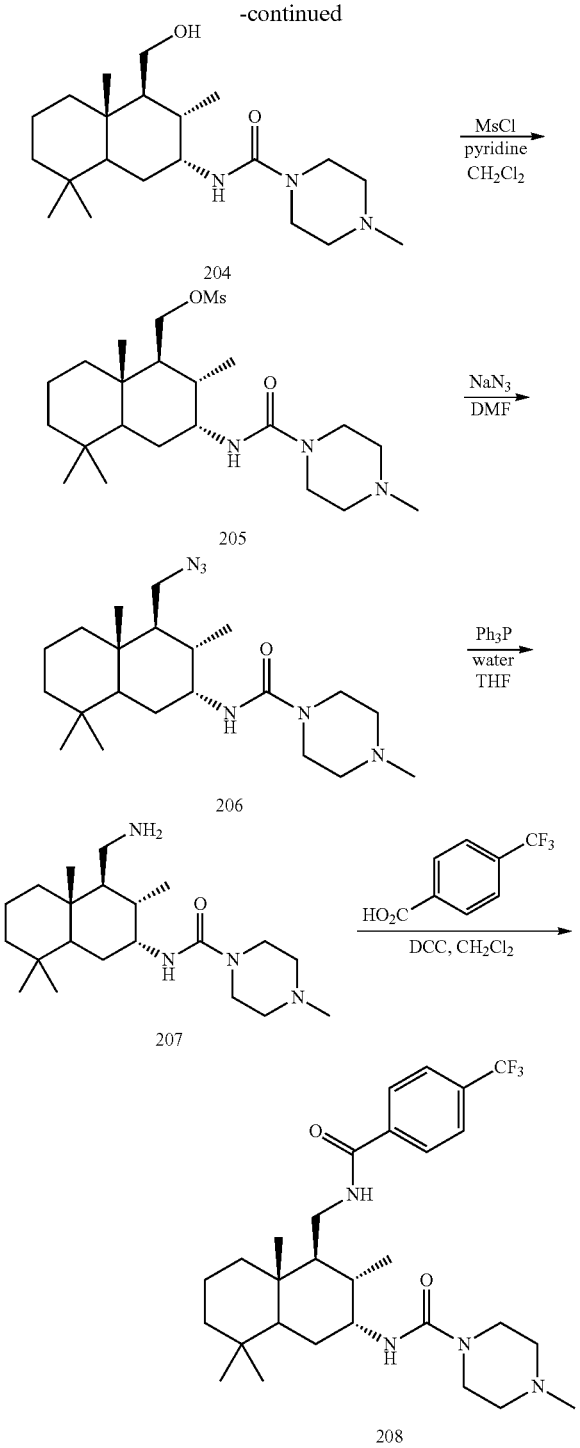

B. A mixture of crude Compound No. 203 (353 mg, 0.58 mmol) and tetrabutylammonium fluoride (TBAF) (1.0 M in THF, 1.8 mL, 1.8 mmol) in THF (10 mL) under argon was heated at reflux for 2 hours then was cooled and concentrated. The residue was purified by chromatography on silica gel (10% MeOH/EtOAc with 1% NH$_4$OH then 20% MeOH/EtOAc with 2% NH$_4$OH) to afford Compound No. 204 (215 mg, 100%) as a white solid.

C. To a solution of Compound No. 204 (211 mg, 0.58 mmol) in pyridine (3 mL) and CH$_2$Cl$_2$ (3 mL) at 0° C. under argon was added MsCl (137 μL, 1.73 mmol). After 1 hour saturated NaHCO$_3$ solution (3 mL) was added and the mixture stirred at room temperature for 30 minutes. The mixture was diluted with EtOAc (75 mL), washed with half-saturated NaCl solution (3×15 mL), dried (MgSO$_4$) and concentrated to afford Compound No. 205 (245 mg, 96%) as an orange foam.

D. A mixture of Compound No. 205 (190 mg, 0.43 mmol) and NaN$_3$ (83 mg, 1.3 mmol) in DMF (3 mL) at 50° C. under argon was stirred for 7 hours then was continued at room temperature. The mixture was diluted with Et$_2$O (75 mL), washed with half-saturated NaCl solution (3×8 mL), dried (MgSO$_4$) and concentrated. The residue was purified by chromatography on silica gel (10% MeOH/EtOAc with 1% NH$_4$OH) to afford Compound No. 206 (141 mg, 84%) as a colourless film.

E. A solution of Compound No. 206 (141 mg, 0.36 mmol), triphenylphosphine (956 mg, 3.6 mmol) and water (65 μL, 3.6 mmol) in THF (10 mL) was stirred at room temperature for 4 days. The mixture was concentrated and the residue was purified by chromatography on silica gel (40% MeOH/EtOAc with 4% NH$_4$OH) to afford Compound No. 207 (126 mg, 96%) as a white solid.

F. A mixture of Compound No. 207 (20 mg, 0.055 mmol), 4-trifluoromethyl benzoic acid (32 mg, 0.16 mmol) and DCC (29 mg, 0.14 mmol) in CH$_2$Cl$_2$ (4 mL) under argon was stirred at room temperature for 22 hours. The mixture was purified by chromatography on silica gel (5% MeOH/EtOAc with 0.5% NH$_4$OH then 10% MeOH/EtOAc with 1% NH$_4$OH) to afford Compound No. 208 (26 mg, 90%) as a white solid. $^1$H NMR (CDCl$_3$): δ7.85 (m, 2H), 7.70 (m, 2H), 6.15 (m, 1H), 4.58 (m, 1H), 4.20 (m, 1H), 3.79 (m, 1H), 3.39 (4H), 3.20 (m, 1H), 2.39 (4H), 2.30 (s, 3H), 2.05 (m, 1H), 1.95 (m, 1H), 1.8-1.4 (6H), 1.3-0.8 (15H). ES-MS m/z 537 ([M+1]$^+$).

EXAMPLE 112

Synthesis of N-((2R,3S,4S,4aS)-4-((4-fluorobenzamido)methyl)-3,4a,8,8-tetramethyldecahydronaphthalen-2-yl)-4-methylpiperazine-1-carboxamide (Compound No. 209)

A. To a solution of Compound No. 190 (1.97 g, 4.12 mmol) and Et$_3$N (2.9 mL, 20.6 mmol) in CH$_2$Cl$_2$ (20 mL) at 0° C. under argon was added 4-methyl-1-piperazinecarbonyl chloride (0.93 g, 4.54 mmol). After 10 minutes the cold bath was removed and the reaction was stirred at room temperature for 18 hours. The reaction was cooled to 0° C. and quenched with saturated NaHCO$_3$ solution (3 mL) and stirred at room temperature for 30 minutes, diluted with CH$_2$Cl$_2$ (120 mL), washed with half-saturate NaCl solution (2×20 mL), dried (MgSO$_4$) and concentrated to afford Compound No. 203 (2.59 g, 100%) as a white foam.

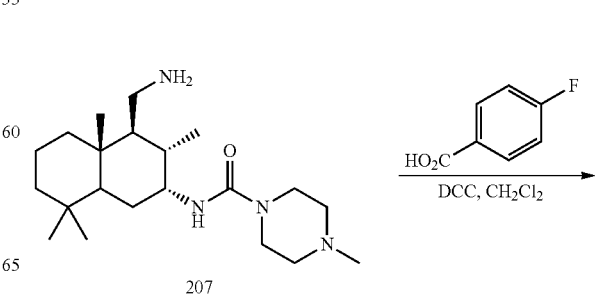

-continued

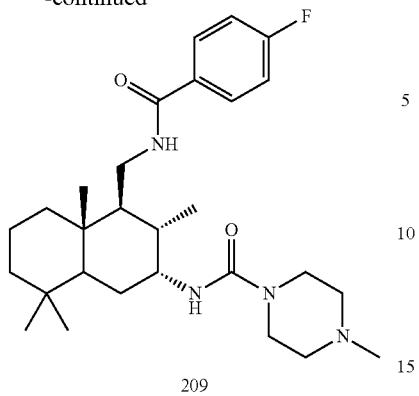

209

A mixture of Compound No. 207 (25 mg, 0.069 mmol), 4-fluorobenzoic acid (30 mg, 0.21 mmol) and DCC (36 mg, 0.17 mmol) in CH₂Cl₂ (4 mL) under argon was stirred at room temperature for 18 hours. The mixture was purified by chromatography on silica gel (5% MeOH/EtOAc with 0.5% NH₄OH then 10% MeOH/EtOAc with 1% NH₄OH) to afford Compound No. 209 (18 mg, 55%) as a white solid. $^1$H NMR (CDCl₃): δ7.75 (m, 2H), 7.10 (m, 2H), 6.05 (m, 1H), 4.59 (m, 1H), 4.20 (m, 1H), 3.78 (m, 1H), 3.39 (4H), 3.19 (m, 1H), 2.39 (4H), 2.30 (s, 3H), 2.05 (m, 1H), 1.95 (m, 1H), 1.8-1.4 (6H), 1.3-0.8 (15H). ES-MS m/z 487 ([M+1]$^+$).

EXAMPLE 113

Synthesis of N-((2R,3S,4S,4aS)-4-(isonicotinamidomethyl)-3,4a,8,8-tetramethyldecahydronaphthalen-2-yl)-4-methylpiperazine-1-carboxamide (Compound No. 210)

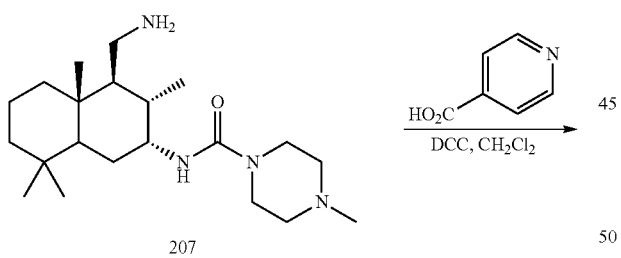

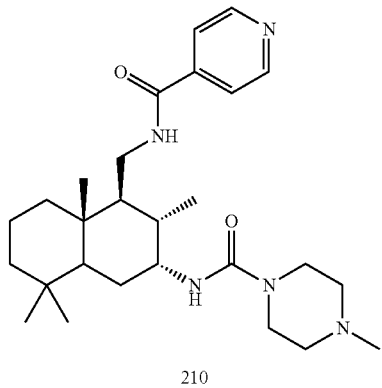

210

A mixture of Compound No. 207 (25 mg, 0.069 mmol), isonicotinic acid (30 mg, 0.21 mmol) and DCC (36 mg, 0.17 mmol) in CH₂Cl₂ (4 mL) under argon was stirred at room temperature for 18 hours. The mixture was purified by chromatography on silica gel (20% MeOH/EtOAc with 2% NH₄OH) to afford Compound No. 210 (22 mg, 69%) as a white solid. $^1$H NMR (CDCl₃): δ8.77 (m, 2H), 7.59 (m, 2H), 6.35 (m, 1H), 4.62 (m, 1H), 4.18 (m, 1H), 3.78 (m, 1H), 3.40 (4H), 3.20 (m, 1H), 2.40 (4H), 2.30 (s, 3H), 2.0 (3H), 1.8-1.4 (5H), 1.3-0.8 (15H). ES-MS m/z 470 ([M+1]$^+$).

EXAMPLE 114

Synthesis of 4-methyl-N-((2R,3S,4S,4aS)-3,4a,8,8-tetramethyl-4-(nicotinamidomethyl)decahydronaphthalen-2-yl)piperazine-1-carboxamide (Compound No. 211)

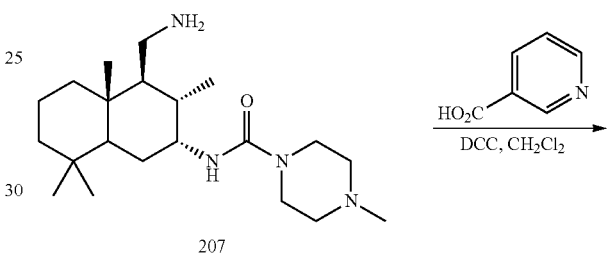

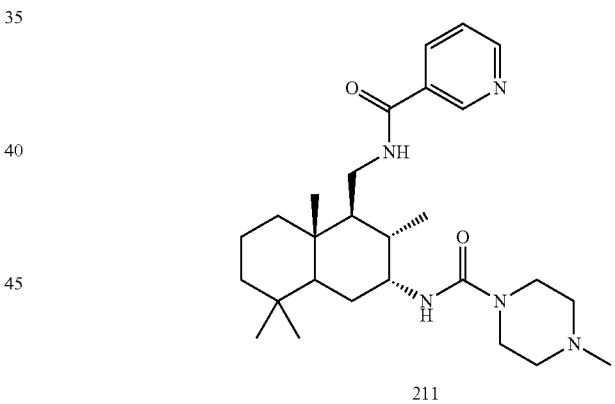

211

A mixture of Compound No. 207 (25 mg, 0.069 mmol), nicotinic acid (26 mg, 0.21 mmol) and DCC (36 mg, 0.17 mmol) in CH₂Cl₂ (4 mL) under argon was stirred at room temperature for 18 hours. The mixture was purified by chromatography on silica gel (10% MeOH/EtOAc with 1% NH₄OH then 20% MeOH/EtOAc with 2% NH₄OH) to afford Compound No. 211 (25 mg, 78%) as a white solid. $^1$H NMR (CDCl₃): δ8.99 (m, 1H), 8.72 (m, 1H), 8.15 (m, 1H), 7.40 (m, 1H), 6.40 (m, 1H), 4.72 (m, 1H), 4.18 (m, 1H), 3.78 (m, 1H), 3.42 (4H), 3.20 (m, 1H), 2.42 (4H), 2.32 (s, 3H), 2.0 (2H), 1.8-1.4 (4H), 1.3-0.8 (17H). ES-MS m/z 470 ([M+1]$^+$).

EXAMPLE 115

Synthesis of N-((2R,3S,4S,4aS)-4-((furan-2-carboxamido)methyl)-3,4a,8,8-tetramethyldecahydronaphthalen-2-yl)-4-methylpiperazine-1-carboxamide (Compound No. 212)

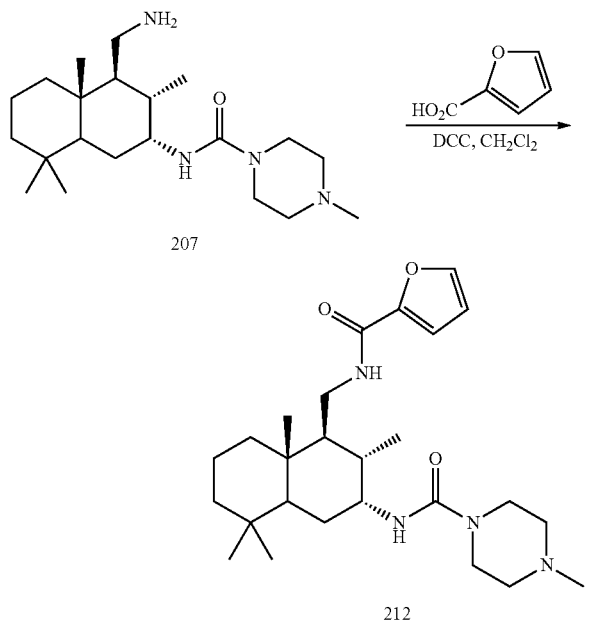

A mixture of Compound No. 207 (25 mg, 0.069 mmol), 2-furoic acid (24 mg, 0.21 mmol) and DCC (36 mg, 0.17 mmol) in CH$_2$Cl$_2$ (4 mL) under argon was stirred at room temperature for 18 hours. The mixture was purified by chromatography on silica gel (5% MeOH/EtOAc with 0.5% NH$_4$OH then 10% MeOH/EtOAc with 1% NH$_4$OH) to afford Compound No. 212 (19 mg, 61%) as a white solid. $^1$H NMR (CDCl$_3$): δ7.42 (m, 1H), 7.18 (m, 1H), 6.52 (m, 1H), 6.30 (m, 1H), 4.59 (m, 1H), 4.19 (m, 1H), 3.78 (m, 1H), 3.39 (4H), 3.15 (m, 1H), 2.40 (4H), 2.28 (s, 3H), 2.05 (m, 1H), 1.95 (m, 1H), 1.8-1.4 (4H), 1.3-0.8 (17H). ES-MS m/z 459 ([M+1]$^+$).

EXAMPLE 116

Synthesis of 4-methyl-N-((2R,3S,4S,4aR)-3,4a,8,8-tetramethyl-4-(2-(4-(trifluoromethyl)benzamido)ethyl)-decahydronaphthalen-2-yl)piperazine-1-carboxamide (Compound No. 215)

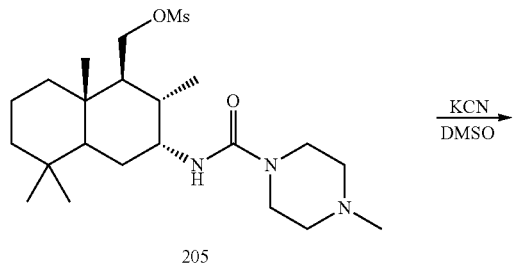

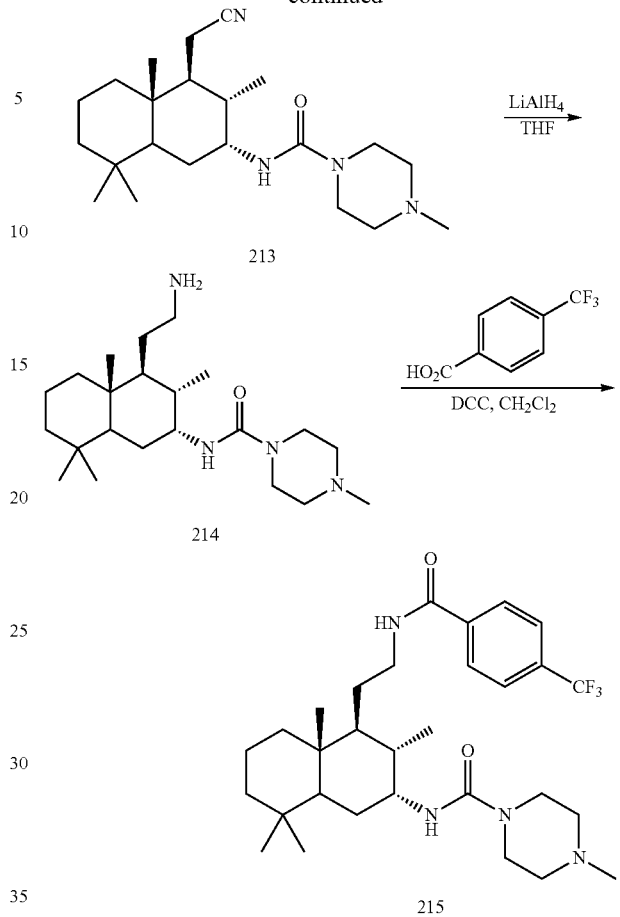

A. A mixture of Compound No. 205 (744 mg, 1.68 mmol) and KCN (342 mg, 5.04 mmol) in DMSO (5 mL) at 60° C. under argon was stirred for 16 hours. The mixture was cooled to room temperature, diluted with Et$_2$O (50 mL) and washed with water (20 mL). The aqueous wash was extracted with Et$_2$O (50 mL) and the combined Et$_2$O layers was washed with brine (10 mL), dried (MgSO$_4$) and concentrated. The residue was purified by chromatography (10% MeOH/EtOAc with 1% NH$_4$OH) to afford Compound No. 213 (327 mg, 52%) as a white foam.

B. To a solution of Compound No. 213 (98 mg, 0.26 mmol) in THF at 0° C. under argon was added LiAlH$_4$ (2.0 M in THF, 0.65 mL, 1.3 mmol) over 1 minute. The reaction was heated at reflux for 2 hours then stirred at room temperature for 16 hours. The mixture was cooled to 0° C. then NaBO$_3$.4H$_2$O was added and the mixture stirred at room temperature for 1 hour. The mixture was filtered through Celite eluting with EtOAc (100 mL) and concentrated. The residue was purified by chromatography on silica gel (5% NH$_4$OH/MeOH) to afford Compound No. 214 (75 mg, 76%) as a white film.

C. A mixture of Compound No. 214 (42 mg, 0.11 mmol), 4-trifluoromethyl benzoic acid (65 mg, 0.33 mmol) and DCC (57 mg, 0.28 mmol) in CH$_2$Cl$_2$ (10 mL) under argon was stirred at room temperature for 18 hours. The mixture was purified by chromatography on silica gel (5% MeOH/EtOAc with 0.5% NH$_4$OH then 10% MeOH/EtOAc with 1% NH$_4$OH) to afford Compound No. 215 (49 mg, 80%) as a white solid. $^1$H NMR (CDCl$_3$): δ7.88 (m, 2H), 7.70 (m, 2H), 6.55 (m, 1H), 4.72 (m, 1H), 4.05 (m, 1H), 3.6-3.3 (6H), 2.39 (4H), 2.28 (s, 3H), 2.0-0.7 (25H). ES-MS m/z 551 ([M+1]$^+$).

EXAMPLE 117

Synthesis of N-((2R,3S,4S,4aR)-4-(2-(4-fluorobenzamido)ethyl)-3,4a,8,8-tetramethyldecahydronaphthalen-2-yl)-4-methylpiperazine-1-carboxamide (Compound No. 216)

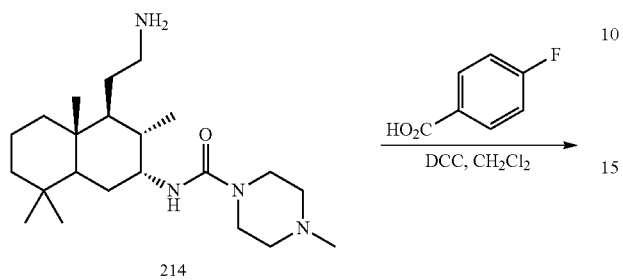

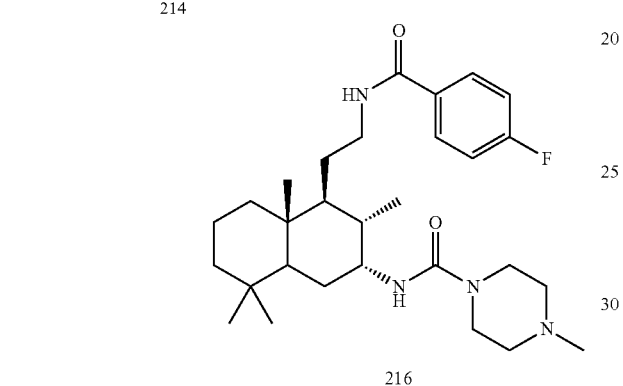

A mixture of Compound No. 214 (25 mg, 0.066 mmol), 4-fluorobenzoic acid (28 mg, 0.20 mmol) and DCC (34 mg, 0.17 mmol) in CH₂Cl₂ (4 mL) under argon was stirred at room temperature for 18 hours. The mixture was purified by chromatography on silica gel (5% MeOH/EtOAc with 0.5% NH₄OH then 10% MeOH/EtOAc with 1% NH₄OH) to afford Compound No. 216 (28 mg, 85%) as a white solid. ¹H NMR (CDCl₃): δ7.78 (m, 2H), 7.10 (m, 2H), 6.25 (m, 1H), 4.72 (m, 1H), 4.05 (m, 1H), 3.50 (m, 1H), 3.40 (4H), 3.35 (m, 1H), 2.40 (4H), 2.0-0.7 (25H). ES-MS m/z 501 ([M+1]⁺).

EXAMPLE 118

Synthesis of N-((2R,3S,4S,4aR)-4-(2-(furan-2-carboxamido)ethyl)-3,4a,8,8-tetramethyldecahydronaphthalen-2-yl)-4-methylpiperazine-1-carboxamide (Compound No. 217)

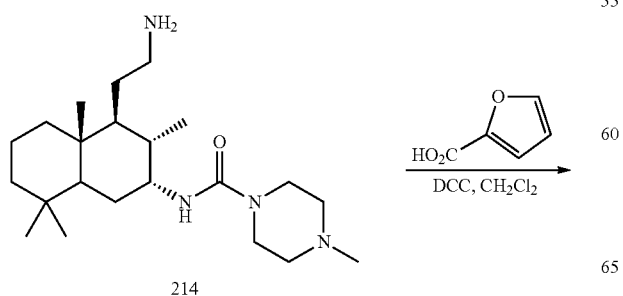

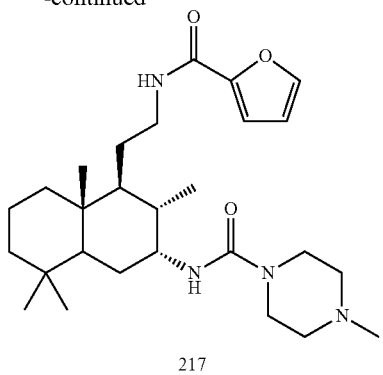

A mixture of Compound No. 214 (25 mg, 0.066 mmol), 2-furoic acid (23 mg, 0.20 mmol) and DCC (34 mg, 0.17 mmol) in CH₂Cl₂ (4 mL) under argon was stirred at room temperature for 18 hours. The mixture was purified by chromatography on silica gel (5% MeOH/EtOAc with 0.5% NH₄OH then 10% MeOH/EtOAc with 1% NH₄OH) to afford Compound No. 217 (26 mg, 84%) as a white solid. ¹H NMR (CDCl₃): δ7.45 (m, 1H), 7.05 (m, 1H), 6.50 (m, 1H), 6.40 (m, 1H), 4.70 (m, 1H), 4.05 (m, 1H), 3.45 (5H), 3.33 (m, 1H), 2.40 (4H), 2.30 (s, 3H), 1.9-1.2 (10H), 1.12 (m, 1H), 1.00 (d, 3H), 0.9-0.6 (11H). ES-MS m/z 473 ([M+1]⁺).

EXAMPLE 119

Synthesis of 4-methyl-N-((2R,3S,4S,4aR)-3,4a,8,8-tetramethyl-4-(2-(nicotinamido)ethyl)decahydronaphthalen-2-yl)piperazine-1-carboxamide (Compound No. 218)

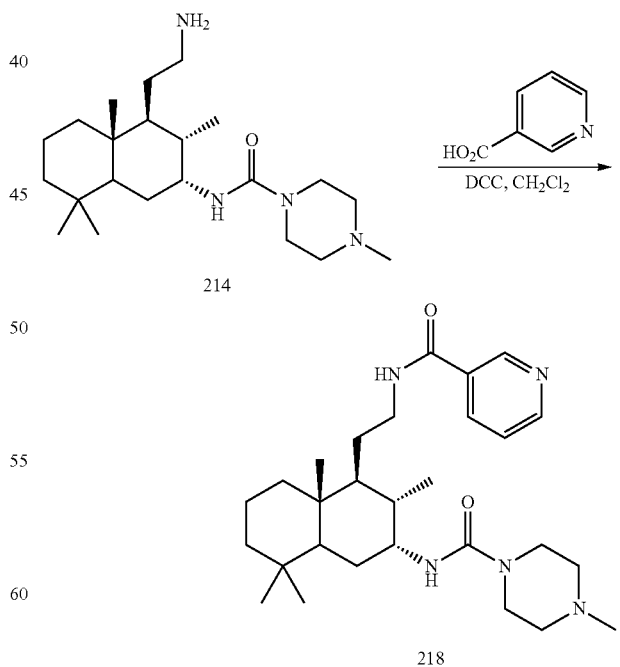

A mixture of Compound No. 214 (25 mg, 0.066 mmol), nicotinic acid (25 mg, 0.20 mmol) and DCC (34 mg, 0.17 mmol) in CH₂Cl₂ (3 mL) under argon was stirred at room temperature for 18 hours. The mixture was purified by chromatography on silica gel (10% MeOH/EtOAc with 1% NH$_4$OH then 20% MeOH/EtOAc with 2% NH$_4$OH) to afford Compound No. 218 (27 mg, 84%) as a white solid. $^1$H NMR (CDCl$_3$): δ8.98 (m, 1H), 8.75 (m, 1H), 8.10 (m, 1H), 7.40 (m, 1H), 6.48 (m, 1H), 4.70 (m, 1H), 4.05 (m, 1H), 3.55 (m, 1H), 3.40 (4H), 3.20 (m, 1H), 2.40 (4H), 2.30 (s, 3H), 2.00 (m, 1H), 1.77 (4H), 1.6-1.2 (5H), 1.2-0.9 (4H), 0.9 (11H). ES-MS m/z 484 ([M+1]$^+$).

EXAMPLE 120

Synthesis of 3-{[(1S,4aS,8aS)-2,5,5,8a-tetramethyl-1,4,4a,5,6,7,8,8a-octahydronaphthalen-1-yl]methoxy}-5-methoxyphenol (Compound No. 220)

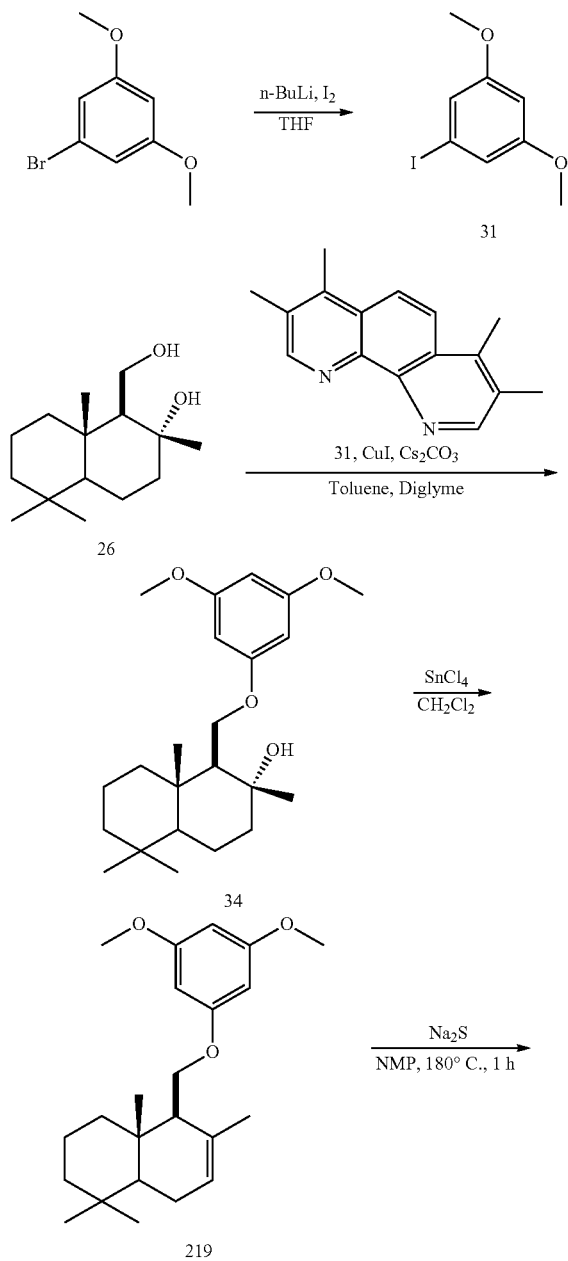

A. A solution of 1-bromo-3,5-dimethoxybenzene (2.17 g, 10.0 mmol) in anhydrous THF (50 mL) was cooled to −78° C. under N$_2$. To the mixture, a 1.6 M solution of n-BuLi in hexanes (12.5 mL, 20.0 mmol) was added, and the mixture was stirred at −78° C. for 30 min. A solution of iodine (5.1 g, 40 mmol) in anhydrous THF (50 mL) was added dropwise to the reaction mixture and the mixture was stirred for 1 h while slowly warming to −30° C. The reaction was quenched with water and the organic layer was separated and concentrated to dryness. The residue was purified by flash column chromatography on silica gel (Hexanes/EtOAc, 4:1) to yield 1-iodo-3,5-dimethoxybenzene (Compound No. 31) (1.45 g, 55% yield) as a pale brown solid.

B. (1S,2R,4aS,8aS)-1-(hydroxymethyl)-2,5,5,8a-tetramethyl-decahydronaphthalen-2-ol (Compound No. 36) (prepared according to Kuchkova et al., Synthesis, 1045-1048, 1997) (0.59 g, 2.4 mmol), Cu(I)I (0.04 g, 0.21 mmol) and 3,4,7,8-tetramethyl-[1,10]phenanthroline (0.10 g, 0.50 mmol) were added to an oven dried tube, which was sealed with a rubber septum, and flushed with a stream of nitrogen for 15 min. Anhydrous toluene (10 mL), anhydrous diglyme (2.0 mL) and 1-iodo-3,5-dimethoxybenzene (Compound No. 31) (0.71 g, 2.7 mmol) were added via a syringe with vigorous stirring under a stream of nitrogen at room temperature. The rubber septum was replaced with the teflon cap and the sealed tube was heated at 130° C. in an oil bath for 18 h. The reaction mixture was allowed to cool to room temperature, then quenched with water and extracted with EtOAc. The organic layer was separated, dried with Na$_2$SO$_4$ and concentrated to dryness under reduced pressure. The residue was purified by flash column chromatography on silica gel (Hexanes/EtOAc, 4:1) to yield (1S,2R,4aS,8aS)-1-(3,5-dimethoxyphenoxymethyl)-2,5,5,8a-tetramethyl-decahydronaphthalen-2-ol (Compound No. 34) (0.65 g, 70% yield) as a pale yellow oil.

C. To a stirred solution of (1S,2R,4aS,8aS)-1-(3,5-dimethoxyphenoxymethyl)-2,5,5,8a-tetramethyl-decahydronaphthalen-2-ol (Compound No. 34) (0.65 g, 1.7 mmol) in CH$_2$Cl$_2$ (20 mL), cooled in a dry ice-acetone bath to −78° C., a solution of SnCl$_4$ (0.8 mL, 6.9 mmol) in CH$_2$Cl$_2$ (10 mL) was added dropwise under N$_2$. As soon as the addition ended, the dry ice-acetone bath was replaced with an ice bath. The mixture was warmed to room temperature and stirred for 3 h. The reaction mixture was quenched with water and the organic layer was separated and concentrated to dryness. The residue was purified by flash column chromatography on silica gel (Hexanes/Toluene, 1:2) to yield (4aS,5S,8aS)-5-(3,5-dimethoxyphenoxymethyl)-1,1,4a,6-tetramethyl-1,2,3,4,4a,5,8,8a-octahydronaphthalene (Compound 219) (0.15 g, 24% yield) as a white solid.

D. A mixture of (4aS,5S,8aS)-5-(3,5-dimethoxyphenoxymethyl)-1,1,4a,6-tetramethyl-1,2,3,4,4a,5,8,8a-octahydronaphthalene (5) (0.15 g, 0.45 mmol), Na$_2$S (0.22 g, 2.7 mmol) and NMP (5.0 mL) were sealed in a microwave vessel and heated at 180° C. with stirring for 1 h. The reaction mixture was cooled to room temperature, quenched with water and extracted with EtOAc. The organic layer was separated and concentrated to dryness. The residue was purified by flash column chromatography on silica gel (Hexanes/EtOAc, 6:1) to yield 3-{[(1S,4aS,8aS)-2,5,5,8a-tetramethyl-1,4,4a,5,6,7,8,8a-octahydronaphthalen-1-yl]methoxy}-5-methoxyphenol (Compound No. 220) (0.058 g, 37% yield) as a pale brown oil. $^1$H NMR (CDCl$_3$): δ6.05 (s, 1H), 6.00 (s, 2H), 5.50 (s, 1H), 4.60 (m, 1H), 4.05 (m, 1H), 3.85 (m, 1H), 3.75 (s, 3H), 2.15 (m, 1H), 2.00-1.80 (m, 3H), 1.68 (s, 3H), 1.61-0.95 (m, 6H), 0.88 (s, 3H), 0.84 (s, 6H); MS m/z 345 (C$_{22}$H$_{32}$O$_3$+1).

EXAMPLE 121

Synthesis of (2R,4aS,8aS)-1-{[(3-hydroxy-5-methoxyphenyl)amino]methyl}-2,5,5,8a-tetramethyl-decahydronaphthalen-2-ol (Compound No. 223)

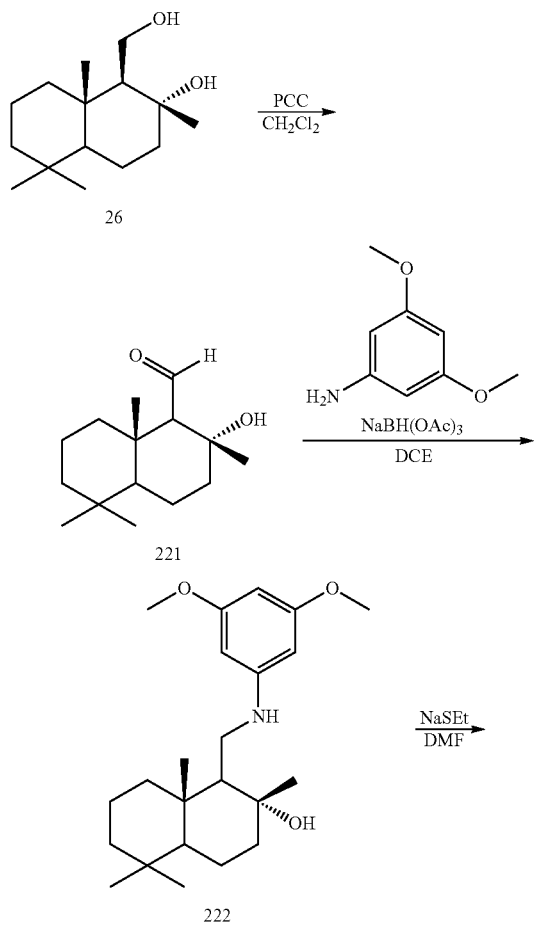

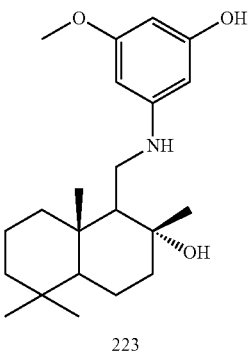

A. (1S,2R,4aS,8aS)-1-(hydroxymethyl)-2,5,5,8a-tetramethyl-decahydronaphthalen-2-ol (Compound No. 26) (prepared according to Kuchkova et al., *Synthesis*, 1045-1048, 1997) (2.0 g, 8.3 mmol) was added to a mixture of pyridinium chlorochromate (3.0 g, 9.5 mmol) in anhydrous CH$_2$Cl$_2$ (40 mL). The mixture was stirred at room temperature for 4 h under N$_2$. The reaction was filtered through a plug of silica and the filtrate concentrated to dryness. The crude product was purified by flash chromatography on silica gel (Hexanes/EtOAc, 6:1) to yield (2R,4aS,8aS)-2-hydroxy-2,5,5,8a-tetramethyl-decahydronaphthalene-1-carbaldehyde (Compound No. 221) (0.73 g, 37% yield) as a pale green solid.

B. A mixture of (2R,4aS,8aS)-2-hydroxy-2,5,5,8a-tetramethyl-decahydronaphthalene-1-carbaldehyde (Compound No. 221) (0.25 g, 1.1 mmol), 3,5-dimethoxyaniline (0.25 g, 1.6 mmol) and sodium triacetoxyborohydride (0.34 g, 1.6 mmol) in dichloroethane (10 mL) was stirred at room temperature for 18 h under N$_2$. The reaction mixture was concentrated to dryness and the residue was purified by flash chromatography on silica gel (Hexanes/EtOAc, 2:1) to yield (2R,4aS,8aS)-1-{[(3,5-dimethoxyphenyl)amino]methyl}-2,5,5,8a-tetramethyl-decahydronaphthalen-2-ol (Compound No. 222) (0.10 g, 26%) as a colorless oil.

C. A mixture of (2R,4aS,8aS)-1-{[(3,5-dimethoxyphenyl)amino]-methyl}-2,5,5,8a-tetramethyl-decahydronaphthalen-2-ol (Compound No. 223) (0.10 g, 0.27 mmol), EtSNa (0.44 g, 5.3 mmol) and DMF (3.0 mL) were sealed in a microwave vessel and heated at 160° C. with stirring for 2 h. The reaction mixture was cooled to room temperature, quenched with water and extracted with EtOAc. The organic layer was separated and then concentrated to dryness. The crude product was purified by flash chromatography on silica gel (Hexanes/EtOAc, 2:1) to yield (2R,4aS,8aS)-1-{[(3-hydroxy-5-methoxyphenyl)amino]methyl}-2,5,5,8a-tetramethyl-decahydronaphthalen-2-ol (Compound No. 223) (0.080 g, 83% yield) as a pale brown solid. 1H NMR (CDCl$_3$): δ5.84 (s, 2H), 5.78 (s, 1H), 3.75 (s, 3H), 3.30-3.12 (m, 3H), 2.10-1.80 (m, 3H), 1.70-0.90 (m, 12H), 0.88 (s, 3H), 0.83 (s, 3H), 0.78 (s, 3H); MS m/z 362 (C$_{22}$H$_{35}$NO$_3$+1).

EXAMPLE 122

Synthesis of 2-[(1S,2R,3R,4aS,8aR)-3-bromo-2,5,5, 8a-tetramethyl-decahydro-naphthalen-1-yl]-N-(3,5-dihydroxyphenyl)-N-methylacetamide (Compound No. 225) and 2-[(1S,4aS,8aS)-2,5,5,8a-tetramethyl-1,4,4a,5,6,7,8,8a-octahydronaphthalen-1-yl]-N-(3,5-dihydroxyphenyl)-N-methylacetamide (Compound No. 226)

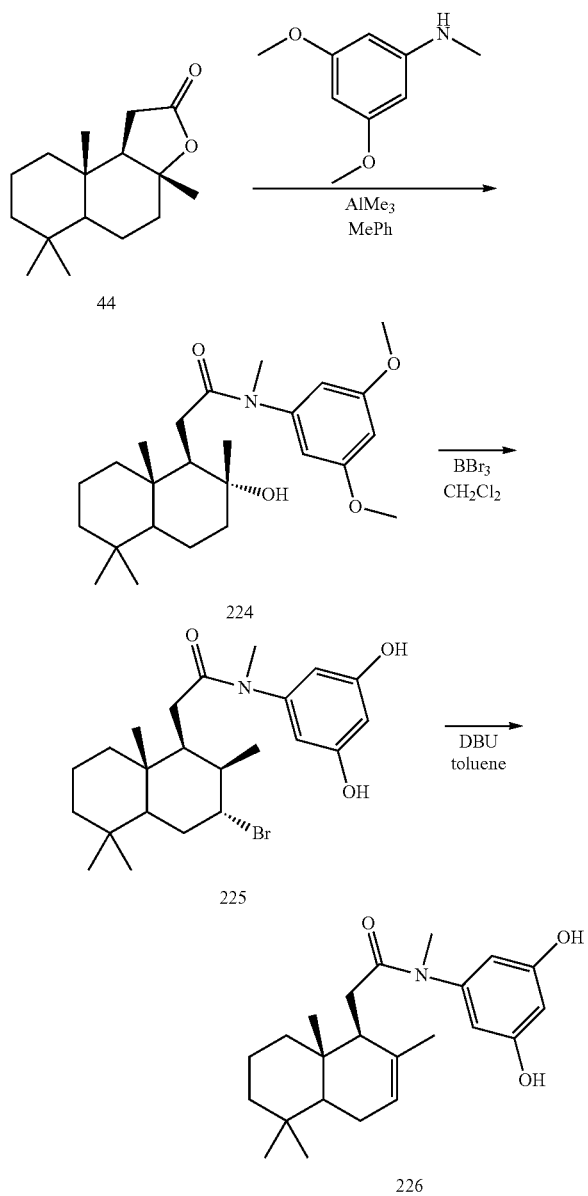

A. To a stirred solution of N-(3,5-dimethoxyphenyl)-N-methylamine (0.43 g, 2.6 mmol) in anhydrous toluene (10 mL) at room temperature, trimethylaluminum (2 M in hexanes, 1.9 mL, 3.8 mmol) was added dropwise. The mixture was stirred at room temperature for 55 minutes. A solution of (3aR,5aS,9aS,9bR)-3a,6,6,9a-tetramethyl-dodecahydronaphtho[2,1-b]furan-2-one (Compound No. 44) (0.71 g, 2.8 mmol) in anhydrous toluene (3.0 mL) was added dropwise and the mixture was heated at 80° C. for 17 h. The reaction was cooled to 0° C. and quenched with 1 M HCl, diluted with water and extracted with EtOAc. The organic phase was separated abd concentrated to dryness. The crude product was purified by flash chromatography on silica gel (Hexanes/EtOAc, 1:1) to yield 2-[(1R,2R,4aS,8aS)-2-hydroxy-2,5,5,8a-tetramethyl-decahydronaphthalen-1-yl]-N-(3,5-dimethoxyphenyl)-N-methylacetamide (Compound No. 224) (0.98 g, 91% yield) as a white semi-solid.

B. A solution of 2-[(1R,2R,4aS,8aS)-2-hydroxy-2,5,5,8a-tetramethyl-decahydronaphthalen-1-yl]-N-(3,5-dimethoxyphenyl)-N-methylacetamide (Compound No. 224) (0.16 g, 0.38 mmol) in anhydrous $CH_2Cl_2$ (3.0 mL) was prepared at −28° C. under $N_2$. To the mixture, $BBr_3$ (1 M in $CH_2Cl_2$, 2.0 mL, 2.0 mmol) was added dropwise. The mixture was stirred at −28° C. to −20° C. for 8 h and then was allowed to slowly warm to room temperature overnight. The solution was cooled to 0° C. and quenched with anhydrous MeOH. The solution was evaporated and the residue co-evaporated with anhydrous MeOH. The residue was dissolved in $CH_2Cl_2$ and was shaken with 1M HCl. The pH was adjusted to 8 using $NaHCO_3$ and the organic phase was separated. The aqueous phase was extracted with $CH_2Cl_2$ and the organic extracts were combined and concentrated to dryness. The residue was purified by flash chromatography on silica gel (Hexanes/EtOAc, 3:2) to yield 2-[(1S,2R,3R,4aS,8aR)-3-bromo-2,5,5,8a-tetramethyl-decahydro-naphthalen-1-yl]-N-(3,5-dihydroxyphenyl)-N-methylacetamide (Compound No. 225) (0.12 g, 69% yield) as an off-white solid. $^1$H NMR ($CD_3OD$): δ6.26 (s, 1H), 6.14 (d, 2H), 4.60 (d, 1H), 3.16 (s, 3H), 2.21-2.00 (m, 3H), 1.93-1.83 (m, 2H), 1.73-1.67 (d, 1H), 1.63-1.52 (m, 2H), 1.51-1.37 (m, 3H), 1.30-1.18 (m, 1H), 1.11-0.99 (m, 1H), 0.87 (d, 3H), 0.84 (s, 3H), 0.81 (s, 3H), 0.70 (s, 3H). MS m/z 450, 452 ($C_{23}H_{34}BrNO_3$−1).

C. A solution of 2-[(1S,2R,3R,4aS,8aR)-3-bromo-2,5,5,8a-tetramethyl-decahydronaphthalen-1-yl]-N-(3,5-dihydroxyphenyl)-N-methylacetamide (Compound No. 225) (0.054 g, 0.119 mmol) in anhydrous toluene (2.0 mL) and DBU (0.10 mL, 0.66 mmol) were heated at 118° C. for 23 h. The mixture was cooled in ice, diluted with $CH_2Cl_2$ and washed with 1 M HCl. The acidic aqueous layer was extracted with $CH_2Cl_2$. The organic phase was washed with diluted brine and this aqueous washing was back extracted with $CH_2Cl_2$. The combined organic extracts were concentrated to dryness. The crude solid was triturated with $CH_2Cl_2$ and collected by filtration to yield 2-[(1S,4aS,8aS)-2,5,5,8a-tetramethyl-1,4,4a,5,6,7,8,8a-octahydronaphthalen-1-yl]-N-(3,5-dihydroxyphenyl)-N-methylacetamide (Compound No. 226) (0.024 g, 56% yield) as an off-white solid. $^1$H NMR ($CD_3OD$): δ6.27 (dd, 1H), 6.15 (d, 2H), 5.35 (br.s, 1H), 3.18 (s, 3H), 2.63-2.56 (m, 1H), 2.20-2.14 (m, 1H), 2.08-1.93 (m, 2H), 1.87-1.75 (m, 1H), 1.71-1.63 (m, 1H), 1.58-1.38 (m, 3H), 1.29-1.15 (m, 2H), 1.04 (ddd, 1H), 0.87 (s, 6H), 0.86 (s, 3H), 0.61 (s, 3H). MS m/z 372 ($C_{23}H_{33}NO_4$+1).

EXAMPLE 123

His-hSHIP1 Activity of Representative Compounds

Test compounds are dissolved in 95% ethanol to form stock solutions. Before screening, the stock solutions are diluted with Phosphatase Assay Buffer (20 mM Tris-HCL, 10 mM $MgCl_2$ pH 7.5, 0.02% Tween 20) to form working assay solutions that contain 10% ethanol. The assay is carried out on 96-well microtiter plates using a modified procedure of that reported by Ong et al., *Blood* 110, 1942-

1949, 2007 and Yang et al., *Org Lett* 7, 1073-1076, 2005, both of which references are incorporated herein by reference in their entirety.

Data were generated by one of two variant methods. Test compounds are screened by one of two approaches described as follows. In the first approach, each reaction contains 5 μL of His-hSHIP1 enzyme (5-20 ng), 10 μL of the substrate, 1,3,4,5-inositol tetrakisphosphate (IP4; 50 μM final), 5 μL of Phosphatase Assay Buffer, and 5 L of test compound at various concentrations in 10% ethanol (0-300 μM final). Control blanks are also prepared by replacing His-hSHIP1 enzyme, IP4, or test compounds with Phosphatase Assay Buffer. After adding the reaction components in a 96-well microtiter plate on ice, the reaction is mixed by briefly shaking the plate vigorously. The reaction is then incubated at 37° C. for 15 min with gentle shaking followed by addition of 100 μL of Biomol Green Reagent (BIOMOL, Pa., USA) to terminate the reaction. The free phosphate released from IP4 by His-hSHIP1 binds to the Biomol Green Reagent, which turns the dye to green color. After incubating the mixture for 20 min at room temperature for color development, the absorbance is read with SpectraMax Plus 96-well plate reader (Molecular Devices, Sunnyvale, Calif., USA) at a wavelength of 650 nm.

In the second approach, a master mix is prepared that contains 50 μL of His-hSHIP1 enzyme (0.4-1.6 ng/μL final), 25 μL of the substrate, IP4 (25 or 250 μM final), and 50 μL of test compound in 3.3% ethanol (100 μL final). Control blanks are also prepared by replacing His-hSHIP1 enzyme, IP4, or test compounds with Phosphate Assay Buffer. A reference compound that has been shown to activate SHIP1 is also included. Each reaction component is preincubated at 37° C. for 30 min before adding to a 96-well microtiter plate. The master mix is then incubated at 37° C. At time 0, 20, 25 and 30 min, 25 μL of the master mix is removed and transferred to a new 96-well microtiter plate, to which 100 μL of Biomol Green Reagent is added to stop the reaction. After incubating the mixture for 20 min at room temperature for color development, the absorbance is read with SpectraMax Plus 96-well plate reader at a wavelength of 650 nm. Phosphate released is plotted against time to calculate the initial velocities (i.e., slope of the graph) at each IP4 concentration. The initial velocities are baseline corrected and the ratio of initial velocities ($IP4_{25}/IP4_{250}$) is calculated and used to rate the test compounds.

According to the above assay(s), the representative compounds listed in Table 2 below were found to activate His-hSHIP1 enzyme at concentrations ≤300 μM.

Scoring of the Compound is Expressed as Follows:

| Scoring | Approach 1 (% increase relative to background) | Approach 2 (Initial velocity Ratio) |
| --- | --- | --- |
| +++ | x ≥65 | higher than reference or reference − 15% |
| ++ | 50 ≤ x < 65 | reference − 16% to reference − 30% |
| + | 0 < x < 50 | reference − 31% or lower |

Data Generated by the Second Method is Distinguished by an Asterisk.

TABLE 2

| Cpd. No. | Scoring |
| --- | --- |
| 4 | ++ |
| 6 | + |

TABLE 2-continued

| Cpd. No. | Scoring |
| --- | --- |
| 8 | + |
| 9 | + |
| 11 | +++ |
| 17 | ++ |
| 22 | + |
| 23 | + |
| 27 | ++ |
| 29 | +++ |
| 30 | + |
| 38 | + |
| 42 | + |
| 43 | + |
| 45 | ++ |
| 46 | ++ |
| 47 | ++ |
| 48 | +++ |
| 50 | ++ |
| 51 | ++ |
| 52 | +++ |
| 53 | ++ |
| 54 | ++ |
| 55 | + |
| 56 | + |
| 57 | +++ |
| 58 | +++ |
| 62 | +++ |
| 65 | +++ |
| 49* | +++ |
| 68* | +++ |
| 20* | +++ |
| 136* | ++ |
| 175* | ++ |
| 176* | ++ |
| 149* | ++ |
| 137* | ++ |
| 137* | ++ |
| 138* | ++ |
| 139* | ++ |
| 157* | ++ |
| 181* | +++ |
| 141* | + |
| 142* | ++ |
| 173* | +++ |
| 118* | +++ |
| 178* | +++ |
| 119* | ++ |
| 179* | + |

EXAMPLE 124

Activity of Representative Compounds on Akt Phosphorylation in Lymphocytes

Phosphorylation of AKT has been shown to be modulated by SHIP1 (Helgason et al., *J Exp Med* 191, 781-794, 2000). Jurkat (PTEN−/SHIP1−) or Molt-4 (PTEN−/SHIP1+) cells are starved in serum free RPMI for overnight. In a 15 mL conical tube, 2-3 million serum starved cells (1 million cells per mL) are treated with various concentrations of test compound (0.1, 1, or 10 μM final in 0.1% DMSO) for 30 min at 37° C. followed by stimulation with 100 ng/mL of IGF-1 for 1 hour at 37° C. After stimulation, cells are washed once with ice-cold DPBS and lysed with Lysis Buffer (20 mM Tris-HCl, pH 7.5, 140 mM NaCl, 1% NP-40, Complete Mini Protease Inhibitor Cocktail, 10 mM NaF, 1 mM $Na_3VO_4$, 1 mM β-glycerolphosphate) on ice for 30 min with vortexing every 10 min. Samples are then centrifuged at 13,000 rpm for 20 min, and supernatants are collected as total cell lysate samples. Protein concentration is determined using bicinchonic acid assay, and about 15 μg of total protein from each sample is loaded and separated on a 4-12% Tris-Glycine gel.

After SDS-PAGE, proteins are transferred from the gel to a nitrocellulose membrane. The membrane is blocked in 5% BSA in PBS containing 0.1% Tween-20 (PBS-T) for 1 hour at room temperature before probing with primary antibodies for overnight at 4° C. The following antibodies are used: mouse anti-SHIP1 (1:500 dilution; Santa Cruz, Calif., USA), rabbit anti-phospho-Akt(Ser473) (1:1000 dilution; Cell Signaling Technologies, MA, USA), rabbit anti-Akt (1:1000; Cell Signaling Technologies, MA, USA), and rabbit anti-actin (1:2000; Cell Signaling Technologies, MA, USA). The membrane is then incubated with goat anti-rabbit or anti-mouse secondary antibodies (1:3000) for 1 hour at room temperature. Target proteins on the membrane are detected with ECL solution and exposed on a film.

According to the above assay, the representative compounds listed in Table 3 below were found to inhibit Akt phosphorylation at ≤10 μM in Molt-4 (SHIP1+), but not Jurkat (SHIP1−) lymphocytes. Scoring in Table 3 is expressed as follows: + (inhibits Akt phosphorylation at 10 μM); − (no effect on Akt phosphorylation at 10 μM).

TABLE 3

| Cpd. No. | Molt-4 (SHIP +) | Jurkat (SHIP1 −) |
|---|---|---|
| 22 | + | − |
| 57 | + | − |
| 22 | + | − |
| 57 | − | − |
| 68 | − | − |
| 20 | − | − |

EXAMPLE 125

Activity of Representative Compounds on Passive Cutaneous Anaphylaxis in Mice

The activity of representative compounds on passive cutaneous anaphylaxis in mice was evaluated according to the procedures disclosed by Ovary, *J Immunol* 81, 355-357, 1958 and Halpern et al., *Br J Pharmacol Chemother* 20, 389-398, 1963, both of which are incorporated herein by reference in their entirety.

To induce a passive cutaneous anaphylaxis, mice undergo intradermal ear inoculation on their right ear with 25 ng in 20 μL of anti-DNP-IgE. The left ears are untreated and serve as negative controls. Twenty-four hours after inoculation, all mice are administered test compound by oral gavage (PO). Sixty minutes after oral administration, mice are given a tail vein injection of 2% Evan's Blue (0.2 μm filtered, in 200 μL saline) followed by a second tail IV injection of 100 μg DNP-HSA (in 200 μL). Sixty minutes following the DNP-HAS injection, mice are euthanized using $CO_2$ inhalation. Subsequently, ear biopsies are performed by taking four millimetre punches from both ears, which then undergo Evan's Blue extraction using formamide incubation in 96 well plates. Eighty μL of eluents are transferred to flat-bottom 96-well plates and absorbance read using SpectraMax M5 spectrophotometer (Molecular Devices, Sunnyvale, Calif., USA) at 620 nm. Background readings from all samples are taken at 740 nm and subtracted from the 620 nm readings. Data are reported as OD.

According to the above assay, the representative compounds listed in Table 4 below were found to inhibit allergen-induced passive cutaneous anaphylaxis at doses less than 20 mg/kg. Scoring in Table 4 is expressed as follows: + (1-30% inhibition); ++ (31-50% inhibition); +++ (>50% inhibition).

TABLE 4

| Cpd. No. | % Inhibition |
|---|---|
| 38 | +++ |
| 57 | +++ |
| 58 | +++ |

EXAMPLE 126

Activity of Representative Compounds on Carrageenan Paw Edema in Mice

The activity of representative compounds on carrageenan paw edema in mice was evaluated according to the procedures disclosed by Winter et al., *Proc Soc Exp Biol Med* 111, 544-547, 1962 which is incorporated herein by reference in its entirety.

To induce edema in the paw, test compounds were administered orally one hour before intraplantar injection of the right hind paw with carrageenan (50 μL of 1% suspension). Hind paw edema, as a measure of inflammation, was recorded using a plethysmometer (Ugo Basile, Italy) 4 hours after λ-carrageenan administration. When tested in this assay, representative Compound No. 48 was found to inhibit allergen-induced carrageenan-induced paw edema by 21% at 30 mg/kg.

\* \* \*

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A method for modulating SHIP1 activity in a mammal, wherein the method comprises administering to the mammal in need thereof an effective amount of a compound of formula (I):

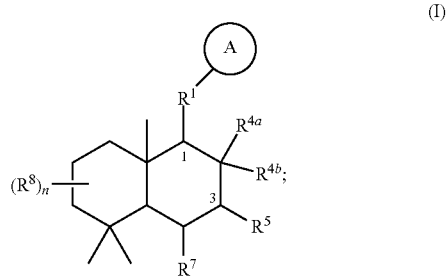

wherein:

is selected from:

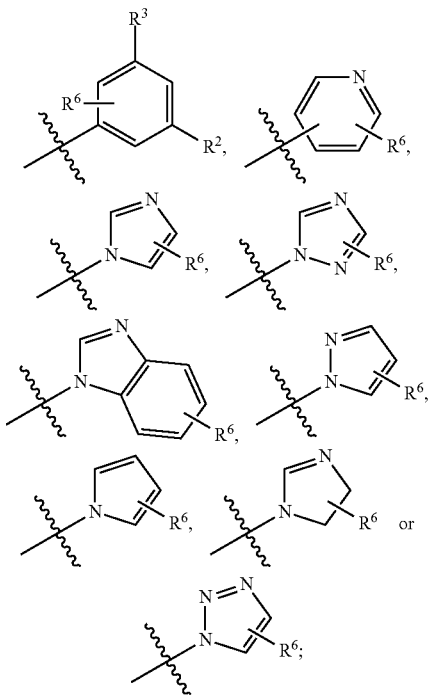

n is 1, 2, 3, 4, 5, or 6;
R$^1$ is —R$^{9a}$—C(R$^{10}$)$_2$—R$^{9b}$—, —R$^{9a}$—C(O)—R$^{9b}$—, —R$^{9a}$—S(O)$_t$—R$^{9b}$— (where t is 0, 1 or 2), —R$^{9a}$—O—R$^{9b}$—, —R$^{9a}$—C(O)N(R$^{11a}$)—R$^{9b}$—, —R$^{9a}$—N(R$^{11a}$)C(O)—R$^{9b}$— or —R$^{9a}$—N(R$^{11a}$)—R$^{9b}$—; provided that when A is

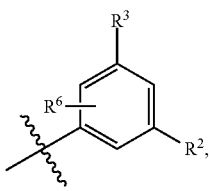

R$^1$ is not —R$^{9a}$—C(R$^{10}$)$_2$—R$^{9b}$—;
R$^2$ and R$^3$ are each independently selected from hydrogen, alkyl or —R$^9$—OR$^{11}$, provided that at least one of R$^2$ and R$^3$ is —R$^9$—OR$^{11}$ when R$^6$ is hydrogen;
R$^{4a}$ and R$^{4b}$ are each independently selected from hydrogen, alkyl, —R$^9$—OR$^{11}$ or —C(O)OR$^{11}$,
R$^5$ is independently selected from hydrogen, oxo, cyano, nitro, halo, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl, optionally substituted heteroarylalkyl,
—R$^9$—OR$^{11}$, —R$^9$—C(O)R$^{11}$, —R$^9$—C(O)OR$^{11}$, —R$^9$—N(R$^{11}$)R$^{12}$, —R$^9$—C(O)N(R$^{11}$)R$^{12}$, —R$^9$—N(R$^{11}$)C(O)R$^{12}$, —R$^9$—N(R$^{11}$)—R$^{14}$—N(R$^{11}$)R$^{12}$, —R$^9$—N(R$^{11}$)C(O)—R$^9$—N(R$^{11}$)R$^{12}$, —R$^9$—N(R$^{11}$)C(O)N(R$^{11}$)—OR$^{12}$, —R$^9$—N(R$^{11}$)C(=NR$^{11}$)N(R$^{11}$)R$^{12}$, —R$^9$—N(R$^{11}$)S(O)$_p$R$^{11}$ (where p is 1 or 2), —R$^9$—N(R$^{11}$)C(S)N(R$^{11}$)R$^{12}$ or —R$^9$—N(R$^{11}$)C(O)—R$^9$—N(R$^{11}$)S(O)$_p$R$^{12}$ (where p is 1 or 2);
each R$^6$ and R$^8$ is independently selected from hydrogen, alkyl, halo or haloalkyl;
R$^7$ is hydrogen, alkyl, halo or haloalkyl;
each R$^9$, R$^{9a}$ and R$^{9b}$ is independently a direct bond or a straight or branched alkylene chain;
each R$^{10}$ is independently hydrogen, alkyl, —OR$^{11}$, —C(O)OR$^{11}$, —C(O)N(R$^{11}$)R$^{12}$, —N(R$^{11}$)R$^{12}$ or —N(R$^{11}$)C(O)R$^{11}$;
each R$^{11}$, R$^{11a}$ and R$^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and
R$^{14}$ is a straight or branched alkylene chain;
or a stereoisomer thereof or a pharmaceutically acceptable salt thereof;
provided that compounds of formula (I) do not include the following compounds:
(1S,2R,4aS,8aS)-1-(3-methoxy-5-methylphenoxymethyl)-2,5,5,8a-tetramethyl-decahydronaphthalen-2-ol;
(1S,2R,4aS,8aS)-1-(3,5-dimethoxyphenoxymethyl)-2,5,5,8a-tetramethyl-decahydronaphthalen-2-ol;
(1S,2R,4aS,8aS)-1-[3,5-bis(propan-2-yloxy)phenoxymethyl]-2,5,5,8a-tetramethyl-decahydronaphthalen-2-ol;
(1R,2R,8aS)-1-((3,5-dimethoxyphenylsulfonyl)methyl)-2,5,5,8a-tetramethyldecahydronaphthalen-2-ol;
(1R,2R,4aS,8aS)-1-{[(3-methoxy-5-methylphenyl)sulfanyl]methyl}-2,5,5,8a-tetramethyl-decahydronaphthalen-2-ol;
(1R,2R,4aS,8aS)-1-{[(3-methoxyphenyl)sulfanyl]methyl}-2,5,5,8a-tetramethyl-decahydronaphthalen-2-ol; and
(1R,2R,4aS,8aS)-1-{[(3,5-dimethoxyphenyl)sulfanyl]methyl}-2,5,5,8a-tetramethyl-decahydronaphthalen-2-ol.

2. A method for modulating SHIP1 activity in a mammal, wherein the method comprises administering to the mammal in need thereof an effective amount of a composition comprising a pharmaceutically acceptable excipient and a compound of formula (I):

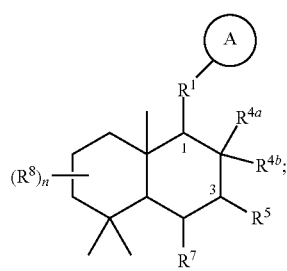

(I)

wherein:

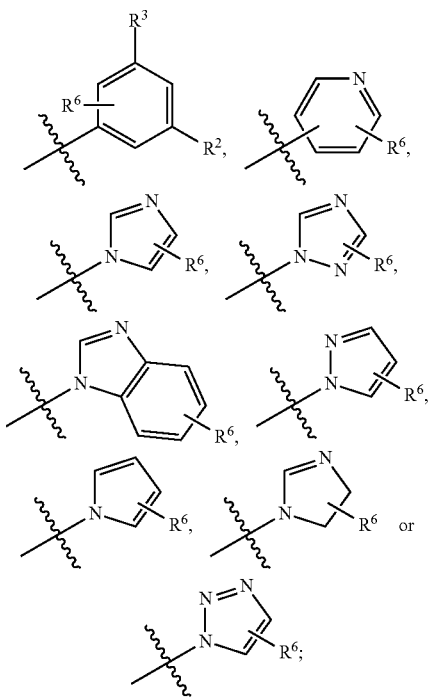

n is 1, 2, 3, 4, 5, or 6;
$R^1$ is $-R^{9a}-C(R^{10})_2-R^{9b}-$, $-R^{9a}-C(O)-R^{9b}-$, $-R^{9a}-S(O)_t-R^{9b}-$ (where t is 0, 1 or 2), $-R^{9a}-O-R^{9b}-$, $-R^{9a}-C(O)N(R^{11a})-R^{9b}-$, $-R^{9a}-N(R^{11a})C(O)-R^{9b}-$ or $-R^{9a}-N(R^{11a})-R^{9b}-$; provided that when A is

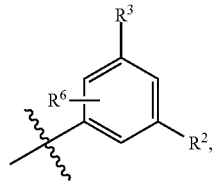

$R^1$ is not $-R^{9a}-C(R^{10})_2R^{9b}-$;
$R^2$ and $R^3$ are each independently selected from hydrogen, alkyl or $-R^9-OR^{11}$, provided that at least one of $R^2$ and $R^3$ is $-R^9-OR^{11}$ when $R^6$ is hydrogen;

$R^{4a}$ and $R^{4b}$ are each independently selected from hydrogen, alkyl, $-R^9-OR^{11}$ or $-C(O)OR^{11}$,
$R^5$ is independently selected from hydrogen, oxo, cyano, nitro, halo, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl, optionally substituted heteroarylalkyl, $-R^9-OR^{11}$, $-R^9-C(O)R^{11}$, $-R^9-C(O)OR^{11}$, $-R^9-N(R^{11})R^{12}$, $-R^9-C(O)N(R^{11})R^{12}$, $-R^9-N(R^{11})C(O)R^{12}$, $-R^9-N(R^{11})-R^{14}-N(R^{11})R^{12}$, $-R^9-N(R^{11})C(O)-R^9-N(R^{11})R^{12}$, $-R^9-N(R^{11})C(O)N(R^{11})-OR^{12}$, $-R^9-N(R^{11})C(=NR^{11})N(R^{11})R^{12}$, $-R^9-N(R^{11})S(O)_pR^{11}$ (where p is 1 or 2), $-R^9-N(R^{11})C(S)N(R^{11})R^{12}$ or $-R^9-N(R^{11})C(O)-R^9-N(R^{11})S(O)_pR^{12}$ (where p is 1 or 2);
each $R^6$ and $R^8$ is independently selected from hydrogen, alkyl, halo or haloalkyl;
$R^7$ is hydrogen, alkyl, halo or haloalkyl;
each $R^9$, $R^{9a}$ and $R^{9b}$ is independently a direct bond or a straight or branched alkylene chain;
each $R^{10}$ is independently hydrogen, alkyl, $-OR^{11}$, $-C(O)OR^{11}$, $-C(O)N(R^{11})R^{12}$, $-N(R^{11})R^{12}$ or $-N(R^{11})C(O)R^{11}$;
each $R^{11}$, $R^{11a}$ and $R^{12}$ is independently hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; and
$R^{14}$ is a straight or branched alkylene chain;
or a stereoisomer thereof or a pharmaceutically acceptable salt thereof;
provided that compounds of formula (I) do not include the following compounds:
(1S,2R,4aS,8aS)-1-(3-methoxy-5-methylphenoxymethyl)-2,5,5,8a-tetramethyl-decahydronaphthalen-2-ol;
(1S,2R,4aS,8aS)-1-(3,5-dimethoxyphenoxymethyl)-2,5,5,8a-tetramethyl-decahydronaphthalen-2-ol;
(1S,2R,4aS,8aS)-1-[3,5-bis(propan-2-yloxy)phenoxymethyl]-2,5,5,8a-tetramethyl-decahydronaphthalen-2-ol;
(1R,2R,8aS)-1-((3,5-dimethoxyphenylsulfonyl)methyl)-2,5,5,8a-tetramethyldecahydronaphthalen-2-ol;
(1R,2R,4aS,8aS)-1-{[(3-methoxy-5-methylphenyl)sulfanyl]methyl}-2,5,5,8a-tetramethyl-decahydronaphthalen-2-ol;
(1R,2R,4aS,8aS)-1-{[(3-methoxyphenyl)sulfanyl]methyl}-2,5,5,8a-tetramethyl-decahydronaphthalen-2-ol; and
(1R,2R,4aS,8aS)-1-{[(3,5-dimethoxyphenyl)sulfanyl]methyl}-2,5,5,8a-tetramethyl-decahydronaphthalen-2-ol.

* * * * *